(12) United States Patent
Aversa et al.

(10) Patent No.: US 10,167,279 B2
(45) Date of Patent: Jan. 1, 2019

(54) COMPOUNDS AND COMPOSITIONS AS RAF KINASE INHIBITORS

(71) Applicant: NOVARTIS AG, Basel (CH)

(72) Inventors: Robert John Aversa, Watertown, MA (US); Matthew T. Burger, Belmont, MA (US); Michael Patrick Dillon, Castro Valley, CA (US); Thomas A. Dineen, Jr., Somerville, MA (US); Yan Lou, Pleasanton, CA (US); Gisele A. Nishiguchi, Arlington, MA (US); Savithri Ramurthy, Emeryville, CA (US); Alice C. Rico, Castro Valley, CA (US); Vivek Rauniyar, Cambridge, MA (US); Martin Sendzik, Belmont, MA (US); Sharadha Subramanian, San Ramon, CA (US); Lina Quattrocchio Setti, Fremont, CA (US); Benjamin R. Taft, Oakland, CA (US); Huw Rowland Tanner, San Francisco, CA (US); Lifeng Wan, Union City, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/510,609

(22) PCT Filed: Sep. 11, 2015

(86) PCT No.: PCT/IB2015/056989
§ 371 (c)(1),
(2) Date: Mar. 10, 2017

(87) PCT Pub. No.: WO2016/038582
PCT Pub. Date: Mar. 17, 2016

(65) Prior Publication Data
US 2018/0170917 A1    Jun. 21, 2018

Related U.S. Application Data

(60) Provisional application No. 62/049,468, filed on Sep. 12, 2014.

(51) Int. Cl.
C07D 405/14  (2006.01)
C07D 405/12  (2006.01)
C07D 305/06  (2006.01)
A61P 35/00   (2006.01)
C07D 413/14  (2006.01)

(52) U.S. Cl.
CPC ............ C07D 405/14 (2013.01); A61P 35/00 (2018.01); C07D 305/06 (2013.01); C07D 405/12 (2013.01); C07D 413/14 (2013.01)

(58) Field of Classification Search
None
See application file for complete search history.

(56) References Cited

U.S. PATENT DOCUMENTS

2014/0275003 A1    9/2014   Busanti et al.

OTHER PUBLICATIONS

Lyne, et al., "Identification of amidoheteroaryls as potent inhibitors of mutant (V600E) B-Raf kinase with in vivo activity", Bioorganic & Medicinal Chemistry Letters, 19(3):1026-1029. (2009).
Babchia ey al., "The PI3K/Akt and mTor/P70S6K Signaling Pathways in Human Uveal Melanoma Cells: Interaction with B-Raf/ERK", Investigative Opthalmology & Visual Science, 51(1):421-429. (2010).

Primary Examiner — Heidi Reese
(74) Attorney, Agent, or Firm — Scott W. Reid

(57) ABSTRACT

The present invention provides compounds of Formula (I) and (II) as described herein, and salts thereof, and therapeutic uses of these compounds for treatment of disorders associated with Raf kinase activity. The invention further provides pharmaceutical compositions comprising these compounds, and compositions comprising these compounds and a therapeutic co-agent.

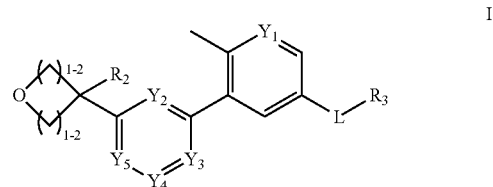

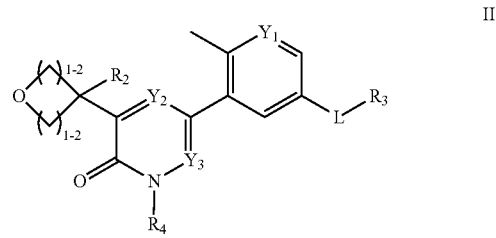

17 Claims, No Drawings

COMPOUNDS AND COMPOSITIONS AS RAF KINASE INHIBITORS

FIELD OF THE INVENTION

The invention provides compounds that inhibit Raf kinases, and are accordingly useful for treating certain disorders associated with excessive Raf kinase activity, including cell proliferation disorders such as cancers. The invention further provides pharmaceutical compositions containing these compounds and methods of using these compounds to treat conditions including cancer.

BACKGROUND

Protein Kinases are involved in very complex signaling cascades that regulate most cellular functions, including cell survival and proliferation. These signaling pathways have been heavily studied, particularly in the context of disorders caused by dysregulated cellular function, such as cancer. The mitogen-activated protein kinase (MAPK) cascade has been studied extensively, for example, and kinases in this pathway (e.g., RAS, RAF, MEK, and ERK) have been exploited as target sites for drug discovery. Mutated B-Raf is found in a significant fraction of malignancies (over 30% of all tumors and 40% of melanomas), and several drug candidates that inhibit a common B-Raf mutant (V600E, an activating mutation found in many cancers, particularly in cutaneous malignant melanoma, thyroid cancer, colorectal cancer, and ovarian cancer) have been reported, including GDC-0879, PLX4032, and PLX4720, while other inhibitors targeting C-Raf or B-Raf (or both) include sorafenib, XL281 RAF265, and BAY43-9006. These examples demonstrate that compounds that inhibit B-Raf or C-Raf are useful to treat various cancers.

The MAPK signaling cascade includes RAS, Raf, MEK and ERK kinases, each of which is actually a group of related proteins. These proteins function collectively as a signal transduction cascade where the number of distinct kinases and their varying substrate specificities create a complex and highly branched pathway. Raf, for example, consists of monomers referred to as A-Raf, B-Raf, and C-Raf (also called Raf-1), each of which functions primarily as a dimer. The RAF complex includes heterodimers as well as homodimers of these three species, bringing the total number of dimeric species in the Raf group to six, with each of these having a number of sites where phosphorylation at serine, threonine or tyrosine can cause either activation or inhibition. Due to the complexity of the pathway and its regulation, it has been reported that inhibitors of B-Raf can cause paradoxical activation of the pathway, apparently due to conformational effects on the kinase domain of Raf that affect dimerization, membrane localization, and interaction with RAS-GTP. In particular, ATP-competitive inhibitors can exhibit opposing effects on the signaling pathway, as either inhibitors or activators, depending on the cellular context. As a result, B-Raf inhibitors effective against tumors having the activating B-Raf mutation V600E may not be as effective as expected in tumors having wild-type B-Raf or KRas mutations.

The present invention provides novel inhibitors of Raf kinases, including A-Raf, B-Raf and/or C-Raf, and use of these compounds to treat disorders associated with excessive or undesired levels of Raf activity, such as certain cancers. The compounds of the invention minimize undesired pathway activation effects, and thus can be more efficacious and more predictable in vivo than the B-Raf inhibitors that cause paradoxical pathway activation even when they have similar in vitro potency. The compounds of the invention bind in a DFG-out mode, making them type 2 inhibitors, which have been reported to be less prone to induce paradoxical activation. The compounds are suited for treatment of BRaf wild-type and KRas mutant tumors, as well as B-Raf V600E mutant tumors.

SUMMARY OF THE INVENTION

In one aspect, the invention provides compounds of the formula I and II:

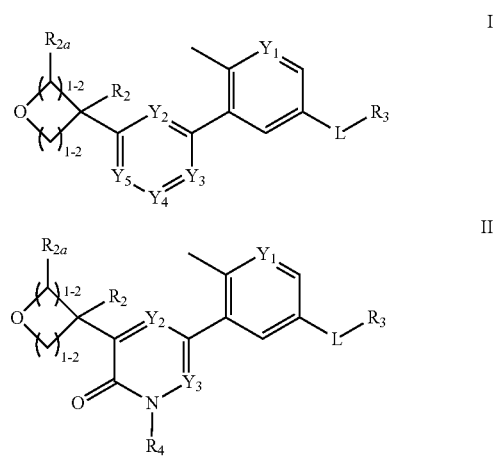

in which:

L is selected from —NHC(O)— and —C(O)NH—;

$Y_1$ is selected from N and CH;

$Y_2$ is selected from N and CH;

$Y_3$ is selected from N and CH;

$Y_4$ is selected from N and $CR_8$; wherein $R_8$ is selected from H, hydroxy-ethoxy, 3-hydroxyoxetan-3-yl, 2,3-dihydroxypropoxy, hydroxy-ethyl-amino, 4-amino-4-methylpiperidin-1-yl, 2-oxooxazolidin-3-yl, methoxy and methyl;

$Y_5$ is selected from N and $CR_1$; or $R_1$ and the nitrogen of $Y_4$ form a 5 member unsaturated ring containing and additional heteroatom selected from N, O and S; or $R_1$ and $R_8$ together with the ring to which they are both attached form 2H-benzo[b][1,4]oxazin-3(4H)-one substituted with one to two $R_{20}$ groups independently selected from methyl and hydroxy-ethyl; or $R_8$ and $Y_3$ together with the ring to which they are both attached form 1H-benzo[d]imidazole substituted with methyl;

$R_1$ is selected from H, ethoxy, isopropoxy, methoxy-ethyl-amino, (2-hydroxyethyl)(methyl)amino, (1-hydroxypropan-2-yl)amino, methoxy-ethoxy, hydroxy-ethoxy, methoxy, (2-hydroxypropyl)amino, (tetrahydro-2H-pyran-4-yl)oxy, (tetrahydro-2H-pyran-4-yl)oxy, (1-ethylpiperidin-4-yl)oxy and pyrazolyl; wherein said pyrazolyl can be unsubstituted or substituted with 1 to 2 methyl groups; each $R_{2a}$ is independently selected from hydrogen and OH;

$R_{2b}$ is selected from H, methyl, halo, fluoro-methyl, hydroxy, hydroxymethyl, difluoromethyl, formyl, methoxy and cyano;

$R_3$ is selected from:

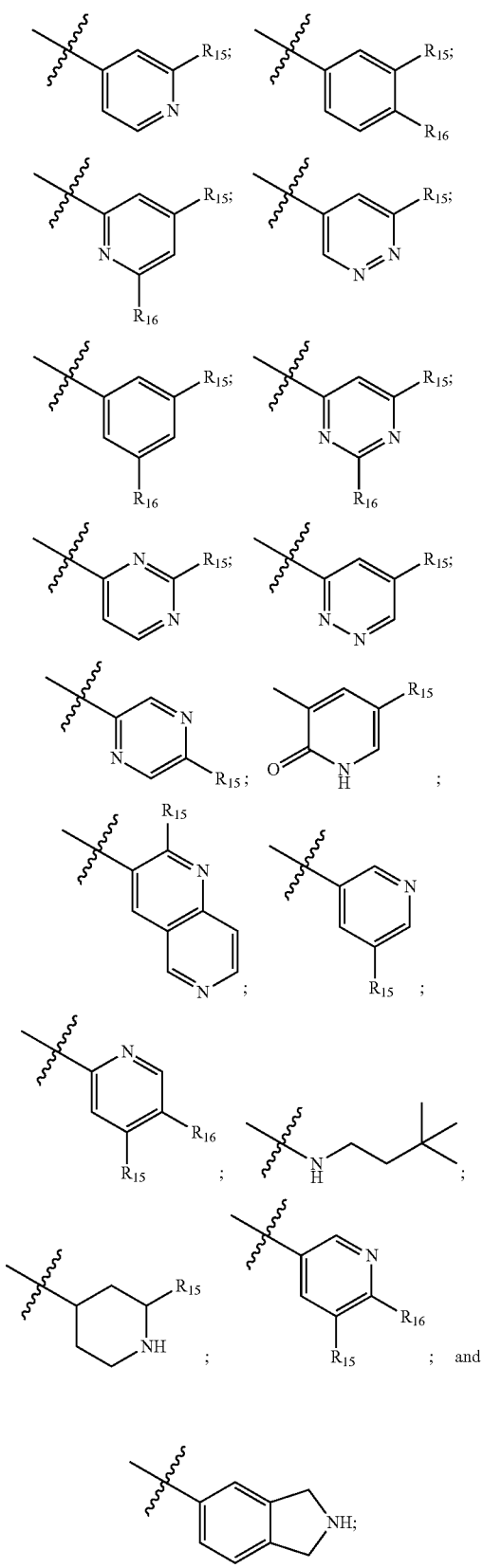

wherein

indicates the point of attachment with L;

$R_4$ is selected from H, methyl, hydroxy-ethyl, hydroxy-propyl and 2,3-dihydroxypropyl;

$R_{15}$ is selected from —$CF_3$, methoxy, —$C(CH_3)_2F$, —$CF_2CH_2F$, —$C(CH_3)_2CN$, —$C(CH_3)F_2$, —$CHF_2$, —$C(CH_3)_2OH$, t-butyl, 1-cyanocyclopropyl, 2-(trifluoromethyl)cyclopropyl, —$C(F_2)C_2H_5$, methyl-sulfonyl, 4-ethyl-piperazin-1-yl, —$C(CH_3)_2NH_2$ and dimethyl-amino-methyl:

$R_{16}$ is selected from H, halo, hydroxy, dimethyl-amino, hydroxy-methyl, amino-methyl, —$C(CH_3)_2NH_2$ and —$CF_3$; with the proviso that a compound of formula II is not 2-(2-cyanopropan-2-yl)-N-(4-methyl-3-(1-methyl-6-oxo-5-(tetrahydro-2H-pyran-4-yl)-1,6-dihydropyridazin-3-yl)phenyl)isonicotinamide or 2-(2-fluoropropan-2-yl)-N-(4-methyl-3-(1-methyl-6-oxo-5-(tetrahydro-2H-pyran-4-yl)-1,6-dihydropyridazin-3-yl)phenyl)isonicotinamide.

In a second aspect, the present invention provides a pharmaceutical composition which contains a compound of Formula I or II or a N-oxide derivative, individual isomers and mixture of isomers thereof; or a pharmaceutically acceptable salt thereof, in admixture with one or more suitable excipients.

In another aspect, the compounds of Formula I or II are inhibitors of Raf kinases as shown by data herein, and are accordingly useful to treat conditions such as melanoma, breast cancer, sarcoma. GI tumors such as gastrointestinal stromal tumors, ovarian cancer, sarcoma, GI tumors such as gastrointestinal stromal tumors, and other malignancies associated with excessive Raf pathway activity, particularly in cancers driven by Ras mutations. In addition, the compounds of the invention exhibit low levels of paradoxical activation of the Raf pathway.

In another aspect, the invention provides pharmaceutical compositions comprising a compound of Formula I or II admixed with at least one pharmaceutically acceptable carrier or excipient, optionally admixed with two or more pharmaceutically acceptable carriers or excipients.

In addition, the invention includes combinations of a compound of Formula I or II with a co-therapeutic agent, optionally including one or more pharmaceutically acceptable carriers, and methods of treatment using a compound of Formula I or II in combination with a co-therapeutic agent. Suitable co-therapeutic agents for use in the invention include, for example, cancer chemotherapeutics including but not limited to inhibitors of PI3K, other inhibitors of the Raf pathway, paclitaxel, docetaxel, temozolomide, platins, doxorubicins, vinblastins, cyclophosphamide, topotecan, gemcitabine, ifosfamide, etoposide, irinotecan, and the like.

In another aspect, the invention provides a method to treat a condition characterized by excessive or undesired levels of activity of Raf, especially B-Raf and/or C-Raf, which comprises administering to a subject in need of such treatment an effective amount of a compound of Formula I or II or any subgenus thereof as described herein, or a pharmaceutical composition comprising such compound. The subject can be a mammal, and is preferably a human. Conditions treatable by the compounds and methods described herein include various forms of cancer, such as solid tumors, melanoma, breast cancer, lung cancer (e.g., non-small cell lung cancer), sarcoma, GI tumors such as gastrointestinal stromal tumors, ovarian cancer, colorectal cancer, thyroid cancer, and pancreatic cancer. The invention thus includes compounds of Formula I or II and the subgenera thereof that are disclosed herein, including each species disclosed herein, for use in therapy, particularly for use to treat cancers such as melanoma, breast cancer, lung cancer, liver cancer, sarcoma, GI tumors such as gastrointestinal stromal tumors, sarcoma, GI tumors such as gastrointestinal stromal tumors, ovarian cancer, colorectal cancer, thyroid cancer, and pancreatic cancer. The invention also includes use of such compounds for manufacture of a medicament for treating these conditions.

The invention includes compounds of Formula I or II and the subgenera of Formula I or II described herein, and all stereoisomers (including diastereoisomers and enantiomers), tautomers and isotopically enriched versions thereof (including deuterium substitutions), as well as pharmaceutically acceptable salts of these compounds. In particular, where a heteroaryl ring containing N as a ring atom is optionally substituted with hydroxyl. e.g., a 2-hydroxypyridine ring, tautomers where the hydroxyl is depicted as a carbonyl (e.g., 2-pyridone) are included. Compounds of the present invention also comprise polymorphs of compounds of formula I (or sub-formulae thereof) and salts thereof.

DETAILED DESCRIPTION

The following definitions apply unless otherwise expressly provided.

As used herein, the term "halogen" (or halo) refers to fluorine, bromine, chlorine or iodine, in particular fluorine or chlorine. Halogen-substituted groups and moieties, such as alkyl substituted by halogen (haloalkyl) can be mono-, poly- or per-halogenated.

As used herein, the term "hetero atoms" refers to nitrogen (N), oxygen (O) or sulfur (S) atoms, in particular nitrogen or oxygen, unless otherwise provided.

As used herein, the term "alkyl" refers to a fully saturated branched or unbranched hydrocarbon moiety having up to 20 carbon atoms. Unless otherwise provided, alkyl refers to hydrocarbon moieties having 1 to 10 carbon atoms, 1 to 6 carbon atoms, or 1 to 4 carbon atoms. Typically, alkyl groups have 1-6 carbon atoms. "Lower alkyl" refers to alkyl groups having 1-4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

A substituted alkyl is an alkyl group containing one or more substituents in place of hydrogen, such as one, two or three substituents, or 1-4 substituents, up to the number of hydrogens present on the unsubstituted alkyl group. Suitable substituents for alkyl groups, if not otherwise specified, may be selected from halogen, CN, oxo, hydroxy, substituted or unsubstituted $C_{1-4}$ alkoxy, substituted or unsubstituted $C_{3-6}$ cycloalkyl, substituted or unsubstituted $C_3$ heterocycloalkyl, substituted or unsubstituted phenyl, amino, ($C_{1-4}$ alkyl) amino, di($C_{1-4}$ alkyl)amino. $C_{1-4}$ alkylthio, $C_{1-4}$ alkylsulfonyl, —C(=O)—$C_{1-4}$ alkyl, COOH, COO($C_{1-4}$ alkyl), —O(C=O)—$C_{1-4}$ alkyl. —NHC(=O)$C_{1-4}$ alkyl and —NHC(=O)O$C_{1-4}$ alkyl groups; wherein the substituents for substituted $C_{1-4}$ alkoxy, substituted $C_{3-6}$ cycloalkyl, Cu heterocycloalkyl, and substituted phenyl are up to three groups selected from halo, $C_{1-4}$ alkyl, $C_{1-4}$ haloalkyl, $C_{1-4}$ alkoxy, amino, hydroxy, and CN. Preferred substituents for alkyl groups include halogen, CN, oxo, hydroxy, $C_{1-4}$ alkoxy, $C_{3-6}$ cycloalkyl, phenyl, amino, ($C_{1-4}$ alkyl)amino, di($C_{1-4}$ alkyl)amino, $C_{1-4}$ alkylthio, $C_{1-4}$ alkylsulfonyl, —C(=O)—$C_{1-4}$ alkyl, COOH, —COO($C_{1-4}$ alkyl), —O(C=O)—$C_{1-4}$ alkyl, —NHC(=O) $C_{1-4}$ alkyl and —NHC(=O)O $C_{1-4}$ alkyl groups.

As used herein, the term "alkylene" refers to a divalent alkyl group having 1 to 10 carbon atoms, and two open valences to attach to other features. Unless otherwise provided, alkylene refers to moieties having 1 to 10 carbon atoms, 1 to 6 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like. A substituted alkylene is an alkylene group containing one or more, such as one, two or three substituents; unless otherwise specified, suitable and preferred substituents are selected from the substituents described as suitable and preferred for alkyl groups.

As used herein, the term "haloalkyl" refers to an alkyl as defined herein, which is substituted by one or more halo groups as defined herein. The haloalkyl can be monohaloalkyl, dihaloalkyl, trihaloalkyl, or polyhaloalkyl including perhaloalkyl. A monohaloalkyl can have one iodo, bromo, chloro or fluoro within the alkyl group. Chloro and fluoro are preferred on alkyl or cycloalkyl groups; fluoro, chloro and bromo are often preferred on aryl or heteroaryl groups. Dihaloalkyl and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms, e.g. trifluoromethyl.

As used herein, the term "alkoxy" refers to alkyl-O—, wherein alkyl is defined above. Representative examples of alkoxy include, but are not limited to, methoxy, ethoxy, propoxy, 2-propoxy, butoxy, tert-butoxy, pentyloxy, hexyloxy, and the like. Typically, alkoxy groups have 1-10, or 1-6 carbons, more commonly 1-4 carbon atoms.

A "substituted alkoxy" is an alkoxy group containing one or more, such as one, two or three substituents on the alkyl portion of the alkoxy. Unless otherwise specified, suitable and preferred substituents are selected from the substituents listed above for alkyl groups, except that hydroxyl and amino are not normally present on the carbon that is directly attached to the oxygen of the substituted 'alkyl-O' group.

Similarly, each alkyl part of other groups like "alkylaminocarbonyl", "alkoxyalkyl", "alkoxycarbonyl", "alkoxycarbonylalkyl", "alkylsulfonyl", "alkylsulfoxyl", "alkylamino", "haloalkyl" shall have the same meaning as described in the above-mentioned definition of "alkyl". When used in this way, unless otherwise indicated, the alkyl group is often a 1-4 carbon alkyl and is not further substituted by groups other than the component named. When such alkyl groups are substituted, suitable substituents are selected from the suitable or preferred substituents named above for alkyl groups unless otherwise specified.

As used herein, the term "haloalkoxy" refers to haloalkyl-O—, wherein haloalkyl is defined above. Representative examples of haloalkoxy include, but are not limited to, fluoromethoxy, difluoromethoxy, trifluoromethoxy, trichloromethoxy, 2-chloroethoxy, 2,2,2-trifluoroethoxy, 1,1,1,3,3,3-hexafluoro-2-propoxy, and the like. Typically, haloalkyl groups have 1-4 carbon atoms.

DESCRIPTION OF PREFERRED EMBODIMENTS

The present invention provides compounds, compositions and methods for the treatment of kinase related disease, particularly Raf kinase related diseases; for example: various forms of cancer, such as solid tumors, melanoma, breast cancer, lung cancer (e.g., non-small cell lung cancer), sarcoma, GI tumors such as gastrointestinal stromal tumors, ovarian cancer, colorectal cancer, thyroid cancer, and pancreatic cancer. Various embodiments of the invention are described herein. It will be recognized that features specified in each embodiment may be combined with other specified features to provide further embodiments of the present invention. The following embodiments are representative of the invention.

In one embodiment, with reference to compounds of formula I or II are compounds of formula Ia:

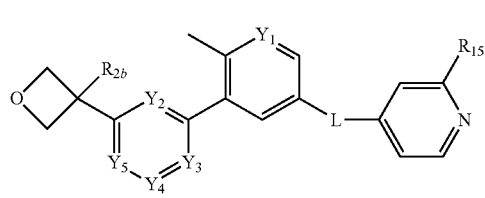

in which: L is selected from —NHC(O)— and —C(O)NH—; $Y_1$ is selected from N and CH; $Y_2$ is selected from N and CH; $Y_3$ is selected from N and CH; $Y_4$ is selected from N and $CR_8$; wherein R is selected from H, hydroxy-ethoxy, 3-hydroxyoxetan-3-yl, 2,3-dihydroxypropoxy, hydroxyethyl-amino, 4-amino-4-methylpiperidin-1-yl, 2-oxooxazolidin-3-yl, methoxy and methyl; $Y_5$ is selected from N and $CR_1$; $R_1$ is selected from H, ethoxy, hydroxy-ethoxy, methoxy, (tetrahydro-2H-pyran-4-yl)oxy and pyrazolyl; wherein said pyrazolyl can be unsubstituted or substituted with 1 to 2 methyl groups; $R_{2b}$ is selected from H, methyl, halo, fluoro-methyl, hydroxy, difluoromethyl, formyl, methoxy and cyano; $R_{15}$ is selected from —$CF_3$, methoxy, —$C(CH_3)_2F$, —$CF_2CH_2F$, —$C(CH_3)_2CN$, —$C(CH_3)F_2$, —$CHF_2$, —$C(CH_3)_2OH$, t-butyl, 1-cyanocyclopropyl, 2-(trifluoromethyl)cyclopropyl, —$C(F_2)C_2H_5$, methyl-sulfonyl, 4-ethylpiperazin-1-yl, —$C(CH_3)_2NH_2$ and dimethyl-amino-methyl; or the pharmaceutically acceptable salt thereof.

In a further embodiment are compounds, or a pharmaceutically acceptable salt thereof, selected from:

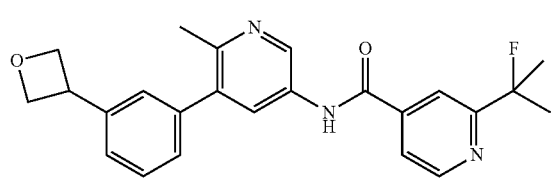

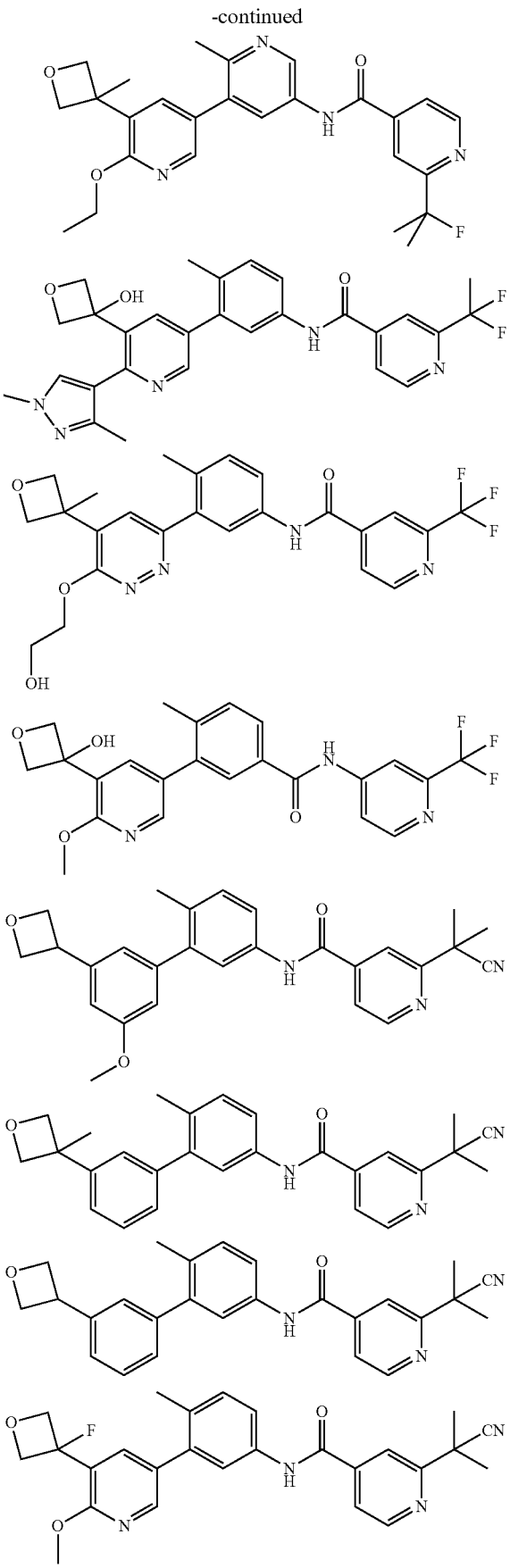

-continued
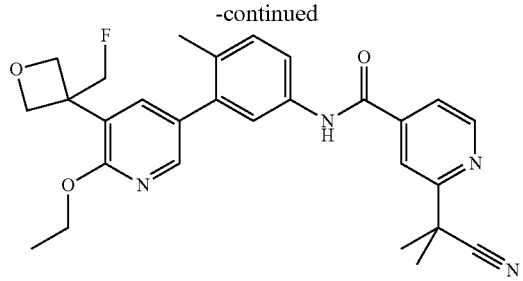
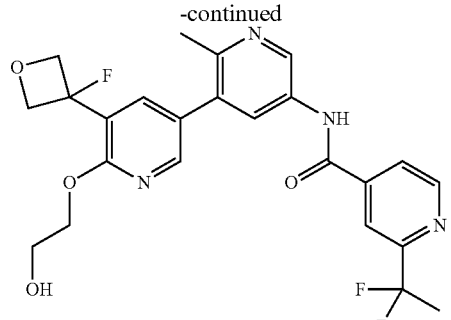
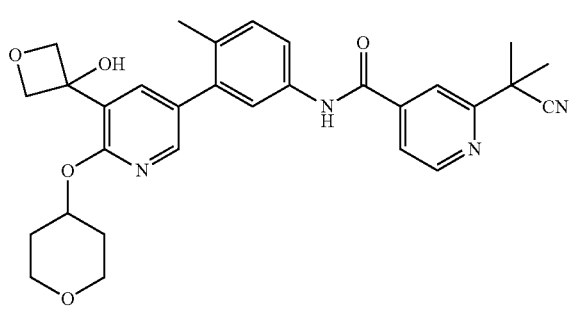
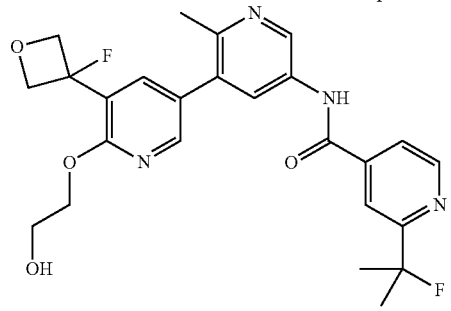
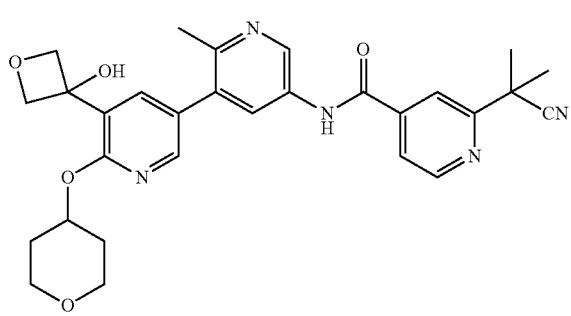
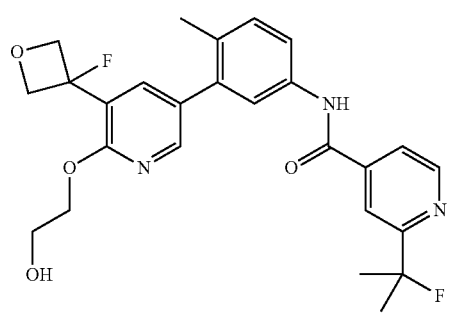
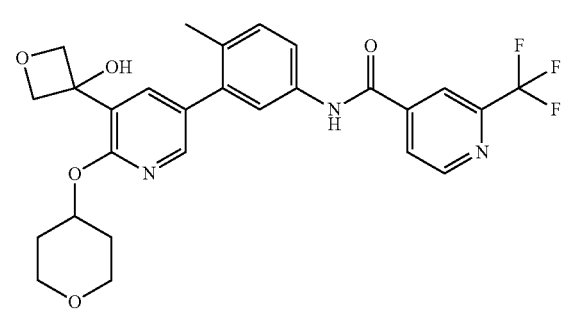
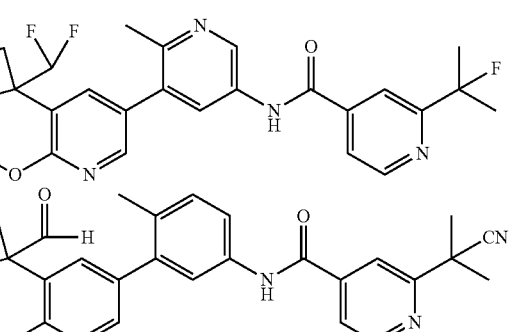
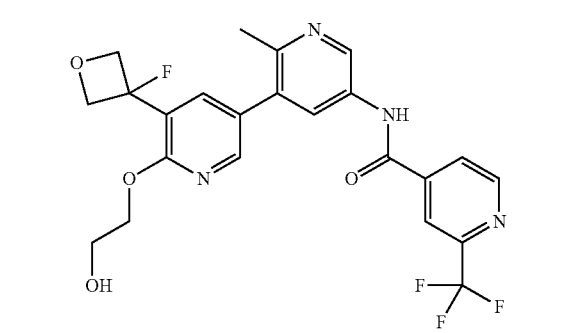
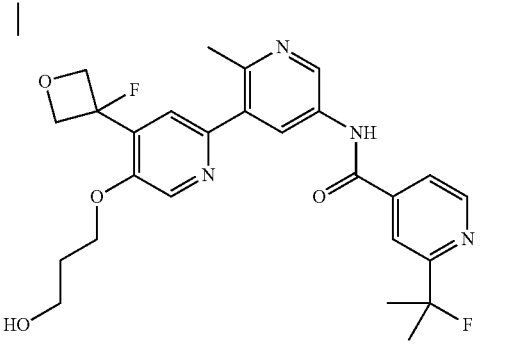

-continued
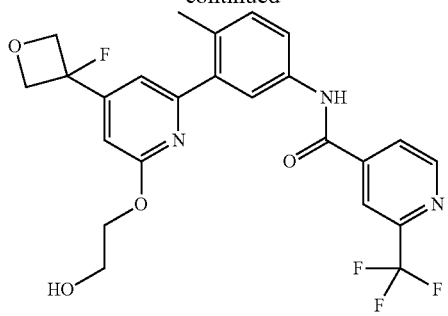
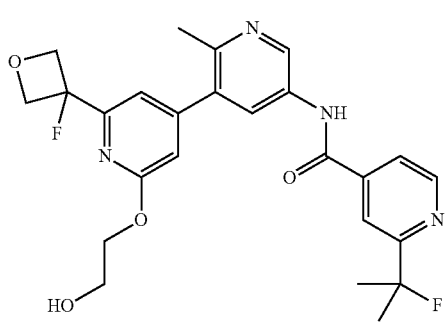
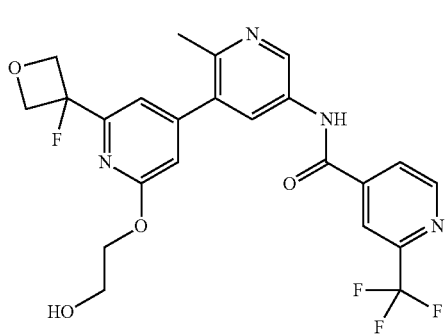
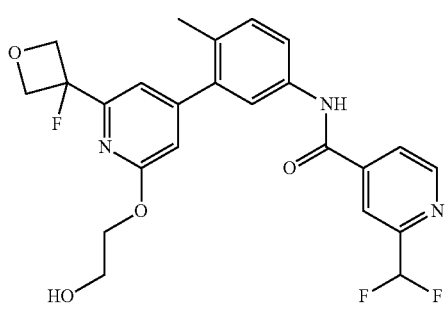
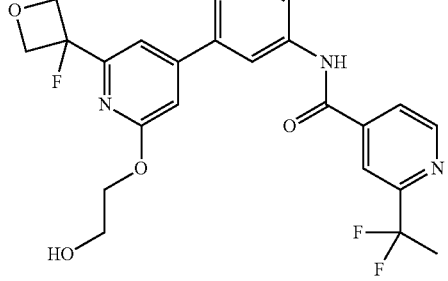
-continued
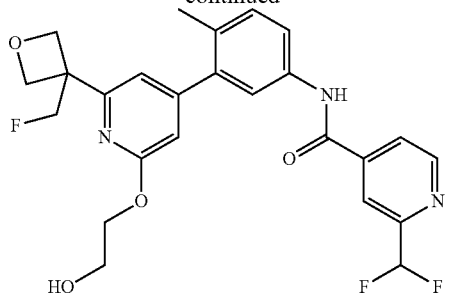
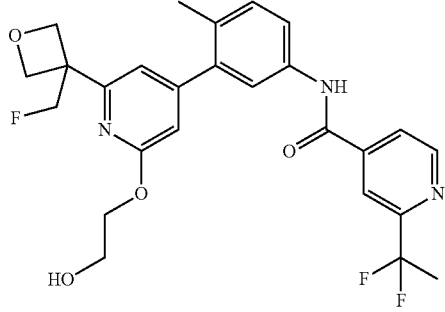
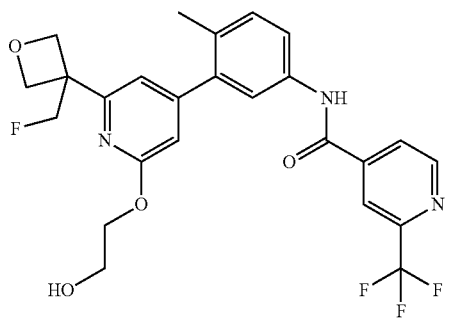
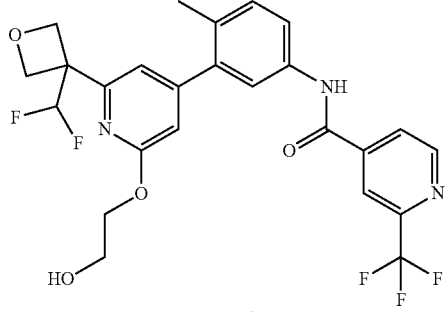
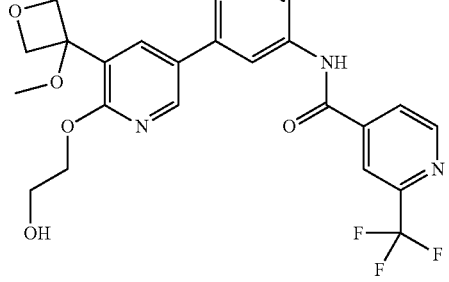

13
-continued
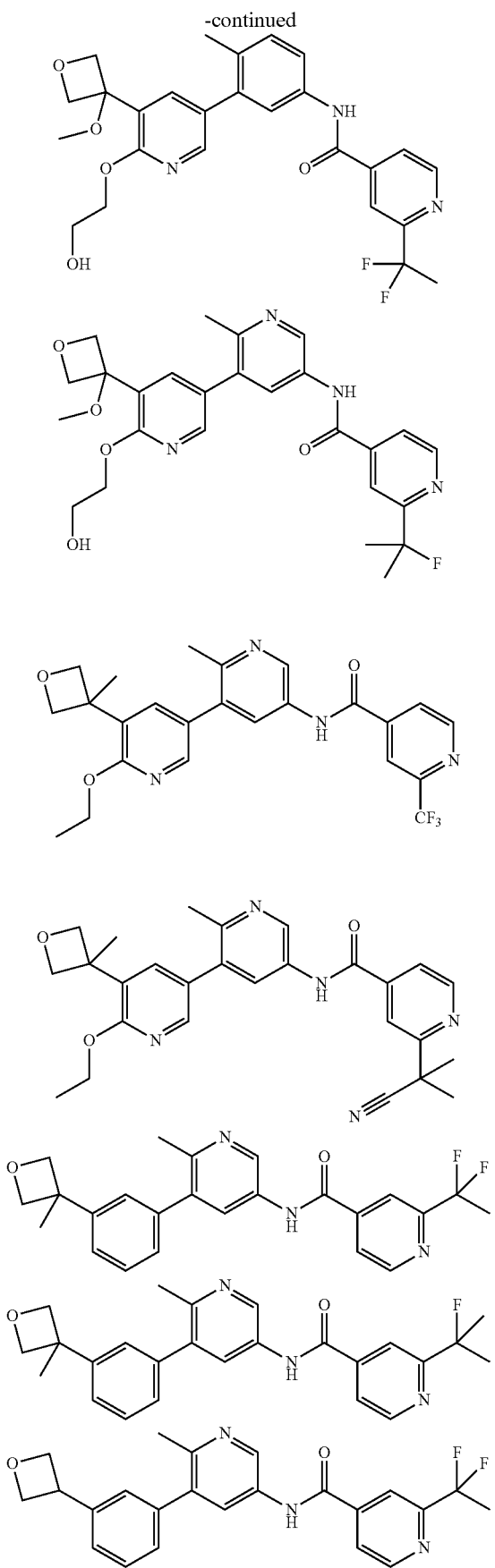
14
-continued
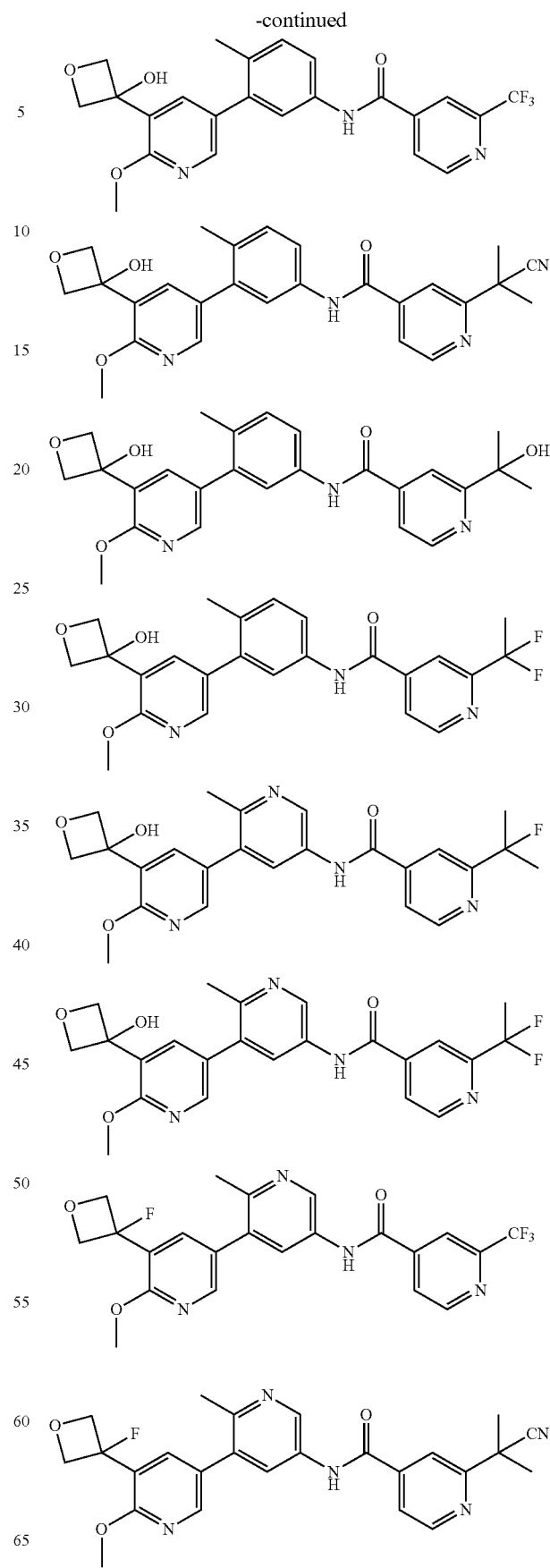

-continued

-continued
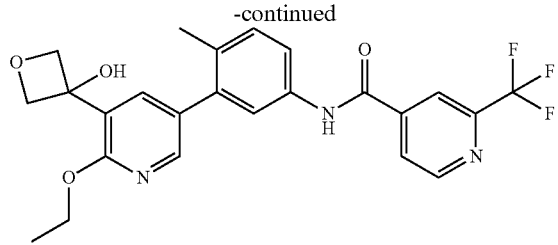
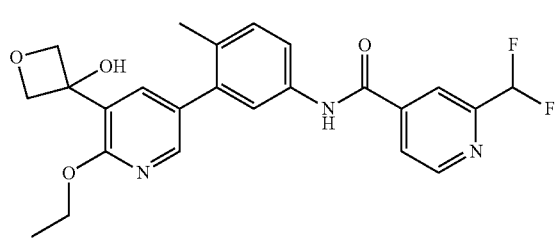
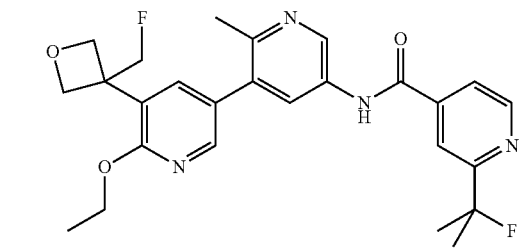
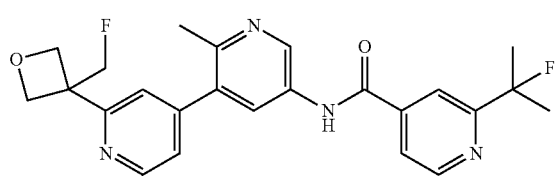
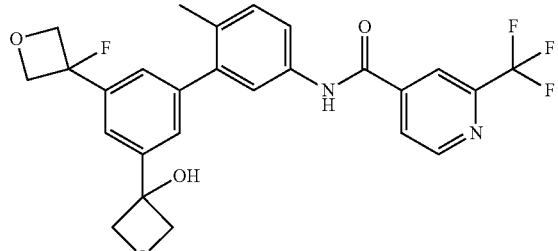
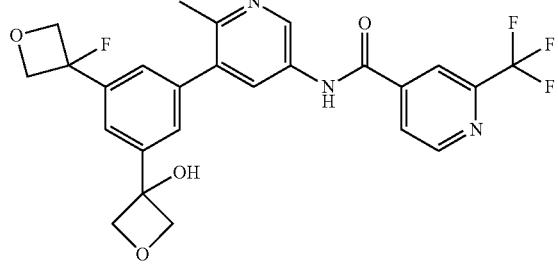
-continued
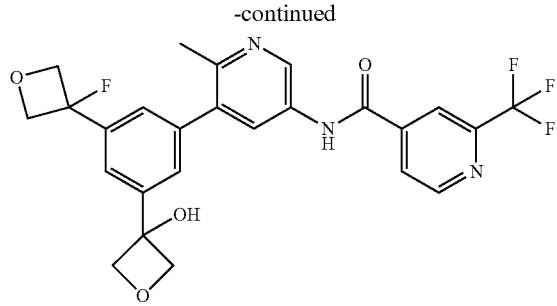
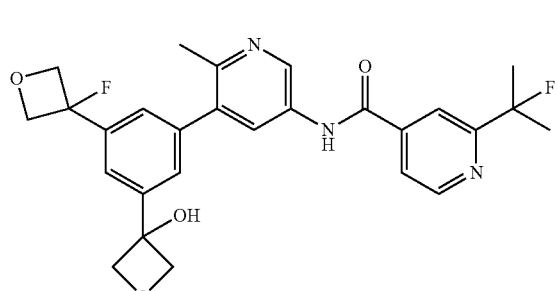
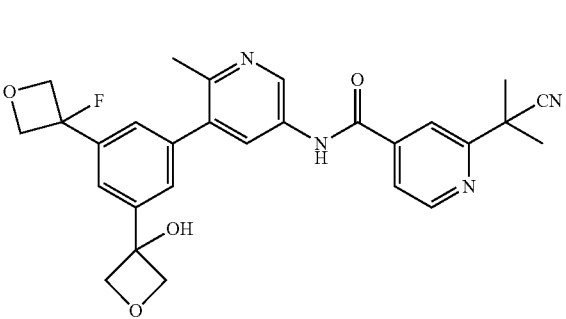
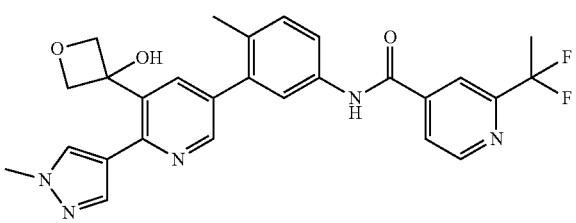
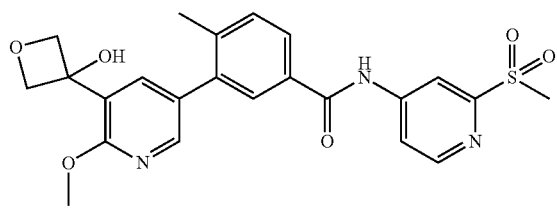
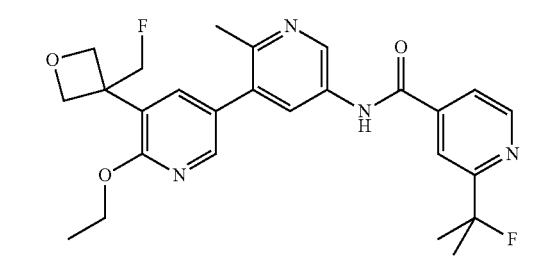

-continued

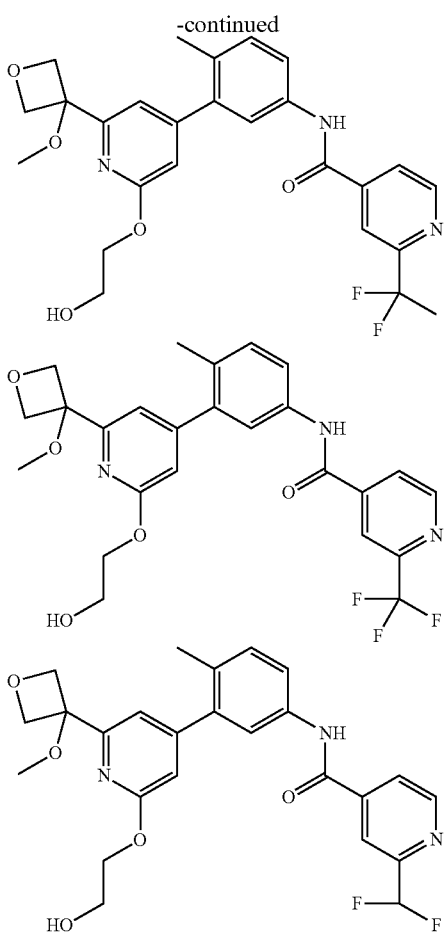

In another embodiment are compounds of formula Ib:

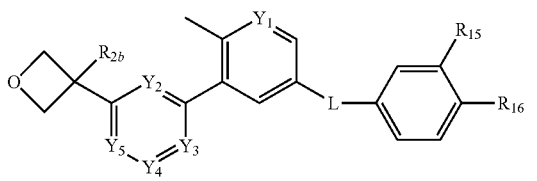

Ib in which: L is selected from —NHC(O)— and —C(O)NH—; $Y_1$ is selected from N and CH; $Y_2$ is selected from N and CH; $Y_3$ is selected from N and CH; $Y_4$ is selected from N and $CR_8$; wherein $R_8$ is selected from H, hydroxy-ethoxy, 3-hydroxyoxetan-3-yl, 2,3-dihydroxypropoxy, hydroxy-ethyl-amino, 4-amino-4-methylpiperidin-1-yl, 2-oxooxazolidin-3-yl, methoxy and methyl; $Y_5$ is selected from N and $CR_1$; $R_1$ is selected from H, ethoxy, hydroxy-ethoxy, methoxy, (tetrahydro-2H-pyran-4-yl)oxy and pyrazolyl; wherein said pyrazolyl can be unsubstituted or substituted with 1 to 2 methyl groups; $R_{2b}$ is selected from H, methyl, halo, fluoro-methyl, hydroxy, difluoromethyl, formyl, methoxy and cyano; $R_{15}$ is selected from —$CF_3$, methoxy, —$C(CH_3)_2F$, —$CF_2CH_2F$, —$C(CH_3)_2CN$, —$C(CH_3)F_2$, —$CHF_2$, —$C(CH_3)_2OH$, t-butyl, 1-cyanocyclopropyl, 2-(trifluoromethyl)cyclopropyl, —$C(F_2)C_2H_5$, methyl-sulfonyl, 4-ethylpiperazin-1-yl, —$C(CH_3)_2NH_2$ and dimethyl-amino-methyl; $R_{16}$ is selected from H, halo, hydroxy, dim- ethyl-amino, hydroxy-methyl, amino-methyl, —$C(CH_3)_2NH_2$ and —$CF_3$; or a pharmaceutically acceptable salt thereof.

In a further embodiment are compounds, or the pharmaceutically acceptable salt thereof, selected from:

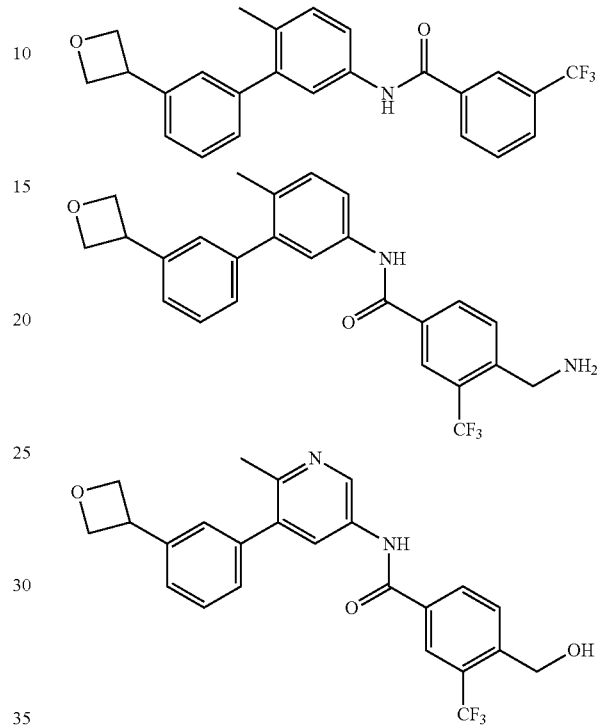

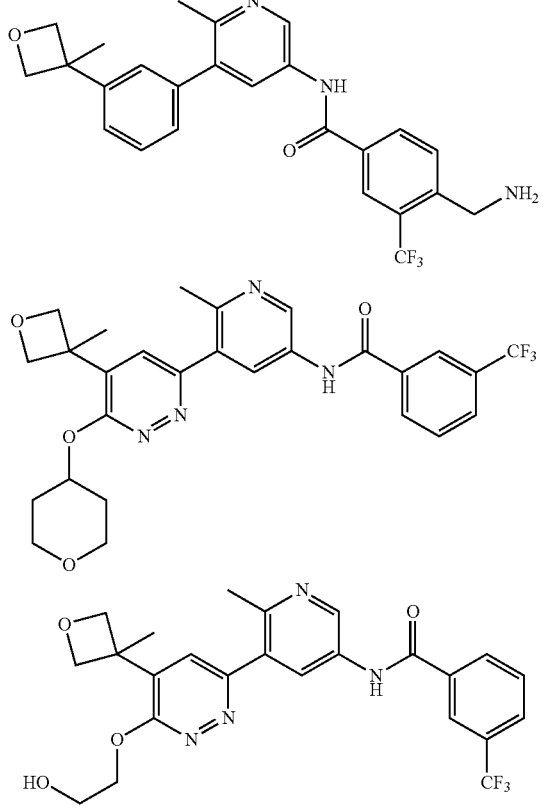

-continued
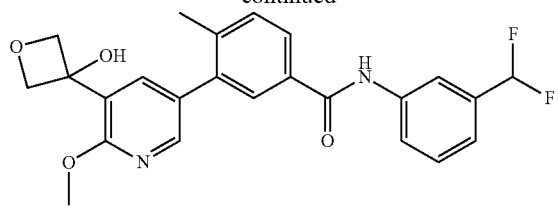
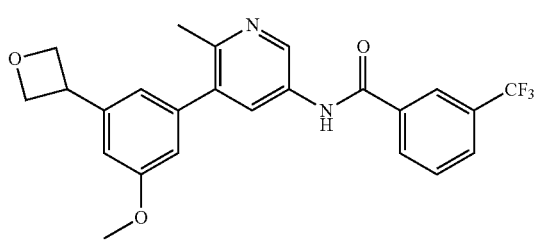
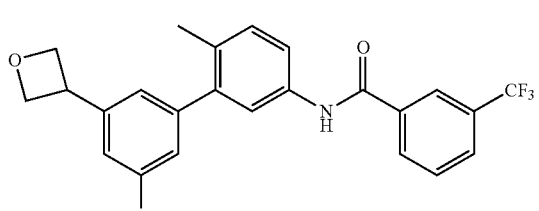
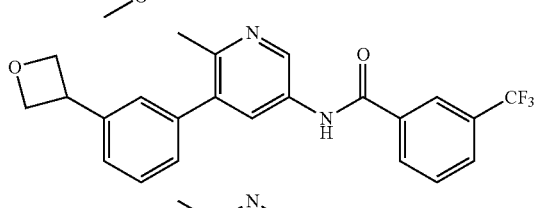
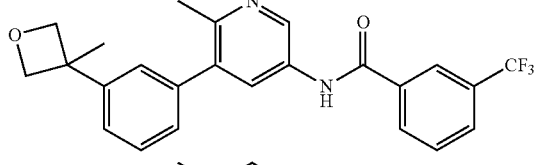
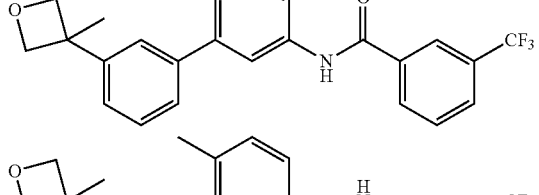
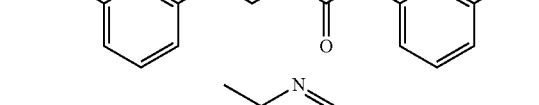
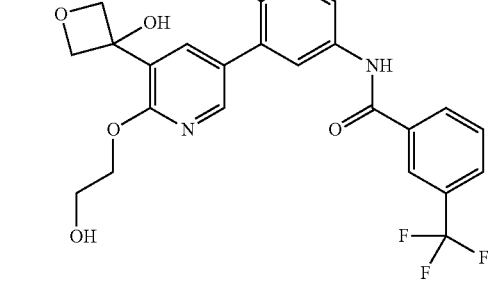
-continued
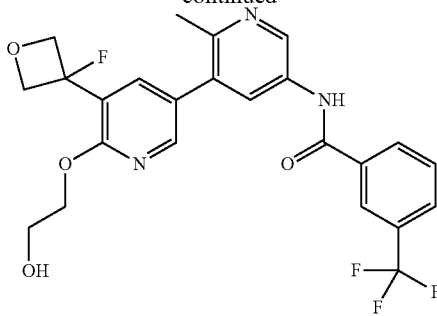
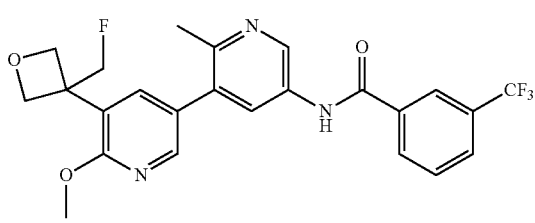
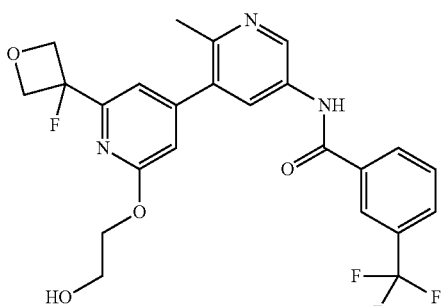
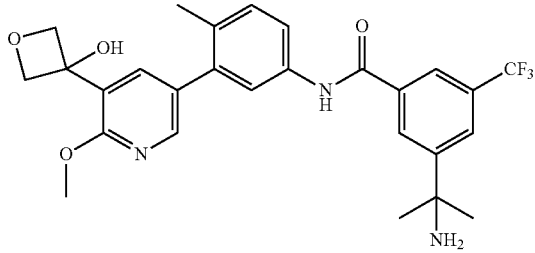
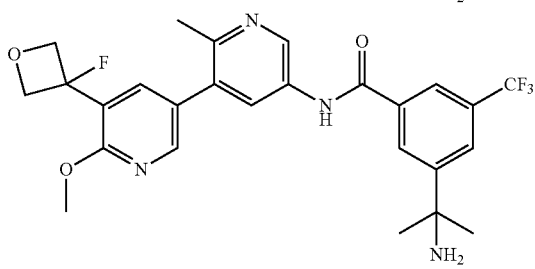
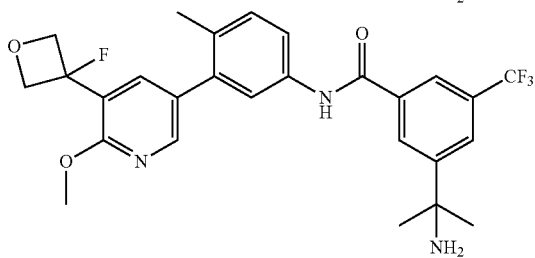

-continued
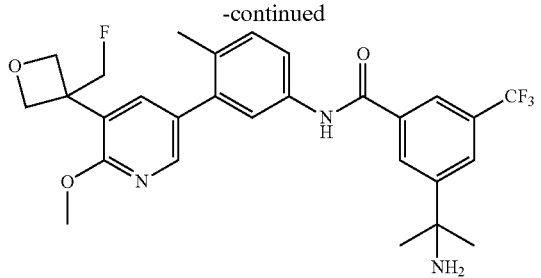
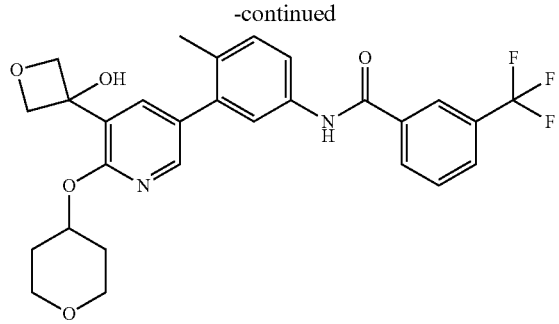
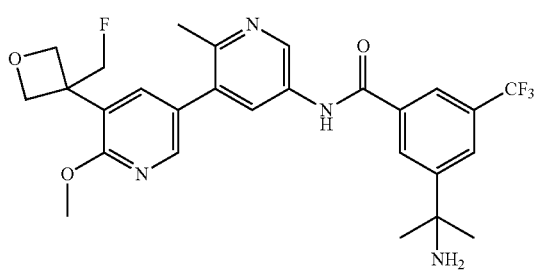
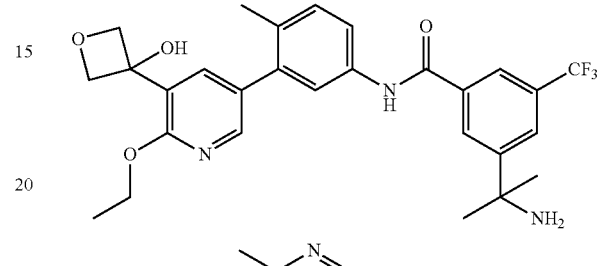
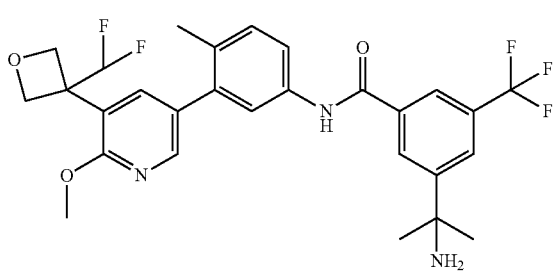
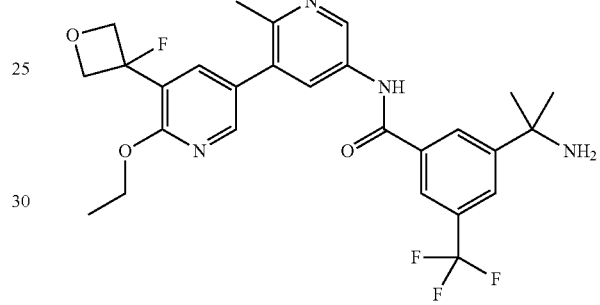
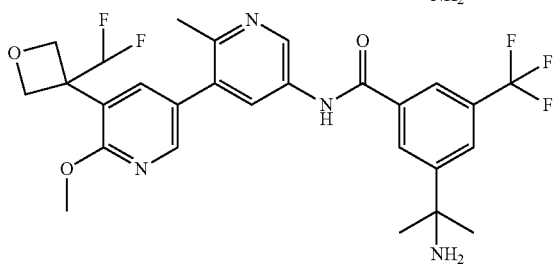
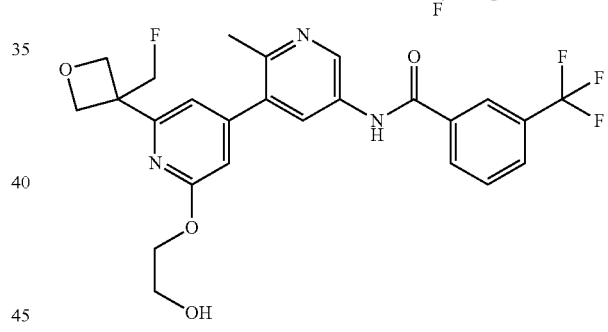
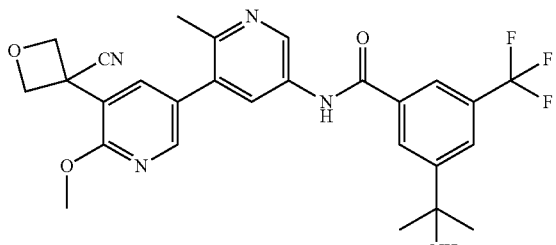
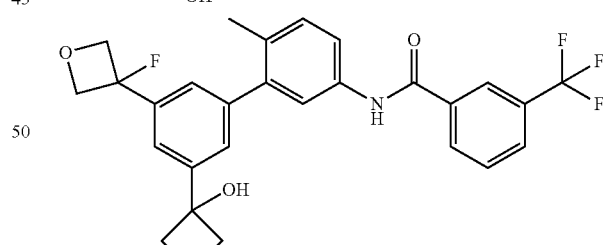
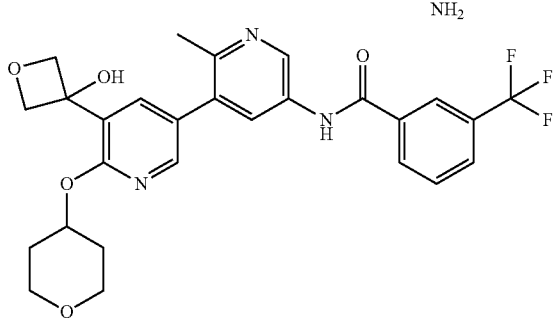
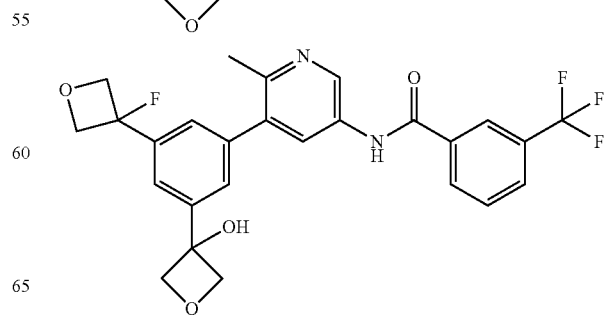

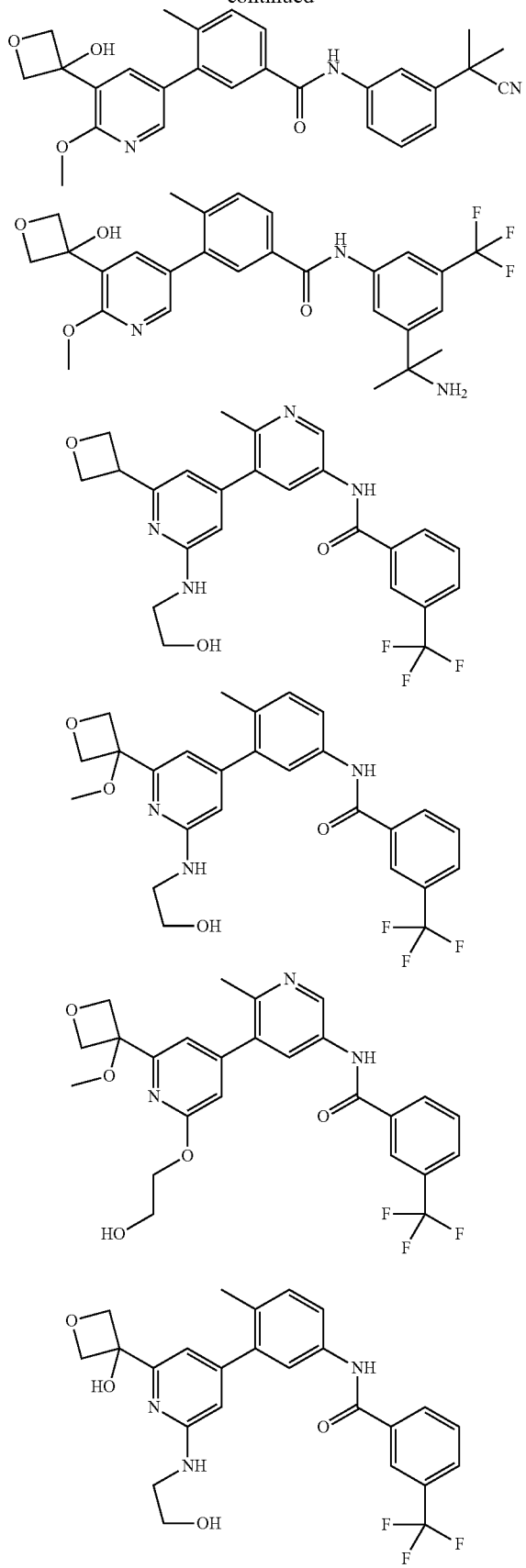

In another embodiment are compounds of formula Ic:

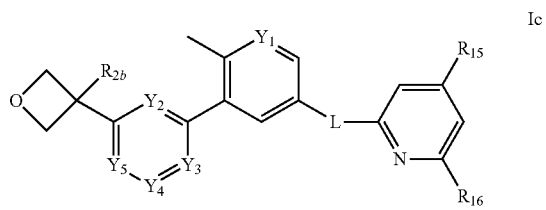

in which: L is selected from —NHC(O)— and —C(O)NH—; $Y_1$ is selected from N and CH; $Y_2$ is selected from N and CH; $Y_3$ is selected from N and CH; $Y_4$ is selected from N and $CR_8$; wherein $R_8$ is selected from H, hydroxy-ethoxy, 3-hydroxyoxetan-3-yl, hydroxy-ethyl-amine, methoxy and methyl; $Y_5$ is selected from N and $CR_1$; $R_1$ is selected from H, ethoxy, hydroxy-ethoxy, methoxy, (tetrahydro-2H-pyran-4-yl)oxy and pyrazolyl; wherein said pyrazolyl can be unsubstituted or substituted with 1 to 2 methyl groups; $R_{2b}$ is selected from H, methyl, halo, fluoro-methyl, hydroxy, difluoromethyl, formyl, methoxy and cyano; $R_{15}$ is selected from —$CF_3$, methoxy, —$C(CH_3)_2F$, —$CF_2CH_2F$, —$C(CH_3)_2CN$, —$C(CH_3)F_2$, —$CHF_2$, —$C(CH_3)_{20}H$, t-butyl, 1-cyanocyclopropyl, 2-(trifluoromethyl)cyclopropyl, —$C(F_2)C_2H_5$, methyl-sulfonyl, 4-ethylpiperazin-1-yl, —$C(CH_3)_2NH_2$ and dimethyl-amino-methyl; $R_{16}$ is selected from H, halo, hydroxy, dimethyl-amino, hydroxy-methyl, amino-methyl, —$C(CH_3)_2NH_2$ and —$CF_3$; or a pharmaceutically acceptable salt thereof.

In a further embodiment are compounds, or the pharmaceutically acceptable salt thereof, selected from:

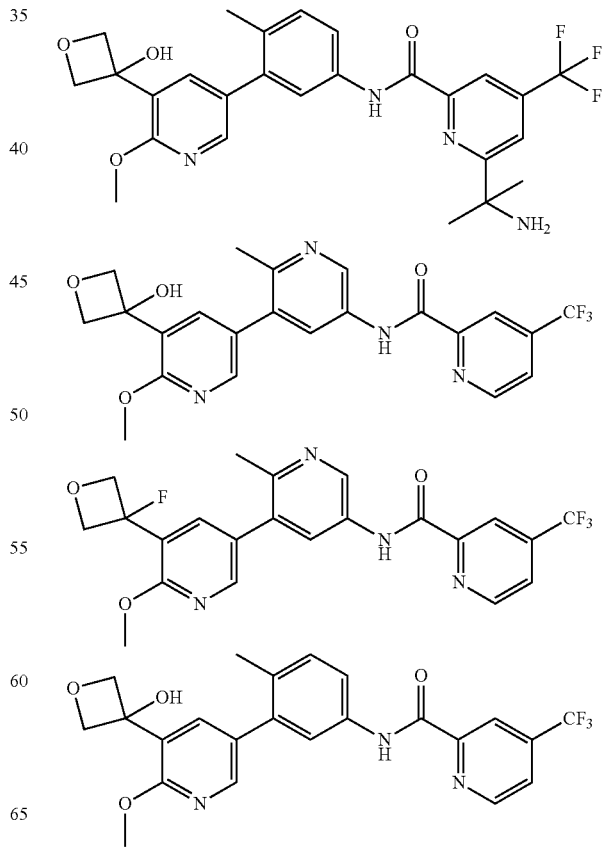

-continued
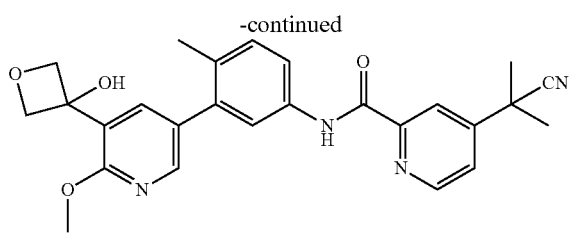
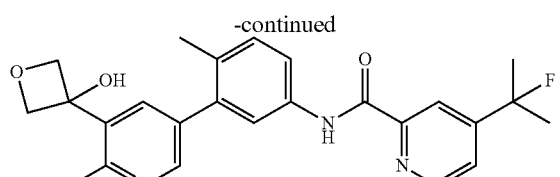
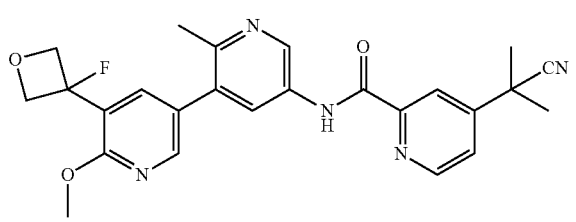
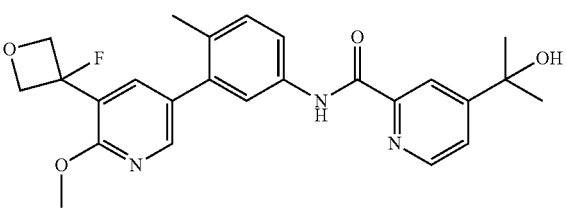
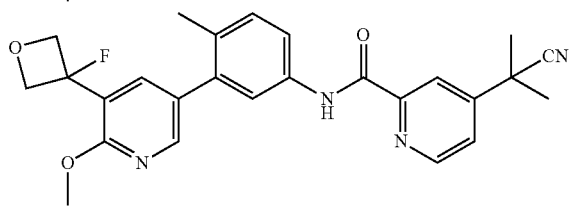
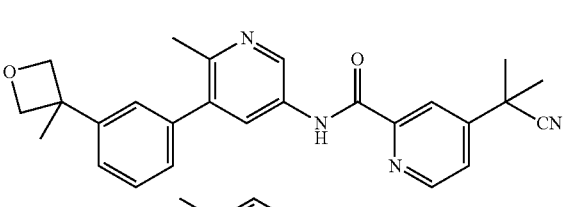
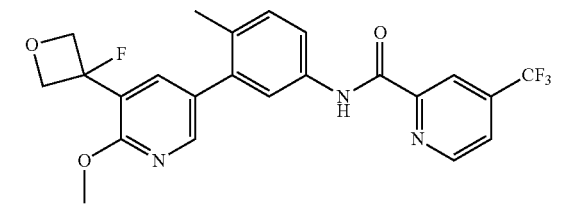
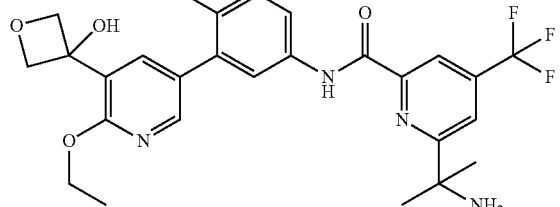
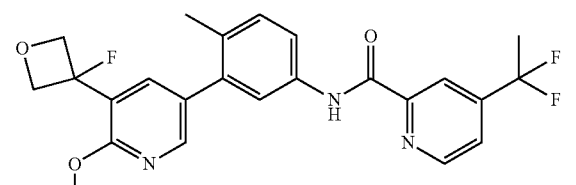
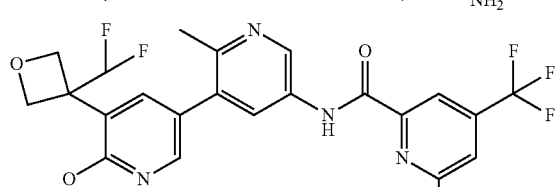
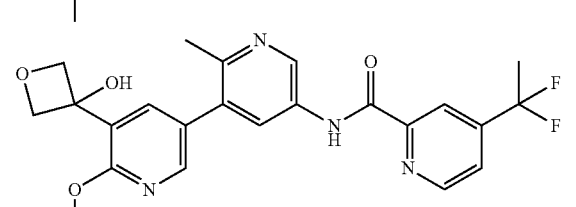
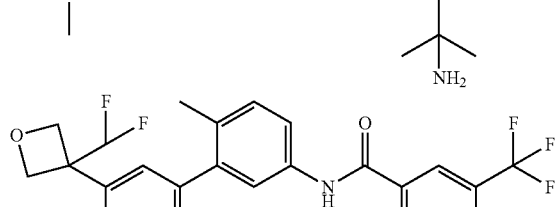
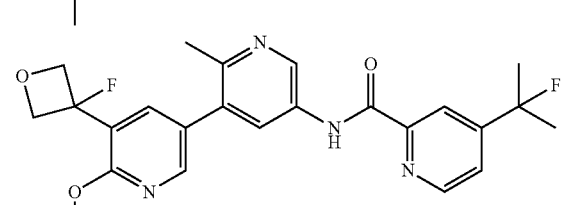
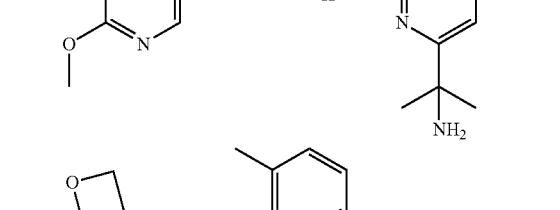
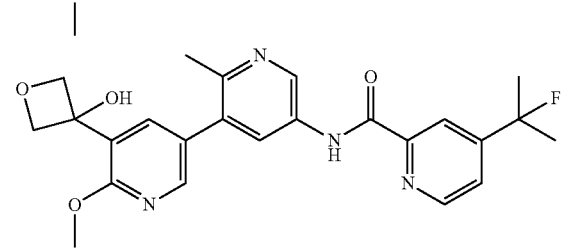
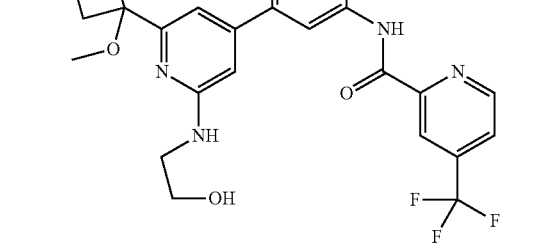

-continued

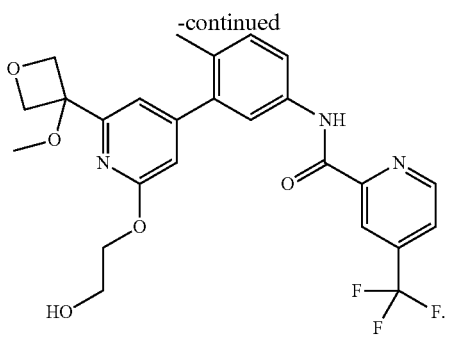

In another embodiment are compounds of formula Id or Ie:

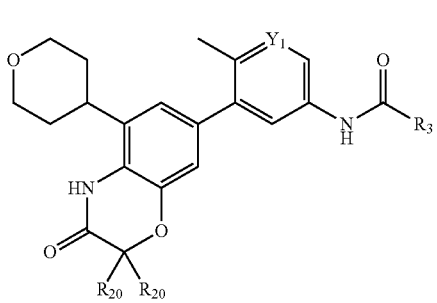

Id

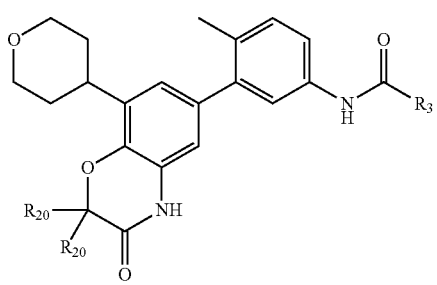

Ie in which: $Y_1$ is selected from N and CH; each $R_{20}$ is independently selected from methyl and hydroxy-ethyl; and $R_3$ is selected from:

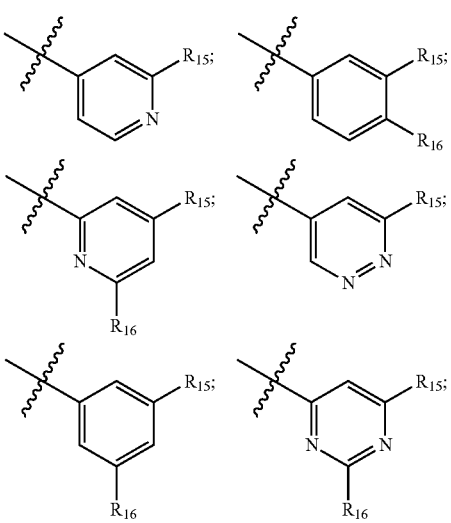

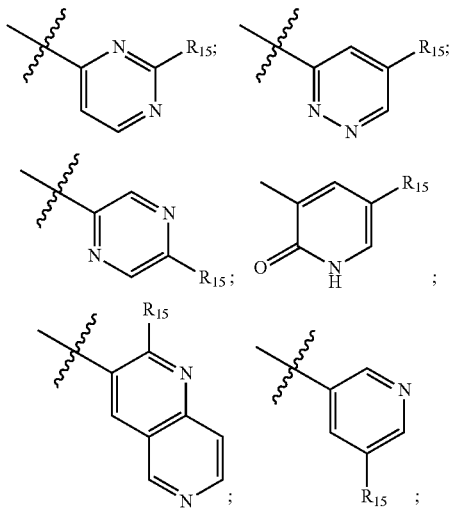

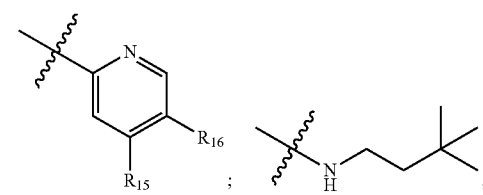

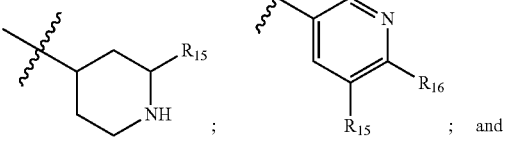

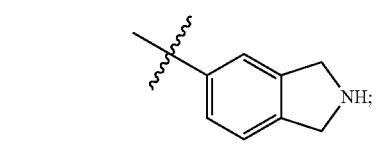

wherein

[attachment symbol]

indicates the point of attachment with L; $R_{15}$ is selected from —$CF_3$, methoxy, —$C(CH_3)_2F$, —$CF_2CH_2F$, —$C(CH_3)_2CN$, —$C(CH_3)F_2$, —$CHF_2$, —$C(CH_3)_2OH$, t-butyl, 1-cyanocyclopropyl, 2-(trifluoromethyl)cyclopropyl, —$C(F_2)C_2H_5$, methyl-sulfonyl, 4-ethylpiperazin-1-yl, —$C(CH_3)_2NH_2$ and dimethyl-amino-methyl; and $R_{16}$ is selected from H, halo, hydroxy, dimethyl-amino, hydroxy-methyl, amino-methyl, —$C(CH_3)_2NH_2$ and —$CF_3$; or a pharmaceutically acceptable salt thereof.

In a further embodiment are compounds, or the pharmaceutically acceptable salt thereof, selected from:

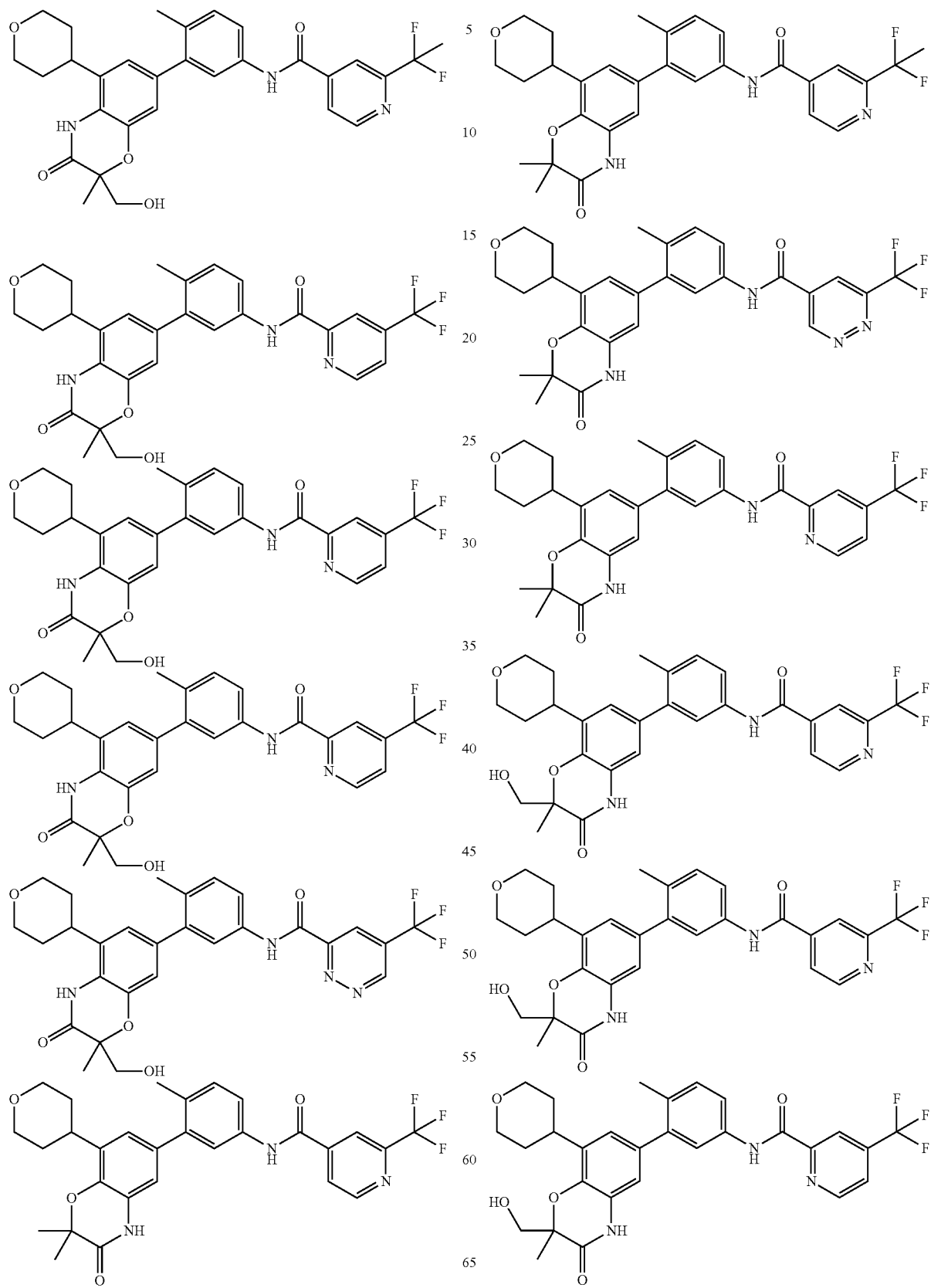

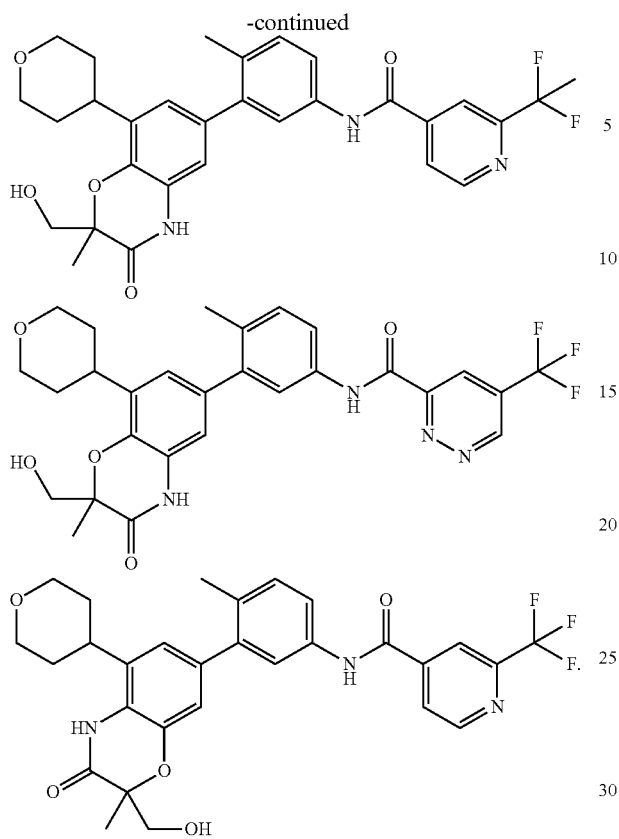

In another embodiment are compounds of formula If:

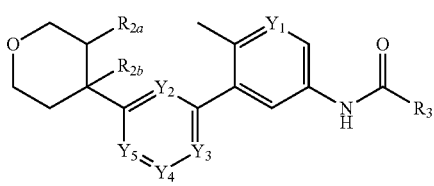

If in which: $Y_1$ is selected from N and CH; $Y_2$ is selected from N and CH; $Y_3$ is selected from N and CH; $Y_4$ is selected from N and $CR_8$; wherein $R_8$ is selected from H, hydroxyethoxy, 3-hydroxyoxetan-3-yl, bis(hydroxy-ethyl)-amino, 4-hydroxy-piperidin1-yl, 2,3-dihydroxypropoxy, hydroxyethyl-amino, 4-amino-4-methylpiperidin-1-yl, 2-oxooxazolidin-3-yl, methoxy and methyl; $Y_5$ is selected from N and $CR_1$; or $R_1$ and the nitrogen of $Y_4$ form a 5 member unsaturated ring containing and additional heteroatom selected from N, O and S; or $R_1$ and $R_8$ together with the ring to which they are both attached form 2H-benzo[b][1,4]oxazin-3(4H)-one substituted with one to two $R_{20}$ groups independently selected from methyl and hydroxy-ethyl; or $R_8$ and $Y_3$ together with the ring to which they are both attached form 1H-benzo[d]imidazole substituted with methyl; $R_1$ is selected from H, ethoxy, isopropoxy, methoxyethyl-amino, (2-hydroxyethyl)(methyl)amino, (1-hydroxypropan-2-yl)amino, methoxy-ethoxy, hydroxy-ethoxy, methoxy, (2-hydroxypropyl)amino, (tetrahydro-2H-pyran-4-yl)oxy, (tetrahydro-2H-pyran-4-yl)oxy, (1-ethylpiperidin-4-yl)oxy and pyrazolyl; wherein said pyrazolyl can be unsubstituted or substituted with 1 to 2 methyl groups; $R_{2a}$ is selected from hydrogen and OH; $R_{2b}$ is selected from H, methyl, halo, fluoro-methyl, hydroxy, hydroxymethyl, difluoromethyl, formyl, methoxy and cyano; $R_3$ is selected from:

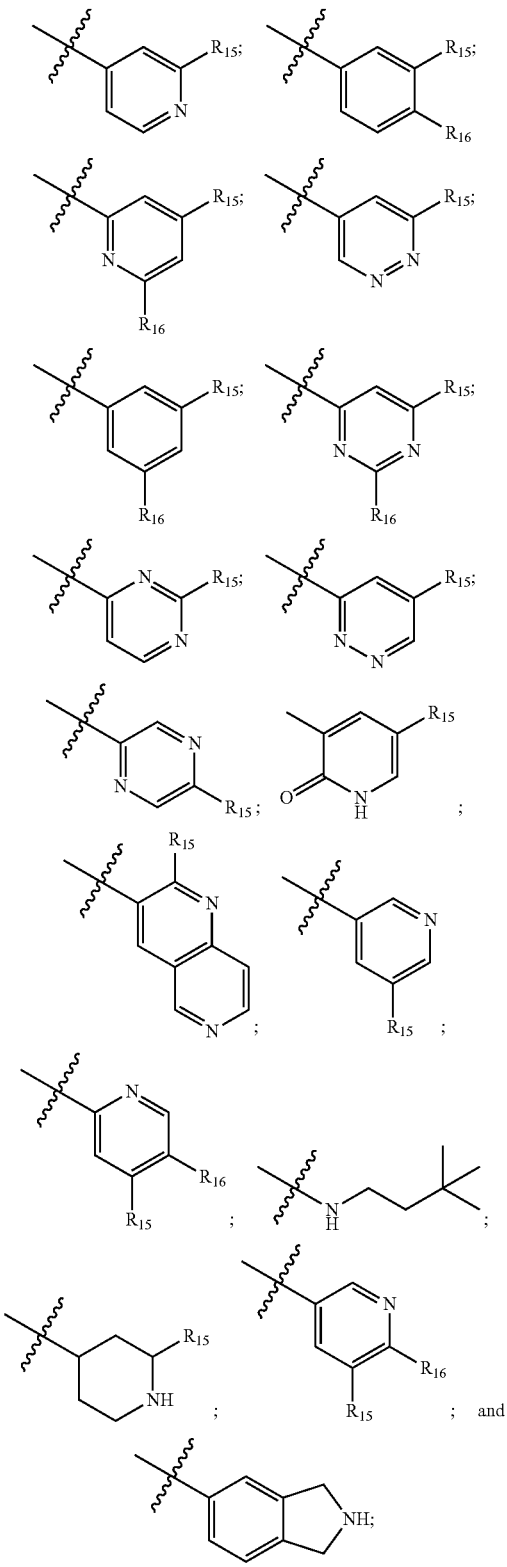

wherein

indicates the point of attachment with L; $R_{15}$ is selected from —$CF_3$, methoxy, —$C(CH_3)_2F$, —$CF_2CH_2F$, —$C(CH_3)_2CN$, —$C(CH_3)F_2$, —$CHF_2$, —$C(CH_3)_2OH$, t-butyl, 1-cyanocyclopropyl, 2-(trifluoromethyl)cyclopropyl, —$C(F_2)C_2H_5$, methyl-sulfonyl, 4-ethylpiperazin-1-yl, —$C(CH_3)_2NH_2$ and dimethyl-amino-methyl; $R_{16}$ is selected from H, halo, hydroxy, dimethyl-amino, hydroxy-methyl, amino-methyl. —$C(CH_3)_2NH_2$ and —$CF_3$; or a pharmaceutically acceptable salt thereof.

In a further embodiment are compounds, or the pharmaceutically acceptable salt thereof, selected from:

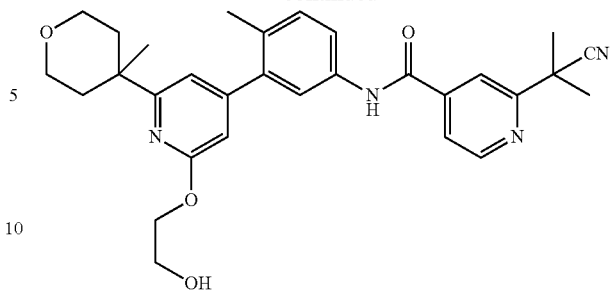

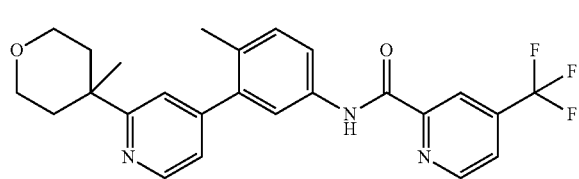

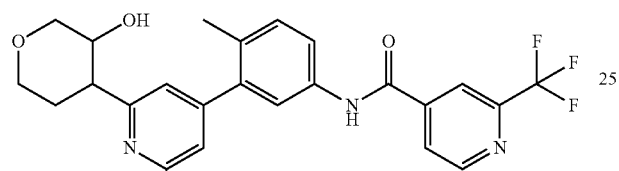

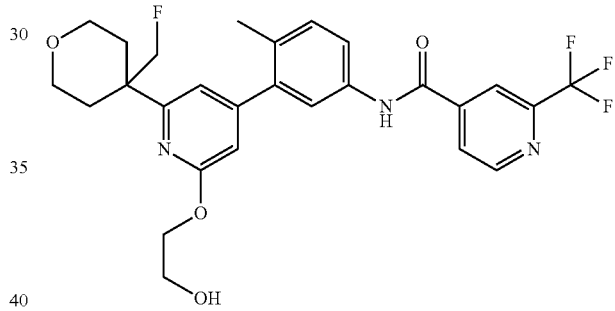

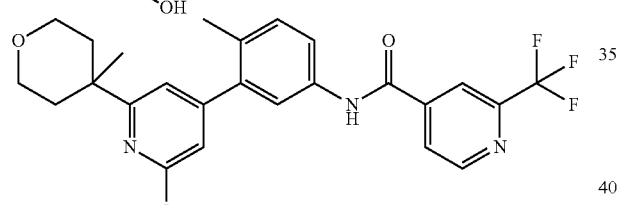

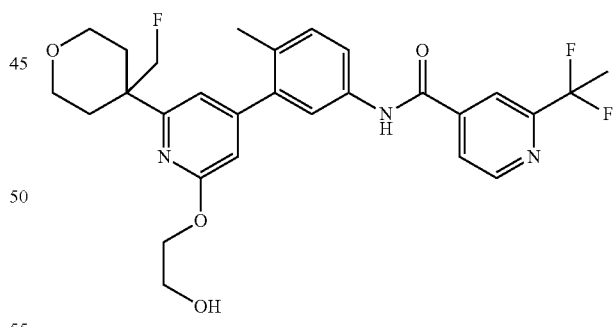

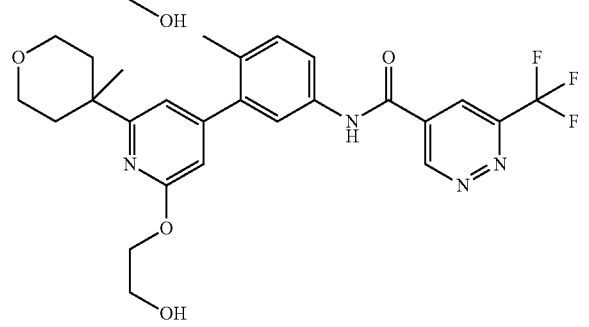

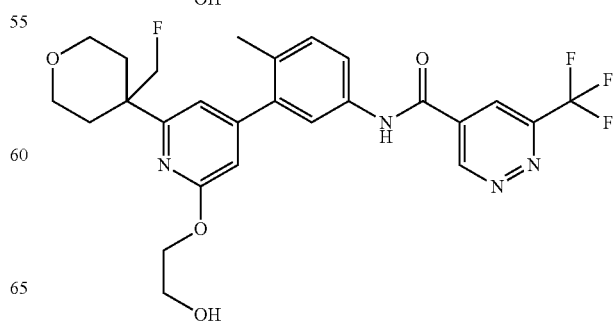

37
-continued
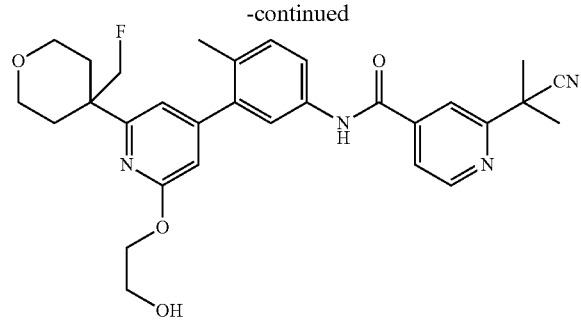
38
-continued
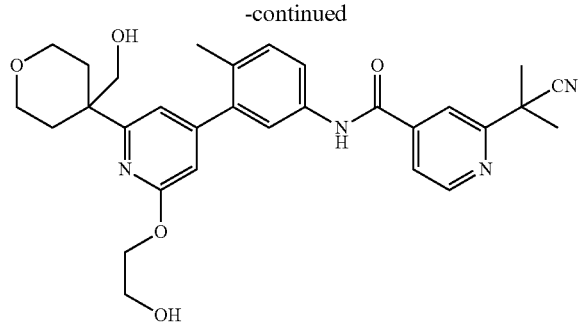
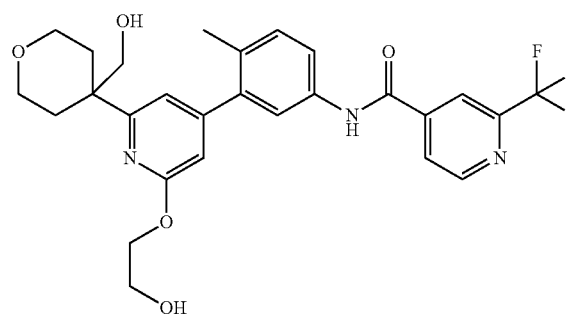
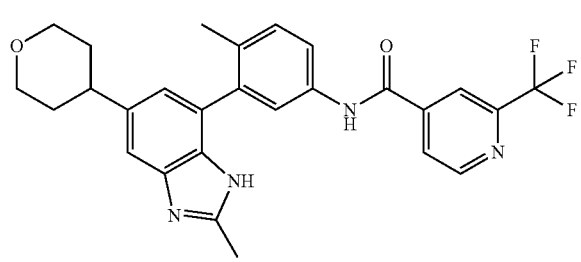
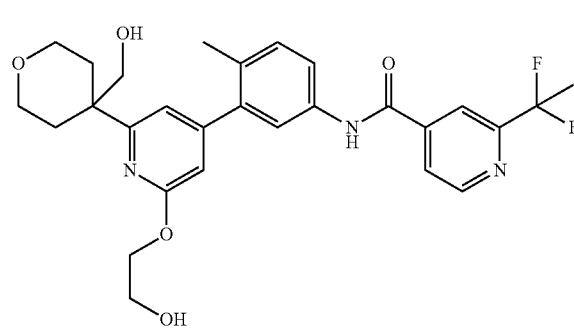
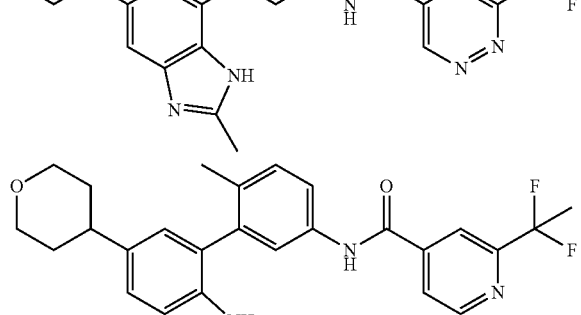
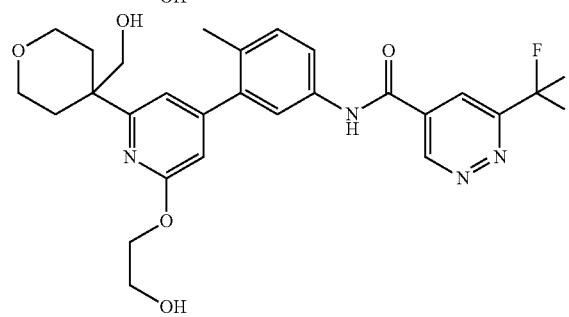

-continued
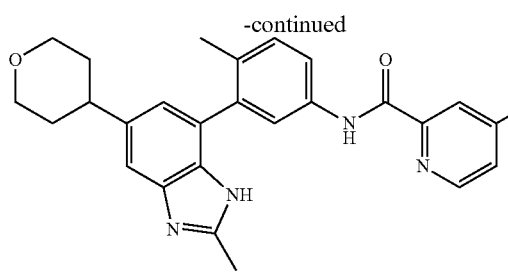
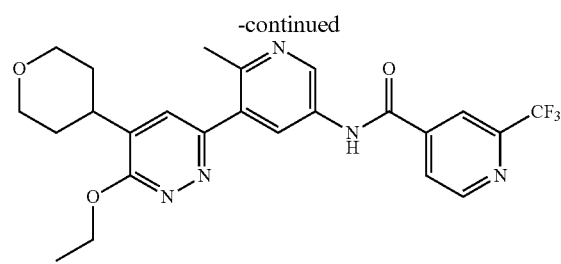
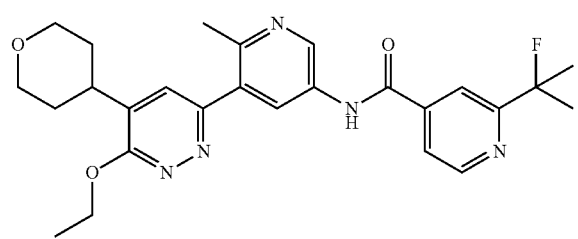
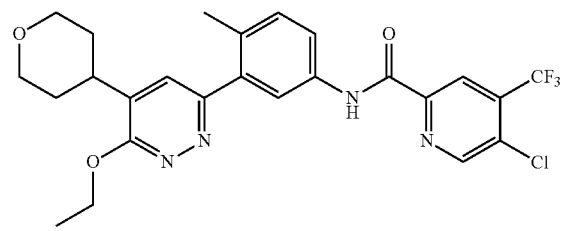
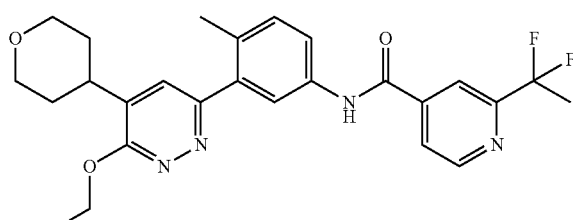
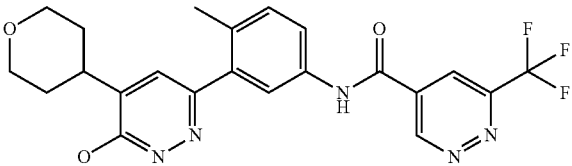
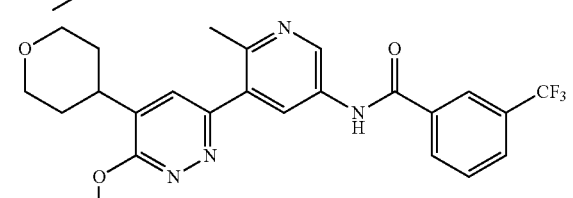
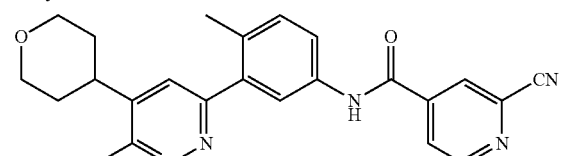
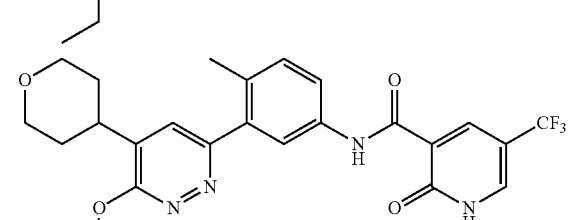
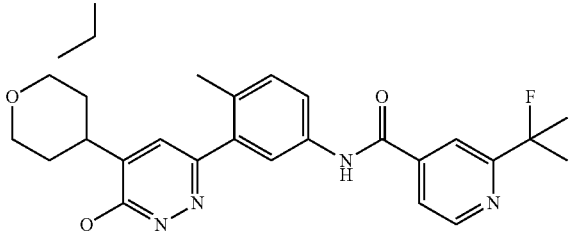
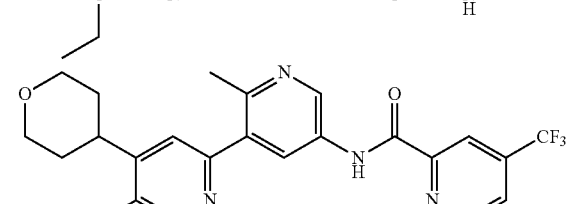
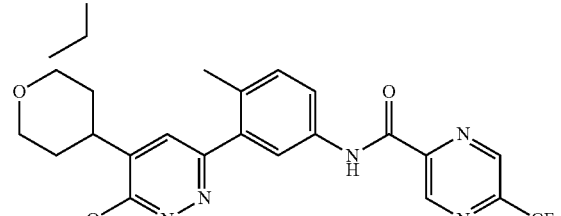
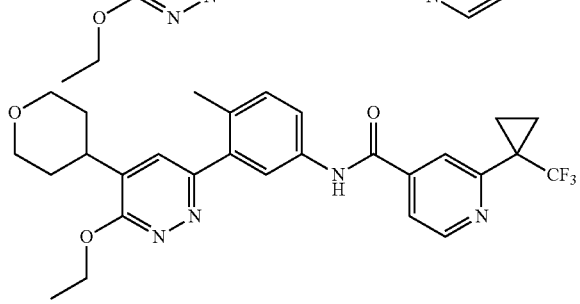
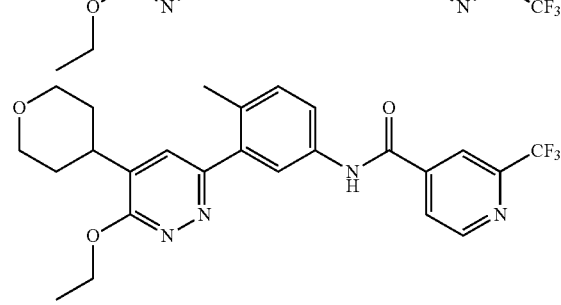

41
-continued
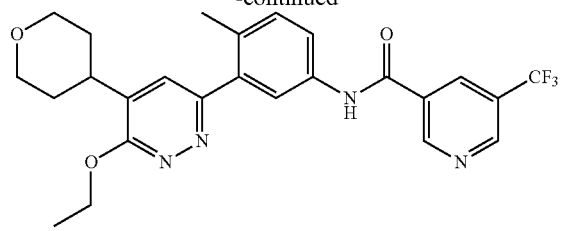
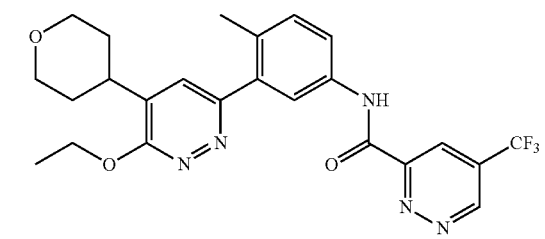
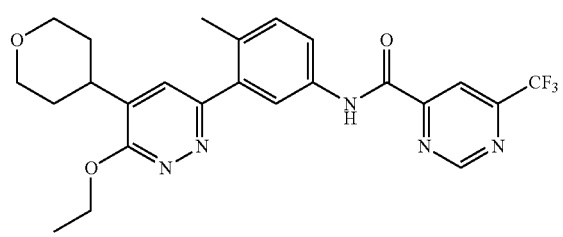
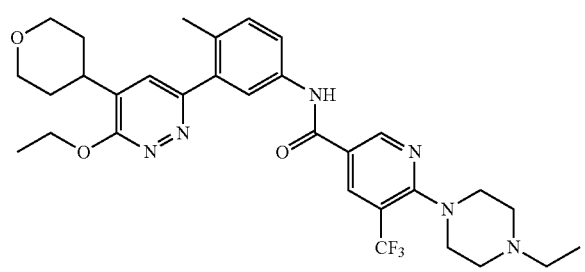
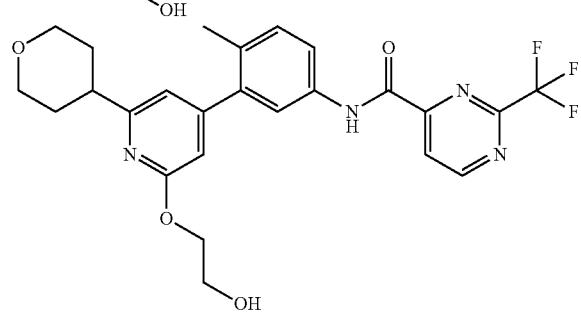
42
-continued
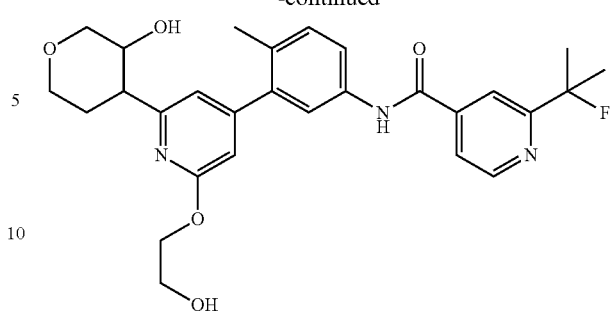
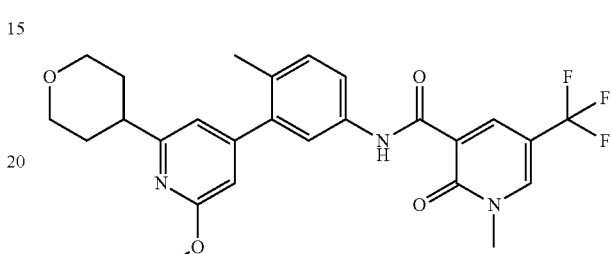
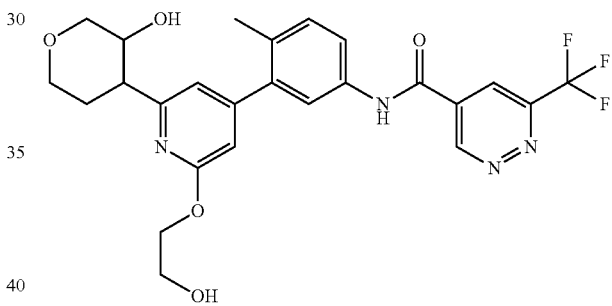
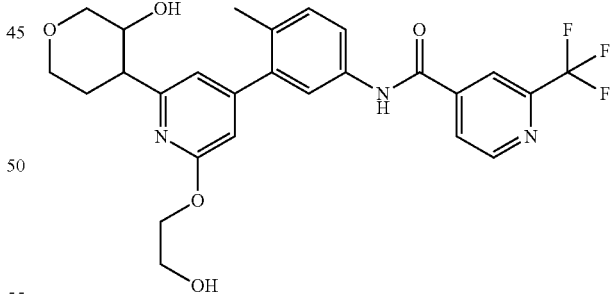
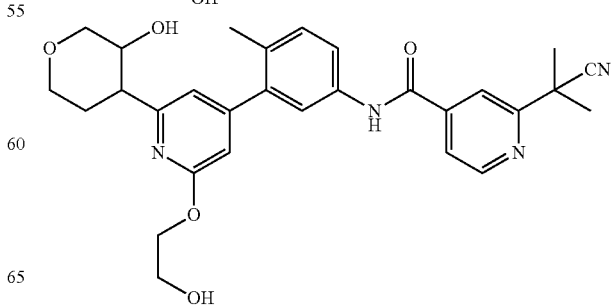

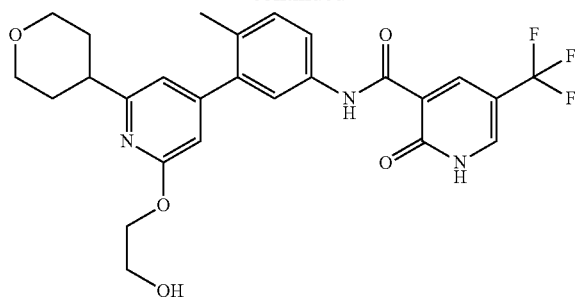
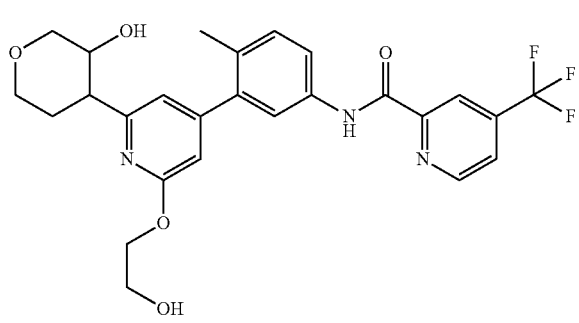
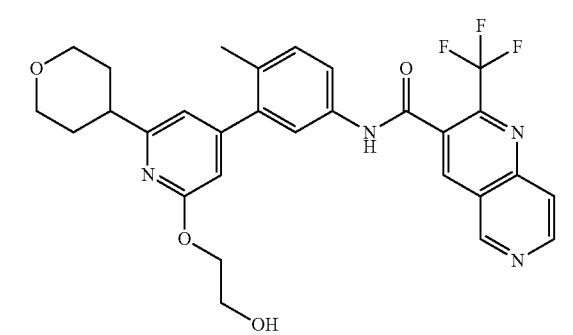
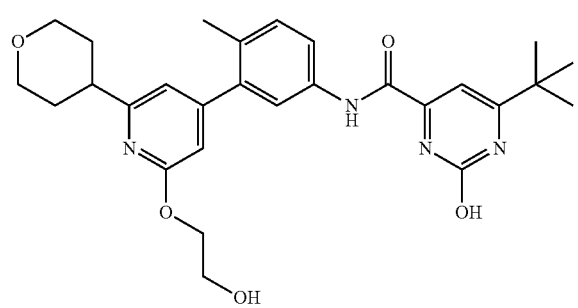
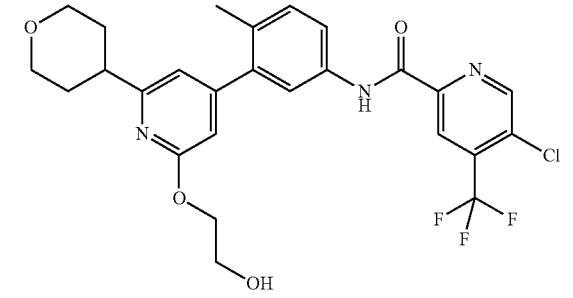
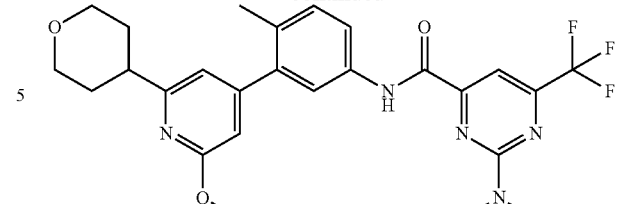
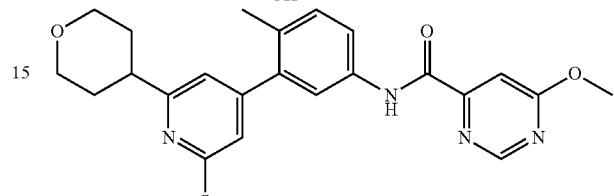
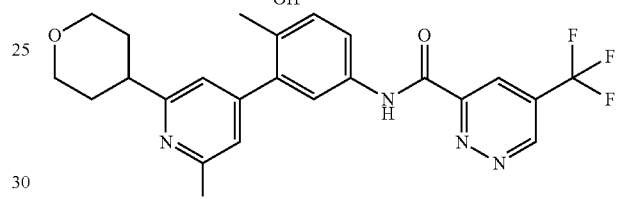
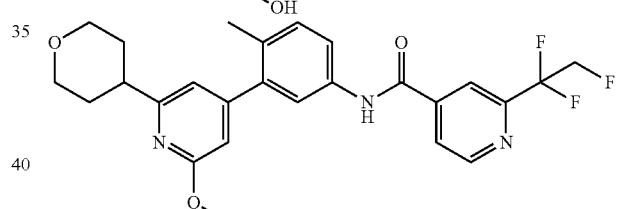
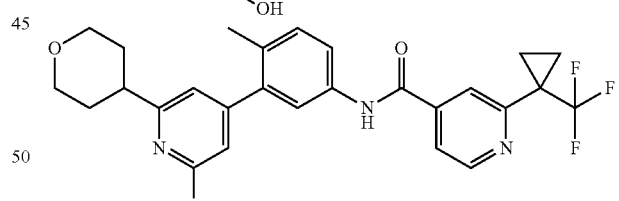
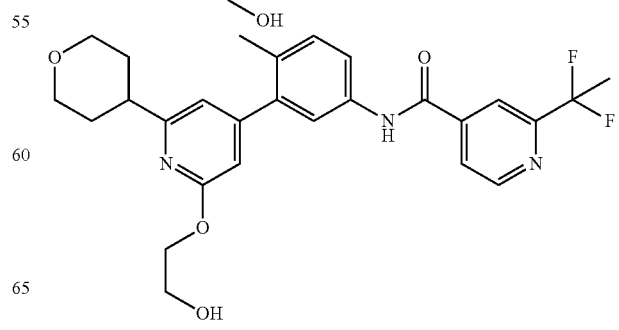

-continued
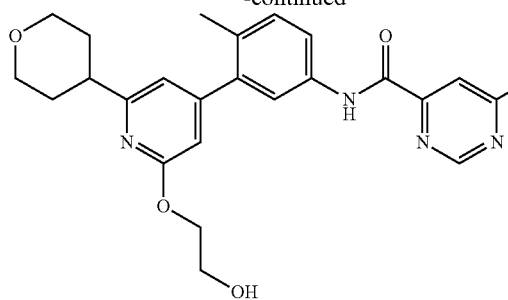
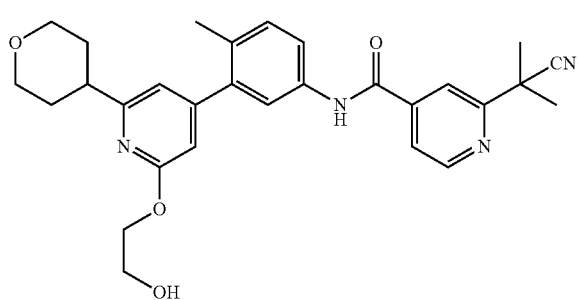
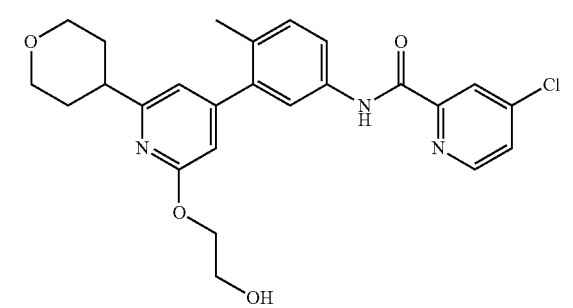
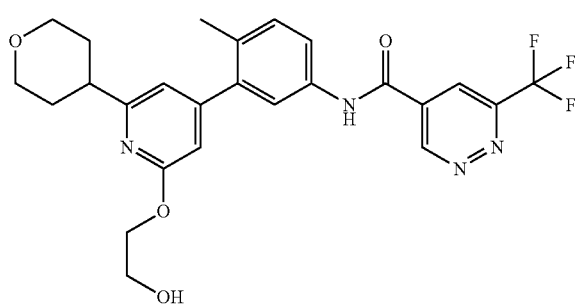
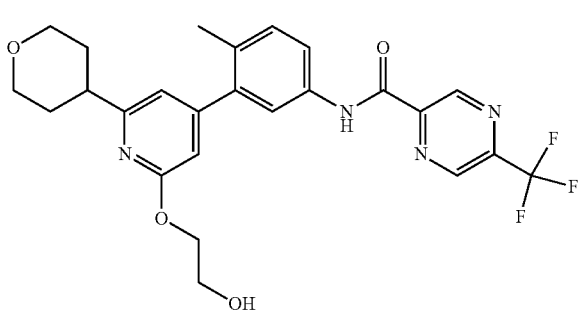
-continued
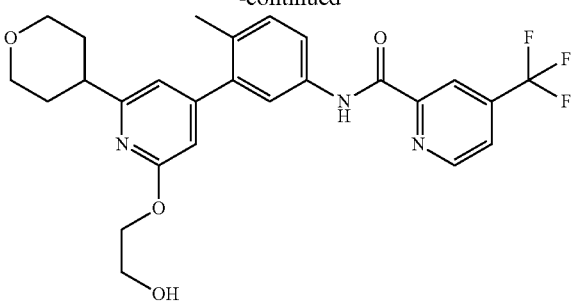
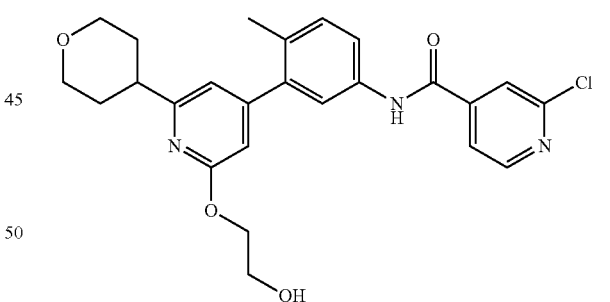
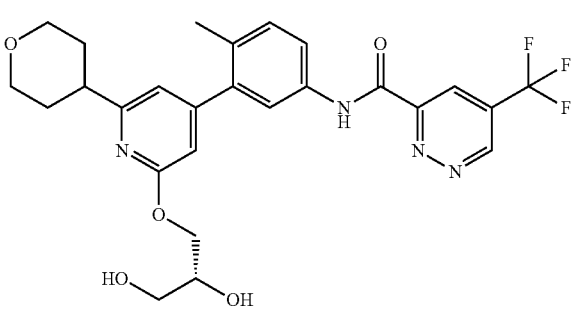

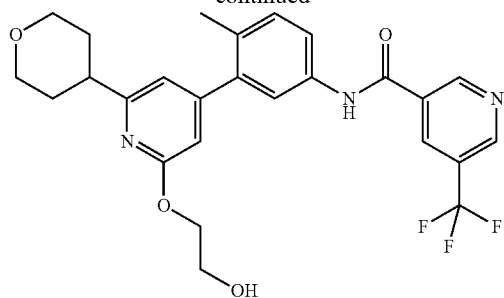
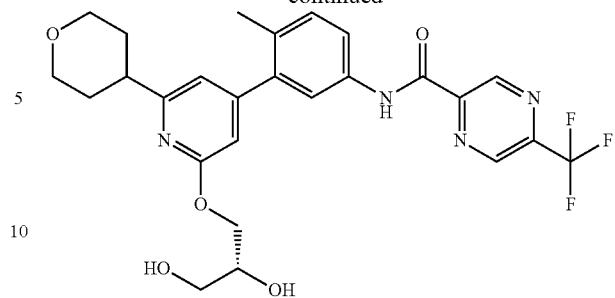
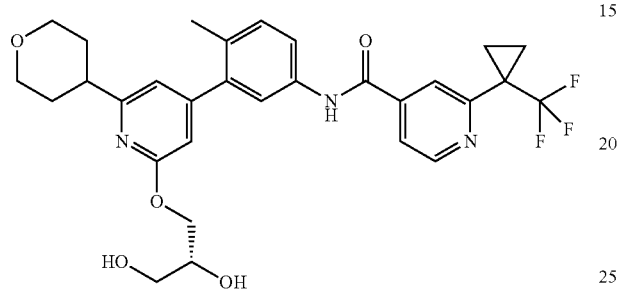
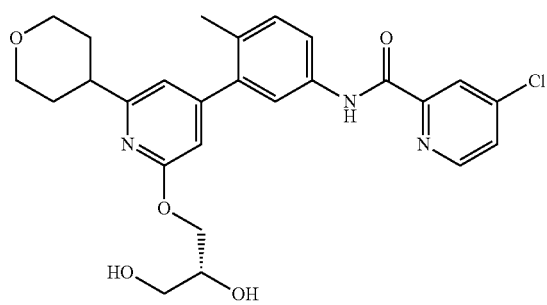
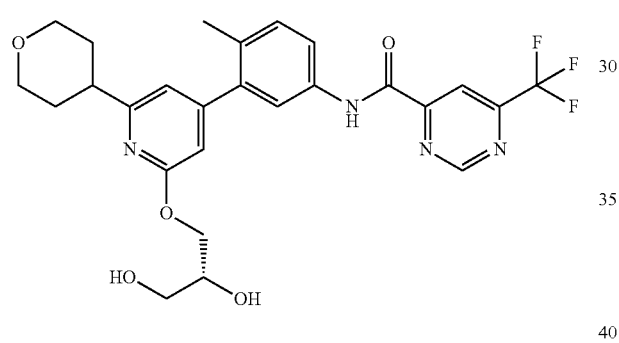
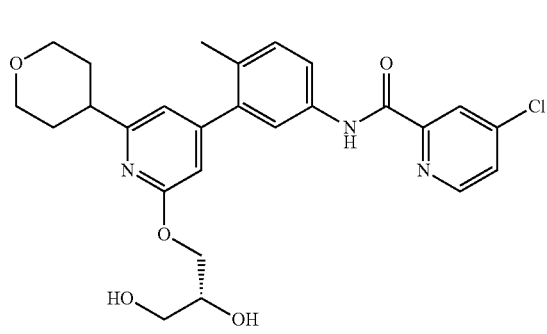
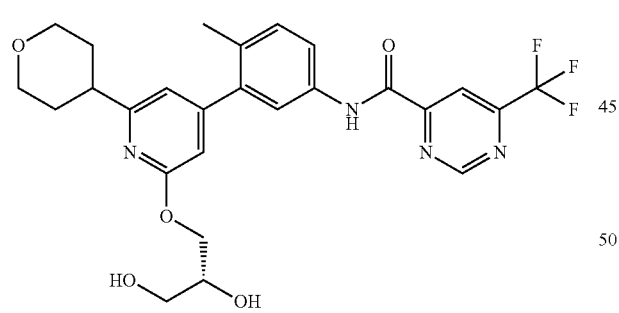
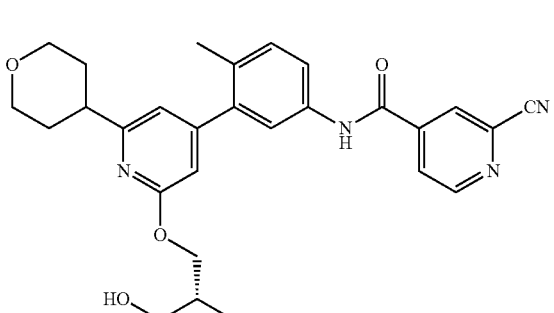
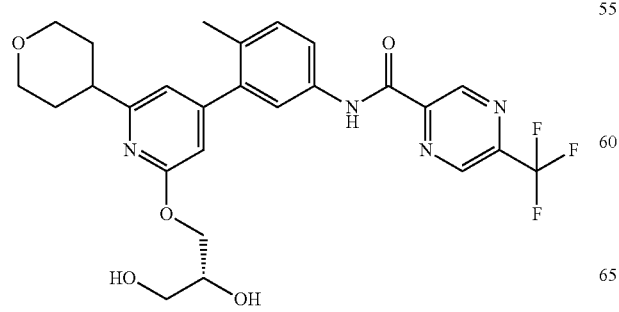
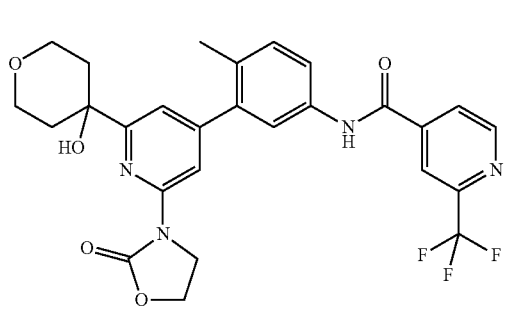

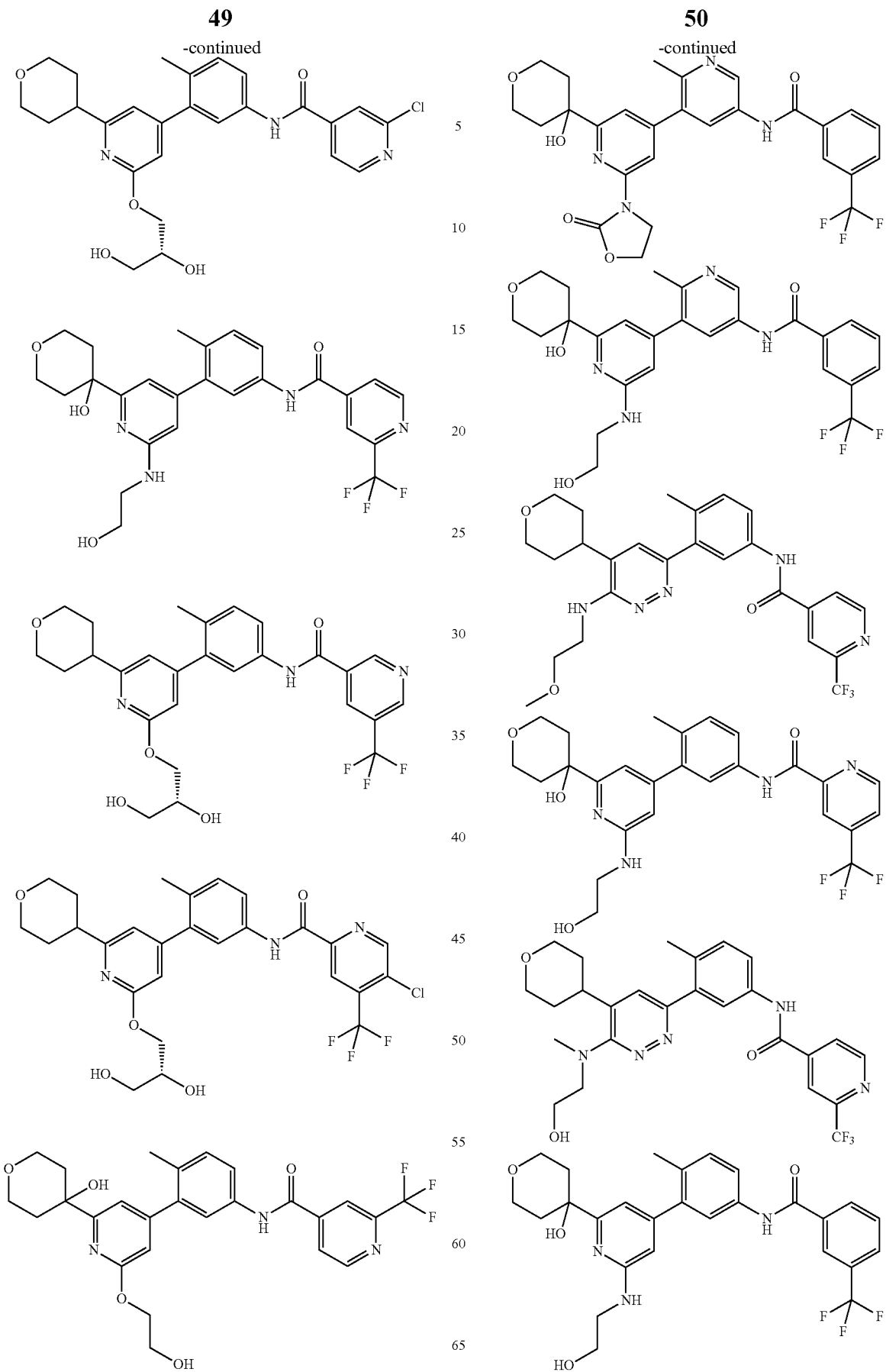

51
-continued
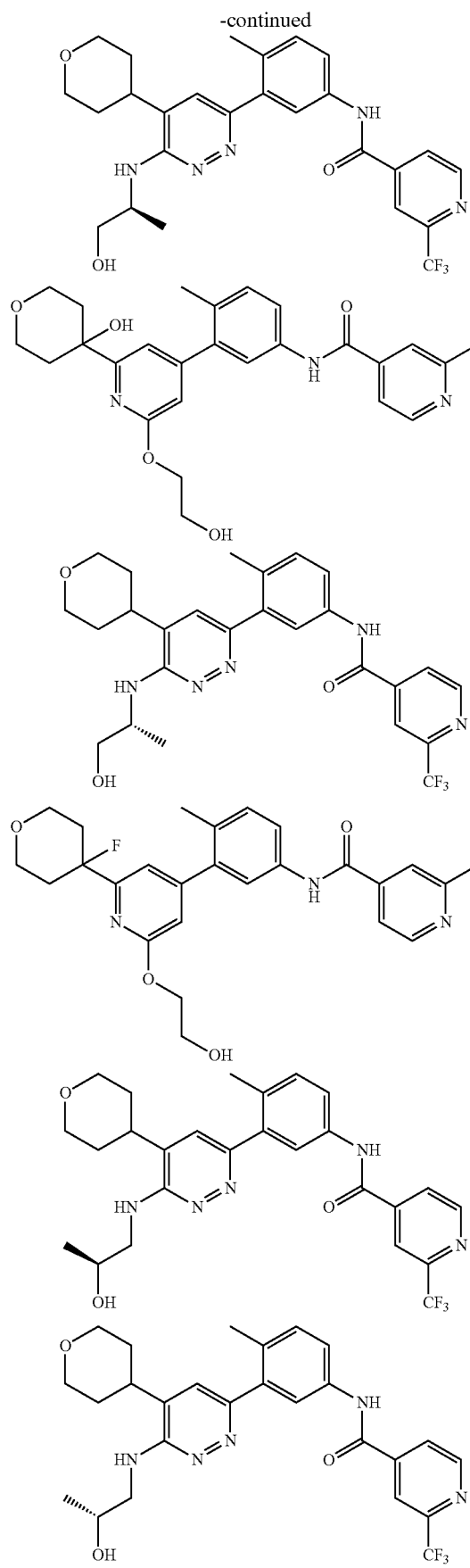
52
-continued
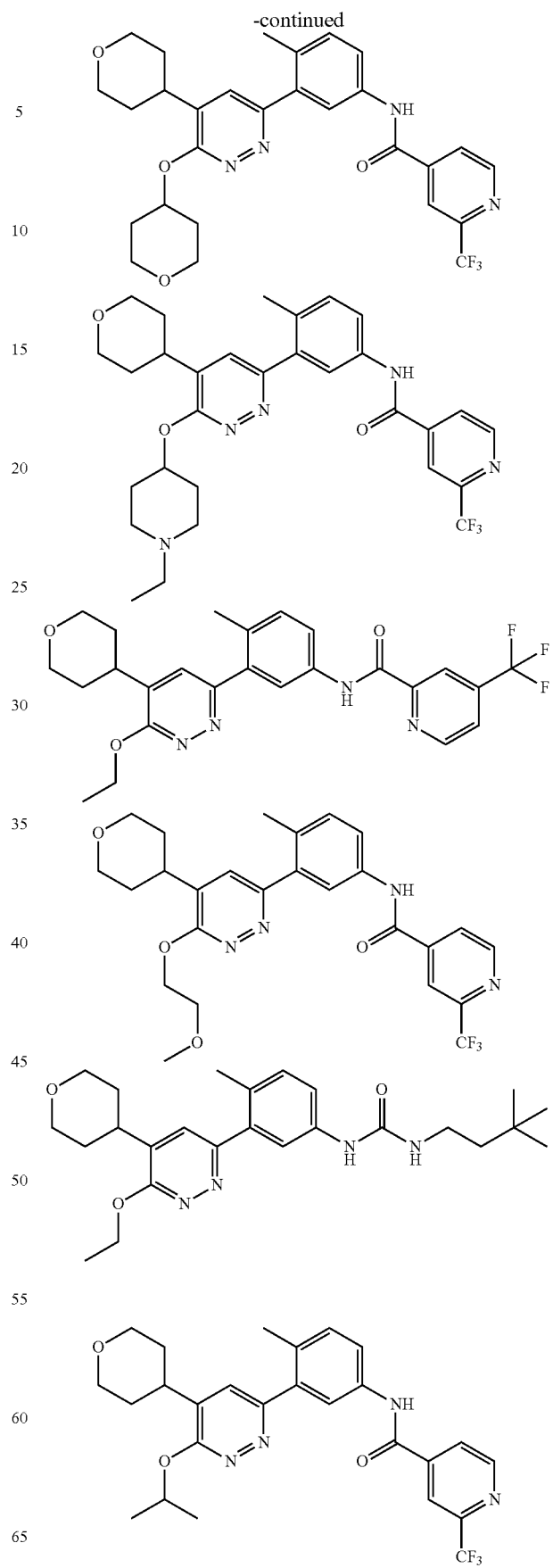

53
-continued
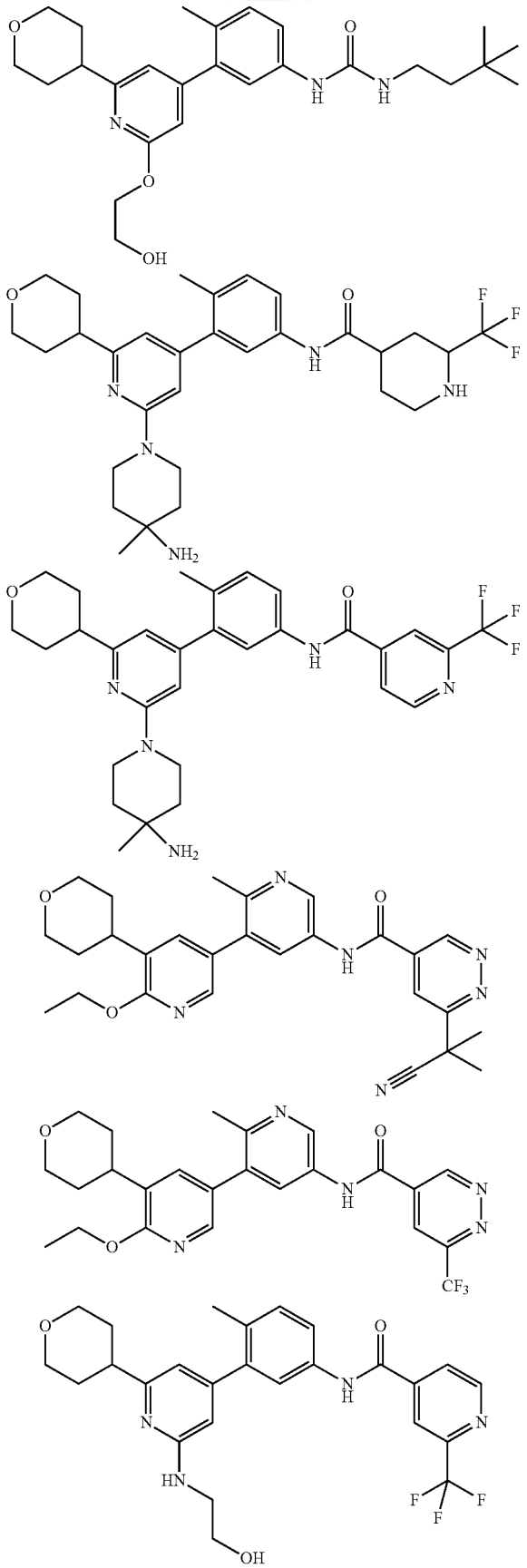
54
-continued
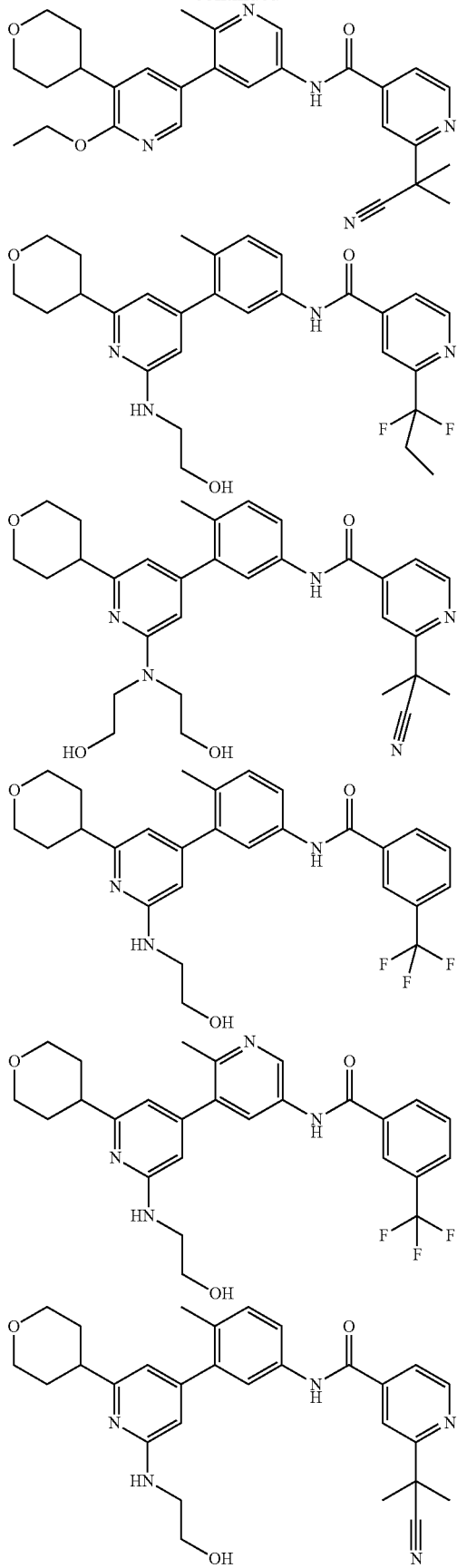

-continued
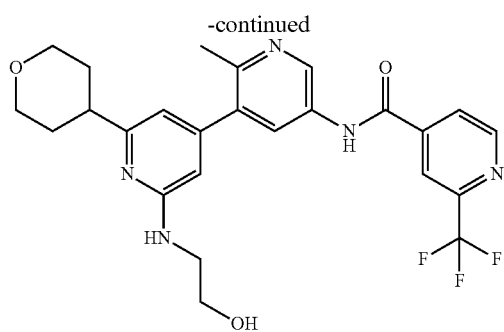
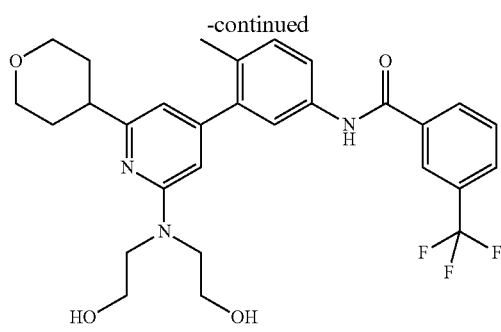
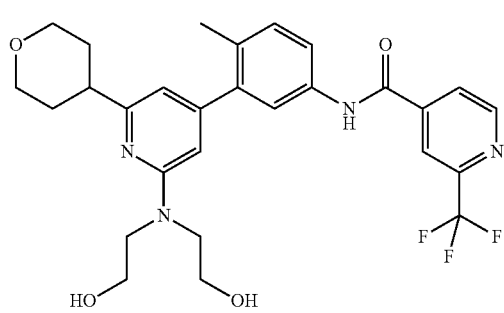
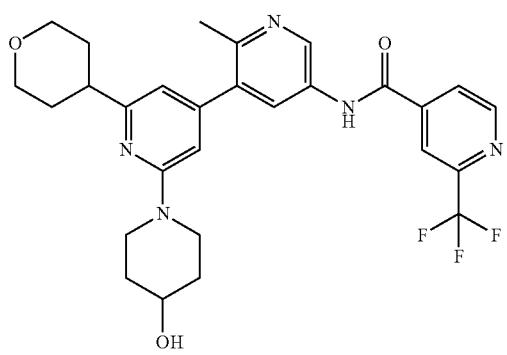
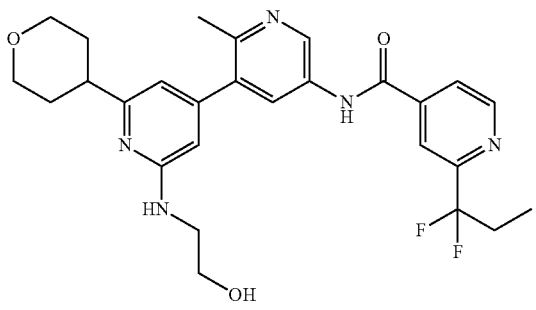
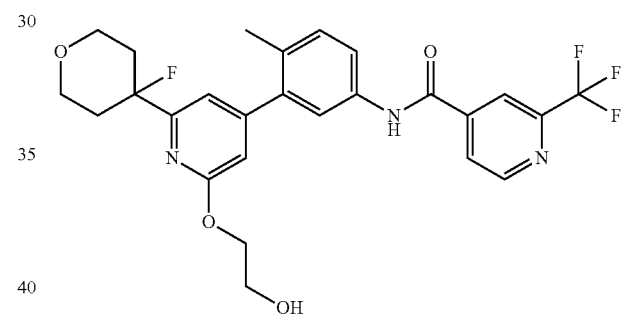
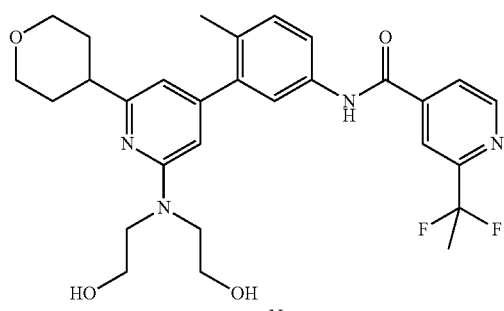
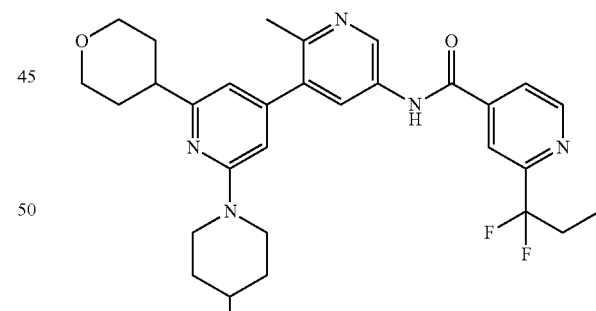
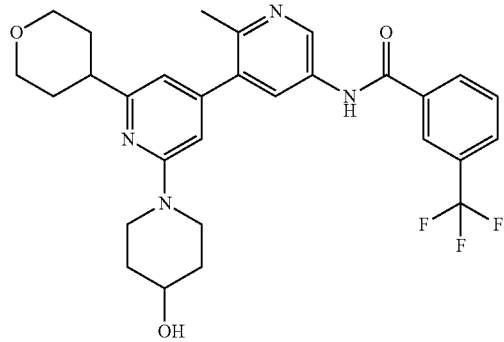
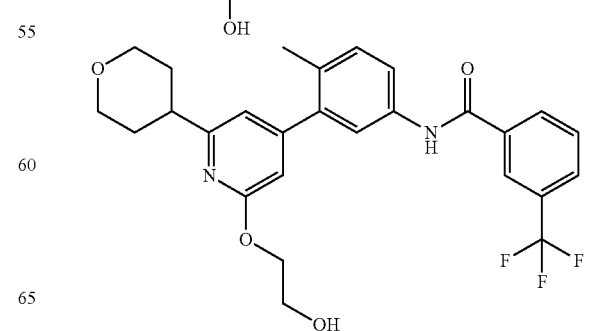

57
-continued
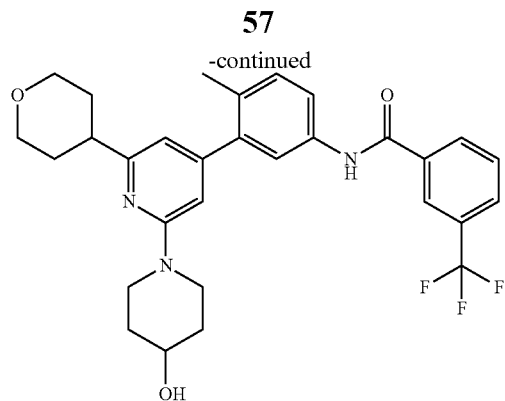
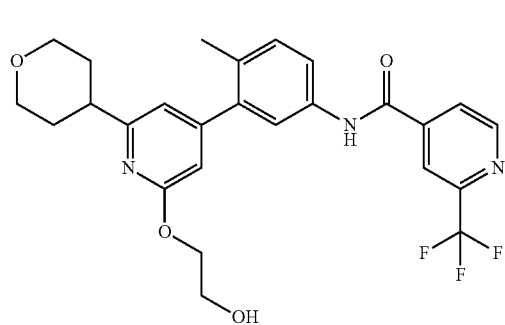
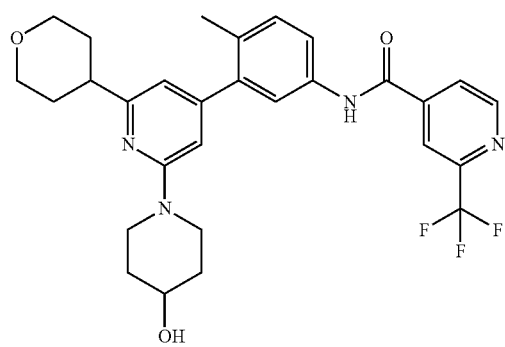
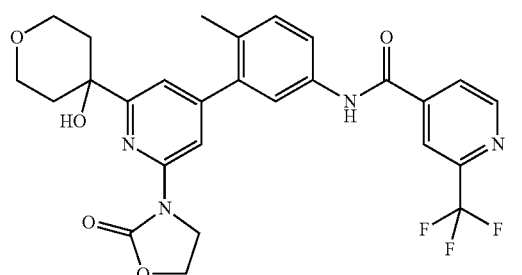
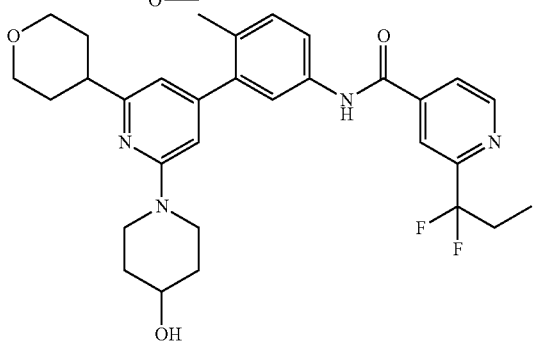
58
-continued
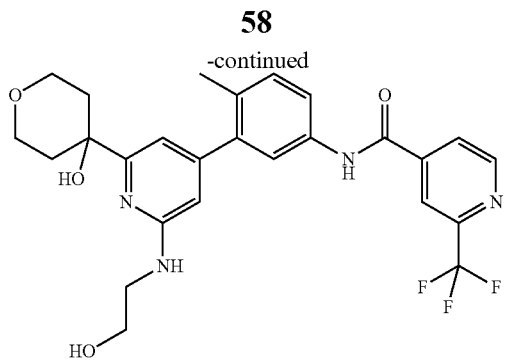
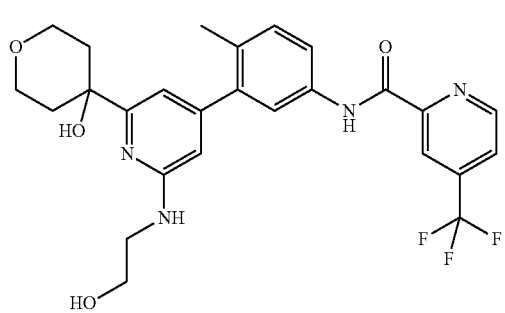
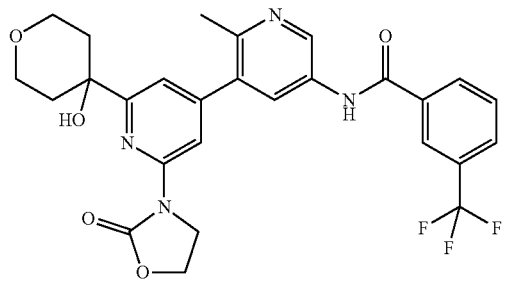
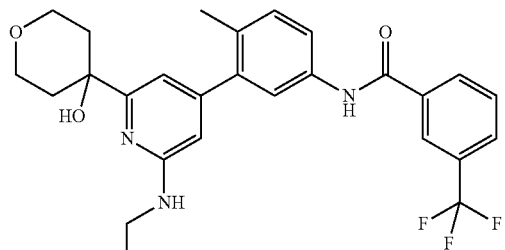
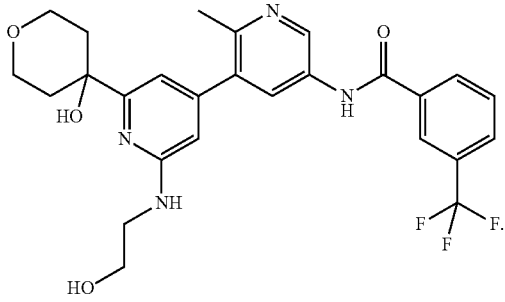
In another embodiment are compounds, or a pharmaceutically acceptable salt thereof, selected from:

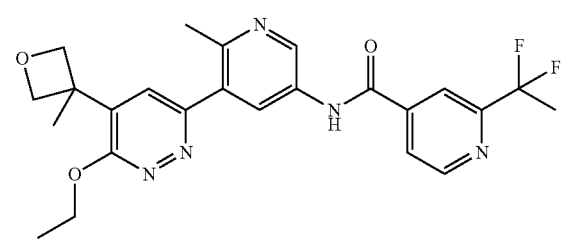
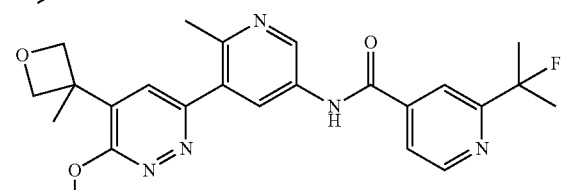
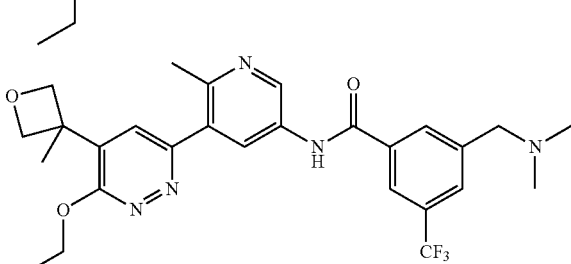
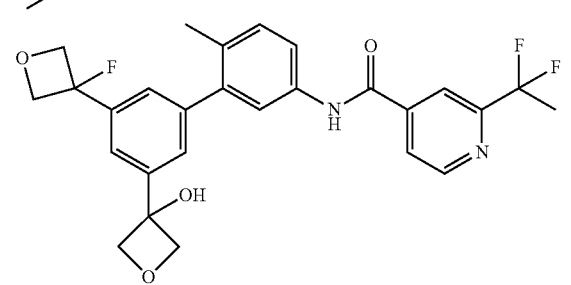
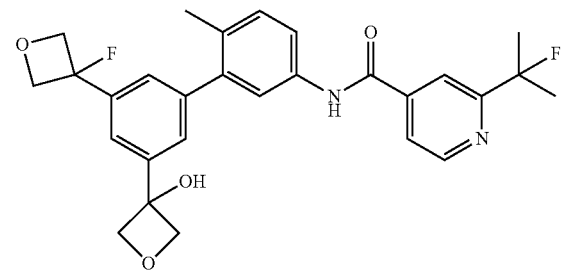
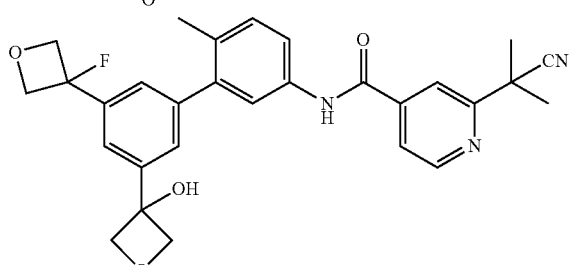
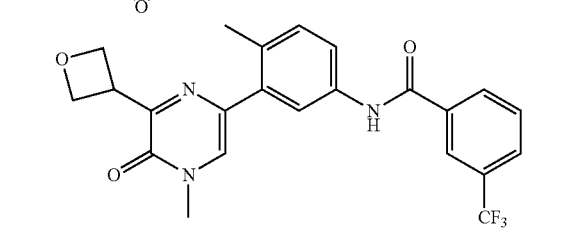
-continued
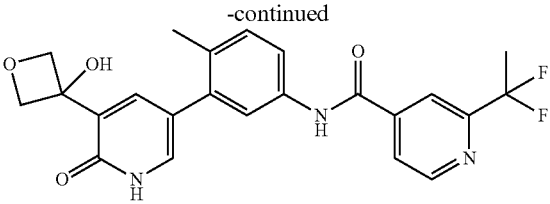
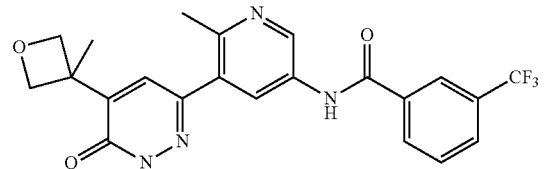
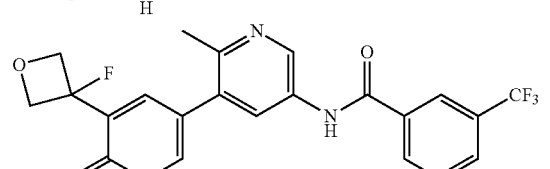
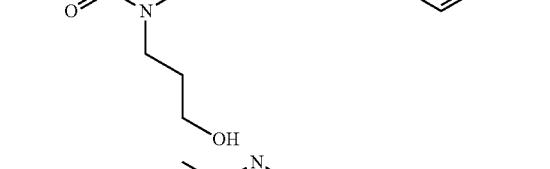
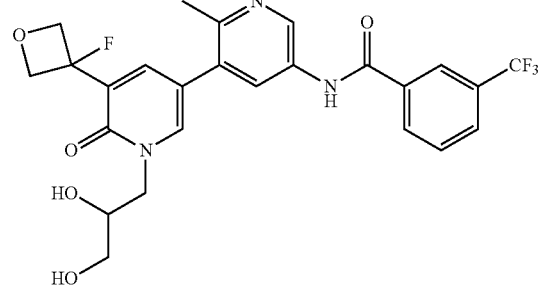
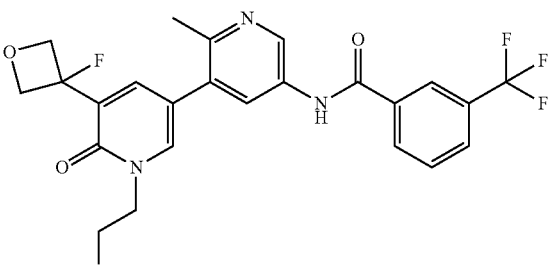
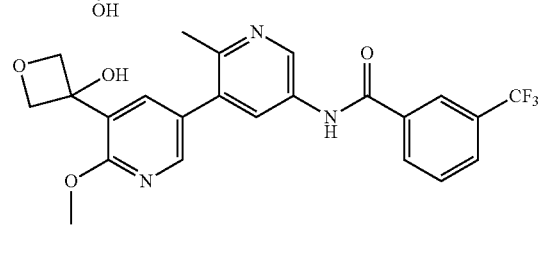
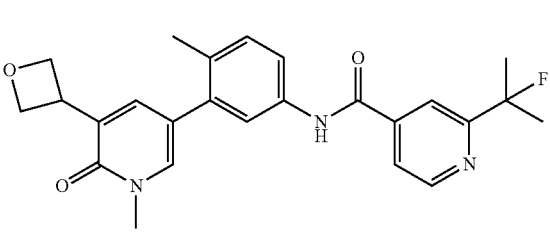

61
-continued
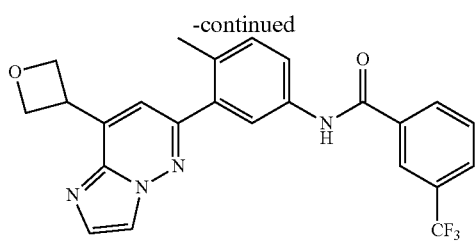
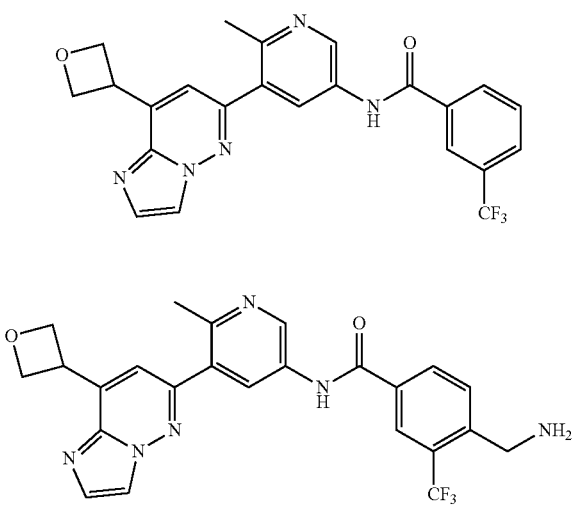
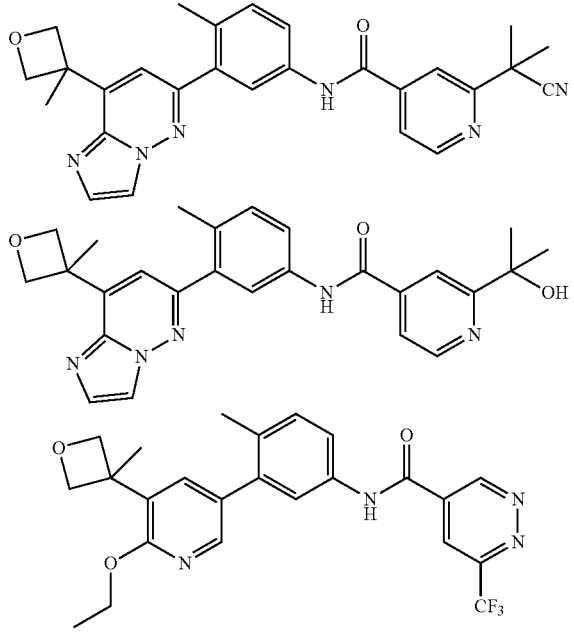
62
-continued
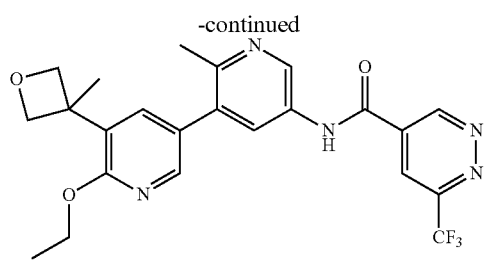
In another embodiment are compounds, or a pharmaceutically acceptable salt thereof, selected from:
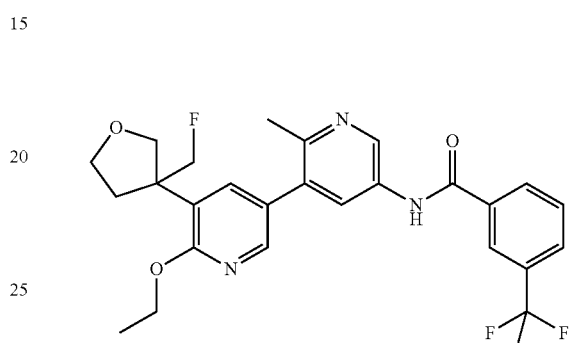
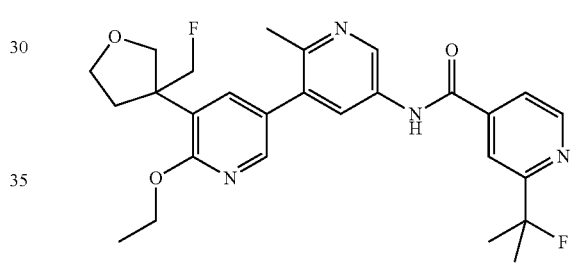
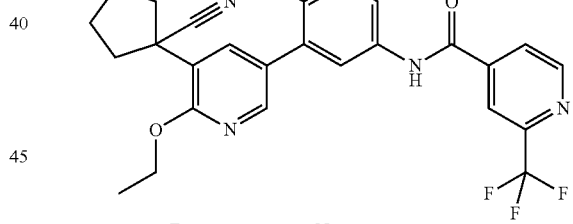
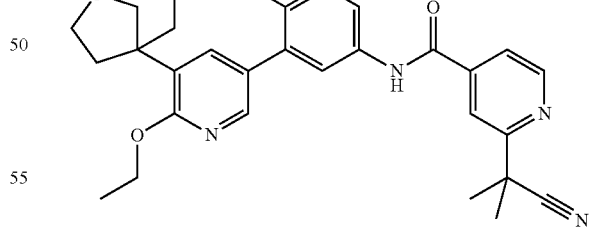
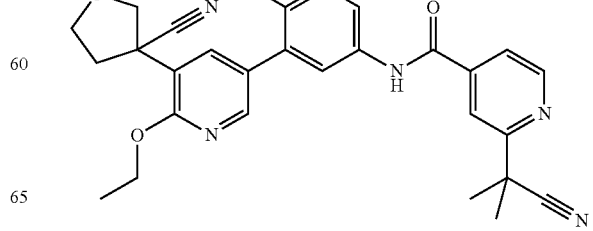

63
-continued
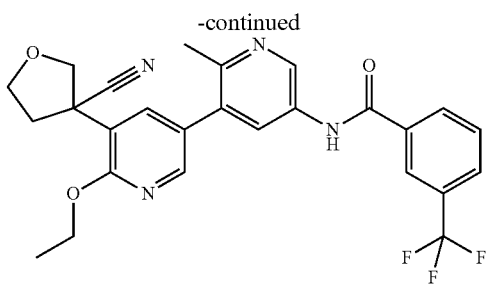
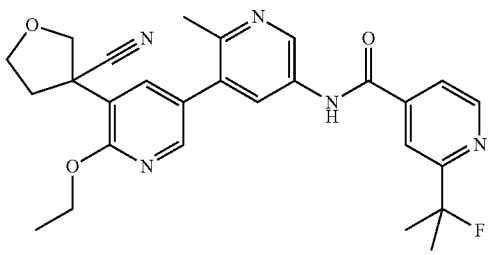
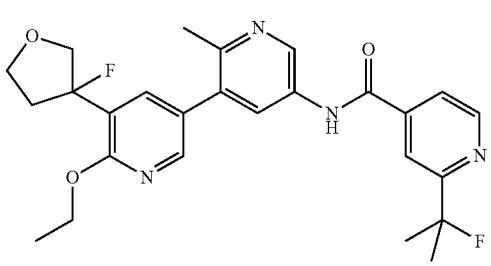
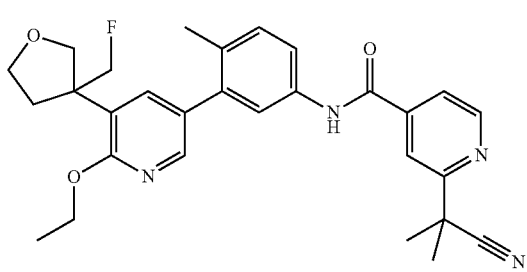
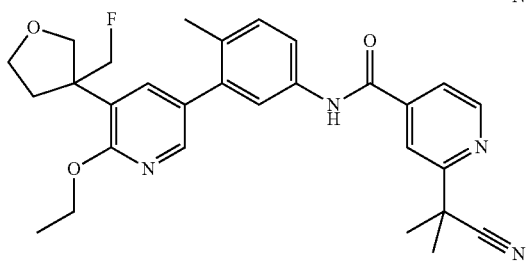
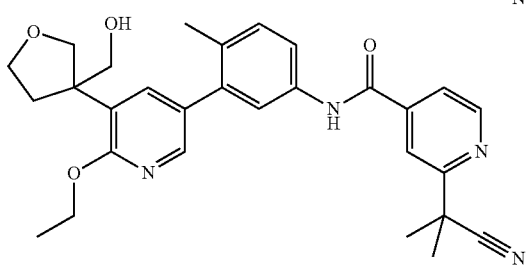
64
-continued
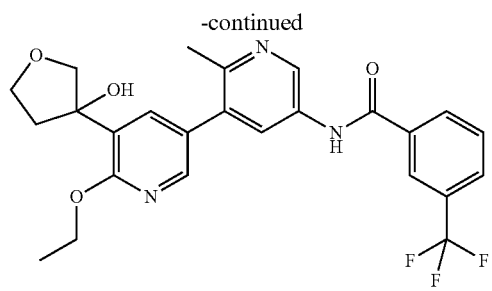
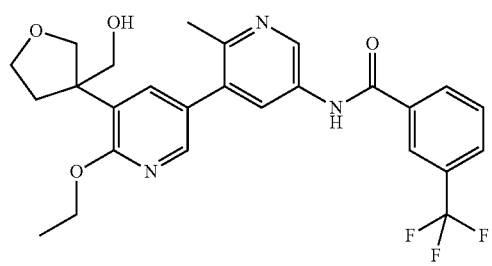
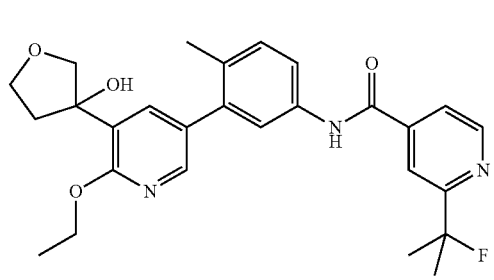
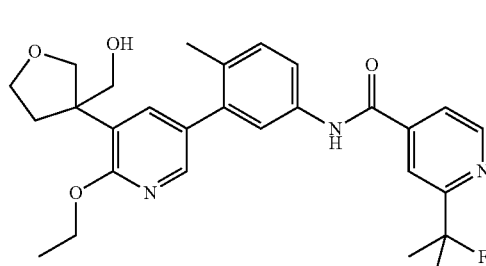
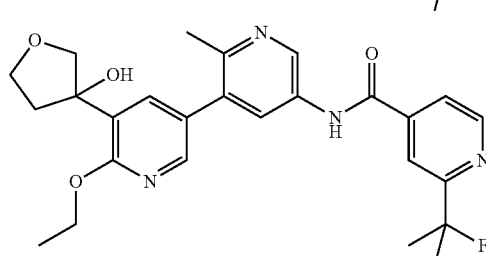
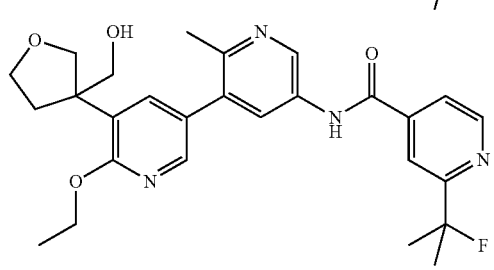

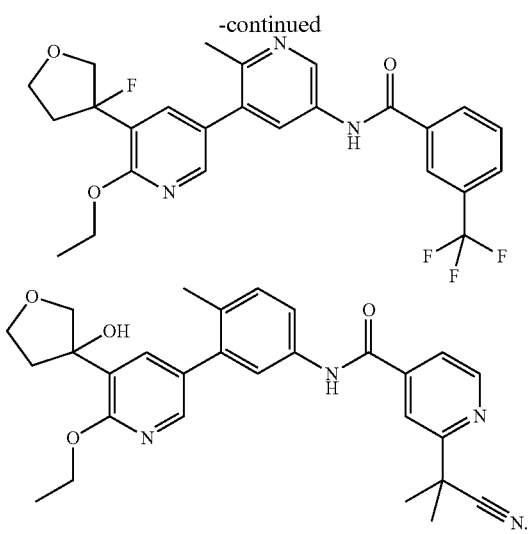

Each of the Example compounds having a measured IC-50 (B-Raf) of less than or equal to 0.01 μM, and a measured IC-50 (c-Raf) of less than 0.005 μM as shown in Table 3, below, is a preferred compound of the invention. The compounds of Examples having a measured IC-50 (B-Raf) of less than or equal to 0.01 μM and measured IC-50 (c-Raf) less than or equal to 0.002 μM according to Table 3 are especially preferred. Thus the use of any one of these compounds for treatment of a condition selected from melanoma, breast cancer, lung cancer (e.g., non-small cell lung cancer, lung adenocarcinoma), sarcoma, GI tumors such as gastrointestinal stromal tumors, ovarian cancer, colorectal cancer, thyroid cancer, and pancreatic cancer is an embodiment of the invention.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog 'R-S' system. When a compound is a pure enantiomer, the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and synthesis procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration unless specified. If the compound contains a disubstituted cycloalkyl, the cycloalkyl substituent may have a cis- or trans-configuration, unless otherwise specified. All tautomeric forms are also intended to be included.

In many cases, the compounds of the present invention are capable of forming acid and/or base salts by virtue of the presence of amino and/or carboxyl groups or groups similar thereto. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlorotheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic or organic bases and can have inorganic or organic counterions.

Inorganic counterions for such base salts include, for example, ammonium salts and metals from columns I to XII of the periodic table. In certain embodiments, the counterion is selected from sodium, potassium, ammonium, alkylammonium having one to four C1-C4 alkyl groups, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Suitable organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, tetrahydrofuran, toluene, chloroform, dichloromethane, methanol, ethanol, isopropanol, or acetonitrile is desirable, where practicable.

Any formula given herein is also intended to represent unlabeled forms (i.e., compounds wherein all atoms are present at natural isotopic abundances, and not isotopically enriched) as well as isotopically enriched or labeled forms of the compounds. Isotopically enriched or labeled compounds have structures depicted by the formulas given herein except that at least one atom of the compound is replaced by an atom having an atomic mass or mass number different from the atomic mass or the atomic mass distribution that occurs naturally. Examples of isotopes that can be incorporated into enriched or labeled compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those in which radioactive isotopes, such as $^3H$ and $^{14}C$, or those in which non-radioactive isotopes, such as $^2H$ and $^{13}C$, are present at levels significantly above the natural abundance for these isotopes. These isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula I or II can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula I or II. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d^6$-acetone, $d^6$-DMSO, as well as solvates with non-enriched solvents.

Compounds of the invention, i.e. compounds of formula I or II that contain groups capable of acting as donors and/or acceptors for hydrogen bonds may be capable of forming co-crystals with suitable co-crystal formers. These co-crystals may be prepared from compounds of formula I or II by known co-crystal forming procedures. Such procedures include grinding, heating, co-subliming, co-melting, or contacting in solution compounds of formula I or II with the co-crystal former under crystallization conditions and isolating co-crystals thereby formed. Suitable co-crystal formers include those described in WO 2004/078163. Hence the invention further provides co-crystals comprising a compound of formula I or II.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease mediated by a Raf kinase such as B-Raf or C-Raf, or associated with activity of a kinase such as B-Raf or C-Raf, or (2) reduce or inhibit the activity of a kinase such as B-Raf or C-Raf in vivo.

In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of a kinase such as B-Raf or C-Raf, or at least partially reduce or alleviate a symptom or a condition associated with excessive Raf kinase activity.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In specific embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the (R)- or (S)-configuration, i.e., for optically active compounds, it is often preferred to use one enantiomer to the substantial exclusion of the other enantiomer. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. 'Substantially pure' or 'substantially free of other isomers' as used herein means the product contains less than 5%, and preferably less than 2%, of other isomers relative to the amount of the preferred isomer, by weight.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another aspect, the present invention provides a pharmaceutical composition comprising a compound of the present invention, or a pharmaceutically acceptable salt thereof, and at least one pharmaceutically acceptable carrier. The pharmaceutical composition can be formulated for particular routes of administration such as oral administration, parenteral administration, and rectal administration, and the like. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions for compounds of Formula I or II are tablets or gelatin capsules comprising an active ingredient of Formula I or II together with at least one of the following pharmaceutically acceptable excipients:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in salt form, exhibit valuable pharmacological activities, e.g. they modulate or inhibit activity of A-Raf, B-Raf and/or C-Raf, as indicated by test data provided in the next sections, and are therefore indicated for therapy or for use as research chemicals. e.g. as tool compounds. These compounds are especially useful for treatment of cancers driven by mutations in the Raf/Raf/MEK/ERK pathway, including cancers characterized by an activating Raf mutation such as Raf V600E, including but not limited to melanoma (e.g., malignant melanoma), breast cancer, lung cancer (e.g., non-small cell lung cancer), sarcoma, GI tumors such as gastrointestinal stromal tumors, ovarian cancer, colorectal cancer, thyroid cancer, and pancreatic cancer.

Thus, as a further embodiment, the present invention provides the use of a compound of formula I or II or any of the embodiments within the scope of Formula I or II as described herein, in therapy. In a further embodiment, the therapy is for a disease which may be treated by inhibition of A-Raf. B-Raf or C-Raf. In another embodiment, the compounds of the invention are useful to treat cancers, including but not limited to melanoma, breast cancer, lung cancer, sarcoma, GI tumors such as gastrointestinal stromal tumors, ovarian cancer, colorectal cancer, thyroid cancer, and pancreatic cancer.

In another embodiment, the invention provides a method of treating a disease which is treatable by inhibition of A-Raf, B-Raf or C-Raf, or a combination thereof, comprising administration of a therapeutically effective amount of a compound of formula I or II or any of the embodiments within the scope of Formula I or II as described herein. In a further embodiment, the disease is selected from the afore-mentioned list, suitably melanoma, breast cancer, lung cancer, sarcoma, GI tumors such as gastrointestinal stromal tumors, ovarian cancer, colorectal cancer, thyroid cancer, and pancreatic cancer. The method typically comprises administering an effective amount of a compound as described herein or a pharmaceutical composition comprising such compound to a subject in need of such treatment. The compound may be administered by any suitable method such as those described herein, and the administration may be repeated at intervals selected by a treating physician.

Thus, as a further embodiment, the present invention provides the use of a compound of formula I or II or any of the embodiments of such compounds described herein for the manufacture of a medicament. In a further embodiment, the medicament is for treatment of a disease which may be treated by inhibition of A-Raf, B-Raf or C-Raf. In another embodiment, the disease is a cancer, e.g., a cancer selected from the afore-mentioned list, including melanoma, breast cancer, lung cancer, sarcoma, GI tumors such as gastrointestinal stromal tumors, ovarian cancer, colorectal cancer, thyroid cancer, and pancreatic cancer.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more therapeutic co-agent(s) (co-therapeutic agents). Suitable co-therapeutic agents for use in the invention include, for example, cancer chemotherapeutics including but not limited to inhibitors of PI3K, other inhibitors of the Raf pathway, paclitaxel, docetaxel, temozolomide, platins, doxorubicins, vinblastins, cyclophosphamide, topotecan, gemcitabine, ifosfamide, etoposide, irinotecan, and the like. The compound of the present invention may be administered separately, by the same or different route of administration, or together in the same pharmaceutical composition as the co-agent(s).

In one embodiment, the invention provides a product comprising a compound of formula I or II and at least one other therapeutic co-agent as a combined preparation for simultaneous, separate or sequential use in therapy. In one embodiment, the therapy is the treatment of a disease or condition mediated by B-Raf or C-Raf, such as cancer. Products provided as a combined preparation include a composition comprising the compound of formula I or II and the other therapeutic co-agent(s) together in the same pharmaceutical composition, or the compound of formula I or II and the other therapeutic co-agent(s) in separate form, e.g. in the form of a kit.

In one embodiment, the invention provides a pharmaceutical composition comprising a compound of formula I or II and another therapeutic co-agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula I or II. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic co-agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula I or II for treating a disease or condition mediated by B-Raf or C-Raf, wherein the medicament is prepared for administration with another therapeutic agent. The invention also provides the use of another therapeutic co-agent for treating a disease or condition, wherein the medicament is administered with a compound of formula I or II.

The invention also provides a compound of formula I or II for use in a method of treating a disease or condition mediated by B-Raf or C-Raf, wherein the compound of formula I or II is prepared for administration with another therapeutic agent. The invention also provides another therapeutic co-agent for use in a method of treating a disease or condition mediated by B-Raf or C-Raf, wherein the other therapeutic co-agent is prepared for administration with a compound of formula I or II. The invention also provides a compound of formula I or II for use in a method of treating a disease or condition mediated by B-Raf or C-Raf, wherein the compound of formula I or II is administered with another therapeutic co-agent. The invention also provides another therapeutic co-agent for use in a method of treating a disease or condition mediated by B-Raf or C-Raf, wherein the other therapeutic co-agent is administered with a compound of formula I or II.

The invention also provides the use of a compound of formula I or II for treating a disease or condition mediated by B-Raf or C-Raf, wherein the patient has previously (e.g. within 24 hours) been treated with another therapeutic agent. The invention also provides the use of another therapeutic agent for treating a disease or condition mediated by B-Raf or C-Raf, wherein the patient has previously (e.g. within 24 hours) been treated with a compound of formula I or II.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the following Reaction Scheme I:

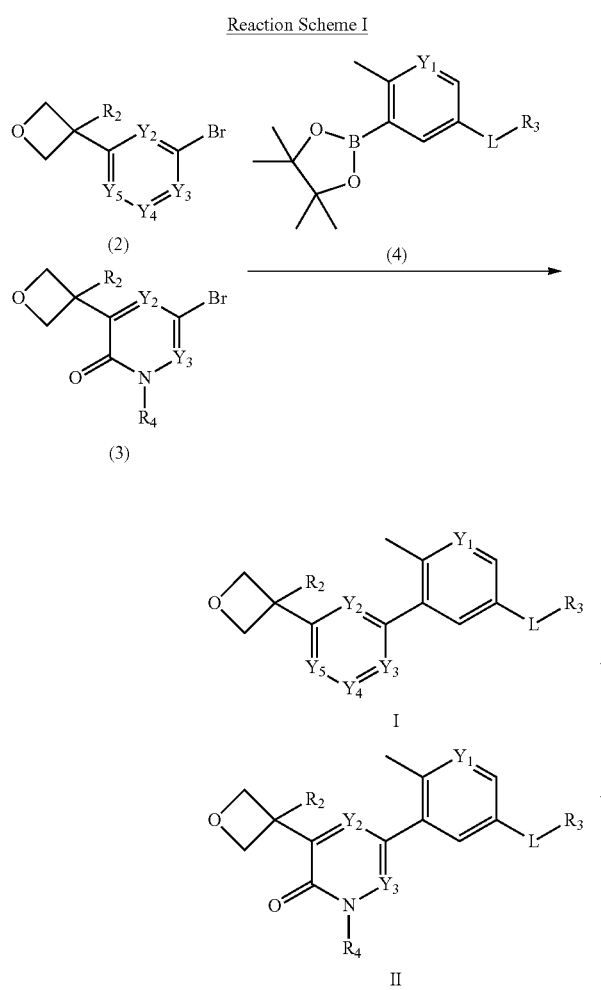

in which L, $R_2$, $R_3$, $R_4$, $Y_1$, $Y_2$, $Y_3$, $Y_4$ and $Y_5$ are as described in the Summary of the Invention. A compound of formula I or Ii can be prepared by reacting a compound of formula 2 or 3 with a compound of formula 4, respectively. The reaction takes place in the presence of a suitable catalyst (for example added PdCl$_2$(dppf)-DCM adduct, and the like) and a suitable solvent (for example DME, and the like). The reaction proceeds at a temperature of about 25° C. to about 150° C. and can take up to about 4 hours to complete.

Compounds of Formula I can be prepared by proceeding as in the following Reaction Scheme II:

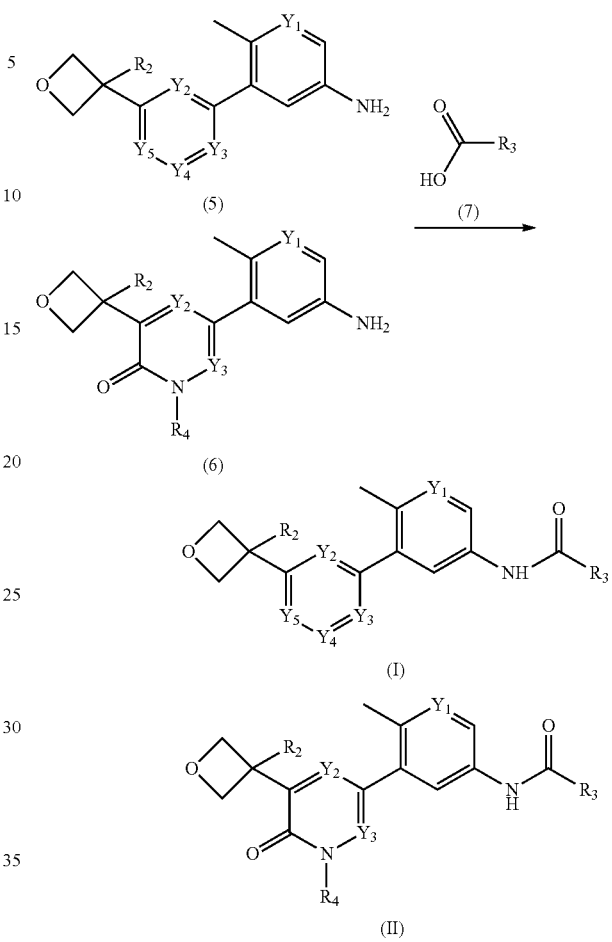

in which L, $R_2$, $R_3$, $R_4$, $Y_1$, $Y_2$, $Y_3$, $Y_4$ and $Y_5$ are as described in the Summary of the Invention. A compound of formula I or II can be prepared by reacting a compound of formula 5 and 6 with a compound of formula 7 in the presence of a suitable base (for example, 2-(3H-[1,2,3] triazolo[4,5-b]pyridin-3-yl)-1,1,3,3-tetramethylisouronium hexafluorophosphate(V), and the like) and suitable solvent (for example, DMF, and the like). The reaction proceeds at about room temperature and can take up to about 8 hours to complete.

Detailed descriptions of the synthesis of specific examples are described, below.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction schemes I and II; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer, for example stereoisomer, of a compound of the invention from a mixture of isomers;
(g) optionally converting a non-derivatized compound of the invention into a pharmaceutically acceptable prodrug derivative; and
(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following intermediates and examples that illustrate the preparation of compounds of Formula I according to the invention.

The following abbreviations may be used herein:

| | |
|---|---|
| DAST | (diethylamino)sulfurtrifluoride |
| DCM | Dichloromethane |
| DIAD | diisopropylazodicarboxylate |
| DIEA | diisopropylethylamine |
| DMA | Dimethylacetamide |
| DMAP | 4-dimethylaminopyridine |
| DME | 1,2-dimethoxyethane |
| DMF | N,N-dimethylformamide |
| DPPF | 1,1'-bis(diphenylphosphino)ferrocene |
| EDC | 1-(3-Dimethylaminopropyl)-3-ethylcarbodiimide hydrochloride |
| EtOAc | ethyl acetate |
| EtOH | Ethanol |
| HOAT | Hydroxyazabenzotriazole |
| HOBt | Hydroxybenzotriazole |
| $K_2CO_3$ | Potassium carbonate |
| MeCN | Acetonitrile |
| $MgSO_4$ | Magnesium sulfate |
| MeOH | Methanol |
| $Na_2CO_3$ | sodium carbonate |
| NaCl | Sodium chloride |
| $NaHCO_3$ | sodium bicarbonate |
| NBS | N-bromosuccinimide |
| NMP | N-methyl-2-pyrrolidone |
| $Pd_2(dba)_3$ | Tris(dibenzylideneacetone)dipalladium(0) |
| $Pd(PPh_3)_4$ | Tetrakis(triphenylphospine)palladium(0) |
| $Pd(dppf)Cl_2$-DCM | Dichloro-(1,2-bis(diphenylphosphino)ethan)-Palladium(II)-dichloromothethane adduct |
| RT or rt | room temperature |
| TBDMSCl | tert-butyldimethylsilylchloride |
| TEA | Triethylamine |
| THF | tetrahydrofuran |

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

Mass spectrometric analysis was performed on LCMS instruments: Waters System (Acuity UPLC and a Micromass ZQ mass spectrometer; Column: Acuity HSS C18 1.8-micron, 2.1×50 mm; gradient: 5-95% acetonitrile in water with 0.05% TFA over a 1.8 min period; flow rate 1.2 mL/min; molecular weight range 200-1500; cone Voltage 20 V; column temperature 50° C.). All masses were reported as those of the protonated parent ions.

Nuclear magnetic resonance (NMR) analysis was performed on some of the compounds with a Varian 400 MHz NMR (Palo Alto, Calif.). The spectral reference was either TMS or the known chemical shift of the solvent.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art in view of the following examples.

Intermediates

Synthesis of 3-(3-bromo-5-methoxyphenyl)oxetane

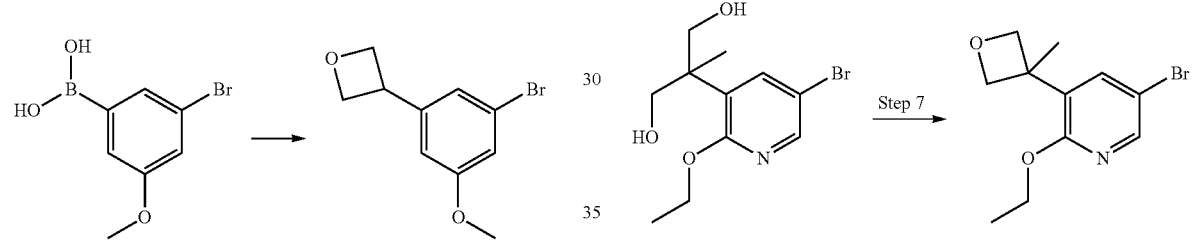

To a solution of (3-bromo-5-methoxyphenyl)boronic acid (2.0 equiv.), 3-iodooxetane (1.0 equiv.), nickel(II) iodide (0.12 equiv.) and (1R,2R)-2-aminocyclohexanol (0.12 equiv.) in 2-propanol (0.38 M) was added NaHMDS (1 M solution, 2.0 equiv.) and the mixture was heated to 80° C. in the microwave for 30 min. The solution was filtered through Celite and washed with ethyl acetate. The filtrate was concentrated to dryness and purified via reverse phase prep-HPLC. The pure fractions were lyophilized to give 3-(3-bromo-5-methoxyphenyl)oxetane in 27% yield. LCMS (m/z) (M+H)=242.9/244.9, Rt=0.78 min.

Synthesis of 3-(6-ethoxy-5-(3-methyloxetan-3-yl) pyridin-3-yl)-4-methylaniline

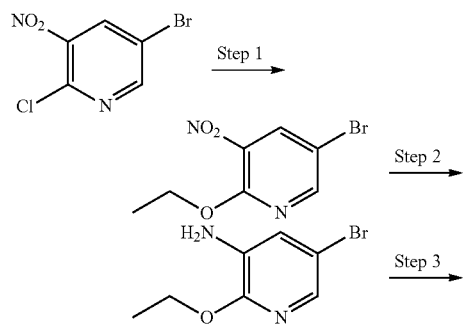

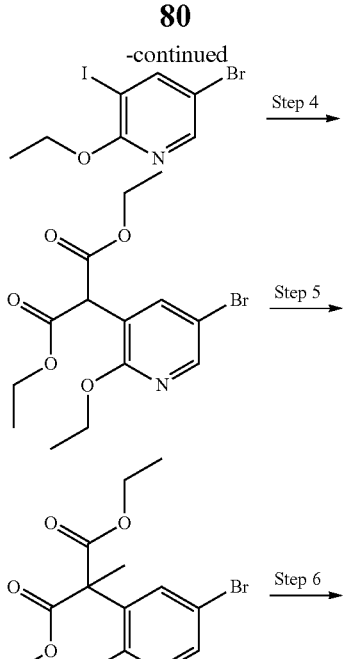

Step 1

Sodium ethoxide (21 wt % in EtOH) (1.2 equiv.) was added to a solution of 5-bromo-2-chloro-3-nitropyridine (1.0 equiv.) in EtOH (0.23 M) at 25° C. and the mixture was heated to 75° C. for 1 h. LCMS shows complete conversion of starting material to product (M+1=247/249, $R_f$=0.95). The reaction was poured onto 1 M citric acid and water, and the ethanol was removed on the roto-vap. The residue was extracted with EtOAc (3×). The combined organics were washed with brine, dried (MgSO$_4$) and concentrated to give 5-bromo-2-ethoxy-3-nitropyridine in quantitative yield as a brown oil which was used without further purification.

Step 2

To a stirred solution of 5-bromo-2-ethoxy-3-nitropyridine (1.0 equiv.) in MeOH and DCM (10:1, 0.27 M) at 25° C. were added zinc (5.5 equiv.) and ammonium chloride (5.0 equiv.) and the mixture was heated to 75° C. and stirred for 4 h. LCMS shows complete consumption of starting material and fairly clean conversion to a desired product (M+1=217/219, $R_f$=0.75). The reaction was cooled to room temp and filtered through a short plug of Celite, washing with DCM, and then concentrated to remove MeOH. The residue was taken up in EtOAc, washed with water and brine and then dried (MgSO$_4$) and concentrated. The residue was quickly passed through a silica column, eluting with 0-50% EtOAc:heptane. Product elutes around 20% EtOAc and was concentrated to give 5-bromo-2-ethoxypyridin-3-amine in 79% yield as a light brown solid. LCMS (m/z) (M+H)=217/219, Rt=0.75 min.

Step 3

To a stirred solution of 5-bromo-2-ethoxypyridin-3-amine (1.0 equiv.) in conc. HCl and Water (1:1.35, 0.07 M) at 0° C. was slowly added NaNO₂ (1.1 equiv.) and the mixture was stirred for 30 min. A solution of KI (3.0 equiv.) in Water (0.07 M) was slowly added to the mixture, which was then allowed to warm to 25° C. and stirred for 30 min. The mixture was poured into a separatory funnel and extracted with EtOAc (3×). LCMS of the organic extracts shows mostly desired product (M+1=327/329, R$_t$=1.11) with a small amount of unreacted starting material. The combined organics were washed with sat. aq. Na₂SO₃ and sat. aq. Na₂CO₃ and then dried (MgSO₄) and concentrated. The residue was purified via Grace flash column chromatography (0-15% EtOAc:heptane). Product co-elutes with the unreacted starting material and was concentrated to give 5-bromo-2-ethoxy-3-iodopyridine in 95% yield as a dark orange oil. LCMS (m/z) (M+H)=327/329, Rt=1.11 min.

Step 4

A mixture of 5-bromo-2-ethoxy-3-iodopyridine (1.0 equiv.), and Cs₂CO₁ (3.0 equiv.) in Dioxane (0.22 M) was degassed with Ar; CuI (0.1 equiv.) and picolinic acid (0.2 equiv.) were added, and the vial was sealed mixture was degassed again. Diethyl malonate (2.0 equiv.) was then added and the mixture was heated at 70° C. overnight. LCMS shows complete consumption of starting material and clean conversion to desired product (M+1=360/362, R$_t$=1.04). The reaction mixture was poured onto sat. aq. NH₄Cl, and extracted with EtOAc (3×). The combined organics were washed with brine, dried (MgSO₄) and concentrated. The residue was purified via ISCO flash column chromatography (0-15% EtOAc:heptane). Product fractions elute around 10% EtOAc and were concentrated to a yellow oil which contained some excess diethyl malonate. Diethyl 2-(5-bromo-2-ethoxypyridin-3-yl)malonate was obtained as an orange oil in 79% yield. LCMS (m/z) (M+H)=360/362, Rt=1.04 min.

Step 5

To a stirred solution of diethyl 2-(5-bromo-2-ethoxypyridin-3-yl)malonate (1.0 equiv.) in DMF (0.15 M) at 0° C. was added NaH (1.5 equiv.) and the mixture was stirred for 10 min. MeI (3.0 equiv.) as then added, and the reaction was allowed to warm to 25° C. and stirred overnight. LCMS shows near complete consumption of starting material and fairly clean conversion to product (M+1=374/376, R$_t$=1.07). The mixture was poured onto water and extracted with EtOAc (3×). The combined organics were washed with water, brine, dried (MgSO₄) and concentrated. The residue was purified via ISCO flash column chromatography (0-20% EtOAc:heptane) and the pure fractions were concentrated to give diethyl 2-(5-bromo-2-ethoxypyridin-3-yl)-2-methylmalonate in 83% yield as an orange oil. LCMS (m/z) (M+H)=374/376, Rt=1.07 min.

Step 6

To a stirred solution of diethyl 2-(5-bromo-2-ethoxypyridin-3-yl)-2-methylmalonate (1.0 equiv.) in DCM (0.13 M) at −78° C. was added DIBAL-H (1.0 M solution in PhMe) (6.0 equiv.) and the mixture was allowed to warm to 0° C. and stirred for 2.5 h. LCMS shows complete consumption starting material with fairly clean conversion to product (M+1=290/292, R$_t$=0.65). The reaction was diluted with EtOAc and quenched with sat. aq. Rochelles salt. The mixture was stirred vigorously overnight, and then extracted with EtOAc (3×). The combined organics were washed with brine, dried and concentrated. The residue was loaded onto Celite (insoluble in DCM/heptane) and purified by ISCO flash column chromatography (0-100% EtOAc:heptane). Pure fractions were concentrated to give 2-(5-bromo-2-ethoxypyridin-3-yl)-2-methylpropane-1,3-diol in 79% yield as a white solid. LCMS (m/z) (M+H)=290/292, Rt=0.65 min.

Step 7

A microwave vial was charged with 2-(5-bromo-2-ethoxypyridin-3-yl)-2-methylpropane-1,3-diol (1.0 equiv.) and PPh₃ (2.0 equiv.) and then sealed and purged with Ar. A solution of DIAD (2.0 equiv.) in Toluene (0.1 M) was then added and the mixture was irradiated at 140° C. for 45 min. LCMS shows near complete conversion to product. The mixture was concentrated and purified via ISCO flash column chromatography (0-25% ethyl acetate/heptanes). The pure fractions were concentrated to give 5-bromo-2-ethoxy-3-(3-methyloxetan-3-yl)pyridine as a colorless oil in 52% yield. LCMS (m/z) (M+H)=272.1/274.1, Rt=0.92 min.

Synthesis of 6-chloro-8-(3-methyloxetan-3-yl)imidazo[1,2-b]pyridazine

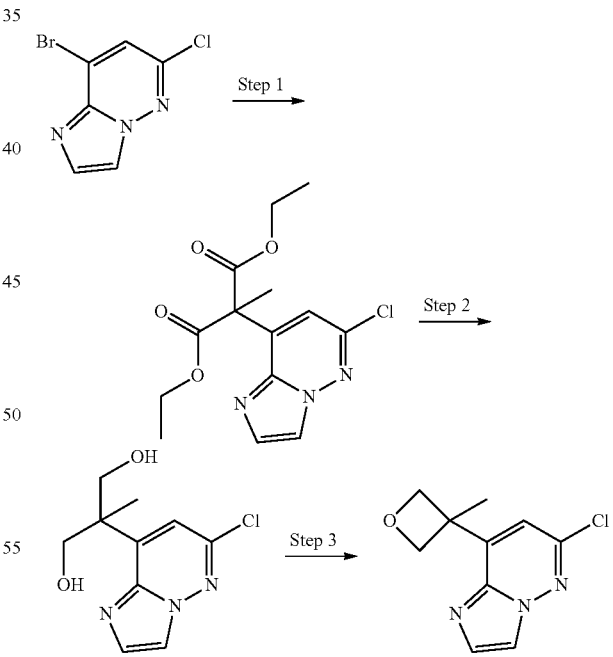

Step 1

To a solution of 8-bromo-6-chloroimidazo[1,2-b]pyridazine (1.0 equiv.) and diethyl 2-methylmalonate (1.0 equiv.) in DMF (0.15 M) was added sodium hydride (2.5 equiv.) at rt. The reaction was stirred for 10 min, then quenched with saturated ammonium chloride and extracted twice with ethyl acetate. The organic phase was dried with magnesium sulfate, filtered and concentrated. The residue was purified via reverse phase prep-HPLC to give diethyl 2-(6-chloroimidazo[1,2-b]pyridazin-8-yl)-2-methylmalonate in 21% yield. LCMS (m/z) (M+H)=326.0, Rt=0.84 min.

Step 2

To a solution of diethyl 2-(6-chloroimidazo[1,2-b]pyridazin-8-yl)-2-methylmalonate (1.0 equiv.) in DCM (0.1 M) at −78° C. was added DIBAL-H (6.0 equiv.) and the solution was slowly warmed to rt. The reaction was quenched by the addition of methanol, Rochelle's salt was added and stirred overnight. The layers were separated, the aqueous phase was extracted one more time with DCM and the organic phases were washed with brine, dried over magnesium sulfate, filtered and concentrated. The residue was purified via reverse phase prep-HPLC to give 2-(6-chloroimidazo[1,2-b]pyridazin-8-yl)-2-methylpropane-1,3-diol as a pale yellow solid. LCMS (m/z) (M+H)=241.9, Rt=0.34 min.

Step 3

To a solution of 2-(6-chloroimidazo[1,2-b]pyridazin-8-yl)-2-methylpropane-1,3-diol in toluene (0.06 M) was added triphenylphosphine (1.1 equiv.), (E)-diisopropyl diazene-1,2-dicarboxylate (1.1 equiv.), and N-ethyl-N-isopropylpropan-2-amine (2.0 equiv.) and the solution was heated to 140° C. for 30 min. The reaction was concentrated under vacuo and purified via reverse phase prep-HPLC to give 6-chloro-8-(3-methyloxetan-3-yl)imidazo[1,2-b]pyridazine as a white solid product in 33% yield. LCMS (m/z) (M+H)=224.0, Rt=0.52 min.

Synthesis of
3-(5-bromo-2-methoxypyridin-3-yl)oxetan-3-ol

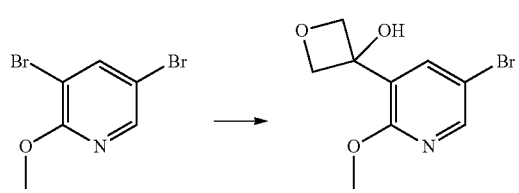

To a solution of 3,5-dibromo-2-methoxypyridine (1.0 equiv.) in a flame-dried flask equipped with a low temperature internal thermometer under argon was added diethyl ether (0.1 M). The solution was cooled to −78° C. and n-butyllithium (1.6 M in hexanes, 1.1 equiv.) was added via syringe while maintaining the internal temperature at −70° C. After stirring for 40 min, the reaction was allowed to slowly warm to rt and stirred for 3 hours. At this point, the reaction was quenched by the addition of sat. sodium bicarbonate and diluted with DCM. The organic phase was washed with brine, dried over magnesium sulfate, filtered and concentrated. The crude residue was purified via silica gel chromatography (ISCO, 0-100% ethyl acetate/heptanes) to give 3-(5-bromo-2-methoxypyridin-3-yl)oxetan-3-ol as an oil in 71% yield. LCMS (m/z) (M+H)=259.9/261.9, Rt 0.54 min.

Synthesis of
5-bromo-3-(3-fluorooxetan-3-yl)-2-methoxypyridine

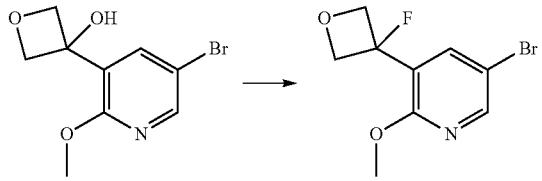

To a solution of 3-(5-bromo-2-methoxypyridin-3-yl)oxetan-3-ol in DCM (0.1 M) at −78° C. under an atmosphere of argon was added DAST (1.5 equiv.). The solution was stirred for 10 min at −78° C., then allowed to warm to rt. Upon warming to rt, the reaction was quenched by the addition of sat. sodium bicarbonate and the solution was diluted with ethyl acetate. The layers were mixed, separated and the organic phase was washed with brine, dried over magnesium sulfate, filtered and concentrated. The residue was purified via silica gel chromatography eluting with 0-50% ethyl acetate/heptanes to give 5-bromo-3-(3-fluorooxetan-3-yl)-2-methoxypyridine in 25% yield. LCMS (m/z) (M+H)=261.9/263.8, Rt=0.77 min.

Synthesis of 5-bromo-2-ethoxy-3-(3-(fluoromethyl)oxetan-3-yl)pyridine

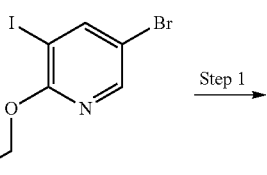

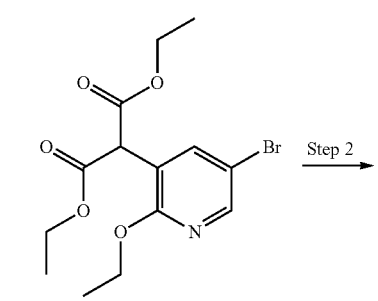

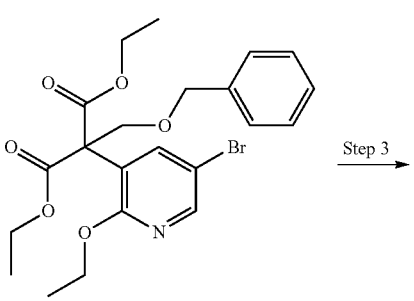

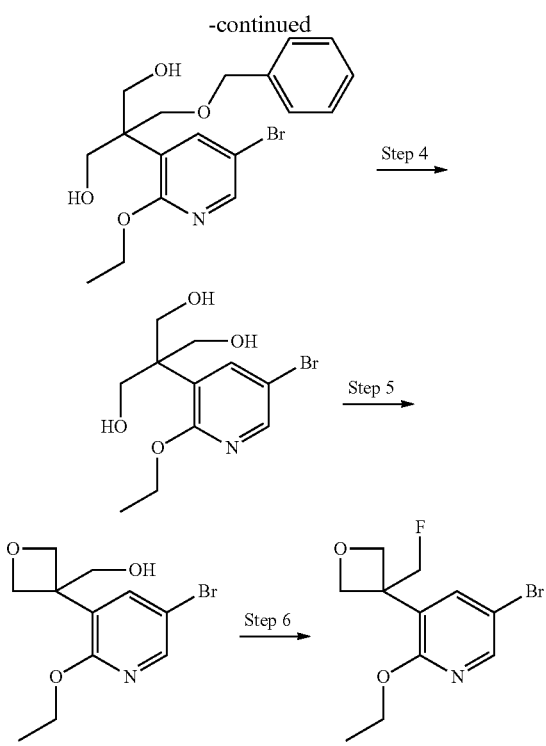

Step 1

A mixture of 5-bromo-2-ethoxy-3-iodopyridine (1.0 equiv.), and $Cs_2CO_3$ (3.0 equiv.) in Dioxane (0.15 M) was degassed with Ar; CuI (0.1 equiv.) and picolinic acid (0.2 equiv.) were added, and the mixture was degassed again. Diethyl malonate (2.0 equiv.) was then added and the mixture was heated at 70° C. overnight. LCMS shows about 80% complete consumption of starting material and clean conversion to desired product (M+1=360/362, $R_t$=1.04). More picolinic acid (0.2 equiv.), CuI (0.1 equiv.), and diethyl malonate (2.0 equiv.) were added, and the reaction was continued for another 5 h. The reaction mixture was poured onto sat. aq. $NH_4Cl$, and extracted with EtOAc (3×). The combined organics were washed with brine, dried ($MgSO_4$) and concentrated. Purification via ISCO flash column chromatography (0-20% EtOAc:heptane) afforded diethyl 2-(5-bromo-2-ethoxypyridin-3-yl)malonate as a colorless oil in 77% yield. LCMS (m/z) (M+H)=359.1/361.9, Rt=1.05 min.

Step 2

A solution of diethyl 2-(5-bromo-2-ethoxypyridin-3-yl)malonate (1.0 equiv.) in DMF (0.16 M) was degassed with Ar, and then cooled to 0° C. NaH (1.5 equiv.) was added and the mixture was allowed to warm to 25° C. over 30 min. Benzyl chloromethyl ether (1.5 equiv.) was then added, and the reaction was stirred over the weekend LCMS shows complete consumption of starting material and fairly clean conversion to desired product (M+1=480/482, $R_t$=1.27). The mixture was poured onto water and extracted three times with ethyl acetate. The combined organics were washed with water, brine, dried over magnesium sulfate, filtered, and concentrated. The crude residue was purified via Grace flash column chromatography over silica gel eluting with heptane and 0-20% EtOAc gradient. Product eluted around 10% EtOAc and was concentrated to diethyl 2-((benzyloxy)methyl)-2-(5-bromo-2-ethoxypyridin-3-yl)malonate in 84% yield as a colorless oil. LCMS (m/z) (M+H)=480.0/482.0, Rt=1.26 min.

Step 3

To a stirred solution of diethyl 2-((benzyloxy)methyl)-2-(5-bromo-2-ethoxypyridin-3-yl)malonate (1.0 equiv.) in DCM (0.1 M) at −78° C. was added DIBAL-H (1.0 M solution in PhMe) (6.0 equiv.) and the mixture was allowed to warm to 0° C. and stirred for 2.5 h. LCMS shows complete consumption starting material with conversion to product (M+1=396/398, $R_t$=0.92). Two more eq of DIBAL-H was added, and the reaction was allowed to warm to room temperature and stirred for another 1.5 h. The reaction was diluted with ethyl acetate and quenched with saturated aqueous Rochelle's salt. The mixture was stirred vigorously overnight, and then extracted three times with ethyl acetate. The combined organics were washed with brine, dried over magnesium sulfate, filtered, and concentrated. The residue was purified via silica gel Grace flash column chromatography, eluting with heptane and 0-75% ethyl acetate gradient. Product fractions elute around 40% EtOAc and were concentrated to give 2-((benzyloxy)methyl)-2-(5-bromo-2-ethoxypyridin-3-yl)propane-1,3-diol in 86% yield as a colorless oil. LCMS (m/z) (M+H)=396.2/398.2, Rt=0.92 min.

Step 4

To a solution of 2-((benzyloxy)methyl)-2-(5-bromo-2-ethoxypyridin-3-yl)propane-1,3-diol (1.0 equiv.) in DCM (0.05 M) at −78° C. was added $BCl_3$ (1 M in DCM) (3.0 equiv.) and the mixture was allowed to warm to 0° C. and stirred for 2 h. LCMS complete consumption of starting material and clean conversion to desired product (M+1=306/308, $R_t$=0.51). The mixture was quenched with MeOH and concentrated directly onto Celite, which was then purified by ISCO flash column chromatography, eluting with DCM and 0-15% MeOH gradient. Product fractions eluted around 5% MeOH and were concentrated to give 2-(5-bromo-2-ethoxypyridin-3-yl)-2-(hydroxymethyl)propane-1,3-diol as a pale yellow oil in quantitative yield. LCMS (m/z) (M+H)=305.8/307.8, Rt=0.51 min.

Step 5

2-(5-bromo-2-ethoxypyridin-3-yl)-2-(hydroxymethyl)propane-1,3-diol (1.0 equiv.) and $PPh_3$ (1.2 equiv.) were added to a microwave vial and purged with argon. A solution of DIAD in toluene (1.2 equiv.) was then added and the mixture was heated thermally at 60° C. overnight. The mixture was concentrated and purified via silica gel chromatography (Grace, 0-100% ethyl acetate/heptanes). The pure fractions were concentrated to give (3-(5-bromo-2-ethoxypyridin-3-yl)oxetan-3-yl)methanol in 38% yield as a colorless oil. LCMS (m/z) (M+H)=288.0/290.0. Rt=0.68 min.

Step 6

To a stirred solution of (3-(5-bromo-2-ethoxypyridin-3-yl)oxetan-3-yl)methanol (1.0 equiv.) in THF (0.04 M) at rt was added $Et_3N$ (12 equiv.), perfluorobutanesulfonyl fluoride (4.0 equiv.), and triethylamine trihydrofluoride (4.0 equiv.) and the mixture was heated to 55° C. and stirred for 2 hours. At this time, more Et₃N (12 equiv.), perfluorobutanesulfonyl fluoride (4.0 equiv.), and triethylamine trihydrofluoride (4.0 equiv.) were added and the reaction was stirred overnight at 55° C. Upon overnight stirring, the reaction was poured onto saturated aqueous sodium bicarbonate and extracted three times with ethyl acetate. The combined organics were washed with brine, dried over magnesium sulfate, filtered and concentrated. The crude residue was absorbed onto Celite and purified via silica gel chromatography (ISCO, eluting with 0-50% ethyl acetate/heptanes). The pure fractions were concentrated to give 5-bromo-2-ethoxy-3-(3-(fluoromethyl)oxetan-3-yl)pyridine in 47% yield. LCMS (m/z) (M+H)=290.0/292.0, Rt=0.89 min.

Synthesis of 5-bromo-3-(3-(fluoromethyl)oxetan-3-yl)-2-methoxypyridine

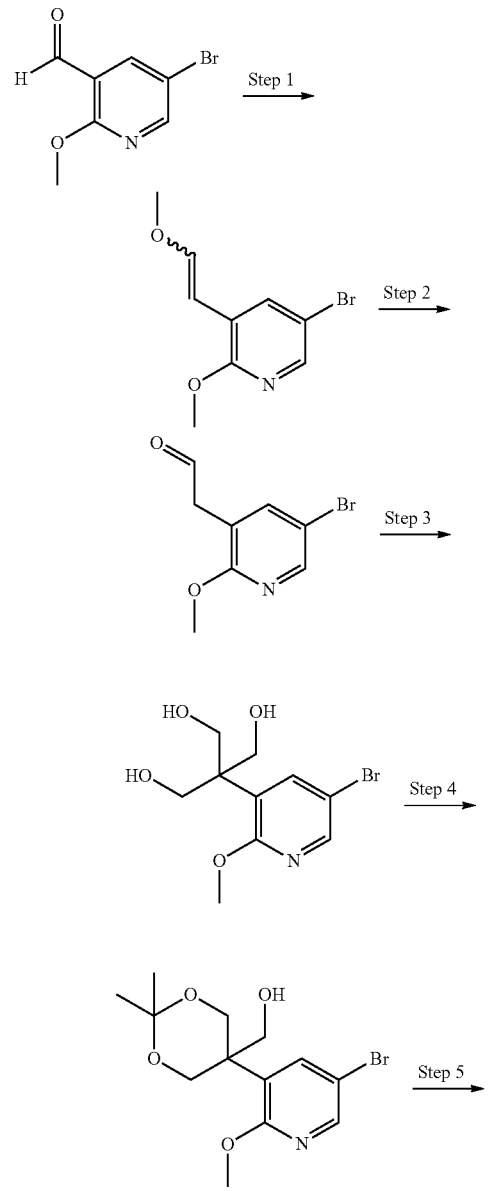

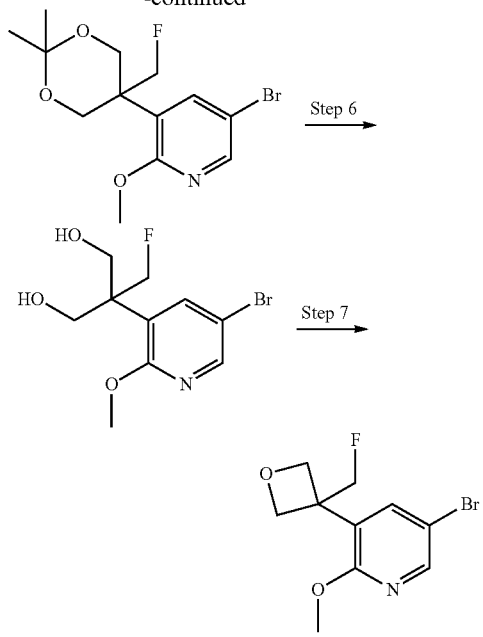

Step 1

To a solution of (methoxymethyl)triphenylphosphonium chloride (1.5 equiv.) in THF (0.3 M) at 0° C. was added NaHMDS (1M in THF, 1.55 equiv.) and the red solution was stirred in the cold bath for 30 min at which point 5-bromo-2-methoxynicotinaldehyde (1.0 equiv.) was added. After stirring in the cold bath for 30 min, the solution was allowed to warm to rt, stirred for 2 hours, then partitioned between ethyl acetate and sat. sodium bicarbonate. The layers were mixed, separated, the organic phase was washed with brine, dried over magnesium sulfate, filtered and concentrated. The residue was purified via silica gel chromatography (0-30% ethyl acetate/n-heptanes) to yield 5-bromo-2-methoxy-3-(2-methoxyvinyl)pyridine contaminated with the starting aldehyde. This mixture was dissolved in methanol and 0.5 equiv. of sodium borohydride were added. After stirring at rt for 10 min, the volatiles were removed in vacuo and the residue was partitioned between ethyl acetate and brine. The organic phase was dried over magnesium sulfate, filtered and concentrated. Purification via silica gel chromatography (ISCO, 0-15% ethyl acetate/n-heptanes) afforded 5-bromo-2-methoxy-3-(2-methoxyvinyl)pyridine in 11% yield as a mixture of enol ethers isomers. LCMS (m/z) (M+H)=244.0/246.0, Rt=0.97 and 1.01 min.

Step 2

To a solution of 5-bromo-2-methoxy-3-(2-methoxyvinyl)pyridine (1.0 equiv.) in acetonitrile (0.35 M) was added 6N HCl (17 equiv.). The solution was stirred at rt overnight. The reaction was neutralized by the addition of solid sodium bicarbonate, then diluted with ethyl acetate and water. The organic phase was washed with brine, dried over magnesium sulfate, filtered and concentrated. The residue was purified via silica gel chromatography (ISCO, 0-40% ethyl acetate/n-heptanes) to give 2-(5-bromo-2-methoxypyridin-3-yl)acetaldehyde as a light colored off-white solid. LCMS (m/z) (M+H)=229.8/231.8, Rt=0.69 min.

Step 3

To a solution of 2-(5-bromo-2-methoxypyridin-3-yl)acetaldehyde (1.0 equiv.) in THF (0.3 M) was added paraformaldehyde (9 equiv.) and calcium hydroxide (10 equiv.) in a glass high pressure vessel. The container was heated to 75° C. behind a safety shield overnight. Upon cooling to rt, the reaction was diluted with DCM and filtered through a pad of Celite, rinsing with DCM and 20% MeOH/DCM. Upon concentration of the volatiles, the residue was purified via silica gel chromatography (ISCO, 0-10% MeOH/DCM) to give 2-(5-bromo-2-methoxypyridin-3-yl)-2-(hydroxymethyl)propane-1,3-diol as white solid in 50% yield. LCMS (m/z) (M+H)=291.9/293.9, Rt=0.42 min.

Step 4

To a solution of 2-(5-bromo-2-methoxypyridin-3-yl)-2-(hydroxymethyl)propane-1,3-diol (1.0 equiv.) in acetone (1M) was added dimethoxypropane (1.5 equiv.) and pTsOH—H$_2$O (0.05 equiv.) and the homogeneous solution was stirred at rt overnight. Diluted with ethyl acetate and water, the organic phase was washed with brine, dried over magnesium sulfate, filtered and concentrated. The residue was purified via silica gel chromatography (ISCO, 0-100% ethyl acetate/n-heptanes) to give (5-(5-bromo-2-methoxypyridin-3-yl)-2,2-dimethyl-1,3-dioxan-5-yl)methanol in 75% yield. LCMS (m/z) (M+H)=331.9/333.9, Rt=0.77 min.

Step 5

To a solution of (5-(5-bromo-2-methoxypyridin-3-yl)-2,2-dimethyl-1,3-dioxan-5-yl)methanol (1.0 equiv.) in THF (0.15 M) was added triethyl amine (12 equiv.), perfluorobutanesulfonyl fluoride (4.0 equiv.) and triethylamine trihydrofluoride (4.0 equiv.). The solution was heated to 55° C. for 2 hours, then cooled to rt, partitioned between ethyl acetate and water, the organic phase was washed with brine, dried over magnesium sulfate, filtered and concentrated. The residue was purified via silica gel chromatography (ISCO, 0-50% ethyl acetate/n-heptanes) to give 5-bromo-3-(5-(fluoromethyl)-2,2-dimethyl-1,3-dioxan-5-yl)-2-methoxypyridine in 75% yield. LCMS (m/z) (M+H)=333.9/335.9, Rt=1.03 min.

Step 6

To a solution of 5-bromo-3-(5-(fluoromethyl)-2,2-dimethyl-1,3-dioxan-5-yl)-2-methoxypyridine (1.0 equiv.) in methanol (0.1 M) was added pTsOH (0.2 equiv.) and the solution was stirred at rt for 2 hours. The reaction was quenched by the addition of sat. sodium carbonate, the volatiles were removed under vacuo and the residue was partitioned between ethyl acetate and water. The organic phase was washed with sat. sodium carbonate, brine, dried over magnesium sulfate, filtered and concentrated. The residue was purified via silica gel chromatography (ISCO, 0-100% ethyl acetate/n-heptanes) to give 2-(5-bromo-2-methoxypyridin-3-yl)-2-(fluoromethyl)propane-1,3-diol in 76% yield. LCMS (m/z) (M+H)=293.8/395.8. Rt=0.57 min.

Step 7

To a solution of 2-(5-bromo-2-methoxypyridin-3-yl)-2-(fluoromethyl)propane-1,3-diol (1.0 equiv.) in toluene (0.14 M) was added triphenylphosphine (1.2 equiv.) and DIAD (1.2 equiv.). The flask was heated to 60° C. overnight, then the volatiles were removed in vacuo and the residue was purified via silica gel chromatography (ISCO, 0-40% ethyl acetate/n-heptanes) to give 5-bromo-3-(3-(fluoromethyl)oxetan-3-yl)-2-methoxypyridine in 60% yield. LCMS (m/z) (M+H)=276.1/278.1, Rt=0.78 min.

Synthesis of 5-bromo-3-(3-(difluoromethyl)oxetan-3-yl)-2-methoxypyridine

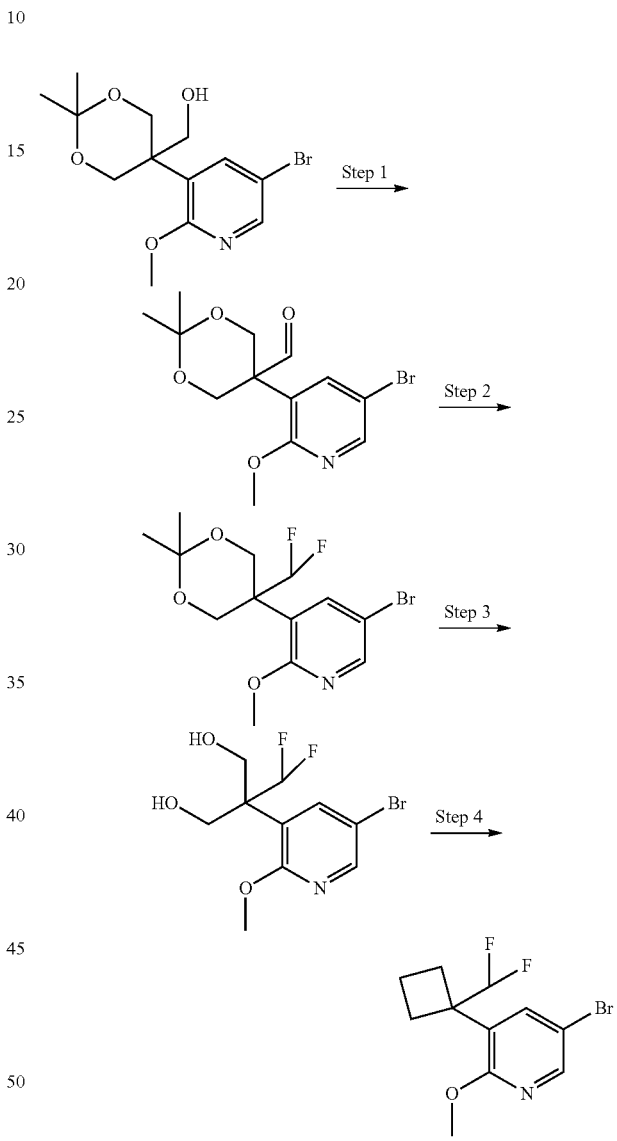

Step 1

To a solution of (5-(5-bromo-2-methoxypyridin-3-yl)-2,2-dimethyl-1,3-dioxan-5-yl)methanol (1.0 equiv.) in DCM (0.08 M) at 0° C. was added Dess-Martin periodinane (1.2 equiv.) and the solution was stirred at 0° C. for 2 hours and allowed to warm to rt. Partitioned between ethyl acetate and 1:1 10% Na$_2$S$_2$O$_3$/NaHCO$_{3(sat.)}$, the organic phase was washed with 1:1 10% Na$_2$S$_2$O$_3$/NaHCO$_{3(sat.)}$, with NaCl$_{(sat.)}$ dried over MgSO$_4$, filtered, concentrated and purified by ISCO SiO$_2$ chromatography eluting with 0-50% ethyl acetate/n-heptanes to give 5-(5-bromo-2-methoxypyridin-3-yl)-2,2-dimethyl-1,3-dioxane-5-carbaldehyde in 82% yield. LCMS (m/z) (M+H)=330.1/332.1, Rt=0.88 min.

Step 2

To a solution of 5-(5-bromo-2-methoxypyridin-3-yl)-2,2-dimethyl-1,3-dioxane-5-carbaldehyde (1.0 equiv.) in DCM (0.12 M) at 0° C. was added DAST (2.0 equiv.) and the reaction was allowed to warm to rt and stirred overnight. The reaction was partitioned between ethyl acetate and sat. sodium bicarbonate, the organic phase was washed with brine, dried over magnesium sulfate, filtered and concentrated. The residue was purified via silica gel chromatography (ISCO, 0-40% ethyl acetate/n-heptanes) to give 5-bromo-3-(5-(difluoromethyl)-2,2-dimethyl-1,3-dioxan-5-yl)-2-methoxypyridine in 18% yield. LCMS (m/z) (M+H)=352.1/354.1, Rt=1.03 min.

Step 3

To a solution of 5-bromo-3-(5-(difluoromethyl)-2,2-dimethyl-1,3-dioxan-5-yl)-2-methoxypyridine (1.0 equiv.) in methanol (0.05 M) was added p-TsOH (0.2 equiv.). The solution was stirred at rt overnight, the volatiles were removed under vacuo, the residue was partitioned between ethyl acetate and sat. sodium carbonate, the organic phase was washed with brine, dried over magnesium sulfate, filtered and concentrated to give 2-(5-bromo-2-methoxypyridin-3-yl)-2-(difluoromethyl)propane-1,3-diol in 93% yield. LCMS (m/z) (M+H)=311.8/313.8, Rt=0.61 min.

Step 4

To a solution of 2-(5-bromo-2-methoxypyridin-3-yl)-2-(difluoromethyl)propane-1,3-diol (1.0 equiv.) in toluene (0.05 M) was added triphenylphosphine (1.2 equiv.) and DIAD (1.2 equiv.) and the solution was heated to 60° C. overnight. Upon cooling to it, the solution was purified via silica gel chromatography (ISCO, 0-40% ethyl acetate/n-heptanes) to give 5-bromo-3-(3-(difluoromethyl)oxetan-3-yl)-2-methoxypyridine in 36% yield. LCMS (m/z) (M+H)=293.8/295.8, Rt=0.61 min.

Synthesis of (3-(5-bromo-2-methoxypyridin-3-yl)oxetan-3-yl)methanol

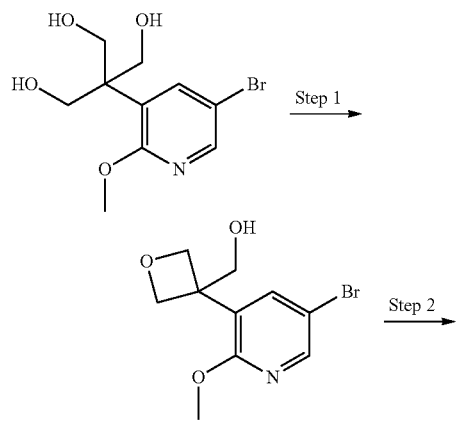

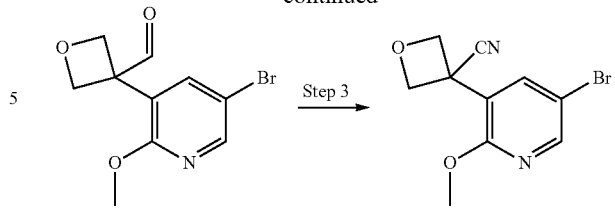

Step 1

A solution of 2-(5-bromo-2-methoxypyridin-3-yl)-2-(hydroxymethyl)propane-1,3-diol (1.0 equiv.), triphenylphosphine (1.6 equiv.) and DIAD (1.6 equiv.) in toluene (0.06 M) was heated to 55 C overnight. Upon overnight stirring, heat was increased to 65° C. and heated for another 24 hours. Upon cooling to rt the volatiles were removed in vacuo and the residue was purified via silica gel chromatography (0-100% ethyl acetate/n-heptanes) to give (3-(5-bromo-2-methoxypyridin-3-yl)oxetan-3-yl)methanol in 48% yield. LCMS (m/z) (M+H)=273.8/275.8, Rt=0.46 min.

Step 2

To a solution of (3-(5-bromo-2-methoxypyridin-3-yl)oxetan-3-yl)methanol in DCM (0.1 M) at 0° C. was added Dess-Martin periodinane and the solution was allowed to warm to rt and stirred for 5 hours. The solution was then partitioned between ethyl acetate and 1:1 10% $Na_2S_2O_3$/$NaHCO_{3(sat.)}$, mixed, separated, washed with 1:1 10% $Na_2S_2O_3$/$NaHCO_{3(sat.)}$, with $NaCl_{(sat.)}$, dried over $MgSO_4$, filtered, concentrated and purified by ISCO $SiO_2$ chromatography (0-100% EtOAc/n-heptanes) to yield 3-(5-bromo-2-methoxypyridin-3-yl)oxetane-3-carbaldehyde as a white solid. LCMS (m/z) (M+H)=271.8/273.8, Rt=0.60 min.

Step 3

To a solution of 3-(5-bromo-2-methoxypyridin-3-yl)oxetane-3-carbaldehyde (1.0 equiv.) and hydroxylamine hydrochloride (1.5 equiv.) was added ethanol (0.07 M) and pyridine (10 equiv.). The reaction was stirred at rt for 2 hours, then the volatiles were removed in vacuo and the residue was partitioned between water and ethyl acetate. The organic phase was washed with brine, dried over magnesium sulfate, filtered and concentrated. The crude oxime was dissolved in THF (0.07 M) and heated in the presence of CDI (4.0 equiv.) at 120° C. for 20 min in the microwave. The volatiles were removed under vacuo and the residue was purified via silica gel chromatography (0-50% ethyl acetate/n-heptanes) to give 3-(5-bromo-2-methoxypyridin-3-yl)oxetane-3-carbonitrile as a white solid in 70% yield. LCMS (m/z) (M+H)=268.8/270.8, Rt=0.71 min.

Synthesis of 2-((5-bromo-3-(3-fluorooxetan-3-yl)pyridin-2-yl)oxy)ethanol

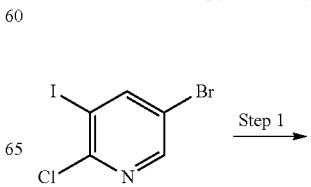

-continued

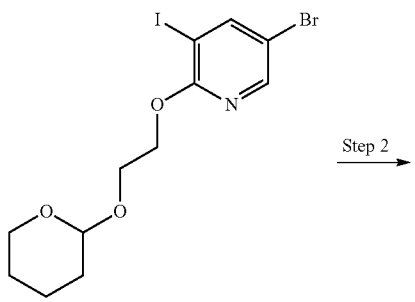

Step 2

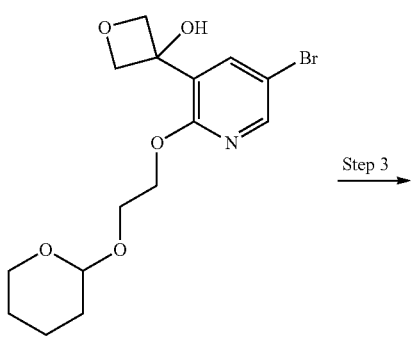

Step 3

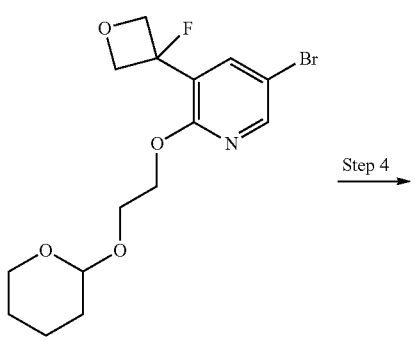

Step 4

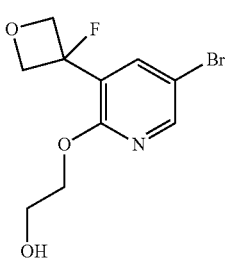

Step 1

Sodium hydride (2.0 equiv.) was added to dioxane (0.3 M). 2-((tetrahydro-2H-pyran-2-yl)oxy)ethanol (2.0 equiv.) was added and the mixture was stirred for 30 min at rt. 5-bromo-2-chloro-3-iodopyridine (1.0 equiv.) was added to the mixture and the reaction was heated to 105° C. for 1 hour. The cooled reaction mixture was quenched by the addition of saturated aqueous sodium bicarbonate and extracted with ethyl acetate. The combined extracts were dried over sodium sulfate, filtered, and concentrated. The crude product was purified by flash chromatography over silica gel (heptanes with 10% ethyl acetate) to give 5-bromo-3-iodo-2-(2-((tetrahydro-2H-pyran-2-yl)oxy)ethoxy)pyridine as a colorless oil in 78% yield. LCMS (m/z) (M+H)=427.8/429.8, Rt=1.12 min.

Step 2

A solution of 5-bromo-3-iodo-2-(2-((tetrahydro-2H-pyran-2-yl)oxy)ethoxy)pyridine (1.0 equiv.) in THF (0.39 M) was cooled to an internal temperature of −50° C. isopropylmagnesium chloride, 2.0M in THF (1.2 equiv.) was added dropwise over 10 min. The faintly pink solution was stirred at an internal temperature of −60 to −40° C. for 30 min, becoming cloudy. Oxetan-3-one (1.5 equiv.) was added dropwise over 5 min, keeping internal temperature at −40 to −35° C. The reaction was allowed to warm to −5° C. over 1 hr. The reaction was quenched by the addition of saturated aqueous sodium bicarbonate and extracted with ethyl acetate. The combined extracts were dried over sodium sulfate, filtered, and concentrated. The crude material was purified by flash chromatography over silica gel (heptanes with ethyl acetate gradient) to give 3-(5-bromo-2-(2-((tetrahydro-2H-pyran-2-yl)oxy)ethoxy)pyridin-3-yl)oxetan-3-ol as a colorless oil in 79% yield. LCMS (m/z) (M+Na)=398.1, Rt=0.74 min.

Step 3

To a solution of 3-(5-bromo-2-(2-((tetrahydro-2H-pyran-2-yl)oxy)ethoxy)pyridin-3-yl)oxetan-3-ol (1.0 equiv.) in CH$_2$Cl$_2$ at −78° C. under Ar was added DAST (2.0 equiv.) at a fast drip. After addition, the solution was stirred under Ar at −78° C. for 15 min. The reaction was allowed to warm to ambient temperature over 30 min. Analysis by TLC (2:1 heptanes:ethyl acetate) indicated all SM was consumed. The reaction was quenched by addition of saturated aqueous NaHCO$_3$, and the mixture was extracted with DCM (2×). The combined extracts were dried over sodium sulfate, filtered, and concentrated. The crude material was purified by flash chromatography over silica gel (heptanes with ethyl acetate gradient) to give 5-bromo-2-ethoxy-3-(3-fluorooxetan-3-yl)pyridine as a colorless oil in 35% yield. LCMS (m/z) (M+H)=375.9/377.9, Rt=0.94 min.

Step 4

5-bromo-3-(3-fluorooxetan-3-yl)-2-(2-((tetrahydro-2H-pyran-2-yl)oxy)ethoxy)pyridine (1.0 equiv.) was dissolved in THF (0.2 M) and then treated with 1.0M aqueous HCl (5.0 equiv.). The mixture was stirred at ambient temperature for 1 hr. The reaction mixture was neutralized with saturated aqueous sodium bicarbonate and extracted with ethyl acetate (2×). The combined extracts were dried over sodium sulfate, filtered, and concentrated. The crude material was purified by flash chromatography over silica gel (heptanes with 25-75% ethyl acetate gradient) to give 2-((5-bromo-3-(3-fluorooxetan-3-yl)pyridin-2-yl)oxy)ethanol as a colorless oil in 74% yield. LCMS (m/z) (M+H)=292.0/294.0, Rt=0.62 min.

Synthesis of 3-(5-bromo-2-(2-hydroxyethoxy)pyridin-3-yl)oxetan-3-ol

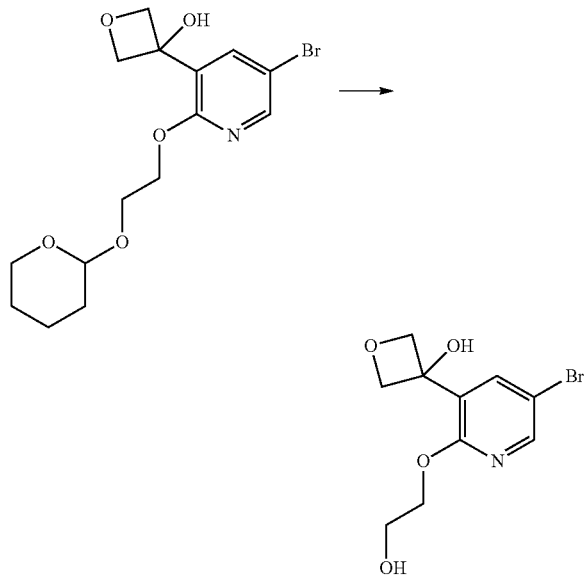

3-(5-bromo-2-(2-((tetrahydro-2H-pyran-2-yl)oxy)ethoxy)pyridin-3-yl)oxetan-3-ol was dissolved in THF (0.2 M) and treated with HCl (5.0 equiv, 1 M aq). The mixture was stirred at ambient temperature for 1 hr. The reaction mixture was neutralized with saturated aqueous sodium bicarbonate and extracted with ethyl acetate (2×). The combined extracts were dried over sodium sulfate, filtered, and concentrated. The crude material was purified by flash chromatography over silica gel (heptanes with ethyl acetate gradient) to give 3-(5-bromo-2-(2-hydroxyethoxy)pyridin-3-yl)oxetan-3-ol in 77%/o yield. LCMS (m/z) (M+H)=289.8/291.8, Rt=0.48 min.

Synthesis of 3-(5-bromo-2-ethoxypyridin-3-yl)oxetan-3-ol

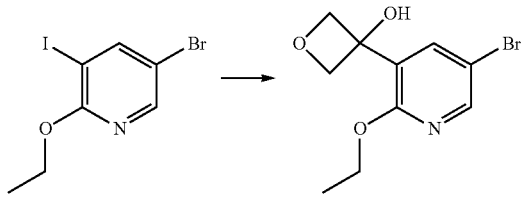

To a stirred solution of 5-bromo-2-ethoxy-3-iodopyridine (1.0 equiv.) in Et$_2$O (0.2 M) at −78° C. was slowly added BuLi (2.5 M in hexanes) (1.1 equiv.) and the mixture was stirred for 30 min. oxetan-3-one (1.15 equiv.) was then slowly added and the mixture was stirred for 15 min and then allowed to warm to room temperature. The reaction mixture was poured onto saturated aqueous ammonium chloride and extracted three times with ethyl acetate. The combined organics were washed with brine, dried over magnesium sulfate, filtered and concentrated. The crude reside was purified via ISCO over silica gel, eluting with heptane and 0-50% EtOAc gradient to give 3-(5-bromo-2-ethoxypyridin-3-yl)oxetan-3-ol in 54% yield. LCMS (m/z) (M+H)=274.0/276.0, Rt=0.72 min.

Synthesis of 5-bromo-2-ethoxy-3-(3-fluorooxetan-3-yl)pyridine

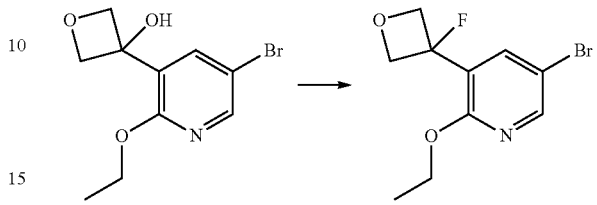

To a solution of 3-(5-bromo-2-ethoxypyridin-3-yl)oxetan-3-ol (1.0 equiv.) in CH$_2$Cl$_2$ (0.1 M) at −78° C. under Ar was added DAST (1.1 equiv.) at a fast drip. After addition, the solution was stirred under Ar at −78° C. for 25 min. The reaction was allowed to warm to ambient temperature over 1 hr. The reaction was quenched by addition of saturated aqueous NaHCO$_3$, and the mixture was extracted with DCM (2×). The combined extracts were dried over sodium sulfate, filtered, and concentrated. The crude material was purified by flash chromatography over silica gel (heptanes with ethyl acetate gradient) to give 5-bromo-2-ethoxy-3-(3-fluorooxetan-3-yl)pyridine in 27% yield as a colorless oil. LCMS (m/z) (M+H)=275.8/277.8, Rt=0.88 min.

Synthesis of 3-(5-bromo-2-((tetrahydro-2H-pyran-4-yl)oxy)pyridin-3-yl)oxetan-3-ol

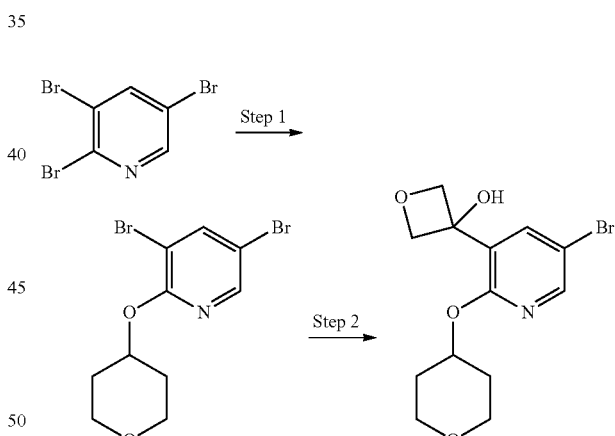

Step 1

A solution of 2,3,5-tribromopyridine (1.0 equiv.) in N,N-dimethylformamide (0.23 M) was treated with sodium hydride (60% dispersion in mineral oil, 1.5 equiv.). The mixture was cooled to 0° C. and 4-hydroxypyran (1.2 equiv.) was added slowly. The resultant mixture was stirred at 0° C. for 2 h and at room temperature for 1 hour, then was added to dilute brine solution and was extracted with ethyl acetate. The organic layer was dried over magnesium sulfate, was filtered, and the solvent was removed in vacuo. Purified by ISCO (0-100% EtOAc/heptane) to yield 3,5-dibromo-2-((tetrahydro-2H-pyran-4-yl)oxy)pyridine in 63% yield. LCMS (m/z) (M+H)=336.0/338.0, Rt=1.04 min.

Step 2

To a solution of 3,5-dibromo-2-((tetrahydro-2H-pyran-4-yl)oxy)pyridine (1.0 equiv.) in Et₂O (0.14 M) at –78° C. was added BuLi (1.4 equiv.) dropwise. The resulting mixture was stirred at –78° C. for 30 min and a solution of oxetan-3-one (2.0 equiv.) in THF was added dropwise. The mixture was stirred at –78° C. for 1 h, warmed to rt and kept at rt for 2 h. Quenched the reaction with sat. NaHCO₃ and extracted with EtOAc. The organic layer was washed with Brine, dried over sodium sulfate and concentrated. Purified by ISCO (0-50%/o EtOAc/heptane) to yield 3-(5-bromo-2-((tetrahydro-2H-pyran-4-yl)oxy)pyridin-3-yl)oxetan-3-ol in 51% yield. LCMS (m/z) (M+H)=329.8/331.8, Rt=0.66 min.

Synthesis of 5-bromo-3-(3-fluorooxetan-3-yl)-1-(3-hydroxypropyl)pyridin-2(1H)-one

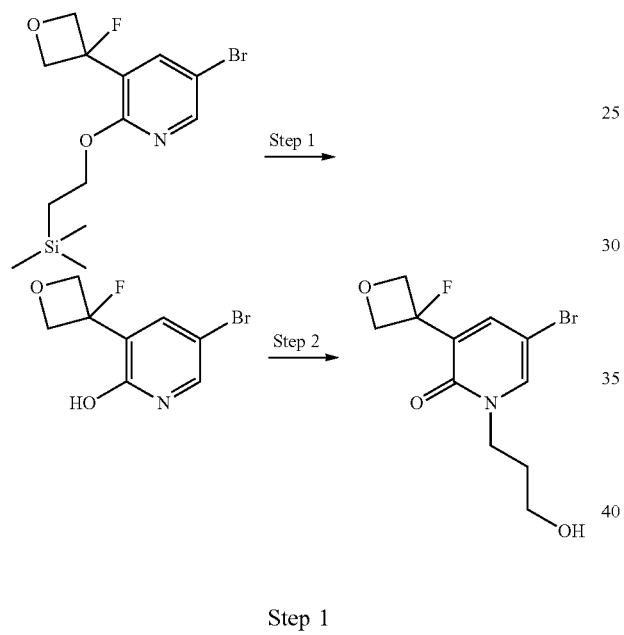

Step 1

To a solution of 5-bromo-3-(3-fluorooxetan-3-yl)-2-(2-(trimethylsilyl)ethoxy)pyridine (1.0 equiv.) in DCM (0.1 M) was added TFA (1.0 equiv.) and the solution was stirred at rt overnight. The volatiles were removed under vacuo and the white solid was stirred in diethyl ether, sonicated for 10 min and allowed to sit overnight. The precipitate was filtered to give 5-bromo-3-(3-fluorooxetan-3-yl)pyridin-2-ol as a white solid in 60% yield. LCMS (m/z) (M+H)=247.8/249.8, Rt=0.43 min.

Step 2

To a solution of 5-bromo-3-(3-fluorooxetan-3-yl)pyridin-2-ol (1.0 equiv.) in DMF (0.4 M) was added potassium carbonate (5.0 equiv.) and 3-bromopropan-1-ol (3.0 equiv.). The solution was stirred at rt overnight. Diluted with ethyl acetate and added solid potassium carbonate. The organic phase was washed with brine, dried over magnesium sulfate, filtered and concentrated to give 5-bromo-3-(3-fluorooxetan-3-yl)-1-(3-hydroxypropyl)pyridin-2(1H)-one in 9% yield. LCMS (m/Z) (M+H)=305.8/307.8, Rt=0.47 min.

Synthesis of 3-(5-bromo-2-methoxypyridin-3-yl)oxetane-3-carbaldehyde

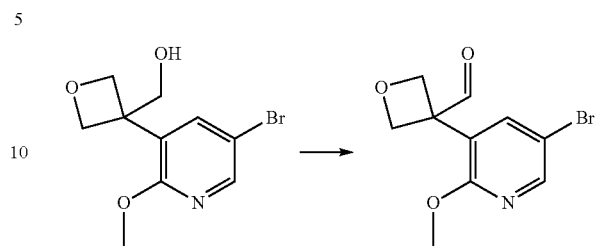

To a solution of (3-(5-bromo-2-methoxypyridin-3-yl)oxetan-3-yl)methanol (1.0 equiv.) in DCM (0.1 M) at 0° C. was added Dess-Martin Periodinane (1.2 equiv.) and the solution was stirred at 0° C. for 1 hour, then allowed to warm to rt and stirred at rt for 5 hours. The reaction was partitioned between ethyl acetate and 1:1 10% Na₂S₂O₃/NaHCO₃₍sat.₎, the organic layer was washed with 1:1 10% Na₂S₂O₃/NaHCO₃₍sat.₎, then brine, dried over magnesium sulfate, filtered and concentrated. The residue was purified via silica gel chromatography (ISCO, 0-100% ethyl acetate/n-heptanes) to give 3-(5-bromo-2-methoxypyridin-3-yl)oxetane-3-carbaldehyde as a white solid in 71% yield. LCMS (m/z) (M+H)=271.8/273.8, Rt=0.60 min.

Synthesis of 2-((6-bromo-4-(3-fluorooxetan-3-yl)pyridin-2-yl)oxy)ethanol

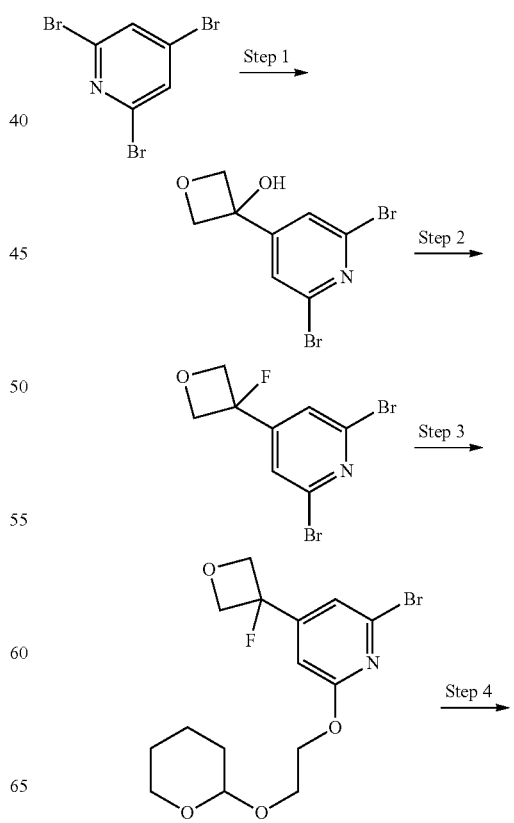

-continued

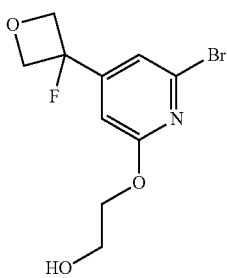

Step 1

A colorless solution of 2,4,6-tribromopyridine (1.0 equiv.) in THF (0.1 M) was cooled to an internal temperature of −73° C. Isopropylmagnesium chloride (1.1 equiv.) was added dropwise over 10 min (gradually turning pink), keeping the internal temperature below −70° C. The light pink solution was stirred at −70° C. to −50° C. over 30 min, gradually turning yellow. The yellow solution was warmed to −30° C. over 30 min (turning lighter yellow then light green). Oxetan-3-one (1.2 equiv.) was added dropwise, and the mixture was allowed to come to ambient temperature, turning light yellow. The reaction mixture was quenched by the addition of saturated aqueous sodium bicarbonate and extracted with ethyl acetate. The combined extracts were dried over sodium sulfate, filtered, concentrated, and purified by flash chromatography over silica gel (heptanes with 25-60% ethyl acetate gradient) to give 3-(2,6-dibromopyridin-4-yl)oxetan-3-ol in 24% yield as a white solid. $^1$H NMR (400 MHz, <cdcl3>) δ ppm 7.80 (s, 2H) 4.87-4.94 (m, 2H) 4.71-4.78 (m, 2H) 2.67 (s, 1H).

Step 2: To a suspension of 3-(2,6-dibromopyridin-4-yl)oxetan-3-ol (1.0 equiv.)) in CH$_2$Cl$_2$ (0.1 M) at −15° C. under nitrogen was added DAST (2.0 equiv.) at a fast drip. After addition, the solution was stirred for 15 min. The reaction was quenched by addition of saturated aqueous NaHCO$_3$, and the mixture was extracted with DCM. The combined extracts were dried over sodium sulfate, filtered, and concentrated. The crude material was purified by flash chromatography over silica gel (heptanes with 5-40% ethyl acetate gradient) to give 2,6-dibromo-4-(3-fluorooxetan-3-yl)pyridine in 83% yield. LCMS (m/z) (M+H)=311.9. Rt=0.74 min.

Step 3

2-((tetrahydro-2H-pyran-2-yl)oxy)ethanol (3.0 equiv.) was added to a mixture of sodium hydride, 60% in mineral oil (3.0 equiv.) and Dioxane (0.22 M) and stirred for 20 min. The mixture was added to 2,6-dibromo-4-(3-fluorooxetan-3-yl)pyridine (1.0 equiv.), and the reaction was stirred at 90° C. for 2 hours. The reaction was cooled to RT and quenched with saturated aqueous NaHCO$_3$, extracted with EtOAc, dried over Na$_2$SO$_4$, filtered, and concentrated to give crude 2-bromo-4-(3-fluorooxetan-3-yl)-6-(2-((tetrahydro-2H-pyran-2-yl)oxy)ethoxy)pyridine in quantitative yield. LCMS (m/z) (M-THP)=291.8/293.8, Rt=0.96 min.

Step 4

To a solution of crude 2-bromo-4-(3-fluorooxetan-3-yl)-6-(2-((tetrahydro-2H-pyran-2-yl)oxy)ethoxy)pyridine (1.0 equiv.) in THF (0.07 M) was added 0.5M aqueous HCl (7.0 equiv.). The mixture was stirred vigorously for 45 min at ambient temperature. The reaction mixture was neutralized with saturated aqueous sodium bicarbonate and extracted with ethyl acetate. The combined extracts were dried over sodium sulfate, filtered, concentrated, and purified by flash chromatography over silica gel (heptanes with 10-60% ethyl acetate) to give 2-((6-bromo-4-(3-fluorooxetan-3-yl)pyridin-2-yl)oxy)ethanol as a colorless oil in 52% yield. LCMS (m/z) (M+H)=292/294, Rt=0.61 min.

Synthesis of 2-((5-bromo-3-(3-methoxyoxetan-3-yl)pyridin-2-yl)oxy)ethanol

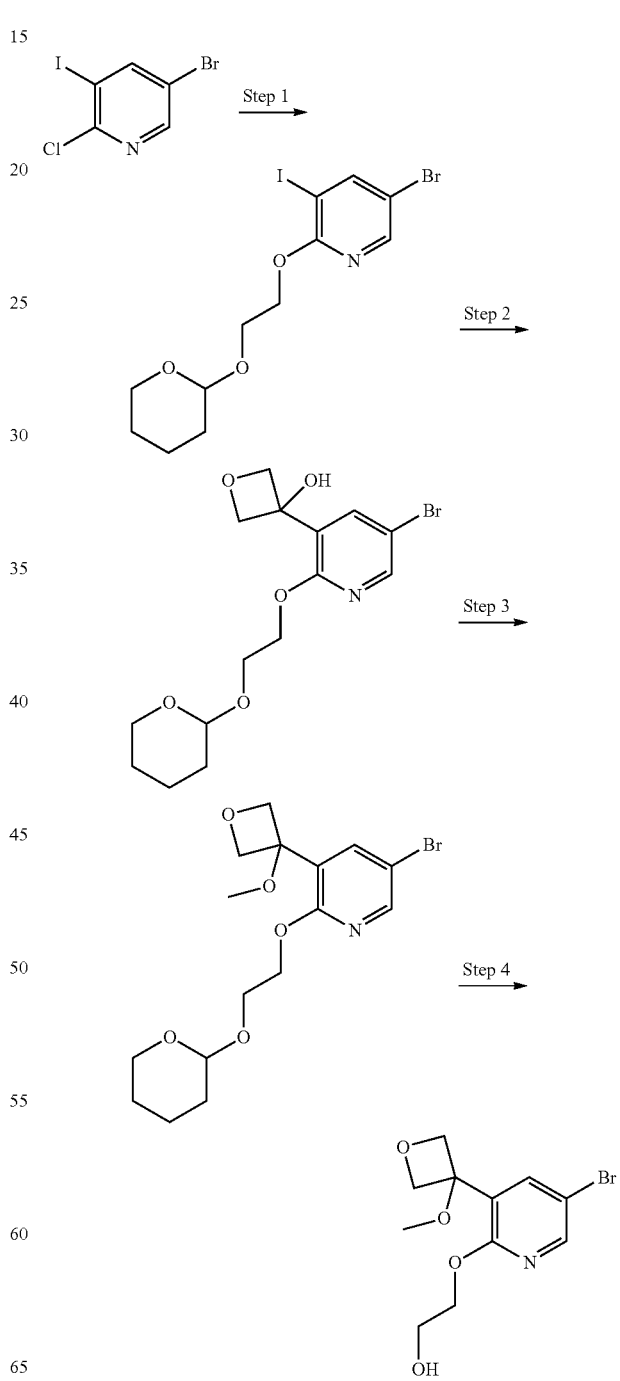

Step 1

Sodium hydride, 60% dispersion (2.0 equiv.) was added to Dioxane (0.3 M). 2-((tetrahydro-2H-pyran-2-yl)oxy)ethanol (2.0 equiv.) was added. The mixture was stirred for 30 min at ambient temperature. 5-bromo-2-chloro-3-iodopyridine (1.0 equiv.) was added, and the mixture was stirred at 105° C. for 1 hr. The cooled reaction mixture was quenched by the addition of saturated aqueous sodium bicarbonate and extracted with ethyl acetate. The combined extracts were dried over sodium sulfate, filtered, and concentrated. The crude product was purified by flash chromatography over silica gel (heptanes with 10% ethyl acetate) to give 5-bromo-3-iodo-2-(2-((tetrahydro-2H-pyran-2-yl)oxy)ethoxy)pyridine as a colorless oil in 78% yield. LCMS (m/z) (M+H)=427.8/429.8. Rt=1.13 min.

Step 2

A solution of 5-bromo-3-iodo-2-(2-((tetrahydro-2H-pyran-2-yl)oxy)ethoxy)pyridine (1.0 equiv.) in THF (0.35 M) was cooled to an internal temperature of −50° C. Isopropylmagnesium chloride, 2.0M in THF (1.2 equiv.) was added dropwise over 10 min. The colorless solution was stirred at an internal temperature of −50 to −30° C. for 30 min. Oxetan-3-one (1.5 equiv.) was added dropwise over 5 min, keeping internal temperature at −40 to −35° C. The reaction was allowed to warm to −5° C. over 0.5 hr, turning cloudy. The reaction was quenched by the addition of saturated aqueous sodium bicarbonate and extracted with ethyl acetate (2×). The combined extracts were dried over sodium sulfate, filtered, and concentrated. The crude material was purified by flash chromatography over silica gel (heptanes with 25-75% ethyl acetate gradient) to give 3-(5-bromo-2-(2-((tetrahydro-2H-pyran-2-yl)oxy)ethoxy)pyridin-3-yl)oxetan-3-ol in 68% yield as a colorless oil. LCMS (m/z) (M+Na)=396.1/398.1, Rt=0.73 min.

Step 3

To sodium hydride (1.1 equiv.) in DMF (0.2 M) was added 3-(5-bromo-2-(2-((tetrahydro-2H-pyran-2-yl)oxy)ethoxy)pyridin-3-yl)oxetan-3-ol (1.0 equiv.). The mixture was stirred for 40 min at ambient temperature. Methyl iodide (1.1 equiv.) was added, and the reaction was stirred for 1.5 hr at ambient temperature. The reaction mixture was diluted with water and extracted with ethyl acetate (2×). The organic phases were concentrated to give 5-bromo-3-(3-methoxyoxetan-3-yl)-2-(2-((tetrahydro-2H-pyran-2-yl)oxy)ethoxy)pyridine in quantitative yield. The crude material was used without further purification

Step 4

To a solution of crude 5-bromo-3-(3-methoxyoxetan-3-yl)-2-(2-((tetrahydro-2H-pyran-2-yl)oxy)ethoxy)pyridine (1.0 equiv.) in THF (0.13 M) was added 0.5M aqueous HCl (4.0 equiv.). The mixture was stirred vigorously for 70 min at ambient temperature. The reaction mixture was neutralized with saturated aqueous sodium bicarbonate and extracted with ethyl acetate. The combined extracts were dried over sodium sulfate, filtered, concentrated, and purified by flash chromatography over silica gel (heptanes with 25-75% ethyl acetate, product comes off around 65% ethyl acetate) to give 2-((5-bromo-3-(3-methoxyoxetan-3-yl)pyridin-2-yl)oxy)ethanol as a colorless oil which crystallized upon standing in 62% yield. LCMS (m/z) (M+H)=304.1/306.1, Rt=0.60 min.

Synthesis of 5-bromo-1-(2,3-dihydroxypropyl)-3-(3-fluorooxetan-3-yl)pyridin-2(1H)-one

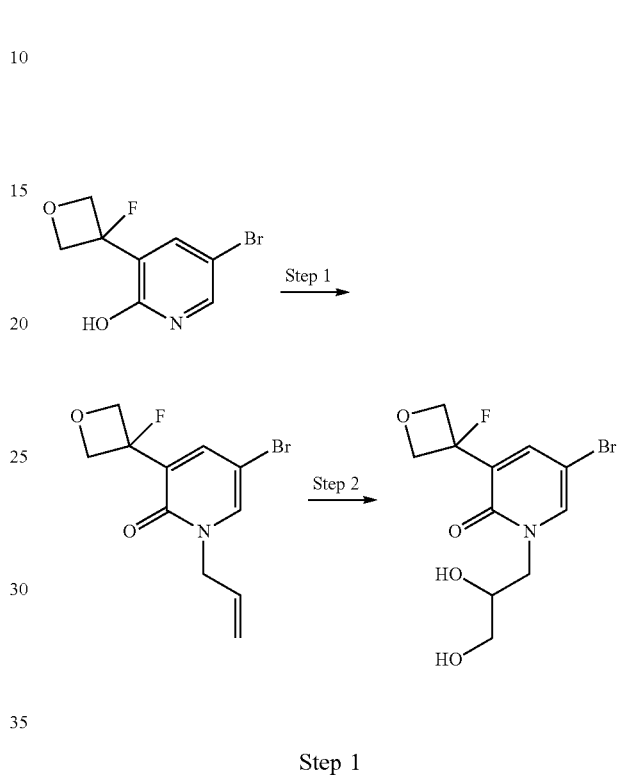

Step 1

To a solution of 5-bromo-3-(3-fluorooxetan-3-yl)pyridin-2-ol (1.0 equiv.) in DMF (0.4 M) was added potassium carbonate (5.0 equiv.) and allyl bromide (3.0 equiv.) and the homogeneous solution was stirred at rt for 4 hours. The mixture was partitioned between ethyl acetate and water, the organic phase was washed with water, brine, dried over magnesium sulfate, filtered and concentrated. The residue was purified via silica gel chromatography (ISCO, 0-55% ethyl acetate/heptanes) to give 1-allyl-5-bromo-3-(3-fluorooxetan-3-yl)pyridin-2(1H)-one in 53% yield. LCMS (m/z) (M+H)=287.8/289.8, Rt=0.61 min.

Step 2

To a solution of 1-allyl-5-bromo-3-(3-fluorooxetan-3-yl)pyridin-2(1H)-one (1.0 equiv.) and NMO (1.5 equiv.) in THF and water (1:1, 0.04 M) was added OsO$_4$ solution (0.05 equiv.) and the homogeneous solution was stirred at rt for 3 hours. Partitioned between ethyl acetate and 1:1 10% Na$_2$S$_2$O$_3$/NaHCO$_{3(sat.)}$, the organic layer was washed with 1:1 10% Na$_2$S$_2$O$_3$/NaHCO$_{3(sat.)}$, then brine, dried with magnesium sulfate, filtered and concentrated to give 5-bromo-1-(2,3-dihydroxypropyl)-3-(3-fluorooxetan-3-yl)pyridin-2(1H)-one as an off-white solid in 86% yield. LCMS (m/z) (M+H)=322.0/324.0. Rt=0.40 min.

Synthesis of 5-bromo-1-(2-((tert-butyldimethylsilyl)oxy)ethyl)-3-(3-fluorooxetan-3-yl)pyridin-2(1H)-one

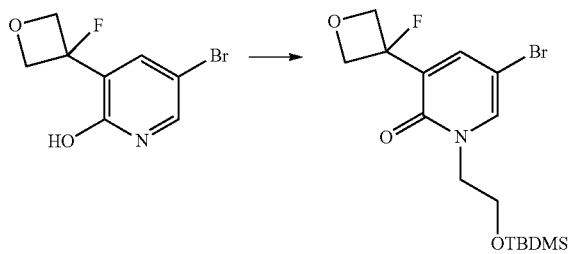 [SMILES: Oc1ncc(Br)cc1C1(F)COC1 ; CC(C)(C)[Si](C)(C)OCCn1cc(Br)cc(C2(F)COC2)c1=O]

To a solution of 5-bromo-3-(3-fluorooxetan-3-yl)pyridin-2-ol (1.0 equiv.) and potassium carbonate (5.0 equiv.) in DMF (0.27 M) was added (2-bromoethoxy)(tert-butyl)dimethylsilane and the solution was stirred at rt for 5 hours. The reaction was partitioned between ethyl acetate and water, the organic layer was washed with water, then brine, dried over magnesium sulfate, filtered and concentrated. The residue was purified via silica gel chromatography (ISCO, 0-100% ethyl acetate/n-heptanes) to give 5-bromo-1-(2-((tert-butyldimethylsilyl)oxy)ethyl)-3-(3-fluorooxetan-3-yl)pyridin-2(1H)-one in 22% yield. LCMS (m/z) (M+H)=406.0-408.0, Rt=1.07 min.

Synthesis of 3-(3-bromo-5-(3-fluorooxetan-3-yl)phenyl)oxetan-3-ol

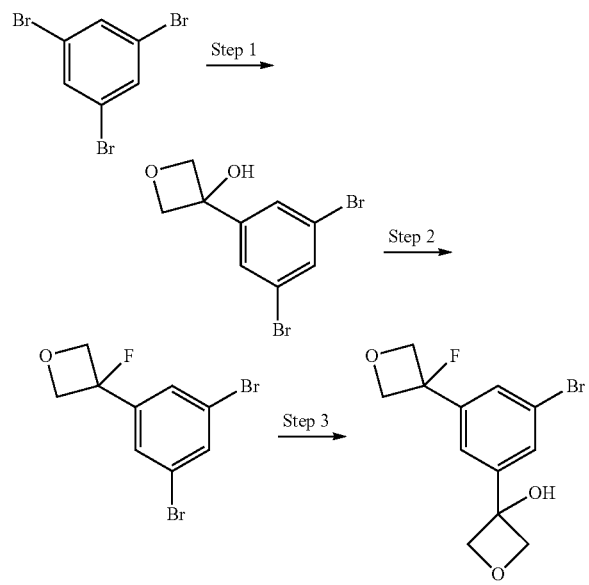

Step 1

To a solution of 1,3,5-tribromobenzene (1.0 equiv.) at −78° C. under argon in diethyl ether (0.2 M) was added n-BuLi (1.0 equiv.) via syringe while keeping the internal temperature below −70° C. Upon completion of the addition, the purple solution was stirred for 1 hour, then oxetan-3-one (1.1 equiv.) was added neat via syringe. The resulting solution was allowed to warm to rt and stirred for one hour. The reaction was quenched by the addition of sat. ammonium chloride, partitioned between ethyl acetate and sat. ammonium chloride, the organic phase was washed with sat. sodium bicarbonate, brine, dried over magnesium sulfate, filtered and concentrated. The residue was purified by sonicating in n-heptanes and the precipitate was filtered and dried under vacuo overnight to give 3-(3,5-dibromophenyl)oxetan-3-ol in 87% yield. 1H NMR (400 MHz, <dmso>) □ ppm 7.62-7.91 (m, 1H) 6.63 (s, 1H) 4.75 (d, J=7.04 Hz, 2H) 4.66 (d, J=7.04 Hz, 2H).

Step 2

To a solution of 3-(3,5-dibromophenyl)oxetan-3-ol (1.0 equiv.) in DCM (0.1 M) at −78° C. was added DAST (2.0 equiv.) and the reaction was stirred at this temperature for 5 min, then allowed to warm to rt. After two hours, the reaction was quenched by pouring onto ice with solid sodium bicarbonate. Partitioned between ethyl acetate and water, the organic phase was washed with sat. sodium bicarbonate, brine, dried over magnesium sulfate, filtered and concentrated. The residue was purified via silica gel chromatography (ISCO, 0-40% ethylacetate/n-heptanes) to give 3-(3,5-dibromophenyl)-3-fluorooxetane in 81% yield. 1H NMR (400 MHz, <dmso>) ppm 7.93 (t, J=1.76 Hz, 1H) 7.77 (dd, J=1.76, 0.98 Hz, 2H) 4.80-5.06 (m, 4H).

Step 3

To a solution of 3-(3,5-dibromophenyl)-3-fluorooxetane (1.0 equiv.) in diethyl ether (0.2 M) at −71° C. (internal temperature) was added n-BuLi (1.0 equiv.) via syringe dropwise. The reaction was stirred at this temperature for one hour, then oxetan-3-one (1.1 equiv.) was added via syringe and the solution was allowed to warm to room temperature and stirred for another hour. Quenched by the addition of sat. ammonium chloride, partitioned between ethyl acetate and water, the organic layer was separated, washed with sat. sodium bicarbonate, brine, dried over magnesium sulfate, filtered and concentrated. The residue was purified via silica gel chromatography (ISCO, 0-100% ethyl acetate/n-heptanes) and the pure fractions were concentrated to give 3-(3-bromo-5-(3-fluorooxetan-3-yl)phenyl)oxetan-3-ol as a white solid in 89% yield. LCMS (m/z) (M+H)=325.8/327.8, Rt=0.68 min.

Synthesis of 2-(3-fluorooxetan-3-yl)-6-(2-hydroxyethoxy)pyridin-4-yl trifluoromethanesulfonate

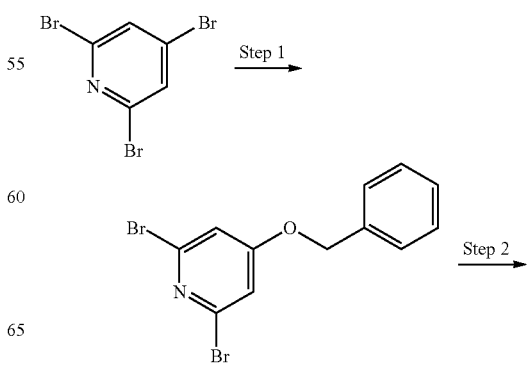

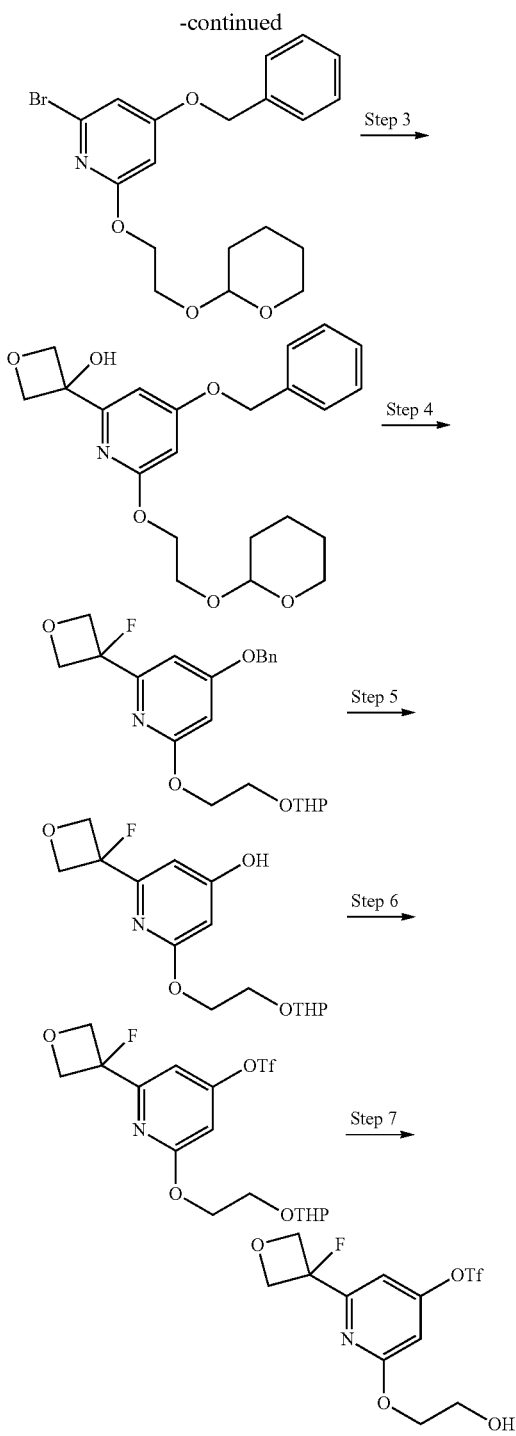

gradient) to give 4-(benzyloxy)-2,6-dichloropyridine, as a white, crystalline solid in 62% yield. LCMS (m/z) (M+H)=344.0, Rt=1.13 min.

Step 2

2-((tetrahydro-2H-pyran-2-yl)oxy)ethanol (1.0 equiv.) was added to a mixture of sodium hydride, 60% in mineral oil (2.1 equiv.) and Dioxane (0.4 M) and stirred for 30 min. This mixture was added to 4-(benzyloxy)-2,6-dibromopyridine (1.0 equiv.), and the reaction was stirred at 80° C. for 30 min. The reaction was cooled to ambient temperature and quenched with saturated aqueous NaHCO$_1$, extracted with EtOAc, dried over Na$_2$SO$_4$, filtered, concentrated, and purified by flash chromatography over silica gel (heptanes with 0-20% ethyl acetate gradient) to give 4-(benzyloxy)-2-bromo-6-(2-((tetrahydro-2H-pyran-2-yl)oxy)ethoxy)pyridine, as a light yellow oil in 76% yield. LCMS (m/z) (M+Na)=430.1/432.1, Rt=1.14 min.

Step 3

A light yellow solution of 4-(benzyloxy)-2-bromo-6-(2-((tetrahydro-2H-pyran-2-yl)oxy)ethoxy)pyridine (1.0 equiv.) in THF (0.2 M) was cooled to an internal temperature of −73° C. n-butyllithium (1.1 equiv.) was added dropwise over 30 min, keeping the internal temperature below −70° C. The reaction was removed from the bath, and oxetan-3-one (1.2 equiv.) was added dropwise. The mixture was allowed to come to ambient temperature. The reaction mixture was quenched by the addition of saturated aqueous sodium bicarbonate and extracted with ethyl acetate. The combined extracts were dried over sodium sulfate, filtered, concentrated, and purified by flash chromatography over silica gel (heptanes with 25-60% ethyl acetate gradient) to give 3-(4-(benzyloxy)-6-(2-((tetrahydro-2H-pyran-2-yl)oxy)ethoxy) pyridin-2-yl)oxetan-3-ol as a colorless oil in 68% yield. LCMS (m/z) (M+H)=402.2, Rt=0.93 min.

Step 4

To a solution of 3-(4-(benzyloxy)-6-(2-((tetrahydro-2H-pyran-2-yl)oxy)ethoxy)pyridin-2-yl)oxetan-3-ol (1.0 equiv.) in CH$_2$Cl$_2$ (0.1 M) at −10° C. under Ar was added DAST (2.0 equiv.) at a fast drip. After addition, the solution was stirred under Ar at −10° C. for 20 min. The reaction was quenched by addition of saturated aqueous NaHCO$_3$, and the mixture was extracted with DCM. The combined extracts were dried over sodium sulfate, filtered, and concentrated. The crude material was purified by flash chromatography over silica gel (heptanes with 0-50% ethyl acetate gradient) to give 4-(benzyloxy)-2-(3-fluorooxetan-3-yl)-6-(2-((tetrahydro-2H-pyran-2-yl)oxy)ethoxy)pyridine as a colorless oil in 78% yield. LCMS (m/z) (M+H)=404.3, Rt=1.14 min.

Step 1

To sodium hydride (1.05 equiv.) in DMF (0.5 M) was added benzyl alcohol (1.05 equiv.). The mixture was stirred at 0° C. for 50 min. 2,4,6-tribromopyridine (1.0 equiv.) was added. The mixture was stirred at 0° C. for 90 min and at ambient temperature for 1 hr. The reaction was quenched by the addition of water and then extracted with ethyl acetate. The combined extracts were dried over sodium sulfate, filtered, concentrated, and purified by flash chromatography over silica gel (heptanes for 5 min then 0-20% ethyl acetate Step 5

To a degassed solution of 4-(benzyloxy)-2-(3-fluorooxetan-3-yl)-6-(2-((tetrahydro-2H-pyran-2-yl)oxy)ethoxy) pyridine (1.0 equiv.) in methanol (0.07 M) was added palladium on carbon (0.05 equiv.). The flask was purged and flushed twice with hydrogen from a balloon. The reaction was stirred for 1 hr under a hydrogen atmosphere. The reaction mixture was degassed and diluted with DCM. The mixture was filtered through Celite. The filtrate was concentrated to give 2-(3-fluorooxetan-3-yl)-6-(2-((tetrahydro- 2H-pyran-2-yl)oxy)ethoxy)pyridin-4-ol, as a colorless oil in 92% yield. LCMS (m/z) (M+H)=314.2. Rt=0.72 min.

Step 6

A solution of 2-(3-fluorooxetan-3-yl)-6-(2-((tetrahydro-2H-pyran-2-yl)oxy)ethoxy)pyridin-4-ol (1.0 equiv.) and pyridine (1.5 equiv.) was cooled in a dry ice/acetone bath. Trifluoromethanesulfonic anhydride (1.25 equiv.) was added in a dropwise fashion over 10 min. After stirring for 10 min, the reaction was allowed to warm to ambient temperature. After 20 min out of the bath (ambient temperature), the reaction mixture was quenched by the addition of saturated aqueous sodium bicarbonate. The mixture was stirred for 10 min and extracted with DCM. The organic phase was dried over sodium sulfate, filtered, concentrated, and purified by flash chromatography over silica gel (heptanes with 10-60% ethyl acetate gradient) to give 2-(3-fluorooxetan-3-yl)-6-(2-((tetrahydro-2H-pyran-2-yl)oxy)ethoxy)pyridin-4-yl trifluoromethanesulfonate, as a colorless oil in 55% yield. LCMS (m/z) (M+Na)=468.0, Rt=1.12 min.

Step 7

To a solution of 2-(3-fluorooxetan-3-yl)-6-(2-((tetrahydro-2H-pyran-2-yl)oxy)ethoxy)pyridin-4-yl trifluoromethanesulfonate (1.0 equiv.) in THF (0.1 M) was added 0.6M aqueous HCl (5.0 equiv.). The mixture was stirred vigorously for 2.5 hr at ambient temperature. The reaction mixture was neutralized with saturated aqueous sodium bicarbonate and extracted with ethyl acetate. The combined extracts were dried over sodium sulfate, filtered, concentrated, and purified by flash chromatography over silica gel (heptanes with 25-75% ethyl acetate) to give 2-(3-fluorooxetan-3-yl)-6-(2-hydroxyethoxy)pyridin-4-yl trifluoromethanesulfonate, as a colorless oil in 69% yield. LCMS (m/z) (M+H)=362.1, Rt=0.84 min.

Synthesis of 2-(2-hydroxyethoxy)-6-(3-hydroxyoxetan-3-yl)pyridin-4-yl trifluoromethanesulfonate

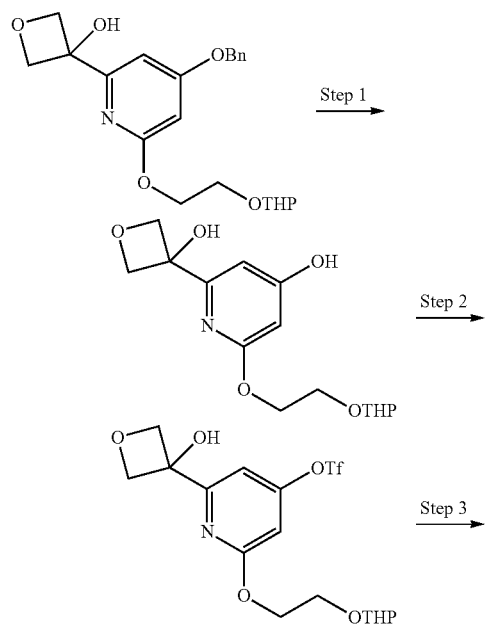

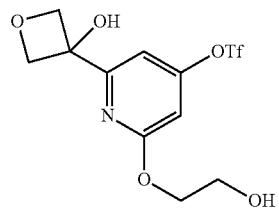 [SMILES: O=S(=O)(Oc1cc(OCCO)nc(C2(F)COC2)c1)C(F)(F)F]

Step 1

To a degassed solution of 3-(4-(benzyloxy)-6-(2-((tetrahydro-2H-pyran-2-yl)oxy)ethoxy)pyridin-2-yl)oxetan-3-ol (1.0 equiv.) in methanol (0.07 M) was added palladium on carbon (0.05 equiv.). The flask was purged and flushed twice with hydrogen from a balloon. The reaction was stirred for 1 hr under a hydrogen atmosphere. The reaction mixture was degassed and diluted with DCM. The mixture was filtered through Celite. The filtrate was concentrated to give 2-(3-hydroxyoxetan-3-yl)-6-(2-((tetrahydro-2H-pyran-2-yl)oxy)ethoxy)pyridin-4-ol which was used without further purification. LCMS (m/z) (M+H)=312.0. Rt=0.47 min.

Step 2

To a stirred solution of 2-(3-hydroxyoxetan-3-yl)-6-(2-((tetrahydro-2H-pyran-2-yl)oxy)ethoxy)pyridin-4-ol (1.0 equiv.) in acetone (0.1 M) at RT were added potassium carbonate (1.5 equiv.) and Comin's regent (1.05 equiv.), and the reaction was allowed stirred for 18 h. The mixture was diluted with DCM and filtered through a pad of $SiO_2$, washing with DCM. The combined filtrates were concentrated and purified by flash chromatography over silica gel (heptanes with 25-75% ethyl acetate gradient) to give 2-(3-hydroxyoxetan-3-yl)-6-(2-((tetrahydro-2H-pyran-2-yl)oxy)ethoxy)pyridin-4-yl trifluoromethanesulfonate in 90% yield. LCMS (m/z) (M+H)=444.3, Rt=0.95 min.

Step 3

To a solution of 2-(3-hydroxyoxetan-3-yl)-6-(2-((tetrahydro-2H-pyran-2-yl)oxy)ethoxy)pyridin-4-yl trifluoromethanesulfonate (1.0 equiv.) in THF (0.15 M) was added 1 M aqueous HCl (5.0 equiv.). The mixture was stirred vigorously for 1.5 hr at ambient temperature. The reaction mixture was neutralized with saturated aqueous sodium bicarbonate and extracted with ethyl acetate. The combined extracts were dried over sodium sulfate, filtered, concentrated, and purified by flash chromatography over silica gel (heptanes with 25-100% ethyl acetate) to give 2-(2-hydroxyethoxy)-6-(3-hydroxyoxetan-3-yl)pyridin-4-yl trifluoromethanesulfonate, as a colorless oil in 69% yield. LCMS (m/z) (M+H)=360.1, Rt=0.69 min.

Synthesis of 2-(2-hydroxyethoxy)-6-(3-methoxyoxetan-3-yl)pyridin-4-yl trifluoromethanesulfonate

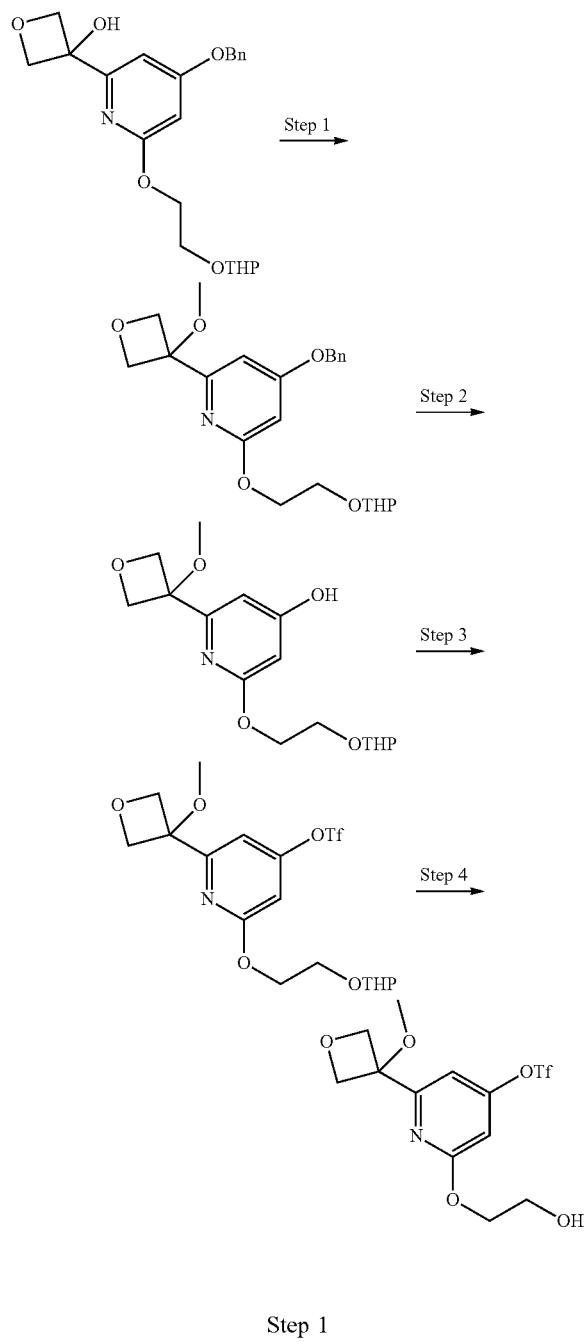

Step 1

To a stirred solution of 3-(4-(benzyloxy)-6-(2-((tetrahydro-2H-pyran-2-yl))ethoxy)ethoxy)pyridin-2-yl)oxetan-3-ol (1.0 equiv.) in DMF (0.15 M) was added sodium hydride (1.1 equiv.). The mixture was stirred for 35 min at ambient temperature. Iodomethane (1.1 equiv.) was added, and the reaction was stirred for 4 hr at ambient temperature. The reaction mixture was diluted with water and extracted twice with ethyl acetate. The organic phases were dried over sodium sulfate, filtered and concentrated to give 4-(benzyloxy)-2-(3-methoxyoxetan-3-yl)-6-(2-((tetrahydro-2H-pyran-2-yl)oxy)ethoxy)pyridine in 99% yield which was used without further purification. LCMS (m/z) (M+H)=416.1, Rt=1.04 min.

Step 2

To a degassed solution of 4-(benzyloxy)-2-(3-methoxyoxetan-3-yl)-6-(2-((tetrahydro-2H-pyran-2-yl)oxy)ethoxy) pyridine (1.0 equiv.) in methanol (0.1 M) was added palladium on carbon (0.05 equiv.). The flask was purged and flushed twice with hydrogen from a balloon. The reaction was stirred for 1 hr under a hydrogen atmosphere. The reaction mixture was degassed and diluted with DCM. The mixture was filtered through Celite. The filtrate was concentrated to give 2-(3-methoxyoxetan-3-yl)-6-(2-((tetrahydro-2H-pyran-2-yl)oxy)ethoxy)pyridin-4-ol which was used without further purification. LCMS (m/z) (M+H)=326.2, Rt=0.56 min.

Step 3

To a stirred solution 2-(3-methoxyoxetan-3-yl)-6-(2-((tetrahydro-2H-pyran-2-yl)oxy)ethoxy)pyridin-4-ol (1.0 equiv.) in acetone (0.1 M) at RT were added potassium carbonate (1.5 equiv.) and Comin's regent (1.05 equiv.), and the reaction was allowed stirred for 2 h. The mixture was diluted with DCM and filtered through a pad of SiO₂, washing with DCM. The combined filtrates were concentrated and purified by flash chromatography over silica gel (heptanes with 10-50% ethyl acetate gradient) to give 2-(3-methoxyoxetan-3-yl)-6-(2-((tetrahydro-2H-pyran-2-yl)oxy)ethoxy)pyridin-4-yl trifluoromethanesulfonate in 70% yield. LCMS (m/z) (M+H)=480.1, Rt=1.07 min.

Step 4

To a solution of 2-(3-methoxyoxetan-3-yl)-6-(2-((tetrahydro-2H-pyran-2-yl)oxy)ethoxy)pyridin-4-yl trifluoromethanesulfonate (1.0 equiv.) in THF (0.1 M) was added 1 M aqueous HCl (5.0 equiv.). The mixture was stirred vigorously for 2.5 hr at ambient temperature. The reaction mixture was neutralized with saturated aqueous sodium bicarbonate and extracted with ethyl acetate. The combined extracts were dried over sodium sulfate, filtered, concentrated, and purified by flash chromatography over silica gel (heptanes with 25-100% ethyl acetate) to give 2-(2-hydroxyethoxy)-6-(3-methoxyoxetan-3-yl)pyridin-4-yl trifluoromethanesulfonate, as a colorless oil in 63% yield. LCMS (m/z) (M+H)=373.9, Rt=0.82 min.

Synthesis of 2-(4-hydroxytetrahydro-2H-pyran-4-yl)-6-(2-oxooxazolidin-3-yl)pyridin-4-yl trifluoromethanesulfonate

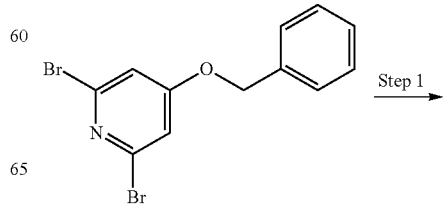

Step 1

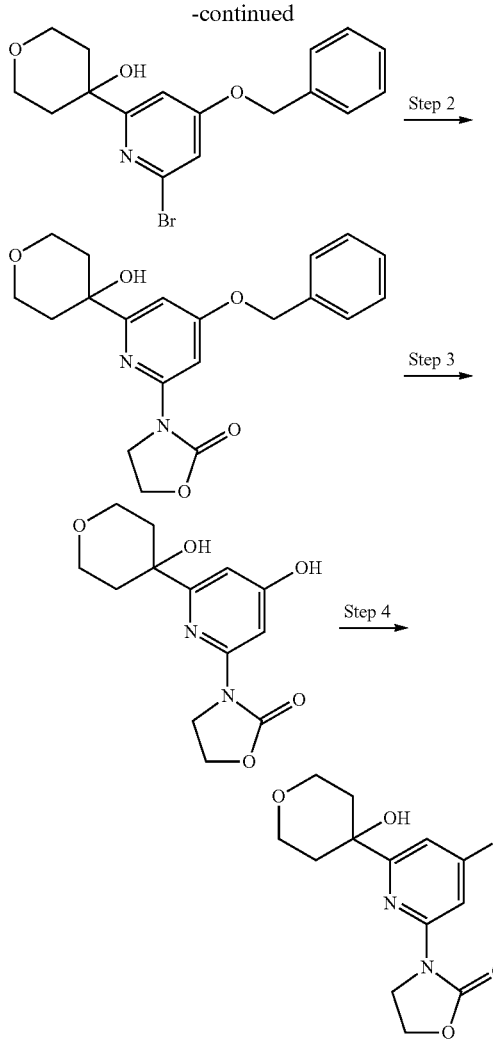

Step 1

A light yellow solution of 4-(benzyloxy)-2,6-dibromopyridine (1.0 equiv.) in THF (0.1 M) was cooled to 0° C. Isopropylmagnesium chloride (1.05 equiv.) was added dropwise, and the mixture was allowed to warm to RT and stirred for 3 h. Dihydro-2H-pyran-4(3H)-one (1.15 equiv.) was then added dropwise, and the mixture was allowed to stir for 1 h. The reaction mixture was quenched by the addition of saturated aqueous sodium bicarbonate and extracted with ethyl acetate. The combined extracts were dried over sodium sulfate, filtered, concentrated, and purified by flash chromatography over silica gel (pentane with 5-50% ethyl acetate gradient) to give 4-(4-(benzyloxy)-6-bromopyridin-2-yl)tetrahydr-2H-pyran-4-ol as a colorless oil in 68% yield. LCMS (m/z) (M+H)=364.0/366.0, Rt=0.93 min.

Step 2

To a degassed mixture of 4-(4-(benzyloxy)-6-bromopyridin-2-yl)tetrahydro-2H-pyran-4-ol (1.0 equiv.), oxazolidin-2-one (1.2 equiv.), N,N-dimethylglycine (0.2 equiv.) and potassium carbonate (2.0 equiv.) in DMF (1 M) was added CuI (0.1 equiv.) and the mixture was stirred at 115° C. for 17 h. The reaction was cooled to ambient temperature and diluted with water and twice extracted with EtOAc. The combined organics were dried over $Na_2SO_4$, filtered, concentrated, and purified by flash chromatography over silica gel (heptanes with 75-100% ethyl acetate gradient) to give 3-(4-(benzyloxy)-6-(4-hydroxytetrahydro-2H-pyran-4-yl)pyridin-2-yl)oxazolidin-2-one, as a white crystalline solid in 73% yield. $^1$H NMR (400 MHz, <cdcl3>) δ ppm 7.86 (d, J=1.96 Hz, 1H) 7.32-7.49 (m, 5H) 6.73 (d, J=1.96 Hz, 1H) 5.16 (s, 2H) 4.39-4.56 (m, 3H) 4.24-4.35 (m, 2H) 3.86-4.01 (m, 4H) 2.00-2.17 (m, 2H) LCMS (m/z) (M+H)=371.0, Rt=0.69 min.

Step 3

To a degassed solution of 3-(4-(benzyloxy)-6-(4-hydroxytetrahydro-2H-pyran-4-yl)pyridin-2-yl)oxazolidin-2-one (1.0 equiv.) in methanol (0.07 M) was added palladium on carbon (0.05 equiv.). The flask was purged and flushed twice with hydrogen from a balloon. The reaction was stirred for 70 min under a hydrogen atmosphere. The reaction mixture was degassed and diluted with DCM. The mixture was filtered through Celite. The filtrate was concentrated to give 3-(4-hydroxy-6-(4-hydroxytetrahydro-2H-pyran-4-yl)pyridin-2-yl)oxazolidin-2-one in quantitative yield. LCMS (m/z) (M+H)=281.0, Rt=0.34 min.

Step 4

To a stirred solution of 3-(4-hydroxy-6-(4-hydroxytetrahydro-2H-pyran-4-yl)pyridin-2-yl)oxazolidin-2-one (1.0 equiv.) in acetone (0.1 M) at RT were added potassium carbonate (1.5 equiv.) and Comin's regent (1.1 equiv.), and the reaction was allowed stirred for 2 h. The mixture was diluted with DCM and filtered through a pad of $SiO_2$, washing with DCM. The combined filtrates were concentrated and purified by flash chromatography over silica gel (heptanes with 40-90% ethyl acetate gradient) to give 2-(4-hydroxytetrahydro-2H-pyran-4-yl)-6-(2-oxoxazolidin-3-yl)pyridin-4-yl trifluoromethanesulfonate in 73% yield. LCMS (m/z) (M+H)=412.9, Rt=0.81 min.

Synthesis of 2-(3-hydroxyoxetan-3-yl)-6-(2-oxoxazolidin-3-yl)pyridin-4-yl trifluoromethanesulfonate

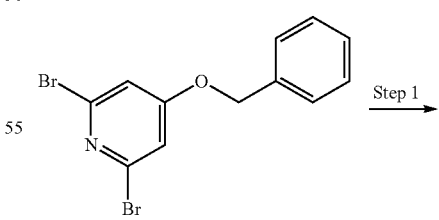

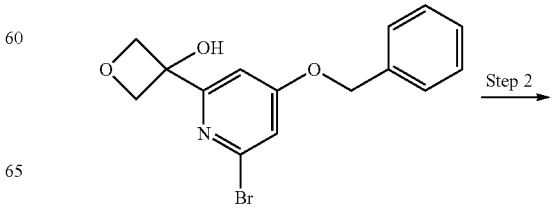

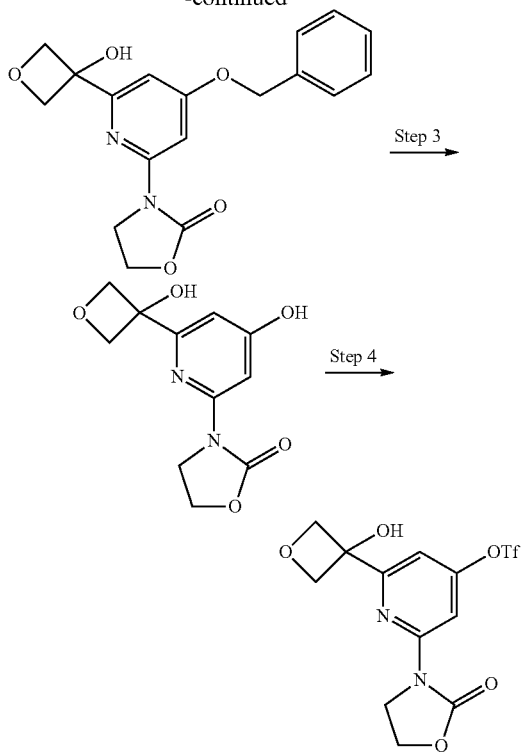

Step 1

A light yellow solution of 4-(benzyloxy)-2,6-dibromopyridine (1.0 equiv.) in THF (0.1 M) was cooled to 0° C. Isopropylmagnesium chloride (1.1 equiv.) was added dropwise, and the mixture was allowed to warm to RT and stirred for 3 h. Oxetan-3-one (1.2 equiv.) was then added dropwise, and the mixture was allowed to stir for 1 h. The reaction mixture was quenched by the addition of saturated aqueous sodium bicarbonate and extracted with ethyl acetate. The combined extracts were dried over sodium sulfate, filtered, concentrated, and purified by flash chromatography over silica gel (pentane with 0-30% ethyl acetate gradient) to give 3-(4-(benzyloxy)-6-bromopyridin-2-yl)oxetan-3-ol as a colorless oil in 27% yield. LCMS (m/z) (M+H)=335.9/337.9, Rt=0.87 min.

Step 2

To a degassed mixture of 3-(4-(benzyloxy)-6-bromopyridin-2-yl)oxetan-3-ol (1.0 equiv.), oxazolidin-2-one (1.2 equiv.), N,N-dimethylglycine (0.2 equiv.) and potassium carbonate (2.0 equiv.) in DMF (1 M) was added CuI (0.1 equiv.) and the mixture was stirred at 115° C. for 17 h. The reaction was cooled to ambient temperature and diluted with water and twice extracted with EtOAc. The combined organics were dried over $Na_2SO_4$, filtered, concentrated, and purified by flash chromatography over silica gel (heptanes with 75-100% ethyl acetate gradient) to give 3-(4-(benzyloxy)-6-(3-hydroxyoxetan-3-yl)pyridin-2-yl)oxazolidin-2-one, as a white crystalline solid in 64% yield. $^1$H NMR (400 MHz, <cdcl3>) δ ppm 7.93 (d, J=1.96 Hz, 1H) 7.32-7.50 (m, 5H) 7.31 (d, J=2.35 Hz, 1H) 5.33 (s, 1H) 5.22 (s, 2H) 4.98-5.05 (m, 2H) 4.70 (d, J=7.04 Hz, 2H) 4.45-4.54 (m, 2H) 4.22-4.33 (m, 2H). LCMS (m/z) (M+H)=343.0, Rt=0.72 min.

Step 3

To a degassed solution of 3-(4-(benzyloxy)-6-(3-hydroxyoxetan-3-yl)pyridin-2-yl)oxazolidin-2-one (1.0 equiv.) in methanol (0.05 M) was added palladium on carbon (0.05 equiv.). The flask was purged and flushed twice with hydrogen from a balloon. The reaction was stirred for 70 min under a hydrogen atmosphere. The reaction mixture was degassed and diluted with DCM. The mixture was filtered through Celite. The filtrate was concentrated to give 3-(4-hydroxy-6-(3-hydroxyoxetan-3-yl)pyridin-2-yl)oxazolidin-2-one in 90% yield. LCMS (m/z) (M+H)=252.9, Rt=0.32 min.

Step 4

To a stirred solution of 3-(4-hydroxy-6-(3-hydroxyoxetan-3-yl)pyridin-2-yl)oxazolidin-2-one (1.0 equiv.) in acetone (0.1 M) at RT were added potassium carbonate (1.5 equiv.) and Comin's regent (1.1 equiv.), and the reaction was allowed stirred for 2 h. The mixture was diluted with DCM and filtered through a pad of $SiO_2$, washing with DCM. The combined filtrates were concentrated and purified by flash chromatography over silica gel (heptanes with 50-100% ethyl acetate gradient) to give 2-(3-hydroxyoxetan-3-yl)-6-(2-oxooxazolidin-3-yl)pyridin-4-yl trifluoromethanesulfonate in 73% yield. LCMS (m/z) (M+H)=384.9. Rt=0.76 min.

Synthesis of 2-((2-hydroxyethyl)amino)-6-(3-methoxyoxetan-3-yl)pyridin-4-yl trifluoromethanesulfonate

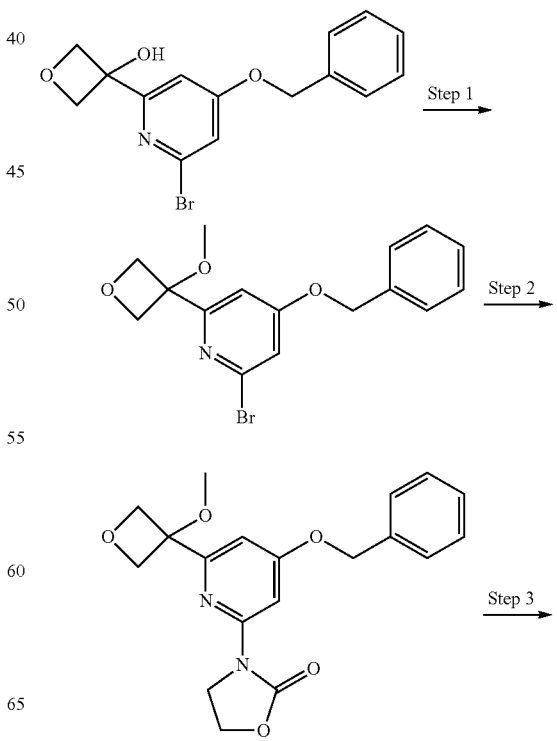

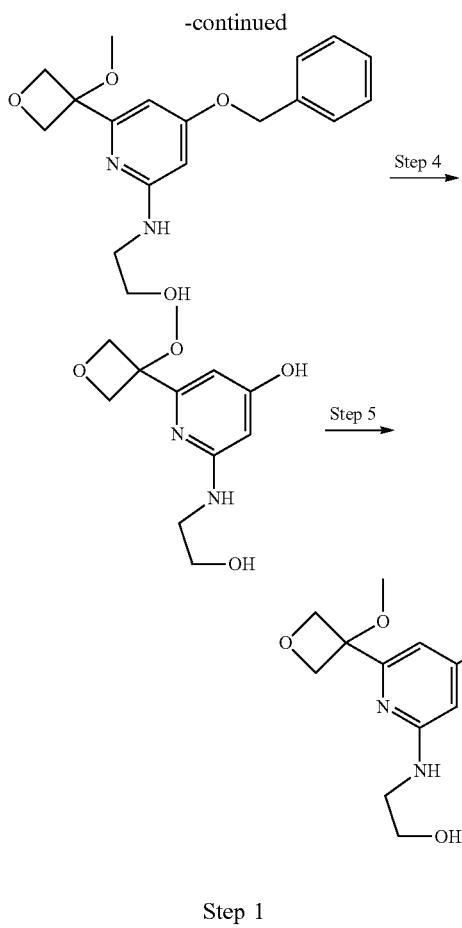

Step 1

To a stirred solution of 3-(4-(benzyloxy)-6-bromopyridin-2-yl)oxetan-3-ol (1.0 equiv.) in DMF (0.15 M) was added sodium hydride (1.1 equiv.). The mixture was stirred for 35 min at ambient temperature. Iodomethane (1.1 equiv.) was added, and the reaction was stirred for 3 hr at ambient temperature. The reaction mixture was diluted with water and extracted twice with ethyl acetate. The organic phases were dried over sodium sulfate, filtered, concentrated, and purified by flash chromatography over silica gel (heptanes with 10-60% ethyl acetate gradient) to give 4-(benzyloxy)-2-bromo-6-(3-methoxyoxetan-3-yl)pyridine in 70% yield. LCMS (m % z) (M+H)=349.9/351.9, Rt=0.99 min.

Step 2

To a degassed mixture of 4-(benzyloxy)-2-bromo-6-(3-methoxyoxetan-3-yl)pyridine (1.0 equiv.), oxazolidin-2-one (1.2 equiv.), N,N-dimethylglycine (0.2 equiv.) and potassium carbonate (2.0 equiv.) in DMF (1 M) was added CuI (0.1 equiv.) and the mixture was stirred at 115° C. for 15 h. The reaction was cooled to ambient temperature and diluted with water and twice extracted with EtOAc. The combined organics were dried over $Na_2SO_4$, filtered, concentrated, and purified by flash chromatography over silica gel (heptanes with 75-100% ethyl acetate gradient) to give 3-(4-(benzyloxy)-6-(3-methoxyoxetan-3-yl)pyridin-2-yl)oxazolidin-2-one, as a white crystalline solid in 60% yield. LCMS (m/z) (M+H)=357.0, Rt=0.88 min.

Step 3

To a solution of 3-(4-(benzyloxy)-6-(3-methoxyoxetan-3-yl)pyridin-2-yl)oxazolidin-2-one (1.0 equiv.) in ethanol (1 M) was added 6 M aqueous NaOH (5.0 equiv.) and the mixture was stirred at 100° C. for 40 min. The reaction was cooled to ambient temperature and diluted with water and twice extracted with EtOAc. The combined organics were dried over $Na_2SO_4$, filtered, concentrated to give 2-((4-(benzyloxy)-6-(3-methoxyoxetan-3-yl)pyridin-2-yl)amino) ethanol in quantitative yield. LCMS (m/z) (M+H)=331.1, Rt=0.61 min.

Step 4

To a degassed solution of 2-((4-(benzyloxy)-6-(3-methoxyoxetan-3-yl)pyridin-2-yl)amino)ethanol (1.0 equiv.) in methanol (0.07 M) was added palladium on carbon (0.05 equiv.). The flask was purged and flushed twice with hydrogen from a balloon. The reaction was stirred for 3 h under a hydrogen atmosphere. The reaction mixture was degassed and diluted with DCM. The mixture was filtered through Celite. The filtrate was concentrated to give 2-((2-hydroxyethyl)amino)-6-(3-methoxyoxetan-3-yl)pyridin-4-ol in 88% yield. LCMS (m/z) (M+H)=241.0, Rt=0.33 min.

Step 5

To a stirred solution of 2-((2-hydroxyethyl)amino)-6-(3-methoxyoxetan-3-yl)pyridin-4-ol (1.0 equiv.) in acetone (0.1 M) at RT were added potassium carbonate (1.5 equiv.) and Comin's regent (1.1 equiv.), and the reaction was allowed stirred for 2 h. The mixture was diluted with DCM and filtered through a pad of $SiO_2$, washing with DCM. The combined filtrates were concentrated and purified by flash chromatography over silica gel (heptanes with 50-100% ethyl acetate gradient) to give 2-((2-hydroxyethyl)amino)-6-(3-methoxyoxetan-3-yl)pyridin-4-yl trifluoromethanesulfonate in 70% yield. LCMS (m/z) (M+H)=373.0, Rt=0.74 min.

Synthesis of 2-(2-hydroxyethoxy)-6-(4-hydroxytetrahydro-2H-pyran-4-yl)pyridin-4-yl trifluoromethanesulfonate

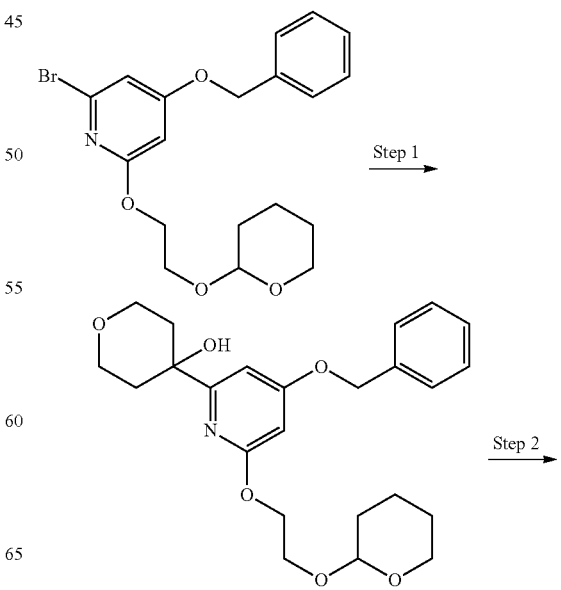

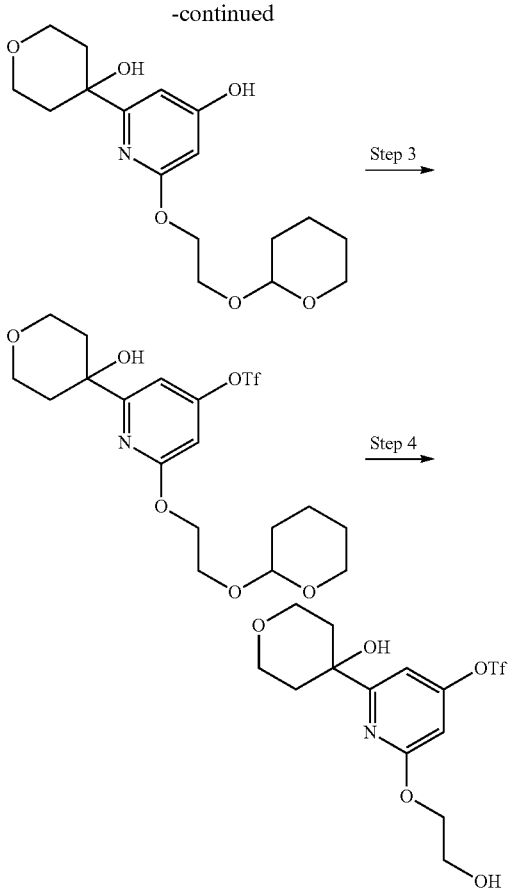

Step 1

A light yellow solution of 4-(benzyloxy)-2-bromo-6-(2-((tetrahydro-2H-pyran-2-yl)oxy)ethoxy)pyridine (1.0 equiv.) in THF (0.5 M) was cooled to −78° C. n-butyllithium (1.1 equiv.) was added dropwise, and the mixture was stirred for 30 min. A 1 M solution of dihydro-2H-pyran-3(4H)-one (1.2 equiv.) in THF was added dropwise, and the mixture was allowed to come to ambient temperature over 1 h. The reaction mixture was quenched by the addition of brine and extracted with ethyl acetate. The combined extracts were dried over sodium sulfate, filtered, concentrated, and purified by flash chromatography over silica gel (heptanes with 0-70% ethyl acetate gradient) to give 4-(4-(benzyloxy)-6-(2-((tetrahydro-2H-pyran-2-yl)oxy)ethoxy)pyridin-2-yl)tetrahydro-2H-pyran-4-ol as a colorless oil in 71% yield. LCMS (m/z) (M+H)=430.2, Rt=0.85 min.

Step 2

To a degassed solution of 4-(4-(benzyloxy)-6-(2-((tetrahydro-2H-pyran-2-yl)oxy)ethoxy)pyridin-2-yl)tetrahydro-2H-pyran-4-ol (1.0 equiv.) in methanol (0.05 M) was added palladium on carbon (0.05 equiv.). The flask was purged and flushed twice with hydrogen from a balloon. The reaction was stirred for 1 hr under a hydrogen atmosphere. The reaction mixture was degassed and diluted with DCM. The mixture was filtered through Celite. The filtrate was concentrated to give 2-(4-hydroxytetrahydro-2H-pyran-4-yl)-6-(2-((tetrahydro-2H-pyran-2-yl)oxy)ethoxy)pyridin-4-ol which was used without further purification. LCMS (m/z) (M+H)=340.3, Rt=0.49 min.

Step 3

To a solution of 2-(4-hydroxytetrahydro-2H-pyran-4-yl)-6-(2-((tetrahydro-2H-pyran-2-yl)oxy)ethoxy)pyridin-4-ol (1.0 equiv.) in acetone (0.1 M) at RT were added potassium carbonate (1.5 equiv.) and Comin's regent (1.1 equiv.), and the reaction was allowed stirred for 2 h. The mixture was diluted with DCM and filtered through a pad of $SiO_2$, washing with DCM. The combined filtrates were concentrated and purified by flash chromatography over silica gel (heptanes with 0-100% ethyl acetate gradient) to give 2-(4-hydroxytetrahydro-2H-pyran-4-yl)-6-(2-((tetrahydro-2H-pyran-2-yl)oxy)ethoxy)pyridin-4-yl trifluoromethanesulfonate in 73% yield. LCMS (m/z) (M+H)=472.0, Rt=0.93 min.

Step 4

To a solution of 2-(4-hydroxytetrahydro-2H-pyran-4-yl)-6-(2-((tetrahydro-2H-pyran-2-yl)oxy)ethoxy)pyridin-4-yl trifluoromethanesulfonate (1.0 equiv.) in THF (0.1 M) was added 0.6 M aqueous HCl (5.0 equiv.). The mixture was stirred vigorously for 2.5 hr at ambient temperature. The reaction mixture was neutralized with saturated aqueous sodium bicarbonate and extracted with ethyl acetate. The combined extracts were dried over sodium sulfate, filtered, concentrated to 2-(2-hydroxyethoxy)-6-(4-hydroxytetrahydro-2H-pyran-4-yl)pyridin-4-yl trifluoromethanesulfonate which was used without further purification. LCMS (m/z) (M+H)=388.2, Rt=0.68 min.

Synthesis of 2-(4-fluorotetrahydro-2H-pyran-4-yl)-6-(2-hydroxyethoxy)pyridin-4-yl trifluoromethanesulfonate

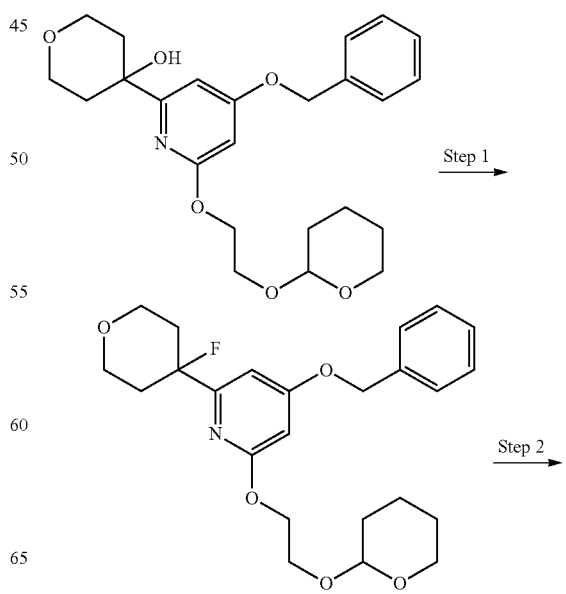

-continued

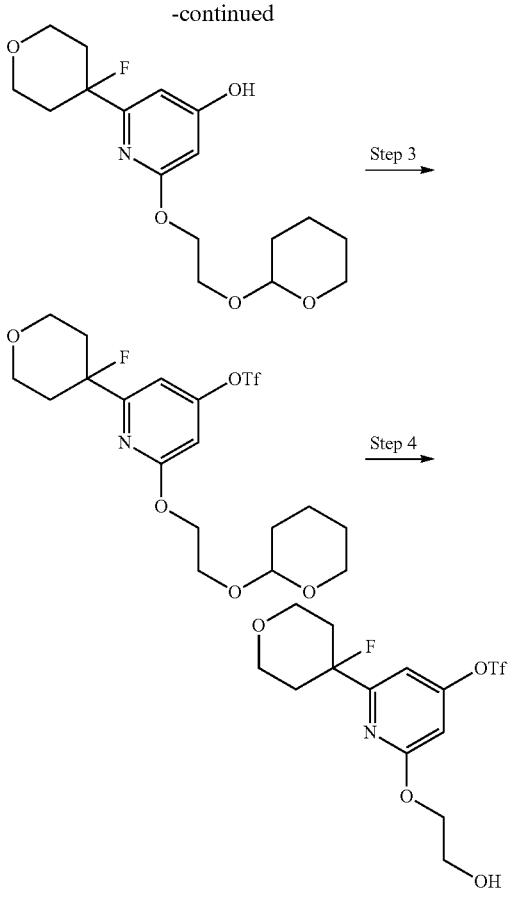

Step 1

To a stirred solution of 4-(4-(benzyloxy)-6-(2-((tetrahydro-2H-pyran-2-yl)oxy)ethoxy)pyridin-2-yl)tetrahydro-2H-pyran-4-ol (1.0 equiv.) in DCM (0.04 M) at −10° C. was added DAST (2.0 equiv.) dropwise, and the mixture was stirred for 20 min. The reaction mixture was quenched by the addition of saturated aqueous sodium bicarbonate, and the mixture was allowed to stir for 15 min while warming to RT. The mixture was extracted with DCM, and the combined extracts were washed with brine, dried over sodium sulfate, filtered, concentrated, and purified by flash chromatography over silica gel (heptanes with 0-50% ethyl acetate gradient) to give 4-(benzyloxy)-2-(4-fluorotetrahydro-2H-pyran-4-yl)-6-(2-((tetrahydro-2H-pyran-2-yl)oxy)ethoxy)pyridine as a colorless oil in 90% yield. LCMS (m/z) (M+H)=432.4, Rt=1.14 min.

Step 2

To a degassed solution of 4-(benzyloxy)-2-(4-fluorotetrahydro-2H-pyran-4-yl)-6-(2-((tetrahydro-2H-pyran-2-yl)oxy)ethoxy)pyridine (1.0 equiv.) in methanol (0.05 M) was added palladium on carbon (0.05 equiv.). The flask was purged and flushed twice with hydrogen from a balloon. The reaction was stirred for 1 hr under a hydrogen atmosphere. The reaction mixture was degassed and diluted with DCM. The mixture was filtered through Celite. The filtrate was concentrated to give 2-(4-fluorotetrahydro-2H-pyran-4-yl)-6-(2-((tetrahydro-2H-pyran-2-yl)oxy)ethoxy)pyridin-4-ol which was used without further purification. LCMS (m/z) (M+H)=342.3, Rt=0.65 min.

Step 3

To a solution of 2-(4-fluorotetrahydro-2H-pyran-4-yl)-6-(2-((tetrahydro-2H-pyran-2-yl)oxy)ethoxy)pyridin-4-ol (1.0 equiv.) in acetone (0.1 M) at RT were added potassium carbonate (1.5 equiv.) and Comin's regent (1.1 equiv.), and the reaction was allowed stirred for 2 h. The mixture was diluted with DCM and filtered through a pad of SiO$_2$, washing with DCM. The combined filtrates were concentrated and purified by flash chromatography over silica gel (heptanes with 0-100% ethyl acetate gradient) to give 2-(4-fluorotetrahydro-2H-pyran-4-yl)-6-(2-((tetrahydr-2H-pyran-2-yl)oxy)ethoxy)pyridin-4-yl trifluoromethanesulfonate in 90% yield. LCMS (m/z) (M+H)=474.3, Rt=1.13 min.

Step 4

To a solution of 2-(4-fluorotetrahydro-2H-pyran-4-yl)-6-(2-((tetrahydro-2H-pyran-2-yl)oxy)ethoxy)pyridin-4-yl trifluoromethanesulfonate (1.0 equiv.) in THF (0.1 M) was added 0.6 M aqueous HCl (5.0 equiv.). The mixture was stirred vigorously for 2.5 hr at ambient temperature. The reaction mixture was neutralized with saturated aqueous sodium bicarbonate and extracted with ethyl acetate. The combined extracts were dried over sodium sulfate, filtered, concentrated to 2-(4-fluorotetrahydro-2H-pyran-4-yl)-6-(2-hydroxyethoxy)pyridin-4-yl trifluoromethanesulfonate which was used without further purification. LCMS (m/z) (M+H)=390.2, Rt=0.85 min.

Synthesis of 5-(6-ethoxy-5-(3-methyloxetan-3-yl)pyridazin-3-yl)-6-methylpyridin-3-amine

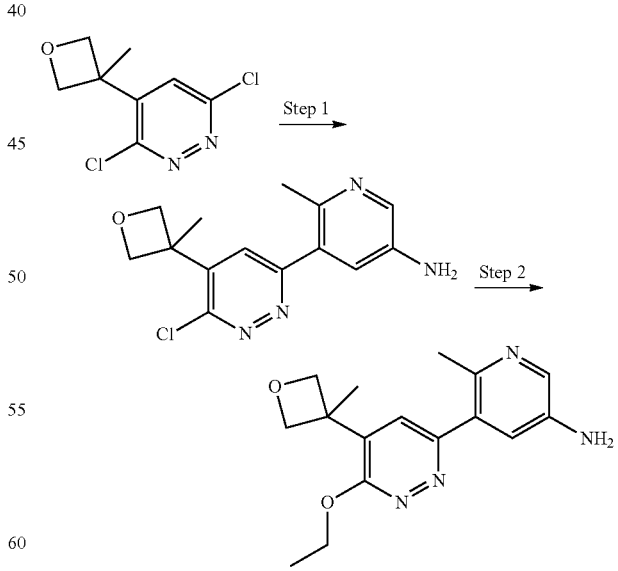

Step 1

To a solution of 3,6-dichloro-4-(3-methyloxetan-3-yl)pyridazine (1.0 equiv.) and 6-methyl-5-(4,4,5,5-tetramethyl- 1,3,2-dioxaborolan-2-yl)pyridin-3-amine (1.0 equiv.) in DME (0.2 M) was added sodium carbonate (3.0 equiv., 2M aqueous solution) and PdCl$_2$(dppf)-DCM adduct (0.05 equiv.) and the reaction was heated at 130° C. in the microwave for 30 min. The organic phase was concentrated to dryness and purified via reverse phase prep-HPLC. The pure fractions were concentrated to give 5-(6-chloro-5-(3-methyloxetan-3-yl)pyridazin-3-yl)-6-methylpyridin-3-amine in 14% yield. LCMS (m/z) (M+H)=290.9, Rt=0.40 min.

Step 2

To a solution of 5-(6-chloro-5-(3-methyloxetan-3-yl)pyridazin-3-yl)-6-methylpyridin-3-amine (1.0 equiv.) in dioxane (0.03 M) was added ethanol (6.0 equiv.) and sodium hydride (6.0 equiv.) and the mixture was heated at 100° C. for 15 min in the microwave. Upon cooling to rt, the reaction was quenched by the addition of water, then extracted with ethyl acetate. The organic phase was dried with magnesium sulfate, filtered and concentrated. The residue was purified via reverse phase prep HPLC to give 5-(6-ethoxy-5-(3-methyloxetan-3-yl)pyridazin-3-yl)-6-methylpyridin-3-amine in 29% yield. LCMS (m/z) (M+H)=301.0, Rt=0.51 min.

Synthesis of 3-(6-ethoxy-5-(3-methyloxetan-3-yl)pyridin-3-yl)-4-methylaniline

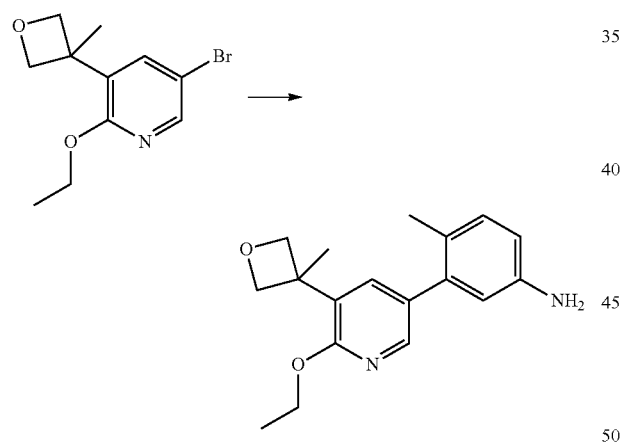

A solution of 5-bromo-2-ethoxy-3-(3-methyloxetan-3-yl)pyridine (1.0 equiv.) and 5-amino-2-methylphenylboronic acid, pinacol ester (1.1 equiv.) in DME (0.09 M) and sodium carbonate (2M aqueous solution, 3.0 equiv.) was purged with argon for 5 min, then PdCl$_2$(dppf)-DCM adduct (0.05 equiv.) was added and the mixture was purged with argon again and the reaction was heated to 100° C. for 2 hours. The mixture was poured into water and extracted with ethyl acetate (3×). The combined organics were washed with brine, dried over magnesium sulfate, filtered and concentrated. The residue was purified by Grace flash column chromatography (0-50% ethyl acetate/heptanes) and the product fractions were concentrated to give 3-(6-ethoxy-5-(3-methyloxetan-3-yl)pyridin-3-yl)-4-methylaniline as a colorless oil. LCMS (m/z) (M+H)=299.2, Rt=0.64 min.

Synthesis of 3-(5-(5-amino-2-methyl)-2-methoxypyridin-3-yl)oxetan-3-ol

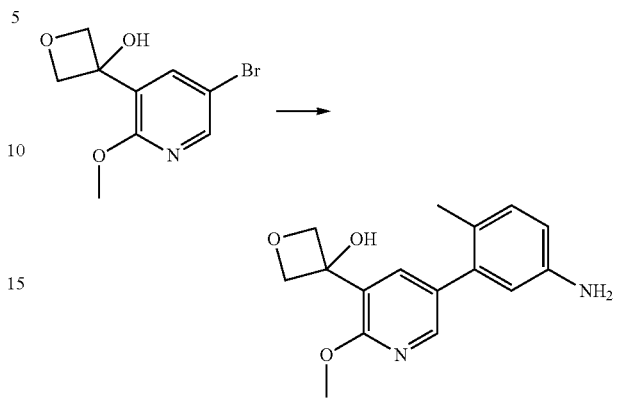

To a solution of 3-(5-bromo-2-methoxypyridin-3-yl)oxetan-3-ol (1.0 equiv.) and 4-methyl-3-(4,4,5,5-tetramethyl-1,3,2-dioxaborolan-2-yl)aniline (1.0 equiv.) in DME (0.17 M) was added PdCl$_2$(dppf)-DCM adduct (0.03 equiv.) and sodium carbonate (2M aqueous solution, 3.0 equiv.). The solution was heated in the microwave at 130° C. for 30 min. Partitioned between ethyl acetate and water, added brine and separated the layers. The organic phase was dried over magnesium sulfate, filtered and concentrated. The residue was purified via silica gel chromatography (0-100% ethyl acetate/heptanes) to give 3-(5-(5-amino-2-methylphenyl)-2-methoxypyridin-3-yl)oxetan-3-ol as a white solid in 77% yield. LCMS (m/z) (M+H)=287.0, Rt=0.44 min.

Synthesis of 3-(5'-amino-6-methoxy-2'-methyl-[3,3'-bipyridin]-5-yl)oxetan-3-ol

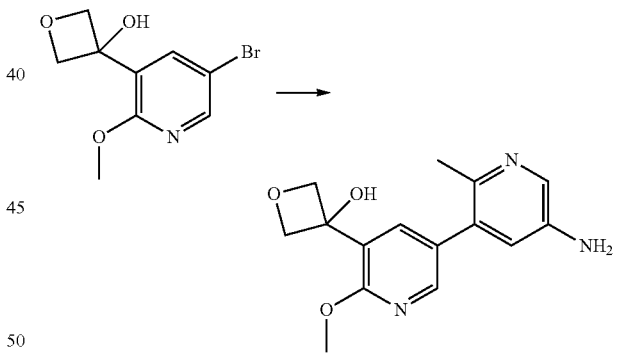

To a solution of 3-(5-bromo-2-methoxypyridin-3-yl)oxetan-3-ol (1.0 equiv.) and 6-methyl-5-(4,4,5,5-tetramethyl-1,3,2-dioxaborolan-2-yl)pyridin-3-amine (1.0 equiv.) in DME (0.17 M) was added PdCl$_2$(dppf)-DCM adduct (0.03 equiv.) and sodium carbonate (2M aqueous solution, 3.0 equiv.). The solution was heated in the microwave at 130° C. for 30 min. Partitioned between ethyl acetate and water, added brine and separated the layers. The organic phase was dried over magnesium sulfate, filtered and concentrated. The residue was purified via silica gel chromatography (0-8% methanol/DCM with 0.1% TEA) to give 3-(5'-amino-6-methoxy-2'-methyl-[3,3'-bipyridin]-5-yl)oxetan-3-ol in 70% yield. LCMS (m/z) (M+H)=288.0, Rt=0.35 min.

The following intermediates of Table 1 were synthesized according to the conditions described above, using appropriate starting materials:

TABLE 1

| Intermediate Name | Intermediate Structure | Physical Data |
| --- | --- | --- |
| 5'-(3-fluorooxetan-3-yl)-6'-methoxy-2-methyl-[3,3'-bipyridin]-5-amine | | LCMS (m/z) (M + H) = 290.0, Rt = 0.47 min. |
| 6-methyl-5-(3-(3-methyloxetan-3-yl)phenyl)pyridin-3-amine | | LCMS (m/z) (M + H) = 255.2, Rt = 0.52 min. |
| 6-methyl-5-(3-(oxetan-3-yl)phenyl)pyridin-3-amine | | LCMS (m/z) (M + H) = 241.1, Rt = 0.47 min. |
| 6-methyl-3'-(oxetan-3-yl)-[1,1'-biphenyl]-3-amine | | |
| 6'-ethoxy-2-methyl-5'-(3-methyloxetan-3-yl)-[3,3'-bipyridin]-5-amine | | LCMS (m/z) (M + H) = 300.2, Rt = 0.55 min. |
| 6'-ethoxy-5'-(3-(fluoromethyl)oxetan-3-yl)-2-methyl-[3,3'-bipyridin]-5-amine | | LCMS (m/z) (M + H) = 318.2, Rt = 0.57 min. |
| 3-(5-(3-fluorooxetan-3-yl)-6-methoxypyridin-3-yl)-4-methylaniline | | LCMS (m/z) (M + H) = 289.0, Rt = 0.57 min. |

TABLE 1-continued

| Intermediate Name | Intermediate Structure | Physical Data |
| --- | --- | --- |
| 6'-ethoxy-5'-(3-fluorooxetan-3-yl)-2-methyl-[3,3'-bipyridin]-5-amine | | LCMS (m/z) (M + H) = 304.2, Rt = 0.53 min. |
| 3-(5-(3-(fluoromethyl)oxetan-3-yl)-6-methoxypyridin-3-yl)-4-methylaniline | | LCMS (m/z) (M + H) = 303.2, Rt = 0.60 min. |
| 5'-(3-(fluoromethyl)oxetan-3-yl)-6'-methoxy-2-methyl-[3,3'-bipyridin]-5-amine | | LCMS (m/z) (M + H) = 304.0, Rt = 0.46 min. |
| 3-(5-(5-amino-2-methylphenyl)-2-methoxypyridin-3-yl)oxetane-3-carbonitrile | | LCMS (m/z) (M + H) = 296.0, Rt = 0.53 min. |
| 3-(5'-amino-6-methoxy-2'-methyl-[3,3'-bipyridin]-5-yl)oxetane-3-carbonitrile | | LCMS (m/z) (M + H) = 297.0, Rt = 0.43 min. |
| 3-(5-(3-(difluoromethyl)oxetan-3-yl)-6-methoxypyridin-3-yl)-4-methylaniline | | LCMS (m/z) (M + H) = 321.0, Rt = 0.59 min. |
| 5'-(3-(difluoromethyl)oxetan-3-yl)-6'-methoxy-2-methyl-[3,3'-bipyridin]-5-amine | | LCMS (m/z) (M + H) = 322.0, Rt = 0.51 min. |

TABLE 1-continued

| Intermediate Name | Intermediate Structure | Physical Data |
| --- | --- | --- |
| 3-(5-(5-amino-2-methylphenyl)-2-((tetrahydro-2H-pyran-4-yl)oxy)pyridin-3-yl)oxetan-3-ol | | LCMS (m/z) (M + H) = 357.3, Rt = 0.50 min. |
| 3-(5'-amino-2'-methyl-6-((tetrahydro-2H-pyran-4-yl)oxy)-[3,3'-bipyridin]-5-yl)oxetan-3-ol | | LCMS (m/z) (M + H) = 358.3, Rt = 0.42 min. |
| 3-(5-(5-amino-2-methylphenyl)-2-ethoxypyridin-3-yl)oxetan-3-ol | | LCMS (m/z) (M + H) = 301.2, Rt = 0.49 min. |
| 5-(6-ethoxy-5-(3-methyloxetan-3-yl)pyridazin-3-yl)-6-methylpyridin-3-amine | | LCMS (m/z) (M + H) = 301.0, Rt = 0.48 min. |
| 3-(3-(5-amino-2-methylpyridin-3-yl)-5-(3-fluorooxetan-3-yl)phenyl)oxetan-3-ol | | LCMS (m/z) (M + H) = 331.0, Rt = 0.40 min. |

TABLE 1-continued
| Intermediate Name | Intermediate Structure | Physical Data |
|---|---|---|
| 3-(5'-amino-5-(3-fluorooxetan-3-yl)-2'-methyl-[1,1'-biphenyl]-3-yl)oxetan-3-ol | | LCMS (m/z) (M + H) = 330.0, Rt = 0.50 min. |
| 4-methyl-3-(8-(3-methyloxetan-3-yl)imidazo[1,2-b]pyridazin-6-yl)aniline | | LCMS (m/z) (M + H) = 295.0, Rt = 0.39 min. |
Synthesis of 2-((5-amino-6'-(3-(fluoromethyl)oxetan-3-yl)-2-methyl-[3,4'-bipyridin]-2'-yl)oxy)ethanol
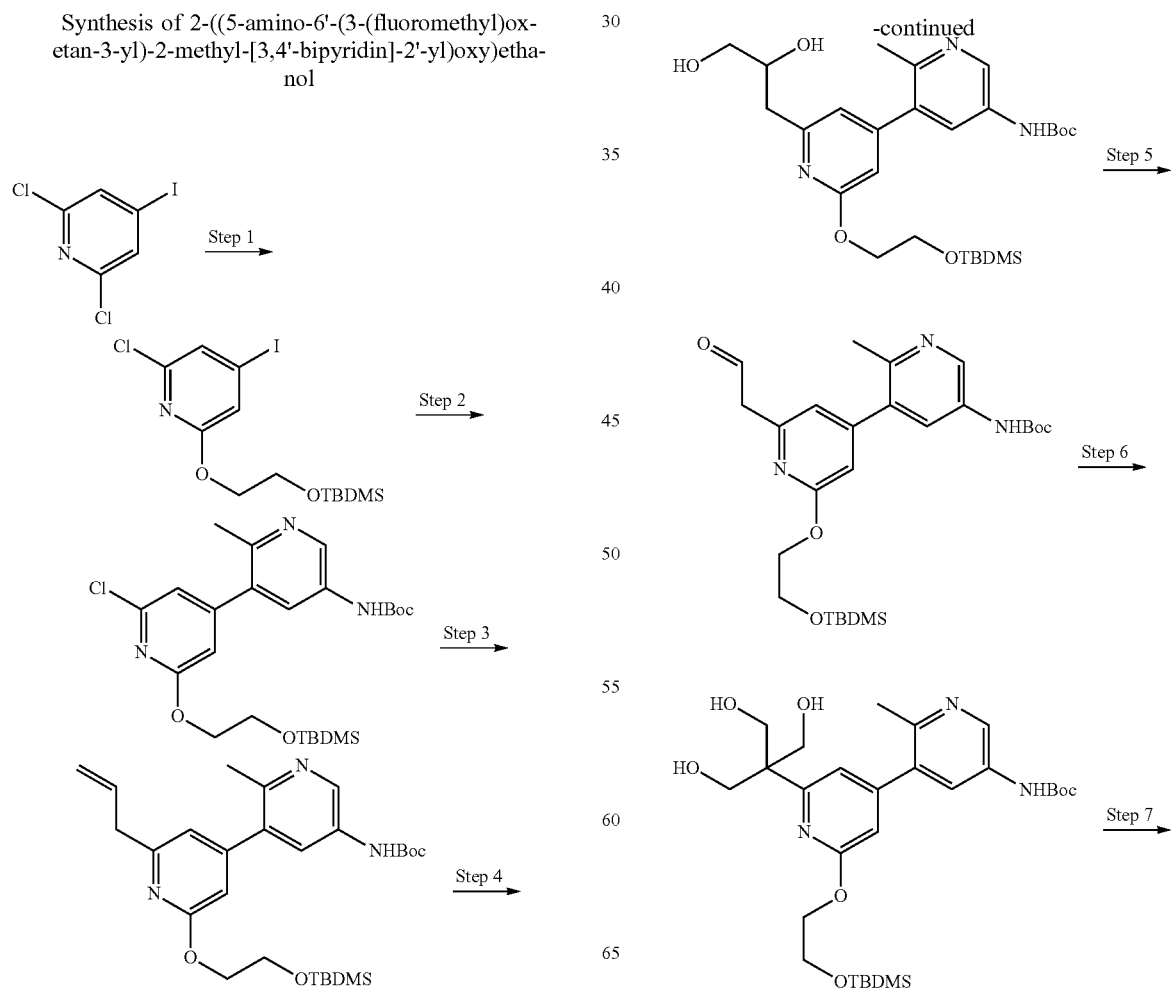

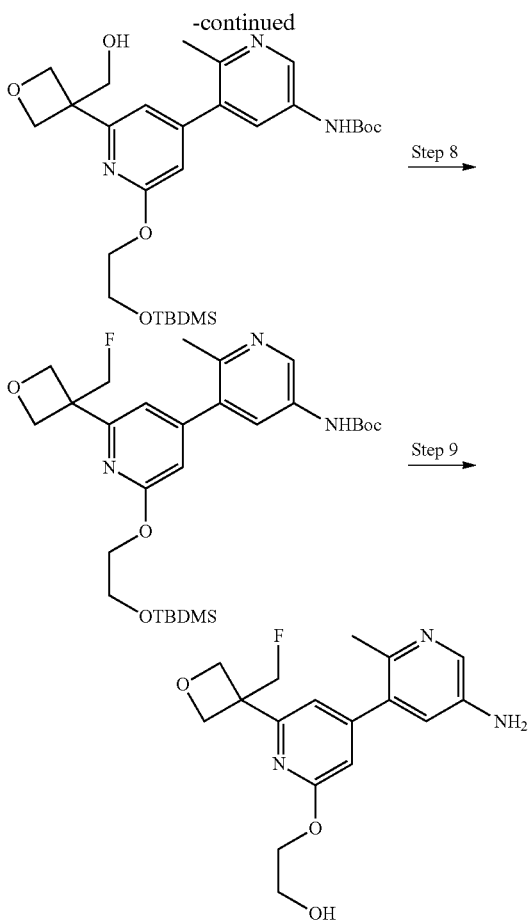

Step 1

A solution of 2,6-dichloro-4-iodopyridine (1.0 equiv.) in THF (0.3 M) was cooled to 0° C. Sodium hydride (1.5 equiv.) was added, followed by 2-((tert-butyldimethylsilyl)oxy)ethanol (1.1 equiv.) via syringe. The solution was stirred for 30 min at 0° C., then allowed to warm to rt and stirred overnight. Cooled to 0° C. and quenched by the addition of sat. sodium bicarbonate. The solution was partitioned between 1:1 n-heptanes/ethyl acetate and sat. sodium bicarbonate. The organic phase was washed with brine, dried over magnesium sulfate, filtered and concentrated. The residue was purified via silica gel chromatography (0-20% ethyl acetate/n-heptanes) to give 2-(2-((tert-butyldimethylsilyl)oxy)ethoxy)-6-chloro-4-iodopyridine in 74% yield. LCMS (m/z) (M+H)=413.9, Rt=1.43 min.

Step 2

To a solution of 2-(2-((tert-butyldimethylsilyl)oxy)ethoxy)-6-chloro-4-iodopyridine (1.0 equiv.), potassium carbonate (3.0 equiv.) and tert-butyl (6-methyl-5-(4,4,5,5-tetramethyl-1,3,2-dioxaborolan-2-yl)pyridin-3-yl)carbamate (1.2 equiv.) in THF and water (4:1, 0.2 M) was added PdCl₂(dppf)-DCM adduct (0.03 equiv.) and the reaction was heated to 90° C. in an oil bath for 3 hours. Upon cooling to rt, the solution was partitioned between ethyl acetate and water, the organic phase was washed with brine, dried over magnesium sulfate, filtered and concentrated. The residue was purified via silica gel chromatography (0-80% ethyl acetate/n-heptanes) to give tert-butyl (2'-(2-((tert-butyldimethylsilyl)oxy)ethoxy)-6-chloro-2-methyl-[34'-bipyridin]-5-yl)carbamate in 82% yield. LCMS (m/z) (M+H)=494.2, Rt=1.11 min.

Step 3

To a degassed solution of tert-butyl (2'-(2-((tert-butyldimethylsilyl)oxy)ethoxy)-6'-chloro-2-methyl-[3,4'-bipyridin]-5-yl)carbamate (1.0 equiv.), 2-allyl-4,4,5,5-tetramethyl-1,3,2-dioxaborolane (1.5 equiv.), cesium fluoride (3.0 equiv.) in acetonitrile (0.14 M) was added PdCl₂(dppf)-DCM adduct (0.1 equiv.) and the reaction was heated to 95° C. for 2 hours. The solution was cooled to rt, filtered and rinsed with ethyl acetate. The organic phase was concentrated to dryness and purified via silica gel chromatography (ISCO, 0-60% ethyl acetate/n-heptanes) to give tert-butyl (2'-allyl-6'-(2-((tert-butyldimethylsilyl)oxy)ethoxy)-2-methyl-[3,4'-bipyridin]-5-yl)carbamate in 70% yield. LCMS (m/z) (M+H)=500.2, Rt=1.14 min.

Step 4

To a solution of tert-butyl (2'-allyl-6'-(2-((tert-butyldimethylsilyl)oxy)ethoxy)-2-methyl-[3,4'-bipyridin]-5-yl)carbamate (1.0 equiv.) in water and acetone (1:9, 0.1 M) was added NMO (1.3 equiv.) followed by OsO₄ solution (0.02 equiv.). The solution was stirred at it overnight. Diluted with ethyl acetate, cooled to 0 C and added sat. Na₂S₂O₃. Stirred for 30 min and partitioned between ethyl acetate. The organic phase was washed with sat. sodium bicarbonate, brine, dried over magnesium sulfate, filtered and concentrated. The residue was purified via silica gel chromatography (ISCO, 0-100% ethyl acetate/n-heptanes) to give tert-butyl (2'-(2-((tert-butyldimethylsilyl)oxy)ethoxy)-6'-(2,3-dihydroxypropyl)-2-methyl-[3,4'-bipyridin]-5-yl)carbamate in 78% yield. LCMS (m/z) (M+H)=534.2. Rt=0.91 min.

Step 5

To a solution of tert-butyl (2'-(2-((tert-butyldimethylsilyl)oxy)ethoxy)-6'-(2,3-dihydroxypropyl)-2-methyl-[3,4'-bipyridin]-5-yl)carbamate (1.0 equiv.) in acetone (0.1 M) and water was added NaIO₄ (2.05 equiv.) and the solution was stirred at rt for 3 hours. Cooled to 0° C. and quenched by the addition of 10% Na₂S₂O₃. Stirred for 10 min and partitioned between ethyl acetate and water. The organic phase was washed with 10% Na₂S₂O₃, brine, dried over magnesium sulfate, filtered and concentrated to give tert-butyl (2'-(2-((tert-butyldimethylsilyl)oxy)ethoxy)-2-methyl-6'-(2-oxoethyl)-[3,4'-bipyridin]-5-yl)carbamate in quantitative yield. LCMS (m/z) (M+H)=502.2, Rt=1.06 min.

Step 6 tert-butyl (2'-(2-((tert-butyldimethylsilyl)oxy)ethoxy)-2-methyl-6'-(2-oxoethyl)-[3,4'-bipyridin]-5-yl)carbamate (1.0 equiv.), paraformaldehyde (12 equiv.) and calcium hydroxide (14 equiv.) were stirred in THF (0.3 M) and heated in a 75° C. oil bath overnight. Upon cooling to rt, the volatiles were removed under vacuo and dissolved in DCM and Methanol. The mixture was filtered through Celite and also 1 uM HPLC filter and the filtrates were concentrated under vacuo. The residue was purified via silica gel chromatography (0-10% methanol/DCM with 0.1% DIEA) to give tert-butyl (2'-(2-((tert-butyldimethylsilyl)oxy)ethoxy)-6'-(1, 3-dihydroxy-2-(hydroxymethyl)propan-2-yl)-2-methyl-[3, 4'-bipyridin]-5-yl)carbamate in 43% yield. LCMS (m/z) (M+H)=564.2, Rt=0.91 min.

Step 7

To tert-butyl (2'-(2-(((tert-butyldimethylsilyl)oxy)ethoxy)-6'-(1,3-dihydroxy-2-(hydroxymethyl)propan-2-yl)-2-methyl-[3,4'-bipyridin]-5-yl)carbamate (1.0 equiv.), triphenylphosphine (1.1 equiv.) was added toluene (0.06 M) and DIAD (1.1 equiv.) and the reaction was heated to 65° C. in an oil bath overnight. The volatiles were removed in vacuo and the residue was purified by silica gel chromatography (ISCO, 0-100% ethyl acetate/n-heptanes, then 10% methanol/DCM with 0.1% DIEA) to give tert-butyl (2'-(2-(((tert-butyldimethylsilyl)oxy)ethoxy)-6'-(3-(hydroxymethyl)oxetan-3-yl)-2-methyl-[3,4'-bipyridin]-5-yl)carbamate in 37% yield. LCMS (m/z) (M+H)=546.3, Rt=1.00 min.

Step 8

To a solution of tert-butyl (2'-(2-((tert-butyldimethylsilyl)oxy)ethoxy)-6'-(3-(hydroxymethyl)oxetan-3-yl)-2-methyl-[3,4'-bipyridin]-5-yl)carbamate (1.0 equiv.) in DCM (0.05 M) at −78° C. was added DAST (2.0 equiv.). After 5 min, the solution was allowed to warm to rt and stirred for 3 hours. Quenched by the addition of sat. sodium bicarbonate, ice and ethyl acetate. The organic phase was washed with brine, dried over magnesium sulfate, filtered and concentrated. The residue was purified via silica gel chromatography (ISCO, 0-10% methanol/DCM with 0.1% DIEA) to give tert-butyl (2'-(2-(((tert-butyldimethylsilyl)oxy)ethoxy)-6'-(3-(fluoromethyl)oxetan-3-yl)-2-methyl-[3,4'-bipyridin]-5-yl)carbamate in 32% yield. LCMS (m/z) (M+H)=548.2, Rt=1.10 min.

Step 9

A solution of tert-butyl (2'-(2-(((tert-butyldimethylsilyl)oxy)ethoxy)-6'-(3-(fluoromethyl)oxetan-3-yl)-2-methyl-[3, 4'-bipyridin]-5-yl)carbamate (1.0 equiv.) was treated with 35% TFA/DCM (0.01 M) and the reaction was stirred for 30 min at rt, then the volatiles were removed in vacuo. Partitioned between ethyl acetate and water, sodium carbonate was added, the organic phase was washed with brine, dried over magnesium sulfate, filtered and concentrated to give 2-((5-amino-6'-(3-(fluoromethyl)oxetan-3-yl)-2-methyl-[3, 4'-bipyridin]-2'-yl)oxy)ethanol in quantitative yield. LCMS (m/z) (M+H)=334.0, Rt=0.41 min.

Synthesis of 5-(5-amino-2-methylphenyl)-1-methyl-3-(oxetan-3-yl)pyridin-2(1H)-one

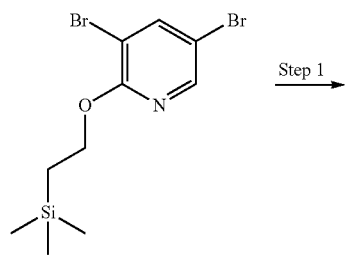

Step 1

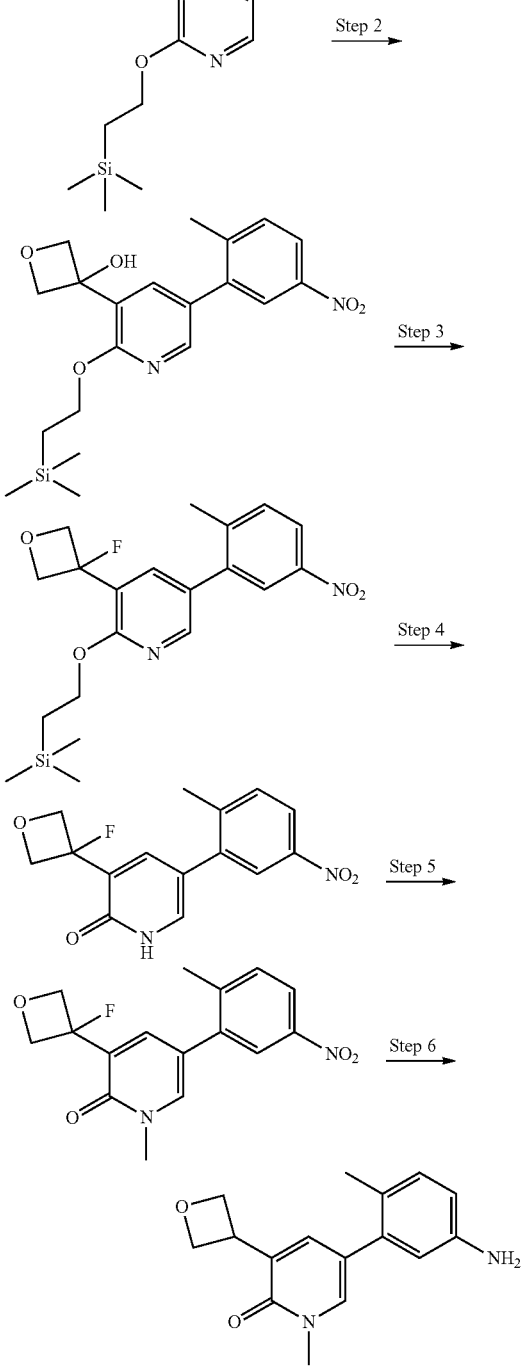

Step 1

To 3,5-dibromo-2-(2-(trimethylsilyl)ethoxy)pyridine (1.0 equiv.) in a flame-dried round-bottomed flask under an argon atmosphere was added MTBE (0.1 M) and cooled to −78° C. n-butyllithium (1.6 M, 1.2 equiv.) was added via syringe with the internal temperature not exceeding −68° C. The solution was stirred for 1 hours at this temperature, then oxetan-3-one (1.4 equiv.) was added in MTBE via syringe. The reaction was allowed to stir cold for 15 min, then warmed to rt slowly and stirred for 5 hours. The reaction was quenched by the addition of sat. sodium bicarbonate and diluted with ethyl acetate. The organic phase was washed with brine, dried over magnesium sulfate, filtered and concentrated. The residue was purified via silica gel chromatography eluting with 0-50%/ethyl acetate/n-heptanes to give 3-(5-bromo-2-(2-(trimethylsilyl)ethoxy)pyridin-3-yl)oxetan-3-ol in 12% yield. LCMS (m/z) (M+H)=345.9/347.9, Rt=1.06 min.

Step 2

To a solution of 3-(5-bromo-2-(2-(trimethylsilyl)ethoxy)pyridin-3-yl)oxetan-3-ol (1.0 equiv.) and 4,4,5,5-tetramethyl-2-(2-methyl-5-nitrophenyl)-1,3,2-dioxaborolane (1.05 equiv.) in DME (0.1 M) was added 2M sodium carbonate (3.0 equiv.) and PdCl$_2$(dppf)-DCM adduct (0.03 equiv.) and the reaction was heated in the microwave at 130° C. for 45 min. The reaction was partitioned between ethyl acetate and water and sat. sodium carbonate, the organic phase was washed with brine, dried over magnesium sulfate, filtered and concentrated. The residue was purified via silica gel chromatography eluting with 0-100% ethyl acetate/n-heptanes to give 3-(5-(2-methyl-5-nitrophenyl)-2-(2-(trimethylsilyl)ethoxy)pyridin-3-yl)oxetan-3-ol as a white solid in 65% yield. LCMS (m/z) (M+H)=403.0, Rt=1.10 min.

Step 3

To a solution of 3-(5-(2-methyl-5-nitrophenyl)-2-(2-(trimethylsilyl)ethoxy)pyridin-3-yl)oxetan-3-ol in DCM (0.07 M) under argon at −78° C. was added DAST (1.3 equiv.) and the reaction was stirred at −78° C. for 30 min, then allowed to warm to rt and stirred for another 30 min. Quenched by the addition of sat. sodium bicarbonate, then diluted with ethyl acetate, washed with sat. sodium bicarbonate, brine, dried over magnesium sulfate, filtered and concentrated. The residue was purified via silica gel chromatography eluting with 0-30% ethyl acetate/n-heptanes to give 3-(3-fluorooxetan-3-yl)-5-(2-methyl-5-nitrophenyl)-2-(2-(trimethylsilyl)ethoxy)pyridine in 44% yield. LCMS (m % z) (M+H)=405.0, Rt=1.27 min.

Step 4

To a solution of 3-(3-fluorooxetan-3-yl)-5-(2-methyl-5-nitrophenyl)-2-(2-(trimethylsilyl)ethoxy)pyridine (1.0 equiv.) in DCM (0.16 M) was added TFA (3.0 equiv.) and the solution was stirred at rt overnight. The volatiles were removed under vacuo and the residue was purified via silica gel chromatography (0-100% ethyl acetate/n-heptanes) to give 3-(3-fluorooxetan-3-yl)-5-(2-methyl-5-nitrophenyl)pyridin-2-ol in 44% yield. LCMS (m/z) (M+H)=304.9, Rt=0.67 min.

Step 5

To a solution of 3-(3-fluorooxetan-3-yl)-5-(2-methyl-5-nitrophenyl)pyridin-2(1H)-one (1.0 equiv.) in DMF (0.09 M) was added cesium carbonate (2.0 equiv.) and iodomethane (1.4 equiv.) and the solution was stirred at rt until consumption of starting material. Partitioned between water and ethyl acetate, the organic phase was washed with water (3×), brine, dried over magnesium sulfate, filtered, and concentrated. The residue was purified via silica gel chromatography eluting with 0-100% ethyl acetate/n-heptanes to give 3-(3-fluorooxetan-3-yl)-1-methyl-5-(2-methyl-5-nitrophenyl)pyridin-2(1H)-one in 50% yield. LCMS (m/z) (M+H)=318.9, Rt=0.73 min.

Step 6

To a degassed solution of 3-(3-fluorooxetan-3-yl)-1-methyl-5-(2-methyl-5-nitrophenyl)pyridin-2(1H)-one (1.0 equiv.) in methanol (0.01 M) was added Pd/C (wet, Degussa, 0.15 equiv.) and the reaction was purged to a hydrogen balloon. The solution was stirred under a hydrogen atmosphere for 5 hours, then filtered and the filtrate was concentrated to give 5-(5-amino-2-methylphenyl)-1-methyl-3-(oxetan-3-yl)pyridin-2(1H)-one in quantitative yield. LCMS (m/z) (M+H)=271.0, Rt=0.41 min.

Synthesis of 3-(2-(3-(difluoromethyl)oxetan-3-yl)-6-(2-((tetrahydro-2H-pyran-2-yl)oxy)ethoxy)pyridin-4-yl)-4-methylaniline

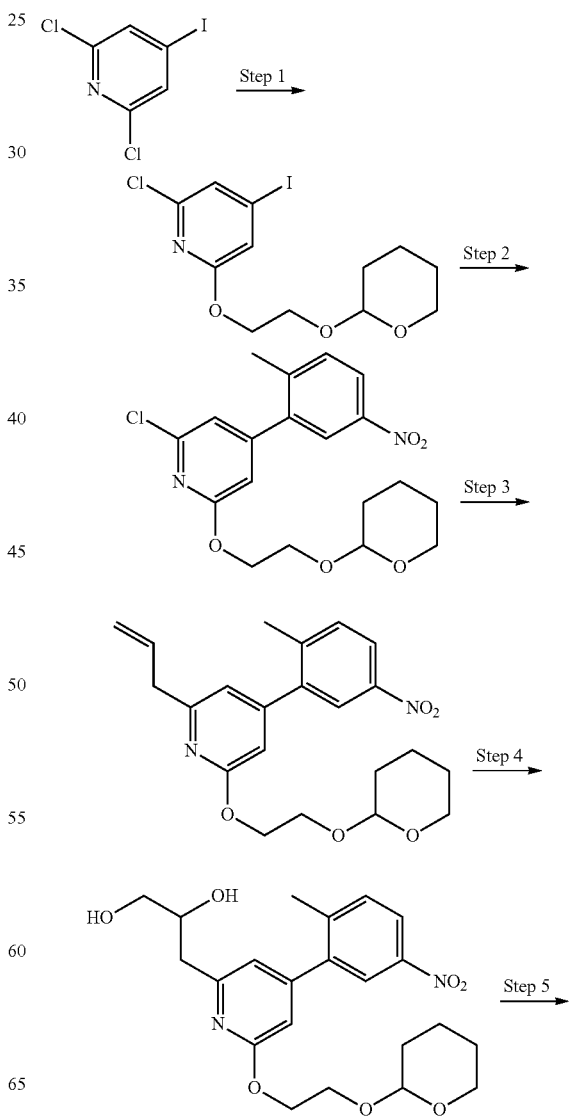

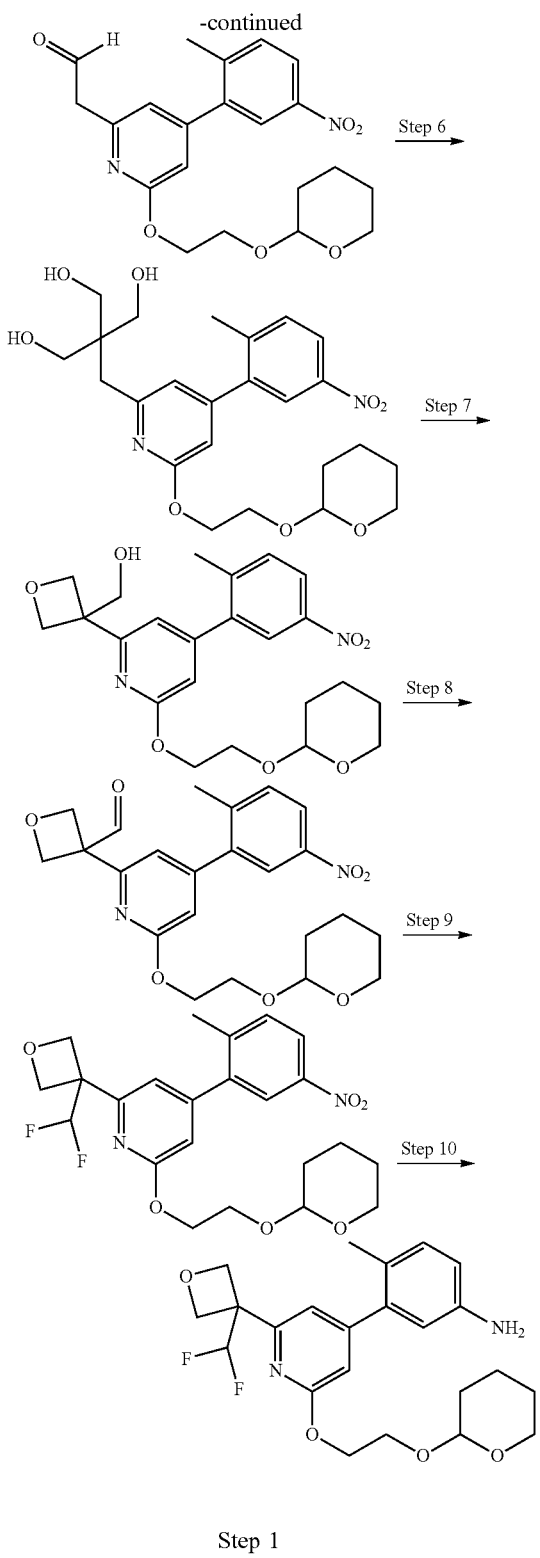

Step 1

To NaH (1.2 equiv.) in Tetrahydrofuran (0.3 M) was added 2-((tetrahydro-2H-pyran-2-yl)oxy)ethanol (1.2 equiv.). The mixture was stirred for 20 min at ambient temperature. The mixture was cooled in an ice/methanol bath. 2,6-dichloro-4-iodopyridine (1.0 equiv.) was added and the reaction was allowed to warm to rt. After 2.5 hr, the reaction was quenched by the addition of saturated aqueous NaHCO$_{3(sat.)}$ and extracted with ethyl acetate. The combined organics were dried over sodium sulfate, filtered, concentrated, and purified by flash chromatography over silica gel (heptanes with 0-20% ethyl acetate gradient) to give 2-chloro-4-iodo-6-(2-((tetrahydro-2H-pyran-2-yl)oxy)ethoxy)pyridine as a colorless oil which crystallized upon standing in 78% yield. LCMS (m/z) (M-THP+H)=299.9, Rt=1.18 min.

Step 2

To 2-chloro-4-iodo-6-(2-((tetrahydro-2H-pyran-2-yl)oxy)ethoxy)pyridine (1.0 equiv.) and (2-methyl-5-nitrophenyl)boronic acid (1.1 equiv.) in DME (0.24 M) was added PdCl$_2$(dppf).CH$_2$Cl$_2$ adduct (0.05 equiv.) and 2M aqueous sodium carbonate (3.0 equiv.). The reaction mixture was stirred at 100° C. for 1.5 hr. The cooled reaction mixture was diluted with water (25 mL) and extracted with ethyl acetate. The combined extracts were dried over sodium sulfate, filtered, and concentrated onto silica gel. This material was purified by flash chromatography over silica gel (heptanes with 5-25% ethyl acetate) to give 2-chloro-4-(2-methyl-5-nitrophenyl)-6-(2-((tetrahydro-2H-pyran-2-yl)oxy)ethoxy)pyridine, as a light yellow oil in 87% yield. LCMS (m/z) (M+Na)=415.1, Rt=1.22 min.

Step 3

To a solution of 2-chloro-4-(2-methyl-5-nitrophenyl)-6-(2-((tetrahydro-2H-pyran-2-yl)oxy)ethoxy)pyridine (1.0 equiv.) in MeCN (0.17 M) was added allylboronic acid pinacol ester (1.3 equiv.). The mixture was degassed by bubbling nitrogen through for 5 min. CsF (3.0 equiv.) was added, and degassing was continued for 5 min. PdCl$_2$(dppf).CH$_2$Cl$_2$ adduct (0.07 equiv.) was added, a reflux condenser was attached, and the flask was submerged in a 100° C. oil bath (the light orange suspension rapidly became a thick slurry—next time run less concentrated) and stirred vigorously for 1 hr. Upon cooling the solution was filtered, rinsing with EtOAc. The organic was concentrated and purified directly by ISCO SiO$_2$ chromatography (0-50% EtOAc/n-heptanes) to yield 2-allyl-4-(2-methyl-5-nitrophenyl)-6-(2-((tetrahydro-2H-pyran-2-yl)oxy)ethoxy)pyridine in 91% yield as a pale yellow oil. LCMS (m/z) (M+H)=399.2. Rt=1.19 min.

Step 4

To a solution of 2-allyl-4-(2-methyl-5-nitrophenyl)-6-(2-((tetrahydro-2H-pyran-2-yl)oxy)ethoxy)pyridine (1.0 equiv.) in acetone and H$_2$O (9:1 (0.1 M)) was added NMO (1.3 equiv.) followed by the OsO$_4$ in t-BuOH (0.02 equiv.). The solution was capped and stirred overnight (18 hr) at ambient temperature. The reaction was diluted with EtOAc, and Na$_2$S$_2$O$_3$ (sat.) was added. After stirring for 30 minutes the solution was poured into EtOAc, mixed, separated, washed with NaHCO$_{3(sat.)}$, dried over sodium sulfate, filtered, concentrated, and purified by ISCO SiO$_2$ chromatography (50-100% EtOAc/n-heptanes) to yield 3-(4-(2-methyl-5-nitrophenyl)-6-(2-((tetrahydro-2H-pyran-2-yl)oxy)ethoxy)pyridin-2-yl)propane-1,2-diol as a white foamy solid in 84% yield. LCMS (m/z) (M+Na)=433.3, Rt=0.81 min.

Step 5

To a solution of 3-(4-(2-methyl-5-nitrophenyl)-6-(2-((tetrahydro-2H-pyran-2-yl)oxy)ethoxy)pyridin-2-yl)propane-1, 2-diol (1.0 equiv.) in acetone was added NaIO$_4$ (2.05 equiv.) and Water (0.07 M). The suspension was stirred at ambient temperature for 3 hr. The solution was cooled in a 0° C. ice bath and was quenched by addition of sodium thiosulfate in water. After stirring for 10 minutes, the solution was partitioned between EtOAc and H$_2$O, mixed, separated, washed with more 10%°/(m/v) aqueous Na$_2$S$_2$O$_3$, NaHCO$_3$ (sat.), dried over sodium sulfate, filtered, concentrated, and dried under high vacuum to give 2-(4-(2-methyl-5-nitrophenyl)-6-(2-((tetrahydro-2H-pyran-2-yl)oxy)ethoxy)pyridin-2-yl) acetaldehyde as an off-white foamy solid in 99% yield. LCMS (m/z) (M+Na)=401.2, Rt=1.02 min.

Step 6

2-(4-(2-methyl-5-nitrophenyl)-6-(2-((tetrahydro-2H-pyran-2-yl)oxy)ethoxy)pyridin-2-yl)acetaldehyde (1.0 equiv.), paraformaldehyde (9.0 equiv.), and calcium hydroxide (10.0 equiv.) were combined in a glass high pressure vessel with 90% headspace in THF (0.3 M). The solution was flushed with nitrogen, sealed and submerged in a 75° C. oil bath and left stirring for 15 hours. The reaction was cooled to ambient temperature and diluted with DCM and filtered through Celite. The filtrate was concentrated and purified by ISCO SiO$_2$ chromatography (0-15% MeOH/CH2Cl2) to give 2-(hydroxymethyl)-2-(4-(2-methyl-5-nitrophenyl)-6-(2-((tetrahydro-2H-pyran-2-yl)oxy)ethoxy)pyridin-2-yl)propane-1,3-diol in 59% yield. LCMS (m/z) (M+Na)=463.2, Rt=0.84 min.

Step 7

To a solution of Ph3P (1.6 equiv.) and 2-(hydroxymethyl)-2-(4-(2-methyl-5-nitrophenyl)-6-(2-((tetrahydro-2H-pyran-2-yl)oxy)ethoxy)pyridin-2-yl)propane-1,3-diol (1.0 equiv.) in Toluene (0.09 M) was added DIAD (1.6 equiv.). The reaction was then stirred at 65° C. for 3 days. The reaction was concentrated to dryness. The residue was purified directly by ISCO SiO$_2$ chromatography (0-100% EtOAc/n-heptanes gradient). The product was re-purified with a DCM-methanol column and then another heptanes-ethyl acetate column to yield (3-(4-(2-methyl-5-nitrophenyl)-6-(2-((tetrahydro-2H-pyran-2-yl)oxy)ethoxy)pyridin-2-yl)oxetan-3-yl)methanol as a colorless residue in 24% yield. LCMS (m/z) (M+Na)=465.1, Rt=0.96 min.

Step 8

A solution of (3-(4-(2-methyl-5-nitrophenyl)-6-(2-((tetrahydro-2H-pyran-2-yl)oxy)ethoxy)pyridin-2-yl)oxetan-3-yl)methanol (1.0 equiv.) in CH$_2$Cl$_2$ (0.12 M) was cooled an ice water bath and treated with Dess-Martin periodinane (1.2 equiv.). The solution was stirred at 0° C. for 30 min, and the bath was removed. After 2 hr at ambient temperature, the reaction mixture was diluted with DCM and quenched with 1:1 10%/o Na$_2$S$_2$O$_3$/NaHCO$_3$(sat.). After stirring for 10 minutes the layers were separated. The organic phase was washed with saturated aqueous sodium bicarbonate, dried over sodium sulfate, filtered, concentrated, and purified by ISCO SiO$_2$ chromatography (heptanes with 0-60% ethyl acetate gradient) to yield 3-(4-(2-methyl-5-nitrophenyl)-6-(2-((tetrahydro-2H-pyran-2-yl)oxy)ethoxy)pyridin-2-yl)oxetane-3-carbaldehyde, as a colorless oil in 62% yield. LCMS (m/z) (M+H)=445.3, Rt=0.96 min.

Step 9

To a solution of 3-(4-(2-methyl-5-nitrophenyl)-6-(2-((tetrahydro-2H-pyran-2-yl)oxy)ethoxy)pyridin-2-yl)oxetane-3-carbaldehyde (1.0 equiv.) in CH$_2$Cl$_2$ (0.1 M) in a −10° C. ice/methanol bath was added DAST (4.0 equiv.) in a dropwise fashion. The bath was removed, and the solution was stirred for 1.5 hr, warming to ambient temperature. The cooled reaction mixture was poured into saturated aqueous sodium bicarbonate and extracted with DCM. The combined extracts were dried over sodium sulfate, filtered, concentrated, and purified by ISCO SiO$_2$ chromatography (heptanes with 0-35% ethyl acetate gradient) to yield 2-(3-(difluoromethyl)oxetan-3-yl)-4-(2-methyl-5-nitrophenyl)-6-(2-((tetrahydro-2H-pyran-2-yl)oxy)ethoxy)pyridine, as a colorless oil in 59% yield. LCMS (m/z) (M+Na)=487.1. Rt=1.14 min.

Step 10

To a degassed solution of 2-(3-(difluoromethyl)oxetan-3-yl)-4-(2-methyl-5-nitrophenyl)-6-(2-((tetrahydro-2H-pyran-2-yl)oxy)ethoxy)pyridine (1.0 equiv.) in methanol (0.04 M) was added palladium on carbon (0.05 equiv.). The flask was purged and flushed twice with hydrogen from a balloon. The reaction was stirred for 5 hr under a hydrogen atmosphere. The reaction mixture was degassed, diluted with DCM, and filtered through Celite. The filter cake was rinsed with additional DCM. The combined filtrates were concentrated to give 3-(2-(3-(difluoromethyl)oxetan-3-yl)-6-(2-((tetrahydro-2H-pyran-2-yl)oxy)ethoxy)pyridin-4-yl)-4-methylaniline, as a colorless oil in 99% yield. LCMS (m/z) (M+H)=435.2, Rt=0.30 min.

Synthesis of 3-(2-(3-(fluoromethyl)oxetan-3-yl)-6-(2-((tetrahydro-2H-pyran-2-yl)oxy)ethoxy)pyridin-4-yl)-4-methylaniline

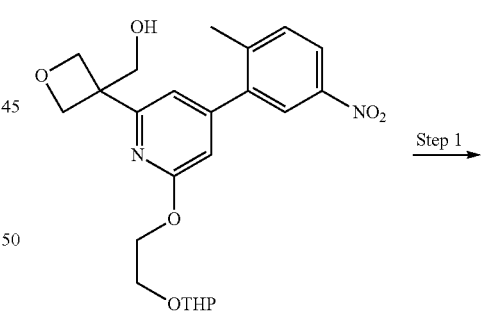

Step 1

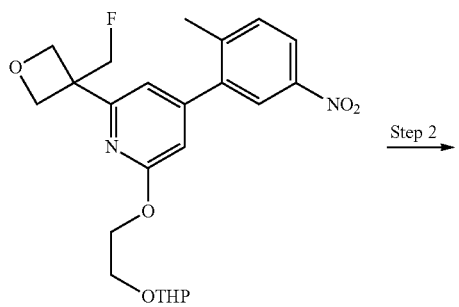

Step 2

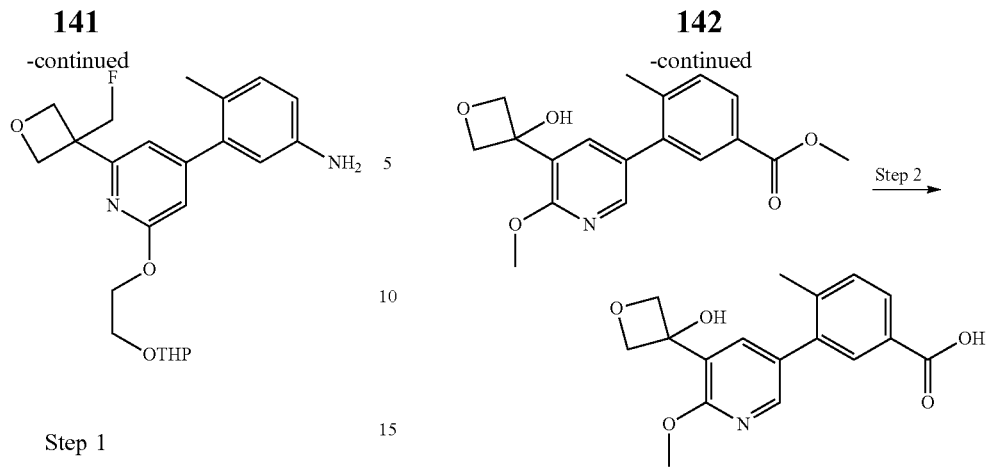

Step 1

To a solution of (3-(4-(2-methyl-5-nitrophenyl)-6-(2-((tetrahydro-2H-pyran-2-yl)oxy)ethoxy)pyridin-2-yl)oxetan-3-yl)methanol (1.0 equiv.) in THF (0.1 M) were added triethylamine (4.0 equiv.), perfluorobutanesulfonyl fluoride (4.0 equiv.), and triethylamine trihydrofluoride (12.0 equiv.) and the reaction was heated to 55° C. in an oil bath for 3 h. Quenched by the addition of sat. sodium bicarbonate and extracted twice with ethyl acetate. The combined organics were dried over sodium sulfate, filtered and concentrated. The residue was purified via silica gel chromatography (ISCO, 0-35% ethyl acetate/heptane) to give 2-(3-(fluoromethyl)oxetan-3-yl)-4-(2-methyl-5-nitrophenyl)-6-(2-((tetrahydro-2H-pyran-2-yl)oxy)ethoxy)pyridine in 43% yield. LCMS (m/z) (M+H)=447.3, Rt=1.11 min.

Step 2

A solution of 2-(3-(fluoromethyl)oxetan-3-yl)-4-(2-methyl-5-nitrophenyl)-6-(2-((tetrahydro-2H-pyran-2-yl)oxy)ethoxy)pyridine (1.0 equiv.) in MeOH (0.03 M) was treated with Pd/C (0.05 eq) and the mixture was purged and flushed twice with H, and then left under a balloon of $H_2$ for 1 h at RT. The reaction mixture was then filtered through Celite, washing with DCM, and concentrated to give 3-(2-(3-(fluoromethyl)oxetan-3-yl)-6-(2-((tetrahydro-2H-pyran-2-yl)oxy)ethoxy)pyridin-4-yl)-4-methylaniline in 97% yield.

$^1$H NMR (400 MHz, <cd3od>) δ ppm 7.14 (d, J=8.22 Hz, 1H) 6.90 (dd, J=8.02, 2.54 Hz, 1H) 6.73-6.82 (m, 2H) 6.63 (d, J=1.17 Hz, 1H) 5.04 (dd, J=6.06, 3.33 Hz, 2H) 4.93 (s, 1H) 4.75-4.84 (m, 3H) 4.70 (dd, J=4.11, 3.33 Hz, 1H) 4.44-4.59 (m, 2H) 4.07 (ddd, J=11.25, 5.58, 3.91 Hz, 1H) 3.90 (ddd, J=11.25, 8.12, 3.33 Hz, 1H) 3.81 (ddd, J=11.05, 6.55, 4.30 Hz, 1H) 3.48-3.59 (m, 1H) 2.17 (s, 3H) 1.79-1.91 (m, 1H) 1.68-1.79 (m, 1H) 1.44-1.68 (m, 4H). LCMS (m % z) (M+H)=417.3, Rt=0.74 min.

Synthesis of 3-(5-(3-hydroxyoxetan-3-yl)-6-methoxypyridin-3-yl)-4-methylbenzoic acid

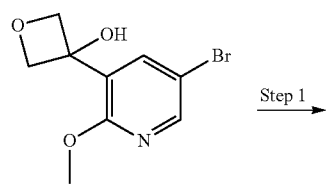

Step 1

Step 1

To a mixture of 3-(5-bromo-2-methoxypyridin-3-yl)oxetan-3-ol (1.0 equiv.), methyl 4-methyl-3-(4,4,5,5-tetramethyl-1,3,2-dioxaborolan-2-yl)benzoate (1.3 equiv.) and $PdCl_2$(dppf).DCM adduct (0.08 equiv.) in DME (0.19 M) was added $Na_2CO_3$ (2M aqueous solution, 3.0 equiv.). The mixture was stirred at 120° C. in microwave for 15 min. The reaction was partitioned between brine and ethyl acetate, the organic layer was dried over sodium sulfate and concentrated to give methyl 3-(5-(3-hydroxyoxetan-3-yl)-6-methoxypyridin-3-yl)-4-methylbenzoate in quantitative yield. The crude material was used for the next step without further purification. LCMS (m/z) (M+H)=330.0, Rt=0.76 min.

Step 2

To a solution of methyl 3-(5-(3-hydroxyoxetan-3-yl)-6-methoxypyridin-3-yl)-4-methylbenzoate (1.0 equiv.) in THF (0.14 M) was added LiOH (3.0 equiv.). The mixture was stirred at it for 4 hr. Concentrated to remove most of THF and the residue was neutralized with 6 N HCl to pH=3 and extracted with EtOAc. The organic layer was washed with brine, dried with sodium sulfate and concentrated to yield 3-(5-(3-hydroxyoxetan-3-yl)-6-methoxypyridin-3-yl)-4-methylbenzoic acid in 85% yield. LCMS (m/z) (M+H)=316.0, Rt=0.62 min.

Synthesis of 6'-ethoxy-2-methyl-5'-(tetrahydro-2H-pyran-4-yl)-[3,3'-bipyridin]-5-amine

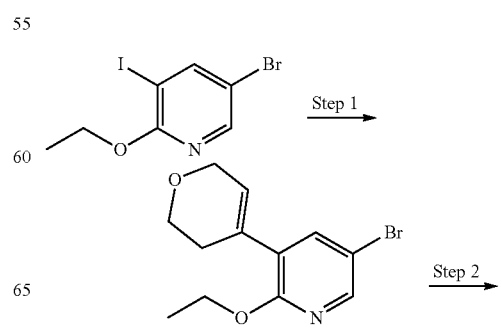

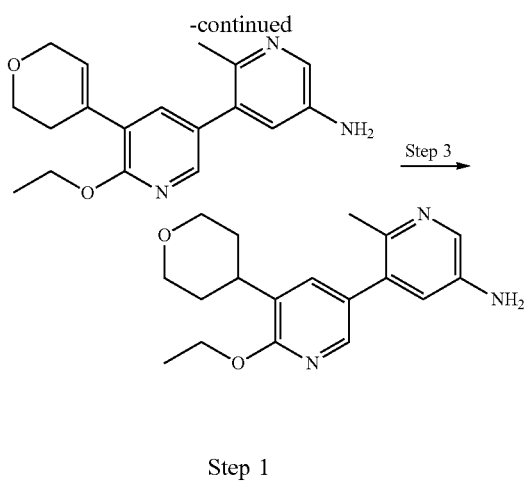

Step 1

A solution of 5-bromo-2-ethoxy-3-iodopyridine (1.0 equiv.), 3,6-dihydro-2H-pyran-4-boronic acid pinacol ester (1.1 equiv.), and K$_3$PO$_4$ (4.0 equiv.) in Dioxane (0.11 M) was purged with Ar for 5 min; PdCl$_2$(dppf).CH$_2$Cl$_2$ adduct (0.05 equiv.) was then added, and the mixture was purged with Ar again, and then the tube was sealed and heated (thermally) at 85° C. for 3.5 h. The mixture was diluted with DCM, absorbed directly onto Celite, and purified by Grace flash column chromatography (silica gel, 0-25% EtOAc: heptane). Product fractions elute around 5% EtOAc and were concentrated to give 5-bromo-3-(3,6-dihydro-2H-pyran-4-yl)-2-ethoxypyridine as a white crystalline solid in 62% yield. LCMS (m/z) (M+H)=283.9/285.9, Rt=1.00 min.

Step 2

A solution of 5-bromo-3-(3,6-dihydro-2H-pyran-4-yl)-2-ethoxypyridine (1.0 equiv.) and 6-methyl-5-(4,4,5,5-tetramethyl-1,3,2-dioxaborolan-2-yl)pyridin-3-amine (1.1 equiv.) in DME (0.1 M) and 2M aqueous sodium carbonate (3.0 equiv.) was purged with argon. PdCl$_2$(dppf).DCM adduct (0.05 equiv.) was added and the mixture was purged with argon again and heated thermally to 100° C. for 1 hour. The solution was poured onto water and extracted with ethyl acetate. The combined organics were washed with brine, dried over magnesium sulfate, filtered and concentrated. The residue was purified by Grace flash column chromatography (silica gel, 0-15% MeOH:DCM). Product fractions elute around 5% MeOH and were concentrated to give 5'-(3,6-dihydro-2H-pyran-4-yl)-6'-ethoxy-2-methyl-[3,3'-bipyridin]-5-amine as a light brown foam in quantitative yield. LCMS (m/z) (M+H)=314.0, Rt=0.54 min.

Step 3

A solution of 5'-(3,6-dihydro-2H-pyran-4-yl)-6'-ethoxy-2-methyl-[3,3'-bipyridin]-5-amine (1.0 equiv.) in methanol (0.12 M) was purged with argon. Pd/C (0.1 equiv.) was added and the mixture was purged with argon once again and then with hydrogen and left under a hydrogen balloon pressure for three days. The solution was filtered through a plug of Celite and washed with methanol. The filtrate was concentrated under vacuo to give 6'-ethoxy-2-methyl-5'-(tetrahydro-2H-pyran-4-yl)-[3,3'-bipyridin]-5-amine in 87% yield. LCMS (m/z) (M+H)=312.3, Rt=0.60 min.

Synthesis of 6'-ethoxy-5'-(3-(fluoromethyl)tetrahydrofuran-3-yl)-2-methyl-[3'-bipyridin]-5-amine

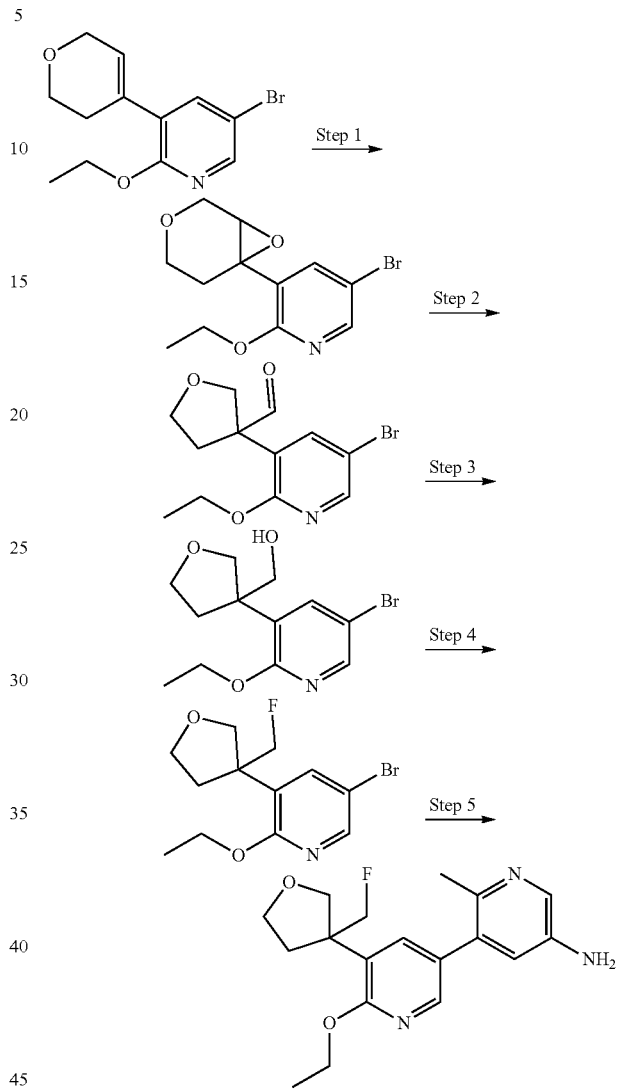

Step 1

To a stirred solution of 5-bromo-3-(3,6-dihydro-2H-pyran-4-yl)-2-ethoxypyridine (1.0 equiv.) in DCM (0.1 M) at 0° C. was added mCPBA (1.1 equiv.) and the mixture was stirred for 3.5 h. The reaction was allowed to warm to 25° C. and stirred at rt overnight. The reaction was poured onto saturated aqueous sodium bicarbonate and extracted three times with ethyl acetate. The combined organics were washed with brine, dried over magnesium sulfate, filtered and concentrated. The residue was used as 3-(3,7-dioxabicyclo[4.1.0]heptan-6-yl)-5-bromo-2-ethoxypyridine without further purification. LCMS (m/z) (M+H)=300.0/302.0, Rt=0.90 min.

Step 2

To a solution of 3-(3,7-dioxabicyclo[4.1.0]heptan-6-yl)-5-bromo-2-ethoxypyridine (1.0 equiv.) in DCM (0.1 M) at 0° C. was added BF$_3$.OEt$_2$ (3.0 equiv.) and the mixture was allowed to warm to 25° C. over 15 min. The reaction was poured onto saturated aqueous sodium bicarbonate and extracted three times with ethyl acetate. The combined organics were washed with brine, dried over magnesium sulfate, filtered and concentrated. The residue was used as 3-(5-bromo-2-ethoxypyridin-3-yl)tetrahydrofuran-3-carbaldehyde without further purification. LCMS (m/z) (M+H)=300.1/302.1, Rt=0.86 min.

Step 3

To a solution of 3-(5-bromo-2-ethoxypyridin-3-yl)tetrahydrofuran-3-carbaldehyde (1.0 equiv.) in MeOH (0.1 M) at 25° C. was added NaBH$_4$(1.1 equiv.) and the mixture was stirred for 15 min. The reaction was poured onto saturated aqueous ammonium chloride partially concentrated to remove excess MeOH. The residue was extracted three times with ethyl acetate. The combined organics were washed with brine, dried over magnesium sulfate, filtered and concentrated. The crude residue was purified by ISCO flash column chromatography over silica gel, eluting with heptane and 0-50% EtOAc gradient. Product fractions elute around 30% EtOAc and were concentrated to (3-(5-bromo-2-ethoxypyridin-3-yl)tetrahydrofuran-3-yl)methanol as a white solid in 82% yield. LCMS (m/z) (M+H)=302.1/304.1, Rt=0.75 min.

Step 4

To a stirred solution of (3-(5-bromo-2-ethoxypyridin-3-yl)tetrahydrofuran-3-yl)methanol (1.0 equiv.) in THF (0.08 M) at 25° C. were sequentially added perfluorobutanesulfonyl fluoride (4.0 equiv.), and triethylamine trihydrofluoride (4.0 equiv.), and Et$_3$N (12 equiv.) and the mixture was heated to 55° C. and stirred overnight. The reaction was poured onto saturated aqueous sodium bicarbonate and extracted three times with ethyl acetate. The combined organics were washed with brine, dried over magnesium sulfate, filtered and concentrated. The crude residue was purified via silica gel chromatography eluting with a 0-20% gradient ethyl acetate/n-heptanes. Product fractions eluted around 10% EtOAc and were concentrated to give 5-bromo-2-ethoxy-3-(3-(fluoromethyl)tetrahydrofuran-3-yl)pyridine as a colorless oil in 30% yield. LCMS (m/z) (M+H)=303.8/305.8, Rt=0.99 min.

Step 5

A solution of 5-bromo-2-ethoxy-3-(3-(fluoromethyl)tetrahydrofuran-3-yl)pyridine (1.0 equiv.) and 6-methyl-5-(4,4,5,5-tetramethyl-1,3,2-dioxaborolan-2-yl)pyridin-3-amine (1.1 equiv.) in DME (0.08 M) and Na$_2$CO$_3$ (2 M aq.) (3.0 equiv.) was purged with Ar for 5 min; PdCl$_2$(dppf).DCM adduct (0.05 equiv.) was then added, and the mixture was purged with Ar again, and then the tube was sealed and heated (thermally) at 100° C. for 1 h. The mixture was poured onto water and extracted three times with ethyl acetate. The combined organics were washed with brine, dried over magnesium sulfate, filtered and concentrated. The residue was used as 6'-ethoxy-5'-(3-(fluoromethyl)tetrahydrofuran-3-yl)-2-methyl-[3,3'-bipyridin]-5-amine without further purification. LCMS (m/z) (M+H)=332.2, Rt=0.61 min.

Synthesis of 3-(5-(5-amino-2-methylphenyl)-2-ethoxypyridin-3-yl)tetrahydrofuran-3-carbonitrile

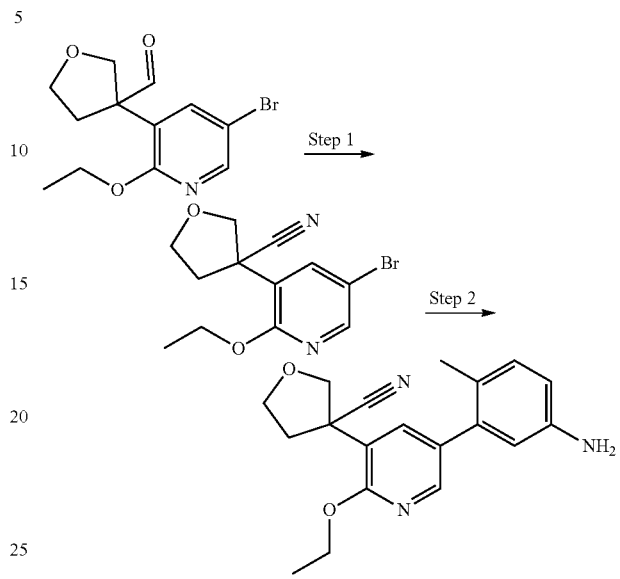

Step 1

To a solution of 3-(5-bromo-2-ethoxypyridin-3-yl)tetrahydrofuran-3-carbaldehyde (1.0 equiv.) in DMF (0.16 M) at 25° C. were sequentially added NH$_2$OH.HCl (1.25 equiv.), Et$_3$N (3.0 equiv.), and T$_3$P (50% in EtOAc) (2.0 equiv.) and the mixture was allowed to warm to 105° C. and stirred overnight. The reaction was poured onto saturated aqueous sodium bicarbonate and extracted three times with ethyl acetate. The combined organics were washed with water, brine, dried over magnesium sulfate, filtered and concentrated. The residue was purified by Grace flash column chromatography over silica gel, eluting with heptane and 0-40% EtOAc gradient. Product fractions elute around 15% EtOAc and were concentrated to 3-(5-bromo-2-ethoxypyridin-3-yl)tetrahydrofuran-3-carbonitrile as a pale yellow oil in 81% yield. LCMS (m/z) (M+H)=297.0/299.0, Rt=0.87 min.

Step 2

A solution of 3-(5-bromo-2-ethoxypyridin-3-yl)tetrahydrofuran-3-carbonitrile (1.0 equiv.) and 5-amino-2-methylphenylboronic acid, pinacol ester (1.3 equiv.) in DME (0.11 M) and Na$_2$CO$_3$ (2 M aq.) (3.0 equiv.) was purged with Ar for 5 min; PdCl$_2$(dppf).DCM adduct (0.05 equiv.) was then added, and the mixture was purged with Ar again, and then the tube was sealed and heated (thermally) at 100° C. for 1 h. The mixture was poured onto water and extracted three times with ethyl acetate. The combined organics were washed with brine, dried over magnesium sulfate, filtered and concentrated. The residue was purified by Grace flash column chromatography over silica gel, eluting with heptane and 0-100% EtOAc gradient. Product fractions were concentrated to give 3-(5-(5-amino-2-methylphenyl)-2-ethoxypyridin-3-yl)tetrahydrofuran-3-carbonitrile as a pale yellow oil. LCMS (m/z) (M+H)=324.2, Rt=0.65 min.

Synthesis of 3-(5'-amino-6-ethoxy-2'-methyl-[3,3'-bipyridin]-5-yl)tetrahydrofuran-3-carbonitrile

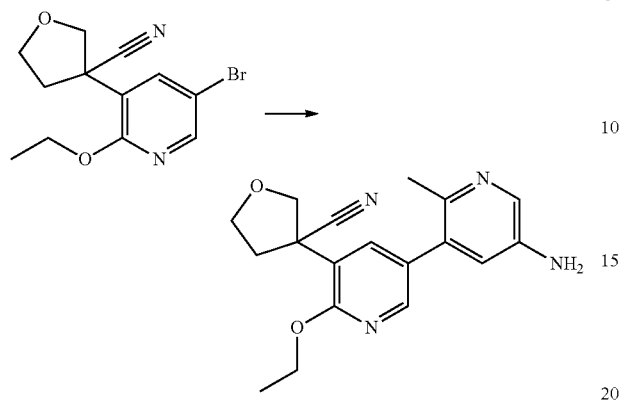

A solution of 3-(5-bromo-2-ethoxypyridin-3-yl)tetrahydrofuran-3-carbonitrile (1.0 equiv.) and 6-methyl-5-(4,4,5-tetramethyl-1,3,2-dioxaborolan-2-yl)pyridin-3-amine (1.1 equiv.) in DME (0.11 M) and Na$_2$CO$_3$ (2 M aq.) (3.0 equiv.) was purged with Ar for 5 min; PdCl$_2$(dppf)-DCM adduct (0.05 equiv.) was then added, and the mixture was purged with Ar again, and then the tube was sealed and heated (thermally) at 100° C. for 1 h. The mixture was poured onto water and extracted three times with ethyl acetate. The combined organics were washed with brine, dried over magnesium sulfate, filtered and concentrated. The residue was purified by Grace flash column chromatography over silica gel, eluting with heptane and 0-100% EtOAc gradient followed by DCM and 0-10% MeOH gradient. Product fractions elute around 7% MeOH and were concentrated to give 3-(5'-amino-6-ethoxy-2'-methyl-[3,3'-bipyridin]-5-yl)tetrahydrofuran-3-carbonitrile as a pale brown oil in 94% yield. LCMS (m/z) (M+H)=325.1, Rt=0.57 min.

Synthesis of 3-(5-bromo-2-ethoxypyridin-3-yl)tetrahydrofuran-3-ol as

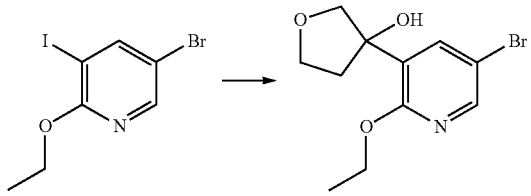 [SMILES: CCOc1ncc(Br)cc1I ; CCOc1ncc(Br)cc1C1(O)CCOC1]

To a stirred solution of 5-bromo-2-ethoxy-3-iodopyridine (1.0 equiv.) in Et$_2$O (0.09 M) at −78° C. was slowly added n-BuLi (2.5 M in hexanes) (1.05 equiv.) and the mixture was stirred for 30 min. 3-oxotetrahydrofuran (1.2 equiv.) was then slowly added and the mixture was stirred for 15 min and then allowed to warm to room temperature. The reaction mixture was poured onto saturated aqueous ammonium chloride and extracted three times with ethyl acetate. The combined organics were washed with brine, dried over magnesium sulfate, filtered and concentrated. The crude reside was purified via Grace flash column chromatography over silica gel, eluting with heptane and 0-50% EtOAc gradient. Product fractions elute around 15% EtOAc and were concentrated to give 3-(5-bromo-2-ethoxypyridin-3-yl)tetrahydrofuran-3-ol as a colorless oil which solidifies on standing in 29%/yield. LCMS (m/z) (M+H)=288.0/290.0, Rt=0.73 min.

Synthesis of 5-bromo-2-ethoxy-3-(3-fluorotetrahydrofuran-3-yl)pyridine

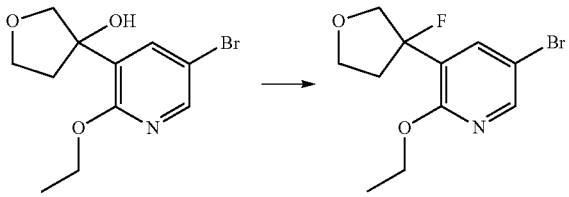 [SMILES: CCOc1ncc(Br)cc1C1(O)CCOC1 ; CCOc1ncc(Br)cc1C1(F)CCOC1]

To a stirred solution of 3-(5-bromo-2-ethoxypyridin-3-yl)tetrahydrofuran-3-ol (1.0 equiv.) in DCM (0.06 M) at −78° C. was added DAST (1.5 equiv.) and the mixture was stirred for 1.5 h. The reaction mixture was quenched with a small amount of 1 M NaOH, warmed to room temperature, poured onto saturated aqueous sodium bicarbonate, and extracted three times with DCM. The combined organics were washed with brine, dried over magnesium sulfate, filtered and concentrated. The crude reside was purified via Grace flash column chromatography over silica gel, eluting with heptane and 0-20% EtOAc gradient to give 5-bromo-2-ethoxy-3-(3-fluorotetrahydrofuran-3-yl)pyridine in 91% yield. LCMS (m/z) (M+H)=290.0/292.0, Rt=0.96 min.

Synthesis of 2,2'-((4-(5-amino-2-methylphenyl)-6-(tetrahydro-2H-pyran-4-yl)pyridin-2-yl)azanediyl)diethanol

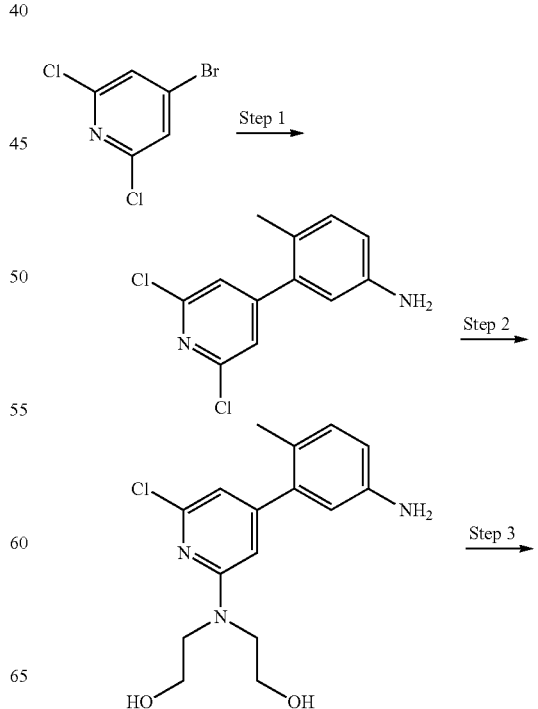

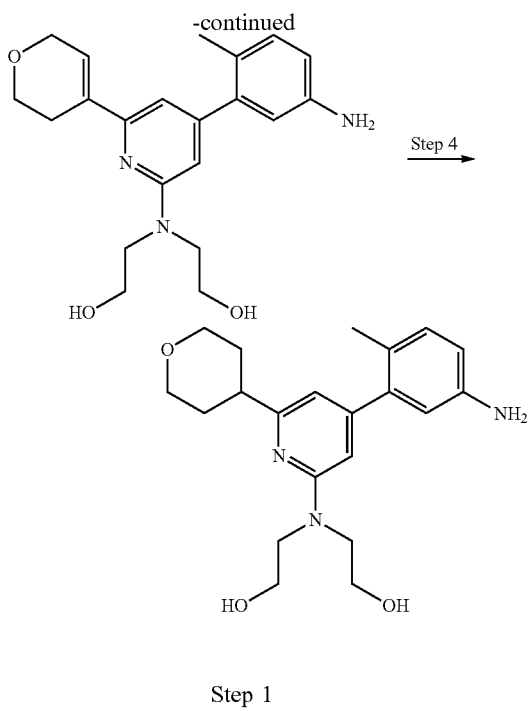

Step 1

To a solution of 4-bromo-2,6-dichloropyridine (1.0 equiv.) in DME and 2M Na$_2$CO$_3$ (3:1, 0.18 M) was added 4-methyl-3-(4,4,5,5-tetramethyl-1,3,2-dioxaborolan-2-yl) aniline (1.0 equiv.) and PdCl$_2$(dppf)-DCM adduct (0.07 equiv.) and the reaction was heated in an oil bath at 85° C. for 2 h. Cooled to rt and partitioned between water and ethyl acetate. The organic phase was washed with brine, concentrated under reduced pressured and the residue was purified via silica gel chromatography (ISCO, 0-50% ethyl acetate/ heptanes) to give 3-(2,6-dichloropyridin-4-yl)-4-methylaniline in 81% yield. LCMS (m/z) (M+H)=253.1/255.1, Rt=0.62 min.

Step 2

3-(2,6-dichloropyridin-4-yl)-4-methylaniline (1.0 equiv.) and 2,2'-azanediyldiethanol (5.0 equiv.) were heated at 105° C. overnight. Upon cooling to rt, the mixture was diluted with ethyl acetate and water. The organic layer was washed with water, brine, and concentrated under reduced pressure to give 2,2'-((4-(5-amino-2-methylphenyl)-6-chloropyridin-2-yl)azanediyl)diethanol in quantitative yield. LCMS (m/z) (M+H)=322.3/324.2. Rt=0.54 min.

Step 3

To a solution of 2,2'-((4-(5-amino-2-methylphenyl)-6-chloropyridin-2-yl)azanediyl)diethanol (1.0 equiv.) in DME and 2M Na$_2$CO$_3$ (3:1, 0.1 M) was added 2-(3,6-dihydro-2H-pyran-4-yl)-4,4,5,5-tetramethyl-1,3,2-dioxaborolane (1.2 equiv.) and PdCl$_2$(dppf)-DCM adduct (0.1 equiv.) and the reaction was heated in an oil bath at 100° C. for 5 h. Cooled to rt and partitioned between water and ethyl acetate. The organic phase was washed with brine, concentrated under reduced pressured and the residue was purified via silica gel chromatography (ISCO, 0-70% MeOH/DCM) to give 2,2'-((4-(5-amino-2-methylphenyl)-6-(3,6-dihydro-2H-pyran-4-yl)pyridin-2-yl)azanediyl)diethanol in 62% yield. LCMS (m/z) (M+H)=370.3, Rt=0.46 min.

Step 4

To a solution of 2,2'-((4-(5-amino-2-methylphenyl)-6-(3, 6-dihydro-2H-pyran-4-yl)pyridin-2-yl)azanediyl)diethanol (1.0 equiv.) in ethanol (0.08 M) was added Pd/C (0.1 equiv.) and the mixture was stirred under a hydrogen balloon overnight. The flask was flushed with argon, Celite was added and the mixture was filtered through a plug of Celite. Rinsed with DCM and the filtrate was concentrated under reduced pressure to give 2,2'-((4-(5-amino-2-methylphenyl)-6-(tetrahydro-2H-pyran-4-yl)pyridin-2-yl)azanediyl) diethanol in 86% yield. LCMS (m/z) (M+H)=372.4. Rt=0.42 min.

Synthesis of 2-((4-(5-amino-2-methylphenyl)-6-(tetrahydro-2H-pyran-4-yl)pyridin-2-yl)amino)ethanol

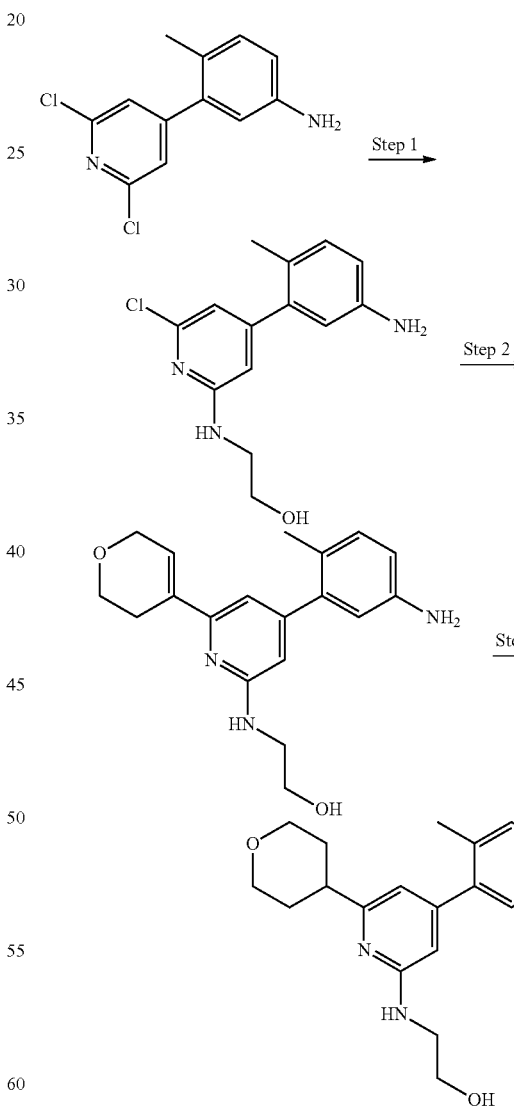

Step 1

3-(2,6-dichloropyridin-4-yl)-4-methylaniline (1.0 equiv.) and 2-aminoethanol (5.0 equiv.) were heated at 105° C. for 2 hours. Upon cooling to rt, the mixture was diluted with ethyl acetate and water. The organic layer was washed with water, brine, and concentrated under reduced pressure to give 2-((4-(5-amino-2-methylphenyl)-6-chloropyridin-2-yl)amino)ethanol in quantitative yield. LCMS (m/z) (M+H)=278.2/280.1, Rt=0.50 min.

Step 2

To a solution of 2-((4-(5-amino-2-methylphenyl)-6-chloropyridin-2-yl)amino)ethanol (1.0 equiv.) in DME and 2M Na₂CO₃ (3:1, 0.1 M) was added 2-(3,6-dihydro-2H-pyran-4-yl)-4,4,5,5-tetramethyl-1,3,2-dioxaborolane (1.2 equiv.) and PdCl₂(dppf)-DCM adduct (0.1 equiv.) and the reaction was heated in an oil bath at 100° C. for 5 h. Cooled to rt and partitioned between water and ethyl acetate. The organic phase was washed with brine, concentrated under reduced pressured and the residue was purified via silica gel chromatography (ISCO, 0-50% MeOH/DCM) to give 2-((4-(5-amino-2-methylphenyl)-6-(3,6-dihydro-2H-pyran-4-yl)pyridin-2-yl)amino)ethanol in 71% yield. LCMS (m/z) (M+H)=326.3, Rt=0.46 min.

Step 3

To a solution of 2-((4-(5-amino-2-methylphenyl)-6-(3,6-dihydro-2H-pyran-4-yl)pyridin-2-yl)amino)ethanol (1.0 equiv.) in ethanol (0.09 M) was added Pd/C (0.1 equiv.) and the mixture was stirred under a hydrogen balloon overnight. The flask was flushed with argon, Celite was added and the mixture was filtered through a plug of Celite. Rinsed with DCM and the filtrate was concentrated under reduced pressure to give 2-((4-(5-amino-2-methylphenyl)-6-(tetrahydro-2H-pyran-4-yl)pyridin-2-yl)amino)ethanol in 97% yield. LCMS (m/z) (M+H)=328.3, Rt=0.42 min.

Synthesis of 2-(5-amino-2-methyl-6'-(tetrahydro-2H-pyran-4-yl)-3,4'-bipyridin-2'-yl)amino)ethanol

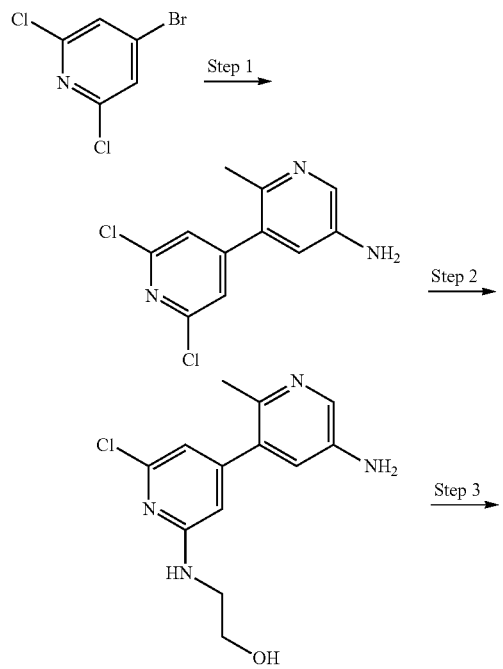

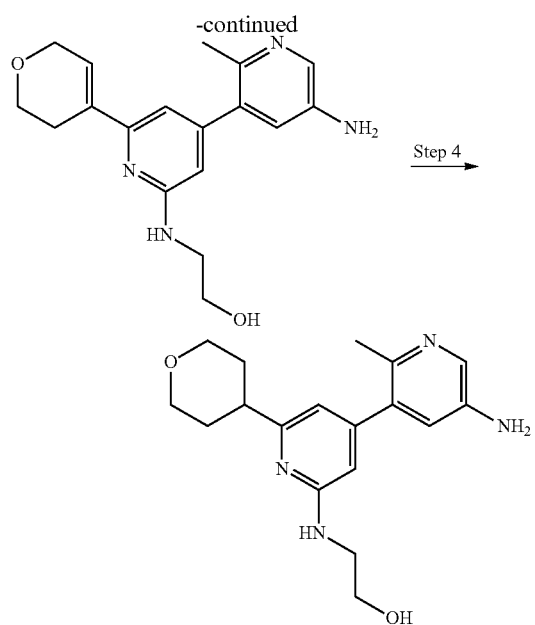

Step 1

To a solution of 4-bromo-2,6-dichloropyridine (1.0 equiv.) in DME and 2M Na₂CO₃ (3:1, 0.18 M) was added 6-methyl-5-(4,4,5,5-tetramethyl-1,3,2-dioxaborolan-2-yl)pyridin-3-amine (1.1 equiv.) and PdCl₂(dppf)-DCM adduct (0.05 equiv.) and the reaction was heated in an oil bath at 85° C. for 2 h. Cooled to rt and partitioned between water and ethyl acetate. The organic phase was washed with brine, concentrated under reduced pressured and the residue was purified via silica gel chromatography (ISCO, 50-100% ethyl acetate/heptanes) to give 2',6'-dichloro-2-methyl-[3,4'-bipyridin]-5-amine in 65% yield. LCMS (m/z) (M+H)=253.9, Rt=0.49 min.

Step 2

2',6'-dichloro-2-methyl-[3,4'-bipyridin]-5-amine (1.0 equiv.) and 2-aminoethanol (8.4 equiv.) were heated in NMP (2M) at 80° C. for 18 hours. Upon cooling to rt, the mixture was diluted with ethyl acetate and water. The organic layer was washed with water, brine, and concentrated under reduced pressure to give 2-((5-amino-6'-chloro-2-methyl-[3,4'-bipyridin]-2'-yl)amino)ethanol in 78% yield. LCMS (m/z) (M+H)=278.9, Rt=0.43 min.

Step 3

To a solution of 2-((5-amino-6'-chloro-2-methyl-[3,4'-bipyridin]-2'-yl)amino)ethanol (1.0 equiv.) in DME and 2M Na₂CO₃ (3:1, 0.2 M) was added 2-(3,6-dihydro-2H-pyran-4-yl)-4,4,5,5-tetramethyl-1,3,2-dioxaborolane (1.1 equiv.) and PdCl₂(dppf)-DCM adduct (0.05 equiv.) and the reaction was heated in the microwave for 10 min at 120° C. Cooled to rt and partitioned between water and ethyl acetate. The organic phase was washed with brine, concentrated under reduced pressured and the residue was purified via silica gel chromatography (ISCO, 0-20% MeOH/DCM) to give 2-((5-amino-6'-(3,6-dihydro-2H-pyran-4-yl)-2-methyl-[3,4'-bipyridin]-2'-yl)amino)ethanol in 38% yield. LCMS (m/z) (M+H)=327.0, Rt=0.32 min.

Step 4

To a solution of 2-((5-amino-6'-(3,6-dihydro-2H-pyran-4-yl)-2-methyl-[3,4'-bipyridin]-2'-yl)amino)ethanol (1.0 equiv.) in ethanol (0.1 M) was added Pd/C (0.1 equiv.) and the mixture was stirred under a hydrogen balloon for 3 hours. The flask was flushed with argon, Celite was added and the mixture was filtered through a plug of Celite. Rinsed with DCM and the filtrate was concentrated under reduced pressure to give 2-((5-amino-2-methyl-6'-(tetrahydro-2H-pyran-4-yl)-[3,4'-bipyridin]-2'-yl)amino)ethanol in quantitative yield. LCMS (m/z) (M+H)=329.1, Rt=0.31 min.

Synthesis of 1-(5-amino-2-methyl-6'-(tetrahydro-2H-pyran-4-yl)-[3,4'-bipyridin]-2'-yl)piperidin-4-ol

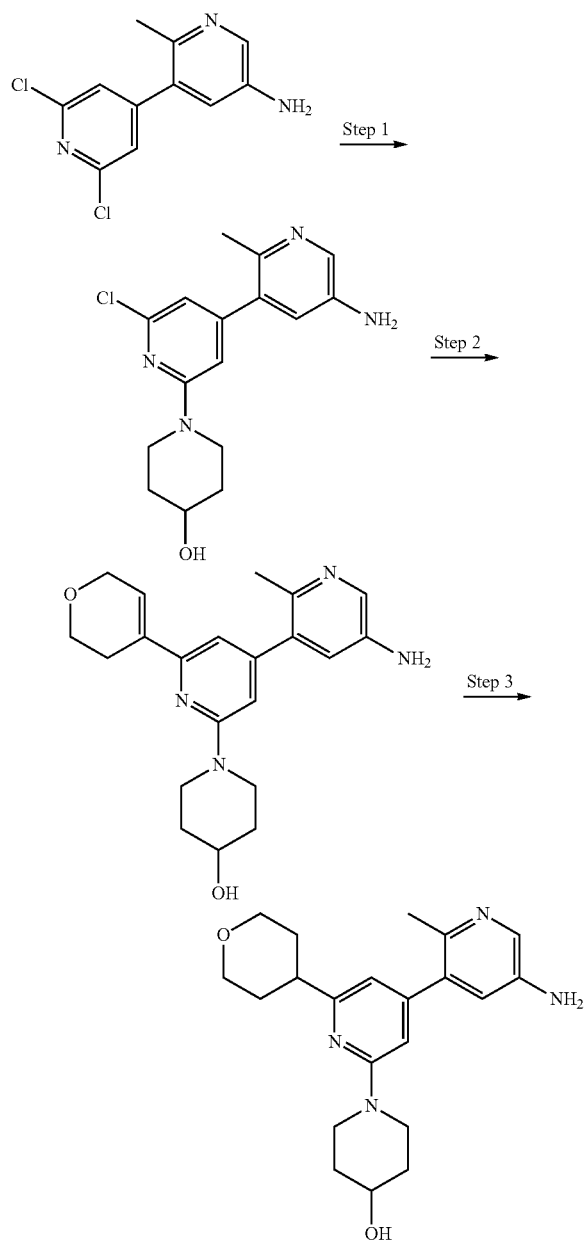

Step 1

2',6'-dichloro-2-methyl-[3,4'-bipyridin]-5-amine (1.0 equiv.) and piperidin-4-ol (3.0 equiv.) were heated in NMP (2M) at 80° C. for 18 hours. Upon cooling to rt, the mixture was diluted with ethyl acetate and water. The organic layer was washed with water, brine, and concentrated under reduced pressure to give 1-(5-amino-6'-chloro-2-methyl-[3,4'-bipyridin]-2'-yl)piperidin-4-ol in 91% yield. LCMS (m/z) (M+H)=319.0, Rt=0.53 min.

Step 2

To a solution of give 1-(5-amino-6'-chloro-2-methyl-[3,4'-bipyridin]-2'-yl)piperidin-4-ol (1.0 equiv.) in DME and 2M $Na_2CO_3$ (3:1, 0.2 M) was added 2-(3,6-dihydro-2H-pyran-4-yl)-4,4,5,5-tetramethyl-1,3,2-dioxaborolane (2.1 equiv.) and $PdCl_2$(dppf)-DCM adduct (0.05 equiv.) and the reaction was heated in the microwave for 20 min at 120° C. Cooled to rt and partitioned between water and ethyl acetate. The organic phase was washed with brine, concentrated under reduced pressured and the residue was purified via silica gel chromatography (ISCO, 0-20/o MeOH/DCM) to give 1-(5-amino-6'-(3,6-dihydro-2H-pyran-4-yl)-2-methyl-[3,4'-bipyridin]-2'-yl)piperidin-4-ol in 70% yield. LCMS (m/z) (M+H)=367.1, Rt=0.40 min.

Step 3

To a solution of 1-(5-amino-6'-(3,6-dihydro-2H-pyran-4-yl)-2-methyl-[3,4'-bipyridin]-2'-yl)piperidin-4-ol (1.0 equiv.) in ethanol (0.1 M) was added Pd/C (0.1 equiv.) and the mixture was stirred under a hydrogen balloon for 21 hours. The flask was flushed with argon, Celite was added and the mixture was filtered through a plug of Celite. Rinsed with DCM and the filtrate was concentrated under reduced pressure to give 1-(5-amino-2-methyl-6'-(tetrahydro-2H-pyran-4-yl)-[3,4'-bipyridin]-2'-yl)piperidin-4-ol in quantitative yield. LCMS (m/z) (M+H)=369.1. Rt=0.33 min.

Synthesis of 1-(4-(5-amino-2-methylphenyl)-6-(tetrahydro-2H-pyran-4-yl)pyridin-2-yl)piperidin-4-ol

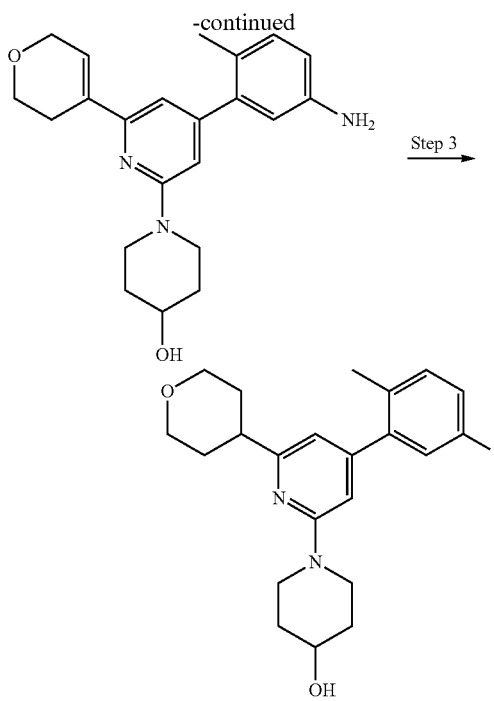

Step 1

3-(2,6-dichloropyridin-4-yl)-4-methylaniline (1.0 equiv.) and piperidin-4-ol (3.0 equiv.) were heated in NMP (2M) at 100° C. for 18 hours. Upon cooling to rt, the mixture was diluted with ethyl acetate and water. The organic layer was washed with water, brine, and concentrated under reduced pressure to give 1-(4-(5-amino-2-methylphenyl)-6-chloropyridin-2-yl)piperidin-4-ol which was used without further purification. LCMS (m/z) (M+H)=318.3/320.1, Rt=0.63 min.

Step 2

To a solution of 1-(4-(5-amino-2-methylphenyl)-6-chloropyridin-2-yl)piperidin-4-ol (1.0 equiv.) in DME (0.2 M) were added 2 M Na$_2$CO$_3$ (5.0 equiv), 2-(3,6-dihydro-2H-pyran-4-yl)-4,4,5,5-tetramethyl-1,3,2-dioxaborolane (2.1 equiv.) and PdCl$_2$(dppf)-DCM adduct (0.05 equiv.) and the reaction was heated in the microwave for 20 min at 120° C. The mixture was diluted with water and extracted twice with ethyl acetate. The organic phase was washed with water and brine, dried over magnesium sulfater, concentrated under reduced pressured and the residue was purified via silica gel chromatography (ISCO, 0-100% EtOAc/heptane) to give 1-(4-(5-amino-2-methylphenyl)-6-(3,6-dihydro-2H-pyran-4-yl)pyridin-2-yl)piperidin-4-ol in 54% yield. LCMS (m/z) (M+H)=366.1, Rt=0.44 min.

Step 3

To a solution of 1-(4-(5-amino-2-methylphenyl)-6-(3,6-dihydro-2H-pyran-4-yl)pyridin-2-yl)piperidin-4-ol (1.0 equiv.) in ethanol (0.1 M) was added Pd/C (0.1 equiv.) and the mixture was purged with H$_2$ and left under a hydrogen atmosphere for 18 hours. The flask was flushed with argon, Celite was added and the mixture was filtered through a plug of Celite. The filtrate was concentrated under reduced pressure to give 1-(4-(5-amino-2-methylphenyl)-6-(tetrahydro-2H-pyran-4-yl)pyridin-2-yl)piperidin-4-ol in 84% yield. LCMS (m/z) (M+H)=368.1, Rt=0.48 min.

Synthesis of 4-methyl-3-(2-(2-((tetrahydro-2H-pyran-2-yl)oxy)ethoxy)-6-(tetrahydro-2H-pyran-4-yl)pyridin-4-yl)aniline

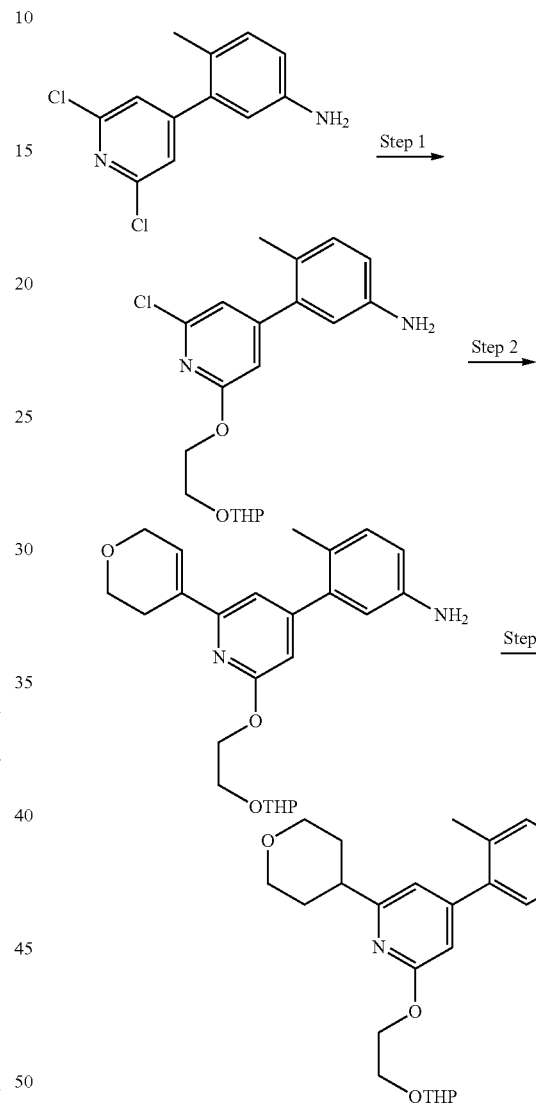

Step 1

To 2-((tetrahydro-2H-pyran-2-yl)oxy)ethanol (1.2 equiv.) in dioxane (0.1 M) was added NaH (1.1 equiv.). The mixture was stirred for 20 min at ambient temperature followed by the addition of a solution of 3-(2,6-dichloropyridin-4-yl)-4-methylaniline (1.0 equiv.) in dioxane. The mixture was heated in at 55° C. for 18 hours. The reaction was quenched by the addition of saturated aqueous NH$_4$Cl and extracted with ethyl acetate. The combined organics were washed with water and brine, dried over sodium sulfate, filtered, concentrated, and purified by flash chromatography over silica gel (heptanes with 0-100% ethyl acetate gradient) to give 3-(2-chloro-6-(2-((tetrahydro-2H-pyran-2-yl)oxy)ethoxy)pyridin-4-yl)-4-methylaniline in 33% yield. LCMS (m/z) (M-THP+H)=278.8, Rt=0.77 min.

Step 2

To a solution of 3-(2-chloro-6-(2-((tetrahydro-2H-pyran-2-yl)oxy)ethoxy)pyridin-4-yl)-4-methylaniline (1.0 equiv.) in DME (0.2 M) were added 2 M Na$_2$CO$_3$ (5.0 equiv), 2-(3,6-dihydro-2H-pyran-4-yl)-4,4,5,5-tetramethyl-1,3,2-dioxaborolane (2.1 equiv.) and PdCl$_2$(dppf)-DCM adduct (0.05 equiv.) and the reaction was heated in the microwave for 20 min at 120° C. The mixture was diluted with water and extracted twice with ethyl acetate. The organic phase was washed with water and brine, dried over magnesium sulfater, concentrated under reduced pressured and the residue was purified via silica gel chromatography (ISCO, 0-100% EtOAc/heptane) to give 3-(2-(3,6-dihydro-2H-pyran-4-yl)-6-(2-((tetrahydro-2H-pyran-2-yl)oxy)ethoxy)pyridin-4-yl)-4-methylaniline in 67% yield. LCMS (m/z) (M+H)=411.2, Rt=0.79 min.

Step 3

To a solution of 3-(2-(3,6-dihydro-2H-pyran-4-yl)-6-(2-((tetrahydro-2H-pyran-2-yl)oxy)ethoxy)pyridin-4-yl)-4-methylaniline (1.0 equiv.) in ethanol (0.1 M) was added Pd/C (0.1 equiv.) and the mixture was purged with H$_2$ and left under a hydrogen atmosphere for 18 hours. The flask was flushed with argon, Celite was added and the mixture was filtered through a plug of Celite. The filtrate was concentrated under reduced pressure to give 4-methyl-3-(2-(2-((tetrahydro-2H-pyran-2-yl)oxy)ethoxy)-6-(tetrahydro-2H-pyran-4-yl)pyridin-4-yl)aniline in 95% yield. LCMS (m/z) (M+H)=413.1, Rt=0.73 min.

Synthesis of 3-(6-ethoxy-5-(tetrahydro-2H-pyran-4-yl)pyridazin-3-yl)-4-methylaniline

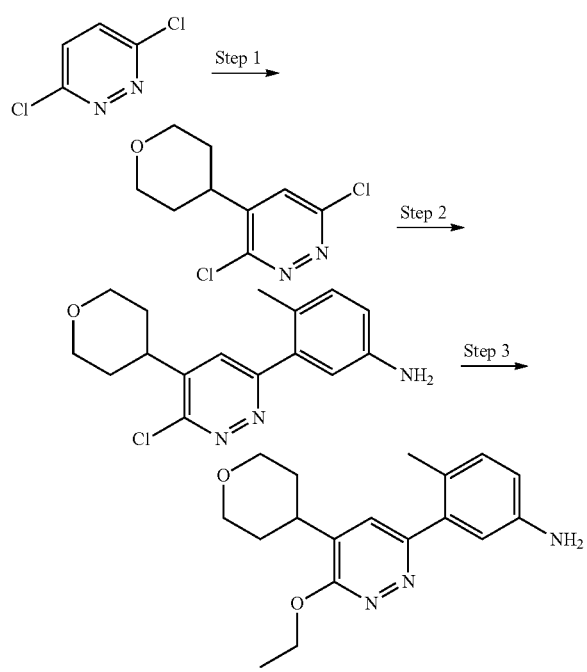

Step 1

A round-bottom flask was charged with 3,6-dichloropyridazine (1 equiv), tetrahydro-2H-pyran-4-carboxylic acid (3.0 equiv), and silver nitrate (0.3 equiv), then a 10% aq. sulfuric acid solution (2 equiv) was added to give a white suspension. The mixture was stirred for 5 min, then a solution of ammonium persulfate (2.1 equiv) in water (1 molar) was added in one portion. After stirring overnight, the mixture was adjusted to pH 11 with aq. ammonium hydroxide and extracted with DCM (3×). The combined organic extracts were dried over sodium sulfate, filtered, and concentrated. The residue was purified by chromatography on silica gel (0-60% EtOAc/heptane) to give a white solid residue. The residue was taken up in heptane, filtered, washed with heptane, and dried with a stream of air on the filter to afford 3,6-dichloro-4-(tetrahydro-2H-pyran-4-yl)pyridazine (50.8% yield) as a white solid. $^1$H NMR (400 MHz, DMSO-d$_6$) δ ppm 8.00 (s, 1H) 3.97 (dt, J=11.28, 3.04 Hz, 2H) 3.39-3.55 (m, 2H) 2.99-3.20 (m, 1H) 1.66-1.82 (m, 4H). LCMS (m/z) (M+H)=232.9, Rt=1.03 min.

Step 2

A vial was charged with 3,6-dichloro-4-(tetrahydro-2H-pyran-4-yl)pyridazine (0.75 g, 3.22 mmol), 4-methyl-3-(4,4,5,5-tetramethyl-1,3,2-dioxaborolan-2-yl)aniline (0.975 g, 4.18 mmol), PdCl$_2$(dppf)-CH$_2$Cl$_2$ adduct (0.263 g, 0.322 mmol), 1,4-Dioxane (Volume: 10.73 ml) and sodium carbonate (2M aq. solution) (4.83 ml, 9.65 mmol) were added. The vial was sealed and heated to 70° C. overnight. After cooling to room temperature, the mixture was diluted with water and extracted with EtOAc (3×). The combined organic extracts were dried over sodium sulfate, filtered, and concentrated. The residue was purified by chromatography on silica gel (40-100% EtOAc/heptane). The major spot was isolated, filtered from heptane, and dried under air to give 3-(6-chloro-5-(tetrahydro-2H-pyran-4-yl)pyridazin-3-yl)-4-methylaniline (445 mg, 1.465 mmol, 45.5% yield) as an off-white solid. $^1$H NMR (400 MHz, DMSO-d6) δ ppm 7.75 (s, 1H) 7.00 (d, J=8.19 Hz, 1H) 6.70 (d, J=2.45 Hz, 1H) 6.63 (dd, J=8.07, 2.45 Hz, 1H) 5.07 (br. s., 2H) 3.98 (dt, J=11.22, 2.95 Hz, 2H) 3.39-3.57 (m, 2H) 3.05-3.22 (m, 1H) 2.13 (s, 3H) 1.71-1.84 (m, 4H). LCMS (m/z) (M+H)=304.0, Rt=0.81 min.

Step 3

A vial was charged with 3-(6-chloro-5-(tetrahydro-2H-pyran-4-yl)pyridazin-3-yl)-4-methylaniline (250 mg, 0.823 mmol), sodium ethoxide (21 wt % solution in ethanol) (922 μl, 2.469 mmol) and ethanol (2 mL) to give a thick suspension. The vial was sealed and placed in a 50° C. heating bath. After 2 h, DMF (0.5 mL) was added, and the heat was raised to 70° C. After another 4 h, the mixture was cooled, diluted with water, and extracted with EtOAc (3×). The combined organic extracts were dried over sodium sulfate filtered, and concentrated. The residue was purified by chromatography on silica gel (50-100% EtOAc/heptane) to give 3-(6-ethoxy-5-(tetrahydro-2H-pyran-4-yl)pyridazin-3-yl)-4-methylaniline (259.3 mg, 0.827 mmol, 101% yield) as a white foam. $^1$H NMR (400 MHz, DMSO-d6) δ ppm 7.43 (s, 1H) 6.96 (d, J=8.19 Hz, 1H) 6.55-6.69 (m, 2H) 4.99 (br. s., 2H) 4.56 (q, J=6.97 Hz, 2H) 3.95 (dd, J=10.33, 2.75 Hz, 2H) 3.46 (td, J=11.19, 3.18 Hz, 2H) 2.97-3.06 (m, 1H) 2.11 (s, 3H) 1.58-1.78 (m, 4H) 1.42 (t, J=7.03 Hz, 3H). LCMS (m/z) (M+H)=314.3, Rt=0.86 min.

159
Synthesis of 5-(6-ethoxy-5-(tetrahydro-2H-pyran-4-yl)pyridazin-3-yl)-6-methylpyridin-3-amine

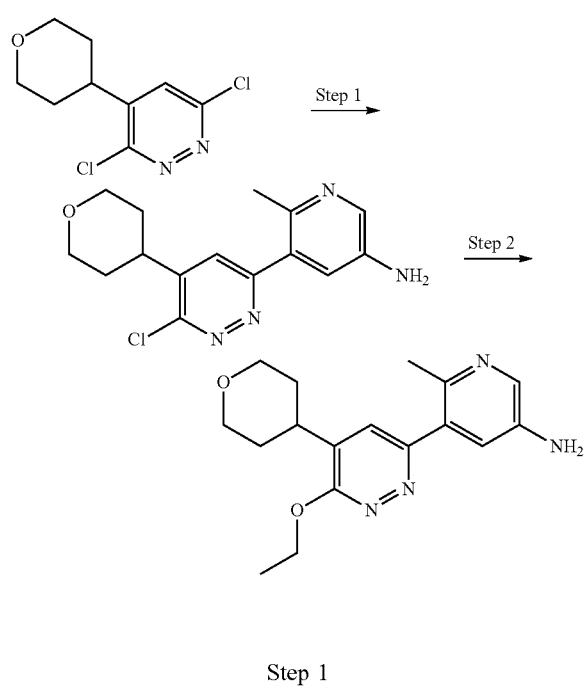

Step 1

A vial was charged with 3,6-dichloro-4-(tetrahydro-2H-pyran-4-yl)pyridazine (0.773 g, 3.32 mmol), 6-methyl-5-(4,4,5,5-tetramethyl-1,3,2-dioxaborolan-2-yl)pyridin-3-amine (1.009 g, 4.31 mmol), $PdCl_2(dppf)-CH_2Cl_2$ adduct (0.271 g, 0.332 mmol), 1,4-Dioxane (Volume: 11.05 ml) and sodium carbonate (2M aq. solution) (4.97 ml, 9.95 mmol) were added. The vial was sealed and heated to 70° C. for 72 h. The mixture was cooled, diluted with water, and extracted with EtOAc (3×). The combined organic extracts were dried over sodium sulfate, filtered, and concentrated. The residue was purified by chromatography on silica gel (0-10% MeOH/DCM) The major spot was isolated with some minor spots to give 5-(6-chloro-5-(tetrahydro-2H-pyran-4-yl)pyridazin-3-yl)-6-methylpyridin-3-amine (1.010 g, 1.988 mmol, 60.0% yield) as a brown solid with ca. 60% purity as assessed LCMS. LCMS (m/z) (M+H)=305.2. Rt=0.71 min.

Step 2

A vial was charged with 5-(6-chloro-5-(tetrahydro-2H-pyran-4-yl)pyridazin-3-yl)-6-methylpyridin-3-amine (598.9 mg, 1.965 mmol), sodium ethoxide (21 wt % solution in ethanol) (2201 µl, 5.90 mmol) and DMF (2 mL) to give a dark solution. The vial was sealed and placed in a 70° C. heating bath for 4 h. The mixture was cooled, diluted with water, and extracted with EtOAc (3×). The combined organic extracts were dried over sodium sulfate filtered, and concentrated. The residue was purified by chromatography on silica gel (0-10% MeOH/DCM) to give 5-(6-ethoxy-5-(tetrahydro-2H-pyran-4-yl)pyridazin-3-yl)-6-methylpyridin-3-amine (320.7 mg, 1.020 mmol, 51.9% yield) as a tan foam of ca. 90% purity by LCMS. LCMS (m/z) (M+H)=315.0, Rt=0.83 min.

160
Synthesis of 2-(1,1,2-trifluoroethyl)isonicotinic acid

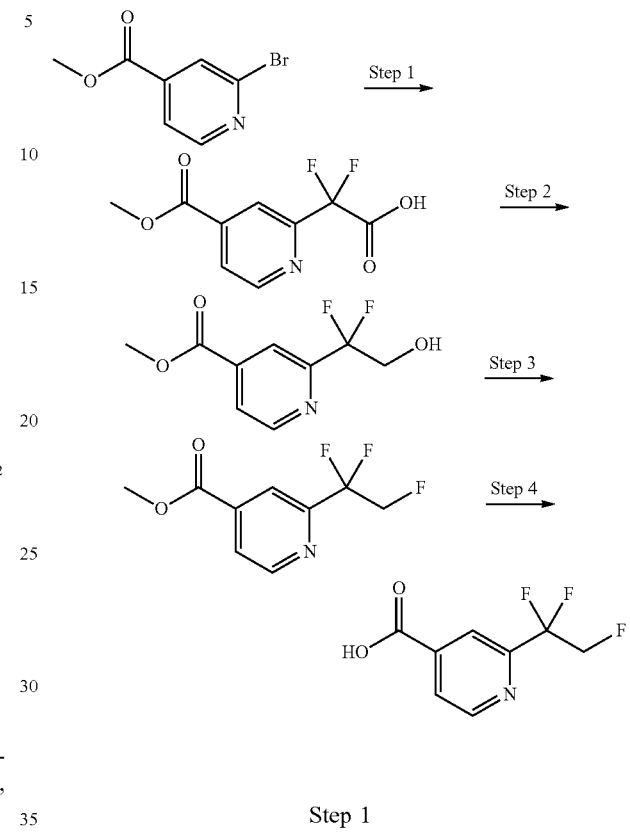

Step 1

To a mixture of copper (3.0 equiv.), methyl 2-bromoisonicotinate (1.0 equiv.) in DMSO (1 M, degassed) was added ethyl 2-bromo-2,2-difluoroacetate (1.2 equiv.) and heated in a flask for 18 h at 62° C. (oil bath). To this rxn mixture was added water (3.0 mL) and DMSO (3.0 mL) and refluxed for 30 min at 100° C. The cooled reaction mixture was diluted with water and filtered off the insoluble particles. It was then partitioned between water and ethyl acetate. The organic phase was washed with saturated $NH_4Cl$, brine, dried over sodium sulfate, filtered, and concentrated. The crude product was purified by flash chromatography over silica gel (DCM with 20% MeOH) to give 2,2-difluoro-2-(4-(methoxycarbonyl)pyridin-2-yl)acetic acid in 26.5% yield. LCMS (m/z) (M+H)=231.9, Rt=1.22 min.

Step 2

To a cooled (−15° C.) solution of 2,2-difluoro-2-(4-(methoxycarbonyl)pyridin-2-yl)acetic acid (1.0 equiv.), 4-methylmorpholine (1.0 equiv.) in dioxane: THF (1:1 ratio) (0.5 M) was added isobutyl carbonochloridate (1.0 equiv.) and stirred for 20 min. To this cold reaction mixture was added $NaBH_4$ (1.0 equiv.) dissolved in water (2.0 mL) and allowed it to come to room temperature and stirred for 30 min. The reaction mixture was quenched by the addition of saturated $NH_4Cl$ and extracted with ethyl acetate. The combined extracts were dried over magnesium sulfate, filtered, and concentrated. The crude product was purified by flash chromatography over silica gel (heptanes with 100% ethyl acetate) to give methyl 2-(1,1-difluoro-2-hydroxy-ethyl)isonicotinate in 43.9% yield. LCMS (m/z) (M+H)=218.2, Rt=0.87 min.

Step 3

To a solution of methyl 2-(1,1-difluoro-2-hydroxyethyl) isonicotinate (1.0 equiv.) in THF (0.1M) were added triethylamine (12.0 equiv.), perfluorobutanesulfonyl fluoride (4.0 equiv.), and triethylamine trihydrofluoride (4.0 equiv.) in sequence. The reaction mixture was heated in for 4 h at 60° C. (heating block). The cooled reaction mixture was poured into saturated NaHCO₃ and vigorously agitated until the effervescence subsided. It was extracted ethyl acetate. The organic phase was dried over magnesium sulfate, filtered, and concentrated. The crude product was purified by flash chromatography over silica gel (heptanes with 50% ethyl acetate) to give methyl 2-(1,1,2-trifluoroethyl)isonicotinate in 95% yield. LCMS (m/z) (M+H)=219.9, Rt=1.23 min.

Step 4

To a solution of methyl 2-(1,1,2-trifluoroethyl)isonicotinate (1.0 equiv.) in THF:MeOH: 3:2 ratio (0.3M) was added LiOH.H₂O (5.0 equiv.) in water (0.5 mL) and stirred at room temperature for 30 min. The reaction mixture was concentrated under reduced pressure and neutralized to pH 1 using 4.0N HCl (aq.). It was extracted ethyl acetate. The organic phase was washed with brine, dried over magnesium sulfate, filtered, and concentrated to 2-(1,1,2-trifluoroethyl)isonicotinic acid in 57.6% yield. LCMS (m/z) (M+H)=205.9. Rt=0.98 min.

Synthesis of
2-(1-(trifluoromethyl)cyclopropyl)isonicotinic acid

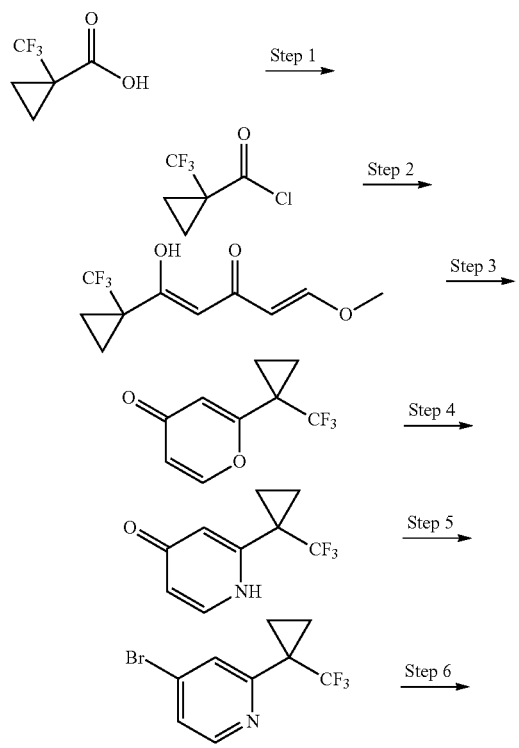

Step 1

A solution of 1-(trifluoromethyl)cyclopropanecarboxylic acid (1 equiv) in DCM (0.65 M) was treated with DMF (4 drops) followed by oxalyl chloride (1.5 equiv) over 20 s. After 4 h, the mixture was concentrated (150 mbar, 24° C.) to give 1-(trifluoromethyl)cyclopropanecarbonyl chloride (88% yield) as a yellow oil containing some DCM. ¹H NMR (400 MHz, CHLOROFORM-d) δ ppm 1.81-1.89 (m, 2H) 1.60-1.69 (m, 2H).

Step 2

A round-bottom flask was charged with (E)-4-methoxy-but-3-en-2-one (2 equiv) and THF (0.1 M) to give a brown solution. The solution was cooled in a dry ice-acetone bath for 15 min, then lithium bis(trimethylsilyl)amide (1.5M in THF, 2 equiv) was added dropwise over 10 min. After 15 min, a solution of 1-(trifluoromethyl)cyclopropanecarbonyl chloride (I equiv) in THF was added dropwise. After 5 min, the cooling bath was removed. The mixture was stirred for 30 min, then quenched with saturated aq. ammonium chloride solution. The volatiles were removed in vacuo. The resulting mixture was diluted with water and extracted with ether (3×). The combined ethereal solution was dried over magnesium sulfate, filtered, and concentrated. The residue was purified by chromatography on silica gel (0-15% EtOAc/heptane) to give (1Z,4E)-1-hydroxy-5-methoxy-1-(1-(trifluoromethyl)cyclopropyl)penta-1,4-dien-3-one (46.9% yield) as a light-yellow oil. ¹H NMR (400 MHz. CHLOROFORM-d) δ ppm 7.47 (d, J=12.35 Hz, 1H) 5.58-5.66 (m, 1H) 5.15 (d, J=12.47 Hz, 1H) 3.58-3.61 (m, 3H) 1.30-1.36 (m, 2H) 1.11-1.18 (m, 2H). LCMS (m/z) (M+H)=. Rt=1.51 min (acidic method) and 1.08 min (basic method).

Step 3

A round-bottom flask was charged with (1Z,4E)-1-hydroxy-5-methoxy-1-(1-(trifluoromethyl)cyclopropyl)penta-1,4-dien-3-one (1 equiv), toluene (0.2M), and trifluoroacetic acid (2 equiv) to give a yellow solution. The mixture was stirred at room temperature for 72 h, then was concentrated. The residue was purified by chromatography on silica gel (30-80% EtOAc/heptane) to give 2-(1-(trifluoromethyl)cyclopropyl)-4H-pyran-4-one (72.2% yield) as a light-orange solid. ¹H NMR (400 MHz, CHLOROFORM-d) δ ppm 7.72 (d, J=5.87 Hz, 1H) 6.50 (d, J=2.45 Hz, 1H) 6.34 (dd, J=5.87, 2.45 Hz, 1H) 1.43-1.54 (m, 2H) 1.28-1.39 (m, 2H).

Step 4

A round-bottom flask was charged with 2-(1-(trifluoromethyl)cyclopropyl)-4H-pyran-4-one (1 equiv) and ammonium hydroxide (0.28 M). The flask was then heated to 60-65° C. for 1.5 h. The mixture was cooled to room temperature and concentrated in vacuo. The residue was purified by chromatography on silica gel (0-10% MeOH/DCM) to give 2-(1-(trifluoromethyl)cyclopropyl)pyridin-4

(1H)-one (94% yield) as a light-yellow solid. $^1$H NMR (400 MHz, CHLOROFORM-d) δ ppm 7.69 (d, J=6.97 Hz, 1H) 6.66 (d, J=2.45 Hz, 1H) 6.47 (dd, J=6.97, 2.45 Hz, 1H) 1.29-1.47 (m, 2H) 1.05-1.28 (m, 2H). LCMS (m/z) 204.0, Rt=0.59 min.

Step 5

A round-bottom flask was charged with 2-(1-(trifluoromethyl)cyclopropyl)pyridin-4(1H)-one (1 equiv), 1,2-dichloroethane (0.4 M), and phosphorus oxybromide (1.2 equiv). The flask was fitted with a reflux condenser and heated to 85° C. by for 2 h. After cooling to room temperature, the mixture was carefully quenched with saturated aq. sodium bicarbonate solution and stirred for 10 min. The mixture was extracted with DCM (3×), and the combined organic extracts were dried over sodium sulfate, filtered, and concentrated. The residue was purified by chromatography on silica gel (0-15% EtOAc/heptane) to give 4-bromo-2-(1-(trifluoromethyl)cyclopropyl)pyridine (0.0% yield) as a clear oil. $^1$H NMR (400 MHz, CHLOROFORM-d) δ ppm 8.36 (d, J=5.26 Hz, 1H) 7.72-7.78 (m, 1H) 7.38 (dd, J=5.32, 1.77 Hz, 1H) 1.40-1.50 (m, 4H).

Step 6

A round-bottom flask was charged with 4-bromo-2-(1-(trifluoromethyl)cyclopropyl)pyridine (1 equiv) and THF (0.2 M). The flask was cooled in a dry ice-acetone bath for 10 min, then n-butyllithium (1.87 M in hexane) (1.05 equiv) was added dropwise. After 30 min, freshly crushed dry ice was added to the flask. After another 10 min, water was carefully added (10 equiv), then the mixture was warmed to room temperature. The mixture was then diluted with ether and extracted with water (3×). The combined aq. layer was adjusted to ca. pH 3-4 with 6N aq. HCl and extracted with DCM (3×). The combined organic extracts were dried over sodium sulfate, filtered, and concentrated to give a white solid. This material was taken up in ether, sonicated for 30 s, then filtered. The collected solid was washed with ether (2×), then dried under a flow of N$_2$ (g) for 5 min to give the desired product as a white solid. The aq. layer was extracted further with DCM/MeOH (ca. 3:1, 7×). The combined organics were concentrated to give a solid which was taken up in ether, filtered, washed with ether (3×), and dried under a stream of N$_2$ (g) for 5 min. The two purified solids were combined to give 2-(1-(trifluoromethyl)cyclopropyl)isonicotinic acid (59% yield) as a white solid. $^1$H NMR (400 MHz, DMSO-d6) δ ppm 13.82 (br. s., 1H) 8.75 (dd, J=5.01, 0.73 Hz, 1H) 7.93 (s, 1H) 7.77 (dd, J=4.89, 1.47 Hz, 1H) 1.41-1.51 (m, 4H).

Synthesis of 4-(1-(trifluoromethyl)cyclopropyl)picolinic acid

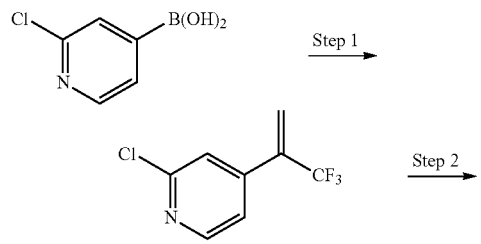

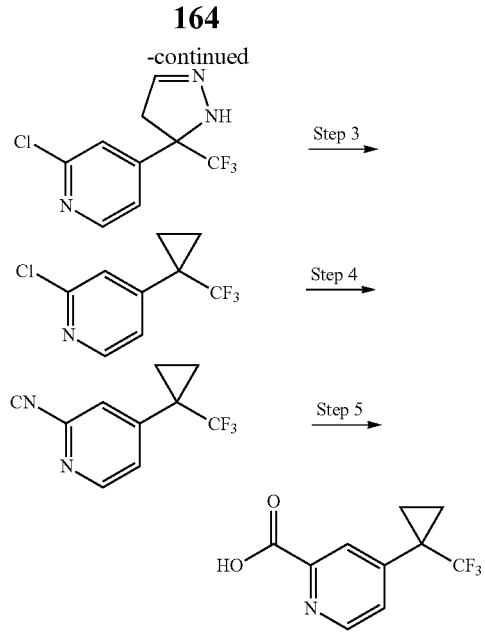

Step 1

A round-bottom flask was charged with (2-chloropyridin-4-yl)boronic acid (1 equiv), potassium carbonate (3.5 equiv), bis(triphenylphosphine)palladium dichloride (0.025 equiv), 2:1 THF/water (0.45 M), and 2-bromo-3,3,3-trifluoroprop-1-ene (1.2 equiv). The flask was fitted with a reflux condenser and heated to 70° C. for 6 h. After cooling to room temperature, the mixture as diluted with water and extracted with EtOAc (3×, decanted away from a gray solid). The combined organic extracts were dried over sodium sulfate, filtered, and concentrated. The residue was purified by chromatography on silica gel (10-60% EtOAc/Heptane) to give 2-chloro-4-(3,3,3-trifluoroprop-1-en-2-yl)pyridine (47.6% yield) as a pale-orange oil. $^1$H NMR (600 MHz, CHLOROFORM-d) δ ppm 8.46 (d, J=5.23 Hz, 1H) 7.44 (s, 1H) 7.32 (d, J=5.14 Hz, 1H) 6.20 (s, 1H) 6.03 (d, J=0.73 Hz, 1H). LCMS (m/z) (M+H)=207.9, Rt=1.39 min.

Step 2

A solution of 2-chloro-4-(3,3,3-trifluoroprop-1-en-2-yl)pyridine (1 equiv) in DCM (0.4 M) was treated with TMS-diazomethane (2M in hexane) (1.5 equiv) at room temperature. After 2 h, trifluoroacetic acid (10 equiv) was added, dropwise at first, resulting in bubbling and some boiling of the solvent. When the exotherm had subsided somewhat, the rest of the TFA was added directly. The mixture was stirred for 2 h then concentrated, and the residue was purified by chromatography on silica gel (25-75% EtOAc/heptane) to give 2-chloro-4-(5-(trifluoromethyl)-4,5-dihydro-1H-pyrazol-5-yl)pyridine (92% yield) as an orange oil. $^1$H NMR (400 MHz, DMSO-d6) δ ppm 8.50 (d, J=5.26 Hz, 2H) 7.68 (s, 1H) 7.56 (dd, J=5.26, 0.61 Hz, 1H) 6.79 (s, 1H) 3.45 (dd, J=18.28, 1.65 Hz, 1H) 3.18-3.31 (m, 1H). LCMS (m/z) (M+H)=249.9, Rt=1.06 min.

Step 3

A 50-mL recovery flask was charged with 2-chloro-4-(5-(trifluoromethyl)-4,5-dihydro-1H-pyrazol-5-yl)pyridine (1 equiv). The flask was fitted with a reflux condenser and heated to 160° C. for 20 h. After cooling to room temperature, the mixture was diluted with acetone (14 mL). LCMS showed very clean ca 1:1 cyclopropane to olefin. The solution was treated in sequence with a solution of 2.5 wt % of osmium tetroxide in t-BuOH (0.005 equiv) and 30% aq. hydrogen peroxide (5 equiv). After 6 h, an additional portion of osmium tetroxide solution (0.005 equiv) and 30% aq. hydrogen peroxide (5 equiv). After stirring overnight, the mixture was carefully quenched by the addition of 1M aq. sodium thiosulfate solution until it remained black. The aq. mixture was then extracted with EtOAc (3×), and the combined organic extracts were washed with saturated aq. sodium thiosulfate solution, and the aq. layer was back extracted with EtOAc (1×). The combined organic extracts were dried over sodium sulfate, filtered, and concentrated. The residue was purified by chromatography on silica gel (0-25% EtOAc/heptane) to give 2-chloro-4-(1-(trifluoromethyl)cyclopropyl)pyridine (49.6% yield) as a clear oil. ¹H NMR (400 MHz. CHLOROFORM-d) δ ppm 8.40 (dd, J=5.13, 0.61 Hz, 1H) 7.40 (d, J=0.61 Hz, 1H) 7.30 (dd, J=5.14, 0.73 Hz, 1H) 1.44-1.51 (m, 2H) 1.08-1.15 (m, 2H). LCMS (m/z) (M+H)=221.9, Rt=1.41 min.

Step 4

A round-bottom flask was charged with 2-chloro-4-(1-(trifluoromethyl)cyclopropyl)pyridine (1 equiv). [1,1'-binaphthalen]-2-yldi-tert-butylphosphine (0.1 equiv), zinc cyanide (0.8 equiv), palladium(II) trifluoroacetate (0.05 equiv), and Zn powder (0.2 equiv). The flask was flushed with N₂ (g), then N,N-dimethylacetamide (0.2 M) was added. The flask was sealed and heated to 80° C. for 2.5 h. After cooling to room temperature, the filtrate was partially concentrated in vacuo, and the residue was taken up in EtOAc and washed with water (2×, emulsion taken with aq. layer) and brine. The aq. layer was back-extracted with EtOAc (2×), and the combined organic extracts were dried over sodium sulfate, filtered, and concentrated. The residue was purified by chromatography on silica gel (0-30% EtOAc/heptane). The product spot was collected with a lower spot (DMAC) to give an oily solid. The material was partitioned between water and EtOAc. The layers were separated, and the organic layer was washed with brine, dried over sodium sulfate, filtered, and concentrated to give 4-(1-(trifluoromethyl)cyclopropyl)picolinonitrile (76% yield, 90% purity) as a gummy solid. ¹H NMR (400 MHz, CHLOROFORM-d) δ ppm 8.64 (dd, J=5.13, 0.86 Hz, 1H) 7.61-7.76 (m, 1H) 7.45-7.56 (m, 1H) 1.40-1.54 (m, 3H) 0.92-1.11 (m, 2H). LCMS (m/z) (M+H)=212.9, Rt=1.30 min.

Step 5

A round-bottom flask was charged with 4-(1-(trifluoromethyl)cyclopropyl)picolinonitrile (1 equiv) and 6M aq. hydrochloric acid (20 equiv). A reflux condenser was attached, and the flask was heated to 100° C. oil overnight. The mixture was cooled to room temperature and adjusted to pH 14 with 6N aq. NaOH. The aq. solution was extracted with ether, and the ethereal layer was back-extracted with water. The combined aq. layers were acidified by ca. pH 3.5 with 1N aq. HCl and extracted with 10% MeOH/DCM (8×). The combined organic extracts were dried over sodium sulfate, filtered, and concentrated to give a light-yellow solid. The mixture was concentrated from DCM/heptane, taken up in heptane, then filtered. The collected solid was washed with heptane (3×), the dried under a flow of N₂ (g) to 4-(1-(trifluoromethyl)cyclopropyl)picolinic acid (74.8% yield) as an off-white solid. ¹H NMR (400 MHz, DMSO-d6) δ ppm 13.39 (br. s., 1H) 8.72 (dd, J=5.01, 0.73 Hz, 1H) 8.04-8.07 (m, 1H) 7.68 (dd, J=5.01, 1.59 Hz, 1H) 1.43-1.50 (m, 2H) 1.27-1.34 (m, 2H). LCMS (m/z) (M+H)=232.2. Rt=0.83.

Synthesis of 7-(5-amino-2-methylphenyl)-2-(hydroxymethyl)-2-methyl-5-(tetrahydro-2H-pyran-4-yl)-2H-benzo[b][1,4]oxazin-3(4H)-one

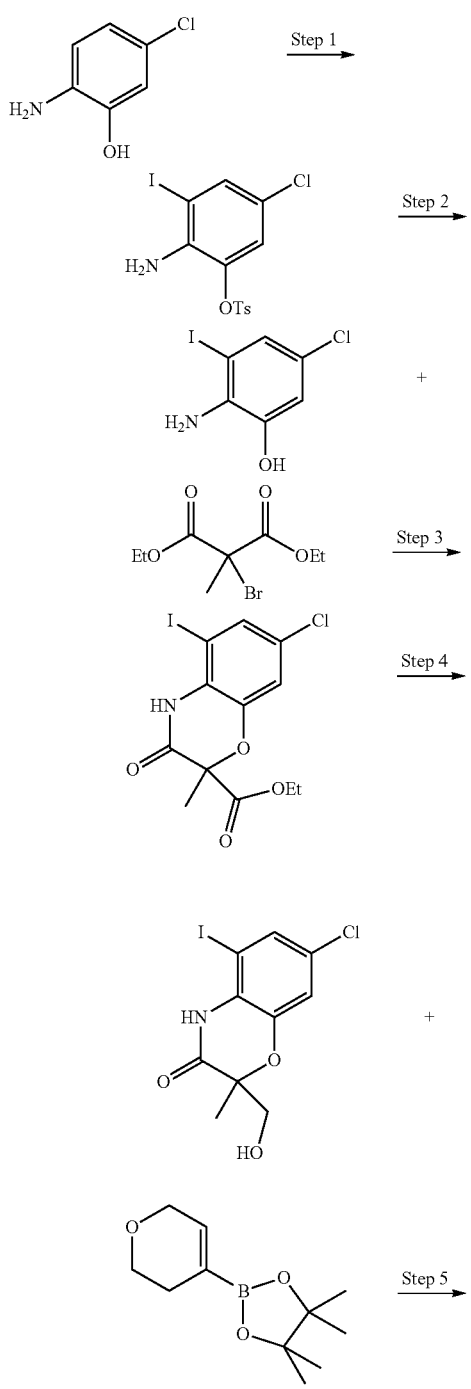

-continued

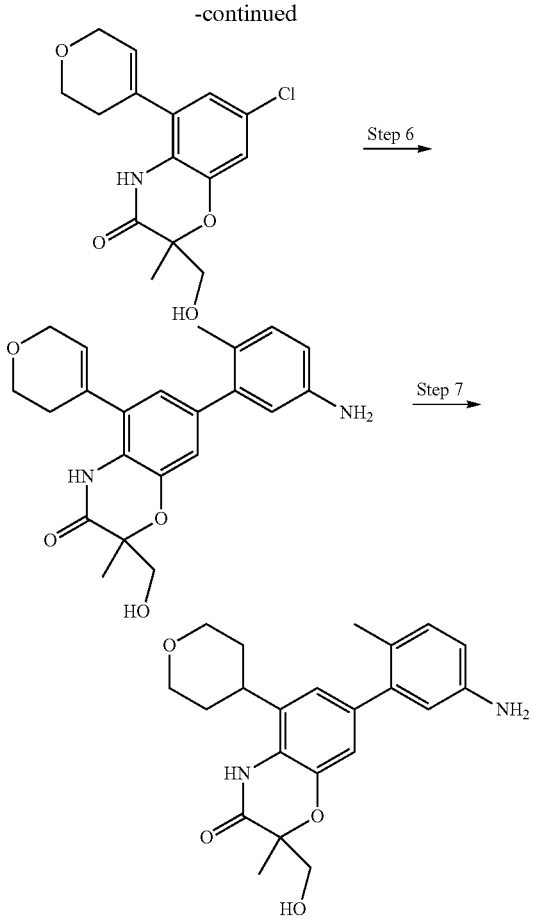

Step 1

2-amino-5-chlorophenol (1.0 equiv.) and triethylamine (1.05 equiv.) were dissolved in DCM (0.5 M) and then to the mixture at room temperature was added p-TsCl (1.0 equiv.). The mixture was agitated at room temperature for 1 h and quenched by addition of water. The product was extracted with DCM and washed with brine and dried (MgSO$_4$), filtered and concentrated in vacuo to afford the desired product 2-amino-5-chlorophenyl 4-methylbenzenesulfonate. The residue was taken to the next step without any further purification. Assume quantitative yield. LCMS (m/z) (M+H)=298.1. Rt=1.50 min.

2-amino-5-chlorophenyl 4-methylbenzenesulfonate from above, Silver Sulfate (1.0 equiv.) were suspended in EtOH (0.2 M) and then 12(1.0 equiv.) was added. The mixture was agitated at room temperature. After 1 h, complete conversion to the desired product was observed. The reaction mixture was filtered through celite and concentrated in vacuo. The residue was dissolved in EtOAc and washed with Sat'd Na$_2$S$_2$O$_5$ twice and then dried (MgSO$_4$), filtered and concentrated in vacuo. The residue 2-amino-5-chloro-3-iodophenyl 4-methylbenzenesulfonate was obtained in quantitative crude yield and was taken to the next step without any further purification. LCMS (m/z) (M+H)=423.8, Rt=1.71 min.

Step 2

2-amino-5-chloro-3-iodophenyl 4-methylbenzenesulfonate from above (29.5 g, 69.7 mmol) was suspended in 3:1 EtOH/THF (0.5 M). To the mixture was added 2.0 M NaOH (3.5 equiv.) and the mixture was then heated to reflux for 30 min and then cooled to room temperature and concentrated in vacuo. The residue was neutralized to pH=7 using 6 N HCl and the product extracted DCM. The organic layer was dried (MgSO$_4$), filtered and concentrated in vacuo. The residue was titutrated with 10:1 heptane/ether and the darkbrown precipitate was collected by filtration, affording 2-amino-5-bromo-3-iodophenol in 55% yield. LCMS (m/z) (M+H)=269.8, Rt=1.26 min.

Step 3

To a solution of 2-amino-5-bromo-3-iodophenol (1.0 equiv.) and KF (7.8 equiv) in DMF (0.5 M) was added diethyl 2-bromo-2-methylmalonate (3.3 equiv.) and the mixture was agitated at 70° C. for 70 min. After the elapsed time, the reaction mixture was cooled to room temperature and poured onto water and extracted with EtOAc. The organic layer was washed with water and brine and dried (MgSO$_4$), filtered and concentrated in vacuo. The residue was dissolved in DCM and the product precipitated upon addition of hepanes. The dark-brown product was collected by suction filtration to afford ethyl 7-chloro-5-iodo-2-methyl-3-oxo-3,4-dihydro-2H-benzo[b][1,4]oxazine-2-carboxylate in 72.7% isolated yield. LCMS (m/z) (M+H)=395.8, Rt=1.51 min.

Step 4 ethyl 7-chloro-5-iodo-2-methyl-3-oxo-3,4-dihydro-2H-benzo[b][1,4]oxazine-2-carboxylate (1.0 equiv) was dissolved in THF (0.2 M) and then super hydride (5.0 equiv.) was added dropwise. The mixture was agitated at room temperature for 1 h. The mixture was quenched by dropwise addition of water. After the effervescence subsided, the mixture was diluted with EtOAc and washed with Sat'd Na$_2$CO$_3$ and the organic layer was dried (MgSO$_4$), filtered and concentrated in vacuo. The residue was once azeotroped with MeOH and then purified by flash chromatography (0-100% EtOAc/heptane) to afford the desired product 7-chloro-2-(hydroxymethyl)-5-iodo-2-methyl-2H-benzo[b][1,4]oxazin-3(4H)-one in 88% isolated yield as a orange-pink solid. LCMS (m/z) (M+H)=353.8, Rt=1.21 min.

Step 5

7-chloro-2-(hydroxymethyl)-5-iodo-2-methyl-2H-benzo[b][1,4]oxazin-3(4H) (1.0 equiv.), PdCl$_2$(dppf).CH$_2$Cl$_2$ adduct (0.1 equiv.), 2-(3,6-dihydro-2H-pyran-4-yl)-4,4,5,5-tetramethyl-1,3,2-dioxaborolane (1.2 equiv.) and 2.0 M Na$_2$CO$_3$ (2.5 equiv.) were combined in Dioxane (0.3 M). The mixture was heated at 105° C. in a heating block for 1 h. After the elapsed time, the reaction mixture was cooled to room temperature and diluted with EtOAc and washed with brine. The organic layer was dried (MgSO$_4$), filtered and concentrated in vacuo. The residue was purified by flash chromatography (0-100% EtOAc/heptane) to afford 7-chloro-5-(3,6-dihydro-2H-pyran-4-yl)-2-(hydroxymethyl)-2-methyl-2H-benzo[b][1,4]oxazin-3(4H)-one in 68.5% isolated yield as a pale orange solid. LCMS (m/z) (M+H)=310.0, Rt=1.16 min.

Step 6

7-chloro-5-(3,6-dihydro-2H-pyran-4-yl)-2-(hydroxymethyl)-2-methyl-2H-benzo[b][1,4]oxazin-3(4H)-one (1.0 equiv), K$_3$PO$_4$ (3.0 equiv.), 4-methyl-3-(4,4,5,5-tetramethyl-1,3,2-dioxaborolan-2-yl)aniline (1.2 equiv.) and X-Phos-Pd-Precatalyst (G2) (0.1 equiv.) were suspended in 18:1 dioxane/water (0.15 M) was added. The mixture was heated in MW at 130° C. for 30 min and after the elapsed time, the reaction mixture was diluted with EtOAc and brine. The organic layer was separated and dried (MgSO$_4$), filtered and concentrated in vacuo and the residue purified by flash chromatography (0-100% EtOAc/DCM) to afford 7-(5-amino-2-methylphenyl)-5-(3,6-dihydro-2H-pyran-4-yl)-2-(hydroxymethyl)-2-methyl-2H-benzo[b][1,4]oxazin-3(4H)-one in 55% isolated yield as a yellowish brown solid. LCMS (m/z) (M+H)=381.0, Rt=0.83 min.

Step 7

7-(5-amino-2-methylphenyl)-5-(3,6-dihydro-2H-pyran-4-yl)-2-(hydroxymethyl)-2-methyl-2H-benzo[b][1]oxazin-3(4H)-one (1.0 equiv.) was dissolved in EtOH (0.016 M) and then Pd—C 10 wt % wet-basis (0.5 equiv) was added. The mixture was evacuated and back-filled with hydrogen gas. This process was repeated twice and the mixture was agitated at room temperature for 5 h and filtered through celite. The filtrate was concentrated in vacuo to afford 7-(5-amino-2-methylphenyl)-2-(hydroxymethyl)-2-methyl-5-(tetrahydro-2H-pyran-4-yl)-2H-benzo[b][1,4]oxazin-3(4H)-one as pale white solid in 79%/yield, which was used without any further purification. LCMS (m/z) (M+H)=383.3, Rt=0.83 min.

Synthesis of N-(3-(6-chloro-5-(tetrahydro-2H-pyran-4-yl)pyridazin-3-yl)-4-methylphenyl)-4-(trifluoromethyl)picolinamide

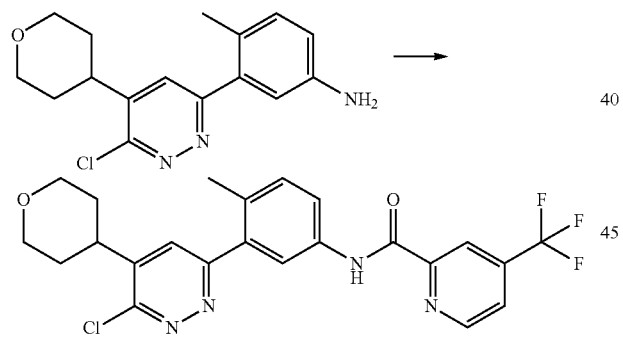

A round-bottom flask was charged with 3-(6-chloro-5-(tetrahydro-2H-pyran-4-yl)pyridazin-3-yl)-4-methylaniline (1 equiv), 4-(trifluoromethyl)-2-pyridylcarboxylic acid (1.2 equiv), EDC.HCl (1.2 equiv), HOAt (1.2 equiv), and DMF (0.2 M) to give a clear, light-yellow solution. After stirring for 2 h at room temperature, the mixture was diluted with saturated aq. sodium bicarbonate and water, then extracted with EtOAc (3×). The combined organic extracts were washed with brine, dried over sodium sulfate, filtered and concentrated. The residue was purified by chromatography on silica gel (25-75% EtOAc/Heptane) to give N-(3-(6-chloro-5-(tetrahydro-2H-pyran-4-yl)pyridazin-3-yl)-4-methylphenyl)-4-(trifluoromethyl)picolinamide (86% yield) as a white solid. $^1$H NMR (400 MHz, DMSO-d$_6$) δ ppm 10.89 (s, 1H) 9.04 (d, J=5.13 Hz, 1H) 8.32-8.41 (m, 1H) 8.10 (dd, J=5.01, 1.10 Hz, 1H) 8.06 (d, J=2.20 Hz, 1H) 8.01 (dd, J=8.25, 2.26 Hz, 1H) 7.89 (s, 1H) 7.40 (d, J=8.44 Hz, 1H) 3.95-4.06 (m, 2H) 3.47-3.56 (m, 2H) 3.12-3.23 (m, 1H) 2.33 (s, 3H) 1.77-1.85 (m, 4H). LCMS (m/z) (M+H)=477.0, Rt=1.57 min.

Synthesis of 6-(4-ethylpiperazin-1-yl)-5-(trifluoromethyl)nicotinic acid

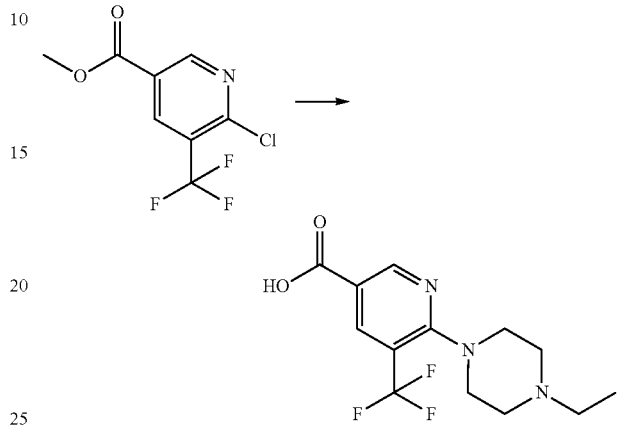

A 60% oil dispersion of sodium hydride (2 equiv) was added to 1,4-Dioxane (0.5 M) in a vial. 1-ethylpiperazine (2 equiv) was added dropwise and the resulting solution was stirred at room temperature for 15 minutes. Methyl 6-chloro-5-(trifluoromethyl)nicotinate (1 equiv) was added and resulting mixture was heated at 60° C. for 4 hours. Lithium hydroxide (1 equiv) and a few drops of water were added to saponify the ester. HCl (4M in 1,4-Dioxane, 1 equiv) was then added and the reaction was quenched with excess MeOH and the volatiles were concentrated. The residue was dissolved in DCM, passed through a filter frit and concentrated. The residue was purified by chromatography on silica gel (0-10% MeOH/DCM) to give 6-(4-ethylpiperazin-1-yl)-5-(trifluoromethyl)nicotinic acid (30.4% yield) as a tan solid. LCMS (m/z) (M+H)=304.3, Rt=0.65 min.

Synthesis of N-(3-(6-chloro-5-(tetrahydro-2H-pyran-4-yl)pyridazin-3-yl)-4-methylphenyl)-2-(trifluoromethyl)isonicotinamide

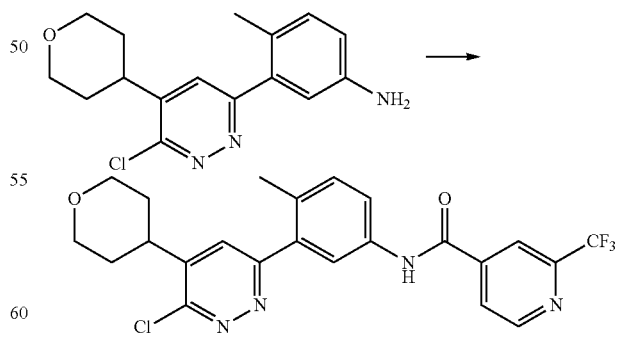

2-(trifluoromethyl)isonicotinic acid (1 equiv) was added to a solution of 3-(6-chloro-5-(tetrahydro-2H-pyran-4-yl)pyridazin-3-yl)-4-methylaniline (1 equiv) in DMF (0.2 M). EDC.HCl (1.2 equiv) and HOAt (1.2 equiv) were then added and the reaction mixture was stirred at room temperature overnight. The reaction was diluted with saturated sodium bicarbonate solution (2 ml) and extracted three times with EtOAc. The combined organics were washed with brine, dried over magnesium sulfate, filtered and concentrated. The residue was purified by chromatography on silica gel (0-1 (P/MeOH/DCM) to give a pale yellow oil, which was dried under high vacuum over the weekend to give N-(3-(6-chloro-5-(tetrahydro-2H-pyran-4-yl)pyridazin-3-yl)-4-methylphenyl)-2-(trifluoromethyl)isonicotinamide (70.8% yield) as pale yellow oil. LCMS (m/z) (M+H)=477.2, Rt=1.46 min.

Synthesis of 6-(5-amino-2-methylphenyl)-2,2-dimethyl-8-(tetrahydro-2H-pyran-4-yl)-2H-benzo[b][1,4]oxazin-3(4H)-one

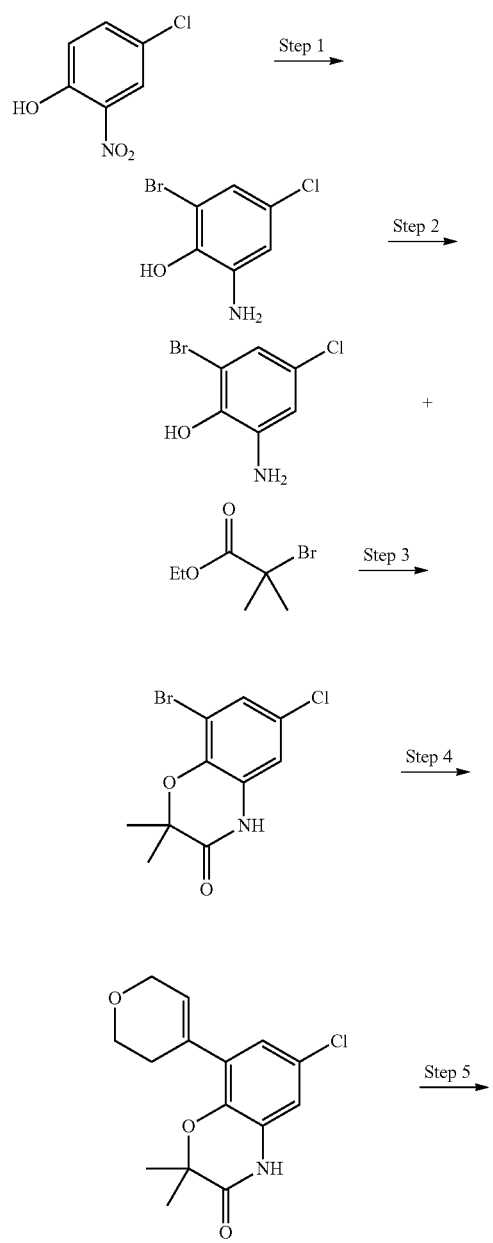

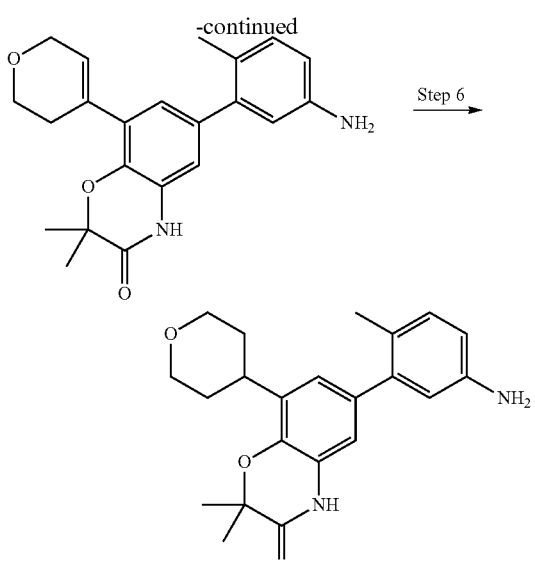

Step 1

4-chloro-2-nitrophenol (1.0 equiv.) was dissolved in Acetic Acid (0.64 M) and cooled in an ice-bath. To the mixture was then added bromine (1.1 equiv.) and the mixture agitated for 3 h while gradually warming to room temperature. Additional bromine (0.3 equiv.) was added. Then, after additional hour, almost complete conversion to the desired product is observed. At this stage, ice-cold water was added and immediately, a yellowish suspension was observed. The mixture was vigorously agitated and then filtered. The yellowish orange precipitate was washed with water and then with heptane and the yellow powder was placed under high-vacuum for 3 days to afford 2-bromo-4-chloro-6-nitrophenol in 76% yield. LCMS (m/z) (M+H)=291.9, Rt=1.45 min.

Step 2

2-bromo-4-chloro-6-nitrophenol (1.0 equiv.) was suspended in EtOH (0.5) and then iron powder (8.0 equiv.) followed by NH$_4$Cl (8.0 equiv.) and Water (1/10 of EtOH volume) was added. The mixture was heated at 90° C. for 75 min and then filtered hot through celite. The filtrate was concentrated in vacuo and there residue dissolved in EtOAc and washed with water and brine. The organic layer was dried (MgSO$_4$), filtered and concentrated in vacuo to give a dark brown residue. This material was suspended in DCM and titurated with heptane. The dark brown suspension was collected by filtration to afford 2-amino-6-bromo-4-chlorophenol in 64% yield. LCMS (m/z) (M+H)=223.8, Rt=1.11 min.

Step 3

K$_2$CO$_3$ (3.0 equiv.), 2-amino-6-bromo-4-chlorophenol (1.0 equiv.), ethyl 2-bromo-2-methylpropanoate (1.2 equiv.) were suspended in Acetone (0.3M) and the mixture agitated at 70° C. overnight. The next morning, the mixture was filtered through celite and the filtrate concentrated in vacuo. The residue was dissolved in DCM and dry-loaded onto silica and purified by flash chromatography (0-100% EtOAc/heptane) and the product fractions combined and concentrated in vacuo and the residue was titutrated with heptane and the off-white (light pink tinge) solid was collected by filtration and represented 8-bromo-6-chloro-2,2-dimethyl-2H-benzo[b][1,4]oxazin-3(4H)-one in 32% yield. LCMS (m/z) (M+H)=291.8. Rt=1.47 min.

Step 4

8-bromo-6-chloro-2,2-dimethyl-2H-benzo[b][1,4]oxazin-3(4H)-one (1.0 equiv.) PdCl$_2$(dppf).CH$_2$Cl$_2$ adduct (0.1 equiv.), 2-(3,6-dihydro-2H-pyran-4-yl)-4,4,5,5-tetramethyl-1,3,2-dioxaborolane (1.0 equiv.) were combined in Dioxane (0.3 M) and then 2.0 M Na$_2$CO$_3$ (3.0 equiv.) was added. The mixture was agitated at 105° C. in a heating block. After 90 min, the reaction mixture was diluted with EtOAc and washed with brine and dried (Na$_2$SO$_4$), filtered and concentrated in vacuo. The residue was purified by flash chromatography (0-50% EtOAc/heptane) to afford 6-chloro-8-(3,6-dihydro-2H-pyran-4-yl)-2,2-dimethyl-2H-benzo[b][1,4]oxazin-3(4H)-one in 36.4% yield as a light orange solid. LCMS (m/z) (M+H)=293.9, Rt=1.33 min.

Step 5

K$_3$PO$_4$ (3.0 equiv.), 6-chloro-8-(3,6-dihydro-2H-pyran-4-yl)-2,2-dimethyl-2H-benzo[b][1,4]oxazin-3(4H)-one (1.0 equiv.), 4-methyl-3-(4,4,5,5-tetramethyl-1,3,2-dioxaborolan-2-yl)aniline (1.2 equiv.) and X-Phos-Pd-Precatalyst (G2) (0.1 equiv.) were suspended in 10:1 Dioxane/Water (0.2 M). The mixture was heated in MW at 130° C. for 30 min and the reaction mixture was diluted with EtOAc and washed with brine and dried (MgSO$_4$), filtered and concentrated in vacuo. The residue was purified by flash chromatography (0-100% EtOAc/heptane) to afford 6-(5-amino-2-methylphenyl)-8-(3,6-dihydro-2H-pyran-4-yl)-2,2-dimethyl-2H-benzo[b][1,4]oxazin-3(4H)-one in 84% yield. LCMS (m/z) (M+H)=365.0, Rt=0.94 min.

Step 6

6-(5-amino-2-methylphenyl)-8-(3,6-dihydro-2H-pyran-4-yl)-2,2-dimethyl-2H-benzo[b][14]oxazin-3(4H)-one (1.0 equiv.) was dissolved in EtOH (0.07 M). To the mixture was added Pd—C (10 wt % wet basis) (0.34 equiv) and the mixture was evacuated and purged with hydrogen (3x). The reaction was agitated at room temperature under 1 atm of hydrogen gas overnight. The next morning the reaction mixture was diluted with DCM and filtered through celite and the filtrate was concentrated in vacuo to afford quantitative yield of 6-(5-amino-2-methylphenyl)-2,2-dimethyl-8-(tetrahydro-2H-pyran-4-yl)-2H-benzo[b][1,4]oxazin-3(4H)-one. LCMS (m/z) (M+H)=366.9, Rt=0.94 min.

Synthesis of 6-(5-amino-2-methylphenyl)-2-(hydroxymethyl)-2-methyl-8-(tetrahydro-2H-pyran-4-yl)-2H-benzo[b][1,4]oxazin-3(4H)-one

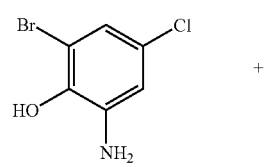

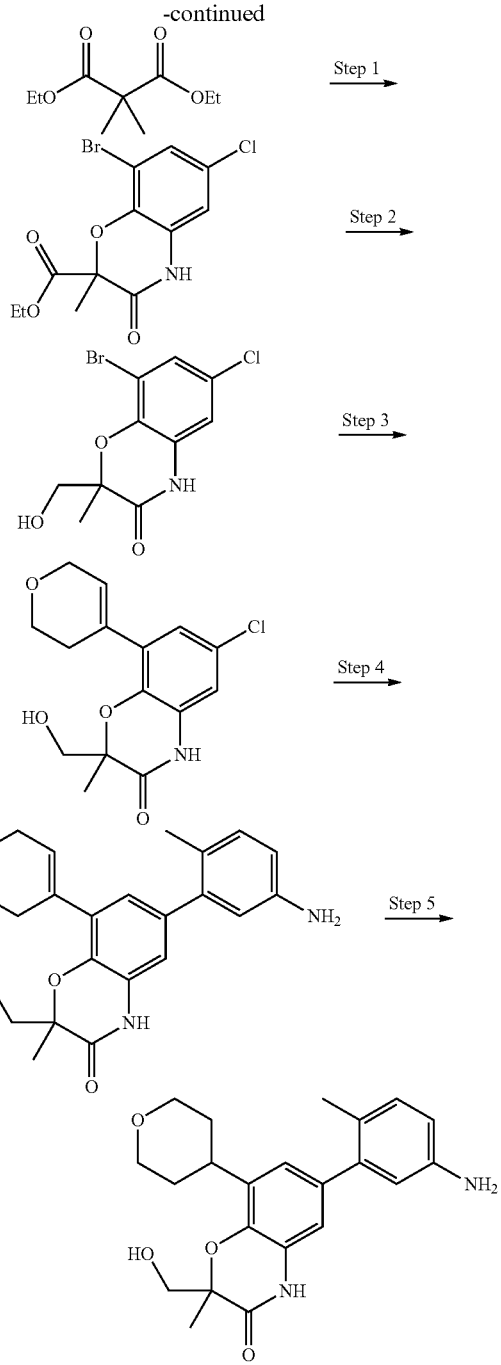

Step 1

To a solution of 2-amino-6-bromo-4-chlorophenol (1.0 equiv.) and KF (7.85 equiv.) in DMF (0.5 M) was added diethyl 2-bromo-2-methylmalonate (3.3 equiv.) and the mixture was agitated at 70° C. for 70 min. The reaction mixture was cooled to room temperature and poured into water and extracted with EtOAc. During work-up, emulsion developed. The entire emulsion was passed through celite and the layer separated. The organic layer was washed with water and brine and dried (MgSO$_4$), filtered and concentrated in vacuo. The residue was purified by flash chromatography (0-50% EtOAc/heptane) to afford the crude product which was titurated with heptane and the off-white solid was collected by filtration to afford ethyl 8-bromo-6-chloro-2-methyl-3-oxo-3,4-dihydro-2H-benzo [b][1,4]oxazine-2-carboxylate in 34.1% yield. LCMS (m/z) (M+H)=349.8, Rt=1.47 min.

Step 2

Ethyl 8-bromo-6-chloro-2-methyl-3-oxo-3,4-dihydro-2H-benzo [b][1,4]oxazine-2-carboxylate (1.0 equiv.) was dissolved in Tetrahydrofuran (0.2 M) and at room temperature was added super hydride (6.0 equiv.). The mixture was agitated at room temperature for 30 min md the reaction was quenched by drop-wise addition of water and then extracted with EtOAc. The organic layer was dried (MgSO$_4$), filtered and concentrated in vacuo and the residue azeotroped with MeOH. The solid was dissolved in DCM and loaded into silica-gel and the product was purified by flash chromatography (0-100% EtOAc/heptane) to afford the desired product 8-bromo-6-chloro-2-(hydroxymethyl)-2-methyl-2H-benzo [b][1,4]oxazin-3(4H)-one in 70.5% yield. LCMS (m/z) (M+H)=307.8. Rt=1.18 min.

Step 3

8-bromo-6-chloro-2-(hydroxymethyl)-2-methyl-2H-benzo [b][1,4]oxazin-3(4H)-one (1.0 equiv.), PdCl$_2$(dppf).CH$_2$Cl$_2$ adduct (0.1 equiv.), 2-(3,6-dihydro-2H-pyran-4-yl)-4,4,5,5-tetramethyl-1,3,2-dioxaborolane (1.2 equiv.) were combined in Dioxane (0.22 M) and then 2.0 M Na$_2$CO$_3$ (3.0 equiv.) was added. The mixture was agitated at 120° C. in MW for 30 min. After the elapsed time, the reaction mixture was cooled to room temperature and diluted with EtOAc and washed with brine and dried (Na$_2$SO$_4$), filtered and concentrated in vacuo and the residue purified by flash chromatography (0-100% EtOAc/heptane) to afford 6-chloro-8-(3,6-dihydro-2H-pyran-4-yl)-2-(hydroxymethyl)-2-methyl-2H-benzo[b][1,4]oxazin-3(4H)-one in 77% yield. LCMS (m/z) (M+H)=310.2, Rt=1.12 min.

Step 4

K$_3$PO$_4$ (3.0 equiv), 6-chloro-8-(3,6-dihydro-2H-pyran-4-yl)-2 (hydroxymethyl)-2-methyl-2H-benzo[b][1,4]oxazin-3 (4H)-one (1.0 equiv.), 4-methyl-3-(4,4,5,5-tetramethyl-1,3,2-dioxaborolan-2-yl)aniline (1.2 equiv.) and X-Phos-Pd-Precatalyst (G2) (0.1 equiv.) were suspended in 10:1 Dioxane/Water (0.2 M) was added. The mixture was heated in MW at 130° C. for 30 min and then the mixture cooled to room temperature and diluted with EtOAc and brine. The organic layer was dried (MgSO$_4$), filtered and concentrated in vacuo and the residue purified by flash chromatography (0-100% EtOAc/DCM) to afford 6-(5-amino-2-methylphenyl)-8-(3,6-dihydro-2H-pyran-4-yl)-2-(hydroxymethyl)-2-methyl-2H-benzo[b][1,4]oxazin-3(4H)-one in 61.5% yield as a yellowish brown solid. LCMS (m/z) (M+H)=381.0, Rt=0.83 min.

Step 5

6-(5-amino-2-methylphenyl)-8-(3,6-dihydro-2H-pyran-4-yl)-2-(hydroxymethyl)-2-methyl-2H-benzo[b][1,4]oxazin-3(4H)-one (0.1 equiv.) was dissolved in EtOH (0.08 M). To the mixture was added Pd—C (10 wt % wet basis) (0.36 equiv.) and the mixture was evacuated and purged with hydrogen (3×). The reaction was agitated at room temperature under 1 atm of hydrogen gas overnight. The next morning the reaction mixture was diluted with DCM and filtered through celite and the filtrate was concentrated in vacuo to afford 6-(5-amino-2-methylphenyl)-2-(hydroxymethyl)-2-methyl-8-(tetrahydro-2H-pyran-4-yl)-2H-benzo[b][1,4]oxazin-3(4H)-one in 84% yield. LCMS (m/z) (M+H)=381.4, Rt=0.83 min.

Synthesis of 4-(4-(2-methyl-5-nitrophenyl)-6-(2-((tetrahydro-2H-pyran-2-yl)oxy)ethoxy)pyridin-2-yl) tetrahydro-2H-pyran-3-ol

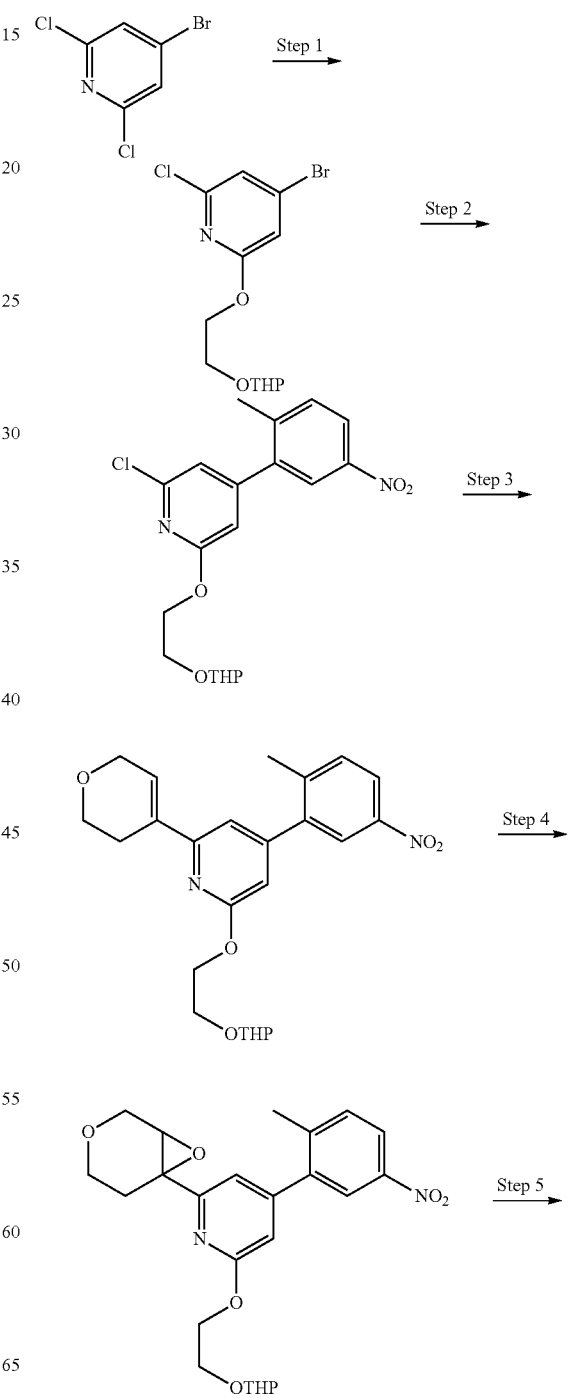

-continued

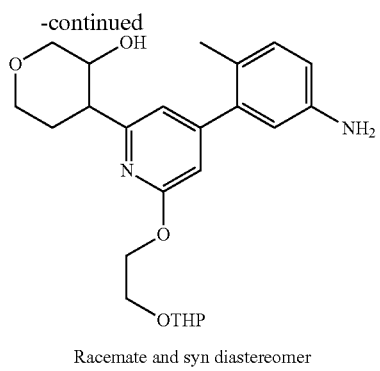

Racemate and syn diastereomer

Step 1

Into a RB flask was charged 2-((tetrahydro-2H-pyran-2-yl)oxy)ethanol (1.2 equiv.) and THF (0.3 M). The mixture was cooled to 0° C. Then NaH (60% in mineral oil) (1.2 equiv.) was added. After the effervescence had subsided, 4-bromo-2,6-dichloropyridine (1.0 equiv) was added neat and the mixture let to warm to room temperature. After 2 h, the reaction mixture was quenched by addition of Sat'd NaHCO$_1$ and then extracted with EtOAc and the organic layer was dried (MgSO$_4$), filtered and concentrated in vacuo and the residue purified by flash chromatography (0-20% EtOAc/heptane) to afford 4-bromo-2-chloro-6-(2-((tetrahydro-2H-pyran-2-yl)oxy)ethoxy)pyridine in 83% yield. 1H NMR (400 MHz, CHLOROFORM-d) δ ppm 7.28 (s, 1H) 7.09 (d, J=1.34 Hz, 4H) 6.92 (d, J=1.22 Hz, 4H) 4.67-4.77 (m, 4H) 4.45-4.57 (m, 8H) 4.04 (ddd, J=11.62, 5.81, 3.48 Hz, 4H) 3.85-3.95 (m, 4H) 3.79 (ddd, J=11.58, 6.39, 3.55 Hz, 4H) 3.49-3.59 (m, 4H) 1.80-1.93 (m, 4H) 1.69-1.79 (m, 4H) 1.47-1.68 (m, 16H); LCMS (m/z) (M+H-THP)=253.8, Rt=1.73 min.

Step 2

Into a 30 mL MW vial were charged PdCl$_2$(dppf).CH$_2$Cl$_2$ adduct (0.1 equiv.), 4,4,5,5-tetramethyl-2-(2-methyl-5-nitrophenyl)-1,3,2-dioxaborolane (1.05 equiv), 4-bromo-2-chloro-6-(2-((tetrahydro-2H-pyran-2-yl)oxy)ethoxy)pyridine (1.0 equiv) and then dioxane (0.3 M). Finally, 2.0 M Na$_2$CO$_3$ (2.5 equiv.) was added. The mixture was agitated in MW at 100° C. for 20 min. After the elapsed time, the reaction mixture was diluted with EtOAc and then washed with brine and dried (MgSO$_4$), filtered and concentrated in vacuo and the residue purified by flash chromatography (0-30% EtOAc/heptane) to afford 2-chloro-4-(2-methyl-5-nitrophenyl)-6-(2-((tetrahydro-2H-pyran-2-yl)oxy)ethoxy)pyridine in 44.2% yield. LCMS (m/z) (M+H-THP)=309.1, Rt=1.33 min.

Step 3

Into a MW vial were charged 2-chloro-4-(2-methyl-5-nitrophenyl)-6-(2-((tetrahydro-2H-pyran-2-yl)oxy)ethoxy)pyridine (1.0 equiv.), K$_3$PO$_4$ (2.0 equiv.), 2-(3,6-dihydro-2H-pyran-4-yl)-4,4,5,5-tetramethyl-1,3,2-dioxaborolane (1.15 equiv.), X-Phos-Palladium precatalyst G2 (0.1 equiv.) were suspended in 10:1 Dioxane/Water (0.3 M). The mixture was placed in MW at 130° C. for 20 min and then the mixture was cooled to room temperature and the reaction mixture was diluted with EtOAc and washed with brine. The organic layer was dried (MgSO$_4$), filtered and concentrated in vacuo and the residue purified by flash chromatography (0-20% EtOAc/heptane) to afford 2-(3,6-dihydro-2H-pyran-4-yl)-4-(2-methyl-5-nitrophenyl)-6-(2-((tetrahydro-2H-pyran-2-yl)oxy)ethoxy)pyridine in 60.1% yield. LCMS (m/z) (M+H-THP)=356.9, Rt=1.77 min.

Step 4

2-(3,6-dihydro-2H-pyran-4-yl)-4-(2-methyl-5-nitrophenyl)-6-(2-((tetrahydro-2H-pyran-2-yl)oxy)ethoxy) (1.0 equiv.) was dissolved in DCM (0.2 M) and then cooled to 0° C. To the mixture was then added m-chloroperbenzoic acid (1.2 equiv.). The mixture was let to gradually warm to room temperature. After 100 min. the reaction mixture was diluted with water and extracted with EtOAc. The organic layer was washed with Sat'd Na$_2$CO$_3$ and then dried (MgSO$_4$), filtered and concentrated in vacuo and the residue 2-(3,7-dioxabicyclo[4.1.0]heptan-6-yl)-4-(2-methyl-5-nitrophenyl)-6-(2-((tetrahydro-2H-pyran-2-yl)oxy)ethoxy)pyridine obtained in quantitative yield was taken to the next step without any further purification. LCMS (m/z) (M+H-THP)=373.0, Rt=1.18 min.

Step 5

2-(3,7-dioxabicyclo[4.1.0]heptan-6-yl)-4-(2-methyl-5-nitrophenyl)-6-(2-((tetrahydro-2H-pyran-2-yl)oxy)ethoxy)pyridine (1.0 equiv.) was charged into a RB flask and suspended in 10:1 DCM/MeOH (0.05 M) and then Triethylamine (2.5 equiv.) was added. Then, Pd—C (10 wt %, wet basis) (0.3 equiv.) was added. The mixture was evacuated and purged with hydrogen (3×) and finally, the mixture was agitated under 1 atm of hydrogen. After 90 min, the reaction mixture was filtered through celite and the filtrate evaporated in vacuo and the residue purified by flash chromatography (0-10% MeOH/DCM) to afford 4-(4-(2-methyl-5-nitrophenyl)-6-(2-((tetrahydro-2H-pyran-2-yl)oxy)ethoxy)pyridin-2-yl)tetrahydro-2H-pyran-3-ol in 45.8% yield. $^1$H NMR (400 MHz, CHLOROFORM-d) δ ppm 7.08 (d, J=8.19 Hz, 1H) 6.75 (d, J=1.10 Hz, 1H) 6.70 (dd, J=8.13, 2.51 Hz, 1H) 6.68 (d, J=1.22 Hz, 1H) 6.58 (d, J=2.57 Hz, 1H) 4.73 (t, J=3.42 Hz, 1H) 4.38-4.60 (m, 2H) 4.04-4.20 (m, 4H) 3.91 (ddd, J=11.25, 8.25, 3.12 Hz, 1H) 3.79-3.87 (m, 1H) 3.50-3.63 (m, 3H) 2.87-3.05 (m, 1H) 2.47 (qt, J=12.66, 4.11 Hz, 1H) 2.17 (s, 3H) 1.43-1.88 (m, 9H); LCMS (m/z) (M+H-THP)=345.0, Rt=1.06 min.

Synthesis of 4-methyl-3-(2-(4-methyltetrahydro-2H-pyran-4-yl)-6-(2-((tetrahydro-2H-pyran-2-yl)oxy)ethoxy)pyridin-4-yl)aniline

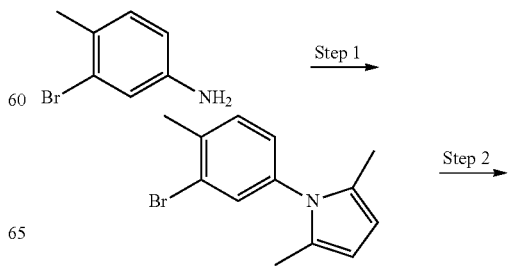

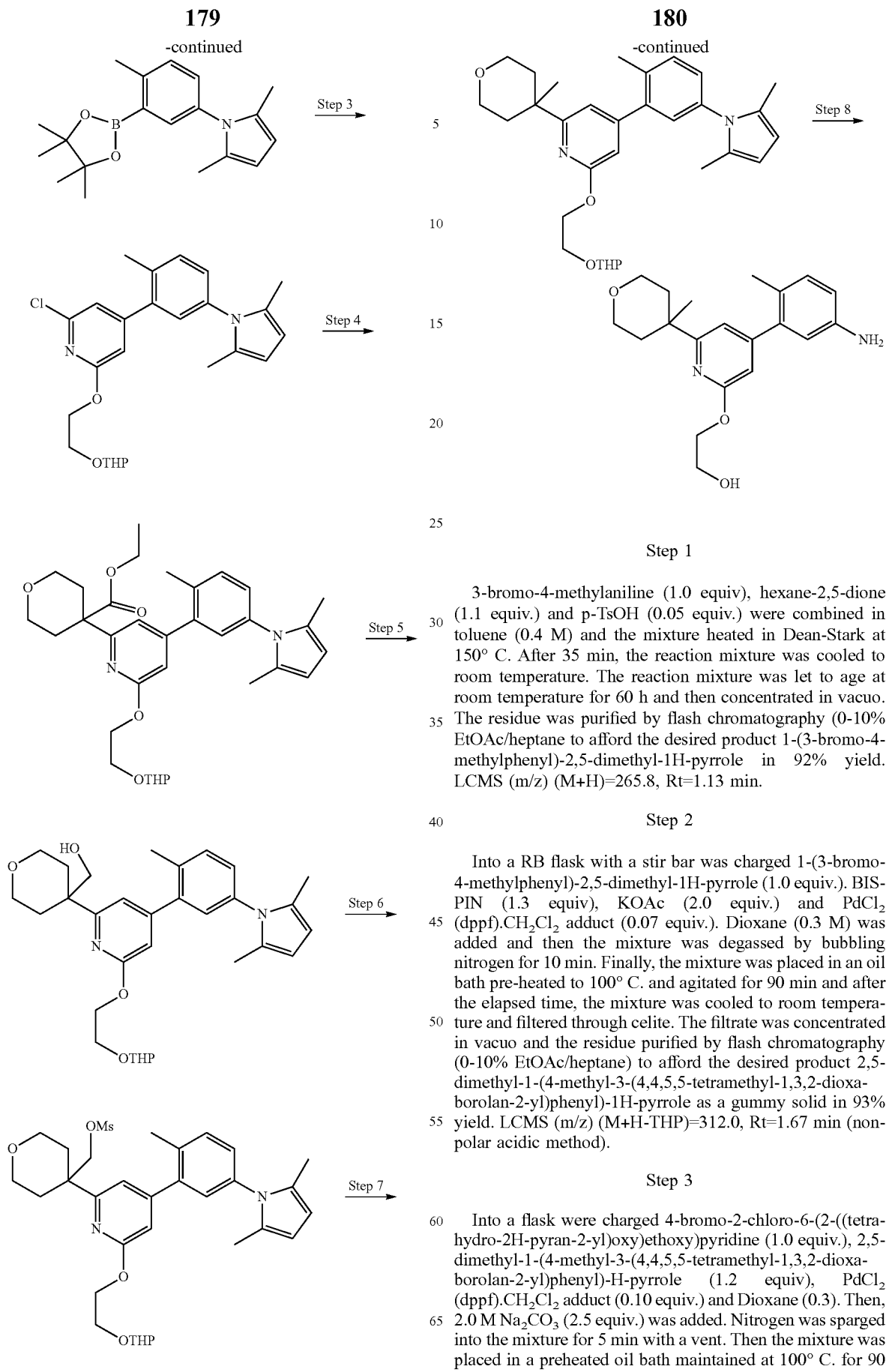

Step 1

3-bromo-4-methylaniline (1.0 equiv.), hexane-2,5-dione (1.1 equiv.) and p-TsOH (0.05 equiv.) were combined in toluene (0.4 M) and the mixture heated in Dean-Stark at 150° C. After 35 min, the reaction mixture was cooled to room temperature. The reaction mixture was let to age at room temperature for 60 h and then concentrated in vacuo. The residue was purified by flash chromatography (0-10% EtOAc/heptane to afford the desired product 1-(3-bromo-4-methylphenyl)-2,5-dimethyl-1H-pyrrole in 92% yield. LCMS (m/z) (M+H)=265.8, Rt=1.13 min.

Step 2

Into a RB flask with a stir bar was charged 1-(3-bromo-4-methylphenyl)-2,5-dimethyl-1H-pyrrole (1.0 equiv.). BIS-PIN (1.3 equiv), KOAc (2.0 equiv.) and $PdCl_2$ (dppf).$CH_2Cl_2$ adduct (0.07 equiv.). Dioxane (0.3 M) was added and then the mixture was degassed by bubbling nitrogen for 10 min. Finally, the mixture was placed in an oil bath pre-heated to 100° C. and agitated for 90 min and after the elapsed time, the mixture was cooled to room temperature and filtered through celite. The filtrate was concentrated in vacuo and the residue purified by flash chromatography (0-10% EtOAc/heptane) to afford the desired product 2,5-dimethyl-1-(4-methyl-3-(4,4,5,5-tetramethyl-1,3,2-dioxaborolan-2-yl)phenyl)-1H-pyrrole as a gummy solid in 93% yield. LCMS (m/z) (M+H-THP)=312.0, Rt=1.67 min (nonpolar acidic method).

Step 3

Into a flask were charged 4-bromo-2-chloro-6-(2-((tetrahydro-2H-pyran-2-yl)oxy)ethoxy)pyridine (1.0 equiv.), 2,5-dimethyl-1-(4-methyl-3-(4,4,5,5-tetramethyl-1,3,2-dioxaborolan-2-yl)phenyl)-H-pyrrole (1.2 equiv), $PdCl_2$ (dppf).$CH_2Cl_2$ adduct (0.10 equiv.) and Dioxane (0.3). Then, 2.0 M $Na_2CO_3$ (2.5 equiv.) was added. Nitrogen was sparged into the mixture for 5 min with a vent. Then the mixture was placed in a preheated oil bath maintained at 100° C. for 90 min and after the elapsed time brine was added to the mixture. The product was extracted with EtOAc and the organic layer was dried (MgSO$_4$), filtered and concentrated in vacuo and the residue purified by flash chromatography (0-10% EtOAc/heptane) to afford the desired product 2-chloro-4-(5-(2,5-dimethyl-1H-pyrrol-1-yl)-2-methylphenyl)-6-(2-((tetrahydro-2H-pyran-2-yl)oxy)ethoxy)pyridine as a light transparent orange viscous syrup in 93% yield. LCMS (m/z) (M+H-THP)=357.3, Rt=1.68 min.

Step 4

Into a 30 mL vial were charged ethyl tetrahydro-2H-pyran-4-carboxylate (1.50 equiv.), 2-chloro-4-(5-(2,5-dimethyl-1H-pyrrol-1-yl)-2-methylphenyl)-6-(2-((tetrahydro-2H-pyran-2-yl)oxy)ethoxy)pyridine (1.0 equiv.), and [(tBu3P)PdBr]2 (0.035 equiv.) Then Toluene (0.3 M) was added. The mixture was sparged with N$_2$ for 5 min and then LiHMDS (1.0 M in toluene) (1.7 equiv.) was added and the mixture was agitated at room temperature overnight. The next morning, the reaction mixture was quenched by addition of water and Sat'd NaHCO$_3$ and the product extracted with EtOAc. The organic layer was dried (MgSO$_4$), filtered and concentrated in vacuo and the residue purified by flash chromatography (0-20% EtOAc/heptane) to afford the desired product ethyl 4-(4-(5-(2,5-dimethyl-1H-pyrrol-1-yl)-2-methylphenyl)-6-(2-((tetrahydro-2H-pyran-2-yl)oxy)ethoxy)pyridin-2-yl)tetrahydro-2H-pyran-4-carboxylate as a colorless solid in 58.8% yield. LCMS (m/z) (M+H)=563.5, Rt=1.63 min.

Step 5

Into a RB flask was added ethyl 4-(4-(5-(2,5-dimethyl-1H-pyrrol-1-yl)-2-methylphenyl)-6-(2-((tetrahydro-2H-pyran-2-yl)oxy)ethoxy)pyridin-2-yl)tetrahydro-2H-pyran-4-carboxylate (1.0 equiv.) and THF (0.15 M). The mixture was cooled in 0° C. LiAlH$_4$ (1.0 M in THF) (1.7 equiv.) was added dropwise and the mixture agitated at same temperature for 20 min and then the reaction mixture was quenched by addition of water and and then 1N NaOH. The mixture was diluted with diethyl ether and MgSO$_4$ was charged into the quenched reaction mixture. The slurry was vigorously agitated for 5 min and then filtered. The filtrate was concentrated m vacuo to afford (4-(4-(5-(2,5-dimethyl-1H-pyrrol-1-yl)-2-methylphenyl)-6-(2-((tetrahydro-2H-pyran-2-yl)oxy)ethoxy)pyridin-2-yl)tetrahydro-2H-pyran-4-yl)methanol in 95% yield. LCMS (m/z) (M+H)=521.2, Rt=1.75 min.

Step 6

Into a flask was charged (4-(4-(5-(2,5-dimethyl-1H-pyrrol-1-yl)-2-methylphenyl)-6-(2-((tetrahydro-2H-pyran-2-yl)oxy)ethoxy)pyridin-2-yl)tetrahydro-2H-pyran-4-yl)methanol (1.0 equiv.) and DCM (0.1 M) and then Et$_3$N (2.0 equiv.) was added. The mixture was cooled to 0° C. To the mixture was added MsCl (1.1 equiv.) and the mixture agitated at same temperature for 30 min and then the reaction mixture was quenched by addition of water and then extracted with DCM. The organic layer was washed with brine and dried (MgSO$_4$), filtered and concentrated in vacuo to afford (4-(4-(5-(2,5-dimethyl-1H-pyrrol-1-yl)-2-methylphenyl)-6-(2-((tetrahydro-2H-pyran-2-yl)oxy)ethoxy)pyridin-2-yl)tetrahydro-2H-pyran-4-yl)methyl methanesulfonate in quantitative yield. LCMS (m/z) (M+H)=599.2, 1.43 min (acidic non-polar method).

Step 7

(4-(4-(5-(2,5-dimethyl-1H-pyrrol-1-yl)-2-methylphenyl)-6-(2-((tetrahydro-2H-pyran-2-yl)oxy)ethoxy)pyridin-2-yl)tetrahydro-2H-pyran-4-yl)methyl methanesulfonate (1.0 equiv.) was dissolved in THF (0.1 M) and treated with Super-Hydride (3.0 equiv.) at room temperature. Then the mixture was agitated at 70° C. for overnight. The next morning, an additional Super-Hydride (4.0 equiv) was added and the mixture agitated at reflux for another 4 h. The reaction mixture was cooled to room temperature and carefully quenched by addition of water and extracted with EtOAc. The organic layer was dried (MgSO$_4$), filtered and concentrated in vacuo and the residue azeotroped with MeOH and then purified by flash chromatography (0-10% EtOAc/heptane) to afford desired product 4-(5-(2,5-dimethyl-1H-pyrrol-1-yl)-2-methylphenyl)-2-(4-methyltetrahydro-2H-pyran-4-yl)-6-(2-((tetrahydro-2H-pyran-2-yl)oxy)ethoxy)pyridine in 48.4% isolated yield. LCMS (m/z) (M+H)=505.2, 1.74 min (acidic non-polar method).

Step 8

4-(5-(2,5-dimethyl-1H-pyrrol-1-yl)-2-methylphenyl)-2-(4-methyltetrahydro-2H-pyran-4-yl)-6-(2-((tetrahydro-2H-pyran-2-yl)oxy)ethoxy)pyridine (1.0 equiv.) and hydroxylamine hydrochloride (12.0 equiv.) were dissolved in EtOH: Water (3:1, 0.05 M). To the mixture was added triethylamine (6.0 equiv.) and then the mixture was placed in a heating block maintained at 80° C. The reaction mixture was agitated at 80° C. overnight. The next morning the reaction mixture was concentrated in vacuo and the product extracted with EtOAc and washed with Sat'd Na$_2$CO$_3$. The organic layer was dried (MgSO$_4$), filtered and concentrated in vacuo to afford quantitative yield of 2-((4-(5-amino-2-methylphenyl)-6-(4-methyltetrahydro-2H-pyran-4-yl)pyridin-2-yl)oxy)ethan-1-ol. LCMS (m/z) (M+H)=343.3, 0.91 min.

Synthesis of 2-((4-(5-amino-2-methylphenyl)-6-(4-methyltetrahydro-2H-pyran-4-yl)pyridin-2-yl)oxy) ethan-1-ol

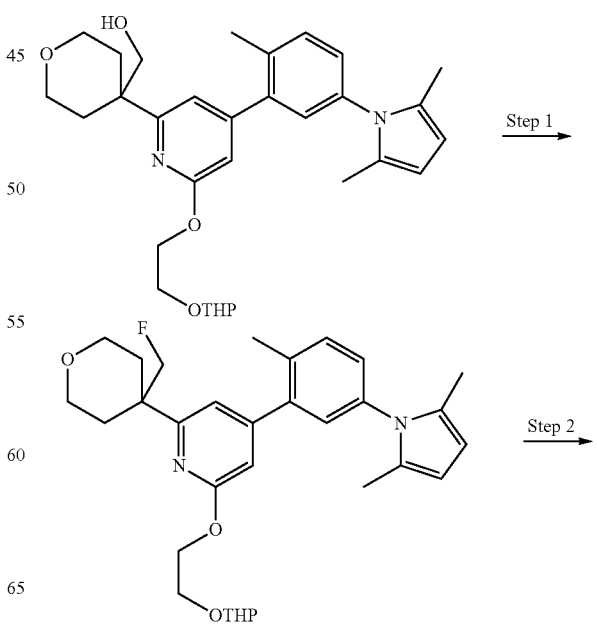

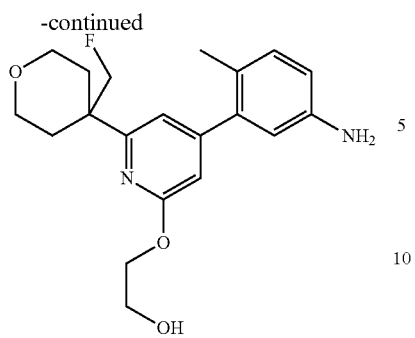

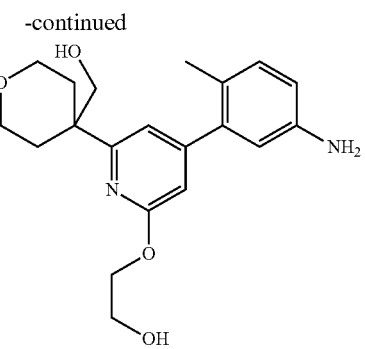

Step 1

(4-(4-(5-(2,5-dimethyl-1H-pyrrol-1-yl)-2-methylphenyl)-6-(2-((tetrahydro-2H-pyran-2-yl)oxy)ethoxy)pyridin-2-yl)tetrahydro-2H-pyran-4-yl)methanol (1.0 equiv.) was dissolved in THF (0.1 M) and then triethylamine (12.0 equiv.) followed by perfluorobutanesulfonyl fluoride (4.0 equiv.) and then triethylamine trihydrofluoride (4.0 equiv.) were added. The mixture was agitated at 60° C. for 7 hour upon which the reaction mixture was carefully poured onto Sat'd Na₂CO₃ and the product was extracted with EtOAc. The organic layer was separated and dried (MgSO₄), filtered and concentrated in vacuo. The residue was purified by flash chromatography (0-30% EtOAc/heptane) to afford the desired product 4-(5-(2,5-dimethyl-1H-pyrrol-1-yl)-2-methylphenyl)-2-(4-(fluoromethyl)tetrahydro-2H-pyran-4-yl)-6-(2-((tetrahydro-2H-pyran-2-yl)oxy)ethoxy)pyridine in 78% isolated yield as a colorless solid. LCMS (m-z) (M+H)=523.2, 1.62 min.

Step 2

4-(5-(2,5-dimethyl-1H-pyrrol-1-yl)-2-methylphenyl)-2-(4-(fluoromethyl)tetrahydro-2H-pyran-4-yl)-6-(2-((tetrahydro-2H-pyran-2-yl)oxy)ethoxy)pyridine (1.0 equiv.) and hydroxylamine hydrochloride (12.0 equiv.) were dissolved in 3:1 EtOH/Water (0.05 M). To the mixture was added triethylamine (6.0 equiv.) and then the mixture heated overnight at 80° C. and the next morning the reaction mixture was concentrated in vacuo. The residue was extracted with EtOAc and the organic layer was washed with Sat'd Na₂CO₃ and then brine and dried (MgSO₄), filtered and concentrated m vacuo to afford quantitative crude yield of 2-((4-(5-amino-2-methylphenyl)-6-(4-methyltetrahydro-2H-pyran-4-yl)pyridin-2-yl)oxy)ethan-1-ol. LCMS (m/z) (M+H)=361.3, 0.87 min.

Synthesis of 2-((4-(5-amino-2-methylphenyl)-6-(4-(hydroxymethyl)tetrahydro-2H-pyran-4-yl)pyridin-2-yloxy)ethan-1-ol

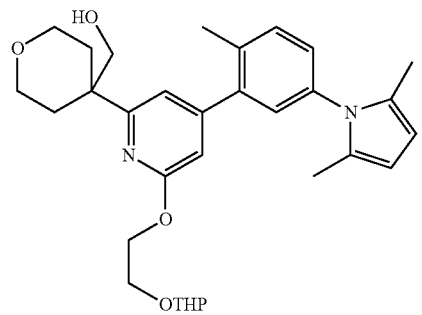

Step 1

(4-(4-(5-(2,5-dimethyl-1H-pyrrol-1-yl)-2-methylphenyl)-6-(2-((tetrahydro-2H-pyran-2-yl)oxy)ethoxy)pyridin-2-yl)tetrahydro-2H-pyran-4-yl)methanol (1.0 equiv.) and hydroxylamine hydrochloride (12.0 equiv.) were dissolved in 3:1 EtOH/Water (0.05 M). To the mixture was added triethylamine (6.0 equiv.) and then the reaction mixture was agitated at 80° C. overnight. The next morning, LCMS indicated desired product was major species. The reaction mixture was concentrated m vacuo and the product extracted with EtOAc and washed with Sat'd Na₂CO₃. The organic layer was dried (MgSO₄), filtered and concentrated in vacuo to afford quantitative yield of crude product 2-((4-(5-amino-2-methylphenyl)-6-(4-(hydroxymethyl)tetrahydro-2H-pyran-4-yl)pyridin-2-yl)oxy)ethan-1-ol, which was taken to the next step without any further purification. LCMS (m/z) (M+H)=359.3, 0.74 min.

Synthesis of tert-butyl (4-methyl-1-(4-(2-methyl-5-(2-(trifluoromethyl)piperidine-4-carboxamido)phenyl)-6-(tetrahydro-2H-pyran-4-yl)pyridin-2-yl)piperidin-4-yl)carbamate

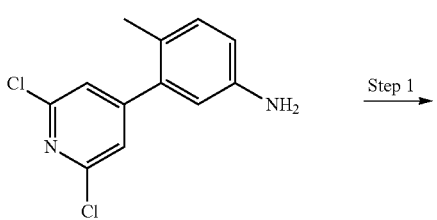

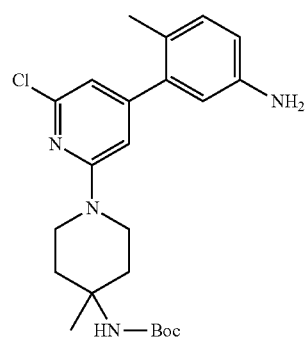

-continued

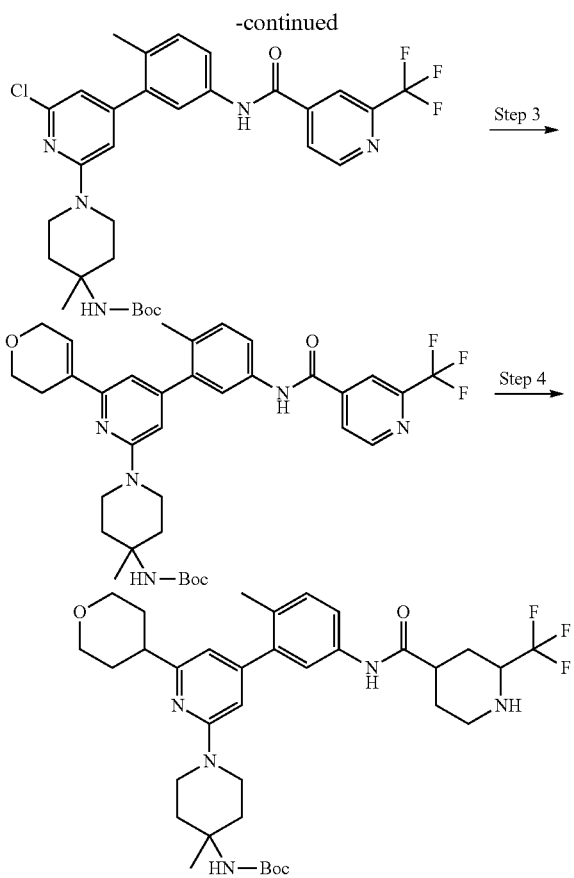

Step 1

A mixture of 3-(2,6-dichloropyridin-4-yl)-4-methylaniline (1.0 equiv.), tert-butyl (4-methylpiperidin-4-yl)carbamate (2.0 equiv.), DIPEA (5.0 equiv.) in DMF (0.4 M, degassed) was irradiated in a microwave for 1 h at 150° C. The cooled reaction mixture was purified by flash chromatography over silica gel (heptanes with 50% ethyl acetate) to give tert-butyl (1-(4-(5-amino-2-methylphenyl)-6-chloropyridin-2-yl)-4-methylpiperidin-4-yl)carbamate in 77% yield. LCMS (m/z) (M+H)=431.2, Rt=1.35 min.

Step 2 tert-butyl (1-(4-(5-amino-2-methylphenyl)-6-chloropyridin-2-yl)-4-methylpiperidin-4-yl)carbamate (1.0 equiv.), 2-(trifluoromethyl)isonicotinic acid (1.0 equiv.), EDC.HCl (1.2 equiv.), HOAT (1.2 equiv.) in DMF (0.4 M) were stirred for 3 h. The reaction mixture was purified by flash chromatography over silica gel (heptanes with 50% ethyl acetate) to give tert-butyl (1-(6-chloro-4-(2-methyl-5-(2-(trifluoromethyl)isonicotinamido)phenyl)pyridin-2-yl)-4-methylpiperidin-4-yl)carbamate in 69% yield. LCMS (m/z) (M+H)=604.2, Rt=1.88 min.

Step 3

A mixture of tert-butyl (1-(6-chloro-4-(2-methyl-5-(2-(trifluoromethyl)isonicotinamido)phenyl)pyridin-2-yl)-4-methylpiperidin-4-yl)carbamate (1.0 equiv.), 2-(3,6-dihydro-2H-pyran-4-yl)-4,4,5,5-tetramethyl-1,3,2-dioxaborolane (2.0 equiv.), Xphos Pd (11) (0.1 equiv.) and $K_2CO_3$ (3.0 equiv.) in acetonitrile: water (2:1) (0.07 M) was irradiated in a microwave vial for 1 h at 120° C. The cooled reaction mixture was partitioned between water and ethyl acetate. The organic phase was washed with brine, concentrated under reduced pressure. The crude product was purified by flash chromatography over silica gel (heptanes with 50% ethyl acetate) to give tert-butyl (1-(6-(3,6-dihydro-2H-pyran-4-yl)-4-(2-methyl-5-(2-(trifluoromethyl)isonicotinamido)phenyl)pyridin-2-yl)-4-methylpiperidin-4-yl)carbamate in 95% yield. LCMS (m/z) (M+H)=652.4, Rt=1.59 min.

Step 4

To a degassed solution of tert-butyl (1-(6-(3,6-dihydro-2H-pyran-4-yl)-4-(2-methyl-5-(2-(trifluoromethyl)isonicotinamido)phenyl)pyridin-2-yl)-4-methylpiperidin-4-yl)carbamate (1.0 equiv.) in ethanol: THF (6:1) (0.1 M) was added 10% palladium on carbon (0.3 equiv.). The flask was purged and flushed three times with hydrogen from a balloon. The reaction was stirred for 48 h under a hydrogen atmosphere. The reaction mixture was degassed, and filtered through Celite and the filter cake was rinsed with DCM. The combined filtrates were concentrated to give tert-butyl (4-methyl-1-(4-(2-methyl-5-(2-(trifluoromethyl)piperidine-4-carboxamido)phenyl)-6-(tetrahydro-2H-pyran-4-yl)pyridin-2-yl)piperidin-4-yl)carbamate in 75% yield. LCMS (m/z) (M+H)=660.5, Rt=1.01 min.

Synthesis of 1-methyl-2-oxo-5-(trifluoromethyl)-1,2-dihydropyridine-3-carboxylic acid

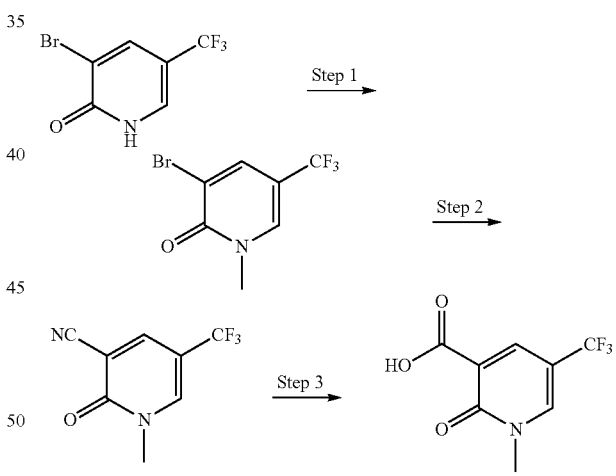

Step 1

Into a 30 mL vial was charged 3-bromo-5-(trifluoromethyl)pyridin-2(1H)-one (1.0 equiv.), K2CO3 (3.5 equiv.) and Acetone (1.0 M). Then iodomethane (3.5 equiv.) was added. The vial was capped and placed in a heating block maintained at 60° C. and agitated overnight. The next morning, the reaction mixture was filtered through celite and concentrated in vacuo. The residue was titurated with heptane/ether (20:1) and sonicated. The tan colored precipitate was collected by suction filtration to afford 3-bromo-1-methyl-5-(trifluoromethyl)pyridin-2(1H)-one in 82% yield. LCMS (m/z) (M+H)=257.9, 0.80 min.

Step 2

Into a vial were charged Pd(Ph₃P)₄ (0.1 equiv.), 3-bromo-1-methyl-5-(trifluoromethyl)pyridin-2(1H)-one (1.0 equiv.) and Zinc Cyanide (1.1 equiv.). The mixture was purged with nitrogen and then agitated overnight at 100° C. overnight. The next morning, the reaction mixture was cooled to room temperature and filtered through celite and the filtrate was diluted with EtOAc and washed twice with water. The organic layer was dried (MgSO₄), filtered and concentrated in vacuo. The residue was purified by flash chromatography (0-50% EtOAc/heptane) to afford 1-methyl-2-oxo-5-(trifluoromethyl)-1,2-dihydropyridine-3-carbonitrile as a white solid. LCMS (m/z) (M+H)=202.9, 0.90 min.

Step 3

Into a MW vial was charged 1-methyl-2-oxo-5-(trifluoromethyl)-1,2-dihydropyridine-3-carbonitrile (1.0 equiv.) and Water (1.25 M) and then cone. Sulfuric acid (12.6 equiv). The vial was capped and agitated in MW at 120° C. for 60 min and then poured over 6N NaOH until neutral pH. The precipitate was collected by filtration and then dissolved in 3N NaOH and washed with EtOAc. The aq. layer was acidified to pH=1 using 4N HCl and the product extracted with EtOAc. The organic layer was dried (MgSO₄), filtered and concentrated in vacuo to afford 1-methyl-2-oxo-5-(trifluoromethyl)-1,2-dihydropyridine-3-carboxylic acid in 55% yield. LCMS (m/z) (M+H)=222.1, 0.88 min.

Synthesis of 4-methyl-3-(2-methyl-5-(tetrahydro-2H-pyran-4-yl)-1H-benzo[d]imidazol-7-yl)aniline

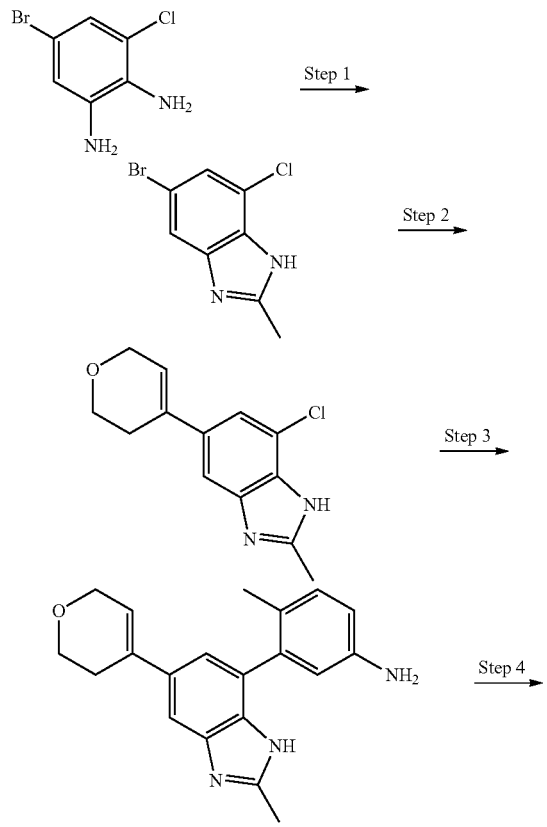

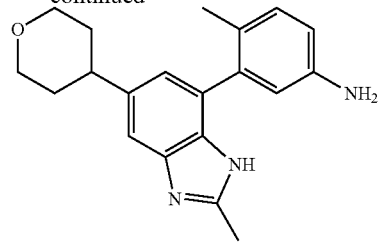

Step 1

Into a 30 mL vial were charged 5-bromo-3-chlorobenzene-1,2-diamine (1.0 equiv), ytterbium(III) trifluoromethanesulfonate (0.1 equiv.) and 1,1,1-trimethoxyethane (1.2 equiv.). The mixture was heated at 90° C. for 1 h and cooled to room temperature and concentrated in vacuo. The residue was purified by flash chromatography (0-5% MeOH/DCM) to afford 5-bromo-7-chloro-2-methyl-1H-benzo[d]imidazole in 100% yield as a yellow solid. LCMS (m/z) (M+H)=247.0, 0.81 min.

Step 2

Into a 30 mL vial were charged 5-bromo-7-chloro-2-methyl-1H-benzo[d]imidazole (1.0 equiv.), 2-(3,6-dihydro-2H-pyran-4-yl)-4,4,5,5-tetramethyl-1,3,2-dioxaborolane (1.2 equiv.), PdCl₂(dppf).CH₂Cl₂ adduct (0.1 equiv), dioxane (0.3 M) and then 2.0 M Na₂CO₃ (3.0 equiv.). The mixture was sparged with nitrogen and then heated in a block at 100° C. for 2 h and then the mixture was cooled to room temperature and diluted with EtOAc and water and filtered through celite. The organic layer was separated and dried (MgSO₄) filtered and concentrated in vacuo and the residue purified by flash chromatography (0-20% MeOH/DCM) to afford 7-chloro-5-(3,6-dihydro-2H-pyran-4-yl)-2-methyl-1H-benzo [d]imidazole in 52.3% yield as an orange solid. LCMS (m/z) (M+H)=248.9, 250.8, 0.78 min.

Step 3

Into a MW vial were charged K₃PO₄ (2.5 equiv), 4-methyl-3-(4,4,5,5-tetramethyl-1,3,2-dioxaborolan-2-yl)aniline (1.2 equiv.), X-Phos G2-palladium precatalyst (0.1 equiv.) and then 10:8:5 mixture of dioxane/DMF/water (0.105 M) solution of 7-chloro-5-(3,6-dihydro-2H-pyran-4-yl)-2-methyl-1H-benzo[d]imidazole (1.0 equiv.) was added. The mixture was sparged with N₂ and then heated in MW at 130° C. for 50 min. The reaction mixture was diluted with EtOAc and water. The organic layer was washed twice with water and brine and dried (MgSO₄), filtered and concentrated in vacuo and the residue purified by flash chromatography (0-20% DCM/MeOH) to afford 3-(5-(3,6-dihydro-2H-pyran-4-yl)-2-methyl-1H-benzo[d]imidazol-7-yl)-4-methylaniline in 79% yield. LCMS (m/z) (M+H)=320.0, 0.73 min.

Step 4

3-(5-(3,6-dihydro-2H-pyran-4-yl)-2-methyl-1H-benzo[d]imidazol-7-yl)-4-methylaniline (1.0 equiv.) was dissolved in EtOH (0.115 M) and then Pd—C (10 Wt %, wet basis) (0.3 equiv.) was added. The mixture was evacuated and purged with hydrogen gas (3×) and finally agitated under hydrogen (balloon pressure) overnight. The next morning the reaction mixture was diluted with EtOAc and filtered through celite. The filtrate was concentrated in vacuo to afford quantitative yield of crude 4-methyl-3-(2-methyl-5-(tetrahydro-2H-pyran-4-yl)-H-benzo[d]imidazol-7-yl)aniline, which was taken to the next step as such without any further purification. LCMS (m/z) (M+H)=322.0, 0.53 min.

Synthesis of (S)-3-(2-((2,2-dimethyl-1,3-dioxolan-4-yl)methoxy)-6-(tetrahydro-2H-pyran-4-yl)pyridin-4-yl)-4-methylaniline

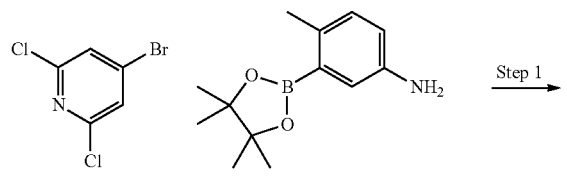

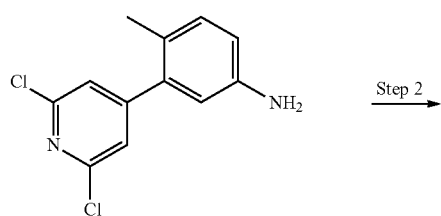

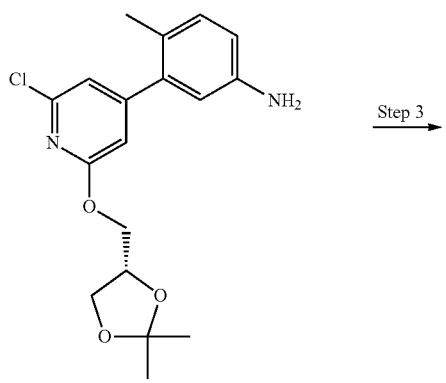

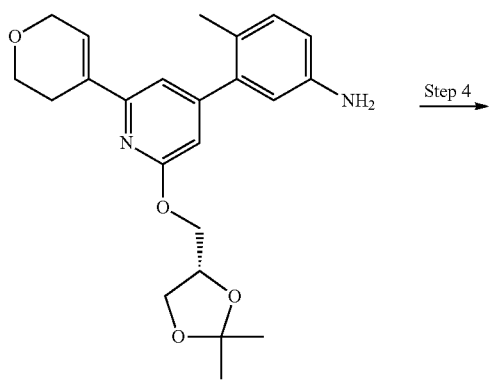

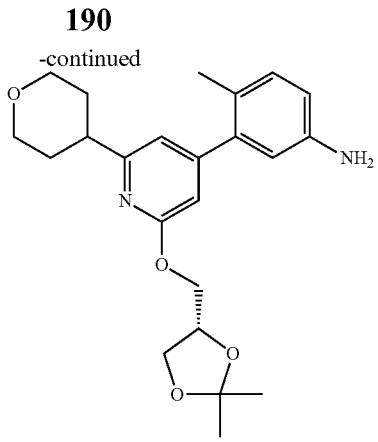

Step 1

A mixture of 4-bromo-2,6-dichloropyridine (1.0 equiv.), 4-methyl-3-(4,4,5,5-tetramethyl-1,3,2-dioxaborolan-2-yl)aniline (1.1 equiv.), PdCl₂(dppf).CH₂Cl₂ adduct (0.1 equiv.) and 2 M Na₂CO₃ (2.5 equiv.) in Dioxane (0.3 M, degassed) was heated in a sealed tube for 4 h at 85° C. (oil bath). The cooled reaction mixture was partitioned between water and ethyl acetate. The organic phase was washed with brine, concentrated under reduced pressured. The crude product was purified by flash chromatography over silica gel (heptanes with 50% ethyl acetate) to give 3-(2,6-dichloropyridin-4-yl)-4-methylaniline in 85% yield. LCMS (m/z) (M+H)=252.9, Rt=1.03 min.

Step 2

Sodium hydride (2.0 equiv.) was added to dioxane (0.6 M). (S)-(2,2-dimethyl-1,3-dioxolan-4-yl)methanol (2.0 equiv.) was added and the mixture was stirred for 30 min at rt. 3-(2,6-dichloropyridin-4-yl)-4-methylaniline (1.0 equiv.) was added to the mixture and the reaction was heated to 50° C. for 2 h. The cooled reaction mixture was quenched by the addition of water and extracted with ethyl acetate. The combined extracts were dried over sodium sulfate, filtered, and concentrated. The crude product was purified by flash chromatography over silica gel (heptanes with 30% ethyl acetate) to give (S)-3-(2-chloro-6-((2,2-dimethyl-1,3-dioxolan-4-yl)methoxy)pyridin-4-yl)-4-methylaniline in 100% yield. LCMS (m/z) (M+H)=349.0, Rt=1.47 min.

Step 3

A mixture of (S)-3-(2-chloro-6-((2,2-dimethyl-1,3-dioxolan-4-yl)methoxy)pyridin-4-yl)-4-methylaniline (1.0 equiv.), 2-(3,6-dihydro-2H-pyran-4-yl)-4,4,5,5-tetramethyl-1,3,2-dioxaborolane (1.2 equiv.), PdCl₂(dppf).CH₂Cl₂ adduct (0.1 equiv.) and 2 M Na₂CO₃ (2.6 equiv.) in Dioxane (0.3 M, degassed) was heated in a microwave vial for 2 h at 105° C. (oil bath). The cooled reaction mixture was partitioned between water and ethyl acetate. The organic phase was washed with brine, dried over sodium sulfate, filtered, and concentrated. The crude product was purified by flash chromatography over silica gel (heptanes with 70% ethyl acetate) to give (S)-3-(2-(3,6-dihydro-2H-pyran-4-yl)-6-((2,2-dimethyl-1,3-dioxolan-4-yl)methoxy)pyridin-4-yl)-4-methylaniline in 92% yield. LCMS (m % z) (M+H)=397.4, Rt=1.42 min.

Step 4

To a degassed solution of (S)-3-(2-(3,6-dihydro-2H-pyran-4-yl)-6-((2,2-dimethyl-1,3-dioxolan-4-yl)methoxy)pyridin-4-yl)-4-methylaniline (1.0 equiv.) in ethanol (0.1 M) was added 10% palladium on carbon (0.3 equiv.). The flask was purged and flushed three times with hydrogen from a balloon. The reaction was stirred for 14 h under a hydrogen atmosphere. The reaction mixture was degassed, and filtered through Celite and the filter cake was rinsed with DCM. The combined filtrates were concentrated to give (S)-3-(2-((2,2-dimethyl-1,3-dioxolan-4-yl)methoxy)-6-(tetrahydro-2H-pyran-4-yl)pyridin-4-yl)-4-methylaniline in 83% yield. LCMS (m/z) (M+H)=399.5, Rt=1.39 min.

Synthesis of 2-oxo-5-(trifluoromethyl)-1,2-dihydropyridine-3-carboxylic acid

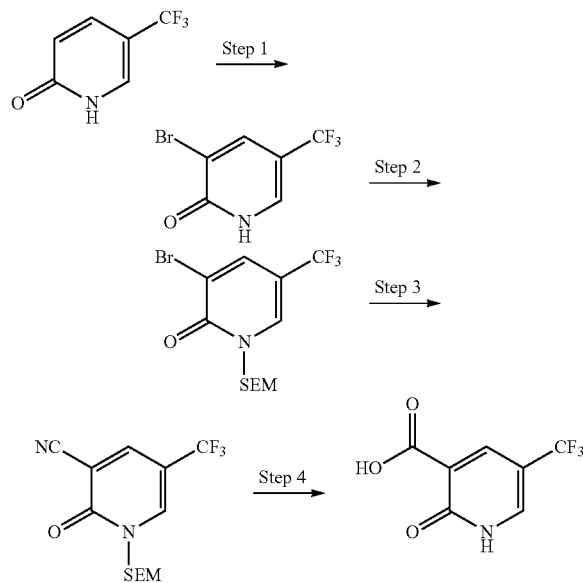

Step 1

To a solution of 5-(trifluoromethyl)pyridin-2(1H)-one (1.0 equiv.) and NaOAc (1.05 equiv.) in glacial AcOH (1.5 M) was added bromine (1.05 equiv.) and the resulting mixture was heated at 80° C. for 2.5 h. The reaction was allow to cool to room temperature and then was evaporated under reduced pressure. The residue was neutralized with saturated NaHCO$_3$ solution and extracted with EtOAc. The organic extracts were combined, dried over MgSO$_4$, filtered, and concentrated in vacuo until a slurry consistency was observed. At this stage, the slurry was diluted with heptanes and the precipitate was collected by filtration to afford 3-bromo-5-(trifluoromethyl)pyridin-2(1H)-one in 92% yield. LCMS (m/z) (M+H)=242.0, 244.0, 0.59 min.

Step 2

To a suspension of 3-bromo-5-(trifluoromethyl)pyridin-2(1H)-one (1.0 equiv.) in THF (0.2 M) at 0° C. was added a 1.0 M THF solution of KOtBu (1.0 equiv.). After 10 minutes, the suspension became a solution and [p-(trimethylsilyl)ethoxy]methyl chloride (1.0 equiv.) was added. The reaction mixture was further agitated for 15 minutes after which, water was added and the layers were separated. The aqueous layer was extracted with ethyl acetate. The combined organic extract was washed with brine, dried over Na$_2$SO$_4$, filtered and concentrated in vacuo. The residue was purified by flash chromatography (0-50/% EtOAc/heptane) to afford 3-bromo-5-(trifluoromethyl)-1-((2-(trimethylsilyl)ethoxy)methyl)pyridin-2(1H)-one in 79% yield as a colorless oil. LCMS (m/z) (M+H)=374.1, 1.70 min.

Step 3

Into a vial were charged Pd(Ph$_3$P)$_4$ (0.1 equiv.), 3-bromo-5-(trifluoromethyl)-1-((2-(trimethylsilyl)ethoxy)methyl)pyridin-2(1H)-one (1.0 equiv.) and Zinc Cyanide (1.1 equiv.) and DMF (0.26 M). The mixture was purged with nitrogen and then agitated overnight at 100° C. The next morning, the reaction mixture was cooled to room temperature and filtered through celite and the filtrate was diluted with EtOAc and washed twice with water. The organic layer was dried (MgSO$_4$), filtered and concentrated in vacuo. The residue was purified by flash chromatography (0-50% EtOAc/heptane) to afford 2-oxo-5-(trifluoromethyl)-1-((2-(trimethylsilyl)ethoxy)methyl)-1,2-dihydropyridine-3-carbonitrile in 82% yield as a white solid. LCMS (m/z) (M+H)=202.9, 0.90 min.

Step 4

2-oxo-5-(trifluoromethyl)-1-((2-(trimethylsilyl)ethoxy)methyl)-1,2-dihydropyridine-3-carbonitrile (1.0 equiv) was suspended in water (1.0 M) and then conc. sulfuric acid (20.95 equiv) was added dropwise with agitation. The mixture was agitated at 120° C. in MW for 30 min. After the elapsed time, the reaction mixture was carefully poured onto 6N NaOH to neutral pH. The white solid was extracted with EtOAc and the organic layer was dried (MgSO$_4$), filtered and concentrated in vacuo and the residue titurated with heptane and the precipitate collected by filtration to afford 2-oxo-5-(trifluoromethyl)-1,2-dihydropyridine-3-carboxylic acid in 55.2% yield. LCMS (m/z) (M+H)=202.9, 0.90 min.

Example 1

2-(2-fluoropropan-2-yl)-N-(6-methyl-5-(3-(oxetan-3-yl)phenyl)pyridin-3-yl)isonicotinamide

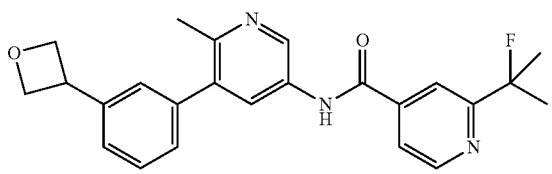 [SMILES: Cc1ncc(NC(=O)c2ccnc(C(C)(C)F)c2)cc1-c1cccc(C2COC2)c1]

A solution of 6-methyl-5-(3-(oxetan-3-yl)phenyl)pyridin-3-amine (1.0 equiv.), 2-(2-fluoropropan-2-yl)isonicotinic acid (1.0 equiv.) and 2-(3H-[1,2,3]triazolo[4,5-b]pyridin-3-yl)-1,1,3,3-tetramethylisouronium hexafluorophosphate(V) in DMF was stirred at rt for 4 hours. Upon completion, the reaction was filtered and purified via reverse phase prep-HPLC and the pure fractions were lyophilized to give 2-(2-fluoropropan-2-yl)-N-(6-methyl-5-(3-(oxetan-3-yl)phenyl)pyridin-3-yl)isonicotinamide in 28% yield. 1H NMR (400 MHz, <dmso>) δ ppm 1.60-1.79 (m, 9H) 4.26-4.41 (m, 1H) 4.61-4.70 (m, 2H) 4.90-5.03 (m, 2H) 7.23-7.58 (m, 4H) 7.83 (dd, J=4.89, 1.37 Hz, 1H) 8.05 (s, 1H) 8.18 (d, J=1.56 Hz, 1H) 8.77 (d, J=5.09 Hz, 1H) 8.91-9.01 (m, 1H) 10.74-11.02 (m, 1H). LCMS (m/z) (M+H)=406.1, Rt=0.65 min.

Example 2

N-(6-methyl-3'-(oxetan-3-yl)-[1,1'-biphenyl]-3-yl)-3-(trifluoromethyl)benzamide

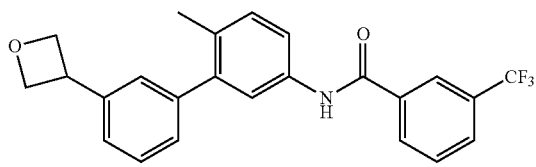 [SMILES: Cc1ccc(NC(=O)c2cccc(C(F)(F)F)c2)cc1-c1cccc(C2COC2)c1]

To a solution of 3-(3-bromophenyl)oxetane (1.0 equiv.) and N-(4-methyl-3-(4,4,5,5-tetramethyl-1,3,2-dioxaborolan-2-yl)phenyl)-3-(trifluoromethyl)benzamide (1.0 equiv.) in DME and 2M sodium carbonate (3:1, 0.1 M) was added PdCl$_2$(dppf)-DCM adduct (0.1 equiv.) and the reaction was heated in the microwave for 30 min at 120° C. Upon cooling to rt, the mixture was partitioned between ethyl acetate and brine. The organic phase was dried with magnesium sulfate, filtered and concentrated. The residue was purified via reverse phase prep-HPLC and the pure fractions were lyophilized to give N-(6-methyl-3'-(oxetan-3-yl)-[1,1'-biphenyl]-3-yl)-3-(trifluoromethyl)benzamide in 48% yield. 1H NMR (400 MHz, <dmso>) δ ppm 2.20 (s, 3H) 2.38-2.59 (m, 4H) 4.19-4.39 (m, 1H) 4.53-4.75 (m, 2H) 4.95 (dd, J=8.61, 5.87 Hz, 2H) 7.22-7.31 (m, 2H) 7.34 (s, 1H) 7.38-7.49 (m, 2H) 7.64 (d, J=1.96 Hz, 1H) 7.71 (dd, J=8.22, 2.35 Hz, 1H) 7.77 (t, J=7.83 Hz, 1H) 7.95 (d, J=7.43 Hz, 1H) 8.20-8.32 (m, 2H) 10.43 (s, 1H). LCMS (m/z) (M+H)=412.2, Rt=1.12 min.

Example 3

N-(6'-ethoxy-2-methyl-5'-(3-methyloxetan-3-yl)-[3,3'-bipyridin]-5-yl)-2-(2-fluoropropan-2-yl)isonicotinamide

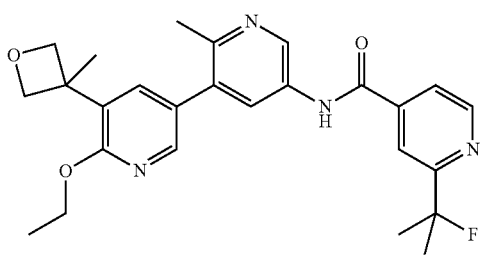 [SMILES: CCOc1ncc(-c2cc(NC(=O)c3ccnc(C(C)(C)F)c3)cnc2C)cc1C1(C)COC1]

To a solution of 6'-ethoxy-2-methyl-5'-(3-methyloxetan-3-yl)-[3,3'-bipyridin]-5-amine (1.0 equiv.), 2-(2-fluoropropan-2-yl)isonicotinic acid (1.2 equiv.), N1-((ethylimino)methylene)-N3,N3-dimethylpropane-1,3-diamine hydrochloride (1.3 equiv.) and 3H-[1,2,3]triazolo[4,5-b]pyridin-3-ol hydrate (1.3 equiv.) in DMA (0.1 M) was added DIEA (3.0 equiv.) and the reaction was stirred at rt overnight. Upon completion, water was added and the solution was filtered and purified via reverse phase prep-HPLC. The pure fractions were lyophilized to give N-(6'-ethoxy-2-methyl-5'-(3-methyloxetan-3-yl)-[3,3'-bipyridin]-5-yl)-2-(2-fluoropropan-2-yl)isonicotinamide in 45% yield. $^1$H NMR (400 MHz, <cd3od>) δ ppm 1.40 (t, J=7.04 Hz, 3H) 1.71 (s, 3H) 1.76 (d, J=2.74 Hz, 6H) 2.68 (s, 3H) 4.46 (q, J=7.04 Hz, 2H) 4.60 (d, J=6.26 Hz, 2H) 5.03 (d, J=6.26 Hz, 2H) 7.54 (d, J=2.35 Hz, 1H) 7.83 (dd, J=5.09, 1.57 Hz, 1H) 8.09-8.20 (m, 2H) 8.45 (d, J=2.35 Hz, 1H) 8.76 (d, J=5.09 Hz, 1H) 9.33 (d, J=2.35 Hz, 1H). LCMS (m/z) (M+H)=465.3, Rt=0.74 min.

Example 4

N-(4-methyl-3-(4-methyl-6-(oxetan-3-yl)-5-oxo-4,5-dihydropyrazin-2-yl)phenyl)-3-(trifluoromethyl)benzamide

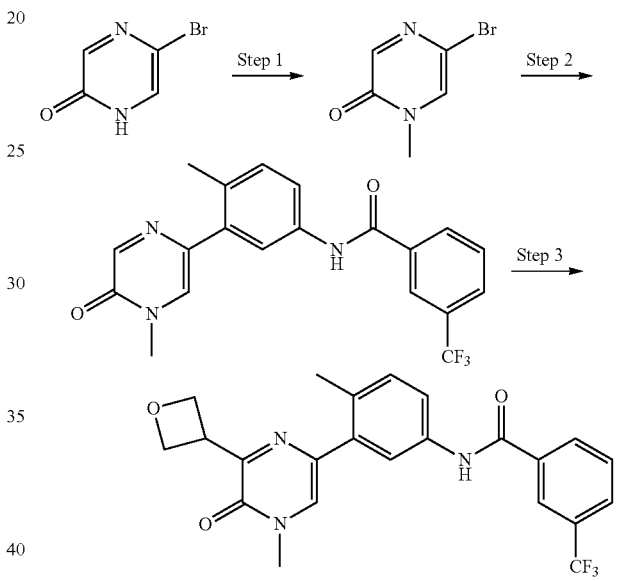

Step 1

To a solution of 5-bromopyrazin-2(1H)-one (1.0 equiv.) in DMF (0.3 M) was added cesium carbonate (1.5 equiv.) and iodomethane (2.0 equiv.) and the suspension was stirred at rt overnight. The reaction was partitioned between water and ethyl acetate, the aqueous phase was extracted once again with ethyl acetate. The organics were combined, washed with water, dried with magnesium sulfate, filtered and concentrated to give 5-bromo-1-methylpyrazin-2(1H)-one in 53% yield as a light yellow solid.

Step 2

To a solution of 5-bromo-1-methylpyrazin-2(1H)-one (1.0 equiv.), N-(4-methyl-3-(4,4,5,5-tetramethyl-1,3,2-dioxaborolan-2-yl)phenyl)-3-(trifluoromethyl)benzamide (1.0 equiv.) and sodium carbonate (2M aq. solution, 3.0 equiv.) in DME (0.27 M) was added PdCl$_2$(dppf)-DCM adduct (0.05 equiv.) and the reaction was heated at 120° C. in the microwave for 20 min. The solution was cooled to rt, then the organic phase was concentrated and purified via reverse phase prep-HPLC to give N-(4-methyl-3-(4-methyl-5-oxo- 4,5-dihydropyrazin-2-yl)phenyl)-3-(trifluoromethyl)benzamide in 41% yield. LCMS (m/z) (M+H)=388.1, Rt=0.81 min.

Step 3

To a solution of N-(4-methyl-3-(4-methyl-5-oxo-4,5-dihydropyrazin-2-yl)phenyl)-3-(trifluoromethyl)benzamide (1.0 equiv.), 3-iodooxetane (4.0 equiv.), sulphuric acid (2.0 equiv.), and FeSO$_4$ (0.6 equiv.) in DMSO (0.06 M) was added hydrogen peroxide (12 equiv.) dropwise. After 2 min, another 0.6 equiv. of FeSO$_4$ was added. Stirred for another 30 min, then added another 6 equiv. of hydrogen peroxide and 0.6 equiv. of FeSO$_4$. The solution was stirred at rt overnight. Quenched by the addition of sodium bicarbonate solution and extracted twice with ethyl acetate. The organic phase was dried with magnesium sulfate, filtered and concentrated to dryness. The crude was purified via reverse phase prep-HPLC and the pure fractions were lyophilized to give N-(4-methyl-3-(4-methyl-6-(oxetan-3-yl)-5-oxo-4,5-dihydropyrazin-2-yl)phenyl)-3-(trifluoromethyl)benzamide as a white solid in 14% yield. 1H NMR (400 MHz, <cdcl3>) δ ppm 2.32-2.52 (m, 3H) 3.59 (d, J=−4.70 Hz, 3H) 4.54-4.78 (m, 1H) 4.87-5.17 (m, 4H) 7.15-7.37 (m, 1H) 7.37-7.52 (m, 1H) 7.57-7.70 (m, 1H) 7.75-7.88 (m, 1H) 7.97-8.25 (m, 1H). LCMS (m/z) (M+H)=444.3, Rt=0.86 min.

Example 5

4-(aminomethyl)-N-(6-methyl-3'-(oxetan-3-yl)-[1,1'-biphenyl]-3-yl)-3-(trifluoromethyl)benzamide

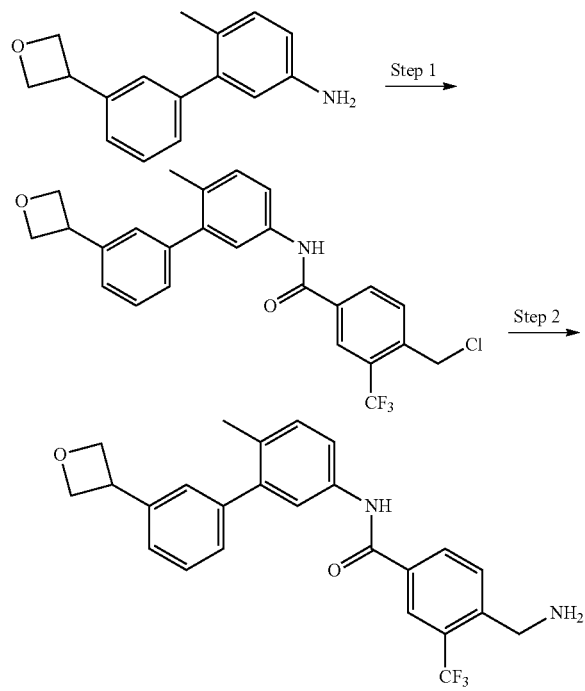

Step 1

To a solution of 6-methyl-3'-(oxetan-3-yl)-[1,1'-biphenyl]-3-amine (1.0 equiv.) and 4-(bromomethyl)-3-(trifluoromethyl)benzoic acid (1.1 equiv.) in DMF (0.1M) was added HOAT (1.0 equiv.) and EDC-HCl (1.0 equiv.) and the reaction was stirred at rt overnight. Upon completion, the solution was purified via reverse phase prep-HPLC to give 4-(chloromethyl)-N-(6-methyl-3'-(oxetan-3-yl)-[1,1'-biphenyl]-3-yl)-3-(trifluoromethyl)benzamide in 71% yield. LCMS (m/z) (M+H)=460.1, Rt=1.16 min.

Step 2

4-(chloromethyl)-N-(6-methyl-3'-(oxetan-3-yl)-[1,1'-biphenyl]-3-yl)-3-(trifluoromethyl)benzamide (1.0 equiv.) was stirred in ammonia in methanol (7M solution, 322 equiv.) at 50° C. overnight. Upon concentration under vacuo, the residue was purified via reverse phase prep-HPLC to give 4-(aminomethyl)-N-(6-methyl-3'-(oxetan-3-yl)-[1,1'-biphenyl]-3-yl)-3-(trifluoromethyl)benzamide in 15% yield. LCMS (m/z) (M+H)=441.3, Rt=0.80 min.

Example 6

N-(4-methyl-3-(8-(oxetan-3-yl)imidazo[1,2-b]pyridazin-6-yl)phenyl)-3-(trifluoromethyl)benzamide

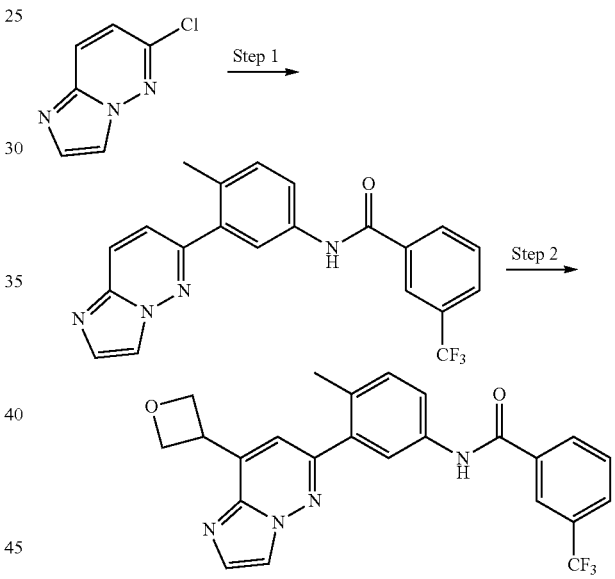

Step 1

To a solution of 6-chloroimidazo[1,2-b]pyridazine (1.0 equiv.) and N-(4-methyl-3-(4,4,5,5-tetramethyl-1,3,2-dioxaborolan-2-yl)phenyl)-3-(trifluoromethyl)benzamide (1.0 equiv.) in DME (0.7M) was added sodium carbonate (3.0 equiv., 2M aqueous solution) and PdCl$_2$(dppf)-DCM adduct (0.05 equiv.) and the reaction was heated at 130° C. in the microwave for 30 min. The organic phase was concentrated to dryness and purified via reverse phase prep-HPLC. The pure fractions were concentrated to give N-(3-(imidazo[1,2-b]pyridazin-6-yl)-4-methylphenyl)-3-(trifluoromethyl)benzamide as a white solid in 77% yield. LCMS (m/z) (M+H)=397.2, Rt=0.79 min.

Step 2

To a solution of N-(3-(imidazo[1,2-b]pyridazin-6-yl)-4-methylphenyl)-3-(trifluoromethyl)benzamide (1.0 equiv.) in DMSO (0.05 M) was added 3-iodooxetane (4.0 equiv.), sulfuric acid (2.0 equiv.), FeSO4 (0.6 equiv.). To this mixture was added hydrogen peroxide (6.0 equiv.) dropwise at rt. After two minutes, added another 0.6 equiv. of FeSO$_4$ and stirred for 30 min. Another 6.0 equiv. of hydrogen peroxide and 0.6 equiv. of FeSO$_4$ was added and the reaction was stirred at rt overnight. The reaction was quenched with sodium bicarbonate (sat. solution) and extracted twice with ethyl acetate. The organic phase was dried with magnesium sulfate, filtered and concentrated. The residue was purified via reverse phase prep-HPLC and the pure fractions were neutralized by pushing through PL-HCO$_3$ resin. Upon concentration, isolated N-(4-methyl-3-(8-(oxetan-3-yl)imidazo[1,2-b]pyridazin-6-yl)phenyl)-3-(trifluoromethyl)benzamide in 9% yield as a white solid. 1H NMR (400 MHz, <cdcl3>) δ ppm 2.42 (s, 3H) 4.82-5.07 (m, 3H) 5.14-5.31 (m, 2H) 7.18-7.29 (m, 1H) 7.36 (d, J=8.22 Hz, 1H) 7.57-7.70 (m, 2H) 7.73-7.88 (m, 3H) 8.02 (s, 2H) 8.05-8.20 (m, 2H). LCMS (m/z) (M+H)=453.2, Rt=0.81 min.

Example 7

4-(hydroxymethyl)-N-(6-methyl-5-(oxetan-3-yl)phenyl)pyridin-3-yl)-3-(trifluoromethyl)benzamide

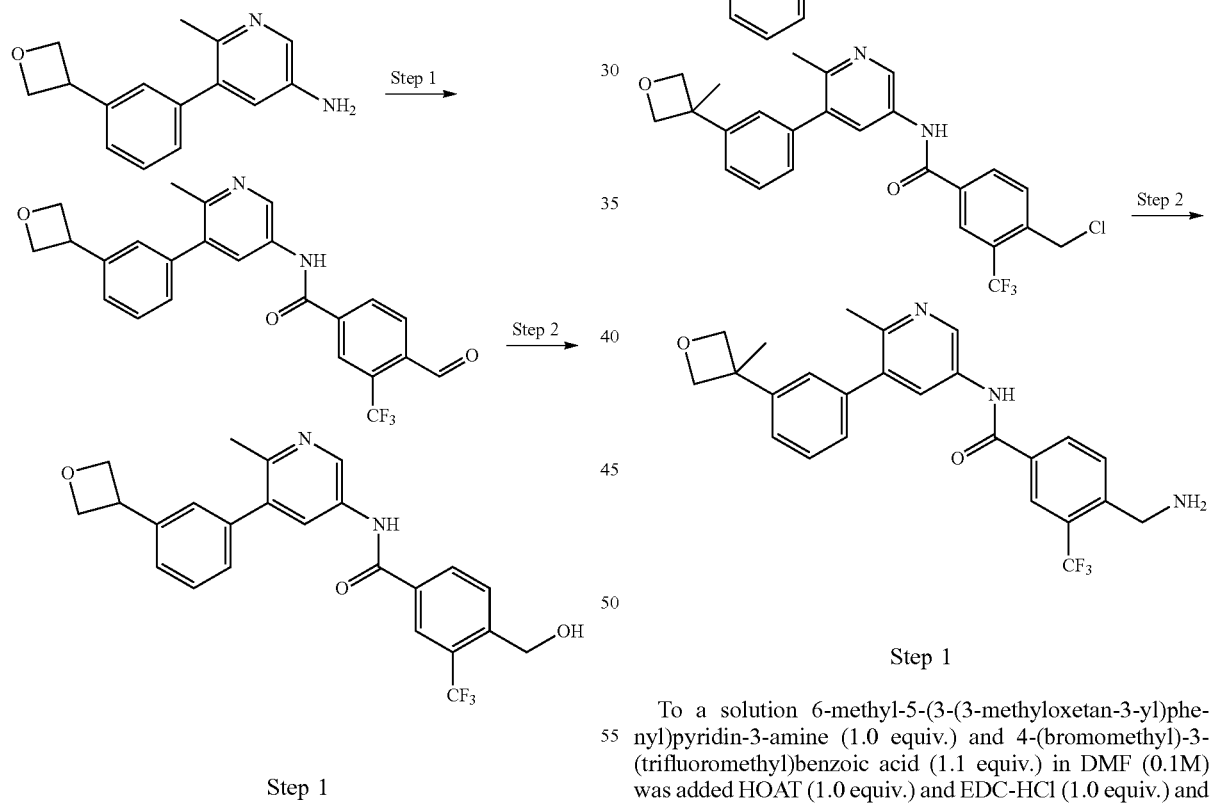

Step 1

To a solution of 6-methyl-5-(3-(oxetan-3-yl)phenyl)pyridin-3-amine (1.0 equiv.) and 4-formyl-3-(trifluoromethyl) benzoic acid (1.0 equiv.) in DMF (0.2M) was added HOAT (1.0 equiv.) and EDC-HCl (1.0 equiv.) and the reaction was stirred at rt overnight. Upon completion, the solution was purified via reverse phase prep-HPLC to give 4-formyl-N-(6-methyl-5-(3-(oxetan-3-yl)phenyl)pyridin-3-yl)-3-(trifluromethyl)benzamide in 33% yield. LCMS (m/z) (M+H)=441.1, Rt=0.75 min.

To a solution of 4-formyl-N-(6-methyl-5-(3-(oxetan-3-yl)phenyl)pyridin-3-yl)-3-(trifluoromethyl)benzamide (1.0 equiv.) in methanol was added sodium borohydride (2.0 equiv.) at rt and the reaction was stirred for 10 min. Upon concentration, the residue was purified via reverse phase prep-HPLC to give 4-(hydroxymethyl)-N-(6-methyl-5-(3-(oxetan-3-yl)phenyl)pyridin-3-yl)-3-(trifluoromethyl)benzamide in 29% yield. 1H NMR (400 MHz, <dmso>) δ ppm 2.41 (s, 3H) 4.20-4.44 (m, 1H) 4.56-4.81 (m, 4H) 4.95 (dd, J=8.61, 5.87 Hz, 2H) 5.65 (t, J=5.67 Hz, 1H) 7.18-7.57 (m, 4H) 7.86-8.08 (m, 2H) 8.15-8.39 (m, 2H) 8.84 (d, J=2.35 Hz, 1H) 10.61 (s, 1H). LCMS (m/z) (M+H)=443.1, Rt=0.67 min.

Example 8

4-(aminomethyl-N-(6-methyl-5-(3(3-methyloxetan-3-yl)phenyl)pyridin-3-yl)-3-(trifluoromethyl)benzamide

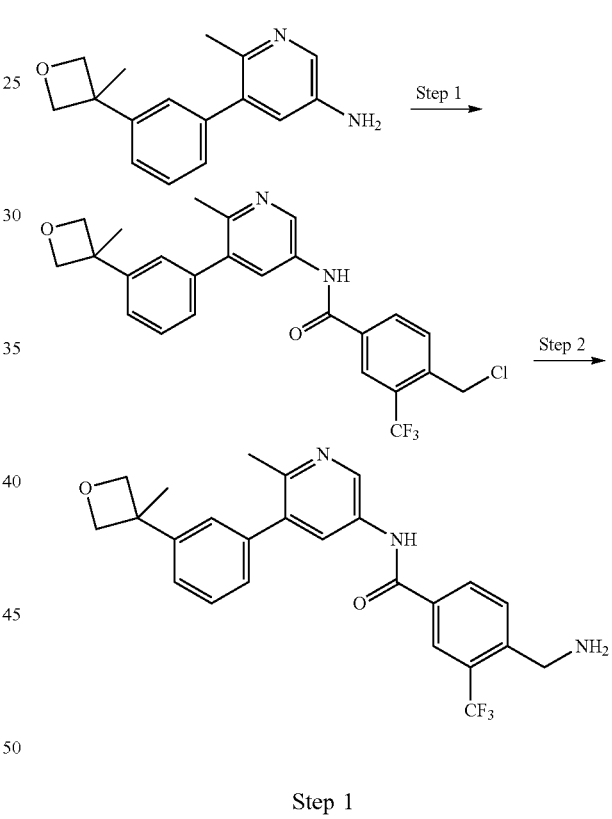

Step 1

To a solution 6-methyl-5-(3-(3-methyloxetan-3-yl)phenyl)pyridin-3-amine (1.0 equiv.) and 4-(bromomethyl)-3-(trifluoromethyl)benzoic acid (1.1 equiv.) in DMF (0.1M) was added HOAT (1.0 equiv.) and EDC-HCl (1.0 equiv.) and the reaction was stirred at rt overnight. Upon completion, the solution was purified via reverse phase prep-HPLC to give 4-(chloromethyl)-N-(6-methyl-5-(3-(3-methyloxetan-3-yl)phenyl)pyridin-3-yl)-3-(trifluoromethyl)benzamide in 39% yield. LCMS (m/z) (M+H)=475.1, Rt=0.89 min.

Step 2

A solution of 4-(chloromethyl)-N-(6-methyl-5-(3-(3-methyloxetan-3-yl)phenyl)pyridin-3-yl)-3-(trifluoromethyl)

benzamide (1.0 equiv.) was stirred in ammonia in methanol (7M solution, 831 equiv.) for 3 days at rt. The reaction was concentrated under vacuo and purified via reverse phase prep-HPLC to give 4-(aminomethyl)-N-(6-methyl-5-(3-(3-methyloxetan-3-yl)phenyl)pyridin-3-yl)-3-(trifluoromethyl) benzamide in 56% yield. 1H NMR (400 MHz, <dmso>) δ ppm 2.41 (s, 3H) 4.08 (s, 2H) 4.56 (d, J=5.87 Hz, 2H) 4.84 (d, J=5.48 Hz, 2H) 7.15-7.34 (m, 3H) 7.41-7.56 (m, 1H) 7.83-8.07 (m, 2H) 8.21-8.40 (m, 2H) 8.85 (d, J=2.35 Hz, 1H) 10.62 (s, 1H). LCMS (m/z) (M+H)=456.2, Rt=0.57 min.

Example 9

N-(6-methyl-5-(8-(oxetan-3-yl)imidazo[1,2-b]pyridazin-6-yl)pyridin-3-yl)-3-(trifluoromethyl)benzamide

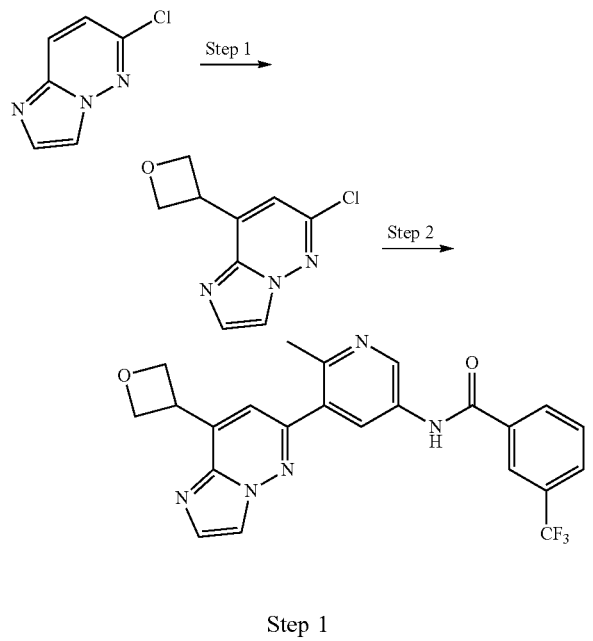

Step 1

To a solution of 6-chloroimidazo[1,2-b]pyridazine (1.0 equiv.) in DMSO (0.1 M) was added 3-iodooxetane (4.0 equiv.), sulfuric acid (2.0 equiv.) and FeSO$_4$ (0.6 equiv.) at rt. To this solution was added hydrogen peroxide (6.0 equiv.) dropwise. After 2 min, another 0.6 equiv. of FeSO$_4$ was added and the reaction was stirred for 30 min. Then, another 6.0 equiv. of hydrogen peroxide and 0.6 equiv. of FeSO$_4$ were added and the reaction was stirred overnight at rt. The mixture was quenched by the addition of sat. sodium bicarbonate and extracted twice with ethyl acetate. The organic phase was dried with magnesium sulfate, filtered and concentrated. The residue was purified via reverse phase prep-HPLC and the pure fractions were neutralized with a PL-HCO$_3$ resin. Upon concentration under vacuo, 6-chloro-8-(oxetan-3-yl)imidazo[1,2-b]pyridazine was isolated in 27% yield. LCMS (m/z) (M+H)=210.0. Rt=0.41 min.

Step 2

To a solution of 6-chloro-8-(oxetan-3-yl)imidazo[1,2-b]pyridazine (1.0 equiv.) and N-(6-methyl-5-(4,4,5,5-tetramethyl-1,3,2-dioxaborolan-2-yl)pyridin-3-yl)-3-(trifluoromethyl)benzamide (1.0 equiv.) in DME (0.1 M) was added sodium carbonate (3.0 equiv., 2M aqueous solution) and PdCl$_2$(dppf)-DCM adduct (0.05 equiv.) and the reaction was heated at 130° C. in the microwave for 30 min. The organic phase was concentrated to dryness and purified via reverse phase prep-HPLC. The pure fractions were concentrated to give N-(6-methyl-5-(8-(oxetan-3-yl)imidazo[1,2-b]pyridazin-6-yl)pyridin-3-yl)-3-(trifluoromethyl)benzamide as a white solid in 41% yield. 1H NMR (400 MHz, <dmso>) δ ppm 2.55 (s, 3H) 4.72-4.91 (m, 1H) 4.91-5.23 (m, 4H) 7.50 (s, 1H) 7.71-7.88 (m, 2H) 7.99 (d, J=7.83 Hz, 1H) 8.19-8.48 (m, 4H) 8.97 (d, J=2.74 Hz, 1H) 10.76 (s, 1H). LCMS (m/z) (M+H)=454.1, Rt=0.65 min.

Example 10

4-(aminomethyl)-N-(6-methyl-5-(8-(oxetan-3-yl)imidazo[1,2-b]pyridazin-6-yl)pyridin-3-yl)-3-(trifluoromethyl)benzamide

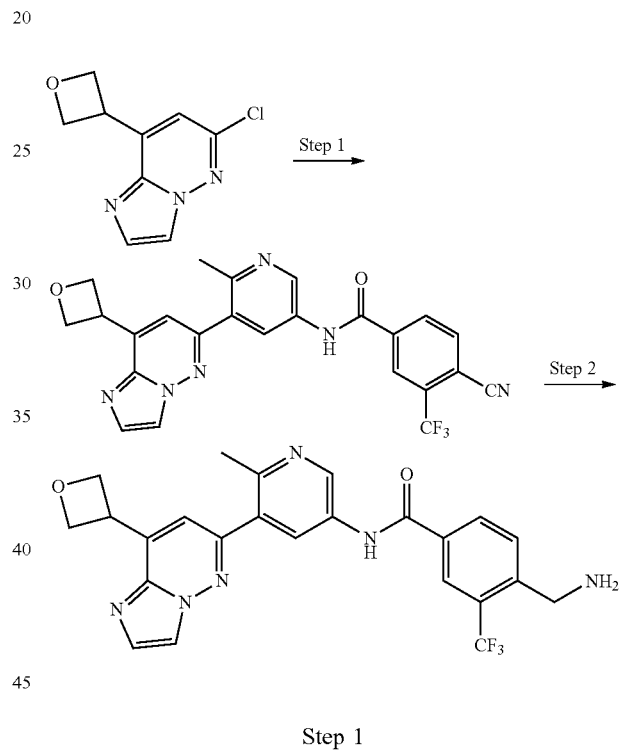

Step 1

To a solution of 6-chloro-8-(oxetan-3-yl)imidazo[1,2-b]pyridazine (1.0 equiv.) and (5-(4-cyano-3-(trifluoromethyl)benzamido)-2-methylpyridin-3-yl)boronic acid (1.0 equiv.) in DME (0.1M) was added sodium carbonate (3.0 equiv., 2M aqueous solution) and PdCl$_2$(dppf)-DCM adduct (0.05 equiv.) and the reaction was heated at 130° C. in the microwave for 30 min. The organic phase was concentrated to dryness and purified via reverse phase prep-HPLC. The pure fractions were concentrated to give 4-cyano-N-(6-methyl-5-(8-(oxetan-3-yl)imidazo[1,2-b]pyridazin-6-yl)pyridin-3-yl)-3-(trifluoromethyl)benzamide as a white solid in 14% yield. LCMS (m/z) (M+H)=479.0. Rt=0.71 min.

Step 2

To a solution of 4-cyano-N-(6-methyl-5-(8-(oxetan-3-yl)imidazo[1,2-b]pyridazin-6-yl)pyridin-3-yl)-3-(trifluoromethyl)benzamide (1.0 equiv.) in ethanol was added nickel(II) chloride (3.0 equiv.) followed by sodium borohydride (15 equiv.) at rt. The solution was stirred for 4 hours, then quenched by the addition of diethyltriamine. The solution was filtered and concentrated to dryness and the residue was purified via reverse phase HPLC to give 4-(aminomethyl)-N-(6-methyl-5-(8-(oxetan-3-yl)imidazo[1,2-b]pyridazin-6-yl)pyridin-3-yl)-3-(trifluoromethyl)benzamide in 27% yield. 1H NMR (400 MHz, <dmso>) δ ppm 2.57 (s, 3H) 3.22 (s, 2H) 3.41 (s, 1H) 4.29 (d, J=3.91 Hz, 4H) 4.86 (d, J=8.61 Hz, 1H) 4.92-5.10 (m, 4H) 7.54 (s, 1H) 7.77-7.98 (m, 2H) 8.26-8.59 (m, 7H) 9.00 (d, J=2.35 Hz, 1H) 10.87 (s, 1H). LCMS (m/z) (M+H)=483.1, Rt=0.55 min.

Example 11

N-(6-methyl-5-(5-(3-methyloxetan-3-yl)-6-((tetrahydro-2H-pyran-4-yl)oxy)pyridazin-3-yl)pyridin-3-yl)-3-(trifluoromethylbenzamide

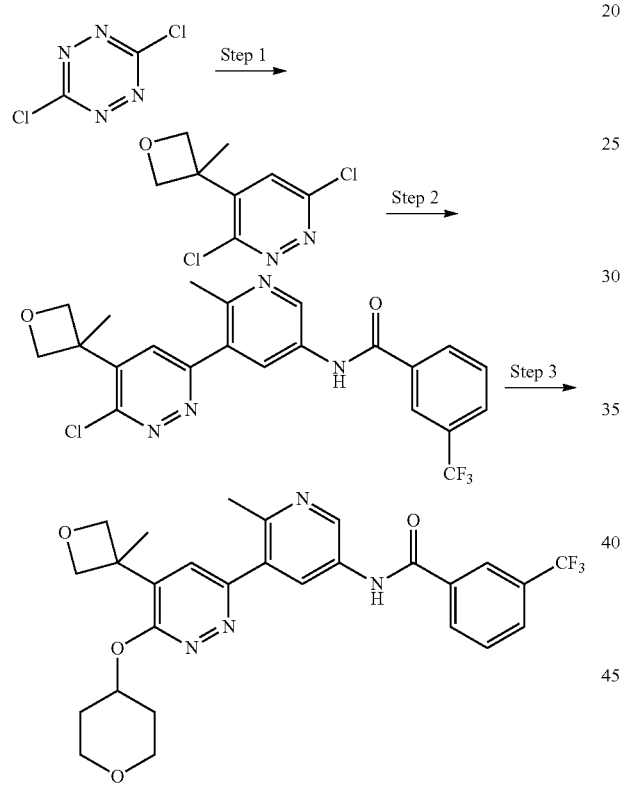

Step 1

To a solution of 3,6-dichloro-1,2,4,5-tetrazine in 1,2-dichloroethane (1.0 M) was added 3-ethynyl-3-methyloxetane (1.0 equiv.) and the reaction was stirred at 140° C. for 2.5 hours. The reaction was concentrated to dryness and used for the next step without further purification. LCMS (m/z) (M+H)=218.9/220.9, Rt=0.53 min.

Step 2

To a solution of 3,6-dichloro-4-(3-methyloxetan-3-yl) pyridazine (1.0 equiv.) and N-(6-methyl-5-(4,4,5,5-tetramethyl-1,3,2-dioxaborolan-2-yl)pyridin-3-yl)-3-(trifluoromethyl)benzamide (1.0 equiv.) in DME (1 M) was added sodium carbonate (3.0 equiv., 2M aqueous solution) and PdCl2(dppf)-DCM adduct (0.05 equiv.) and the reaction was heated at 130° C. in the microwave for 30 min. The organic phase was concentrated to dryness and purified via reverse phase prep-HPLC. The pure fractions were concentrated to give N-(5-(6-chloro-5-(3-methyloxetan-3-yl)pyridazin-3-yl)-6-methylpyridin-3-yl)-3-(trifluoromethyl)benzamide in 24% yield. LCMS (m/z) (M+H)=463.0, Rt=0.76 min.

Step 3

To a solution of N-(5-(6-chloro-5-(3-methyloxetan-3-yl) pyridazin-3-yl)-6-methylpyridin-3-yl)-3-(trifluoromethyl) benzamide (1.0 equiv.) in THF (0.03 M) was added tetrahydro-2H-pyran-4-ol (6.0 equiv.) and sodium hydride (6.0 equiv.) and the mixture was heated at 90° C. for 4 hours. Upon cooling to it, the reaction was quenched by the addition of water, then extracted with ethyl acetate. The organic phase was dried with magnesium sulfate, filtered and concentrated. The residue was purified via reverse phase prep HPLC to give N-(6-methyl-5-(5-(3-methyloxetan-3-yl)-6-((tetrahydro-2H-pyran-4-yl)oxy)pyridazin-3-yl)pyridin-3-yl)-3-(trifluoromethyl)benzamide in 40% yield. 1H NMR (400 MHz, <dmso>) δ ppm 1.59-1.84 (m, 5H) 1.97-2.12 (m, 3H) 3.56 (ddd, J=11.54, 8.02, 3.13 Hz, 3H) 3.72-3.86 (m, 2H) 4.45 (d, J=6.26 Hz, 2H) 4.91 (d, J=5.87 Hz, 2H) 5.42-5.56 (m, 1H) 7.64 (s, 1H) 7.78 (t, J=7.83 Hz, 1H) 7.97 (t, J=7.83 Hz, 1H) 8.17-8.38 (m, 3H) 8.89 (d, J=2.35 Hz, 1H) 10.71 (s, 1H). LCMS (m/z) (M+H)=529.1, Rt=0.75 min.

Example 12

2-(1,1-difluoroethyl)-N-(3-(6-(1,3-dimethyl-1H-pyrazol-4-yl)-5-(3-hydroxyoxetan-3-yl)pyridin-3-yl)-4-methylphenyl)isonicotinamide

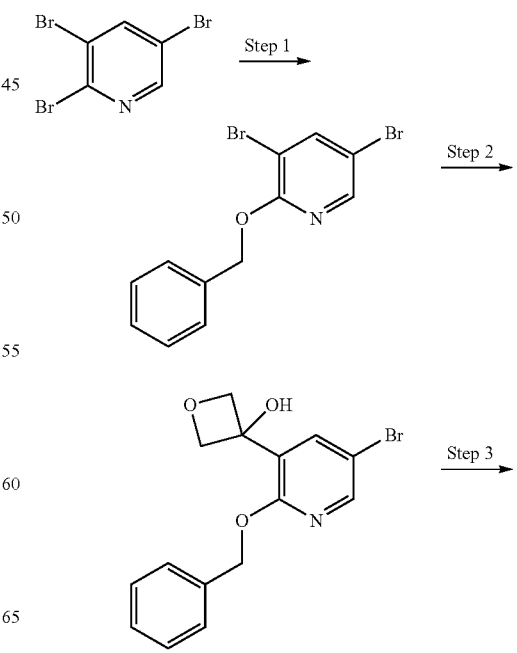

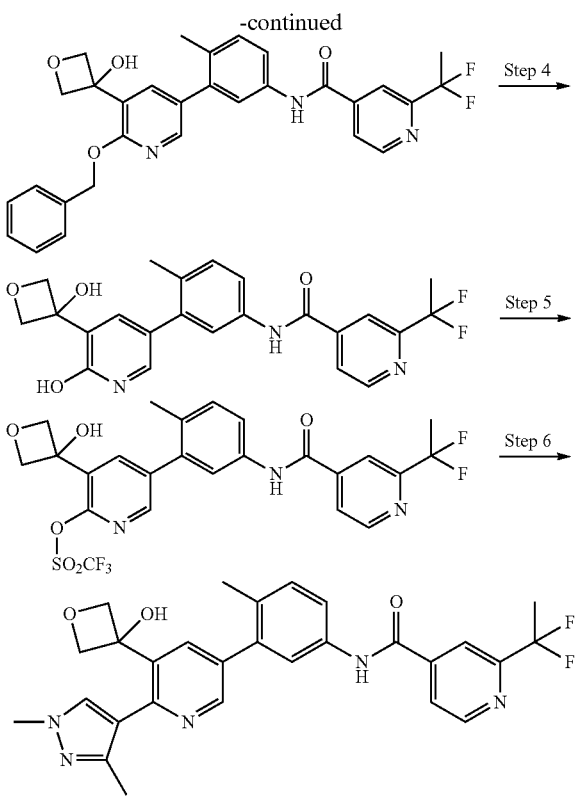

Step 1

A solution of 2,3,5-tribromopyridine (1.0 equiv.) in N,N-dimethylformamide (0.2 M) was treated with sodium hydride (60% dispersion in mineral oil, 1.3 equiv.). The mixture was cooled to 0° C. and BzOH (1.0 equiv.) was added slowly. The resultant mixture was stirred at 0° C. for 2 h and room temperature for 1 hour, then was added to dilute brine solution and was extracted with ethyl acetate. The organic layer was dried over magnesium sulfate, filtered, and the solvent was removed in vacuo. Purified by ISCO (0-100% EtOAc/heptane) to yield 2-(benzyloxy)-3,5-dibromopyridine in 55% yield. LCMS (m/z) (M+H)=342.0/344.0, Rt=1.20 min.

Step 2

To a flame-dried two-neck flask was added 2-(benzyloxy)-3,5-dibromopyridine (1.0 equiv.) and Et$_2$O (1.7 M). The mixture was cooled to −78° C. and butyl Lithium (2.6 equiv.) was added dropwise to ensure internal temperature not to exceed −70° C. After stirred at −78° C. for 30 min, a solution of oxetan-3-one (2.6 equiv.) in THF was added dropwise to ensure internal temperature not to exceed −70° C. The mixture was stirred at −78° C. for 1 h, warmed to rt by removing the ice bath and kept at rt for additional 3 h. Quenched with sat. NaHCO$_3$ and extracted with DCM. The organic phase was washed with brine, drived over sodium sulfate and concentrated. The residue was purified via ISCO SiO$_2$ chromatography (0-100% EtOAc/n-heptanes) to yield 3-(2-(benzyloxy)-5-bromopyridin-3-yl)oxetan-3-ol in 21% yield). LCMS (m/z) (M+H)=335.8/337.8, Rt=0.88 min.

Step 3

A solution of 3-(2-(benzyloxy)-5-bromopyridin-3-yl)oxetan-3-ol (1.0 equiv.), 2-(1,1-difluoroethyl)-N-(4-methyl-3-(4,4,5,5-tetramethyl-1,3,2-dioxaborolan-2-yl)phenyl)isonicotinamide (1.1 equiv.), PdCl$_2$(dppf)-DCM adduct (0.03 equiv.) and 2M aqueous sodium carbonate (3.0 equiv.) in DME (0.09 M) was heated in the microwave at 130° C. for 45 min. The reaction was partitioned between ethyl acetate and water, the organic phase was washed with brine, dried over magnesium sulfate, filtered and concentrated. The crude material was purified via silica gel chromatography (0-100% ethyl acetate/n-heptanes) to give N-(3-(6-(benzyloxy)-5-(3-hydroxyoxetan-3-yl)pyridin-3-yl)-4-methylphenyl)-2-(1,1-difluoroethyl)isonicotinamide in 92% yield. LCMS (m/Z) (M+H)=532.1. Rt=1.01 min.

Step 4

A solution of N-(3-(6-(benzyloxy)-5-(3-hydroxyoxetan-3-yl)pyridin-3-yl)-4-methylphenyl)-2-(1,1-difluoroethyl)isonicotinamide (1.0 equiv.) in methanol (0.08 M) was purged to a balloon of argon. To this solution was added Pd/C (0.1 equiv.) and a hydrogen balloon was attached. The reaction was left stirring under hydrogen for 2 hours. The reaction was degassed and purged to argon, then filtered, rinsed with ethyl acetate and the filtrate was concentrated under vacuo to give 2-(1,1-difluoroethyl)-N-(3-(6-hydroxy-5-(3-hydroxyoxetan-3-yl)pyridin-3-yl)-4-methylphenyl)isonicotinamide in 88% yield. LCMS (m/z) (M+H)=442.0, Rt=0.68 min.

Step 5

To a solution of 2-(1,1-difluoroethyl)-N-(3-(6-hydroxy-5-(3-hydroxyoxetan-3-yl)pyridin-3-yl)-4-methylphenyl)isonicotinamide (1.0 equiv.) and lutidine (5.0 equiv.) in pyridine (0.07 M) at 0° C. was added triflic anhydride and the reaction was stirred at 0° C. for 2 hours, then allowed to warm to rt and stirred for 4 hours. The volatiles were removed in vacuo and the residue was purified via silica gel chromatography (ISCO, 0-100% ethyl acetate/n-heptanes) to give 5-(5-(2-(1,1-difluoroethyl)isonicotinamido)-2-methylphenyl)-3-(3-hydroxyoxetan-3-yl)pyridin-2-yl trifluoromethanesulfonate in 48% yield. LCMS (m/z) (M+H)=574.2, Rt=0.97 min.

Step 6

To a solution of 5-(5-(2-(1,1-difluoroethyl)isonicotinamido)-2-methylphenyl)-3-(3-hydroxyoxetan-3-yl)pyridin-2-yl trifluoromethanesulfonate (1.0 equiv.) in DME (0.03 M) was added 1,3-dimethyl-4-(4,4,5,5-tetramethyl-1,3,2-dioxaborolan-2-yl)-1H-pyrazole (1.4 equiv.), followed by PdCl$_2$(dppf)-DCM adduct (0.1 equiv.) and 2M aqueous sodium carbonate (15 equiv.). The solution was heated in the microwave at 120° C. for 20 min. The organic phase was concentrated to dryness and the residue was purified via reverse phase HPLC. The pure product fractions were diluted with ethyl acetate, sodium carbonate was added and the organic phase was washed with brine, dried over magnesium sulfate, filtered and concentrated. The product was redissolved in acetonitrile and water (1:1) and lyophilized to give 2-(1,1-difluoroethyl)-N-(3-(6-(1,3-dimethyl-1H-pyrazol-4-yl)-5-(3-hydroxyoxetan-3-yl)pyridin-3-yl)-4-methylphenyl)isonicotinamide in 12% yield. $^1$H NMR (400 MHz, <dmso>) □□ ppm 2.05 (t, J=20.0 Hz, 3H) 2.30 (s, 3H) 2.31 (s, 3H) 3.81 (s, 3H) 4.52 (d, J=5.0 Hz, 2H) 4.66 (d, J=5.0 Hz, 2H) 6.71 (s, 1H) 7.38 (d, J=5.0 Hz, 1H) 7.67 (d, J=2.0 Hz, 1H) 7.74-7.76 (m, 2H) 7.95 (s, 1H) 8.04 (d, J=5.0 Hz, 1H) 8.19

(s, 1H) 8.59 (d, J=2.0 Hz, 1H) 8.88 (d, J=5.0 Hz, 1H) 10.68 (s, 1H). LCMS (m/z) (M+H)=520.1, Rt=0.65 min.

Example 13

2-(1,1-difluoroethyl)-N-(3-(5-(3-hydroxyoxetan-3-yl)-6-oxo-1,6-dihydropyridin-3-yl)-4-methylphenyl)isonicotinamide

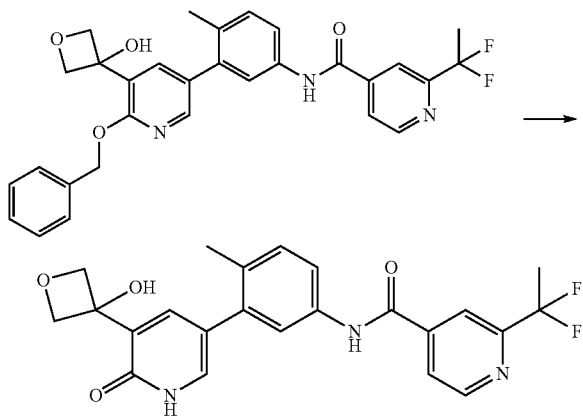

To a solution of N-(3-(6-(benzyloxy)-5-(3-hydroxyoxetan-3-yl)pyridin-3-yl)-4-methylphenyl)-2-(1,1-difluoroethyl)isonicotinamide (1.0 equiv.) in methanol (0.04M) was added Pd/C (0.1 equiv.) and the reaction was stirred at rt under a hydrogen balloon for 2 hours. The reaction was degassed and purged to argon then filtered and rinsed with ethyl acetate. The volatiles were removed under vacuo and the residue was purified via reverse phase prep-HPLC to give 2-(1,1-difluoroethyl)-N-(3-(5-(3-hydroxyoxetan-3-yl)-6-oxo-1,6-dihydropyridin-3-yl)-4-methylphenyl)isonicotinamide in 89% yield. ¹H NMR (400 MHz, <dmso>) δ ppm 2.05 (t, J=20.0 Hz, 3H) 2.26 (s, 3H) 4.52 (d, J=5.0 Hz, 2H) 5.01 (d, J=5.0 Hz, 2H) 6.15 (s, 1H) 7.29 (d, J=10.0 Hz, 1H) 7.38 (s, 1H) 7.56 (d, J=5.0 Hz, 1H) 7.62 (d, J=5.0 Hz, 1H) 7.68-7.70 (m, 1H) 8.02-8.03 (m, 1H) 8.18 (s, 1H) 8.88 (d, J=5.0 Hz, 1H) 10.62 (s, 1H) 11.96 (s, 1H). LCMS (m/z) (M+H)=442.0, Rt=0.66 min.

Example 14

N-(3-(6-(2-hydroxyethoxy)-5-(3-methyloxetan-3-yl)pyridazin-3-yl)-4-methylphenyl)-2-(trifluoromethyl)isonicotinamide

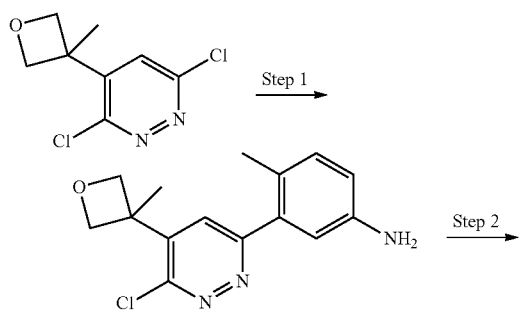

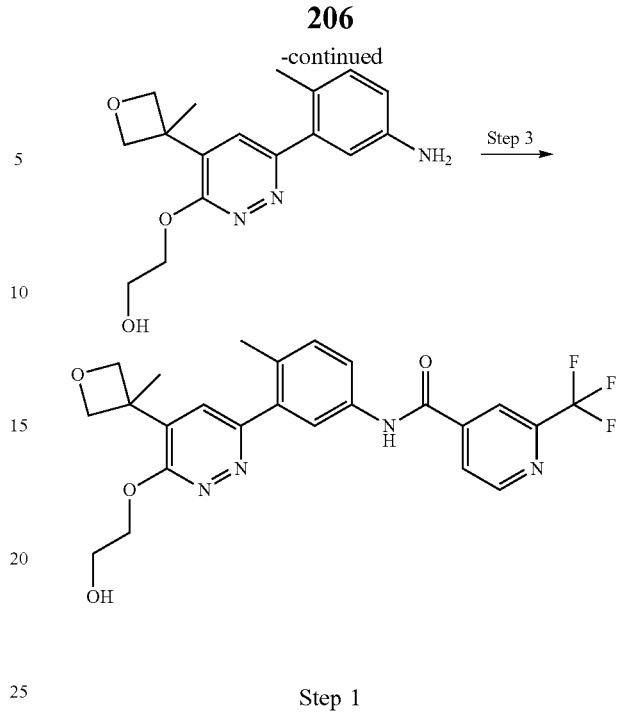

Step 1

To a solution of 3,6-dichloro-4-(3-methyloxetan-3-yl)pyridazine (1.0 equiv.) in DME (0.5 M) was added 4-methyl-3-(4,4,5,5-tetramethyl-1,3,2-dioxaborolan-2-yl)aniline (1.1 equiv.), followed by PdCl₂(dppf)-DCM adduct (0.05 equiv.) and 2M aqueous sodium carbonate (3.0 equiv.). The solution was heated in the microwave at 130° C. for 30 min. The organic phase was concentrated to dryness and the residue was purified via reverse phase HPLC to give 3-(6-chloro-5-(3-methyloxetan-3-yl)pyridazin-3-yl)-4-methylaniline in 13% yield. LCMS (m/z) (M+H)=289.9. Rt=0.49 min.

Step 2

To a solution of 3-(6-chloro-5-(3-methyloxetan-3-yl)pyridazin-3-yl)-4-methylaniline (1.0 equiv.) in THF (0.03 M) was added ethane-1,2-diol (6.0 equiv.) and sodium hydride (6.0 equiv.) and the mixture was heated to 100° C. in the microwave for 15 min. Upon cooling to rt, partitioned between water and ethyl acetate, the organic phase was dried with sodium sulfate, filtered and concentrated. The residue was purified via reverse phase prep-HPLC to give 2-((6-(5-amino-2-methylphenyl)-4-(3-methyloxetan-3-yl)pyridazin-3-yl)oxy)ethanol in 51% yield. LCMS (m/z) (M+H)=316.0, Rt=0.41 min.

Step 3

To a solution of 2-((6-(5-amino-2-methylphenyl)-4-(3-methyloxetan-3-yl)pyridazin-3-yl)oxy)ethanol (1.0 equiv.) in DMF (0.01M) was added 2-(3H-[1,2,3]triazolo[4,5-b]pyridin-3-yl)-1,1,3,3-tetramethylisouronium hexafluorophosphate(V) (1.0 equiv.) and 2-(trifluoromethyl)isonicotinic acid (1.0 equiv.) and the reaction was stirred at rt. Upon completion, the solution was purified via reverse phase prep-HPLC to give N-(3-(6-(2-hydroxyethoxy)-5-(3-methyloxetan-3-yl)pyridazin-3-yl)-4-methylphenyl)-2-(trifluoromethyl)isonicotinamide as a white solid in 14% yield. LCMS (m/z) (M+H)=489.0, Rt=0.73 min.

Example 15

N-(6-methyl-5-(5-(3-methyloxetan-3-yl)-6-oxo-1,6-dihydropyridazin-3-yl)pyridin-3-yl)-3-(trifluoromethyl)benzamide

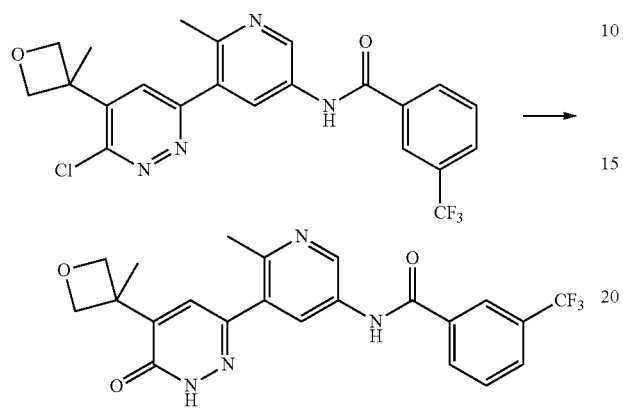

To a solution of N-(5-(6-chloro-5-(3-methyloxetan-3-yl)pyridazin-3-yl)-6-methylpyridin-3-yl)-3-(trifluoromethyl)benzamide (1.0 equiv.) and tert-butyldimethylsilanol (4.0 equiv.) in THF (0.03 M) was added sodium hydride (4.0 equiv.) and the reaction was heated to 90° C. After 2 hours, the reaction was cooled to rt and quenched by the addition of sat. ammonium chloride. The aqueous phase was concentrated and purified via reverse phase prep-HPLC to give N-(6-methyl-5-(5-(3-methyloxetan-3-yl)-6-oxo-1,6-dihydropyridazin-3-yl)pyridin-3-yl)-3-(trifluoromethyl)benzamide in 5% yield. LCMS (m/z) (M+H)=445.1, Rt=0.65 min.

Example 16

N-(5-(6-(2-hydroxyethoxy)-5-(3-methyloxetan-3-yl)pyridazin-3-yl)-6-methylpyridin-3-yl)-3-(trifluoromethyl)benzamide

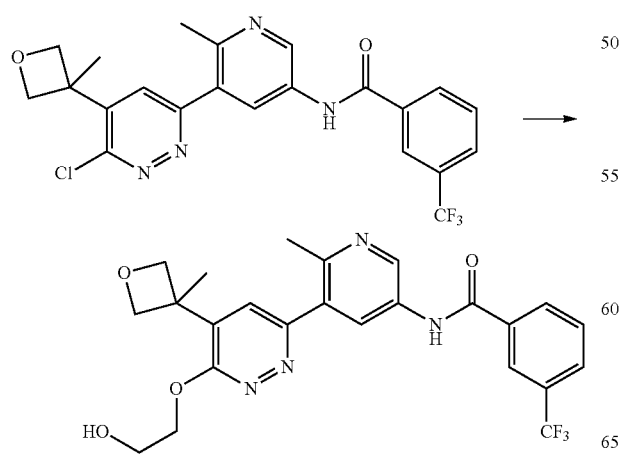

To a solution of N-(5-(6-chloro-5-(3-methyloxetan-3-yl)pyridazin-3-yl)-6-methylpyridin-3-yl)-3-(trifluoromethyl)benzamide (1.0 equiv.) in THF (0.03 M) was added ethane-1,2-diol (6.0 equiv.) and sodium hydride (6.0 equiv.) and the mixture was heated to 90° C. for 4 hours. Upon cooling to rt, partitioned between ethyl acetate and water, the organic phase was dried with sodium sulfate, filtered and concentrated. The residue was purified via reverse phase pre-HPLC to give N-(5-(6-(2-hydroxyethoxy)-5-(3-methyloxetan-3-yl)pyridazin-3-yl)-6-methylpyridin-3-yl)-3-(trifluoromethyl)benzamide in 42% yield. LCMS (m/z) (M+H)=489.1, Rt=0.66 min.

Example 17

3-(5-(3-hydroxyoxetan-3-yl)-6-methoxypyridin-3-yl)-4-methyl-N-(2-(trifluoromethyl)pyridin-4-yl)benzamide

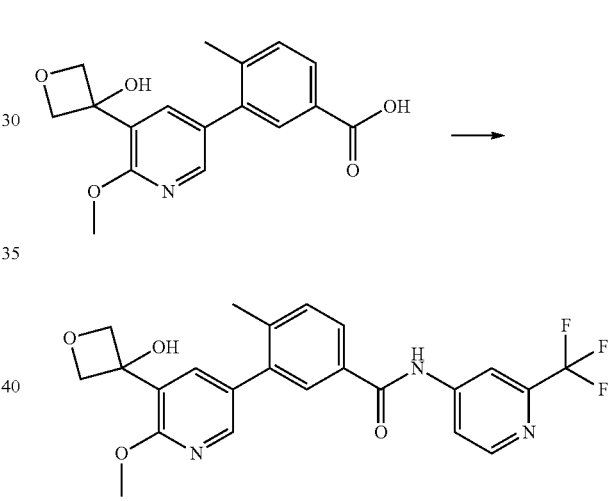

To a stirred solution of 3-(5-(3-hydroxyoxetan-3-yl)-6-methoxypyridin-3-yl)-4-methylbenzoic acid (1.0 equiv.) in DCM (0.08 M) at 0° C. was added 1-chloro-N,N,2-trimethyl-1-propenylamine (1.4 equiv.) and the mixture was allowed to stir at 0° C. for 1 h. The solution was subsequently added to a solution of 4-amino-2-(trifluoromethyl)pyridine (1.3 equiv.) and Et₃N (3.0 equiv.) in DCM and the reaction was allowed to warm to RT and stirred for 1 h. The volatiles were concentrated under vacuo and purified by neutral prep HPLC to give 3-(5-(3-hydroxyoxetan-3-yl)-6-methoxypyridin-3-yl)-4-methyl-N-(2-(trifluoromethyl)pyridin-4-yl)benzamide in 18% yield. $^1$H NMR (400 MHz, <dmso>) δ ppm 2.33 (s, 3H) 3.93 (s, 3H) 4.56-4.69 (m, 2H) 4.97-5.08 (m, 2H) 6.10-6.18 (m, 1H) 7.46-7.58 (m, 1H) 7.69-7.78 (m, 1H) 7.86-7.96 (m, 2H) 8.01-8.10 (m, 1H) 8.11-8.23 (m, 1H) 8.26-8.32 (m, 1H) 8.61-8.70 (m, 1H) 10.78-10.88 (m, 1H). LCMS (m/z) (M+H)=460.1, Rt=0.84 min.

Example 18

N-(3-(difluoromethyl)phenyl)-3-(5-(3-hydroxyoxetan-3-yl)-6-methoxypyridin-3-yl)-4-methylbenzamide

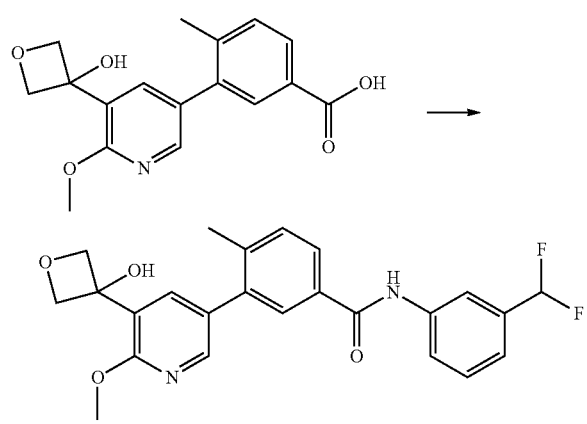

A solution of 3-(5-(3-hydroxyoxetan-3-yl)-6-methoxypyridin-3-yl)-4-methylbenzoic acid (1.0 equiv.), 3-(difluoromethyl)aniline (1.3 equiv.), N1-((ethylimino)methylene)-N3,N3-dimethylpropane-1,3-diamine hydrochloride (2.0 equiv.) and 1H-benzo[d][1,2,3]triazol-1-ol hydrate (2.0 equiv.) in DMF (0.19 M) was stirred at rt overnight. Diluted with DMSO and purified via reverse-phase neutral prep-HPLC to give N-(3-(difluoromethyl)phenyl)-3-(5-(3-hydroxyoxetan-3-yl)-6-methoxypyridin-3-yl)-4-methylbenzamide in 24% yield. $^1$H NMR (400 MHz, <dmso>) δ ppm 2.27 (s, 3H) 3.89 (s, 3H) 4.59 (s, 2H) 4.90-5.01 (m, 2H) 6.09 (s, 1H) 6.81-7.15 (m, 1H) 7.18-7.28 (m, 1H) 7.38-7.47 (m, 2H) 7.63-7.72 (m, 1H) 7.79-7.89 (m, 3H) 7.96-8.03 (m, 1H) 8.09-8.18 (m, 1H) 10.25-10.37 (m, 1H). LCMS (m/z) (M+H)=441.2, Rt=0.85 min.

Example 19

6-(2-aminopropan-2-yl)-N-(3-(5-(3-hydroxyoxetan-3-yl)-6-m ethoxypyridin-3-yl)-4-methylphenyl)-4-(trifluoromethyl)picolinamide

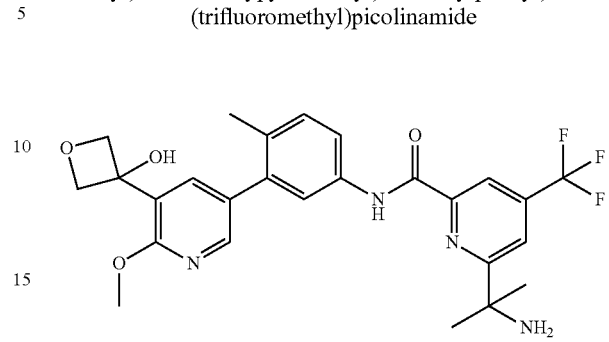

To a solution of 3-(5-(5-amino-2-methylphenyl)-2-methoxypyridin-3-yl)oxetan-3-ol (1.0 equiv.) and 4-(trifluoromethyl)-6-(2-(3-(trimethylsilyl)propanamido)propan-2-yl)picolinic acid (1.3 equiv.) in DMF was added HOBT (2.0 equiv.) and EDC (2.0 equiv.) and the reaction was stirred at rt for 16 h. Water was added and the precipitate was filtered off. The solid was dissolved in DCM, dried over sodium sulfate and filtered. To the filtrate was added TFA and the solution was stirred until complete deprotection. The reaction was concentrated under vacuo and purified via reverse phase prep-HPLC. The pure fractions were concentrated to give 6-(2-aminopropan-2-yl)-N-(3-(5-(3-hydroxyoxetan-3-yl)-6-m ethoxypyridin-3-yl)-4-methylphenyl)-4-(trifluoromethyl)picolinamide in 25% yield. $^1$H NMR (400 MHz, <dmso>) δ ppm 1.55 (s, 6H) 2.23 (s, 3H) 3.93 (s, 3H) 4.63 (d, J=7.04 Hz, 2H) 5.00 (d, J=7.04 Hz, 2H) 6.15 (s, 1H) 7.30-7.41 (m, 1H) 7.68 (s, 2H) 7.77-7.86 (m, 1H) 8.13 (d, J=2.35 Hz, 1H) 8.17-8.24 (m, 2H) 10.46-10.59 (m, 1H). LCMS (m/z) (M+H)=517.2, Rt=0.72 min.

The compounds listed in Table 2, below, were prepared using methods similar to those described for the preparation of the above examples using the appropriate starting materials:

TABLE 2

| Example | Structure | Name | Physical Data |
|---|---|---|---|
| 20 | 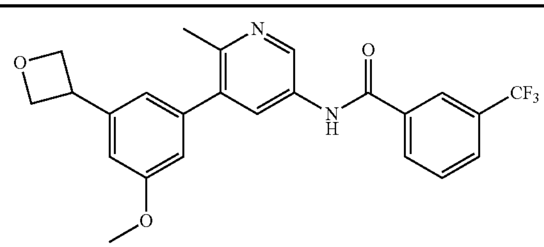 | N-(5-(3-methoxy-5-(oxetan-3-yl)phenyl)-6-methylpyridin-3-yl)-3-(trifluoromethyl)-benzamide | 1H NMR (400 MHz, <cdcl3>) δ ppm 1.68 (br. s., 2H) 2.36-2.69 (m, 3H) 3.66-4.03 (m, 3H) 4.26 (quin, J = 7.34 Hz, 1H) 4.81 (t, J = 5.87 Hz, 2H) 5.11 (t, J = 6.85 Hz, 2H) 6.81 (s, 1H) 6.89-7.09 (m, 2 H) 7.67 (t, J = 7.83 Hz, 1H) 7.85 (d, J = 7.83 Hz, 1H) 7.97-8.29 (m, 4 H) 8.67 (s, 1H). LCMS (m/z) (M + H) = 443.2, Rt = 0.75 min. |
| 21 | 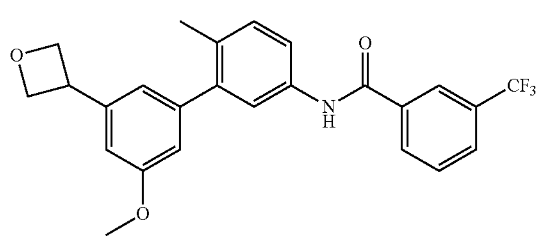 [SMILES: COc1cc(-c2cc(NC(=O)c3cccc(C(F)(F)F)c3)ccc2C)cc(C2COC2)c1] | N-(3'-methoxy-6-methyl-5'-(oxetan-3-yl)-[1,1'-biphenyl-3-yl)-3-(trifluoromethyl)-benzamide | 1H NMR (400 MHz, <cdcl3>) δ ppm 2.28 (s, 3H) 3.86 (s, 3H) 4.24 (quin, J = 7.43 Hz, 1H) 4.69-4.90 (m, 2H) 5.09 (t, J = 7.04 Hz, 2 H) 6.78 (s, 1H) 6.94 (br. s., 2H) 7.19-7.35 (m, 2H) 7.41-7.52 (m, 1H) 7.55-7.71 (m, 2H) 7.81 (d, J = 9.39 Hz, 2H) 8.00-8.20 (m, 2 H). LCMS (m/z) (M + H) = 442.3, Rt = 1.03 min. |

TABLE 2-continued

| Example | Structure | Name | Physical Data |
|---|---|---|---|
| 22 | 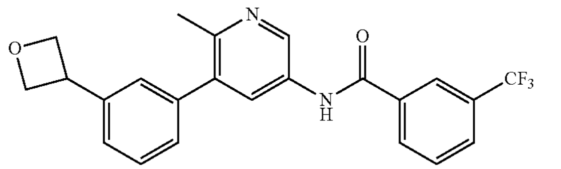 [SMILES: Cc1ncc(NC(=O)c2cccc(C(F)(F)F)c2)cc1-c1cccc(C2COC2)c1] | N-(6-methyl-5-(3-(oxetan-3-yl)phenyl)pyridin-2-yl)-3-(trifluoromethyl)-benzamide | 1H NMR (400 MHz, <cdcl3>) δ ppm 2.52 (s, 3H) 4.29 (quin, J = 7.53 Hz, 1H) 4.82 (t, J = 6.26 Hz, 2H) 5.12 (dd, J = 8.41, 6.06 Hz, 2 H) 7.20-7.32 (m, 2H) 7.38 (s, 1 H) 7.42-7.52 (m, 2H) 7.66 (t, J = 7.83 Hz, 1H) 7.84 (d, J = 7.43 Hz, 1H) 7.96-8.26 (m, 4H) 8.65 (d, J = 2.35 Hz, 1H). LCMS (m/z) (M + H) = 413.2, Rt = 0.71 min. |
| 23 | 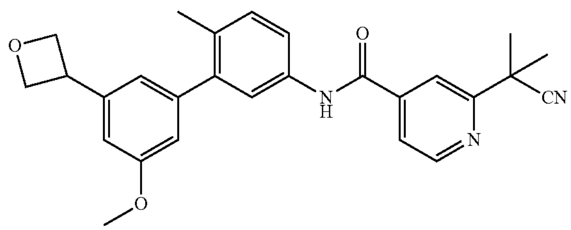 [SMILES: COc1cc(-c2cc(NC(=O)c3ccnc(C(C)(C)C#N)c3)ccc2C)cc(C2COC2)c1] | 2-(2-cyanopropan-2-yl)-N-(3'-methoxy-6-methyl-5'-(oxetan-3-yl)-[1,1'-biphenyl]-3-yl)isonicotinamide | 1H NMR (400 MHz, <cdcl3>) δ ppm 1.74 (s, 6H) 2.40 (s, 3H) 3.84 (s, 3H) 4.24 (quin, J = 7.34 Hz, 1H) 4.74 (t, J = 6.26 Hz, 2H) 5.07 (dd, J = 7.83, 6.26 Hz, 2H) 6.86 (br. s,, 1H) 7.01 (d, J = 8.22 Hz, 2H) 7.15 (s, 1H) 7.25-7.44 (m, 4H) 7.70 (s, 3H) 8.00 (br. s,. 1 H) 8.32 (d, J = 7.83 Hz, 1H) 8.67 (d, J = 4.70 Hz, 1H). LCMS (m/z) (M + H) = 442.2, Rt = 0.87 min. |
| 24 | 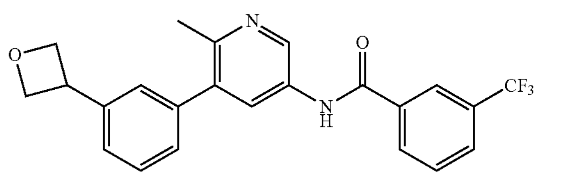 | N-(6-methyl-5-(3-(3-methyloxetan-3-yl)phenyl)pyridin-1-yl)-3-(trifluoromethyl)benzamide | 1H NMR (400 MHz, <cdcl3>) δ ppm 1.64-1.94 (m, 3H) 2.49 (s, 3H) 4.53-4.85 (m, 2H) 5.00 (d, J = 5.48 Hz, 2H) 7.10-7.32 (m, 3 H) 7.38-7.52 (m, 1H) 7.57-7.71 (m, 1H) 7.82 (d, J = 7.43 Hz, 1H) 8.05-8.23 (m, 3H) 8.41 (s, 1H) 8.64 (d, J = 1.96 Hz, 1H). LCMS (m/z) (M + H) = 427.3, Rt = 0.75 min. |
| 25 | 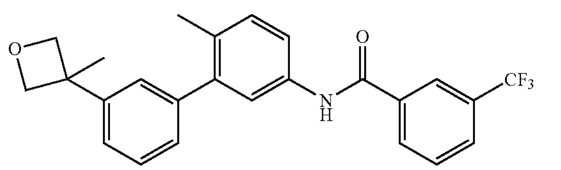 [SMILES: Cc1ccc(NC(=O)c2cccc(C(F)(F)F)c2)cc1-c1cccc(C2(C)COC2)c1] | N-(6-methyl-3'-(3-methyloxetan-3-yl)-[1,1'-biphenyl]-3-yl)-3-(trifluoromethyl)benzamide | 1H NMR (400 MHz, <cdcl3>) δ ppm 1.77 (s, 3H) 2.10-2.36 (m, 3H) 4.51-4.77 (m, 2H) 5.01 (d, J = 5.48 Hz, 2H) 7.12-7.34 (m, 3 H) 7.35-7.50(m, 2H) 7.56-7.70 (m, 2H) 7.75-7.90 (m, 2H) 8.06 (d, J = 7.83 Hz, 1H) 8.13 (s, 1H). LCMS (m/z) (M + H) = 426.3, Rt = 1.07 min. |
| 26 | 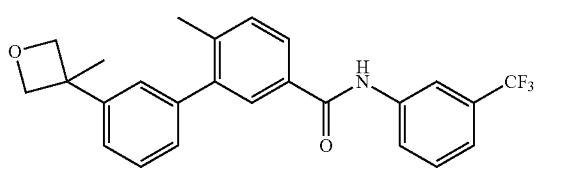 [SMILES: Cc1ccc(C(=O)Nc2cccc(C(F)(F)F)c2)cc1-c1cccc(C2(C)COC2)c1] | 6-methyl-3'-(3-methyloxetan-3-yl)-N-(3-(trifluoromethyl)phenyl)-[1,1'-biphenyl]-3-carboxamide | 1H NMR (400 MHz, <cdcl3>) δ ppm 1.77 (s, 3H) 2.34 (s, 3H) 4.67 (d, J = 5.48 Hz, 2H) 5.01 (d, J = 5.48 Hz, 2H) 7.16 (s, 1H) 7.19-7.30 (m, 4H) 7.34-7.55 (m, 4H) 7.73 (s, 1H) 7.79 (dd, J = 8.02, 1.37 Hz, 1H) 7.84-7.97 (m, 1H). LCMS (m/z) (M + H) = 426.2, Rt = 1.09 min. |
| 27 | 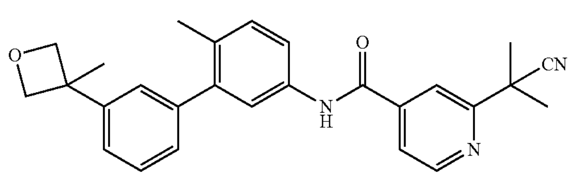 [SMILES: Cc1ccc(NC(=O)c2ccnc(C(C)(C)C#N)c2)cc1-c1cccc(C2(C)COC2)c1] | 2-(2-cyanopropan-2-yl)-N-(6-methyl-3'-(3-methyloxetan-3-yl)-[1,1'-biphenyl]-3-yl)isonicotinamide | 1H NMR (400 MHz, <cdcl3>) δ ppm 1.62-1.86 (m, 9H) 2.41 (s, 3H) 4.64 (d, J = 5.48 Hz, 2H) 4.94 (d, J = 5.48 Hz, 2H) 7.06-7.40 (m, 7H) 7.43-7.61 (m, 1H) 7.74 (s, 1 H) 7.93 (br. s,, 1H) 8.31 (d, J = 7.83 Hz, 1H) 8.67 (d, J = 4.70 Hz, 1H). LCMS (m/z) (M + H) = 426.3, Rt = 0.90 min. |
| 28 | 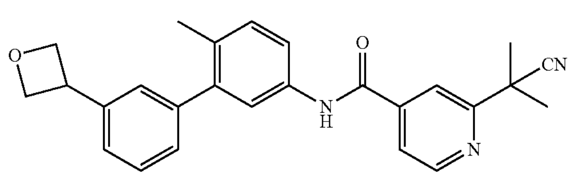 [SMILES: Cc1ccc(NC(=O)c2ccnc(C(C)(C)C#N)c2)cc1-c1cccc(C2COC2)c1] | 2-(2-cyanopropan-2-yl)-N-(6-methyl-3'-(oxetan-3-yl)-[1,1'-biphenyl]-3-yl)isonicotinamide | 1H NMR (400 MHz, <cdcl3>) δ ppm 1.74 (s, 6H) 2.41 (s, 3H) 4.28 (quin, J = 7.43 Hz, 1H) 4.76 (t, J = 6.26 Hz, 2H) 5.09 (dd, J = 8.22, 6.26 Hz, 2H) 7.08-7.61 (m, 12H) 7.70 (s, 1H) 7.94 (br. s., 1H) 8.32 (d, J = 7.83 Hz, 1H) 8.66 (d, J = 4.69 Hz, 1H). LCMS (m/z) (M + H) = 412.2, Rt = 0.87 min. |

TABLE 2-continued

| Example | Structure | Name | Physical Data |
|---|---|---|---|
| 29 | 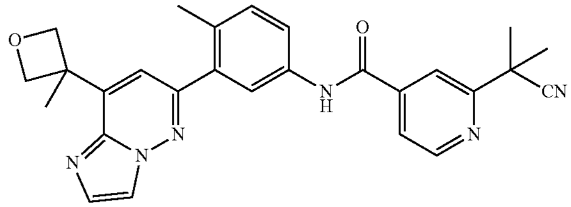 [SMILES: Cc1ccc(NC(=O)c2ccnc(C(C)(C)C#N)c2)cc1-c1cc(C2(C)COC2)c2nccn2n1] | 2-(2-cyanopropan-2-yl)-N-(4-methyl-3-(8-(3-methyloxetan-3-yl)imidazo[1,2-b]pyridazin-6-yl)phenyl)isonicotinamide | 1H NMR (400 MHz, <dmso>) δ ppm 1.75 (s, 6H) 1.84 (s, 3H) 2.34 (s, 3H) 4.62 (d, J = 5.87 Hz, 2 H) 5.09 (d, J = 6.26 Hz, 2H) 7.18 (s, 1H) 7.39 (d, J = 8.61 Hz, 1H) 7.76 (d, J = 0.78 Hz, 1H) 7.79-7.91 (m, 3H) 8.00 (s, 1H) 8.30 (d, J = 1.17 Hz, 1H) 8.79 (d, J = 5.09 Hz, 1H) 10.63 (s, 1H). LCMS (m/z) (M + H) = 467.1, Rt = 0.73 min. |
| 30 | 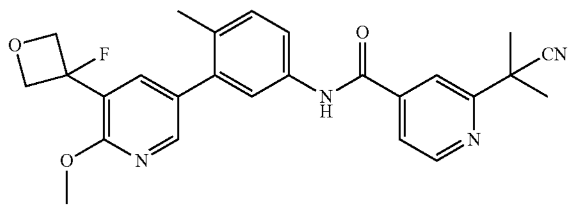 [SMILES: COc1ncc(-c2cc(NC(=O)c3ccnc(C(C)(C)C#N)c3)ccc2C)cc1C1(F)COC1] | 2-(2-cyanopropan-2-yl)-N-(3-(5-(3-fluorooxetan-3-yl)-6-methoxypyridin-3-yl)-4-methylphenyl)isonicotinamide | $^1$H NMR (400 MHz, <dmso>) δ ppm 1.76 (s, 6H) 2.24 (s, 3H) 3.97 (s, 3H) 4.89-4.95 (m, 2H) 5.11-5.20 (m, 2H) 7.35 (d, J = 8.0 Hz, 1H), 7.64 (d, J = 4.0 Hz, 1H), 7.74 (dd, J = 8.0, 2.0 Hz, 1H) 7.85-7.88 (m, 2H) 8.01 (s, 1H) 8.26-8.27 (m, 1H) 8.80-8.81 (m, 1H) 10.58 (s, 1H). LCMS (m/z) (M + H) = 461.2, Rt = 0.93 min. |
| 31 | 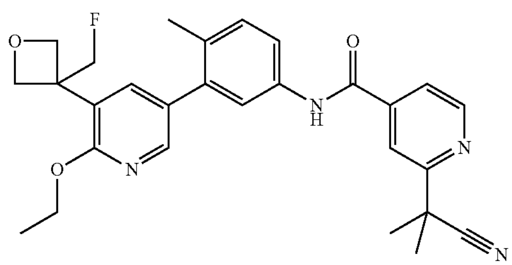 [SMILES: CCOc1ncc(-c2cc(NC(=O)c3ccnc(C(C)(C)C#N)c3)ccc2C)cc1C1(CF)COC1] | 2-(2-cyanopropan-2-yl)-N-(3-(6-ethoxy-5-(3-(fluoromethyl)oxetan-3-yl)pyridin-3-yl)-4-methylphenyl)isonicotinamide | $^1$H NMR (400 MHz, <cd3od>) δ ppm 1.38 (t, J = 7.04 Hz, 3H) 1.81 (s, 6H) 2.26 (s, 3H) 4.41 (q, J = 7.04 Hz, 2H) 4.72-4.84 (m, 4 H) 5.01 (dd, J = 6.46, 2.93 Hz, 2H) 7.32 (d, J = 8.22 Hz, 1H) 7.44 (d, J = 1.96 Hz, 1H) 7.59 (d, J = 1.96 Hz, 1H) 7.65 (dd, J = 8.22, 2.35 Hz, 1H) 7.81 (dd, J = 5.09, 1.17 Hz, 1 H) 8.02-8.10 (m, 2H) 8.75 (d, J = 5.09 Hz, 1H). LCMS (m/z) (M + H) = 489.1, Rt = 1.03 min. |
| 32 | 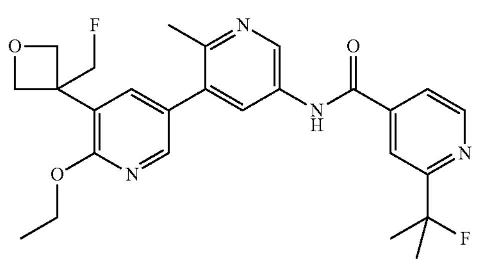 [SMILES: CCOc1ncc(-c2cc(NC(=O)c3ccnc(C(C)(C)F)c3)cnc2C)cc1C1(CF)COC1] | N-(6'-ethoxy-5'-(3-(fluoromethyl)oxetan-3-yl)-2-methyl-[3,3'-bipyridin]-5-yl)-2-(2-fluoropropan-2-yl)isonicotinamide | $^1$H NMR (400 MHz, <cd3od>) δ ppm 1.40 (t, J = 7.04 Hz, 3H) 3.67-1.82 (m, 6H) 2.68 (s, 3H) 4.47 (d, J = 7.04 Hz, 2H) 4.75-4.81 (m, 3H) 4.92 (s, 1H) 5.02 (dd, J = 6.65, 3.13 Hz, 2H) 7.60 (d, J = 2.35 Hz, 1 H) 7.83 (dd, J = 5.09, 1.57 Hz, 1H) 8.14 (s, 1H) 8.23 (d, J = 2.35 Hz, 1 H) 8.45 (d, J = 2.35 Hz, 1H) 8.76 (d, J = 5.09 Hz, 1H) 9.34 (d, J = 2.35 Hz, 1H). LCMS (m/z) (M + H) = 483.2, Rt = 0.76 min. |
| 33 | 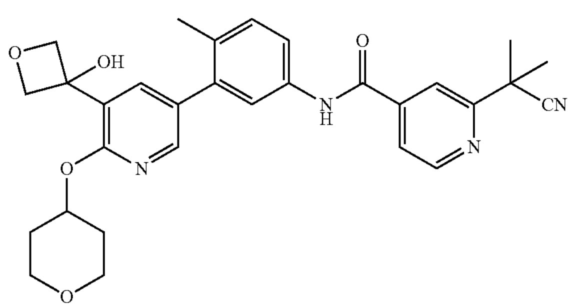 [SMILES: Cc1ccc(NC(=O)c2ccnc(C(C)(C)C#N)c2)cc1-c1cnc(OC2CCOCC2)c(C2(O)COC2)c1] | 2-(2-cyanopropan-2-yl)-N-(3-(5-(3-hydroxyoxetan-3-yl)-6-((tetrahydro-2H-pyran-4-yl)oxy)pyridin-3-yl)-4-methylphenyl)isonicotinamide | $^1$H NMR (400 MHz, <dmso>) δ ppm 1.70 (s, 8H) 1.89-2.01 (m, 2 H) 2.18 (s, 3H) 3.41-3.56 (m, 2 H) 3.71-3.86 (m, 2H) 4.53-4.66 (m, 2H) 4.98-5.05 (m, 2H) 5.23-5.35 (m, 1H) 6.10-6.19 (m, 1H) 7.19-7.3.1 (m, 1H) 7.55-7.66 (m, 3H) 7.75-7.83 (m, 1H) 7.89-7.97 (m, 1H) 8.00-8.08 (m, 1H) 8.70-8.77 (m, 1H) 10.42-10.52 (m, 1H). LCMS (m/z) (M + H) = 529.3, Rt = 0.84 min. |

TABLE 2-continued

| Example | Structure | Name | Physical Data |
|---|---|---|---|
| 34 | 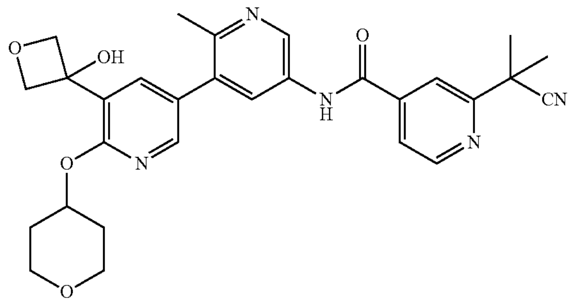 [SMILES: Cc1ncc(NC(=O)c2ccnc(C(C)(C)C#N)c2)cc1-c1cnc(OC2CCOCC2)c(C2(O)COC2)c1] | 2-(2-cyanopropan-2-yl)-N-(5'-(3-hydroxyoxetan-3-yl)-2-methyl-6'-((tetrahydro-2H-pyran-4-yl)oxy)-[3,3'-bipyridin]-5-yl)isonicotinamide | $^1$H NMR (400 MHz, <dmso>) δ ppm 1.70 (s, 8H) 1.90-2.03 (m, 2 H) 2.39 (s, 3H) 3.43-3.57 (m, 2 H) 3.72-3.89 (m, 2H) 4.51-4.64 (m, 2H) 4.97-5.09 (m, 2H) 5.24-5.37 (m, 1H) 6.08-6.21 (m, 1H) 7.65-7.73 (m, 1H) 7.78-7.85 (m, 1H) 7.90-8.02 (m, 2H) 8.07-8.15 (m, 1H) 8.69-8.80 (m, 2H) 10.63-10.75 (m, 1H). LCMS (m/z) (M + H) = 530.3, Rt = 0.60 min. |
| 35 | 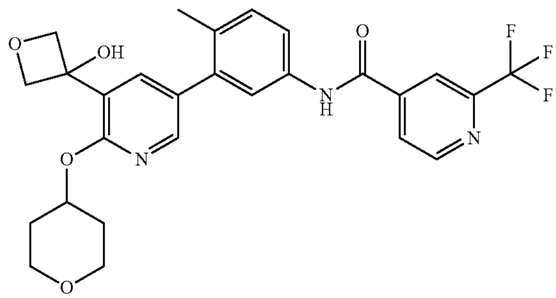 | N-(3-(5-(3-hydroxyoxetan-3-yl)-6-((tetrahydro-2H-pyran-4-yl)oxy)pyridin-3-yl)-4-methylphenyl)-2-(trifluoromethyl)isonicotinamide | $^1$H NMR (400 MHz, <dmso>) δ ppm 1.54-1.76 (m, 2H) 1.89-1.99 (m, 2H) 2.18 (s, 3H) 3.44-3.58 (m, 2H) 3.73-3.86 (m, 2H) 4.52-4.65 (m, 2H) 4.95-5.08 (m, 2H) 5.20-5.36 (m, 1H) 6.07-6.16 (m, 1H) 7.19-7.35 (m, 1H) 7.56-7.71 (m, 3H) 8.00-8.08 (m, 1H) 8.08-8.16 (m, 1H) 8.25-8.32 (m, 1H) 8.87-8.97 (m, 1H) 10.55-10.66 (m, 1H). LCMS (m/z) (M + H) = 530.3, Rt = 0.88 min. |
| 36 | 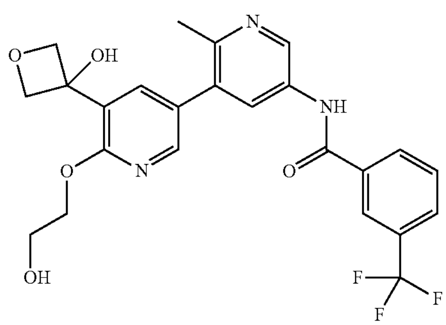 [SMILES: Cc1ncc(NC(=O)c2cccc(C(F)(F)F)c2)cc1-c1cnc(OCCO)c(C2(F)COC2)c1] | N-(6'-(2-hydroxyethoxy)-5'-(3-hydroxyoxetan-3-yl)-2-methyl-[3,3'-bipyridin]-5-yl)-3-(trifluoromethyl)benzamide | $^1$H NMR (400 MHz, <cd3od>) δ ppm 2.52 (s, 3H) 3.95 (dd, J = 5.48, 4.30 Hz, 2H) 4.51-4.58 (m, 2H) 4.84 (d, J = 7.83 Hz, 2H) 5.21-5.27 (m, 2H) 7.74-7.80 (m, 2H) 7.94 (d, J = 7.82 Hz, 1H) 8.16 (d, J = 2.35 Hz, 1H) 8.19 (d, J = 2.35 Hz, 1H) 8.26 (d, J = 7.83 Hz, 1H) 8.32 (s, 3H) 8.85 (d, J = 2.35 Hz, 1 H). LCMS (m/z) (M + H) = 490.0, Rt = 0.61 min. |
| 37 | 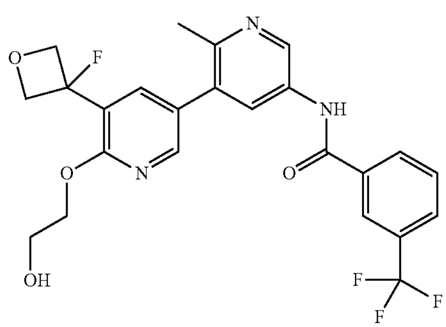 | N-(5'-(3-fluorooxetan-3-yl)-6'-(2-hydroxyethoxy)-2-methyl-[3,3'-bipyridin]-5-yl)-3-(trifluoromethyl)benzamide | $^1$H NMR (400 MHz, <cd3od>) δ ppm 2.51 (s, 3H) 3.91-4.01 (m, 2 H) 4.51-4.64 (m, 2H) 4.96-5.11 (m, 2H) 5.23-5.40 (m, 2H) 7.74-7.81 (m, 1H) 7.84-7.87 (m, 1H) 7.94 (d, J = 7.83 Hz, 1H) 8.15 (d, J = 2.35 Hz, 1H) 8.23-8.29 (m, 2 H) 8.32 (s, 1H) 8.86 (d, J = 2.74 Hz, 1H). LCMS (m/z) (M + H) = 492.0, Rt = 0.69 min. |
| 38 | 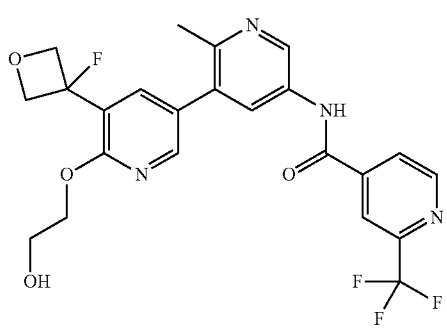 | N-(5'-(3-fluorooxetan-3-yl)-6'-(2-hydroxyethoxy)-2-methyl-[3,3'-bipyridin]-5-yl)-2-(trifluoromethyl)isonicotinamide | $^1$H NMR (400 MHz, <cd3od>) δ ppm 2.51 (s, 3H) 3.90-4.00 (m, 2 H) 4.53-4.63 (m, 2H) 4.97-5.09 (m, 2H) 5.25-5.40 (m, 2H) 7.84-7.88 (m, 1H) 8.14-8.19 (m, 2H) 8.27 (dd, J = 2.35, 1.57 Hz, 1H) 8.36 (s, 1H) 8.87 (d, J = 2.35 Hz, 1 H) 8.95 (d, J = 4.69 Hz, 1H). LCMS (m/z) (M + H) = 493.0, Rt = 0.60 min. |

TABLE 2-continued

| Example | Structure | Name | Physical Data |
|---|---|---|---|
| 39 | 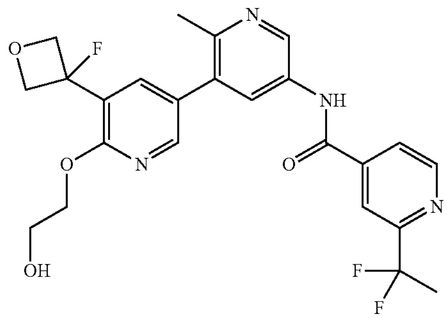 [SMILES: Cc1ncc(NC(=O)c2ccnc(C(C)(F)F)c2)cc1-c1cnc(OCCO)c(C2(F)COC2)c1] | 7-(1,1-difluoroethyl)-N-(5'-(3-fluorooxetan-3-yl)-6'-(2-hydroxyethoxy)-2-methyl-[3,3'-bipyridin]-5-yl)isonotinamide | $^1$H NMR (400 MHz, <cd3od>) δ ppm 2.06 (t, J = 18.78 Hz, 3H) 2.51 (s, 3H) 3.90-3.99 (m, 2H) 4.52-4.64 (m, 2H) 4.96-5.10 (m, 2H) 5.24-5.39 (m, 2H) 7.84-7.87 (m, 1H) 8.01 (dd, J = 5.09, 1.57 Hz, 1 H) 8.36 (d, J = 2.74 Hz, 1H) 8.24 (dd, J = 1.57, 0.78 Hz, 1H) 8.27 (dd, J = 2.35, 1.57 Hz, 1H) 8.85 (dd, J = 5.09, 0.78 Hz, 1H) 8.87 (d, J = 2.35 Hz, 1H). LCMS (m/z) (M + H) = 489.1, Rt = 0.59 min. |
| 40 | 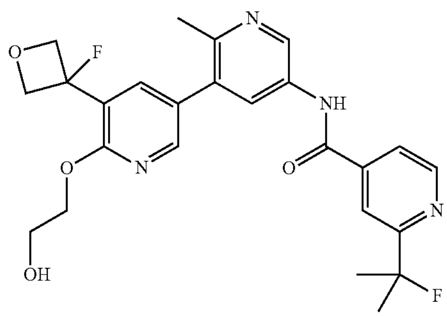 [SMILES: Cc1ncc(NC(=O)c2ccnc(C(C)(C)F)c2)cc1-c1cnc(OCCO)c(C2(F)COC2)c1] | N-(5'-(3-fluorooxetan-3-yl)-6'-(2-hydroxyethoxy)-2-methyl-[3,3'-bipyridin]-5-yl)-2-(2-fluoropropan-2-yl)isonicotinamide | 1H NMR (400 MHz, <cd3od>) δ ppm 1.69-1.81 (m, 6H) 2.51 (s, 3 H) 3.90-3.99 (m, 2H) 4.53-4.62 (m, 2H) 4.97-5.11 (m, 2H) 5.25-5.39 (m, 2H) 7.82 (dd, J = 5.09, 1.96 Hz, 1H) 7.85-7.88 (m, 1H) 8.10-8.13 (m, 1H) 8.16 (d, J = 2.35 Hz, 1H) 8.27 (dd, J = 2.35, 1.57 Hz, 1H) 8.72-8.76 (m, 1H) 8.87 (d, J = 2.35 Hz, 1H). LCMS (m/z) (M + H) = 485.3, Rt = 0.53 min. |
| 41 | 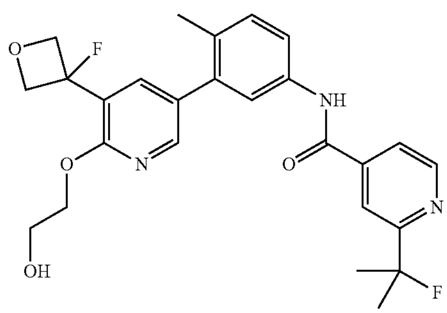 [SMILES: Cc1ccc(NC(=O)c2ccnc(C(C)(C)F)c2)cc1-c1cnc(OCCO)c(C2(F)COC2)c1] | N-(3-(5-(3-fluorooxetan-3-yl)-6-(2-hydroxyethoxy)pyridin-3-yl)-4-methylphenyl)-2-(2-fluoropropan-2-yl)isonicotinamide | $^1$H NMR (400 MHz, <cd3od>) δ ppm 1.69-1.81 (m, 6H) 2.29 (s, 3 H) 3.92-3.99 (m, 2H) 4.52-4.58 (m, 2H) 4.97-5.10 (m, 2H) 5.24-5.39 (m, 2H) 7.35 (d, J = 8.22 Hz, 1 H) 7.64 (d, J = 1.96 Hz, 1H) 7.68 (dd, J = 8.22, 2.35 Hz, 1H) 7.76-7.81 (m, 2H) 8.08 (s, 1H) 8.20 (t, J = 1.96 Hz, 1H) 8.71 (dd, J = 5.09, 0.78 Hz, 1H). LCMS (m/z) (M + H) = 484.1, Rt = 0.84 min. |
| 42 | 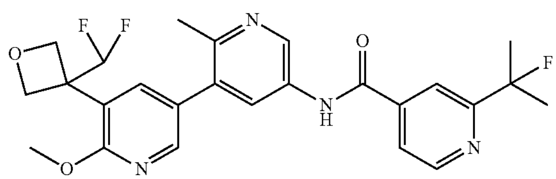 [SMILES: COc1ncc(-c2cc(NC(=O)c3ccnc(C(C)(C)F)c3)cnc2C)cc1C1(C(F)F)COC1] | N-(5'-(3-(difluoromethyl)oxetan-3-yl)-6'-methoxy-2-methyl-[3,3'-bipyridin]-5-yl)-2-(2-fluoropropan-2-yl)isonicotinamide | $^1$H NMR (400 MHz, <dmso>) δ ppm 2.05 (t, J = 20.0 Hz, 3H) 2.43 (s, 3H) 3.92 (s, 3H) 4.82 (d, J = 5.0 Hz, 2H) 4.93 (d, J = 5.0 Hz, 2H) 6.46 (t, J = 55.0 Hz, 1H) 7.70 (d, J = 2.0 Hz, 1H) 7.84-7.85 (m, 1H) 8.04-8.05 (m, 2H) 8.26 (d, J = 2.0 Hz, 1H) 8.78 (d, J = 5.0 Hz, 1H) 8.88 (d, J = 2.0, 1H) 10.80 (s, 1H). LCMS (m/z) (M + H) = 487.0, Rt = 0.70 min. |
| 43 | 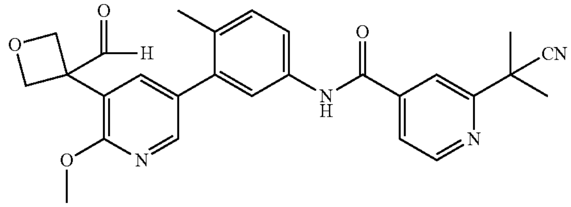 [SMILES: COc1ncc(-c2cc(NC(=O)c3ccnc(C(C)(C)C#N)c3)ccc2C)cc1C1(C=O)COC1] | 2-(2-cyanopropan-2-yl)-N-(3-(5-(3-formyloxetan-3-yl)-6-methoxypyridin-3-yl)-4-methylphenyl)isonicotinamide | $^1$H NMR (400 MHz, CDCl3) δ ppm 9.96 (s, 1H) 8.80 (d, J = 8.0 Hz, 1H) 8.16 (m, 1H) 7.97 (s, 1H) 7.86 (s, 1H) 7.68 (dd, J = 4.0, 2.0, 1H) 7.58 (dd, J = 8.0, 4.0, 1H) 7.53-7.54 (m, 1H) 7.33-7.35 (m, 2H) 5.11 (d, J = 8.0 Hz, 1H) 5.03 (d, J = 8.0 Hz, 1H) 3.97 (s, 3H) 2.30 (s, 3H) 1.82 (s, 6H). LCMS (m/z) (M + H) = 471.0, Rt = 0.87 min. |

TABLE 2-continued

| Example | Structure | Name | Physical Data |
|---|---|---|---|
| 44 | 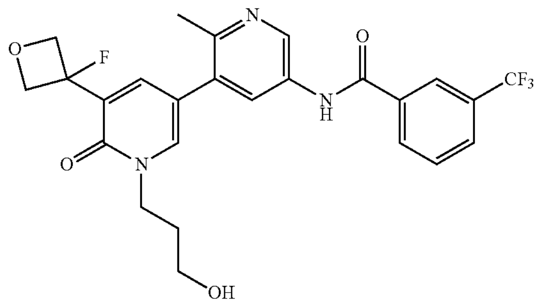 [SMILES: Cc1ncc(NC(=O)c2cccc(C(F)(F)F)c2)cc1-c1cc(C2(F)COC2)c(=O)n(CCCO)c1] | N-(5'-(3-fluorooxetan-3-yl)-1'-(3-hydroxypropyl)-2-methyl-6'-oxo-1',6'-dihydro-[3,3'-bipyridin]-5-yl)-3-(trifluoromethyl)benzamide | $^1$H NMR (400 MHz, <dmso>) δ ppm 1.85 (quin, J = 6.55 Hz, 2H) 2.48 (s, 3H) 3.41-3.49 (m, 2H) 4.05 (t, J = 7.04 Hz, 2H) 4.58-4.63 (m, 1H) 4.78-4.89 (m, 2H) 5.03-5.14 (m, 2H) 7.78-7.80 (m, 1H) 7.81-7.85 (m, 1H) 7.96 (s, 1H) 7.98-8.02 (m, 1H) 8.03-8.05 (m, 1H) 8.29 (d, J = 7.82 Hz, 1H) 8.33 (s, 1H) 8.84 (d, J = 2.35 Hz, 1H) 10.67 (s, 1H). LCMS (m/z) (M + H) = 506.0, Rt = 0.62 min. |
| 45 | 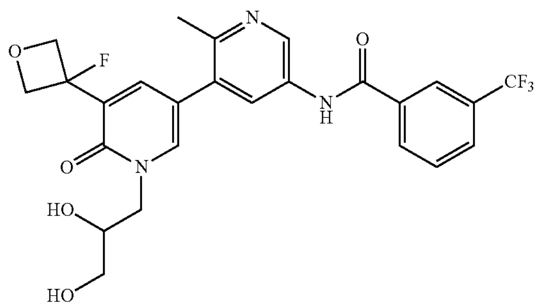 [SMILES: Cc1ncc(NC(=O)c2cccc(C(F)(F)F)c2)cc1-c1cc(C2(F)COC2)c(=O)n(CC(O)CO)c1] | N-(1'-(2,3-dihydroxypropyl)-5'-(3-fluorooxetan-3-yl)-2-methyl-6'-oxo-1',6'-dihydro-[3,3'-bipyridin]-5-yl)-3-(trifluoromethyl)benzamide | $^1$H NMR (400 MHz, <dmso>) δ ppm 2.48 (s, 4H) 3.34-3.44 (m, 4 H) 3.62-3.72 (m, 1H) 3.76-3.86 (m, 1H) 4.36 (dd, J = 12.91, 3.13 Hz, 4H) 4.75 (t, J = 5.67 Hz, 4H) 4.79-4.90 (m, 2H) 5.00-5.15 (m, 3H) 7.78-7.86 (m, 3H) 8.00 (d, J = 7.83 Hz, 1H) 8,05 (d, J = 2.35 Hz, 4H) 8.29 (d, J = 7.82 Hz, 1H) 8.33 (s, 1H) 8.83 (d, J = 2.35 Hz, 1 H) 10.68 (s, 1H). LCMS (m/z) (M + H) = 522.1, Rt = 0.59 min. |
| 46 | 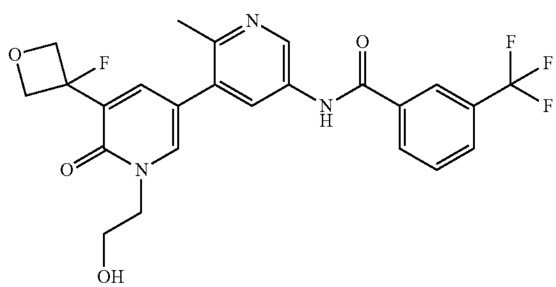 [SMILES: Cc1ncc(NC(=O)c2cccc(C(F)(F)F)c2)cc1-c1cc(C2(F)COC2)c(=O)n(CCO)c1] | N-(5'-(3-fluorooxetan-3-yl)-1'-(2-hydroxyethyl)-2-methyl-6'-oxo-1',6'-dihydro-[3,3'-bipyridin]-5-yl)-3-(trifluoromethyl)benzamide | LCMS (m/z) (M + H) = 492.0, Rt = 0.62 min. |
| 47 | 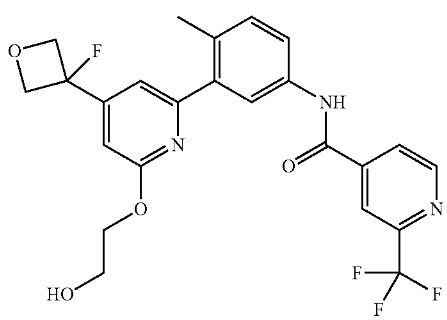 [SMILES: Cc1ccc(NC(=O)c2ccnc(C(F)(F)F)c2)cc1-c1cc(C2(F)COC2)cc(OCCO)n1] | N-(3-(4-(3-fluorooxetan-3-yl)-6-(2-hydroxyethoxy)pyridin-2-yl)-4-methylphenyl)-2-(trifluoromethyl)isonicotinamide | $^1$H NMR (400 MHz, <cd3od> δ ppm 8.93 (d, J = 5.09 Hz, 1H) 8.33 (s, 1H) 8.13-8.18 (m, 1H) 7.87 (d, J = 2.35 Hz, 1H) 7.74 (dd, J = 8.22, 2.35 Hz, 1H) 7.32-7.39 (m, 2H) 7.03 (d, J = 1.17 Hz, 1H) 5.04-5.18 (m, 2H) 4.91 (d, J = 9.00 Hz, 2H) 4.42-4.51 (m, 2H) 3.87-3.96 (m, 2H). LCMS (m/z) (M + H) = 492.2, Rt = 0.86 min. |
| 48 | 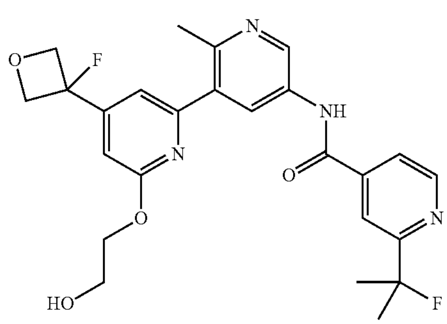 [SMILES: Cc1ncc(NC(=O)c2ccnc(C(C)(C)F)c2)cc1-c1cc(C2(F)COC2)cc(OCCO)n1] | N-(4-(3-fluorooxetan-3-yl)-6-(2-hydroxyethoxy)-2'-methyl-[2,3'-bipyridin]-5-yl)-2-(2-fluoropropan-2-yl)isonicotinamide | $^1$H NMR (400 MHz, <cd3od> δ ppm 8.91 (d, J = 2.35 Hz, 1H) 8.74 (dt, J = 5.09, 0.98 Hz, 1H) 8.38 (d, J = 2.35 Hz, 1H) 8.11-8.15 (m, 1 H) 7.83 (dd, J = 5.09, 1.57 Hz, 1H) 7.43 (d, J = 1.17 Hz, 1H) 7.09 (d, J = 1.56 Hz, 1H) 5.06-5.17 (m, 2 H) 4.90-4.99 (m, 2H) 4.47-4.52 (m, 2H) 3.90-3.96 (m, 2H) 2.65 (s, 3H) 1.70-1.82 (m, 6H). LCMS (m/z) (M + H) = 485.2, Rt = 0.63 min. |

TABLE 2-continued

| Example | Structure | Name | Physical Data |
|---|---|---|---|
| 49 | 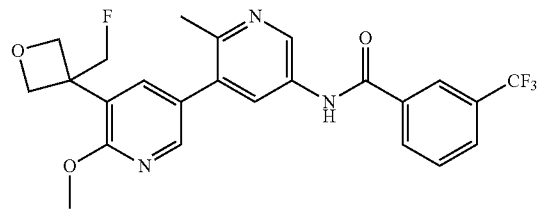 [SMILES: COc1ncc(-c2cc(NC(=O)c3cccc(C(F)(F)F)c3)cnc2C)cc1C1(CF)COC1] | N-(5'-(3-(fluoromethyl)oxetan-3-yl)-6'-methoxy-2-methyl-[3,3'-bipyridin]-5-yl)-3-(trifluoromethyl)benzamide | $^1$H NMR (400 MHz, <dmso>) δ ppm 2.44 (s, 3H) 3.92 (s, 3H) 4.67 (d, J = 6.70 Hz, 2H) 4.79 (d, J = 48.0, 2H) 4.88-4.90 (m, 2H) 7.60 (d, J = 4.0, 1H) 7.81 (t, J = 8.0 Hz, 1H) 8.00 (d, J = 8.0 Hz, 1H) 8.04 (d, J = 2.0 Hz, 1H) 8.20 (d, J = 2.0 Hz, 1H) 8.29 (d, J = 8.0 Hz, 1H) 8.33 (s, 1H) 8.87 (d, J = 2.0 Hz, 1H) 10.68 (s, 1H). LCMS (m/z) (M + H) = 476.2, Rt = 0.77 min. |
| 50 | 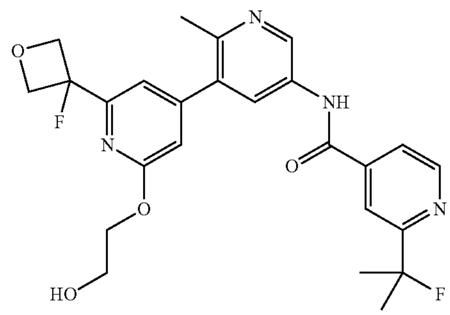 [SMILES: Cc1ncc(NC(=O)c2ccnc(C(C)(C)F)c2)cc1-c1cc(OCCO)nc(C2(F)COC2)c1] | N-(2'-(3-fluorooxetan-3-yl)-6'-(2-hydroxyethoxy)-2-methyl-[3,4'-bipyridin]-5-yl)-2-(2-fluoropropan-2-yl)isonicotinamide | $^1$H NMR (400 MHz, <cd3od> δ ppm 8.89 (d, J = 2.74 Hz, 1H) 8.74 (dt, J = 5.09, 0.98 Hz, 1H) 8.17 (d, J = 2.74 Hz, 1H) 8.09-8.13 (m, 1H) 7.82 (dd, J = 5.09, 1.96 Hz, 1H) 7.19 (t, J = 1.37 Hz, 1H) 6.92 (d, J = 1.17 Hz, 1H) 5.16-5.30 (m, 2H) 4.95-5.07 (m, 2H) 4.54-4.63 (m, 2H) 3.97 (dd, J = 5.28, 4.11 Hz, 2H) 2.50 (s, 3H) 1.70-1.82 (m, 6H). LCMS (m/z) (M + H) = 485.2, Rt = 0.66 min. |
| 51 | 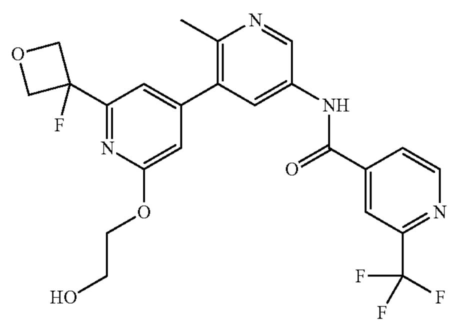 [SMILES: Cc1ncc(NC(=O)c2ccnc(C(F)(F)F)c2)cc1-c1cc(OCCO)nc(C2(F)COC2)c1] | N-(2'-(3-fluorooxetan-3-yl)-6'-(2-hydroxyethoxy)-2-methyl-[3,4'-bipyridin]-5-yl)-2-(trifluoromethyl)isonicotinamide | $^1$H NMR (400 MHz, <cd3od> δ ppm 8.95 (d, J = 5.09 Hz, 1H) 8.90 (d, J = 2.35 Hz, 1H) 8.36 (s, 1H) 8.14-8.21 (m, 2H) 7.18 (t, J = 1.37 Hz, 1H) 6.92 (d, J = 1.17 Hz, 1H) 5.16-5.30 (m, 2H) 4.94-5.07 (m, 2H) 4.55-4.63 (m, 2H) 3.92-4.02 (m, 2H) 2.51 (s, 3H). LCMS (m/z) (M + H) = 493.2, Rt = 0.66 min. |
| 52 | 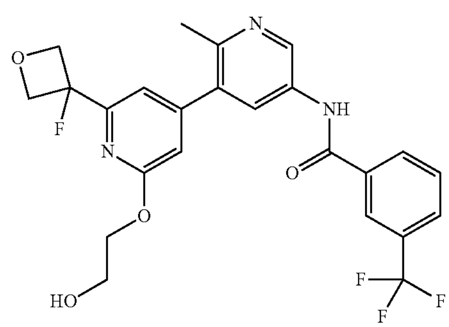 [SMILES: Cc1ncc(NC(=O)c2cccc(C(F)(F)F)c2)cc1-c1cc(OCCO)nc(C2(F)COC2)c1] | N-(2'-(3-fluorooxetan-3-yl)-6'-(2-hydroxyethoxy)-2-methyl-[3,4'-bipyridin]-5-yl)-3-(trifluoromethyl)benzamide | $^1$H NMR (400 MHz, <cd3od> δ ppm 8.89 (d, J = 2.35 Hz, 1H) 8.32 (s, 1H) 8.26 (d, J = 7.82 Hz, 1H) 8.17 (d, J = 2.35 Hz, 1H) 7.94 (d, J = 8.22 Hz, 1H) 7.77 (t, J = 7.83 Hz, 1H) 7.19 (t, J = 1.37 Hz, 1H) 6.92 (d, J = 1.17 Hz, 1H) 5.17-5.31 (m, 2H) 4.94-5.07 (m, 2H) 4.55-4.63 (m, 2H) 3.93-4.03 (m, 2H) 2.50 (s, 3H). LCMS (m/z) (M + H) = 492.2, Rt = 0.74 min. |
| 53 | 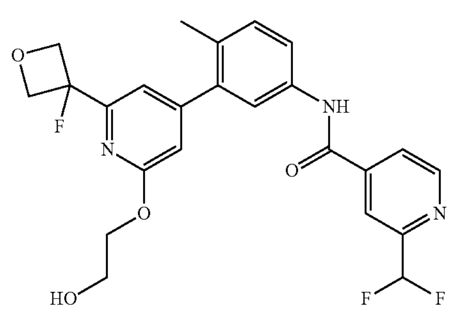 [SMILES: Cc1ccc(NC(=O)c2ccnc(C(F)F)c2)cc1-c1cc(OCCO)nc(C2(F)COC2)c1] | 2-(difluoromethyl-N-(3-(2-(3-fluorooxetan-3-yl)-6-(2-hydroxyethoxy)pyridin-4-yl)-4-methylphenyl)isonicotinamide | $^1$H NMR (400 MHz, <cd3od> δ ppm 8.85 (d, J = 5.09 Hz, 1H) 8.20 (s, 1H) 8.03 (dd, J = 5.09, 0.78 Hz, 1H) 7.71 (dd, J = 8.22, 2.35 Hz, 1H) 7.67 (d, J = 2.35 Hz, 1H) 7.36 (d, J = 8.22 Hz, 1H) 7.13 (t, J = 1.37 Hz, 1H) 6.68-7.02 (m, 2H) 5.16-5.30 (m, 2H) 4.94-5.05 (m, 2H) 4.53-4.63 (m, 2H) 3.97 (dd, J = 5.48, 4.30 Hz, 2H) 2.29 (s, 3H). LCMS (m/z) (M + H) = 474.2, Rt = 0.88 min. |

TABLE 2-continued

| Example | Structure | Name | Physical Data |
|---|---|---|---|
| 54 | 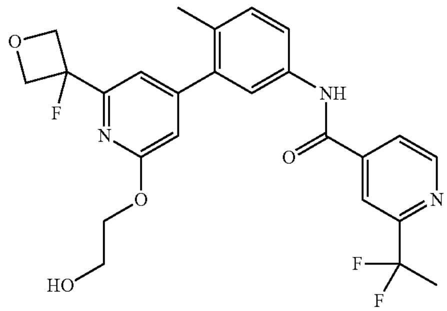 [SMILES: Cc1ccc(NC(=O)c2ccnc(C(C)(F)F)c2)cc1-c1cc(OCCO)nc(C2(F)COC2)c1] | 2-(1,1-difluoroethyl)-N-(3-(2-(3-fluorooxetan-3-yl)-6-(2-hydroxyethoxy)pyridin-4-yl)-4-methylphenyl)isonicotinamide | ¹H NMR (400 MHz, <cd3od>) δ ppm 8.82 (d, J = 5.09 Hz, 1H) 8.20 (s, 1H) 7.98 (d, J = 5.09 Hz, 1H) 7.71 (dd, J = 8.41, 2.15 Hz, 1H) 7.67 (d, J = 2.35 Hz, 1H) 7.36 (d, J = 8.22 Hz, 3H) 7.33 (t, J = 1.37 Hz, 1H) 6.84 (d, J = 1.17 Hz, 3H) 5.15-5.31 (m, 2H) 4.93-5.08 (m, 2H) 4.57 (dd, J = 5.28, 4.11 Hz, 2H) 3.92-4.04 (m, 2H) 2.29 (s, 3H) 2.06 (t, J = 18.78 Hz, 3H). LCMS (m/z) (M+H) = 488.2, Rt = 0.93 min. |
| 55 | 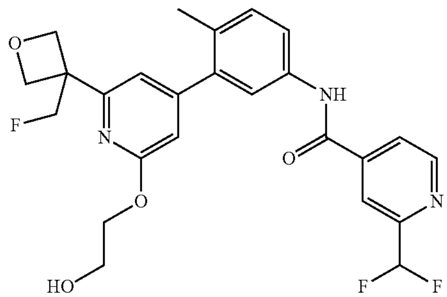 [SMILES: Cc1ccc(NC(=O)c2ccnc(C(F)F)c2)cc1-c1cc(OCCO)nc(C2(CF)COC2)c1] | 2-(difluoromethyl)-N-(3-(2-(3-(fluoromethyl)oxetan-3-yl)-6-(2-hydroxyethoxy)pyridin-4-yl)-4-methylphenyl)isonicotinamide | ¹H NMR (400 MHz, <cd3od>) δ ppm 8.85 (d, J = 5.48 Hz, 1H) 8.20 (s, 1H) 8.03 (d, J = 5.09 Hz, 1 H) 7.71 (dd, J = 8.41, 2.54 Hz, 1H) 7.66 (d, J = 2.35 Hz, 1H) 7.36 (d, J = 8.22 Hz, 1H) 6.68-7.00 (m, 3 H) 5.10 (dd, J = 6.26, 3.13 Hz, 2H) 4.96 (s, 1H) 4.85 (s, 2 H) 4.59 (s, 2 H) 4.42-4.51 (m, 2H) 3.88-3.99 (m, 2H) 2.30 (s, 3H). LCMS (m/z) (M+H) = 488.2, Rt = 0.76 min. |
| 56 | 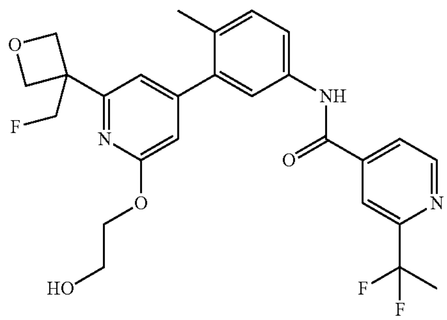 [SMILES: Cc1ccc(NC(=O)c2ccnc(C(C)(F)F)c2)cc1-c1cc(OCCO)nc(C2(CF)COC2)c1] | 2-(1,1-difluoroethyl)-N-(3-(2-(3-(fluoromethyl)oxetan-3-yl)-6-(2-hydroxyethoxy)pyridin-4-yl)-4-methylphenyl)isonicotinamide | ¹H NMR (400 MHz, <cd3od>) δ ppm 8.83 (dd, J = 5.09, 0.78 Hz, 1 H) 8.20 (d, J = 0.78 Hz, 1H) 7.97-8.01 (m, 1H) 7.71 (dd, J = 8.22, 2.35 Hz, 1H) 7.66 (d, J = 2.35 Hz, 1 H) 7.36 (d, J = 8.22 Hz, 1H) 6.96 (d, J = 0.78 Hz, 1H) 6.76 (d, J = 1.17 Hz, 1H) 5.10 (dd, J = 6.26, 3.13 Hz, 2H) 4.96 (s, 1H) 4.85 (s, 1H) 4.43-4.50 (m, 2H) 3.93 (dd, J = 5.48, 4.30 Hz, 2H) 2.30 (s, 3H) 1.99-2.14 (m, 3H). LCMS (m/z) (M + H) = 502.2, Rt = 0.81 min. |
| 57 | 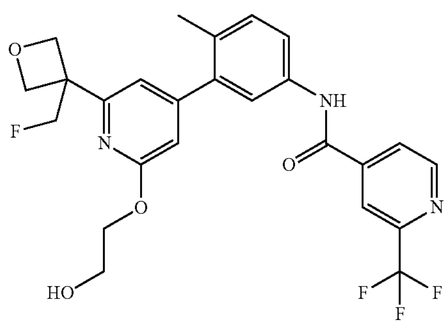 [SMILES: Cc1ccc(NC(=O)c2ccnc(C(F)(F)F)c2)cc1-c1cc(OCCO)nc(C2(CF)COC2)c1] | N-(3-(2-(3-(fluoromethyl)oxetan-3-yl)-6-(2-hydroxyethoxy)pyridin-4-yl)-4-methylphenyl)-2-(trifluoromethyl)isonicotinamide | ¹H NMR (400 MHz, <cd3od>) δ ppm 8.93 (d, J = 5.09 Hz, 1H) 8.32 (s, 1H) 8.14 (dd, J = 4.89, 1.37 Hz, 1H) 7.71 (dd, J = 8.41, 2.15 Hz, 1 H) 7.66 (d, J = 2.35 Hz, 1H) 7.36 (d, J = 8.22 Hz, 1H) 6.96 (d, J = 1.17 Hz, 1H) 6.76 (d, J = 1.17 Hz, 1H) 5.10 (dd, J = 6.26, 3.13 Hz, 2H) 4.96 (s, 1H) 4.85 (d, J = 5.09 Hz, 2 H) 4.43-4.51 (m, 2H) 3.93 (dd, J = 5.48, 4.30 Hz, 2H) 2.30 (s, 3H). LCMS (m/z) (M + H) = 506.2, Rt = 0.79 min. |
| 58 | 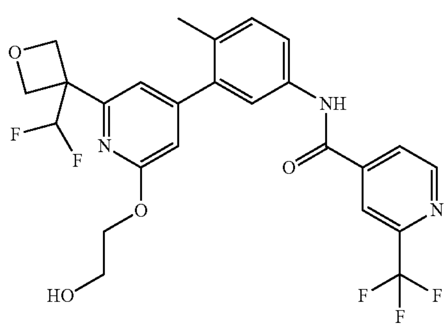 [SMILES: Cc1ccc(NC(=O)c2ccnc(C(F)(F)F)c2)cc1-c1cc(OCCO)nc(C2(C(F)F)COC2)c1] | N-(3-(2-(3-(difluoromethyl)oxetan-3-yl)-6-(2-hydroxyethoxy)pyridin-4-yl)-4-methylphenyl)-2-(trifluoromethyl)isonicotinamide | ¹H NMR (400 MHz, <cd3od>) δ ppm 8.93 (d, J = 5.09 Hz, 1H) 8.32 (s, 1H) 8.15 (dd, J = 4.89, 1.37 Hz, 1H) 7.73 (dd, J = 8.22, 2.35 Hz, 1H) 7.67 (d, J = 2.35 Hz, 1H) 7.37 (d, J = 8.22 Hz, 1H) 7.00 (d, J = 0.78 Hz, 1H) 6.81 (d, J = 1.17 Hz, 1H) 6.22-6.60 (m, 1H) 5.05-5.12 (m, 2H) 5.00-5.05 (m, 2H) 4.43-4.51 (m, 2H) 3.92 (dd, J = 5.48, 4.30 Hz, 2H) 2.30 (s, 3H). LCMS (m/z) (M + H) = 524.2, Rt = 0.86 min. |

TABLE 2-continued

| Example | Structure | Name | Physical Data |
|---|---|---|---|
| 59 | 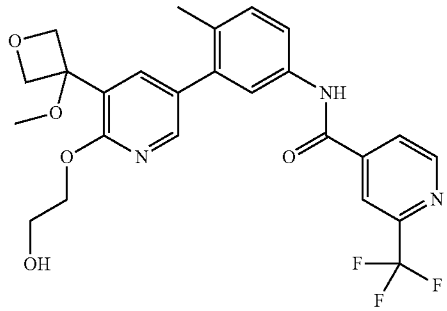 | N-(3-(6-(2-hydroxyethoxy)-5-(3-methoxyoxetan-3-yl)pyridin-3-yl)-4-methylphenyl)-2-(trifluoromethyl)isonicotinamide | ¹H NMR (400 MHz, <cd3od>) δ ppm 8.93 (d, J = 5.09 Hz, 1H) 8.32 (s, 1H) 8.17 (d, J = 2.35 Hz, 1H) 8.12-8.16 (m, 1H) 7.64-7.73 (m, 3H) 7.36 (d, J = 8.22 Hz, 1H) 5.12 (d, J = 8.61 Hz, 2H) 4.90 (d, J = 8.22 Hz, 2H) 4.46-4.52 (m, 2H) 3.87-3.94 (m, 2H) 3.19 (s, 3H) 2.30 s, 3H). LCMS (m/z) (M + H) = 504.2, Rt = 0.87 min. |
| 60 | 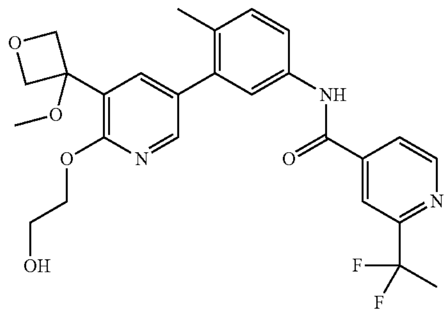 | 2-(1,1-difluoroethyl)-N-(3-(6-(2-hydroxyethoxy)-5-(3-methoxyoxetan-3-yl)pyridin-3-yl)-4-methylphenyl)isonicotinamide | ¹H NMR (400 MHz, <cd3od>) δ ppm 8.82 (dd, J = 5.09, 0.78 Hz, 1 H) 8.20 (s, 1H) 8.17 (d, J = 2.35 Hz, 1H) 7.98 (dd, J = 5.09, 1.57 Hz, 1 H) 7.64-7.71 (m, 3H) 7.36 (d, J = 8.22 Hz, 1H) 5.12 (d, J = 8.22 Hz, 2H) 4.90 (d, J = 8.22 Hz, 2H) 4.45-4.52 (m, 2H) 3.87-3.94 (m, 2H) 3.19 (s, 3H) 2.30 (s, 3H) 2.05 (t, J = 18.78 Hz, 3H). LCMS (m/z) (M + H) = 500.2, Rt = 0.85 min. |
| 61 | 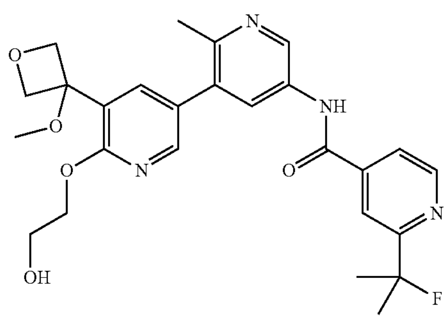 [SMILES: COC1(c2cc(-c3cc(NC(=O)c4ccnc(C(C)(C)F)c4)cnc3C)cnc2OCCO)COC1] | 2-(2-fluoropropan-2-yl)-N-(6'-(2-hydroxyethoxy)-5'-(3-methoxyoxetan-3-yl)-2-methyl-[3,3'-bipyridin]-5-yl)isonicotinamide | ¹H NMR (400 MHz, <cd3od>) δ ppm 8.87 (d, J = 2.35 Hz, 1H) 8.74 (dt, J = 5.09, 0.98 Hz, 1H) 8.23 (d, J = 2.35 Hz, 1H) 8.17 (d, J = 2.74 Hz, 1H) 8.12 (s, 1H) 7.82 (dd, J = 5.09, 1.57 Hz, 1H) 7.77 (d, J = 2.74 Hz, 1H) 5.13 (d, J = 8.61 Hz, 2H) 4.91 (d, J = 8.22 Hz, 2H) 4.47-4.55 (m, 2H) 3.88-3.94 (m, 2H) 3.20 (s, 3H) 2.52 (s, 3H) 1.68-1.82 (m, 6H). LCMS (m/z) (M + H) = 497.2, Rt = 0.58 min. |
| 62 | 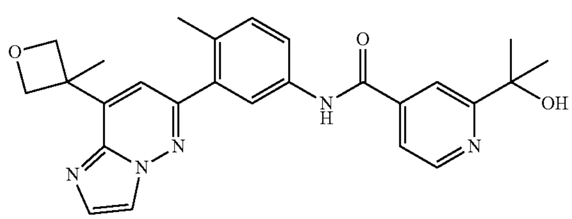 [SMILES: Cc1ccc(NC(=O)c2ccnc(C(C)(C)O)c2)cc1-c1cc(C2(C)COC2)c2nccn2n1] | 2-(2-hydroxypropan-2-yl)-N-(4-methyl-3-(8-(3-methyloxetan-3-yl)imidazo[1,2-b]pyridazin-6-yl)phenyl)isonicotinamide | ¹H NMR (400 MHz, <dmso>) δ ppm 1.45 (s, 6H) 1.83 (s, 3H) 2.32 (s, 3H) 4.61 (d, J = 6.26 Hz, 2 H) 5.07 (d, J = 6.26 Hz, 2H) 7.19 (s, 1H) 7.31-7.40 (m, 1H) 7.66-7.73 (m, 1H) 7.77 (d, J = 0.78 Hz, 1 H) 7.79-7.85 (m, 1H) 7.87 (d, J = 1.96 Hz, 1H) 8.13 (s, 1H) 8.30 (d, J = 0.78 Hz, 1H) 8.65 (d, J = 5.09 Hz, 1H) 10.49-10.69 (m, 1H). LCMS (m/z) (M + H) = 458.1, Rt = 0.55 min. |
| 63 | 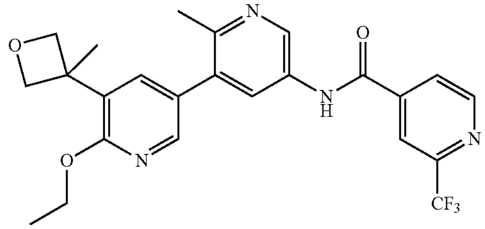 | N-(6'-ethoxy-2-methyl-5'-(3-methyloxetan-3-yl)-[3,3'-bipyridin]-5-yl)-2-(trifluoromethyl)isonicotinamide | ¹H NMR (400 MHz, <cd3od>) δ ppm 1.40 (t, J = 7.04 Hz, 3H) 1.76 (s, 3H) 2.65 (s, 3H) 4.46 (q, J = 7.04 Hz, 2H) 4.59 (d, J = 6.26 Hz, 2H) 5.03 (d, J = 5.87 Hz, 2H) 7.52 (d, J = 2.35 Hz, 1H) 8.14 (d, J = 2.35 Hz, 1H) 8.18 (d, J = 3.91 Hz, 1H) 8.34-8.42 (m, 2H) 8.97 (d, J = 4.70 Hz, 1H) 9.23 (d, J = 2.35 Hz, 1H). LCMS (m/z) (M + H) = 473.3, Rt = 0.75 min. |

TABLE 2-continued

| Example | Structure | Name | Physical Data |
|---|---|---|---|
| 64 | 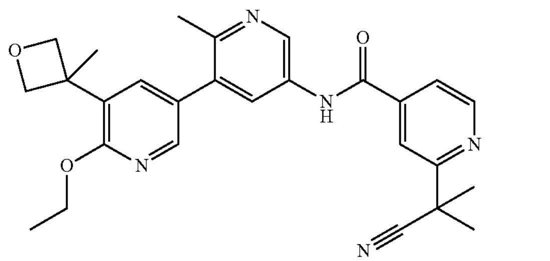 [SMILES: CCOc1ncc(-c2cc(NC(=O)c3ccnc(C(C)(C)C#N)c3)cnc2C)cc1C1(C)COC1] | 2-(2-cyanopropan-2-yl)-N-(6'-ethoxy-2-methyl-5'-(3-methyloxetan-3-yl)-[3,3'-bipyridin]-5-yl)isonicotinamide | ¹H NMR (400 MHz, <cd3od>) δ ppm 1.40 (t, J = 7.04 Hz, 3H) 1.76 (s, 3H) 1.82 (s, 6H) 2.66 (s, 3H) 4.46 (q, J = 7.30 Hz, 2H) 4.59 (d, J = 5.87 Hz, 2H) 5.03 (d, J = 5.87 Hz, 2H) 7.53 (d, J = 2.35 Hz, 1H) 7.87 (dd, J = 5.09, 1.57 Hz, 1H) 8.11-8.16 (m, 2H) 8.39 (d, J = 2.35 Hz, 1H) 8.82 (d, J = 5.09 Hz, 1H) 9.25 (d, J = 2.35 Hz, 1H). LCMS (m/z) (M + H) = 472.3, Rt = 0.72 min. |
| 65 | 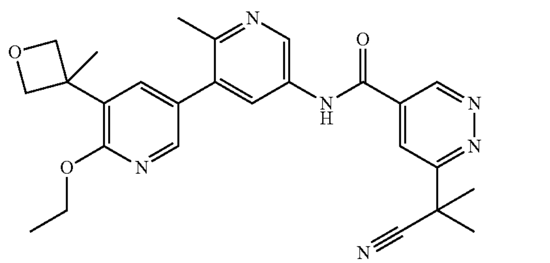 [SMILES: CCOc1ncc(-c2cc(NC(=O)c3cnnc(C(C)(C)C#N)c3)cnc2C)cc1C1(C)COC1] | 6-(2-cyanopropan-2-yl)-N-(6'-ethoxy-2-methyl-5'-(3-methyloxetan-3-yl)-[3,3'-bipyridin]-5-yl)pyridazine-4-carboxamide | ¹H NMR (400 MHz, <cd3od>) δ ppm 1.40 (t, J = 7.04 Hz, 3H) 1.76 (s, 3H) 1.93 (s, 6H) 2.66 (s, 3H) 4.46 (q, J = 7.04 Hz, 2H) 4.60 (d, J = 5.87 Hz, 2H) 5.03 (d, J = 6.26 Hz, 2H) 7.53 (d, J = 2.35 Hz, 1H) 8.14 (d, J = 1.96 Hz, 1H) 8.37 (d, J = 2.35 Hz, 1H) 8.41 (d, J = 1.96 Hz, 1H) 9.23 (d, J = 2.35 Hz, 1H) 9.67 (d, J = 1.57 Hz, 1H). LCMS (m/z) (M + H) = 473.2, Rt = 0.68 min. |
| 66 | 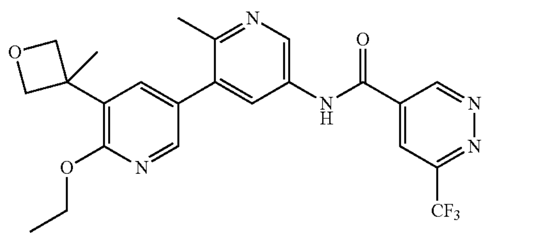 [SMILES: CCOc1ncc(-c2cc(NC(=O)c3cnnc(C(F)(F)F)c3)cnc2C)cc1C1(C)COC1] | N-(6'-ethoxy-2-methyl-5'-(3-methyloxetan-3-yl)-[3,3'-bipyridin]-5-yl)-6-(trifluoromethyl)pyridazine-4-carboxamide | ¹H NMR (400 MHz, <cd3od>) δ ppm 1.40 (t, J = 7.04 Hz, 3H) 1.76 (s, 3H) 2.65 (s, 3H) 4.46 (q, J = 7.04 Hz, 2H) 4.59 (d, J = 6.26 Hz, 2H) 5.03 (d, J = 6.26 Hz, 2H) 7.52 (d, J = 2.35 Hz, 1H) 8.13 (d, J = 2.35 Hz, 1H) 8.35 (d, J = 2.35 Hz, 1H) 8.63 (d, J = 1.96 Hz, 1H) 9.19 (d, J = 2.35 Hz, 1H) 9.92 (d, J = 1.96 Hz, 1H). LCMS (m/z) (M + H) = 474.1, Rt = 0.71 min. |
| 67 | 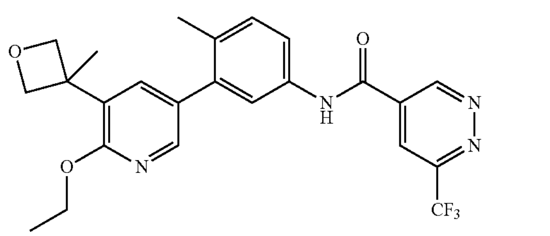 [SMILES: CCOc1ncc(-c2cc(NC(=O)c3cnnc(C(F)(F)F)c3)ccc2C)cc1C1(C)COC1] | N-(3-(6-ethoxy-5-(3-methyloxetan-3-yl)pyridin-3-yl)-4-methylphenyl)-6-(trifluoromethyl)pyridazine-4-carboxamide | ¹H NMR (400 MHz, <cd3od>) δ ppm 1.39 (t, J = 7.04 Hz, 3H) 1.75 (s, 3H) 2.28 (s, 3H) 4.41 (d, J = 7.04 Hz, 2H) 4.58 (d, J = 6.26 Hz, 2H) 5.02 (d, J = 5.87 Hz, 2H) 7.34 (d, J = 8.22 Hz, 1H) 7.38 (d, J = 2.35 Hz, 1H) 7.63 (d, J = 2.35 Hz, 1H) 7.68 (dd, J = 8.41, 2.15 Hz, 1H) 7.99 (d, J = 2.35 Hz, 1H) 8.58 (d, J = 1.96 Hz, 1H) 9.87 (d, J = 1.57 Hz, 1H). LCMS (m/z) (M + H) = 473.1, Rt = 1.01 min. |
| 68 | 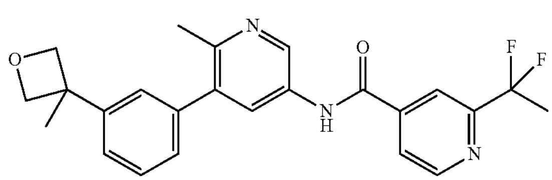 | 2-(1,1-difluoroethyl)-N-(6-methyl-5-(3-(3-methyloxetan-3-yl)phenyl)pyridin-3-yl)isonicotinamide | 1H NMR (400 MHz, <dmso>) δ ppm 1.65 (s, 3H) 2.03 (t, J = 19.17 Hz, 3H) 2.43 (s, 3H) 4.55 (d, J = 5.48 Hz, 2H) 4.79-4.88 (m, 2H) 7.23-7.36 (m, 3H) 7.48 (s, 1H) 7.99-8.09 (m, 2H) 8.16-8.23 (m, 1H) 8.82-8.93 (m, 1H) 10.84 (s, 1H). LCMS (m/z) (M + H) = 424.1, Rt = 0.68 min. |
| 69 | 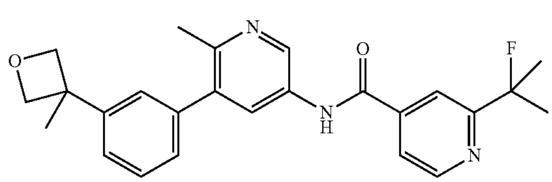 [SMILES: Cc1ncc(NC(=O)c2ccnc(C(C)(C)F)c2)cc1-c1cccc(C2(C)COC2)c1] | 2-(2-fluoropropan-2-yl)-N-(6-methyl-5-(3-(3-methyloxetan-3-yl)phenyl)pyridin-3-yl)isonicotinamide | 1H NMR (400 MHz, <dmso>) δ ppm 1.66 (d, J = 3.13 Hz, 6H) 1.72 (s, 3H) 4.56 (d, J = 5.87 Hz, 2H) 4.83 (s, 2H) 7.24-7.37 (m, 3H) 7.44-7.55 (m, 1H) 7.83 (dd, J = 4.89, 1.37 Hz, 1H) 8.04 (s, 1H) 8.15 (s, 1H) 8.77 (d, J = 5.09 Hz, 1H) 8.92-8.98 (m, 1H) 10.75-11.02 (m, 1H). LCMS (m/z) (M + H) = 420.2, Rt = 0.69 min. |

TABLE 2-continued

| Example | Structure | Name | Physical Data |
|---|---|---|---|
| 70 | 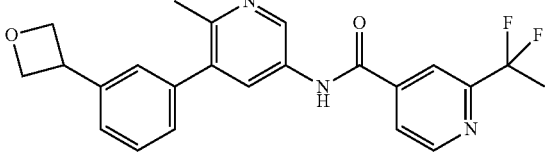 | 2-(1,1-difluoroethyl)-N-(6-methyl-5-(3-(oxetan-3-yl)phenyl)pyridin-3-yl)isonicotinamide | 1H NMR (400 MHz, <dmso>) δ ppm 2.04 (s, 3H) 2.46 (br. s., 6 H) 4.32 (s, 1H) 4.66 (t, J = 6.26 Hz, 2H) 4.90-5.03 (m, 2H) 7.31-7.39 (m, 1H) 7.44 (s, 1H) 7.47-7.55 (m, 2H) 8.01-8.07 (m, 1H) 8.12-8.24 (m, 2H) 8.83-8.98 (m, 2H) 10.78-11.04 (m, 1H). LCMS (m/z) (M + H) = 410.1, Rt = 0.64 min. |
| 71 | 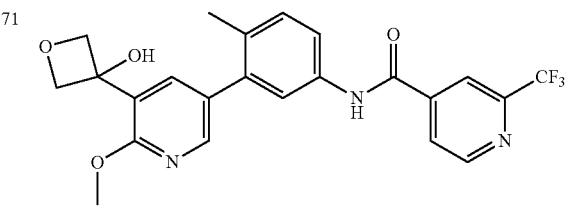 | N-(3-(5-(3-hydroxyoxetan-3-yl)-6-methoxypyridin-3-yl)-4-methylphenyl)-2-(trifluoromethyl)isonicotinamide | $^1$H NMR (400 MHz, <dmso>) δ ppm 2.25 (s, 3H) 3.94 (s, 3H), 4.62-4.66 (m, 2H) 5.00-5.04 (m, 2H) 7.34 (d, J = 9.19 Hz, 1H) 7.60-7.69 (m, 2H) 7.72 (dd, J = 8.14, 2.32 Hz, 1H) 8.13 (d, J = 2.35 Hz, 1 H) 8.18-8.21 (m, 1H) 8.35-8.38 (m, 1H) 8.99 (dt, J = 4.99, 0.71 Hz, 1H) 10.68 (s, 1H). LCMS (m/z) (M + H) = 460.1, Rt = 0.83 min. |
| 72 | 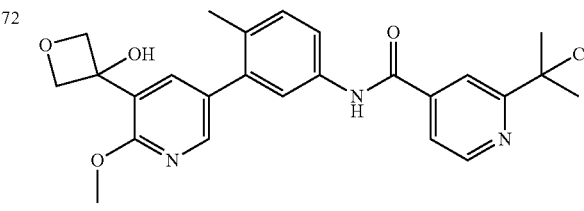 | 2-(2-cyanopropan-2-yl)-N-(3-(5-(3-hydroxyoxetan-3-yl)-6-methoxypyridin-3-yl)-4-methylphenyl)isonicotinamide | $^1$H NMR (400 MHz, <dmso>) δ ppm 1.76 (s, 6H) 2.24 (s, 3H) 3.94 (s, 3H) 4.62-4.66 (m, 2H) 5.00-5.04 (m, 2H) 7.34 (d, J = 9.19 Hz, 1H) 7.65 (d, J = 2.25 Hz, 1H) 7.67 (d, J = 2.40 Hz, 1H) 7.69 (dd, J = 9.29, 2.40 Hz, 1H) 7.86 (dd, J = 5.06, 1.59 Hz, 1H) 7.99-8.02 (m, 1H) 8.13 (d, J = 2.40 Hz, 1H) 8.81 (dd, J = 5.04, 0.88 Hz, 1H) 10.55 (s, 1H). LCMS (m/z) (M + H) = 459.3, Rt = 0.80 min. |
| 73 | 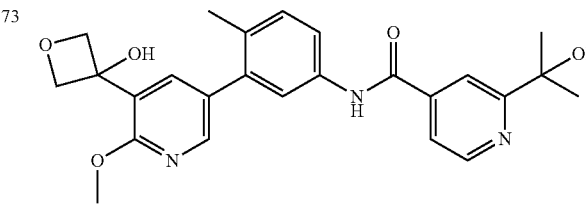 | N-(3-(5-(3-hydroxyoxetan-3-yl)-6-methoxypyridin-3-yl)-4-methylphenyl)-2-(2-hydroxypropan-2-yl)isonicotinamide | $^1$H NMR (400 MHz, <dmso>) δ ppm 1.49 (s, 6H) 2.24 (s, 3H) 3.94 (s, 3H) 4.58-4.69 (m, 2H) 4.99-5.09 (m, 2H) 7.32 (d, J = 9.29 Hz, 1H) 7.64-7.76 (m, 4H) 8.13 (d, J = 2.40 Hz, 1H) 8.14-8.17 (m, 1H) 8.69 (dd, J = 5.09, 0.83 Hz, 1 H) 10.53 (d, 1H). LCMS (m/z) (M + H) = 450.3, Rt = 0.62 min. |
| 74 | 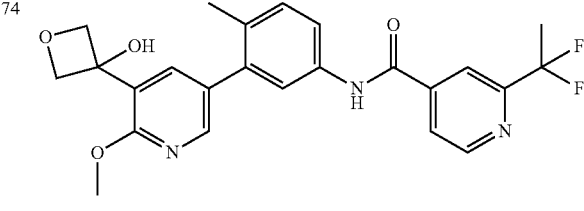 | 2-(1,1-difluoroethyl)-N-(3-(5-(3-hydroxyoxetan-3-yl)-6-methoxypyridin-3-yl)-4-methylphenyl)isonicotinamide | $^1$H NMR (400 MHz, <dmso>) δ ppm 2.05 (t, J = 20.0 Hz, 3H), 2.24 (s, 3H) 3.94 (s, 3H) 4.62-4.66 (m, 2H) 5.00-5.04 (m, 2H) 7.33 (d, J = 8.80 Hz, 1H) 7.66-7.74 (m, 3H) 8.01-8.05 (m, 1H) 8.13 (d, J = 2.40 Hz, 1H) 8.17-8.20 (m, 1H) 8.86-8.89 (m, 1H) 10.64 (s, 1H). LCMS (m/z) (M + H) = 456.3, Rt = 0.83 min. |
| 75 | 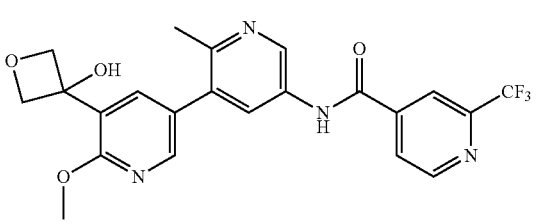 [SMILES: COc1ncc(-c2cc(NC(=O)c3ccnc(C(F)(F)F)c3)cnc2C)cc1C1(O)COC1] | N-(5'-(3-hydroxyoxetan-3-yl)-6'-methoxy-2-methyl-[3,3'-bipyridin]-5-yl)-2-(trifluoromethyl)isonicotinamide | $^1$H NMR (400 MHz, <dmso>) δ ppm 2.49 (s, 3H) 3.96 (s, 3H) 4.63-4.67 (m, 2H) 5.01-5.04 (m, 2H) 7.78 (d, J = 2.40 Hz, 1H) 8.13 (d, J = 2.59 Hz, 1H) 8.22 (d, J = 2.40 Hz, 2H) 8.39-8.41 (m, 1H) 8.90 (d, J = 2.45 Hz, 1H) 9.03 (d, J = 4.99 Hz, 1H) 10.98 (s, 1H). LCMS (m/z) (M + H) = 461.2, Rt = 0.59 min. |

TABLE 2-continued

| Example | Name | Physical Data |
|---|---|---|
| 76 | 2-(2-fluoropropan-2-yl)-N-(5'-(3-hydroxyoxetan-3-yl)-6'-methoxy-2-methyl-[3,3'-bipyridin]-5-yl)isonicotinamide | ¹H NMR (400 MHz, <dmso>) δ ppm 1.72 (d, J = 20.0 Hz, 6H) 2.51 (s, 3H) 3.96 (s, 3H) 4.63-4.67 (m, 2H) 5.01-5.04 (m, 2H) 7.79 (d, J = 2.40 Hz, 1H) 7.84-7.86 (m, 1H) 8.06-8.08 (m, 1H) 8.18-8.19 (m, 1H) 8.24 (d, J = 2.40 Hz, 1H) 8.80 (d, J = 5.04 Hz, 1H) 8.95 (d, J = 2.45 Hz, 1H) 10.92 (s, 1H). LCMS (m/z) (M + H) = 461.2, Rt = 0.57 min. |
| 77 | 2-(1,1-difluoroethyl)-N-(5'-(3-hydroxyoxetan-3-yl)-6'-methoxy-2-methyl-[3,3'-bipyridin]-5-yl)isonicotinamide | ¹H NMR (400 MHz, <dmso>) δ 2.06 (t, J = 20.0 Hz, 3H) 2.51 (s, 3 H) 3.96 (s, 3H) 4.63-4.67 (m, 2 H) 5.01-5.05 (m, 2H) 7.79 (d, J = 2.40 Hz, 1H) 8.06 (d, J = 1.66 Hz, 1H) 8.15-8.26 (m, 3H) 8.92 (dd, J = 5.01, 0.81 Hz, 1H) 8.94 (d, J = 2.45 Hz, 1H) 10.98 (s, 1H). LCMS (m/z) (M + H) = 457.1, Rt = 0.57 min. |
| 78 | N-(5'-(3-hydroxyoxetan-3-yl)-6'-methoxy-2-methyl-[3,3'-bipyridin]-5-yl)-4-(trifluoromethyl)picolinamide | ¹H NMR (400 MHz, <dmso>) δ 2.56 (s, 3H) 3.96 (s, 3H) 4.64-4.68 (m, 2H) 5.01-5.05 (m, 2H) 7.80 (d, J = 2.40 Hz, 1H) 8.14 (dd, J = 5.04, 1.08 Hz, 1H) 8.24 (d, J = 2.40 Hz, 1H) 8.36-8.39 (m, 2 H) 9.07 (dt, J = 5.05, 0.75 Hz, 1H) 9.12 (d, J = 2.49 Hz, 1H) 11.27 (s, 1 H). LCMS (m/z) (M + H) = 461.1, Rt = 0.63 min. |
| 79 | N-(5'-(3-fluorooxetan-3-yl)-6'-methoxy-2-methyl-[3,3'-bipyridin]-5-yl)-2-(trifluoromethyl)isonicotinamide | ¹H NMR (400 MHz, <dmso>) δ 2.45-2.56 (s, 3H) 3.98 (s, 3H) 4.87-4.99 (m, 2H) 5.10-5.22 (m, 2H) 8.31-8.42 (m, 2H) 7.97-7.98 (m, 1H) 8.06 (d, J = 4.0 Hz, 1H) 8.21-8.22 (m, 1H) 8.33-8.34 (m, 1H) 8.39-8.40 (m, 1H) 8.87 (d, J = 2.30 Hz, 1H) 9.01-9.03 (m, 1H) 10.92 (s, 1H). LCMS (m/z) (M + H) = 463.1, Rt = 0.69 min. |
| 80 | 2-(2-cyanopropan-2-yl)-N-(5'-(3-fluorooxetan-3-yl)-6'-methoxy-2-methyl-[3,3'-bipyridin]-5-yl)isonicotinamide | ¹H NMR (400 MHz, <dmso>) δ 1.77 (s, 6H) 2.45 (s, 3H) 3.98 (s, 3 H) 4.86-4.99 (m, 2H) 5.10-5.22 (m, 2H) 7.88-7.90 (m, 1H) 7.97-7.98 (m, 1H) 8.03-8.05 (m, 2H) 8.33-8.34 (m, 1H) 8.82-8.93 (m, 2 H) 10.79 (s, 1H). LCMS (m/z) (M + H) = 462.1, Rt = 0.66 min. |
| 81 | N-(5'-(3-fluorooxetan-3-yl)-6'-methoxy-2-methyl-[3,3'-bipyridin]-5-yl)-2-(2-hydroxypropan-2-yl)isonicotinamide | ¹H NMR (400 MHz, <dmso>) δ 1.48 (s, 6H) 2.44 (s, 3H) 3.98 (s, 3 H) 4.88-4.96 (m, 2H) 5.12-5.21 (m, 2H) 5.39 (s, 1H) 7.71-7.73 (m, 1H) 7.97-7.98 (m, 1H) 8.06 (d, J = 4.0 Hz, 1H) 8.16-8.17 (m, 1H) 8.33-8.32 (m, 1H) 8.69-8.71 (m, 1H) 8.88 (d, J = 4.0 Hz, 1H) 10.74 (s, 1H). LCMS (m/z) (M + H) = 453.1, Rt = 0.50 min. |
| 82 | N-(5'-(3-fluorooxetan-3-yl)-6'-methoxy-2-methyl-[3,3'-bipyridin]-5-yl)-2-(2-fluoropropan-2-yl)isonicotinamide | ¹H NMR (400 MHz, <dmso>) δ 1.71 (d, J = 20.0 Hz, 6H) 2.44 (s, 3H) 3.98 (s, 3H) 4.87-4.97 (m, 2 H) 5.11-5.22 (m, 2H) 7.83-7.85 (m, 1H) 7.97-7.98 (m, 1H) 8.04-8.07 (m, 2H) 8.33-8.34 (m, 1H) 8.77-8.79 (m, 1H) 8.88 (d, J = 2.0 Hz, 1H) 10.79 (s, 1H). LCMS (m/z) (M + H) = 455.1, Rt = 0.68 min. |

TABLE 2-continued

| Example | Structure | Name | Physical Data |
|---|---|---|---|
| 83 | 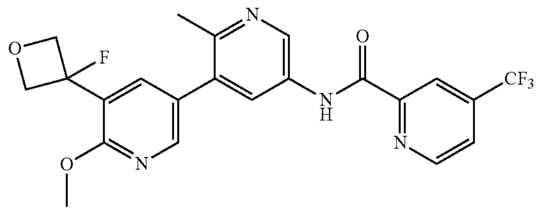 [SMILES: COc1ncc(-c2cc(NC(=O)c3cc(C(F)(F)F)ccn3)cnc2C)cc1C1(F)COC1] | N-(5'-(3-fluorooxetan-3-yl)-6'-methoxy-2-methyl-[3,3'-bipyridin]-5-yl)-4-(trifluoromethyl)picolinamide | $^1$H NMR (400 MHz, <dmso>) δ 2.45 (s, 3H) 3.98 (s, 3H) 4.87-4.99 (m, 2H) 5.12-5.21 (m, 2H) 7.97-7.98 (m, 1H) 8.11-8.13 (m, 1H) 8.20 (m, 1H) 8.33-8.37 (m, 2H) 9.03-9.07 (m, 2H) 11.09 (s, 1H). LCMS (m/z) (M + H) = 463.0, Rt = 0.74 min. |
| 84 | 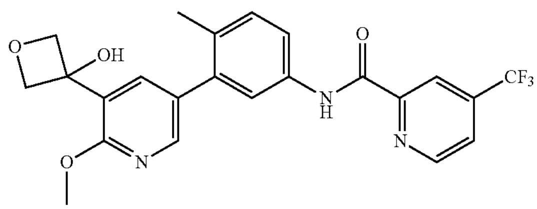 [SMILES: COc1ncc(-c2cc(NC(=O)c3cc(C(F)(F)F)ccn3)ccc2C)cc1C1(O)COC1] | N-(3-(5-(3-hydroxyoxetan-3-yl)-6-methoxypyridin-3-yl)-4-methylphenyl)-4-(trifluoromethyl)picolinamide | $^1$H NMR (400 MHz, <dmso>) δ 2.25 (s, 3H) 3.95 (s, 3H) 4.62-4.67 (m, 2H) 5.01-5.05 (m, 2H) 6.15 (s, 1H) 7.32 (d, J = 8.71 Hz, 1H) 7.68 (d, J = 2.40 Hz, 1H) 7.82-7.88 (m, 2H) 8.08-8.11 (m, 1H) 8.14 (d, J = 2.35 Hz, 1H) 8.34 (dt, J = 1.75, 0.81 Hz, 1H) 9.03 (dt, J = 5.05, 0.75 Hz, 1H) 10.81 (s, 1H). LCMS (m/z) (M + H) = 460.0, Rt = 0.91 min. |
| 85 | 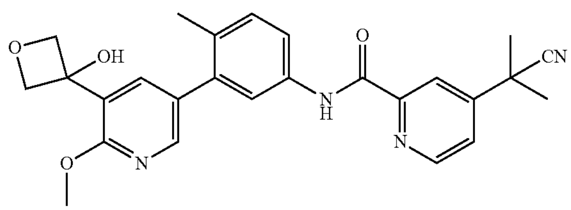 [SMILES: COc1ncc(-c2cc(NC(=O)c3cc(C(C)(C)C#N)ccn3)ccc2C)cc1C1(O)COC1] | 4-(2-cyanopropan-2-yl)-N-(3-(5-(3-hydroxyoxetan-3-yl)-6-methoxypyridin-3-yl)-4-methylphenyl)picolinamide | $^1$H NMR (400 MHz, <dmso>) δ 1.76 (s, 6H) 2.25 (s, 3H) 3.95 (s, 3H) 4.62-4.67 (m, 2H) 5.00-5.05 (m, 2H) 6.15 (s, 1H) 7.31 (d, J = 8.31 Hz, 1H) 7.68 (d, J = 2.40 Hz, 1H) 7.81-7.88 (m, 3H) 8.14 (d, J = 2.40 Hz, 1H) 8.26 (dd, J = 2.05, 0.78 Hz, 1H) 8.79 (dd, J = 5.18, 0.78 Hz, 1H) 10.70 (s, 1H). LCMS (m/z) (M + H) = 459.1, Rt = 0.85 min. |
| 86 | 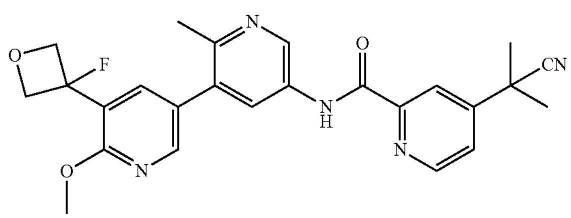 [SMILES: COc1ncc(-c2cc(NC(=O)c3cc(C(C)(C)C#N)ccn3)cnc2C)cc1C1(F)COC1] | 4-(2-cyanopropan-2-yl)-N-(5'-(3-fluorooxetan-3-yl)-6'-methoxy-2-methyl-[3,3'-bipyridin]-5-yl)picolinamide | $^1$H NMR (400 MHz, <dmso>) δ 1.77 (s, 6H) 2.45 (s, 3H) 3.98 (s, 3H) 4.88-4.96 (m, 2H) 5.14-5.24 (m, 2H) 7.86 (dd, J = 5.18, 2.05 Hz, 1H) 7.96-7.98 (m, 1H) 8.20 (d, J = 2.40 Hz, 1H) 8.28 (dd, J = 2.05, 0.78 Hz, 1H) 8.34 (t, J = 2.20 Hz, 1H) 8.82 (dd, J = 5.18, 0.73 Hz, 1H) 9.05 (d, J = 2.49 Hz, 1H) 10.98 (s, 1H). LCMS (m/z) (M + H) = 462.1, Rt = 0.69 min. |
| 87 | 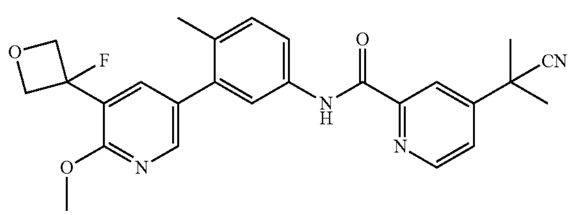 [SMILES: COc1ncc(-c2cc(NC(=O)c3cc(C(C)(C)C#N)ccn3)ccc2C)cc1C1(F)COC1] | 4-(2-cyanopropan-2-yl)-N-(3-(5-(3-fluorooxetan-3-yl)-6-methoxypyridin-3-yl)-4-methylphenyl)picolinamide | $^1$H NMR (400 MHz, <dmso>) δ ppm 1.76 (s, 6H) 2.25 (s, 3H) 3.97 (s, 3H) 4.88-4.96 (m, 2H) 5.12-5.21 (m, 2H) 7.33 (d, J = 8.95 Hz, 1H) 7.80-7.92 (m, 4H) 8.27-8.29 (m, 2H) 8.79 (d, J = 8.95 Hz, 1H) 10.70 (s, 1H). LCMS (m/z) (M + H) = 461.1, Rt = 1.07 min. |
| 88 | 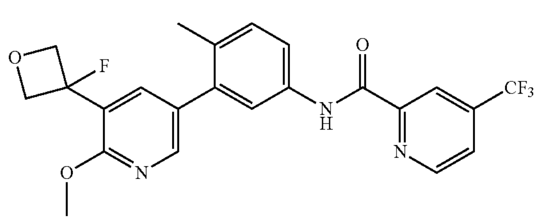 [SMILES: COc1ncc(-c2cc(NC(=O)c3cc(C(F)(F)F)ccn3)ccc2C)cc1C1(F)COC1] | N-(3-(5-(3-fluorooxetan-3-yl)-6-methoxypyridin-3-yl)-4-methylphenyl)-4-(trifluoromethyl)picolinamide | $^1$H NMR (400 MHz, <dmso>) δ ppm 2.25 (s, 3H) 3.97 (s, 3H) 4.88-4.96 (m, 2H) 5.12-5.21 (m, 2H) 7.34 (d, J = 8.0 Hz, 1H) 7.83 (d, J = 2.20 Hz, 1H) 7.87-7.92 (m, 2H) 8.08-8.10 (m, 1H) 8.27-8.28 (m, 1H), 8.34-8.35 (m, 1H) 9.04 (m, 4.0 Hz, 1H) 10.81 (s, 1H). LCMS (m/z) (M + H) = 462.0, Rt = 1.14 min. |

TABLE 2-continued

| Example | Structure | Name | Physical Data |
|---|---|---|---|
| 89 | 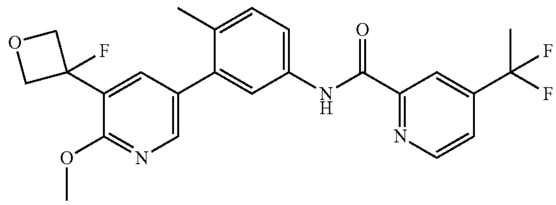 [SMILES: COc1ncc(-c2cc(NC(=O)c3cc(C(C)(F)F)ccn3)ccc2C)cc1C1(F)COC1] | 4-(1,1-difluoroethyl)-N-(3-(5-(3-fluorooxetan-3-yl)-6-methoxypyridin-3-yl)-4-methylphenyl)picolinamide | ¹H NMR (400 MHz, <dmso>) δ ppm 2.05 (t, J = 20.0 Hz, 3H) 2.25 (s, 3H) 3.97 (s, 3H) 4.87-4.97 (m, 2H) 5.12-5.22 (m, 2H) 7.33 (d, J = 9.15 Hz, 1H) 7.83 (d, J = 2.40 Hz, 1H) 7.85-7.92 (m, 3H) 8.23 (dd, J = 1.81, 0.78 Hz, 1H) 8.28 (t, J = 2.20 Hz, 1H) 8.89 (dd, J = 5.04, 0.73 Hz, 1H) 10.74 (s, 1H). LCMS (m/z) (M + H) = 458.1, Rt = 1.11 min. |
| 90 | 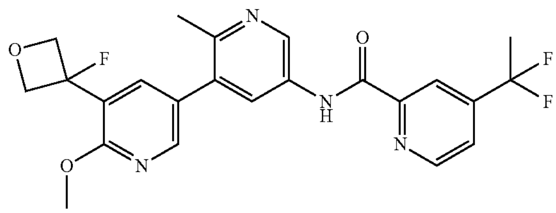 [SMILES: COc1ncc(-c2cc(NC(=O)c3cc(C(C)(F)F)ccn3)cnc2C)cc1C1(F)COC1] | 4-(1,1-difluoroethyl)-N-(5'-(3-fluorooxetan-3-yl)-6'-methoxy-2-methyl-[3,3'-bipyridin]-5-yl)picolinamide | ¹H NMR (400 MHz, <dmso>) δ ppm 2.05 (t, J = 20.0 Hz, 3H) 2.44 (s, 3H) 3.98 (s, 3H) 4.87-4.97 (m, 2H) 5.11-5.22 (m, 2H) 7.89 (dd, J = 5.06, 1.83 Hz, 1H) 7.97 (t, J = 2.32 Hz, 1H) 8.20 (d, J = 2.49 Hz, 1H) 8.25 (dd, J = 1.83, 0.81 Hz, 1H) 8.34 (t, J = 2.20 Hz, 1H) 8.92 (dd, J = 5.06, 0.76 Hz, 1H) 9.05 (d, J = 2.45 Hz, 1H) 11.02 (s, 1H). LCMS (m/z) (M + H) = 459.1, Rt = 0.73 min. |
| 91 | 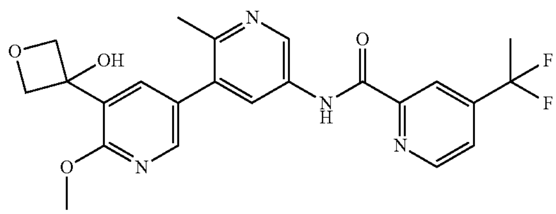 [SMILES: COc1ncc(-c2cc(NC(=O)c3cc(C(C)(F)F)ccn3)cnc2C)cc1C1(O)COC1] | 4-(1,1-difluoroethyl)-N-(5'-(3-fluorooxetan-3-yl)-6'-methoxy-2-methyl-[3,3'-bipyridin]-5-yl)picolinamide | ¹H NMR (400 MHz, <dmso>) δ ppm 2.05 (t, J = 20.0 Hz, 3H) 2.45 (s, 3H) 3.95 (s, 3H) 4.63-4.67 (m, 2H) 5.01-5.05 (m, 2H) 6.17 (s, 1H) 7.76 (d, J = 2.40 Hz, 1H) 7.89 (dd, J = 5.06, 1.83 Hz, 1H) 8.20 (dd, J = 5.09, 2.45 Hz, 2H) 8.25 (dd, J = 1.83, 0.81 Hz, 1H) 8.92 (dd, J = 5.06, 0.76 Hz, 1H) 9.02 (d, J = 2.49 Hz, 1H) 11.02 (s, 1H). LCMS (m/z) (M + H) = 457.1, Rt = 0.61 min. |
| 92 | 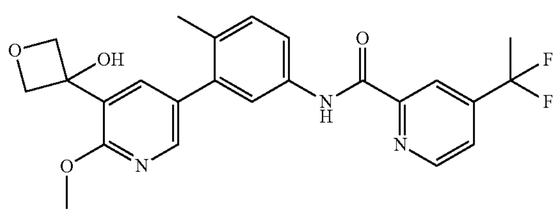 [SMILES: COc1ncc(-c2cc(NC(=O)c3cc(C(C)(F)F)ccn3)ccc2C)cc1C1(O)COC1] | 4-(1,1-difluoroethyl)-N-(3-(5-(3-hydroxyoxetan-3-yl)-6-methoxypyridin-3-yl)-4-methylphenyl)picolinamide | ¹H NMR (400 MHz, <dmso>) δ ppm 2.05 (t, J = 19.27 Hz, 3H) 2.25 (s, 3H) 3.95 (s, 3H) 4.61-4.71 (m, 2H) 5.00-5.10 (m, 2H) 6.15 (s, 1H) 7.32 (d, J = 8.41 Hz, 1H) 7.68 (d, J = 2.40 Hz, 1H) 7.81-7.93 (m, 3H) 8.14 (d, J = 2.35 Hz, 1H) 8.22-8.27 (m, 1H) 8.88-8.93 (m, 1H) 10.73 (s, 1H). LCMS (m/z) (M + H) = 456.1, Rt = 0.93 min. |
| 93 | 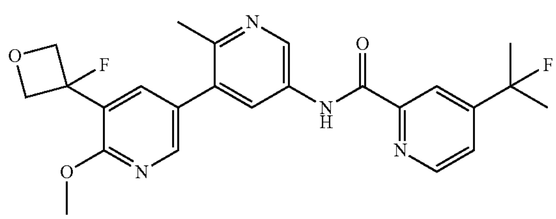 [SMILES: COc1ncc(-c2cc(NC(=O)c3cc(C(C)(C)F)ccn3)cnc2C)cc1C1(F)COC1] | N-(5'-(3-fluorooxetan-3-yl)-6'-methoxy-2-methyl-[3,3'-bipyridin]-5-yl)-4-(2-fluoropropan-2-yl)picolinamide | ¹H NMR (400 MHz, <dmso>) δ ppm 1.71 (d, J = 24.0 Hz, 6H) 2.44 (s, 3H) 3.98 (s, 3H) 4.87-4.95 (m, 2H) 5.12-5.22 (m, 2H) 7.73 (dd, J = 5.18, 1.86 Hz, 1H) 7.97 (t, J = 2.35 Hz, 1H) 8.16 (dd, J = 1.88, 0.86 Hz, 1H) 8.20 (d, J = 2.49 Hz, 1H) 8.34 (t, J = 2.20 Hz, 1H) 8.77 (d, J = 5.09 Hz, 1H) 9.05 (d, J = 2.45 Hz, 1H) 10.94 (s, 1H). LCMS (m/z) (M + H) = 455.1, Rt = 0.75 min. |
| 94 | 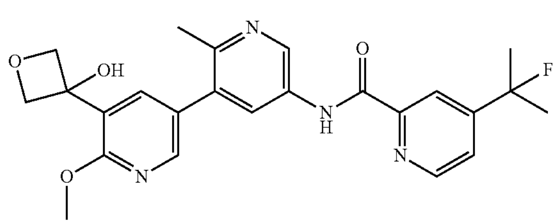 | 4-(2-fluoropropan-2-yl)-N-(5'-(3-hydroxyoxetan-3-yl)-6'-methoxy-2-methyl-[3,3'-bipyridin]-5-yl)picolinamide | ¹H NMR (400 MHz, <dmso>) δ ppm 1.71 (d, J = 24.0 Hz, 6H) 2.45 (s, 3H) 3.95 (s, 3H) 4.63-4.67 (m, 2H) 5.01-5.05 (m, 2H) 7.73 (dd, J = 5.45, 1.93 Hz, 1H) 7.76 (d, J = 2.40 Hz, 1H) 8.16 (dd, J = 1.91, 0.83 Hz, 1H) 8.19-8.23 (m, 2H) 8.77 (dt, J = 5.11, 0.75 Hz, 1H) 9.03 (d, J = 2.49 Hz, 1H) 10.96 (s, 1H). LCMS (m/z) (M + H) = 453.1, Rt = 0.62 min. |

TABLE 2-continued

| Example | Structure | Name | Physical Data |
|---|---|---|---|
| 95 | 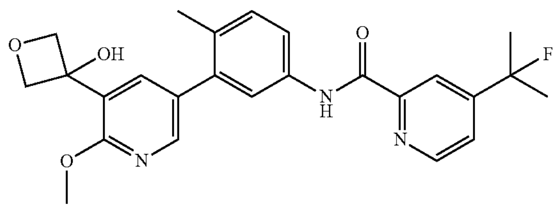 | 4-(2-fluoropropan-2-yl)-N-(3-(5-(3-hydroxyoxetan-3-yl)-6-methoxypyridin-3-yl)-4-methylphenyl)picolinamide | $^1$H NMR (400 MHz, <dmso>) δ ppm 1.68 (s, 3H) 1.73 (s, 3H) 2.25 (s, 3H) 2.50 (dt, J = 3.74, 1.90 Hz, 21H) 3.24-3.44 (m, 3H) 3.32 (s, 14H) 3.94 (s, 3H) 4.63-4.67 (m, 2H) 5.01-5.05 (m, 2H) 6.15 (s, 1H) 7.31 (d, J = 8.75 Hz, 1H) 7.68 (d, J = 2.40 Hz, 1H) 7.70 (dd, J = 5.33, 1.66 Hz, 1H) 7.80-7.87 (m, 2H) 8.12-8.16 (m, 2H) 8.74 (dt, J = 5.12, 0.74 Hz, 1H) 10.66 (s, 1H). LCMS (m/z) (M + H) = 452.1, Rt = 0.94 min. |
| 96 | 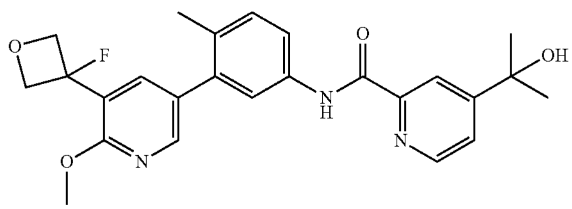 | N-(3-(5-(3-fluorooxetan-3-yl)-6-methoxypyridin-3-yl)-4-methylphenyl)-4-(2-hydroxypropan-2-yl)picolinamide | $^1$H NMR (400 MHz, <dmso>) δ ppm 1.46 (s, 6H) 2.24 (s, 3H) 3.97 (s, 3H) 4.90-4.96 (m, 2H) 5.11-5.22 (m, 2H) 5.45 (s, 1H) 7.32 (d, J = 9.10 Hz, 1H) 7.71 (dd, J = 5.14, 1.86 Hz, 1H) 7.82 (d, J = 2.40 Hz, 1H) 7.87-7.91 (m, 2H) 8.25 (dd, J = 1.88, 0.81 Hz, 1H) 8.28 (t, J = 2.20 Hz, 1H) 8.65 (dd, J = 5.14, 1.86 Hz, 1H) 10.62 (s, 1H). LCMS (m/z) (M + H) = 452.1, Rt = 0.93 min. |
| 97 | 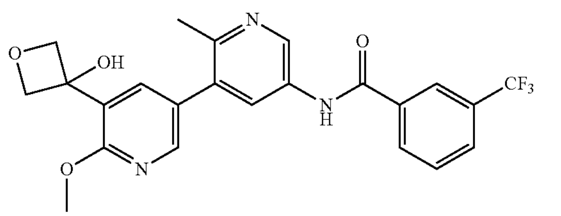 [SMILES: COc1ncc(-c2cc(NC(=O)c3cccc(C(F)(F)F)c3)cnc2C)cc1C1(O)COC1] | N-(5'-(3-hydroxyoxetan-3-yl)-6'-methoxy-2-methyl-[3,3'-bipyridin]-5-yl)-3-(trifluoromethyl)benzamide | $^1$H NMR (400 MHz, <dmso>) δ ppm 2.46 (s, 3H) 3.96 (s, 2H) 4.62-4.67 (m, 1H) 5.01-5.05 (m, 1H) 7.77 (d, J = 2.40 Hz, 1H) 7.82 (t, J = 8.0 Hz, 1H) 8.00 (d, J = 8.0 Hz, 1H) 8.10 (d, J = 2.54 Hz, 1H) 8.21 (d, J = 2.40 Hz, 1H) 8.29 (d, J = 8.0 Hz, 1H) 8.33 (s, 1H) 8.89 (d, J = 2.45 Hz, 1H) 10.72 (s, 1H). LCMS (m/z) (M + H) = 460.2, Rt = 0.63 min. |
| 98 | 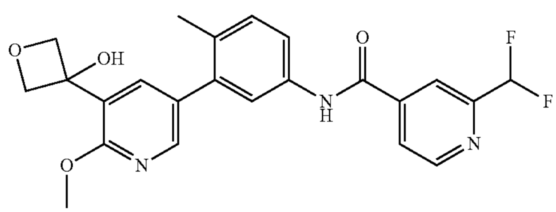 [SMILES: COc1ncc(-c2cc(NC(=O)c3ccnc(C(F)F)c3)ccc2C)cc1C1(O)COC1] | 2-(difluoromethyl)-N-(3-(5-(3-hydroxyoxetan-3-yl)-6-methoxypyridin-3-yl)-4-methylphenyl)isonicotinamide | $^1$H NMR (400 MHz, <dmso>) δ ppm 2.24 (s, 3H) 3.94 (s, 3H) 4.62-4.66 (m, 2H) 5.00-5.04 (m, 2H) 6.16 (s, 1H) 7.08 (t, J = 56.0, 1H) 7.33 (d, J = 9.10 Hz, 1H) 7.66-7.75 (m, 3H) 8.06 (dt, J = 5.07, 0.86 Hz, 1H) 8.13 (d, J = 2.40 Hz, 1H) 8.16-8.19 (m, 1H) 8.90 (dd, J = 5.04, 0.78 Hz, 1H) 10.65 (s, 1H). LCMS (m/z) (M + H) = 442.1, Rt = 0.77 min. |
| 99 | 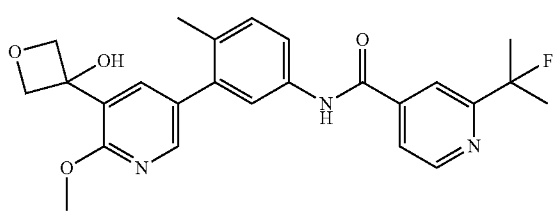 [SMILES: COc1ncc(-c2cc(NC(=O)c3ccnc(C(C)(C)F)c3)ccc2C)cc1C1(O)COC1] | 2-(2-fluoropropan-2-yl)-N-(3-(5-(3-hydroxyoxetan-3-yl)-6-methoxypyridin-3-yl)-4-methylphenyl)isonicotinamide | $^1$H NMR (400 MHz, <dmso>) δ ppm 1.68 (d, J = 20.0 Hz, 6H) 2.24 (s, 3H) 3.94 (s, 3H) 4.61-4.70 (m, 2H) 4.98-5.08 (s, 2H) 6.15 (s, 1H) 7.32 (d, J = 9.15 Hz, 1H) 7.65-7.76 (m, 3H) 7.82 (dd, J = 5.06, 1.69 Hz, 1H) 8.00-8.05 (m, 1H) 8.13 (d, J = 2.35 Hz, 1H) 8.75 (dt, J = 5.04, 0.98 Hz, 1H) 10.56 (s, 1H). LCMS (m/z) (M + H) = 452.1, Rt = 0.80 min. |
| 100 | 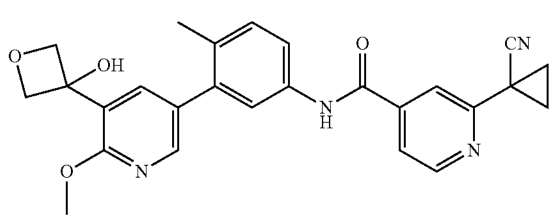 [SMILES: COc1ncc(-c2cc(NC(=O)c3ccnc(C4(C#N)CC4)c3)ccc2C)cc1C1(O)COC1] | 2-(1-cyanocyclopropyl-N-(3-(5-(3-hydroxyoxetan-3-yl)-6-methoxypyridin-3-yl)-4-methylphenyl)isonicotinamide | $^1$H NMR (400 MHz, <dmso>) δ ppm 1.77 (d, J = 3.52 Hz, 2H) 1.88 (d, J = 3.47 Hz, 2H) 2.24 (s, 3H) 3.94 (s, 3H) 4.62-4.66 (m, 2H) 5.02 (d, J = 7.63 Hz, 2H) 7.33 (d, J = 8.0 Hz, 1H) 7.65-7.71 (m, 3H) 7.79 (dd, J = 4.0, 1.6 Hz, 1H) 7.92-7.93 (m, 1H) 8.14 (d, J = 4.0 Hz, 1H) 8.70 (dd, J = 4.0, 1.6 Hz, 1H) 10.58 (s, 1H). LCMS (m/z) (M + H) = 457.1, Rt = 0.76 min. |

TABLE 2-continued

| Example | Structure | Name | Physical Data |
|---|---|---|---|
| 101 | 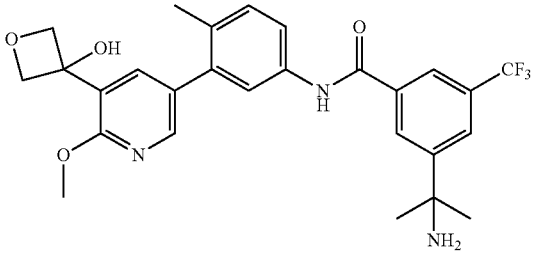 [SMILES: COc1ncc(-c2cc(NC(=O)c3cc(C(C)(C)N)cc(C(F)(F)F)c3)ccc2C)cc1C1(O)COC1] | 3-(2-aminopropan-2-yl)-N-(3-(5-(3-hydroxyoxetan-3-yl)-6-methoxypyridin-3-yl)-4-methylphenyl)-5-(trifluoromethyl)benzamide | 1H NMR (400 MHz, <dmso>) δ ppm 1.46 (s, 6H) 2.24 (s, 3H) 3.94 (s, 3H) 4.62-4.67 (m, 2H) 5.02 (d, J = 7.43 Hz, 2H) 6.16 (s, 1H) 7.32 (d, J = 8.0, 1H) 7.63-7.75 (m, 3H) 8.10-8.16 (m, 3H) 8.34-8.38 (m, 1H) 10.42 (s, 1H). LCMS (m/z) (M + H) = 516.3, Rt = 0.71 min. |
| 102 | 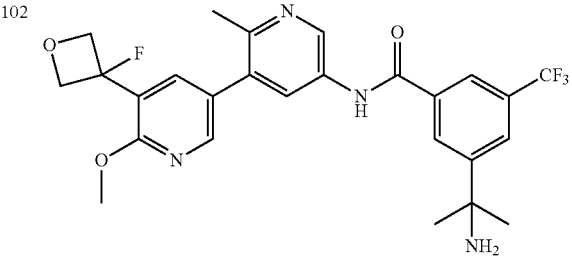 | 3-(2-aminopropan-2-yl)-N-(5'-(3-fluorooxetan-3-yl)-6'-methoxy-2-methyl-[3,3'-bipyridin]-5-yl)-5-(trifluoromethyl)benzamide | $^1$H NMR (400 MHz, <dmso>) δ ppm 1.46 (s, 6H) 2.45 (s, 3H) 3.98 (s, 3H) 4.87-4.97 (m, 2H) 5.11-5.22 (m, 2H) 7.98 (t, J = 2.32 Hz, 1H) 8.05 (d, J = 2.45 Hz, 1H) 8.13-8.15 (m, 1H) 8.15-8.18 (m, 1H) 8.34-8.35 (m, 1H) 8.39 (s, 1H) 8.89 (d, J = 2.45 Hz, 1H) 10.63 (s, 1H). LCMS (m/z) (M + H) = 519.3, Rt = 0.59 min. |
| 103 | 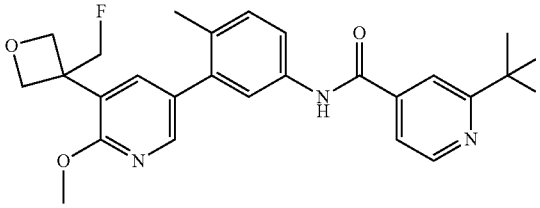 | 2-(1,1-difluoroethyl)-N-(3-(5-(3-(fluoromethyl)oxetan-3-yl)-6-methoxypyridin-3-yl)-4-methylphenyl)isonicotinamide | $^1$H NMR (400 MHz, <dmso>) δ ppm 2.05 (t, J = 20.0 Hz, 3H) 2.23 (s, 3H) 3.91 (s, 3H) 4.68 (d, J = 6.70 Hz, 2H) 4.78 (d, J = 48.0, 2H) 4.87-4.89 (m, 2H) 7.33 (d, J = 8.0 Hz, 1H) 7.52 (d, J = 2.0 Hz, 1H) 7.64 (d, J = 2.0 Hz, 1H) 7.74 (dd, J = 8.0, 2.0 Hz, 1H) 8.02 (d, J = 4.0 Hz, 1H) 8.13 (d, J = 2.0 Hz, 1H) 8.18 (s, 1H) 8.88 (d, J = 4.0 Hz, 1H) 10.64 (s, 1H). LCMS (m/z) (M + H) = 472.2, Rt = 0.96 min. |
| 104 | 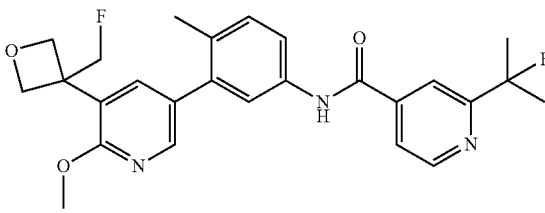 | N-(3-(5-(3-(fluoromethyl)oxetan-3-yl)-6-methoxypyridin-3-yl)-4-methylphenyl)-2-(2-fluoropropan-2-yl)isonicotinamide | $^1$H NMR (400 MHz, <dmso>) δ ppm 1.71 (d, J = 20.0 Hz, 6H) 2.23 (s, 3H) 3.90 (s, 3H) 4.62 (d, J = 6.70 Hz, 2H) 4.78 (d, J = 48.0, 2H) 4.87-4.89 (m, 2H) 7.32 (d, J = 8.0 Hz, 1H) 7.52 (d, J = 2.0 Hz, 1H) 7.64 (d, J = 2.0 Hz, 1H) 7.74 (dd, J = 8.0, 2.0 Hz, 1H) 7.82 (dd, J = 4.0, 2.0 Hz, 1H) 8.02 (s, 1H) 8.13 (d, J = 2.0 Hz, 1H) 8.76 (d, J = 4.0 Hz, 1H) 10.56 (s, 1H). LCMS (m/z) (M + H) = 468.3, Rt = 0.95 min. |
| 105 | 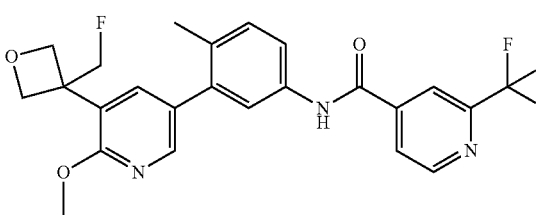 | N-(3-(5-(3-(fluoromethyl)oxetan-3-yl)-6-methoxypyridin-3-yl)-4-methylphenyl)-2-(trifluoromethyl)isonicotinamide | $^1$H NMR (400 MHz, <dmso>) δ ppm 2.24 (s, 3H) 3.91 (s, 3H) 4.66 (d, J = 6.75 Hz, 2H) 4.78 (d, J = 48.0 Hz, 2H) 4.88 (dd, J = 6.82, 3.15 Hz, 2H) 7.34 (d, J = 9.05 Hz, 1H) 7.51 (d, J = 2.35 Hz, 1H) 7.64 (d, J = 2.25 Hz, 1H) 7.74 (dd, J = 8.0, 2.0 Hz, 1H) 8.13 (d, J = 2.35 Hz, 1H) 8.20 (d, J = 4.0 Hz, 1H) 8.35-8.38 (m, 1H) 8.99 (d, J = 4.99 Hz, 1H) 10.69 (s, 1H). LCMS (m/z) (M + H) = 476.2, Rt = 0.98 min. |

TABLE 2-continued

| Example | Structure | Name | Physical Data |
|---|---|---|---|
| 106 | 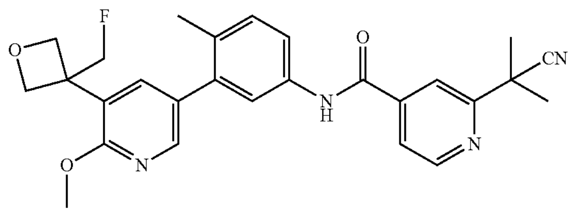 [SMILES: COc1ncc(-c2cc(NC(=O)c3ccnc(C(C)(C)C#N)c3)ccc2C)cc1C1(CF)COC1] | 2-(2-cyanopropan-2-yl)-N-(3-(5-(3-(fluoromethyl)oxetan-3-yl)-6-methoxypyridin-3-yl)-4-methylphenyl)isonicotinamide | $^1$H NMR (400 MHz, <dmso>) δ ppm 1.75 (s, 6H) 2.21 (s, 3H) 3.89 (s, 3H) 4.65 (d, J = 6.75 Hz, 2H) 4.76 (d, J = 48.0 Hz, 1H) 4.86 (dd, J = 6.68, 3.15 Hz, 2H) 7.32 (d, J = 8.66 Hz, 1H) 7.49 (d, J = 2.35 Hz, 1H) 7.60 (d, J = 2.45 Hz, 1H) 7.71 (dd, J = 8.0, 2.0 Hz, 1H) 7.84 (dd, J = 8.0, 2.0 Hz, 1H) 7.97-8.00 (m, 1H) 8.11 (d, J = 2.30 Hz, 1H) 8.79 (dd, J = 5.04, 0.88 Hz, 1H) 10.54 (s, 1H). LCMS (m/z) (M + H) = 475.3, Rt = 0.94 min. |
| 107 | 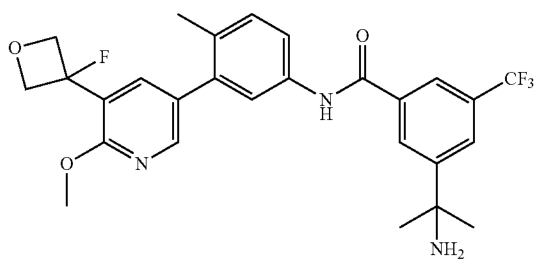 [SMILES: COc1ncc(-c2cc(NC(=O)c3cc(C(C)(C)N)cc(C(F)(F)F)c3)ccc2C)cc1C1(F)COC1] | 3-(2-aminopropan-2-yl)-N-(3-(5-(3-fluorooxetan-3-yl)-6-methoxypyridin-3-yl)-4-methylphenyl)-5-(trifluoromethyl)benzamide | $^1$H NMR (400 MHz, <dmso>) δ ppm 1.63 (s, 6H), 2.24 (s, 3H) 3.97 (s, 3H) 4.88-4.96 (m, 2H) 5.11-5.20 (m, 2H) 7.35 (d, J = 8.0 Hz, 1H) 7.66 (d, J = 4.0 Hz, 1H) 7.78 (dd, J = 8.0, 4.0 Hz, 1H) 7.88 (t, J = 4.0 Hz, 1H) 8.11 (s, 1H) 8.27-8.28 (m, 2H) 8.43 (s, 1H) 10.53 (s, 1H). LCMS (m/z) (M + H) = 518.1, Rt = 0.82 min. |
| 108 | 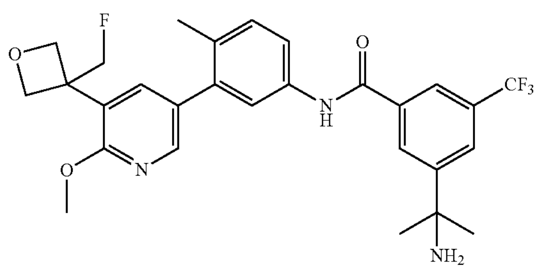 [SMILES: COc1ncc(-c2cc(NC(=O)c3cc(C(C)(C)N)cc(C(F)(F)F)c3)ccc2C)cc1C1(CF)COC1] | 3-(2-aminopropan-2-yl)-N-(3-(5-(3-(fluoromethyl)oxetan-3-yl)-6-methoxypyridin-3-yl)-4-methylphenyl)-5-(trifluoromethyl)benzamide | $^1$H NMR (400 MHz, <dmso>) δ ppm 1.61 (s, 6H) 2.23 (s, 3H) 3.91 (s, 3H) 4.67 (d, J = 8.0 Hz, 2H) 4.78 (d, J = 48.0 Hz, 2H) 4.88-4.90 (m, 2H) 7.33 (d, J = 8.0 Hz, 1H) 7.52 (d, 4.0 Hz, 1H) 7.64 (d, 4.0 Hz, 1H) 7.74-7.77 (m, 1H) 8.11 (s, 1H) 8.14 (d, J = 4.0 Hz, 1H) 8.25 (s, 1H) 8.42 (s, 1H) 10.52 (s, 1H). LCMS (m/z) (M + H) = 532.1, Rt = 0.82 min. |
| 109 | 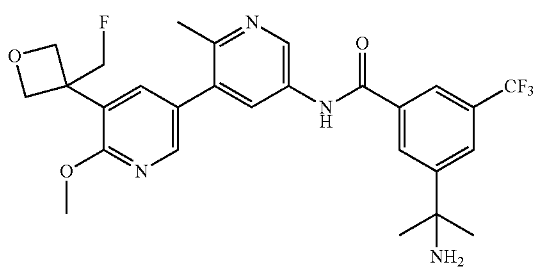 [SMILES: COc1ncc(-c2cc(NC(=O)c3cc(C(C)(C)N)cc(C(F)(F)F)c3)cnc2C)cc1C1(CF)COC1] | 3-(2-aminopropan-2-yl)-N-(5'-(3-(fluoromethyl)oxetan-3-yl)-6'-methoxy-2-methyl-[3,3'-bipyridin]-5-yl)-5-(trifluoromethyl)benzamide | $^1$H NMR (400 MHz, <dmso>) δ ppm 1.74 (s, 6H), 2.52 (s, 3H) 3.92 (s, 3H) 4.67 (d, J = 8.0 Hz, 2H) 4.80 (d, J = 48.0 Hz, 2H) 4.89-4.91 (m, 2H) 7.65 (d, J = 2.0 Hz, 1H) 8.16 (s, 1H) 8.24 (d, J = 2.0 Hz, 1H) 8.30 (s, 1H) 8.38 (s, 1H) 8.61 (s, 1H) 8.80 (s, 2H) 9.06 (m, 1H) 11.13 (s, 1H). LCMS (m/z) (M + H) = 533.1, Rt = 0.59 min. |
| 110 | 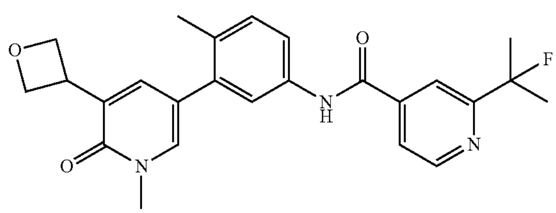 [SMILES: Cc1ccc(NC(=O)c2ccnc(C(C)(C)F)c2)cc1-c1cc(C2COC2)c(=O)n(C)c1] | 2-(2-fluoropropan-2-yl)-N-(4-methyl-3-(1-methyl-5-(oxetan-3-yl)-6-oxo-1,6-dihydropyridin-3-yl)phenyl)isonicotinamide | $^1$H NMR (400 MHz, <dmso>) δ ppm 10.55 (s, 1H) 8.76 (d, J = 4.0, 1H) 8.03 (s, 1H) 7.82 (dd, J = 8.0, 2.0, 1H) 7.69-7.71 (m, 2H) 7.66 (d, J = 2.0, 1H) 7.46-7.47 (m, 1H) 7.30 (d, J = 8.0, 1H) 4.83 (dd, J = 10.0, 8.0, 1H) 4.65 (dd, J = 10.0, 8.0, 1H) 4.27 (quintet, J = 8.0, 1H) 3.50 (s, 3H) 2.28 (s, 3H) 1.71 (d, J = 24.0, 6H). LCMS (m/z) (M + H) = 436.1, Rt = 0.75 min. |
| 111 | 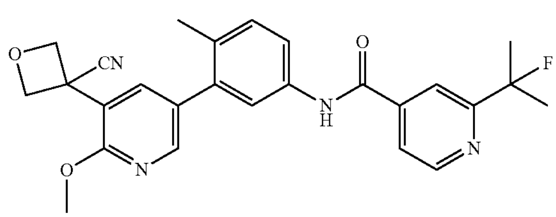 | N-(3-(5-(3-cyanooxetan-3-yl)-6-methoxypyridin-3-yl)-4-methylphenyl)-2-(2-fluoropropan-2-yl)isonicotinamide | $^1$H NMR (400 MHz, <dmso>) δ ppm 10.58 (s, 1H) 10.76 (d, J = 4.0, 1H) 8.24 (d, J = 2.0, 1H) 8.03 (s, 1H) 7.98 (d, J = 2.0, 1H) 7.82 (dd, J = 4.0, 2.0, 1H) 7.75 (dd, J = 8.0, 2.0, 1H) 7.68 (d, J = 2.0, 1H) 7.34 (d, J = 8.0, 1H) 5.05-5.09 (m, 4H) 3.99 (s, 3H) 2.25 (s, 3H) 1.71 (d, J = 24.0, 6H). LCMS (m/z) (M + H) = 461.1, Rt = 0.93 min. |

TABLE 2-continued

| Example | Structure | Name | Physical Data |
|---|---|---|---|
| 112 | 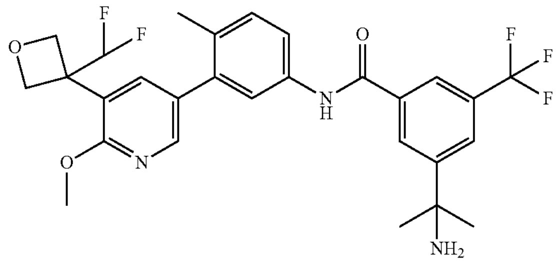 [SMILES: COc1ncc(-c2cc(NC(=O)c3cc(C(C)(C)N)cc(C(F)(F)F)c3)ccc2C)cc1C1(C(F)F)COC1] | 3-(2-aminopropan-2-yl)-N-(3-(5-(3-(difluoromethyl)oxetan-3-yl)-6-methoxypyridin-3-yl)-4-methylphenyl)-5-(trifluoromethyl)benzamide | $^1$H NMR (400 MHz, <dmso>) δ ppm 10.43 (s, 1H) 8.36 (s, 1H) 8.18 (d, J = 4.0 Hz, 1H) 8.13 (s, 1H) 8.11 (s, 1H) 7.75 (dd, J = 8.0, 4.0, 1H) 7.63 (d, J = 2.0 Hz, 1H) 7.60 (d, J = 4.0, 1H) 7.33 (d, J = 8.0, 1H) 6.45 (t, J = 56.0, 1H) 4.92 (d, J = 8.0, 2H) 4.83 (d, J = 8.0, 1H) 3.91 (s, 3H) 2.23 (s, 3H) 1.46 (s, 6H). LCMS (m/z) (M + H) = 550.1, Rt = 0.84 min. |
| 113 | 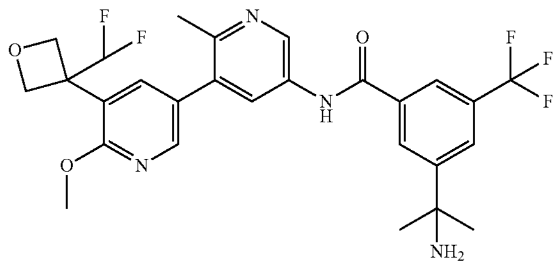 | 3-(2-aminopropan-2-yl)-N-(5'-(3-(difluoromethyl)oxetan-3-yl)-6'-methoxy-2-methyl-[3,3'-bipyridin]-5-yl)-5-(trifluoromethyl)benzamide | $^1$H NMR (400 MHz, <dmso>) δ ppm 10.64 (s, 1H) 8.88 (d, J = 4.0, 1H) 8.39 (s, 1H) 8.26 (d, J = 2.0, 1H) 8.18 (s, 1H) 8.14 (s, 1H) 8.02 (d, J = 4.0, 1H) 7.70 (d, J = 4.0, 1H) 6.46 (t, J = 56.0 Hz, 1H) 4.93 (d, J = 8.0 Hz, 2H) 4.83 (d, J = 8.0 Hz, 2H) 3.92 (s, 3H) 2.43 (s, 3H) 1.48 (s, 6H). LCMS (m/z) (M + H) = 551.1, Rt = 0.62 min. |
| 114 | 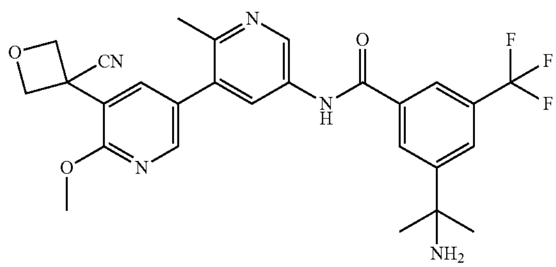 [SMILES: COc1ncc(-c2cc(NC(=O)c3cc(C(C)(C)N)cc(C(F)(F)F)c3)cnc2C)cc1C1(C#N)COC1] | 3-(2-aminopropan-2-yl)-N-(5'-(3-cyanooxetan-3-yl)-6'-methoxy-2-methyl-[3,3'-bipyridin]-5-yl)-5-(trifluoromethyl)benzamide | $^1$H NMR (400 MHz, <dmso>) δ ppm 10.66 (s, 1H) 8.88 (d, J = 4.0 Hz, 1H) 8.39 (s, 1H) 8.32 (d, J = 4.0 1H) 8.21 (s, 1H) 8.14 (s, 1H) 8.06 (d, J = 4.0 Hz, 1H) 7.98 (d, J = 4.0 Hz, 1H) 5.06-5.09 (m, 4H) 4.00 (s, 3H) 2.46 (s, 3H) 1.50 (s, 6H). LCMS (m/z) (M + H) = 526.1, Rt = 0.58 min. |
| 115 | 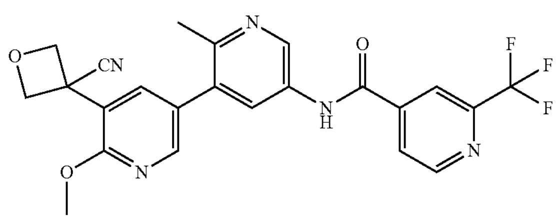 [SMILES: COc1ncc(-c2cc(NC(=O)c3ccnc(C(F)(F)F)c3)cnc2C)cc1C1(C#N)COC1] | N-(5'-(3-cyanooxetan-3-yl)-6'-methoxy-2-methyl-[3,3'-bipyridin]-5-yl)-2-(trifluoromethyl)isonicotinamide | $^1$H NMR (400 MHz, <dmso>) δ ppm 10.92 (s, 1H) 9.02 (d, J = 4.0, 1H) 8.86 (d, J = 4.0, 1H) 8.39 (s, 1H) 8.32 (d, J = 2.0, 1H) 8.22 (d, J = 4.0, 1H) 8.08 (d, J = 4.0, 1H) 7.98 (d, J = 4.0, 1H) 5.06-5.09 (m, 4H) 4.00 (s, 3H) 2.46 (s, 3H). LCMS (m/z) (M + H) = 470.0, Rt = 0.66 min. |
| 116 | 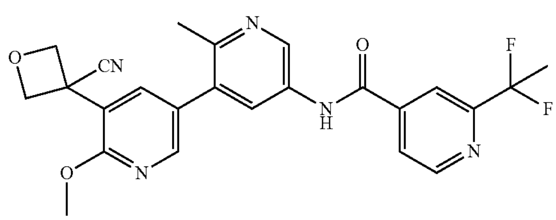 [SMILES: COc1ncc(-c2cc(NC(=O)c3ccnc(C(C)(F)F)c3)cnc2C)cc1C1(C#N)COC1] | N-(5'-(3-cyanooxetan-3-yl)-6'-methoxy-2-methyl-[3,3'-bipyridin]-5-yl)-2-(1,1-difluoroethyl)isonicotinamide | $^1$H NMR (400 MHz, <dmso>) δ ppm 10.87 (s, 1H) 8.91 (d, J = 8.0 Hz, 1H) 8.88 (d, J = 4.0 Hz, 1H) 8.32 (d, J = 2.0 Hz, 1H) 8.21-8.22 (m, 1H) 8.08 (d, J = 4.0 Hz, 1H) 8.05 (dd, J = 8.0, 2.0, 1H) 7.98 (d, J = 4.0, 1H) 5.06-5.09 (m, 4H) 4.00 (s, 3H) 2.46 (s, 3H) 2.06 (t, J = 20.0 Hz, 3H). LCMS (m/z) (M + H) = 466.0, Rt = 0.64 min. |
| 117 | 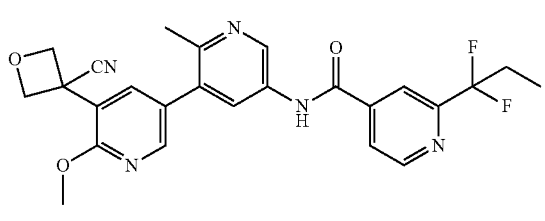 [SMILES: CCC(F)(F)c1cc(C(=O)Nc2cnc(C)c(-c3cnc(OC)c(C4(C#N)COC4)c3)c2)ccn1] | N-(5'-(3-cyanooxetan-3-yl)-6'-methoxy-2-methyl-[3,3'-bipyridin]-5-yl)-2-(1,1-difluoropropyl)isonicotinamide | $^1$H NMR (400 MHz, <dmso>) δ ppm 10.87 (s, 1H) 8.92 (d, J = 8.0 Hz, 1H) 8.88 (d, J = 4.0 Hz, 1H) 8.32 (d, J = 2.0 Hz, 1H) 8.20 (m, 1H) 8.08 (d, J = 4.0 Hz, 1H) 8.05 (dd, J = 8.0 Hz, 2.0, 1H) 7.98 (d, J = 4.0 Hz, 1H) 5.06-5.08 (m, 4H) 2.86 (s, 3H) 2.46 (s, 3H) 2.33-2.39 (m, 2H) 0.95 (t, J = 8.0 Hz, 3H). LCMS (m/z) (M + H) = 480.0, Rt = 0.70 min. |

TABLE 2-continued

| Example | Name | Physical Data |
|---|---|---|
| 118 | N-(5'-(3-hydroxyoxetan-3-yl)-2-methyl-6'-((tetrahydro-2H-pyran-4-yl)oxy)-[3,3'-bipyridin]-5-yl)-3-(trifluoromethyl)benzamide | $^1$H NMR (400 MHz, <dmso>) δ ppm 1.54-1.74 (m, 2H) 1.95 (ddd, J = 9.59, 6.65, 3.33 Hz, 2H) 2.41 (s, 3H) 3.51 (td, J = 7.53, 3.72 Hz, 2H) 3.79 (ddd, J = 11.35, 7.04, 3.52 Hz, 2H) 4.59 (d, J = 7.04 Hz, 2 H) 5.03 (d, J = 7.04 Hz, 2H) 5.25-5.43 (m, 1H) 7.61-7.81 (m, 2H) 7.94 (d, J = 7.83 Hz, 1H) 8.05 (d, J = 1.96 Hz, 1H) 8.12 (d, J = 2.35 Hz, 1H) 8.18-8.33 (m, 2H) 8.82 (d, J = 2.35 Hz, 1H) 10.67 (s, 1H). LCMS (m/z) (M + H) = 530.2, Rt = 0.70 min. |
| 119 | N-(3-(5-(3-hydroxyoxetan-3-yl)-6-((tetrahydro-2H-pyran-4-yl)oxy)pyridin-3-yl)-4-methylphenyl)-3-(trifluoromethyl)benzamide | $^1$H NMR (400 MHz, <dmso>) δ ppm 1.57-1.73 (m, 2H) 1.90-2.01 (m, 2H) 2.17 (s, 3H) 3.44-3.59 (m, 2H) 3.70-3.90 (m, 2H) 4.53-4.63 (m, 2H) 4.95-5.08 (m, 2H) 5.22-5.35 (m, 1H) 6.07-6.19 (m, 1H) 7.20-7.30 (m, 1H) 7.57-7.67 (m, 3H) 7.68-7.78 (m, 1H) 7.86-7.95 (m, 1H) 7.99-8.07 (m, 1H) 8.15-8.27 (m, 2H) 10.34-10.43 (m, 1H). LCMS (m/z) (M + H) = 529.2, Rt = 0.97 min. |
| 120 | 3-(2-aminopropan-2-yl)-N-(3-(6-ethoxy-5-(3-hydroxyoxetan-3-yl)pyridin-3-yl)-4-methylphenyl)-5-(trifluoromethyl)benzamide | $^1$H NMR (400 MHz, <dmso>) δ ppm 1.33 (t, J = 7.04 Hz, 3H) 1.42 (s, 6H) 1.88 (s, 2H) 2.22 (s, 3H) 4.38 (d, J = 7.04 Hz, 2H) 4.61 (d, J = 7.04 Hz, 2H) 5.02 (d, J = 7.04 Hz, 2H) 6.11 (s, 1H) 7.30 (d, J = 8.61 Hz, 1H) 7.60-7.67 (m, 2 H) 7.67-7.75 (m, 1H) 8.09 (d, J = 2.35 Hz, 3H) 8.34 (s, 1H) 10.39 (s, 1H). LCMS (m/z) (M + H) = 530.2, Rt = 0.77 min. |
| 121 | 2-(2-cyanopropan-2-yl)-N-(3-(6-ethoxy-5-(3-hydroxyoxetan-3-yl)pyridin-3-yl)-4-methylphenyl)isonicotinamide | $^1$H NMR (400 MHz, <dmso>) δ ppm 1.33 (t, J = 7.04 Hz, 3H) 1.75 (s, 6H) 2.22 (s, 3H) 4.38 (d, J = 7.04 Hz, 2H) 4.58-4.65 (m, 2 H) 4.98-5.06 (m, 2H) 6.11 (s, 1 H) 7.27-7.35 (m, 1H) 7.61-7.71 (m, 3H) 7.81-7.88 (m, 1H) 7.94-8.01 (m, 1H) 8.04-8.12 (m, 1H) 8.75-8.83 (m, 1H) 10.45-10.57 (m, 1H). LCMS (m/z) (M + H) = 473.1, Rt = 0.86 min. |
| 122 | N-(3-(6-ethoxy-5-(3-hydroxyoxetan-3-yl)pyridin-3-yl)-4-methylphenyl)-2-(2-fluoropropan-2-yl)isonicotinamide | $^1$H NMR (400 MHz, <dmso>) δ ppm 1.27-1.40 (m, 3H) 1.61-1.75 (m, 6H) 2.22 (s, 3H) 4.31-4.46 (m, 2H) 4.56-4.63 (m, 2H) 4.99-5.06 (m, 2H) 6.11 (s, 1H) 7.26-7.35 (m, 1H) 7.59-7.66 (m, 2H) 7.67-7.74 (m, 1H) 7.76-7.84 (m, 1H) 7.97-8.03 (m, 1H) 8.06-8.11 (m, 1H) 8.69-8.76 (m, 1H) 10.50-10.57 (m, 1H). LCMS (m/z) (M + H) = 466.1, Rt = 0.85 min. |

TABLE 2-continued

| Example | Structure | Name | Physical Data |
|---|---|---|---|
| 123 | 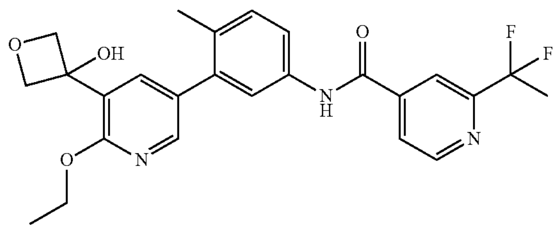 [SMILES: CCOc1ncc(-c2cc(NC(=O)c3ccnc(C(C)(F)F)c3)ccc2C)cc1C1(O)COC1] | 2-(1,1-difluoroethyl)-N-(3-(6-ethoxy-5-(3-hydroxyoxetan-3-yl)pyridin-3-yl)-4-methylphenyl)isonicotinamide | $^1$H NMR (400 MHz, <dmso>) δ ppm 1.33 (t, J = 7.04 Hz, 3H) 1.94-2.13 (m, 3H) 2.22 (s, 3H) 4.38 (d, J = 7.04 Hz, 2H) 4.61 (d, J = 7.43 Hz, 2H) 5.02 (d, J = 7.04 Hz, 2H) 6.11 (s, 1H) 7.23-7.35 (m, 1H) 7.64 (d, J = 2.35 Hz, 3H) 7.98-8.03 (m, 1H) 8.09 (d, J = 2.35 Hz, 1H) 8.13-8.21 (m, 1H) 8.82-8.94 (m, 1H) 10.53-10.65 (m, 1H). LCMS (m/z) (M + H) = 470.0, Rt = 0.86 min. |
| 124 | 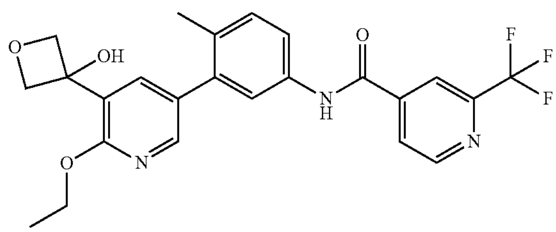 [SMILES: CCOc1ncc(-c2cc(NC(=O)c3ccnc(C(F)(F)F)c3)ccc2C)cc1C1(O)COC1] | N-(3-(6-ethoxy-5-(3-hydroxyoxetan-3-yl)pyridin-3-yl)-4-methylphenyl)-2-(trifluoromethyl)isonicotinamide | $^1$H NMR (400 MHz, <dmso>) δ ppm 1.33 (t, J = 7.04 Hz, 3H) 2.23 (s, 3H) 4.39 (d, J = 7.04 Hz, 2H) 4.58-4.68 (m, 2H) 4.96-5.07 (m, 2H) 6.12 (s, 1H) 7.20-7.38 (m, 1H) 7.64 (s, 3H) 8.03-8.12 (m, 1H) 8.15-8.22 (m, 1H) 8.30-8.38 (m, 1H) 8.92-9.04 (m, 1H) 10.55-10.70 (m, 1H). LCMS (m/z) (M + H) = 474.0, Rt = 0.88 min. |
| 125 | 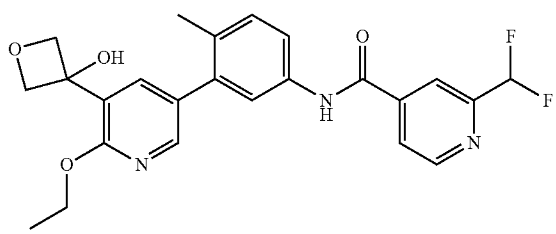 [SMILES: CCOc1ncc(-c2cc(NC(=O)c3ccnc(C(F)F)c3)ccc2C)cc1C1(O)COC1] | 2-(difluoromethyl)-N-(3-(6-ethoxy-5-(3-hydroxyoxetan-3-yl)pyridin-3-yl)-4-methylphenyl)isonicotinamide | $^1$H NMR (400 MHz, <dmso>) δ ppm 1.33 (s, 3H) 2.22 (s, 3H) 4.30-4.45 (m, 2H) 4.56-4.67 (m, 2H) 4.96-5.08 (m, 2H) 6.11 (s, 1H) 6.89-7.35 (m, 2H) 7.60-7.75 (m, 3H) 7.98-8.21 (m, 3H) 8.78-8.95 (m, 1H) 10.55-10.66 (m, 1H). LCMS (m/z) (M + H) = 456.0, Rt = 0.81 min. |
| 126 | 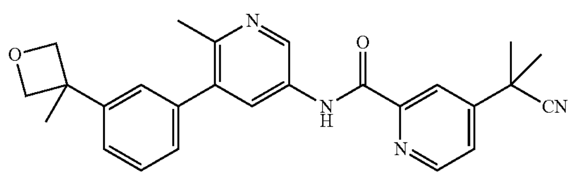 [SMILES: Cc1ncc(NC(=O)c2cc(C(C)(C)C#N)ccn2)cc1-c1cccc(C2(C)COC2)c1] | 4-(2-cyanopropan-2-yl)-N-(6-methyl-5-(3-(3-methyloxetan-3-yl)phenyl)pyridin-3-yl)picolinamide | 1H NMR (400 MHz, <dmso>) δ ppm 1.66 (s, 3H) 1.75 (s, 6H) 4.56 (d, J = 5.48 Hz, 2H) 4.78-4.91 (m, 2H) 7.26-7.38 (m, 3H) 7.44-7.56 (m, 1H) 7.86 (dd, J = 5.48, 1.96 Hz, 1H) 8.27 (d, J = 1.56 Hz, 1H) 8.34-8.44 (m, 1H) 8.77-8.84 (m, 1H) 9.08-9.16 (m, 1H) 10.98-11.36 (m, 1H). LCMS (m/z) (M + H) = 427.1, Rt = 0.70 min. |
| 127 | 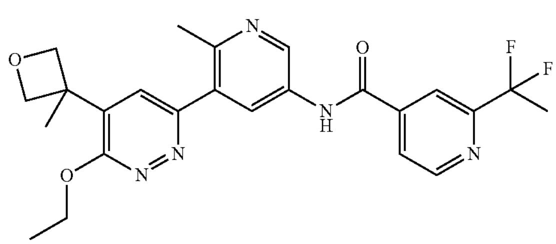 | 2-(1,1-difluoroethyl)-N-(5-(6-ethoxy-5-(3-methyloxetan-3-yl)pyridazin-3-yl)-6-methylpyridin-3-yl)isonicotinamide | 1H NMR (400 MHz, <dmso>) δ ppm 1.36 (t, J = 6.85 Hz, 2H) 1.59-1.76 (m, 6H) 3.80 (s, 3H) 4.45 (d, J = 6.26 Hz, 2H) 4.54 (d, J = 7.04 Hz, 2H) 4.90 (d, J = 6.26 Hz, 2H) 7.65 (s, 1H) 7.84 (d, J = 3.91 Hz, 1H) 8.05 (s, 1H) 8.25 (d, J = 1.96 Hz, 1H) 8.77 (d, J = 5.09 Hz, 1H) 8.92 (d, J = 2.35 Hz, 1H) 10.83 (s, 1H). LCMS (m/z) (M + H) = 466.1, Rt = 0.66 min. |
| 128 | 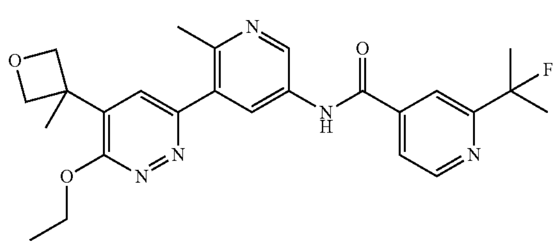 | N-(5-(6-ethoxy-5-(3-methyloxetan-3-yl)pyridazin-3-yl)-6-methylpyridin-3-yl)-2-(2-fluoropropan-2-yl)isonicotinamide | LCMS (m/z) (M + H) = 470.1, Rt = 0.67 min. |

TABLE 2-continued

| Example | Structure | Name | Physical Data |
|---|---|---|---|
| 129 | 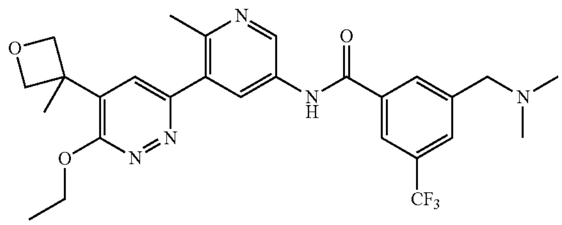 [SMILES: CCOc1nnc(-c2cc(NC(=O)c3cc(CN(C)C)cc(C(F)(F)F)c3)cnc2C)cc1C1(C)COC1] | 3-((dimethylamino)methyl)-N-(5-(6-ethoxy-5-(3-methyloxetan-3-yl)pyridazin-3-yl)-6-methylpyridin-3-yl)-5-(trifluoromethyl)benzamide | LCMS (m/z) (M + H) = 530.1, Rt = 0.59 min. |
| 130 | 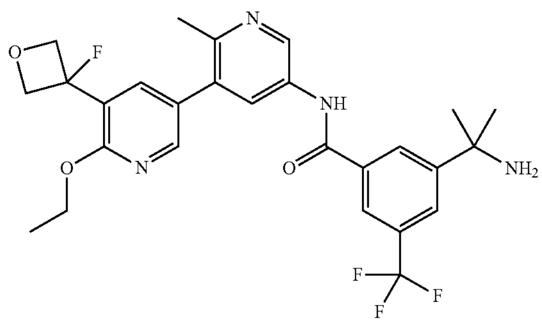 [SMILES: CCOc1ncc(-c2cc(NC(=O)c3cc(C(C)(C)N)cc(C(F)(F)F)c3)cnc2C)cc1C1(F)COC1] | 3-(2-aminopropan-2-yl)-N-(6'-ethoxy-5'-(3-fluorooxetan-3-yl)-2-methyl-[3,3'-bipyridin]-5-yl)-5-(trifluoromethyl)benzamide | $^1$H NMR (400 MHz, <cd3od>) δ ppm 1.47 (t, J = 7.04 Hz, 3H) 1.86 (s, 6H) 2.62 (s, 3H) 4.56 (q, J = 7.04 Hz, 2H) 4.95-5.09 (m, 2H) 5.19-5.36 (m, 2H) 7.86-7.90 (m, 1H) 8.12 (s, 1H) 8.31 (dd, J = 2.35, 1.56 Hz, 1H) 8.35 (d, J = 2.35 Hz, 1H) 8.44 (d, J = 0.78 Hz, 1H) 8.47-8.50 (m, 1H) 9.14 (d, J = 2.35 Hz, 1H). LCMS (m/z) (M + H) = 533.1, Rt = 0.65 min. |
| 131 | 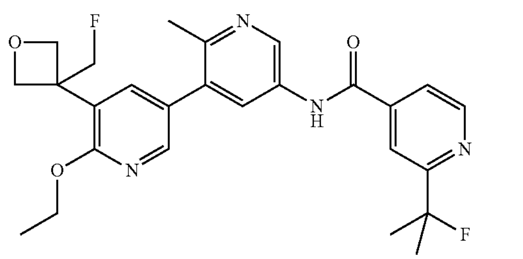 [SMILES: CCOc1ncc(-c2cc(NC(=O)c3ccnc(C(C)(C)F)c3)cnc2C)cc1C1(CF)COC1] | N-(6'-ethoxy-5'-(3-(fluoromethyl)oxetan-3-yl)-2-methyl-[3,3'-bipyridin]-5-yl)-2-(2-fluoropropan-2-yl)isonicotinamide | $^1$H NMR (400 MHz, <cd3od>) δ ppm 1.40 (t, J = 7.04 Hz, 3H) 1.67-1.82 (m, 6H) 2.68 (s, 3H) 4.47 (d, J = 7.04 Hz, 2H) 4.75-4.81 (m, 3H) 4.92 (s, 1H) 5.02 (dd, J = 6.65, 3.13 Hz, 2H) 7.60 (d, J = 2.35 Hz, 1H) 7.83 (dd, J = 5.09, 1.57 Hz, 1H) 8.14 (s, 1H) 8.23 (d, J = 2.35 Hz, 1H) 8.45 (d, J = 2.35 Hz, 1H) 8.76 (d, J = 5.09 Hz, 1H) 9.34 (d, J = 2.35 Hz, 1H). LCMS (m/z) (M + H) = 483.3, Rt = 0.80 min. |
| 132 | 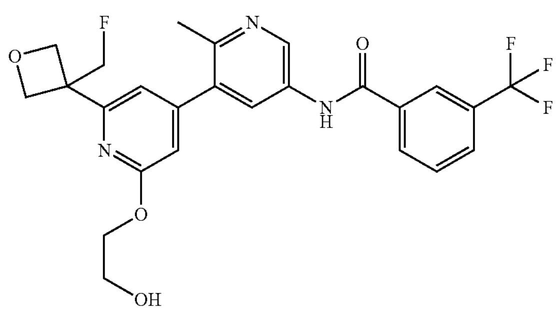 [SMILES: Cc1ncc(NC(=O)c2cccc(C(F)(F)F)c2)cc1-c1cc(OCCO)nc(C2(CF)COC2)c1] | N-(2'-(3-(fluoromethyl)oxetan-3-yl)-6'-(2-hydroxyethoxy)-2-methyl-[3,4'-bipyridin]-5-yl)-3-(trifluoromethyl)benzamide | $^1$H NMR (400 MHz, <dmso>) δ ppm 10.72 (s, 1H) 8.92 (d, J = 2.24 Hz, 1H) 8.33 (s, 1H) 8.29 (d, J = 7.83 Hz, 1H) 8.10 (d, J = 2.35 Hz, 1H) 8.00 (dd, J = 7.82, 0.78 Hz, 1H) 7.82 (t, J = 7.83 Hz, 1H) 7.09 (d, J = 1.17 Hz, 1H) 6.83 (d, J = 1.17 Hz, 1H) 4.99 (s, 1H) 4.94 (dd, J = 6.06, 3.33 Hz, 2H) 4.87 (s, 1H) 4.71 (d, J = 6.26 Hz, 2H) 4.30-4.37 (m, 2H) 3.71-3.78 (m, 2H) 3.41 (br. s., 6H) 2.45 (s, 3H). LCMS (m/z) (M + H) = 506.1, Rt = 0.72 min. |
| 133 | 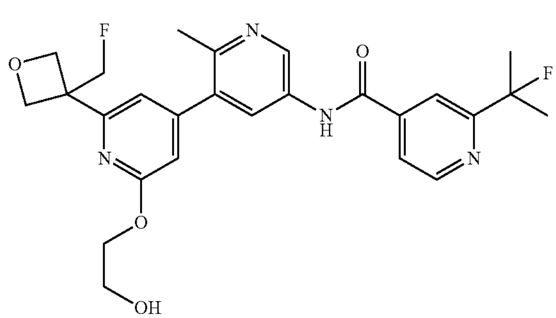 [SMILES: Cc1ncc(NC(=O)c2ccnc(C(C)(C)F)c2)cc1-c1cc(OCCO)nc(C2(CF)COC2)c1] | N-(2'-(3-(fluoromethyl)oxetan-3-yl)-6'-(2-hydroxyethoxy)-2-methyl-[3,4'-bipyridin]-5-yl)-2-(2-fluoropropan-2-yl)isonicotinamide | $^1$H NMR (400 MHz, <dmso>) δ ppm 10.80 (s, 1H) 8.90 (d, J = 2.35 Hz, 1H) 8.78 (dt, J = 5.09, 0.98 Hz, 1H) 8.03-8.10 (m, 2H) 7.84 (dd, J = 5.09, 1.56 Hz, 1H) 7.09 (d, J = 1.17 Hz, 1H) 6.82 (d, J = 1.17 Hz, 1H) 4.98 (s, 1H) 4.94 (dd, J = 6.26, 3.13 Hz, 2H) 4.86 (s, 1H) 4.84 (t, J = 5.67 Hz, 1H) 4.71 (d, J = 6.26 Hz, 2H) 4.32-4.37 (m, 2H) 3.75 (q, J = 5.48 Hz, 2H) 2.44 (s, 3H) 1.64-1.77 (m, 6H). LCMS (m/z) (M + H) = 499.2, Rt = 0.65 min. |

TABLE 2-continued

| Example | Name | Physical Data |
|---|---|---|
| 134 | N-(3'-(3-fluorooxetan-3-yl)-5'-(3-hydroxyoxetan-3-yl)-6-methyl-[1,1'-biphenyl]-3-yl)-3-(trifluoromethyl)benzamide | $^1$H NMR (400 MHz, <dmso>) δ ppm 10.47 (s, 1H) 8.24-8.32 (m, 2H) 7.97 (d, J = 7.82 Hz, 1H) 7.73-7.82 (m, 3H) 7.69 (d, J = 2.35 Hz, 1H) 7.64 (t, J = 1.37 Hz, 1H) 7.45-7.48 (m, 1H) 7.33 (d, J = 8.22 Hz, 1H) 6.54 (s, 1H) 4.95-5.07 (m, 4H) 4.73-4.84 (m, 4H) 2.24 (s, 3H). LCMS (m/z) (M + H) = 502.2, Rt = 0.90 min. |
| 135 | N-(3'-(3-fluorooxetan-3-yl)-5'-(3-hydroxyoxetan-3-yl)-6-methyl-[1,1'-biphenyl]-3-yl)-2-(trifluoromethyl)isonicotinamide | $^1$H NMR (400 MHz, <dmso>) δ ppm 10.69 (s, 1H) 8.99 (d, J = 5.09 Hz, 1H) 8.37 (s, 1H) 8.20 (dd, J = 4.69, 1.17 Hz, 1H) 7.72-7.79 (m, 2H) 7.69 (d, J = 1.96 Hz, 1H) 7.64 (t, J = 1.37 Hz, 1H) 7.45-7.49 (m, 1H) 7.36 (d, J = 8.61 Hz, 1H) 6.54 (s, 1H) 4.94-5.08 (m, 4H) 4.72-4.86 (m, 4H) 2.25 (s, 3H). LCMS (m/z) (M + H) = 503.2, Rt = 0.91 min. |
| 136 | 2-(1,1-difluoroethyl)-N-(3'-(3-fluorooxetan-3-yl)-5'-(3-hydroxyoxetan-3-yl)-6-methyl-[1,1'-biphenyl]-3-yl)isonicotinamide | $^1$H NMR (400 MHz, <dmso>) δ ppm 10.65 (s, 1H) 8.82-8.91 (m, 1H) 8.15-8.21 (m, 1H) 8.03 (dd, J = 5.09, 1.56 Hz, 1H) 7.72-7.80 (m, 2H) 7.70 (d, J = 2.35 Hz, 1H) 7.64 (t, J = 1.57 Hz, 1H) 7.44-7.50 (m, 1H) 7.35 (d, J = 8.61 Hz, 1H) 6.54 (s, 1H) 4.94-5.07 (m, 4H) 4.74-4.85 (m, 4H) 2.25 (s, 3H) 1.99-2.11 (m, 3H). LCMS (m/z) (M + H) = 499.2, Rt = 0.90 min. |
| 137 | N-(3'-(3-fluorooxetan-3-yl)-5'-(3-hydroxyoxetan-3-yl)-6-methyl-[1,1'-biphenyl]-3-yl)-2-(2-fluoropropan-2-yl)isonicotinamide | $^1$H NMR (400 MHz, <dmso>) δ ppm 10.57 (s, 1H) 8.75 (dt, J = 5.09, 0.98 Hz, 1H) 8.02 (s, 1H) 7.82 (dd, J = 5.09, 1.57 Hz, 1H) 7.72-7.79 (m, 2H) 7.69 (d, J = 2.35 Hz, 1H) 7.64 (t, J = 1.37 Hz, 1H) 7.43-7.50 (m, 1H) 7.34 (d, J = 8.61 Hz, 1H) 6.54 (s, 1H) 4.94-5.07 (m, 4H) 4.74-4.85 (m, 4H) 2.25 (s, 3H) 1.65-1.75 (m, 6H). LCMS (m/z) (M + H) = 495.2, Rt = 0.88 min. |
| 138 | 2-(2-cyanopropan-2-yl)-N-(3'-(3-fluorooxetan-3-yl)-5'-(3-hydroxyoxetan-3-yl)-6-methyl-[1,1'-biphenyl]-3-yl)isonicotinamide | $^1$H NMR (400 MHz, <dmso>) δ ppm 10.56 (s, 1H) 8.80 (dd, J = 5.09, 0.78 Hz, 1H) 7.98-8.04 (m, 1H) 7.87 (dd, J = 5.09, 1.57 Hz, 1H) 7.76-7.78 (m, 1H) 7.74 (dd, J = 8.22, 2.35 Hz, 1H) 7.68 (d, J = 2.35 Hz, 1H) 7.64 (t, J = 1.37 Hz, 1H) 7.47 (d, J = 0.78 Hz, 1H) 7.35 (d, J = 8.61 Hz, 1H) 6.54 (s, 1H) 4.95-5.07 (m, 4H) 4.74-4.84 (m, 4H) 2.25 (s, 3H) 1.76 (s, 6H). LCMS (m/z) (M + H) = 502.3, Rt = 0.77 min. |

TABLE 2-continued

| Example | Structure | Name | Physical Data |
|---|---|---|---|
| 139 | 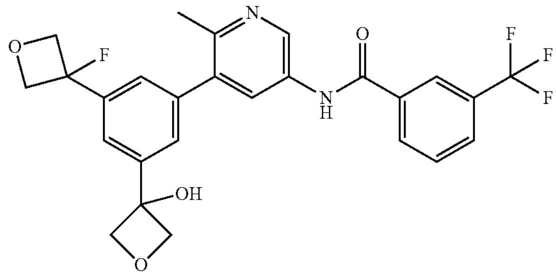 [SMILES: Cc1ncc(NC(=O)c2cccc(C(F)(F)F)c2)cc1-c1cc(C2(O)COC2)cc(C2(F)COC2)c1] | N-(5-(3-(3-fluorooxetan-3-yl)-5-(3-hydroxyoxetan-3-yl)phenyl)-6-methylpyridin-3-yl)-3-(trifluoromethyl)benzamide | $^1$H NMR (400 MHz, <dmso>) δ ppm 10.68 (s, 1H) 8.89 (d, J = 2.35 Hz, 1H) 8.26-8.35 (m, 3H) 8.08-8.12 (m, 1H) 8.00 (d, J = 7.82 Hz, 1H) 7.77-7.85 (m, 2H) 7.70 (t, J = 1.57 Hz, 1H) 7.55 (q, J = 1.56 Hz, 1H) 6.57 (s, 1H) 4.93-5.10 (m, 4H) 4.74-4.85 (m, 4H) 2.45 (s, 3H). LCMS (m/z) (M + H) = 503.0, Rt = 0.71 min. |
| 140 | 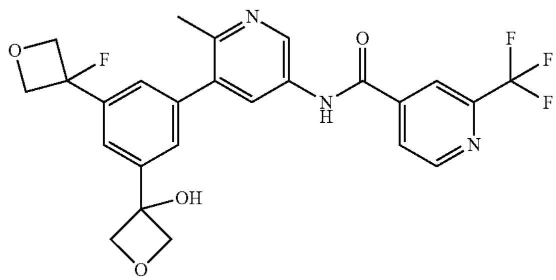 | N-(5-(3-(3-fluorooxetan-3-yl)-5-(3-hydroxyoxetan-3-yl)phenyl)-6-methylpyridin-3-yl)-3-(trifluoromethyl)isonicotinamide | $^1$H NMR (400 MHz, <dmso>) δ ppm 10.90 (s, 1H) 9.02 (d, J = 4.69 Hz, 1H) 8.84-8.93 (m, 1H) 8.39 (s, 1H) 8.22 (dd, J = 4.69, 1.17 Hz, 1H) 8.03-8.15 (m, 1H) 7.80-7.84 (m, 1H) 7.70 (t, J = 1.37 Hz, 1 H) 7.56 (q, J = 1.56 Hz, 1H) 6.85 (s, 1H) 4.92-5.16 (m, 4H) 4.70-4.91 (m, 4H) 2.46 (s, 3H). LCMS (m/z) (M + H) = 504.0, Rt = 0.63 min. |
| 141 | 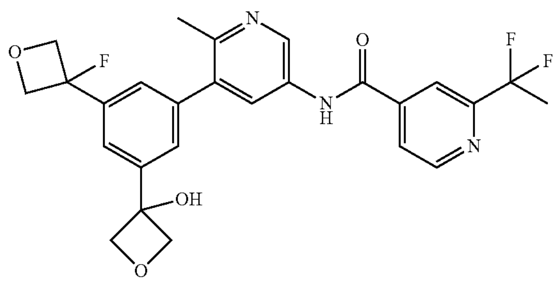 [SMILES: Cc1ncc(NC(=O)c2ccnc(C(C)(F)F)c2)cc1-c1cc(C2(O)COC2)cc(C2(F)COC2)c1] | 2-(1,1-difluoroethyl)-N-(5-(3-(3-fluorooxetan-3-yl)-5-(3-hydroxyoxetan-3-yl)phenyl)-6-methylpyridin-3-yl)isonicotinamide | $^1$H NMR (400 MHz, <dmso>) δ ppm 10.85 (s, 1H) 8.87-8.93 (m, 2H) 8.22 (s, 1H) 8.08-8.11 (m, 1 H) 8.05 (dd, J = 5.09, 1.57 Hz, 1H) 7.81 (d, J = 0.78 Hz, 1H) 7.70 (t, J = 1.57 Hz, 1H) 7.53-7.57 (m, 1 H) 6.57 (s, 1H) 4.93-5.11 (m, 4 H) 4.74-4.86 (m, 4H) 2.45 (s, 3 H) 2.06 (t, J = 19.17 Hz, 3H). LCMS (m/z) (M + H) = 500.1, Rt = 0.60 min. |
| 142 | 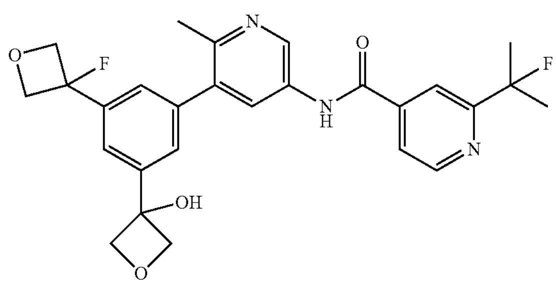 [SMILES: Cc1ncc(NC(=O)c2ccnc(C(C)(C)F)c2)cc1-c1cc(C2(O)COC2)cc(C2(F)COC2)c1] | N-(5-(3-(3-fluorooxetan-3-yl)-5-(3-hydroxyoxetan-3-yl)phenyl)-6-methylpyridin-3-yl)-2-(2-fluoropropan-2-yl)isonicotinamide | $^1$H NMR (400 MHz, <dmso>) δ ppm 10.78 (s, 1H) 8.86-8.93 (m, 1H) 8.72-8.81 (m, 1H) 8.00-8.13 (m, 2H) 7.85 (dd, J = 4.89, 1.76 Hz, 1H) 7.81 (d, J = 0.78 Hz, 1 H) 7.69 (t, J = 1.56 Hz, 1H) 7.55 (q, J = 1.56 Hz, 1H) 6.57 (s, 1H) 4.93-5.10 (m, 4H) 4.75-4.86 (m, 4H) 2.45 (s, 3H) 1.66-1.76 (m, 6H). LCMS (m/z) (M + H) = 496.1, Rt = 0.62 min. |
| 143 | 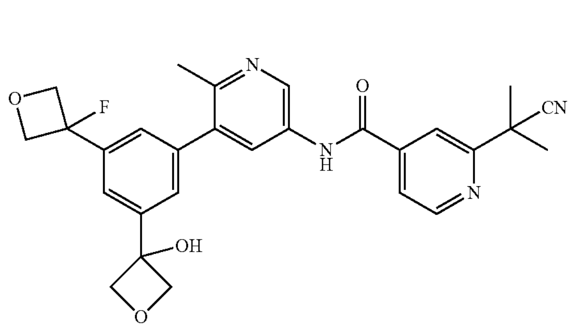 [SMILES: Cc1ncc(NC(=O)c2ccnc(C(C)(C)C#N)c2)cc1-c1cc(C2(O)COC2)cc(C2(F)COC2)c1] | 2-(2-cyanopropan-2-yl)-N-(5-(3-(3-fluorooxetan-3-yl)-5-(3-hydroxyoxetan-3-yl)phenyl)-6-methylpyridin-3-yl)isonicotinamide | $^1$H NMR (400 MHz, <dmso>) δ ppm 10.78 (s, 1H) 8.86-8.90 (m, 1H) 8.83 (dd, J = 5.09, 0.78 Hz, 1 H) 8.06-8.10 (m, 1H) 8.02-8.05 (m, 1H) 7.89 (dd, J = 5.09, 1.56 Hz, 1H) 7.79-7.83 (m, 1H) 7.70 (t, J = 1.56 Hz, 1H) 7.53-7.57 (m, 1 H) 6.57 (s, 1H) 4.93-5.10 (m, 4 H) 4.75-4.85 (m, 4H) 2.46 (s, 3 H) 1.77 (s, 6H). LCMS (m/z) (M + H) = 503.1, Rt = 0.60 min. |

TABLE 2-continued

| Example | Name | Physical Data |
|---|---|---|
| 144 | 2-(1,1-difluoroethyl)-N-(3-(5-(3-hydroxyoxetan-3-yl)-6-(1-methyl-1H-pyrazol-4-yl)pyridin-3-yl)-4-methylphenyl)isonicotinamide | 1H NMR (400 MHz, <dmso>) δ ppm 2.05 (t, J = 20.0 Hz, 3H) 2.30 (s, 3H) 3.91 (s, 3H) 4.70 (d, J = 5.0 Hz, 2H) 4.76 (d, J = 5.0 Hz, 2H) 6.78 (s, 1H) 7.38 (d, J = 5.0 Hz, 1H) 7.72-7.76 (m, 3H) 7.94 (s, 1H) 8.03 (d, J = 5.0 Hz, 1H) 8.19 (s, 2H) 8.55 (m, 1H) 8.88 (d, J = 5.0, 1H) 10.69 (s, 1H). LCMS (m/z) (M + H) = 506.1, Rt = 0.64 min. |
| 145 | 3-(5-(3-hydroxyoxetan-3-yl)-6-methoxypyridin-3-yl)-4-methyl-N-(2-(methylsulfonyl)pyridin-4-yl)benzamide | $^1$H NMR (400 MHz, <dmso>) δ ppm 2.32-2.35 (m, 3H) 3.25 (s, 3 H) 3.93 (s, 3H) 4.59-4.68 (m, 2 H) 4.96-5.06 (m, 2H) 6.09-6.17 (m, 1H) 7.48-7.54 (m, 1H) 7.70-7.76 (m, 1H) 7.89-7.97 (m, 2H) 8.08-8.14 (m, 1H) 8.15-8.22 (m, 1H) 8.45-8.52 (m, 1H) 8.60-8.69 (m, 1H) 10.86-10.95 (m, 1 H). LCMS (m/z) (M + H) = 470.0, Rt = 0.71 min. |
| 146 | N-(3-(2-cyanopropan-2-yl)phenyl)-3-(5-(3-hydroxyoxetan-3-yl)-6-methoxypyridin-3-yl)-4-methylbenzamide | $^1$H NMR (400 MHz, <dmso>) δ ppm 1.67 (s, 6H) 2.32 (s, 3H) 3.93 (s, 3H) 4.63 (d, J = 7.04 Hz, 2 H) 5.01 (d, J = 7.04 Hz, 2H) 6.14 (s, 1H) 7.16-7.28 (m, 1H) 7.35-7.44 (m, 1H) 7.45-7.54 (m, 1H) 7.72 (d, J = 2.35 Hz, 1H) 7.77-7.83 (m, 1H) 7.84-7.97 (m, 3H) 8.18 (d, J = 2.35 Hz, 1H) 10.29 (s, 1 H). LCMS (m/z) (M + H) = 458.2, Rt = 0.86 min. |
| 147 | 6-(2-aminopropan-2-yl)-N-(3-(6-ethoxy-5-(3-hydroxyoxetan-3-yl)pyridin-3-yl)-4-methylphenyl)-4-(trifluoromethyl)picolinamide | $^1$H NMR (400 MHz, <dmso>) δ ppm 1.33 (s, 3H) 1.62 (s, 6H) 2.24 (s, 3H) 4.26-4.48 (m, 2H) 4.57-4.67 (m, 2H) 4.96-5.07 (m, 2H) 6.05-6.18 (m, 1H) 7.28-7.42 (m, 1H) 7.61-7.69 (m, 2H) 7.74-7.85 (m, 1H) 8.05-8.16 (m, 1H) 8.20-8.30 (m, 2H) 10.51-10.61 (m, 1H). LCMS (m/z) (M + H) = 531.0, Rt = 0.78 min. |
| 148 | 6-(2-aminopropan-2-yl)-N-(5'-(3-(difluoromethyl)oxetan-3-yl)-6'-methoxy-2-methyl-[3,3'-bipyridin]-5-yl)-4-(trifluoromethyl)picolinamide | $^1$H NMR (400 MHz, <dmso>) δ ppm 10.70 (s, 1H) 8.99 (d, J = 2.35 Hz, 1H) 8.27 (d, J = 2.35 Hz, 1H) 8.20 (d, J = 5.09 Hz, 2H) 8.10 (d, J = 2.35 Hz, 1H) 7.72 (d, J = 2.35 Hz, 1H) 6.46 (d, J = 56.0 Hz, 1H) 5.76 (s, 1H) 4.93 (d, J = 7.04 Hz, 2 H) 4.83 (d, J = 7.04 Hz, 2H) 3.92 (s, 3H) 2.45 (s, 3H) 1.53 (s, 6H). LCMS (m/z) (M + H) = 552.2, Rt = 0.63 min. |
| 149 | 6-(2-aminopropan-2-yl)-N-(3-(5-(3-(difluoromethyl)oxetan-3-yl)-6-methoxypyridin-3-yl)-4-methylphenyl)-4-(trifluoromethyl)picolinamide | $^1$H NMR (400 MHz, <dmso>) δ ppm 10.52 (s, 1H) 8.12-8.23 (m, 3H) 7.86 (dd, J = 8.22, 2.35 Hz, 1 H) 7.71 (d, J = 2.35 Hz, 1H) 7.62 (d, J = 2.35 Hz, 1H) 7.36 (d, J = 8.61 Hz, 1H) 6.45 (t, J = 56.0 Hz, 1H) 4.92 (d, J = 7.04 Hz, 2H) 4.83 (d, J = 7.04 Hz, 2H) 3.91 (s, 3H) 2.23 (s, 3H) 1.52 (s, 6H). LCMS (m/z) (M + H) = 551.2, Rt = 0.84 min. |

TABLE 2-continued

| Example | Structure | Name | Physical Data |
|---|---|---|---|
| 150 | 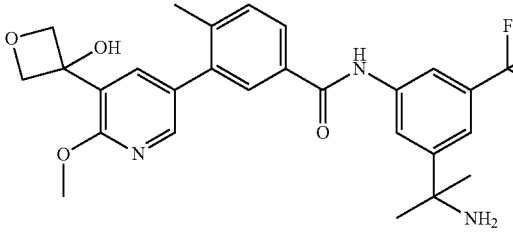 | N-(3-(2-aminopropan-2-yl)-5-(trifluoromethyl)phenyl)-3-(5-(3-hydroxyoxetan-3-yl)-6-methoxypyridin-3-yl)-4-methylbenzamide | LCMS (m/z) (M + H) = 516.1, Rt = 0.73 min. |
| 151 | 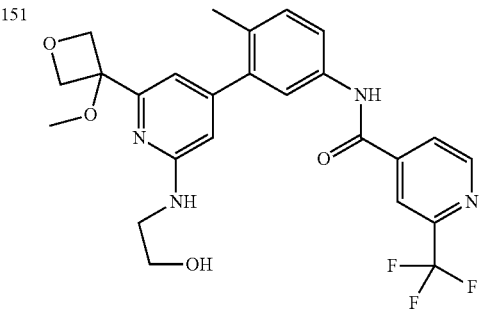 | N-(3-(2-((2-hydroxyethyl)amino)-6-(3-methoxyoxetan-3-yl)pyridin-3-yl)-4-methylphenyl)-2-(trifluoromethyl)isonicotinamide | $^1$H NMR (400 MHz, <cd3od>) δ ppm 8.92 (d, J = 5.09 Hz, 1H) 8.31 (s, 1H) 8.14 (dd, J = 5.09, 1.57 Hz, 1H) 7.68 (dd, J = 8.22, 2.35 Hz, 1 H) 7.64 (d, J = 2.35 Hz, 1H) 7.33 (d, J = 8.22 Hz, 1H) 6.66 (d, J = 1.17 Hz, 1H) 6.48 (d, J = 1.56 Hz, 1H) 5.07-5.12 (m, 2H) 4.81-4.85 (m, 2H) 3.75-3.82 (m, 2H) 3.54-3.61 (m, 2H) 3.27 (s, 3H) 2.29 (s, 3H). LCMS (m/z) (M + H) = 503.0, Rt = 0.71 min. |
| 152 | 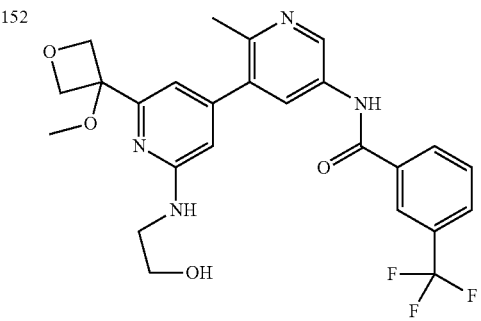 | N-(2'-((2-hydroxyethyl)amino)-6'-(3-methoxyoxetan-3-yl)-2-methyl-[3,4'-bipyridin]-5-yl)-3-(trifluoromethyl)benzamide | $^1$H NMR (400 MHz, <cd3od>) δ ppm 8.88 (d, J = 2.35 Hz, 1H) 8.30-8.34 (m, 1H) 8.26 (d, J = 7.83 Hz, 1H) 8.17 (d, J = 2.74 Hz, 1H) 7.94 (dd, J = 7.82, 0.78 Hz, 1H) 7.77 (t, J = 7.83 Hz, 1H) 6.74 (d, J = 1.17 Hz, 1H) 6.56 (d, J = 1.17 Hz, 1H) 5.09 (d, J = 7.04 Hz, 2H) 4.85 (d, J = 0.78 Hz, 2H) 3.77-3.84 (m, 2H) 3.57-3.63 (m, 2H) 3.30 (s, 3H) 2.52 (s, 3H). LCMS (m/z) (M + H) = 503.1, Rt = 0.62 min. |
| 153 | 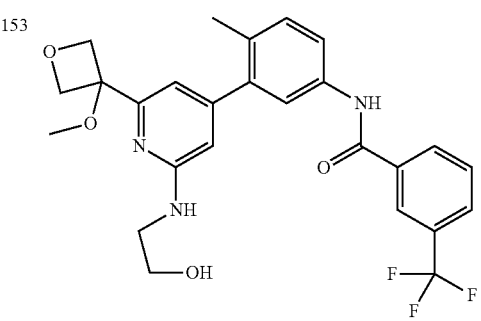 | N-(3-(2-((2-hydroxyethyl)amino)-6-(3-methoxyoxetan-3-yl)pyridin-4-yl)-4-methylphenyl)-3-(trifluoromethyl)benzamide | $^1$H NMR (400 MHz, <cd3od>) δ ppm 8.28 (s, 1H) 8.22 (d, J = 7.83 Hz, 1H) 7.91 (d, J = 7.83 Hz, 1H) 7.72-7.79 (m, 1H) 7.62-7.68 (m, 2H) 7.33 (d, J = 8.22 Hz, 1H) 6.70 (s, 1H) 6.51 (s, 1H) 5.09 (d, J = 7.04 Hz, 2H) 4.85 (d, J = 6.65 Hz, 2H) 3.79 (t, J = 5.48 Hz, 2H) 3.55-3.62 (m, 2H) 3.28 (s, 3H) 2.30 (s, 3H). LCMS (m/z) (M + H) = 502.0, Rt = 0.79 min. |
| 154 | 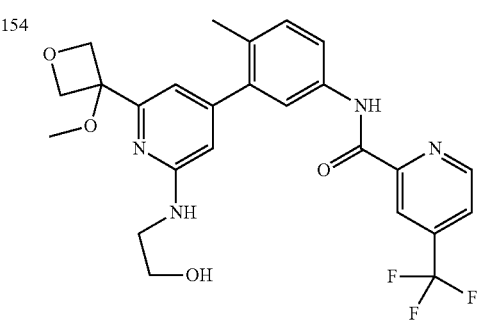 | N-(3-(2-((2-hydroxyethyl)amino)-6-(3-methoxyoxetan-3-yl)pyridin-4-yl)-4-methylphenyl)-4-(trifluoromethyl)picolinamide | $^1$H NMR (400 MHz, <cd3od>) δ ppm 8.98 (d, J = 5.09 Hz, 1H) 8.45 (d, J = 0.78 Hz, 1H) 7.94 (dt, J = 5.09, 0.98 Hz, 1H) 7.74 (dq, J = 4.50, 2.28 Hz, 2H) 7.31-7.37 (m, 1H) 6.68 (d, J = 1.56 Hz, 1 H) 6.49 (d, J = 1.17 Hz, 1H) 5.06-5.13 (m, 2H) 4.84 (dd, J = 6.65, 0.78 Hz, 2H) 3.79 (t, J = 5.67 Hz, 2 H) 3.55-3.62 (m, 2H) 3.28 (s, 3 H) 2.29 (s, 3H). LCMS (m/z) (M + H) = 503.1, Rt = 0.79 min. |

TABLE 2-continued

| Example | Structure | Name | Physical Data |
|---|---|---|---|
| 155 | 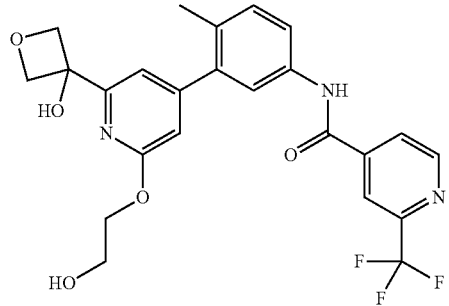 [SMILES: Cc1ccc(NC(=O)c2ccnc(C(F)(F)F)c2)cc1-c1cc(OCCO)nc(C2(O)COC2)c1] | N-(3-(2-(2-hydroxyethoxy)-6-(3-hydroxyoxetan-3-yl)pyridin-4-yl)-4-methylphenyl)-2-(trifluoromethyl)isonicotinamide | $^1$H NMR (400 MHz, <cd3od>) δ ppm 8.92 (d, J = 5.09 Hz, 1H) 8.32 (s, 1H) 8.14 (d, J = 4.30 Hz, 1H) 7.70 (dd, J = 8.22, 2.35 Hz, 1H) 7.67 (d, J = 1.96 Hz, 1H) 7.36 (d, J = 8.22 Hz, 1H) 7.25 (d, J = 1.17 Hz, 1H) 6.76 (d, J = 1.17 Hz, 1H) 5.16 (d, J = 6.26 Hz, 2H) 4.83 (d, J = 6.26 Hz, 2H) 4.52-4.62 (m, 2H) 3.92-4.00 (m, 2H) 2.29 (s, 3H). LCMS (m/z) (M + H) = 490.0, Rt = 0.82 min. |
| 156 | 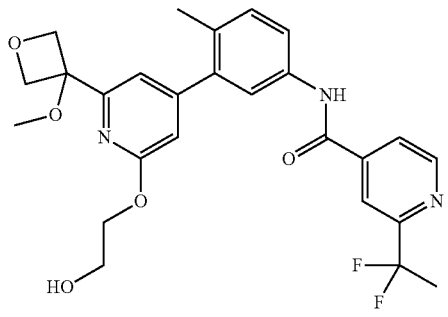 | 2-(1,1-difluoroethyl)-N-(3-(2-(2-hydroxyethoxy)-6-(3-methoxyoxetan-3-yl)pyridin-4-yl)-4-methylphenyl)isonicotinamide | $^1$H NMR (400 MHz, <cd3od>) δ ppm 8.80-8.85 (m, 1H) 8.18-8.21 (m, 1H) 7.98 (d, J = 5.09 Hz, 1H) 7.71 (dd, J = 8.22, 2.35 Hz, 1H) 7.67 (d, J = 2.35 Hz, 1H) 7.36 (d, J = 8.22 Hz, 1H) 7.08 (d, J = 1.17 Hz, 1H) 6.81 (d, J = 1.17 Hz, 1H) 5.12 (dd, J = 6.65, 0.78 Hz, 2H) 4.89 (d, J = 0.78 Hz, 2H) 4.51-4.57 (m, 2H) 3.92-4.00 (m, 2H) 3.31 (s, 3H) 2.29 (s, 3H) 2.05 (t, J = 18.78 Hz, 3H). LCMS (m/z) (M + H) = 500.2, Rt = 0.88 min. |
| 157 | 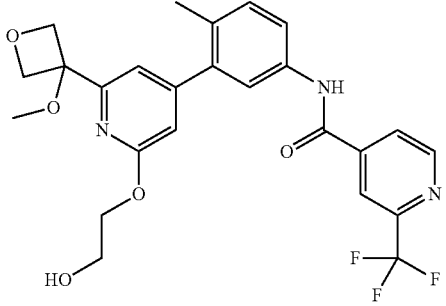 [SMILES: COC1(c2cc(-c3cc(NC(=O)c4ccnc(C(F)(F)F)c4)ccc3C)cc(OCCO)n2)COC1] | N-(3-(2-(2-hydroxyethoxy)-6-(3-methoxyoxetan-3-yl)pyridin-4-yl)-4-methylphenyl)-2-(trifluoromethyl)isonicotinamide | $^1$H NMR (400 MHz, <cd3od>) δ ppm 8.93 (d, J = 5.09 Hz, 1H) 8.32 (s, 1H) 8.14 (d, J = 3.52 Hz, 1H) 7.69-7.74 (m, 1H) 7.68 (d, J = 2.35 Hz, 1H) 7.36 (d, J = 8.61 Hz, 1H) 7.08 (d, J = 1.17 Hz, 1H) 6.80 (d, J = 1.17 Hz, 1H) 5.12 (d, J = 6.65 Hz, 2H) 4.90 (s, 2H) 4.51-4.58 (m, 2H) 3.91-4.00 (m, 2H) 3.31 (s, 3H) 2.30 (s, 3H). LCMS (m/z) (M + H) = 504.0, Rt = 0.90 min. |
| 158 | 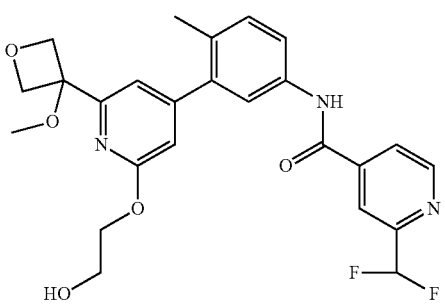 [SMILES: COC1(c2cc(-c3cc(NC(=O)c4ccnc(C(F)F)c4)ccc3C)cc(OCCO)n2)COC1] | 2-(difluoromethyl)-N-(3-(2-(2-hydroxyethoxy)-6-(3-methoxyoxetan-3-yl)pyridin-4-yl)-4-methylphenyl)isonicotinamide | $^1$H NMR (400 MHz, <cd3od>) δ ppm 8.85 (dd, J = 5.09, 0.78 Hz, 1H) 8.19 (s, 1H) 8.03 (d, J = 5.09 Hz, 1H) 7.71 (dd, J = 8.22, 2.35 Hz, 1H) 7.67 (d, J = 2.35 Hz, 1H) 7.36 (d, J = 8.22 Hz, 1H) 7.08 (d, J = 1.17 Hz, 1H) 6.69-7.00 (m, 2H) 5.12 (dd, J = 6.65, 0.78 Hz, 2H) 4.89 (d, J = 0.78 Hz, 2H) 4.52-4.57 (m, 2H) 3.95 (dd, J = 5.48, 4.30 Hz, 2H) 3.31 (s, 3H) 2.29 (s, 3H). LCMS (m/z) (M + H) = 486.2, Rt = 0.83 min. |
| 159 | 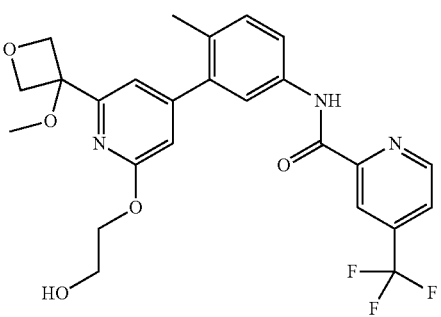 [SMILES: COC1(c2cc(-c3cc(NC(=O)c4cc(C(F)(F)F)ccn4)ccc3C)cc(OCCO)n2)COC1] | N-(3-(2-(2-hydroxyethoxy)-6-(3-methoxyoxetan-3-yl)pyridin-4-yl)-4-methylphenyl)-4-(trifluoromethyl)picolinamide | $^1$H NMR (400 MHz, <cd3od>) δ ppm 1H NMR (400 MHz, <cd3od>) d ppm 8.98 (d, J = 5.09 Hz, 1H) 8.42-8.47 (m, 1H) 7.94 (dd, J = 5.09, 1.17 Hz, 1H) 7.75-7.80 (m, 2H) 7.37 (d, J = 9.39 Hz, 1H) 7.09 (d, J = 1.17 Hz, 1H) 6.82 (d, J = 1.17 Hz, 1H) 5.12 (dd, J = 6.65, 0.78 Hz, 2H) 4.89 (dd, J = 6.65, 0.78 Hz, 2H) 4.51-4.85 (m, 2H) 3.92-3.99 (m, 2H) 3.32 (s, 3H) 2.30 (s, 3H). LCMS (m/z) (M + H) = 504.1, Rt = 1.01 min. |

TABLE 2-continued

| Example | Structure | Name | Physical Data |
|---|---|---|---|
| 160 | 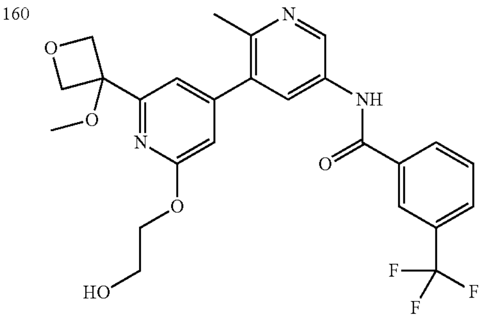 | N-(2'-(2-hydroxyethoxy)-6'-(3-methoxyoxetan-3-yl)-2-methyl-[3,4'-bipyridin]-5-yl)-3-(trifluoromethyl)benzamide | $^1$H NMR (400 MHz, <cd3od>) δ ppm 8.89 (d, J = 2.35 Hz, 1H) 8.32 (s, 1H) 8.26 (d, J = 7.82 Hz, 1H) 8.18 (d, J = 2.35 Hz, 1H) 7.91-7.97 (m, 1H) 7.73-7.81 (m, 1H) 7.15 (d, J = 1.56 Hz, 1H) 6.88 (d, J = 1.56 Hz, 1H) 5.12 (dd, J = 6.65, 0.78 Hz, 2H) 4.90 (dd, J = 6.65, 0.78 Hz, 2H) 4.53-4.59 (m, 2H) 3.93-3.99 (m, 2H) 3.33 (s, 3H) 2.51 (s, 3H). LCMS (m/z) (M + H) = 504.1, Rt = 0.58 min. |

Example 161

6-(2-cyanopropan-2-yl)-N-(6-ethoxy-2-methyl-5'-tetrahydro-2H-pyran-4-yl)-[3,3'-bipyridin]-5-yl)pyridazine-4-carboxamide

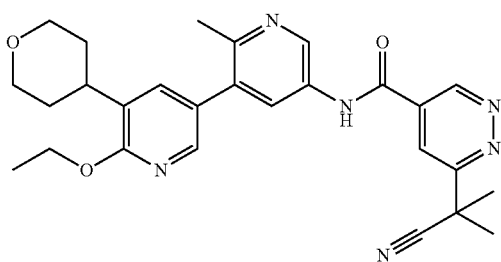

To a solution of 6-(2-cyanopropan-2-yl)pyridazine-4-carboxylic acid (1.2 equiv.) and 6'-ethoxy-2-methyl-5'-(tetrahydro-2H-pyran-4-yl)-[3,3'-bipyridin]-5-amine (1.0 equiv.) in DMA at rt was added HOAt (1.3 equiv.), EDC (1.3 equiv.) and DIEA (3.0 equiv.) and the mixture was stirred overnight at rt. The solution was diluted with water, filtered and purified via reverse phase prep-HPLC. The pure fractions were lyophilized to give 6-(2-cyanopropan-2-yl)-N-(6'-ethoxy-2-methyl-5'-(tetrahydro-2H-pyran-4-yl)-[3,3'-bipyridin]-5-yl)pyridazine-4-carboxamide in 7% yield. $^1$H NMR (400 MHz, <cd3od>) δ ppm 1.44 (t, J=7.04 Hz, 3H) 1.84 (dd, J=8.80, 3.33 Hz, 4H) 1.93 (s, 6H) 2.62 (s, 3H) 3.19 (br. s., 1H) 3.60 (td, J=11.05, 3.72 Hz, 2H) 4.06 (d, J=10.56 Hz, 2H) 4.48 (q, J=7.04 Hz, 2H) 7.67 (d, J=1.96 Hz, 1H) 8.09 (d, J=2.35 Hz, 1H) 8.31 (d, J=1.96 Hz, 1H) 8.41 (d, J=0.96 Hz, 1H) 9.15 (s, 1H) 9.66 (d, J=1.96 Hz, 1H). LCMS (m/z) (M+H)=487.1. Rt=0.71 min.

Example 162

N-(3-(2-(2-hydroxyethoxy)-6-(3-hydroxytetrahydro-2H-pyran-4-yl)pyridin-4-yl)-4-methylphenyl)-2-(trifluoromethyl)isonicotinamide

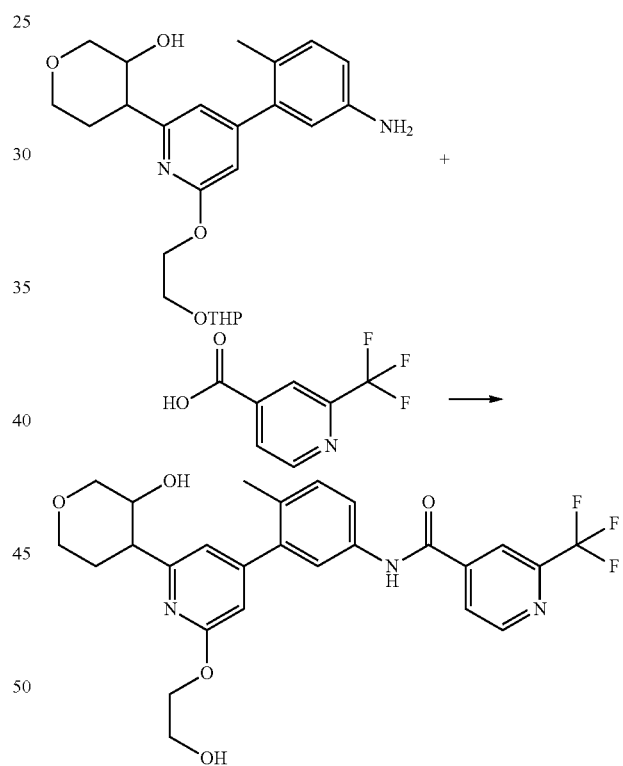

Into a 20 mL vial was charged 4-(trifluoromethyl)picolinic acid (1.0 equiv), HOAT (1.2 equiv), EDC.HCl (1.2 equiv.) and 4-(4-(5-amino-2-methylphenyl)-6-(2-((tetrahydro-2H-pyran-2-yl)oxy)ethoxy)pyridin-2-yl)tetrahydro-2H-pyran-3-ol (1.0 equiv.). The mixture was dissolved in DMF (0.2 M) and agitated at room temperature for 1 h and then diluted with EtOAc and brine. The organic layer was passed through a plug of anhydrous $Na_2SO_4$ and then concentrated in vacuo. The residue was dissolved in MeOH (0.05) and treated with 4 N HCl in dioxane (40 equiv.). The mixture was agitated at room temperature for 30 min and concentrated in vacuo. The residue was dissolved in DMSO and purified by reverse phase HPLC and the product fractions were combined and lyophillized to afford. The product fractions were combined and lyophillized to afford N-(3-(2-(2-hydroxyethoxy)-6-(3-hydroxytetrahydro-2H-pyran-4-yl)pyridin-4-yl)-4-methylphenyl)-2-(trifluoromethyl)isonicotinamide in 30.4% yield. $^1$H NMR (400 MHz, DMSO-d6) δ ppm 10.84 (s, 1H) 9.03 (d, J=5.01 Hz, 1H) 8.32-8.37 (m, 1H) 8.09 (dd, J=5.07, 1.16 Hz, 1H) 7.82-7.93 (m, 2H) 7.32 (d, J=9.29 Hz, 1H) 6.87 (d, J=0.73 Hz, 1H) 6.62 (d, J=1.10 Hz, 1H) 4.26-4.41 (m, 2H) 3.92-4.04 (m, 2H) 3.81 (dd, J=1 1.62, 2.08 Hz, 1H) 3.75 (t, J=5.20 Hz, 2H) 3.55 (dd, J=11.55, 1.16 Hz, 1H) 3.47 (td, J=11.58, 2.14 Hz, 2H) 2.98 (dt, J=12.29, 3.09 Hz, 1H) 2.19-2.31 (m, 4H) 1.60-1.75 (m, 1H); LCMS (m/z) (M+H)=518.0, Rt=1.33 min.

The compounds listed in Table 3, below, were prepared using methods similar to those described for the preparation of the above examples using the appropriate starting materials:

TABLE 3

| Example | Structure | Name | Physical Data |
|---|---|---|---|
| 163 | 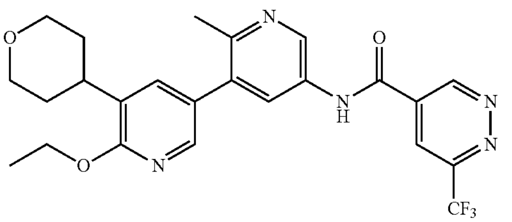 [SMILES: CCOc1ncc(-c2cc(NC(=O)c3cnnc(C(F)(F)F)c3)cnc2C)cc1C1CCOCC1] | N-(6'-ethoxy-2-methyl-5'-(tetrahydro-2H-pyran-4-yl)-[3,3'-bipyridin]-5-yl)-6-(trifluoromethyl)pyridazine-4-carboxamide | $^1$H NMR (400 MHz, <cd3od>) δ ppm 1.44 (t, J = 7.04 Hz, 3H) 1.75-1.89 (m, 4H) 2.65 (s, 3H) 3.20 (d, J = 5.09 Hz, 1H) 3.61 (td, J = 11.05, 3.33 Hz, 2H) 4.06 (d, J = 10.56 Hz, 2H) 4.49 (q, J = 7.04 Hz, 2H) 7.68 (d, J = 2.35 Hz, 1H) 8.10 (d, J = 2.35 Hz, 1H) 8.35 (d, J = 2.35 Hz, 1H) 8.63 (d, J = 1.96 Hz, 1H) 9.22 (d, J = 2.35 Hz, 1H) 9.92 (d, J = 1.96 Hz, 1H). LCMS (m/z) (M + H) = 488.1, Rt = 0.74 min. |
| 164 | 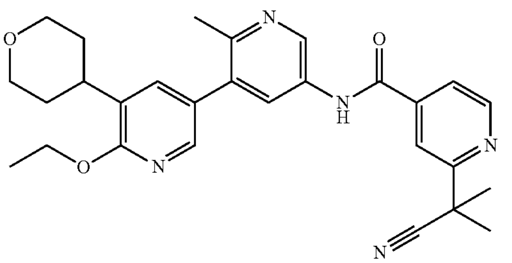 [SMILES: CCOc1ncc(-c2cc(NC(=O)c3ccnc(C(C)(C)C#N)c3)cnc2C)cc1C1CCOCC1] | 2-(2-cyanopropan-2-yl)-N-(6'-ethoxy-2-methyl-5'-(tetrahydro-2H-pyran-4-yl)-[3,3'-bipyridin]-5-yl)isonicotinamide | $^1$H NMR (400 MHz, <cd3od>) δ ppm 1.44 (s, 3H) 1.76-1.88 (m, 10H) 2.67 (s, 3H) 3.14-3.24 (m, 1H) 3.61 (td, J = 11.15, 3.52 Hz, 2H) 4.06 (d, J = 10.96 Hz, 2H) 4.49 (q, J = 7.04 Hz, 2H) 7.70 (d, J = 2.35 Hz, 1H) 7.88 (dd, J = 5.09, 1.57 Hz, 1H) 8.12 (d, J = 2.35 Hz, 1H) 8.14 (s, 1H) 8.40 (d, J = 1.96 Hz, 1H) 8.82 (d, J = 5.09 Hz, 1H) 9.29 (d, J = 2.35 Hz, 1H). LCMS (m/z) (M + H) = 486.2, Rt = 0.76 min. |
| 165 | 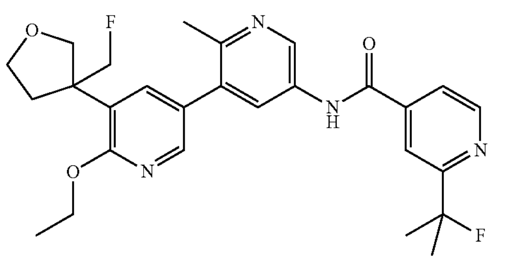 [SMILES: CCOc1ncc(-c2cc(NC(=O)c3ccnc(C(C)(C)F)c3)cnc2C)cc1C1(CF)CCOC1] | N-(6'-ethoxy-5'-(3-(fluoromethyl)tetrahydrofuran-3-yl)-2-methyl-[3,3'-bipyridin]-5-yl)-2-(2-fluoropropan-2-yl)isonicotinamide | $^1$H NMR (400 MHz, <cd3od>) δ ppm 1.46 (t, J = 7.04 Hz, 3H) 1.67-1.81 (m, 6H) 2.24-2.35 (m, 1H) 2.37-2.45 (m, 1H) 2.69 (s, 3H) 3.89-3.96 (m, 2H) 4.03 (d, J = 8.22 Hz, 1H) 4.28 (d, J = 9.39 Hz, 1H) 4.45-4.57 (m, 3H) 4.67 (d, J = 4.30 Hz, 1H) 7.71 (d, J = 2.35 Hz, 1H) 7.84 (dd, J = 5.09, 1.57 Hz, 1H) 8.14 (s, 1H) 8.22 (d, J =2.35 Hz, 1H) 8.46 (d, J = 1.96 Hz, 1H) 8.76 (d, J = 5.09 Hz, 1H) 9.37 (d, J = 2.35 Hz, 1H). LCMS (m/z) (M + H) = 497.3, Rt = 0.78 min. |
| 166 | 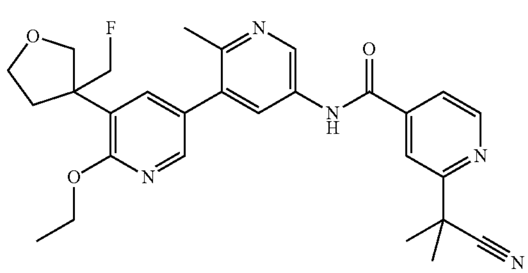 [SMILES: CCOc1ncc(-c2cc(NC(=O)c3ccnc(C(C)(C)C#N)c3)cnc2C)cc1C1(CF)CCOC1] | 2-(2-cyanopropan-2-yl)-N-(6'-ethoxy-5'-(3-(fluoromethyl)tetrahydrofuran-3-yl)-2-methyl-[3,3'-bipyridin]-5-yl)isonicotinamide | $^1$H NMR (400 MHz, <cd3od>) δ ppm 1.46 (t, J = 7.24 Hz, 3H) 1.82 (s, 6H) 2.23 -2.35 (m, 1H) 2.41 (s, 1H) 2.68 (s, 3H) 3.93 (dd,J = 9.19, 5.28 Hz, 2H) 4.02 (d, J = 8.22 Hz, 1H) 4.28 (d, J = 9.00 Hz, 1H) 4.46-4.56 (m, 3H) 4.67 (d, J = 4.30 Hz, 1H) 7.70 (d, J = 2.35 Hz, 1H) 7.88 (dd, J = 5.09, 1.57 Hz, 1H) 8.14 (s, 1H) 8.21 (d, J = 1.96 Hz, 1H) 8.42 (d, J = 2.35 Hz, 1H) 8.82 (d, J = 5.09 Hz, 1H) 9.34 (d, J = 2.35 Hz, 1H). LCMS (m/z) (M + H) = 504.3, Rt = 0.76 min. |

TABLE 3-continued

| Example | Structure | Name | Physical Data |
|---|---|---|---|
| 167 | 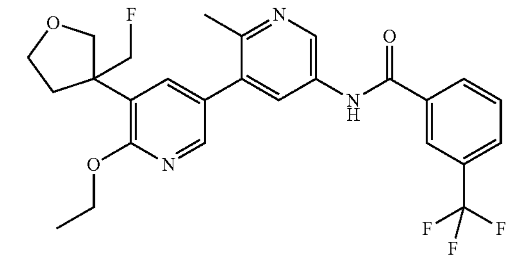 [SMILES: CCOc1ncc(-c2cc(NC(=O)c3cccc(C(F)(F)F)c3)cnc2C)cc1C1(CF)CCOC1] | N-(6'-ethoxy-5'-(3-(fluoromethyl)tetrahydrofuran-3-yl)-2-methyl-[3,3'-bipyridin]-5-yl)-3-(trifluoromethyl)benzamide | $^1$H NMR (400 MHz, <cd3od>) δ ppm 1.42-1.50 (m, 3H) 2.23-2.35 (m, 1H) 2.36-2.46 (m, 1H) 2.67 (s, 3H) 3.89-3.97 (m, 2H) 3.99-4.09 (m, 1H) 4.28 (d, J = 9.39 Hz, 1H) 4.43-4.59 (m, 4H) 4.64-4.72 (m, 1H) 7.71 (d, J = 2.35 Hz, 1H) 7.75-7.84 (m, 1H) 7.97 (d, J = 7.83 Hz, 1H) 8.22 (d, J = 2.35 Hz, 1H) 8.29 (d, J = 7.83 Hz, 1H) 8.35 (s, 1H) 8.44 (d, J = 1.96 Hz, 1H) 9.36 (d, J = 2.35 Hz, 1H). LCMS (m/z) (M + H) = 504.3, Rt = 0.86 min. |
| 168 | 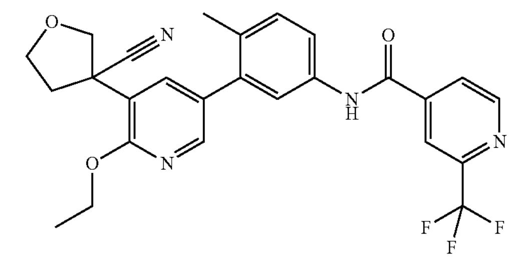 [SMILES: CCOc1ncc(-c2cc(NC(=O)c3ccnc(C(F)(F)F)c3)ccc2C)cc1C1(C#N)CCOC1] | N-(3-(5-(3-cyanotetrahydrofuran-3-yl)-6-ethoxypyridin-3-yl)-4-methylphenyl)-2-(trifluoromethyl)isonicotinamide | $^1$H NMR (400 MHz, <cd3od>) δ ppm 1.49 (t, J = 7.04 Hz, 3H) 2.28 (s, 3H) 2.64-2.73 (m, 1H) 2.75-2.86 (m, 1H) 4.02-4.11 (m, 2H) 4.12-4.20 (m, 1H) 4.50-4.62 (m, 3H) 7.35 (d, J = 8.22 Hz, 1H) 7.63 (d, J = 1.96 Hz, 1H) 7.67 (dd, J = 8.41, 2.15 Hz, 1H) 7.75 (d, J = 1.96 Hz, 1H) 8.12 (d, J = 4.30 Hz, 1H) 8.16 (d, J = 2.35 Hz, 1H) 8.30 (s, 1H) 8.91 (d, J = 5.09 Hz, 1 H). LCMS (m/z) (M + H) = 497.1, Rt = 1.04 min. |
| 169 | 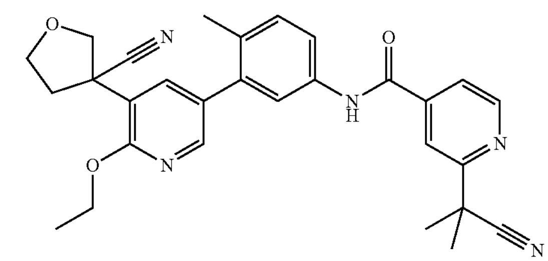 [SMILES: CCOc1ncc(-c2cc(NC(=O)c3ccnc(C(C)(C)C#N)c3)ccc2C)cc1C1(C#N)CCOC1] | 2-(2-cyanopropan-2-yl)-N-(3-(5-(3-cyanotetrahydrofuran-3-yl)-6-ethoxypyridin-3-yl)-4-methylphenyl)isonicotinamide | $^1$H NMR (400 MHz, <cd3od>) δ ppm 1.49 (t, J = 7.04 Hz, 3H) 1.81 (s, 6H) 2.28 (s, 3H) 2.62-2.73 (m, 1H) 2.74-2.85 (m, 1H) 4.01-4.11 (m, 2H) 4.12-4.21 (m, 1H) 4.50-4.59 (m, 3H) 7.34 (d, J = 8.22 Hz, 1H) 7.61 (d, J = 1.96 Hz, 1 H) 7.66 (dd, J = 8.22, 2.35 Hz, 1H) 7.75 (d, J = 1.96 Hz, 1H) 7.81 (dd, J = 5.09, 1.17 Hz, 1H) 8.07 (s, 1H) 8.16 (d, J = 1.96 Hz, 1H) 8.76 (d, J = 5.09 Hz, 1H). LCMS (m/z) (M + H) = 496.2, Rt = 1.00 min. |
| 170 | 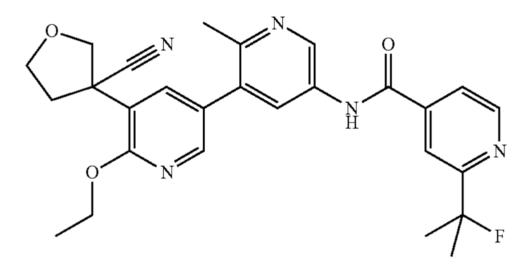 [SMILES: CCOc1ncc(-c2cc(NC(=O)c3ccnc(C(C)(C)F)c3)cnc2C)cc1C1(C#N)CCOC1] | N-(5'-(3-cyanotetrahydrofuran-3-yl)-6'-ethoxy-2-methyl-[3,3'-bipyridin]-5-yl)-2-(2-fluoropropan-2-yl)isonicotinamide | $^1$H NMR (400 MHz, <cd3od>) δ ppm 1.51 (t, J = 7.04 Hz, 3H) 1.67-1.81 (m, 6H) 2.66 (s, 3H) 2.71 (s, 1H) 2.81 (d, J = 5.09 Hz, 1H) 4.04-4.12 (m, 2H) 4.14-4.21 (m, 1H) 4.55 (d, J = 9.00 Hz, 1H) 4.60 (q, J = 7.04 Hz, 2H) 7.83 (dd, J = 5.09, 1.57 Hz, 1H) 7.89 (d, J = 2.35 Hz, 1 H) 8.13 (s, 1H) 8.31 (d, J = 2.35 Hz, 1H) 8.43 (d, J = 2.35 Hz, 1 H) 8.76 (d, J = 5.09 Hz, 1H) 9.28 (d, J = 1.96 Hz, 1H). LCMS (m/z) (M + H) = 490.2, Rt = 0.75 min. |
| 171 | 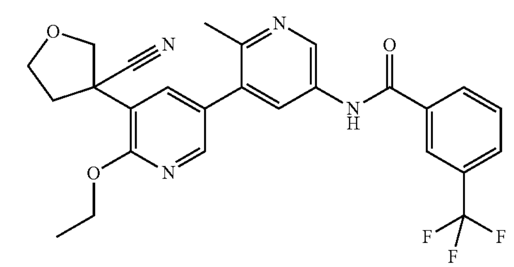 [SMILES: CCOc1ncc(-c2cc(NC(=O)c3cccc(C(F)(F)F)c3)cnc2C)cc1C1(C#N)CCOC1] | N-(5'-(3-cyanotetrahydrofuran-3-yl)-6'-ethoxy-2-methyl-[3,3'-bipyridin]-5-yl)-3-(trifluoromethyl)benzamide | $^1$H NMR (400 MHz, <cd3od>) δ ppm 1.51 (t, J = 7.24 Hz, 3H) 2.65 (s, 3H) 2.67-2.74 (m, 1H) 2.81 (dd, J = 7.43, 5.09 Hz, 1H) 4.05-4.12 (m, 2H) 4.14-4.21 (m, 1H) 4.55 (d, J = 9.00 Hz, 1 H) 4.60 (q, J = 7.04 Hz, 2H) 7.73-7.82 (m, 1H) 7.89 (d, J = 1.96 Hz, 1H) 7.96 (d, J = 7.83 Hz, 1H) 8.28 (d, J = 7.83 Hz, 1H) 8.31 (d, J = 2.35 Hz, 1H) 8.34 (s, 1H) 8.40 (d, J = 2.35 Hz, 1H) 9.25 (d, J = 2.35 Hz, 1H). LCMS (m/z) (M + H) = 497.1, Rt = 0.85 min. |

TABLE 3-continued

| Example | Structure | Name | Physical Data |
|---|---|---|---|
| 172 | 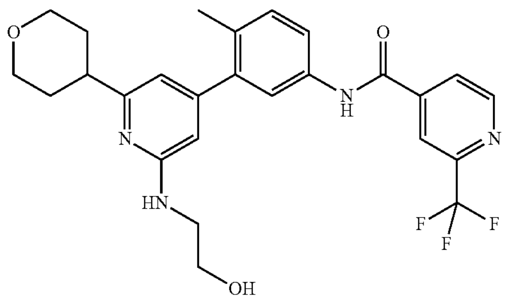 [SMILES: Cc1ccc(NC(=O)c2ccnc(C(F)(F)F)c2)cc1-c1cc(NCCO)nc(C2CCOCC2)c1] | N-(3-(2-((2-hydroxyethyl)amino)-6-(tetrahydro-2H-pyran-4-yl)pyridin-4-yl)-4-methylphenyl)-2-(trifluoromethyl)isonicotinamide | $^1$H NMR (400 MHz, <cd3od>) δ ppm 1.80-1.96 (m, 4H) 2.27 (s, 3H) 2.77-2.89 (m, 1H) 3.49 (t, J = 5.48 Hz. 2H) 3.56 (td, J = 11.54, 2.74 Hz, 2H) 3.75 (td, J = 5.28 Hz, 2H) 4.05 (dd, J = 10.56, 3.52 Hz, 2H) 6.35 (d, J = 1.17 Hz, 1H) 6.45 (d, J = 1.17 Hz, 1H) 7.30 (d, J = 8.22 Hz, 1H) 7.59 (d, J = 2.35 Hz, 1H) 7.65 (dd, J = 8.22, 2.35 Hz, 1H) 8.12 (d, J = 3.52 Hz, 1H) 8.29 (s, 1H) 8.90 (d, J = 5.09 Hz, 1 H). LCMS (m/z) (M + H) = 501.3, Rt = 0.78 min. |
| 173 | 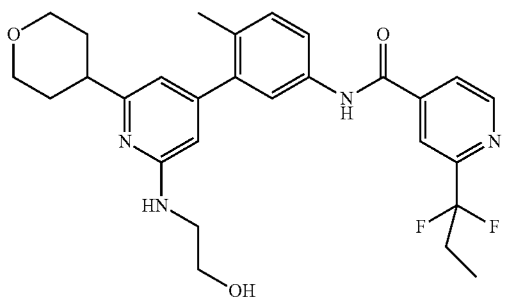 [SMILES: CCC(F)(F)c1cc(C(=O)Nc2ccc(C)c(-c3cc(NCCO)nc(C4CCOCC4)c3)c2)ccn1] | 2-(1,1-difluoropropyl)-N-(3-(2-((2-hydroxyethyl)amino)-6-(tetrahydro-2H-pyran-4-yl)pyridin-4-yl)-4-methylphenyl)isonicotinamide | $^1$H NMR (400 MHz, <cd3od>) δ ppm 1.03 (t, J = 7.43 Hz, 3H) 1.85-1.95 (m, 3H) 2.29 (s, 3H) 2.40 (td, J = 16.73, 7.63 Hz, 2H) 2.79-2.89 (m, 1H) 3.50-3.52 (m, 2H) 3.58 (td, J = 11.54, 3.13 Hz, 2H) 3.77 (t, J = 5.28 Hz, 2 H) 4.07 (d, J = 10.56 Hz, 2H) 6.38 (d, J = 1.17 Hz, 1H) 6.48 (d, J = 1.17 Hz, 1H) 7.32 (d, J = 8.22 Hz, 1H) 7.61 (d, J = 2.35 Hz, 1H) 7.67 (dd, J = 8.22, 2.35 Hz, 1H) 7.98 (d, J = 3.52 Hz, 1H) 8.18 (s, 1H) 8.83 (d, J = 5.87 Hz, 1 H). LCMS (m/z) (M + H) = 511.4, Rt = 0.78 min. |
| 174 | 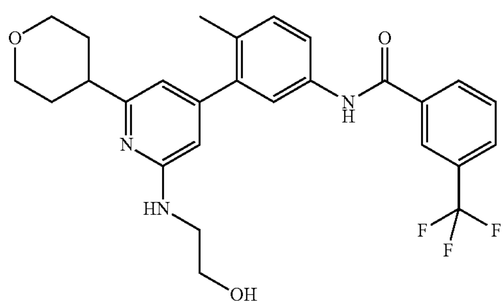 [SMILES: Cc1ccc(NC(=O)c2cccc(C(F)(F)F)c2)cc1-c1cc(NCCO)nc(C2CCOCC2)c1] | N-(3-(2-((2-hydroxyethyl)amino)-6-(tetrahydro-2H-pyran-4-yl)pyridin-4-yl)-4-methylphenyl)-3-(trifluoromethyl)benzamide | $^1$H NMR (400 MHz, <cd3od>) δ ppm 1.79-2.02 (m, 4H) 2.29 (s, 3H) 2.75-2.93 (m, 1H) 3.51 (t, J = 5.28 Hz, 2H) 3.58 (td, J = 11.54, 2.74 Hz, 2H) 3.77 (t, J = 5.28 Hz, 2H) 4.03-4.12 (m, 2H) 6.38 (d, J = 1.17 Hz, 1 H) 6.48 (d, J = 1.17 Hz, 1H) 7.31 (d, J = 8.22 Hz, 1H) 7.60 (d, J = 2.35 Hz, 1H) 7.64 (dd, J = 8.22, 2.35 Hz, 1H) 7.71- 7.80 (m, 1H) 7.91 (d, J = 7.83 Hz, 1H) 8.22 (d, J = 7.83 Hz, 1H) 8.28 (s, 1H). LCMS (m/z) (M + H) = 500.4, Rt = 0.85 min. |
| 175 | 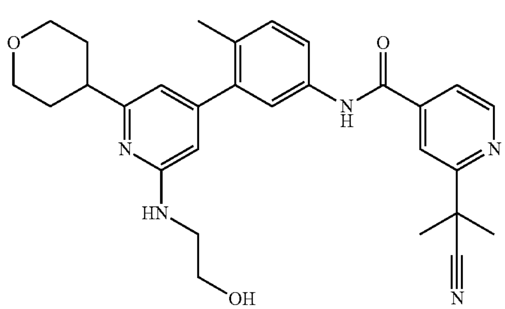 [SMILES: Cc1ccc(NC(=O)c2ccnc(C(C)(C)C#N)c2)cc1-c1cc(NCCO)nc(C2CCOCC2)c1] | 2-(2-cyanopropan-2-yl)-N-(3-(2-((2-hydroxyethyl)amino)-6-(tetrahydro-2H-pyran-4-yl)pyridin-4-yl)-4-methylphenyl)isonicotinamide | $^1$H NMR (400 MHz, <cd3od>) δ ppm 1.84 (s, 6H) 1.86-1.96 (m, 4H) 2.29 (s, 3H) 2.80-2.89 (m, 1H) 3.49-3.53 (m, 2H) 3.58 (td, J = 11.54, 2.74 Hz, 2H) 3.77 (t, J = 5.48 Hz, 2H) 4.07 (dd, J = 10.56, 3.13 Hz, 2H) 6.38 (d, J = 1.56 Hz, 1H) 6.48 (d, J = 1.17 Hz, 1H) 7.32 (d, J = 8.22 Hz, 1 H) 7.60 (d, J = 2.35 Hz, 1H) 7.66 (dd, J = 8.22, 2.35 Hz, 1H) 7.83 (dd, J = 5.09, 1.57 Hz, 1H) 8.08 (s, 1H) 8.78 (dd, J = 5.09, 1.17 Hz, 1H). LCMS (m/z) (M + H) = 500.4, Rt = 0.74 min. |

TABLE 3-continued

| Example | Structure | Name | Physical Data |
|---------|-----------|------|---------------|
| 176 | 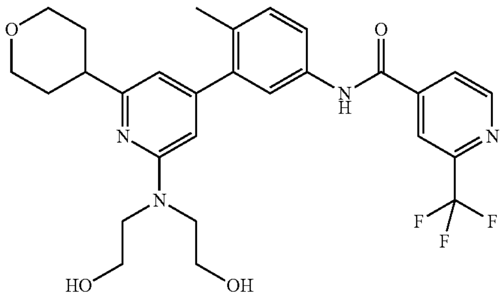 [SMILES: Cc1ccc(NC(=O)c2ccnc(C(F)(F)F)c2)cc1-c1cc(C2CCOCC2)nc(N(CCO)CCO)c1] | N-(3-(2-(bis(2-hydroxyethyl)amino)-6-(tetrahydro-2H-pyran-4-yl)pyridin-4-yl)-4-methylphenyl) isonicotinamide | $^1$H NMR (400 MHz, <cd3od>) δ ppm 1.81-1.89 (m, 2H) 1.90-2.02 (m, 2H) 2.30 (s, 3H) 2.81-2.92 (m, 1H) 3.59 (td, J = 11.74, 2.35 Hz, 2H) 3.71-3.78 (m, 4H) 3.80-3.87 (m, 4H) 4.07 (dd, J = 11.35, 2.74 Hz, 2H) 6.50 (d, J = 3.13 Hz, 2H) 7.33 (d, J = 8.22 Hz, 1H) 7.62 (d, J = 2.35 Hz, 1H) 7.68 (dd, J = 8.22, 2.35 Hz, 1H) 8.14 (d, J = 5.09 Hz, 1H) 8.32 (s, 1H) 8.93 (d, J = 5.09 Hz, 1H). LCMS (m/z) (M + H) = 545.4, Rt = 0.75 min. |
| 177 | 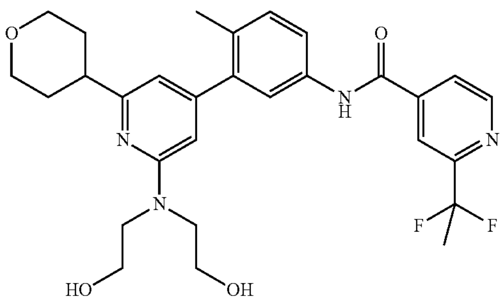 [SMILES: Cc1ccc(NC(=O)c2ccnc(C(C)(F)F)c2)cc1-c1cc(C2CCOCC2)nc(N(CCO)CCO)c1] | N-(3-(2-(bis(2-hydroxyethyl)amino)-6-(tetrahydro-2H-pyran-4-yl)pyridin-4-yl)-4-methylphenyl)-2-(1,1-difluoroethyl) isonicotinamide | $^1$H NMR (400 MHz, <cd3od>) δ ppm 1.81-1.89 (m, 2H) 1.89-1.99 (m, 2H) 2.06 (t, J = 18.58 Hz, 3H) 2.30 (s, 3H) 2.86 (tt, J = 11.54, 3.91 Hz, 1H) 3.59 (td, J = 11.74, 2.35 Hz, 2H) 3.71-3.79 (m, 4H) 3.80-3.87 (m, 4H) 4.07 (dd, J = 11.15, 2.54 Hz, 2H) 6.51 (d, J = 3.13 Hz, 2H) 7.32 (d, J = 8.22 Hz, 1H) 7.62 (d, J = 2.35 Hz, 1H) 7.67 (dd, J = 8.22, 2.35 Hz, 1H) 7.98 (d, J = 5.09 Hz, 1H) 8.20 (d, J = 0.78 Hz, 1H) 8.82 (dd, J = 5.09, 0.78 Hz, 1H). LCMS (m/z) (M + H) = 541.3, Rt = 0.74 min. |
| 178 | 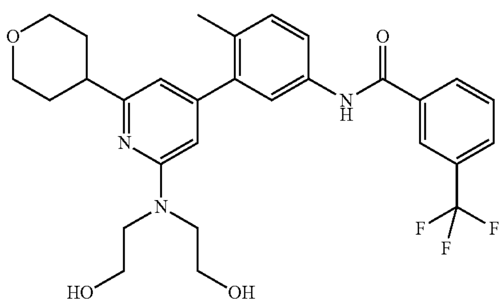 [SMILES: Cc1ccc(NC(=O)c2cccc(C(F)(F)F)c2)cc1-c1cc(C2CCOCC2)nc(N(CCO)CCO)c1] | N-(3-(2-(bis(2-hydroxyethyl)amino)-6-(tetrahydro-2H-pyran-4-yl)pyridin-4-yl)-4-methylphenyl)-3-trifluoromethyl) benzamide | $^1$H NMR (400 MHz, <cd3od>) δ ppm 1.82-1.89 (m, 2H) 1.90-2.02 (m, 2H) 2.29 (s, 3H) 2.86 (tt, J = 11.74, 3.91 Hz, 1H) 3.59 (td, J = 11.74, 2.35 Hz, 2H) 3.71-3.78 (m, 4H) 3.80-3.89 (m, 4H) 4.07 (dd, J = 11.15, 2.54 Hz, 2H) 6.51 (d, J = 2.74 Hz, 2H) 7.32 (d, J = 8.22 Hz, 1H) 7.61 (d, J = 2.35 Hz, 1H) 7.65 (dd, J = 8.22, 1.96 Hz, 1H) 7.72-7.80 (m, 1H) 7.91 (d, J = 7.83 Hz, 1H) 8.22 (d, J = 7.83 Hz, 1H) 8.28 (s, 1H). LCMS (m/z) (M + H) = 544.2, Rt = 0.82 min. |
| 179 | 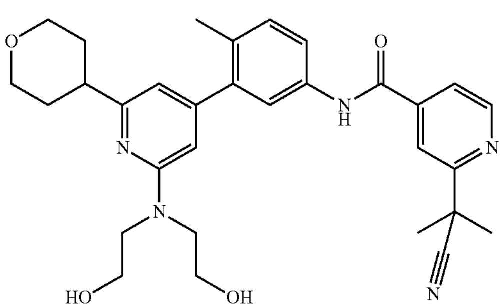 [SMILES: Cc1ccc(NC(=O)c2ccnc(C(C)(C)C#N)c2)cc1-c1cc(C2CCOCC2)nc(N(CCO)CCO)c1] | N-(3-(2-(bis(2-hydroxyethyl)amino)-6-(tetrahydro-2H-pyran-4-yl)pyridin-4-yl)-4-methylphenyl)-2-(2-cyanopropan-2-yl) isonicotinamide | $^1$H NMR (400 MHz, <cd3od>) δ ppm 1.82-1.85 (m, 7H) 1.85-1.89 (m, 1H) 1.90-2.01 (m, 2H) 2.30 (s, 3H) 2.81-2.91 (m, 1H) 3.59 (td, J = 11.74, 2.35 Hz, 2H) 3.70-3.79 (m, 4H) 3.80-3.87 (m, 4H) 4.01-4.12 (m, 2H) 6.51 (d, J = 3.13 Hz, 2H) 7.33 (d, J = 8.22 Hz, 1H) 7.60 (d, J = 2.35 Hz, 1H) 7.67 (dd, J = 8.41, 2.15 Hz, 1H) 7.83 (dd, J = 5.09, 1.57 Hz, 1H) 8.05-8.13 (m, 1H) 8.78 (dd, J = 5.09, 1.17 Hz, 1H). LCMS (m/z) (M + H) = 544.3, Rt = 0.71 min. |

TABLE 3-continued

| Example | Structure | Name | Physical Data |
|---|---|---|---|
| 180 | 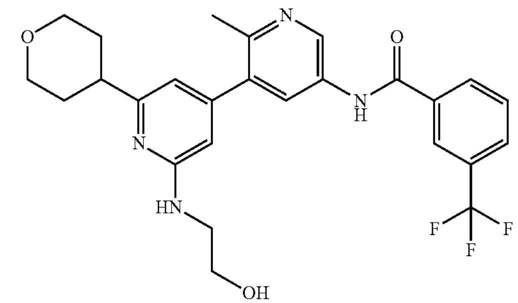 [SMILES: Cc1ncc(NC(=O)c2cccc(C(F)(F)F)c2)cc1-c1cc(NCCO)nc(C2CCOCC2)c1] | N-(2'-((2-hydroxyethyl)amino)-2-methyl-6'-(tetrahydro-2H-pyran-4-yl)-[3,4'-bipyridin]-5-yl)-3-(trifluoromethyl)benzamide | 1H NMR (500 MHz, Methanol-d4) δ 8.90 (d, J = 2.4 Hz, 1H), 8.39 (d, J = 2.5 Hz, 1H), 8.31 (s, 1H), 8.25 (d, J = 8.0 Hz, 1H), 7.94 (d, J = 7.9 Hz, 1H), 7.77 (t, J = 7.9 Hz, 1H), 7.03 (s, 1H), 6.90 (s, 1H), 4.15-4.04 (m, 2H), 3.86 (t, J = 4.9 Hz, 2H), 3.70-3.52 (m, 5H), 2.56 (s, 3H), 2.02-1.84 (m, 5H). LCMS (m/z) (M + H) = 501.0, Rt = 0.65 min. |
| 181 | 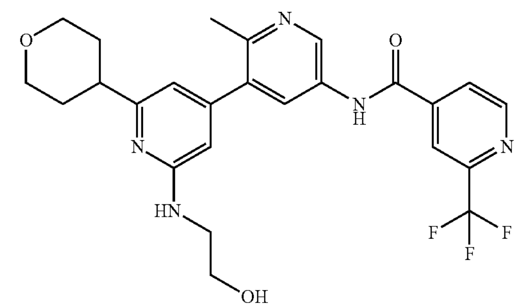 [SMILES: Cc1ncc(NC(=O)c2ccnc(C(F)(F)F)c2)cc1-c1cc(NCCO)nc(C2CCOCC2)c1] | N-(2'-((2-hydroxyethyl)amino)-2-methyl-6'-(tetrahydro-2H-pyran-4-yl)-[3,4'-bipyridin]-5-yl)-2-(trifluoromethyl)isonicotinamide | $^1$H NMR (500 MHz, Methanol-d$_4$) δ 8.27 (d, J = 8.0 Hz, 1H), 7.97 (d, J = 7.6 Hz, 1H), 4.11 (d, J = 10.9 Hz, 2H), 3.94-3.84 (m, 2H), 3.67 (d, J = 4.4 Hz, 2H), 3.60 (t, J = 11.4 Hz, 2H), 2.59 (s, 3H), 2.03-1.84 (m, 5H). LCMS (m/z) (M + H) = 502.0, Rt = 0.56 min. |
| 182 | 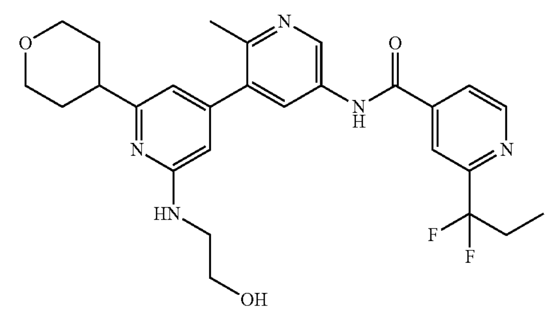 [SMILES: CCC(F)(F)c1cc(C(=O)Nc2cnc(C)c(-c3cc(NCCO)nc(C4CCOCC4)c3)c2)ccn1] | 2-(1,1-difluoropropyl)-N-(2'-((2-hydroxyethyl)amino)-2-methyl-6'-(tetrahydro-2H-pyran-4-yl)-[3,4'-bipyridin]-5-yl)isonicotinamide | $^1$H NMR (500 MHz, Methanol-d4) δ 8.86 (dd, J = 7.5, 3.8 Hz, 2H), 8.37 (d, J = 2.6 Hz, 1H), 8.20 (d, J = 1.6 Hz, 1H), 8.03-7.95 (m, 1H), 7.02 (s, 1H), 6.90 (s, 1H), 4.09 (dt, J = 11.9, 2.6 Hz, 2H), 3.90-3.81 (m, 2H), 3.69-3.52 (m, 5H), 2.56 (s, 3H), 2.39 (td, J = 16.5, 8.1 Hz, 3H), 2.02-1.81 (m, 5H), 1.01 (t, J = 7.5 Hz, 3H). LCMS (m/z) (M + H) = 512.0, Rt = 0.60 min. |
| 183 | 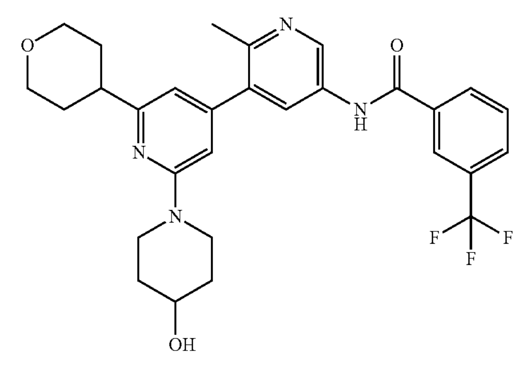 [SMILES: Cc1ncc(NC(=O)c2cccc(C(F)(F)F)c2)cc1-c1cc(C2CCOCC2)nc(N2CCC(O)CC2)c1] | N-(2'-(4-hydroxypiperidin-1-yl)-2-methyl-6'-(tetrahydro-2H-pyran-4-yl)-[3,4'-bipyridin]-5-yl)-3-(trifluoromethyl)benzamide | $^1$H NMR (400 MHz, Methanol-d4) δ 9.13 (d, J = 2.5 Hz, 1H), 8.40 (d, J = 2.4 Hz, 1H), 8.33 (t, J = 1.8 Hz, 1H), 8.29-8.23 (m, 1H), 7.96 (dd, J = 8.3, 1.8 Hz, 1H), 7.78 (t, J = 7.9 Hz, 1H), 6.99 (s, 1H), 6.77 (s, 1H), 4.14 (dt, J = 13.5, 4.6 Hz, 3H), 4.09 (s, 2H), 3.95 (tt, J = 8.2, 3.9 Hz, 1H), 3.69-3.36 (m, 6H), 3.17-2.99 (m, 1H), 2.61 (s, 3H), 2.10-1.84 (m, 7H), 1.62 (ddt, J = 13.6, 9.1, 4.5 Hz, 2H). LCMS (m/z) (M + H) = 541.1, Rt = 0.65 min. |
| 184 | 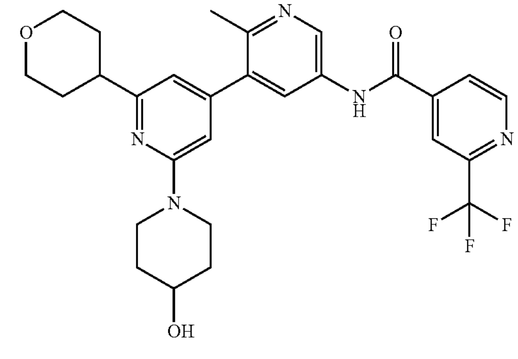 [SMILES: Cc1ncc(NC(=O)c2ccnc(C(F)(F)F)c2)cc1-c1cc(C2CCOCC2)nc(N2CCC(O)CC2)c1] | N-(2'-(4-hydroxypiperidin-1-yl)-2-methyl-6'-(tetrahydro-2H-pyran-4-yl)-[3,4'-bipyridin]-5-yl)-2-(trifluoromethyl)isonicotinamide | $^1$H NMR (400 MHz, Methanol-d4) δ 9.06 (d, J = 2.5 Hz, 1H), 8.96 (d, J = 5.2 Hz, 1H), 8.38 (d, J = 2.4 Hz, 1H), 8.36-8.31 (m, 1H), 8.16 (dd, J = 4.9, 1.6 Hz, 1H), 7.04 (s, 1H), 6.79 (d, J = 1.2 Hz, 1H), 4.19-4.03 (m, 4H), 3.96 (tt, J = 8.1, 3.9 Hz, 1H), 3.66-3.39 (m, 5H), 3.15-2.99 (m, 1H), 2.60 (s, 3H), 2.08-1.95 (m, 2H), 1.94-1.81 (m, 4H), 1.63 (dtd, J = 12.8, 8.7, 3.7 Hz, 2H). LCMS (m/z) (M + H) = 542.1, Rt = 0.58 min. |

TABLE 3-continued

| Example | Structure | Name | Physical Data |
|---|---|---|---|
| 185 | 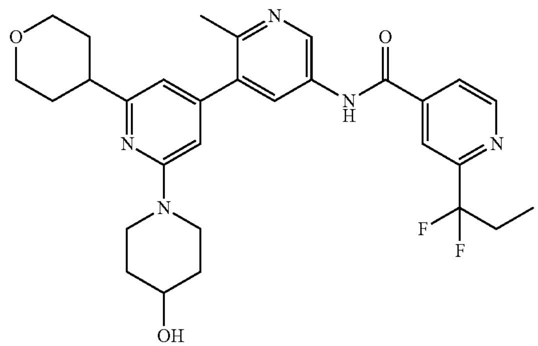 [SMILES: CCC(F)(F)c1cc(C(=O)Nc2cnc(C)c(-c3cc(C4CCOCC4)nc(N4CCC(O)CC4)c3)c2)ccn1] | 2-(1,1-difluoropropyl)-N-(2'-(4-hydroxypiperidin-1-yl)-2-methyl-6'-(tetrahydro-2H-pyran-4-yl)-[3,4'-bipyridin]-5-yl)isonicotinamide | $^1$H NMR (400 MHz, Methanol-d4) δ 9.10 (d, J = 2.4 Hz, 1H), 8.92-8.83 (m, 1H), 8.40 (d, J = 2.3 Hz, 1H), 8.25-8.20 (m, 1H), 8.01 (dd, J = 5.0, 1.7 Hz, 1H), 7.04 (s, 1H), 6.79 (d, J = 1.2 Hz, 1H), 4.19-4.04 (m, 4H), 3.96 (tt, J = 8.1, 3.9 Hz, 1H), 3.65-3.38 (m, 5H), 3.17-3.02 (m, 1H), 2.61 (s, 3H), 2.39 (tq, J = 16.7, 7.5 Hz, 2H), 2.06-1.84 (m, 7H), 1.64 (dtd, J = 12.9, 8.8, 3.8 Hz, 2H), 1.02 (t, J = 7.3 Hz, 3H). LCMS (m/z) (M + H) = 552.2, Rt = 0.61 min. |
| 186 | 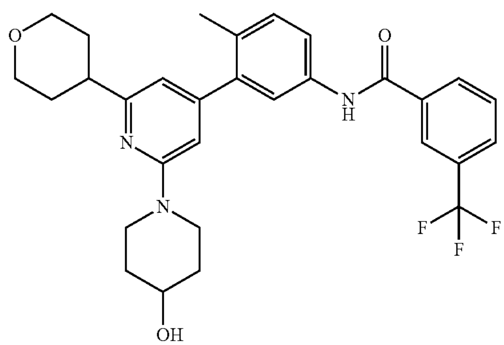 [SMILES: Cc1ccc(NC(=O)c2cccc(C(F)(F)F)c2)cc1-c1cc(C2CCOCC2)nc(N2CCC(O)CC2)c1] | N-(3-(2-(4-hydroxypiperidin-1-yl)-6-(tetrahydro-2H-pyran-4-yl)pyridin-4-yl)-4-methylphenyl)-3-(trifluoromethyl)benzamide | $^1$H NMR (400 MHz, Methanol-d4) δ 8.26 (d, J = 1.9 Hz, 1H), 8.21 (d, J = 7.9 Hz, 1H), 7.94-7.87 (m, 1H), 7.81 (t, J = 2.6 Hz, 1H), 7.74 (t, J = 7.9 Hz, 1H), 7.61 (dt, J = 8.3, 2.4 Hz, 1H), 7.38 (d, J = 8.3 Hz, 1H), 7.17 (d, J = 1.4 Hz, 1H), 6.88 (d, J = 1.2 Hz, 1H), 4.06 (dddd, J = 21.8, 11.4, 6.0, 2.8 Hz, 6H), 3.57 (tt, J = 11.2, 2.4 Hz, 4H), 3.22-3.07 (m, 2H), 2.33 (s, 3H), 2.05 (ddd, J = 13.6, 7.3, 3.8 Hz, 2H), 1.98-1.84 (m, 5H), 1.70 (dtd, J = 12.6, 8.3, 3.7 Hz, 2H). LCMS (m/z) (M + H) = 540.2, Rt = 0.82 min. |
| 187 | 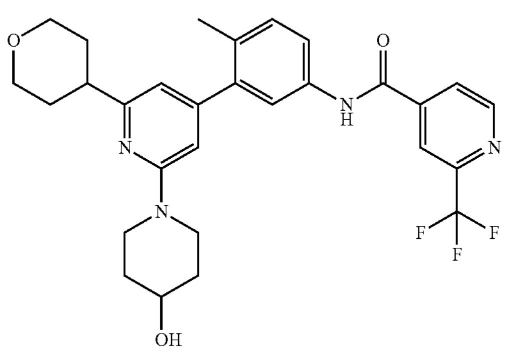 [SMILES: Cc1ccc(NC(=O)c2ccnc(C(F)(F)F)c2)cc1-c1cc(C2CCOCC2)nc(N2CCC(O)CC2)c1] | N-(3-(2-(4-hydroxypiperidin-1-yl)-6-(tetrahydro-2H-pyran-4-yl)pyridin-4-yl)-4-methylphenyl)-2-(trifluoromethyl)isonicotinamide | $^1$H NMR (400 MHz, Methanol-d4) δ 8.92 (d, J = 5.0 Hz, 1H), 8.35-8.26 (m, 1H), 8.13 (dd, J = 5.1, 1.6 Hz, 1H), 7.81 (d, J = 2.3 Hz, 1H), 7.65 (dd, J = 8.3, 2.3 Hz, 1H), 7.39 (d, J = 8.4 Hz, 1H), 7.14 (s, 1H), 6.85 (d, J = 1.3 Hz, 1H), 4.17-3.94 (m, 5H), 3.57 (tdd, J = 11.2, 7.8, 3.0 Hz, 4H), 3.23-3.09 (m, 1H), 2.34 (s, 3H), 2.04 (ddt, J = 13.6, 7.1, 3.6 Hz, 2H), 1.99-1.80 (m, 4H), 1.70 (dtd, J = 12.6, 8.4, 3.7 Hz, 2H). LCMS (m/z) (M + H) = 541.2, Rt = 0.75 min. |
| 188 | 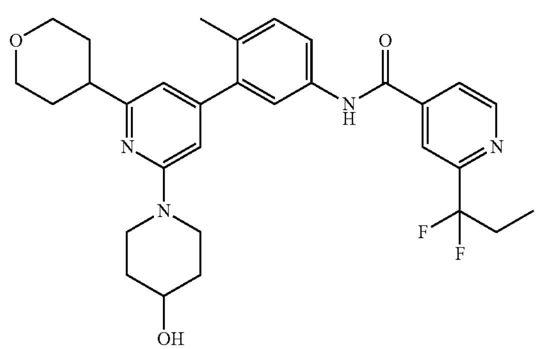 [SMILES: CCC(F)(F)c1cc(C(=O)Nc2ccc(C)c(-c3cc(C4CCOCC4)nc(N4CCC(O)CC4)c3)c2)ccn1] | 2-(1,1-difluoropropyl)-N-(3-(2-(4-hydroxypiperidin-1-yl)-6-(tetrahydro-2H-pyran-4-yl)pyridin-4-yl)-4-methylphenyl)-2-isonicotinamide | $^1$H NMR (400 MHz, Methanol-d4) δ 8.83 (d, J = 5.1 Hz, 1H), 8.16 (t, J = 1.3 Hz, 1H), 7.96 (dd, J = 5.0, 1.6 Hz, 1H), 7.82 (d, J = 2.3 Hz, 1H), 7.64 (dd, J = 8.3, 2.3 Hz, 1H), 7.39 (d, J = 8.3 Hz, 1H), 7.16 (d, J = 1.4 Hz, 1H), 6.87 (d, J = 1.3 Hz, 1H), 4.15-3.93 (m, 5H), 3.63-3.52 (m, 4H), 3.22-3.10 (m, 1H), 2.49-2.29 (m, 5H), 2.03 (ddd, J = 13.7, 6.9, 3.5 Hz, 2H), 1.98-1.80 (m, 4H), 1.70 (dtd, J = 12.5, 8.4, 3.8 Hz, 2H), 1.01 (t, J = 7.4 Hz, 3H). LCMS (m/z) (M + H) = 551.2, Rt = 0.77 min. |

TABLE 3-continued

| Example | Structure | Name | Physical Data |
|---|---|---|---|
| 189 | 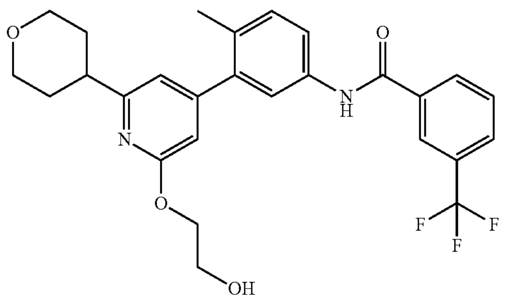 [SMILES: Cc1ccc(NC(=O)c2cccc(C(F)(F)F)c2)cc1-c1cc(OCCO)nc(C2CCOCC2)c1] | N-(3-(2-(2-hydroxyethoxy)-6-(tetrahydro-2H-pyran-4-yl)pyridin-4-yl)-4-methylphenyl)-3-(trifluoromethyl)benzamide | ¹H NMR (400 MHz, Methanol-d4) δ 8.26 (s, 1H) 8.20 (d, J = 7.8 Hz, 1H) 7.89 (d, J = 7.8 Hz, 1H) 7.73 (t, J = 7.9 Hz, 1H) 7.68-7.57 (m, 2H) 7.32 (dd, J = 8.4, 6.0 Hz, 1H) 7.00-6.57 (m, 3H) 4.80-4.66 (m, 2H) 4.51-4.40 (m, 2H) 4.13-4.01 (m, 3H) 3.96-3.85 (m, 2H) 3.58 (td, J = 11.6, 2.6 Hz, 3H) 2.98 (tt, J = 11.5, 4.2 Hz, 1H) 2.28 (s, 3H) 2.04-1.80 (m, 6H). LC-MS: Rt-0.95, Mass-501.2 |
| 190 | 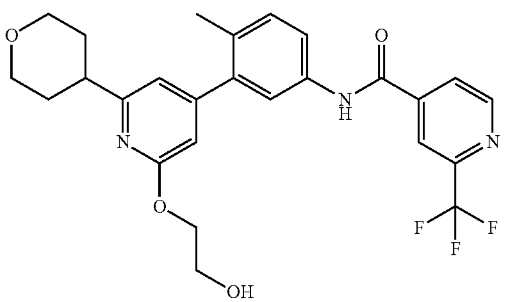 [SMILES: Cc1ccc(NC(=O)c2ccnc(C(F)(F)F)c2)cc1-c1cc(OCCO)nc(C2CCOCC2)c1] | N-(3-(2-(2-hydroxyethoxy)-6-(tetrahydro-2H-pyran-4-yl)pyridin-4-yl)-4-methylphenyl)-2-(trifluoromethyl)isonicotinamide | ¹H NMR (400 MHz, Methanol-d4) δ 8.91 (d, J = 5.1 Hz, 1H) 8.30 (t, J = 1.1 Hz, 1H) 8.12 (dd, J = 5.1, 1.6 Hz, 1H) 7.71-7.64 (m, 2H) 7.34 (d, J = 9.1 Hz, 1H) 6.91 (d, J = 1.2 Hz, 1H) 6.75 (d, J = 1.2 Hz, 1H) 4.52-4.39 (m, 2H) 4.07 (ddd, J = 11.4, 4.3, 1.8 Hz, 2H) 3.96-3.86 (m, 2H) 3.59 (td, J = 11.6, 2.6 Hz, 2H) 2.97 (tt, J = 11.5, 4.3 Hz, 1H) 2.28 (s, 3H) 2.03-1.80 (m, 5H). LC-MS: Rt-0.86, Mass-502.1 |
| 191 | 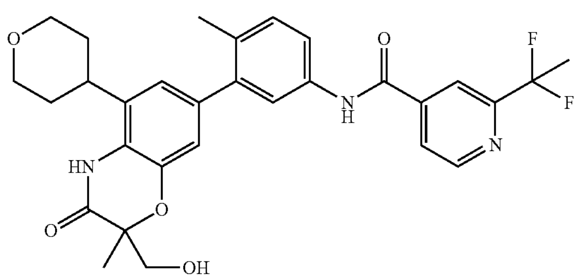 [SMILES: Cc1ccc(NC(=O)c2ccnc(C(C)(F)F)c2)cc1-c1cc2c(c(C3CCOCC3)c1)NC(=O)C(C)(CO)O2] | 2-(1,1-difluoroethyl)-N-(3-(2-(hydroxymethyl)-2-methyl-3-oxo-5-(tetrahydro-2H-pyran-4-yl)-3,4-dihydro-2H-benzo[b][1,4]oxazin-7-yl)-4-methylphenyl)isonicotinamide | ¹H NMR (400 MHz, DMSO-d6) δ ppm 10.58 (s, 1H) 10.39 (s, 1 H) 8.88 (d, J = 5.13 Hz, 1H) 8.18 (s, 1H) 8.03 (dd, J = 5.01, 1.34 Hz, 1H) 7.59-7.72 (m, 2H) 7.29 (d, J = 8.44 Hz, 1H) 6.81 (dd, J = 16.81, 1.77 Hz, 2H) 5.10 (t, J = 5.99 Hz, 1H) 3.91 (d, J = 11.25 Hz, 2H) 3.77 (dd, J = 11.62, 6.11 Hz, 1H) 3.53 (dd, J = 11.62, 5.75 Hz, 3H) 3.14- 3.28 (m, 1H) 2.25 (s, 3H) 2.00-2.13 (m, 3H) 1.55-1.72 (m, 4H) 1.34 (s, 3H); LCMS (m/z) (M + H) = 552.1, Rt = 1.27 min. |
| 192 | 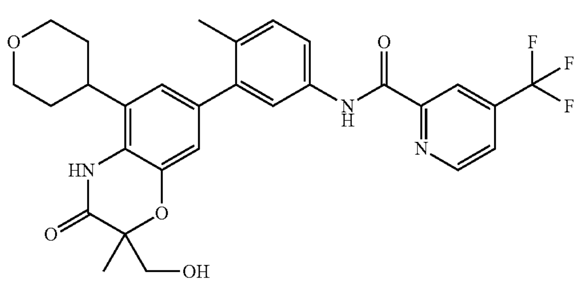 [SMILES: Cc1ccc(NC(=O)c2cc(C(F)(F)F)ccn2)cc1-c1cc2c(c(C3CCOCC3)c1)NC(=O)C(C)(CO)O2] | N-(3-(2-(hydroxymethyl)-2-methyl-3-oxo-5-(tetrahydro-2H-pyran-4-yl)-3,4-dihydro-2H-benzo[b][1,4]oxazin-7-yl)-4-methylphenyl)-4-(trifluoromethyl)picolinamide | ¹H NMR (400 MHz, DMSO-d6) δ ppm 10.78 (s, 1H) 10.39 (s, 1 H) 9.03 (d, J = 5.01 Hz, 1H) 8.28-8.42 (m, 1H) 8.09 (dd, J = 5.07, 1.16 Hz, 1H), 7.81 (dq, J = 4.40, 2.20 Hz, 2H) 7.28 (d, J = 9.17 Hz, 1H) 6.83 (dd, J = 16.99, 1.83 Hz, 2H) 3.87-4.03 (m, 2H) 3.77 (d, J = 11.49 Hz, 1 H) 3.46-3.57 (m, 3H) 3.26 (d, J = 8.19 Hz, 1H) 2.26 (s, 3H) 1.58-1.72 (m, 4H) 1.34 (s, 3 H); LCMS (m/z) (M + H) = 556.1, Rt = 1.42 min. |
| 193 | 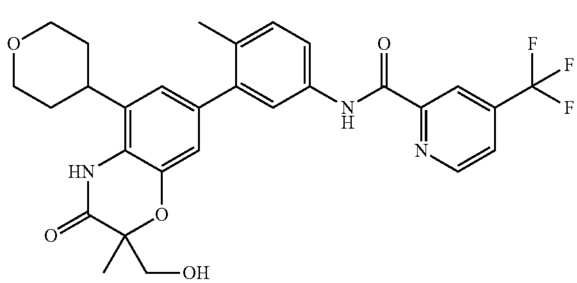 [SMILES: Cc1ccc(NC(=O)c2cc(C(F)(F)F)ccn2)cc1-c1cc2c(c(C3CCOCC3)c1)NC(=O)C(C)(CO)O2] | N-(3-(2-(hydroxymethyl)-2-methyl-3-oxo-5-(tetrahydro-2H-pyran-4-yl)-3,4-dihydro-2H-benzo[b][1,4]oxazin-7-yl)-4-methylphenyl)-4-(trifluoromethyl)picolinamide carboxamide (, single enantiomer, Peak 1 in Chiral SFC) | ¹H NMR (400 MHz, DMSO-d6) δ ppm 10.78 (s, 1H) 10.39 (s, 1 H) 9.03 (d, J = 5.01 Hz, 1H) 8.28-8.42 (m, 1H) 8.09 (dd, J = 5.07, 1.16 Hz, 1H), 7.81 (dq, J = 4.40, 2.20 Hz, 2H) 7.28 (d, J = 9.17 Hz, 1H) 6.83 (dd, J = 16.99, 1.83 Hz, 2H) 3.87-4.03 (m, 2H) 3.77 (d, J = 11.49 Hz, 1 H) 3.46-3.57 (m, 3H) 3.26 (d, J = 8.19 Hz, 1H) 2.26 (s, 3H) 1.58-1.72 (m, 4H) 1.34 (s, 3 H); LCMS (m/z) (M + H) = 556.1, Rt = 1.42 min |

TABLE 3-continued

| Example | Structure | Name | Physical Data |
|---|---|---|---|
| 194 | 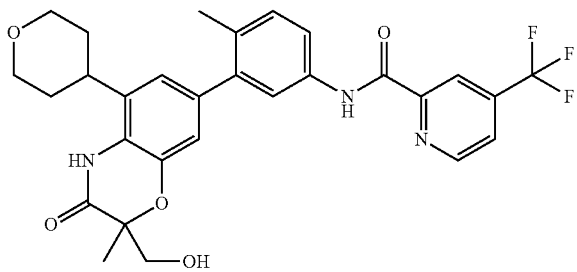 [SMILES: Cc1ccc(NC(=O)c2cc(C(F)(F)F)ccn2)cc1-c1cc2c(c(C3CCOCC3)c1)NC(=O)C(C)(CO)O2] | N-(3-(2-(hydroxymethyl)-2-methyl-3-oxo-5-(tetrahydro-2H-pyran-4-yl)-3,4-dihydro-2H-benzo[b][1,4]oxazin-7-yl)-4-methylphenyl)-4-(trifluoromethyl)picolinamide carboxamide (, single enantiomer, Peak 2 in Chiral SFC) | $^1$H NMR (400 MHz, DMSO-d6) δ ppm 10.78 (s, 1H) 10.39 (s, 1H) 9.03 (d, J = 5.01 Hz, 1H) 8.28-8.42 (m, 1H) 8.09 (dd, J = 5.07, 1.16 Hz, 1H), 7.81 (dq, J = 4.40, 2.20 Hz, 2H) 7.28 (d, J = 9.17 Hz, 1H) 6.83 (dd, J = 16.99, 1.83 Hz, 2H) 3.87-4.03 (m, 2H) 3.77 (d, J = 11.49 Hz, 1H) 3.46-3.57 (m, 3H) 3.26 (d, J = 8.19 Hz, 1H) 2.26 (s, 3H) 1.58-1.72 (m, 4H) 1.34 (s, 3H); LCMS (m/z) (M + H) = 556.1, Rt = 1.42 min |
| 195 | 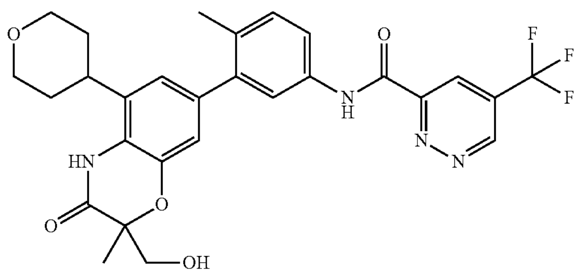 [SMILES: Cc1ccc(NC(=O)c2cc(C(F)(F)F)cnn2)cc1-c1cc2c(c(C3CCOCC3)c1)NC(=O)C(C)(CO)O2] | N-(3-(2-(hydroxymethyl)-2-methyl-3-oxo-5-(tetrahydro-2H-pyran-4-yl)-3,4-dihydro-2H-benzo[b][1,4]oxazin-7-yl)-4-methylphenyl)-5-(trifluoromethyl)pyridazine-3-carboxamide | $^1$H NMR (400 MHz, DMSO-d6) δ ppm 11.22 (s, 1H) 10.39 (s, 1H) 9.95 (d, J = 1.71 Hz, 1H) 8.58 (dd, J = 2.20, 0.73 Hz, 1H) 7.77-7.92 (m, 2H) 7.30 (d, J = 7.83 Hz, 1H) 6.83 (dd, J = 16.44, 1.77 Hz, 2H) 5.11 (t, J = 5.93 Hz, 1H) 3.92 (d, J = 11.00 Hz, 2H) 3.77 (dd, J = 11.62, 6.11 Hz, 1H) 3.46-3.60 (m, 3H) 3.19-3.26 (m, 1H) 2.27 (s, 3H) 1.56-1.73 (m, 4H) 1.34 (s, 3H); LCMS (m/z) (M + H) = 557.1, Rt = 1.31 min |
| 196 | 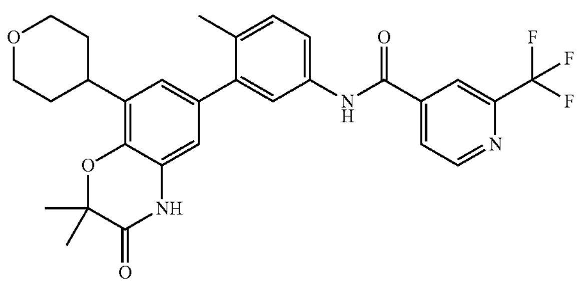 [SMILES: Cc1ccc(NC(=O)c2ccnc(C(F)(F)F)c2)cc1-c1cc2c(c(C3CCOCC3)c1)OC(C)(C)C(=O)N2] | N-(3-(2,2-dimethyl-3-oxo-8-(tetrahydro-2H-pyran-4-yl)-3,4-dihydro-2H-benzo[b][1,4]oxazin-6-yl)-4-methylphenyl)-2-(trifluoromethyl)isonicotinamide | $^1$H NMR (400 MHz, DMSO-d6) δ ppm 10.65 (d, J = 2.32 Hz, 2H) 8.99 (d, J = 5.01 Hz, 1H) 8.37 (s, 1H) 8.20 (d, J = 5.01 Hz, 1H) 7.69 (dd, J = 8.25, 2.14 Hz, 1H) 7.64 (d, J = 2.08 Hz, 1H) 7.30 (d, J = 8.44 Hz, 1H) 6.83 (d, J = 1.83 Hz, 1H) 6.75 (d, J = 1.96 Hz, 1H) 3.95 (dd, J = 11.19, 2.75 Hz, 2H) 3.46 (td, J = 11.43, 1.96 Hz, 2H) 3.32 (s, 1H) 3.13 (tt, J = 11.52, 3.94 Hz, 1H) 2.23 (s, 3H) 1.57-1.82 (m, 4H) 1.45 (s, 6H); LCMS (m/z) (M + H) = 540.1, Rt = 1.45 min. |
| 197 | 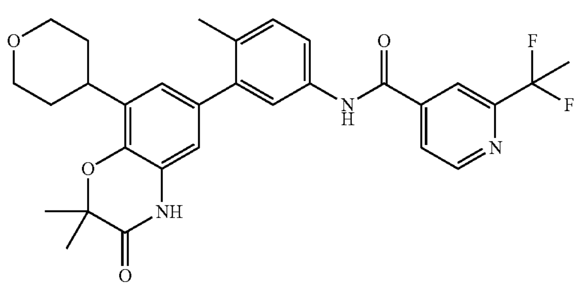 [SMILES: Cc1ccc(NC(=O)c2ccnc(C(C)(F)F)c2)cc1-c1cc2c(c(C3CCOCC3)c1)OC(C)(C)C(=O)N2] | 2-(1,1-difluoroethyl)-N-(3-(2,2-dimethyl-3-oxo-8-(tetrahydro-2H-pyran-4-yl)-3,4-dihydro-2H-benzo[b][1,4]oxazin-6-yl)-4-methylphenyl)isonicotinamide | $^1$H NMR (400 MHz, DMSO-d6) δ ppm 10.61 (br. s., 1H) 8.87 (d, J = 5.01 Hz, 1H) 8.18 (s, 1H) 8.03 (dd, J = 5.01, 1.47 Hz, 1H) 7.58-7.77 (m, 2H) 7.29 (d, J = 8.44 Hz, 1H) 6.82 (d, J = 1.96 Hz, 1H) 6.74 (d, J = 1.96 Hz, 1H) 3.86-4.02 (m, 2H) 3.45 (td, J = 11.49, 2.20 Hz, 2H) 3.02-3.18 (m, 1H) 2.22 (s, 3H) 2.05 (t, J = 19.13 Hz, 3H) 1.59-1.79 (m, 4H) 1.44 (s, 6H); LCMS (m/z) (M + H) = 536.1, Rt = 1.42 min. |
| 198 | 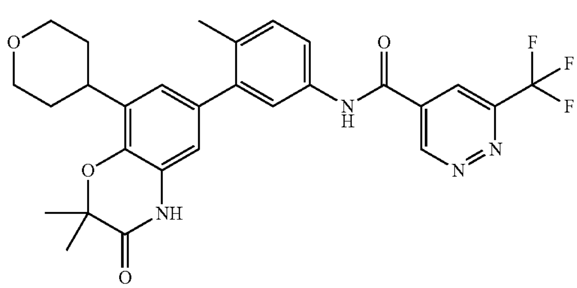 [SMILES: Cc1ccc(NC(=O)c2cnnc(C(F)(F)F)c2)cc1-c1cc2c(c(C3CCOCC3)c1)OC(C)(C)C(=O)N2] | N-(3-(2,2-dimethyl-3-oxo-8-(tetrahydro-2H-pyran-4-yl)-3,4-dihydro-2H-benzo[b][1,4]oxazin-6-yl)-4-methylphenyl)-6-(trifluoromethyl)pyridazine-4-carboxamide | $^1$H NMR (400 MHz, DMSO-d6) δ ppm 10.65 (s, 1H) 9.92 (d, J = 1.83 Hz, 1H) 8.65 (d, J = 1.71 Hz, 1H) 7.52-7.75 (m, 2H) 7.29 (d, J = 8.19 Hz, 1H) 6.61-6.88 (m, 2H) 3.78-4.06 (m, 2H) 3.46 (td, J = 11.40, 2.26 Hz, 2H) 3.03-3.19 (m, 1H) 2.23 (s, 3H) 1.59-1.82 (m, 4H) 1.44 (s, 6H); LCMS (m/z) (M + H) = 541.1, Rt = 1.39 min. |

TABLE 3-continued

| Example | Structure | Name | Physical Data |
|---|---|---|---|
| 199 | 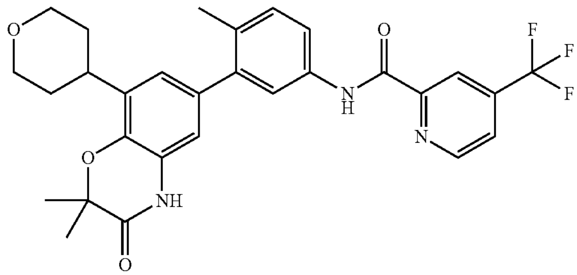 [SMILES: Cc1ccc(NC(=O)c2cc(C(F)(F)F)ccn2)cc1-c1cc2c(c(C3CCOCC3)c1)OC(C)(C)C(=O)N2] | N-(3-(2,2-dimethyl-3-oxo-8-(tetrahydro-2H-pyran-4-yl)-3,4-dihydro-2H-benzo[b][1,4]oxazin-6-yl)-4-methylphenyl)-4-(trifluoromethyl)picolinamide | $^1$H NMR (400 MHz, DMSO-d6) δ ppm 10.78 (br. s., 1H) 10.64 (br. S., 1H) 9.03 (d, J = 5.01 Hz, 1H) 8.27-8.43 (m, 1H) 8.09 (dd, J = 5.01, 1.10 Hz, 1H) 7.70-7.88 (m, 2H) 7.22-7.34 (m, 1H) 6.84 (d, J = 1.83 Hz, 1 H) 6.77 (d, J = 2.08 Hz, 1H) 3.88-4.04 (m, 2H) 3.46 (td, J = 11.49, 2.08 Hz, 2H) 3.13 (tt, J = 11.60, 3.87 Hz, 1H) 2.23 (s, 3H) 1.62-1.83 (m, 4H) 1.45 (s, 6H); LCMS (m/z) (M + H) = 540.1, Rt = 1.56 min |
| 200 | 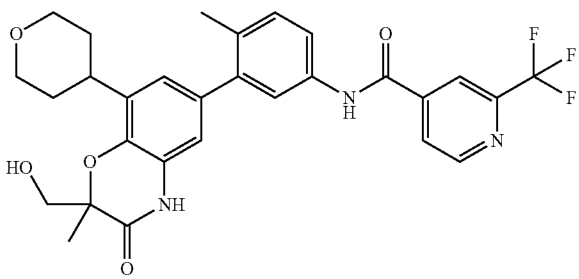 | N-(3-(2-(hydroxymethyl)-2-methyl-3-oxo-8-(tetrahydro-2H-pyran-4-yl)-3,4-dihydro-2H-benzo[b][1,4]oxazin-6-yl)-4-methylphenyl)-2-(trifluoromethyl)isonicotinamide | $^1$H NMR (400 MHz, DMSO-d6) δ ppm 10.64 (br. s., 1H) 8.99 (d, J = 5.01 Hz, 1H) 8.37 (s, 1H) 8.19 (dd, J = 5.01, 1.10 Hz, 1H) 7.68 (dd, J = 8.25, 2.26 Hz, 1H) 7.63 (d, J = 2.20 Hz, 1H) 7.30 (d, J = 8.44 Hz, 1H) 6.79 (d, J = 1.83 Hz, 1H) 6.71 (d, J = 1.96 Hz, 1H) 5.09 (t, J = 5.87 Hz, 1 H) 3.90-4.03 (m, 2H) 3.80 (dd, J = 11.49, 6.24 Hz, 1H) 3.56 (dd, J = 11.55, 5.56 Hz, 1 H) 3.37-3.50 (m, 2H) 3.05-3.23 (m, 1H) 2.23 (s, 3H) 1.59-1.79 (m, 4H) 1.36 (s, 3H); LCMS (m/z) (M + H) = 540.1, Rt = 1.45 min. |
| 201 | 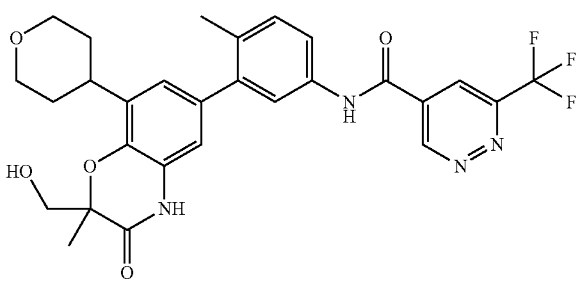 [SMILES: Cc1ccc(NC(=O)c2cnnc(C(F)(F)F)c2)cc1-c1cc2c(c(C3CCOCC3)c1)OC(C)(CO)C(=O)N2] | N-(3-(2-(hydroxymethyl)-2-methyl-3-oxo-8-(tetrahydro-2H-pyran-4-yl)-3,4-dihydro-2H-benzo[b][1,4]oxazin-6-yl)-4-methylphenyl)-6-(trifluoromethyl)pyridazine-4-carboxamide | $^1$H NMR (400 MHz, DMSO-d6) δ ppm 10.64 (br. s., 1H) 9.92 (d, J = 1.96 Hz, 1H) 8.68 (d, J = 1.96 Hz, 1H) 7.67 (dd, J = 8.25, 2.26 Hz, 1H) 7.62 (d, J = 2.20 Hz, 1H) 7.31 (d, J = 8.44 Hz, 1 H) 6.79 (d, J = 1.83 Hz, 1H) 6.71 (d, J = 1.96 Hz, 1H) 5.09 (t, J = 5.81 Hz, 1H) 3.90-4.03 (m, 2H) 3.80 (dd, J = 11.49, 6.11 Hz, 1H) 3.56 (dd, J = 11.55, 5.44 Hz, 1H) 3.39-3.50 (m, 2H) 3.04-3.23 (m, 1H) 2.16-2.27 (m, 3H) 1.62-1.80 (m, 4H) 1.36 (s, 3H); LCMS (m/z) (M + H) = 557.1, Rt = 1.24 min. |
| 202 | 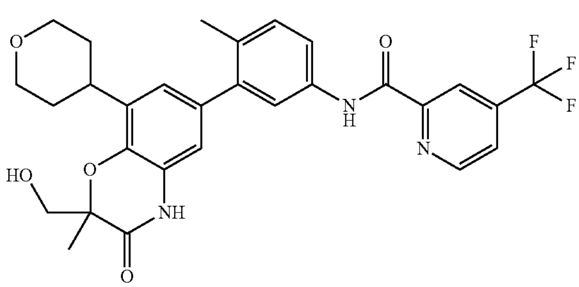 [SMILES: Cc1ccc(NC(=O)c2cc(C(F)(F)F)ccn2)cc1-c1cc2c(c(C3CCOCC3)c1)OC(C)(CO)C(=O)N2] | N-(3-(2-(hydroxymethyl)-2-methyl-3-oxo-8-(tetrahydro-2H-pyran-4-yl)-3,4-dihydro-2H-benzo[b][1,4]oxazin-6-yl)-4-methylphenyl)-4-(trifluoromethyl)picolinamide | $^1$H NMR (400 MHz, DMSO-d6) δ ppm 10.78 (s, 1H) 10.62 (br. s., 1H) 9.03 (d, J = 5.01 Hz, 1 H) 8.29-8.42 (m, 1H) 8.09 (dd, J = 5.01, 1.10 Hz, 1H) 7.71-7.85 (m, 2H) 7.28 (d, J = 9.29 Hz, 1 H) 6.81 (d, J = 1.96 Hz, 1H) 6.73 (d, J = 1.96 Hz, 1H) 5.10 (br. s., 1H) 3.90-4.05 (m, 2H) 3.81 (dd, J = 11.25, 2.81 Hz, 1 H) 3.56 (d, J = 10.27 Hz, 1H) 3.39-3.50 (m, 2H) 3.17 (tt, J = 10.27, 5.26 Hz, 1H) 2.23 (s, 3 H) 1.61-1.80 (m, 4H) 1.36 (s, 3H); LCMS (m/z) (M + H) = 556.1, Rt = 1.40 min. |

TABLE 3-continued

| Example | Structure | Name | Physical Data |
|---|---|---|---|
| 203 | 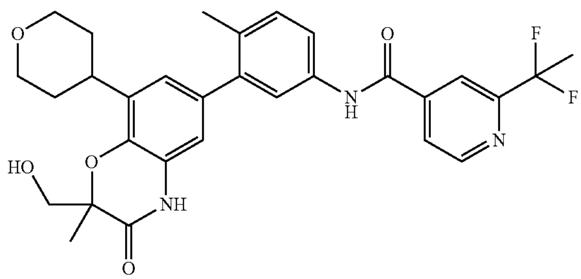 | 2-(1,1-difluoroethyl)-N-(3-(2-(hydroxymethyl)-2-methyl-3-oxo-8-(tetrahydro-2H-pyran-4-yl)-3,4-dihydro-2H-benzo[b][1,4]oxazin-6-yl)-4-methylphenyl)isonicotinamide | ¹H NMR (400 MHz, DMSO-d6) δ ppm 10.78 (s, 1H) 10.39 (s, 1H) 9.03 (d, J = 5.01 Hz, 1H) 8.28-8.42 (m, 1H) 8.09 (dd, J = 5.07, 1.16 Hz, 1H) 7.81 (dq, J = 4.40, 2.20 Hz, 2H) 7.28 (d, J = 9.17 Hz, 1H) 6.83 (dd, J = 16.99, 1.83 Hz, 2H) 3.87-4.03 (m, 2H) 3.77 (d, J = 11.49 Hz, 1 H) 3.46-3.57 (m, 3H) 3.26 (d, J = 8.19 Hz, 1H) 2.26 (s, 3H) 1.58-1.72 (m, 4H) 1.34 (s, 3H); LCMS (m/z) (M + H) = 556.1, Rt = 1.42 min |
| 204 | 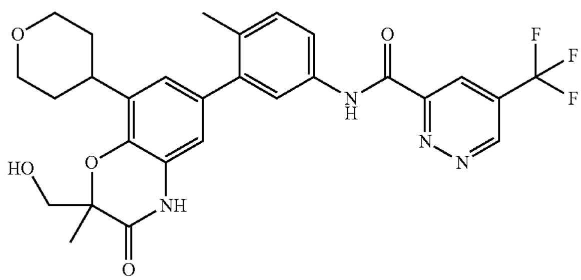 [SMILES: Cc1ccc(NC(=O)c2cc(C(F)(F)F)cnn2)cc1-c1cc2c(c(C3CCOCC3)c1)OC(C)(CO)C(=O)N2] | N-(3-(2-(hydroxymethyl)-2-methyl-3-oxo-8-(tetrahydro-2H-pyran-4-yl)-3,4-dihydro-2H-benzo[b][1,4]oxazin-6-yl)-4-methylphenyl)-5-(trifluoromethyl)pyridazine-3-carboxamide | ¹H NMR (400 MHz, DMSO-d6) δ ppm 10.78 (s, 1H) 10.39 (s, 1H) 9.03 (d, J = 5.01 Hz, 1H) 8.28-8.42 (m, 1H) 8.09 (dd, J = 5.07, 1.16 Hz, 1H) 7.81 (dq, J = 4.40, 2.20 Hz, 2H) 7.28 (d, J = 9.17 Hz, 1H) 6.83 (dd, J = 16.99, 1.83 Hz, 2H) 3.87-4.03 (m, 2H) 3.77 (d, J = 11.49 Hz, 1 H) 3.46-3.57 (m, 3H) 3.26 (d, J = 8.19 Hz, 1H) 2.26 (s, 3H) 1.58-1.72 (m, 4H) 1.34 (s, 3H); LCMS (m/z) (M + H) = 556.1, Rt = 1.42 min |
| 205 | 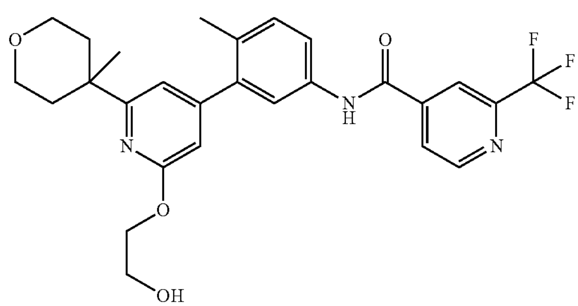 [SMILES: Cc1ccc(NC(=O)c2ccnc(C(F)(F)F)c2)cc1-c1cc(OCCO)nc(C2(C)CCOCC2)c1] | N-(3-(2-(2-hydroxyethoxy)-6-(4-methyltetrahydro-2H-pyran-4-yl)pyridin-4-yl)-4-methylphenyl)-2-(trifluoromethyl)isonicotinamide | ¹H NMR (400 MHz, DMSO-d6) δ ppm 10.69 (s, 1H) 8.99 (d, J = 5.01 Hz, 1H) 8.36 (s, 1H) 8.14-8.20 (m, 1H) 7.75 (dd, J = 8.25, 2.26 Hz, 1H) 7.66 (d, J = 2.20 Hz, 1H) 7.35 (d, J = 8.44 Hz, 1H) 6.94 (d, J = 0.98 Hz, 1H) 6.59 (d, J = 0.98 Hz, 1H) 4.81 (t, J = 5.50 Hz, 1H) 4.32 (t, J = 5.26 Hz, 2H) 3.64-3.81 (m, 4 H) 3.49 (ddd, J = 11.37, 8.01, 3.12 Hz, 2H) 2.15-2.30 (m, 6H) 1.66 (ddd, J = 13.27, 8.07, 3.48 Hz, 2H) 1.28 (s, 3H); LCMS (m/z) (M + H) = 5.16, Rt = 1.43 min. |
| 206 | 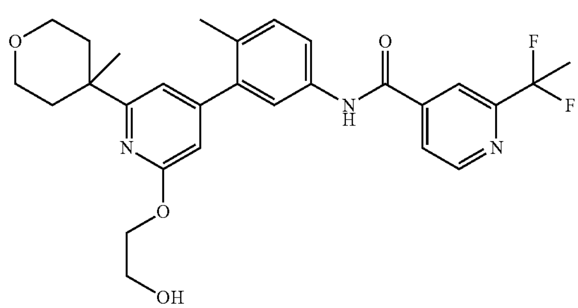 [SMILES: Cc1ccc(NC(=O)c2ccnc(C(C)(F)F)c2)cc1-c1cc(OCCO)nc(C2(C)CCOCC2)c1] | 2-(1,1-difluoroethyl)-N-(3-(2-(2-hydroxyethoxy)-6-(4-methyltetrahydro-2H-pyran-4-yl)pyridin-4-yl)-4-methylphenyl)isonicotinamide | ¹H NMR (400 MHz, DMSO-d6) δ ppm 10.64 (s, 1H) 8.88 (d, J = 5.01 Hz, 1H) 8.18 (s, 1H) 8.03 (dd, J = 5.32, 1.41 Hz, 1H) 7.76 (dd, J = 8.25, 2.26 Hz, 1H) 7.67 (d, J = 2.20 Hz, 1H) 7.34 (d, J = 8.44 Hz, 1H) 6.94 (d, J = 0.98 Hz, 1H) 6.59 (d, J = 0.98 Hz, 1 H) 4.81 (t, J = 5.50 Hz, 1H) 4.32 (t, J = 5.20 Hz, 2H) 3.65-3.85 (m, 4H) 3.49 (ddd, J = 11.34, 7.98, 3.06 Hz, 2H) 2.19-2.28 (m, 5H) 1.98-2.11 (m, 3H) 1.66 (ddd, J = 13.33, 8.07, 3.42 Hz, 2H) 1.28 (s, 3H); LCMS (m/z) (M + H) = 512.1, Rt = 1.40 min. |

TABLE 3-continued

| Example | Structure | Name | Physical Data |
|---|---|---|---|
| 207 | 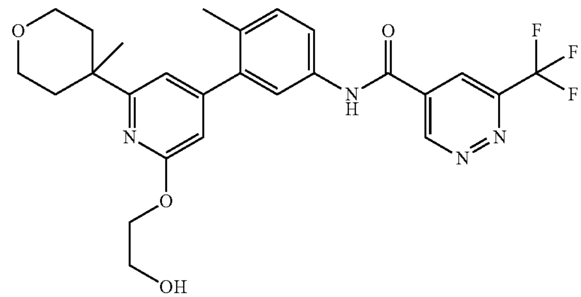 | N-(3-(2-(2-hydroxyethoxy)-6-(4-methyltetrahydro-2H-pyran-4-yl)pyridin-4-yl)-4-methylphenyl)-6-(trifluoromethyl)pyridazine-4-carboxamide | ¹H NMR (400 MHz, DMSO-d6) δ ppm 10.86 (s, 1H) 9.92 (d, J = 1.96 Hz, 1H) 8.68 (d, J = 2.08 Hz, 1H) 7.75 (dd, J = 8.25, 2.26 Hz, 1H) 7.66 (d, J = 2.20 Hz, 1 H) 7.37 (d, J = 8.44 Hz, 1H) 6.94 (d, J = 0.98 Hz, 1H) 6.59 (d, J = 0.98 Hz, 1H) 4.81 (t, J = 5.50 Hz, 1H) 4.33 (t, J = 5.20 Hz, 2H) 3.65-3.84 (m, 4H) 3.49 (ddd, J = 11.37, 7.95, 3.18 Hz, 2H) 2.16-2.27 (m, 5H) 1.66 (ddd, J = 13.30, 8.04, 3.48 Hz, 2 H) 1.28 (s, 3H); LCMS (m/z) (M + H) = 512.1, Rt = 1.40 min. |
| 208 | 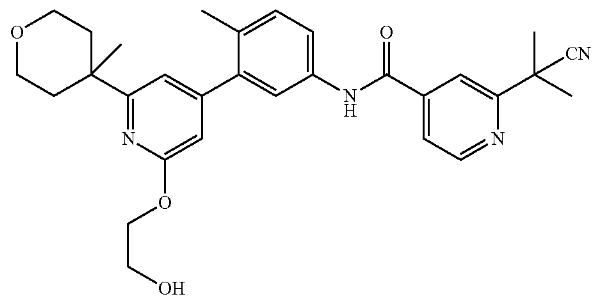 [SMILES: Cc1ccc(NC(=O)c2ccnc(C(C)(C)C#N)c2)cc1-c1cc(OCCO)nc(C2(C)CCOCC2)c1] | 2-(2-cyanopropan-2-yl)-N-(3-(2-(2-hydroxyethoxy)-6-(4-methyltetrahydro-2H-pyran-4-yl)pyridin-4-yl)-4-methylphenyl)isonicotinamide | ¹H NMR (400 MHz, DMSO-d6) δ ppm 10.55 (s, 1H) 8.81 (dd, J = 5.07, 0.67 Hz, 1H) 8.00 (s, 1H) 7.86 (dd, J = 5.01, 1.47 Hz, 1H) 7.74 (dd, J = 8.31, 2.20 Hz, 1H) 7.65 (d, J = 2.20 Hz, 1H) 7.34 (d, J = 8.44 Hz, 1H) 6.94 (d, J = 0.98 Hz, 1H) 6.59 (d, J = 0.98 Hz, 1H) 4.82 (t, J = 5.50 Hz, 1H) 4.32 (t, J = 5.26 Hz, 2H) 3.63-3.82 (m, 4H) 3.49 (ddd, J = 11.40, 7.98, 3.12 Hz, 2H) 2.18-2.29 (m, 5H) 1.72-1.88 (m, 7H) 1.66 (ddd, J = 13.27, 8.01, 3.42 Hz, 2H) 1.28 (s, 3H); LCMS (m/z) (M + H) = 515.1, Rt = 1.36 min. |
| 209 | 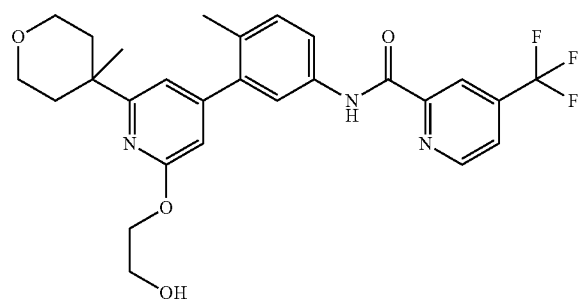 [SMILES: Cc1ccc(NC(=O)c2cc(C(F)(F)F)ccn2)cc1-c1cc(OCCO)nc(C2(C)CCOCC2)c1] | N-(3-(2-(2-hydroxyethoxy)-6-(4-methyltetrahydro-2H-pyran-4-yl)pyridin-4-yl)-4-methylphenyl)-4-(trifluoromethyl)picolinamide | ¹H NMR (400 MHz, DMSO-d6) δ ppm 10.83 (s, 1H) 9.03 (d, J = 5.01 Hz, 1H) 8.29-8.43 (m, 1H) 8.09 (dd, J = 5.07, 1.16 Hz, 1H) 7.90 (dd, J = 8.31, 2.32 Hz, 1H) 7.85 (d, J = 2.20 Hz, 1H) 7.33 (d, J = 8.44 Hz, 1H) 6.95 (d, J = 0.98 Hz, 1H) 6.61 (d, J = 0.98 Hz, 1H) 4.82 (t, J = 5.56 Hz, 1 H) 4.33 (t, J = 5.20 Hz, 2H) 3.65-3.87 (m, 4H) 3.50 (ddd, J = 11.37, 8.01, 3.12 Hz, 2H) 2.10-2.30 (m, 5H) 1.67 (ddd, J = 13.24, 8.04, 3.42 Hz, 2H) 1.28 (s, 3H); LCMS (M + H) = 516.1, Rt = 1.55 min. |
| 210 | 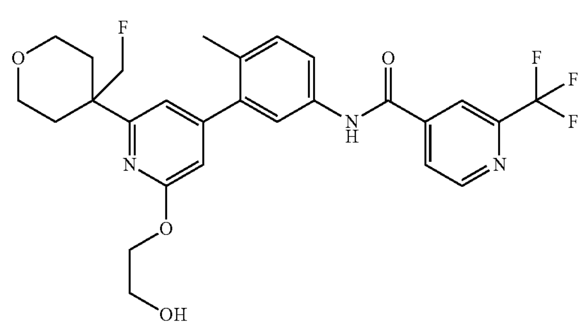 [SMILES: Cc1ccc(NC(=O)c2ccnc(C(F)(F)F)c2)cc1-c1cc(OCCO)nc(C2(CF)CCOCC2)c1] | N-(3'-(2-hydroxyethoxy)-6-methyl-5'-(4-methyltetrahydro-2H-pyran-4-yl)-[1,1'-biphenyl]-3-yl)-2-(trifluoromethyl)isonicotinamide | ¹H NMR (400 MHz, DMSO-d6) δ ppm 10.70 (s, 1H) 8.99 (d, J = 5.01 Hz, 1H) 8.36 (s, 1H) 8.19 (dd, J = 4.95, 0.92 Hz, 1H) 7.77 (dd, J = 8.31, 2.20 Hz, 1H) 7.67 (d, J = 2.20 Hz, 1H) 7.35 (d, J = 8.44 Hz, 1H) 7.04 (d, J = 0.61 Hz, 1H) 6.66 (d, J = 0.86 Hz, 1 H) 4.82 (t, J = 5.50 Hz, 1H) 4.42-4.63 (m, 2H) 4.33 (t, J = 5.20 Hz, 2H) 3.67-3.85 (m, 4H) 3.37-3.51 (m, 2H) 2.17-2.31 (m, 5H) 1.81 (ddd, J = 13.79, 10.00, 3.97 Hz, 2H); LCMS (m/z) (M + H) = 534.3, Rt = 1.26 min. |

TABLE 3-continued

| Example | Structure | Name | Physical Data |
|---|---|---|---|
| 211 | 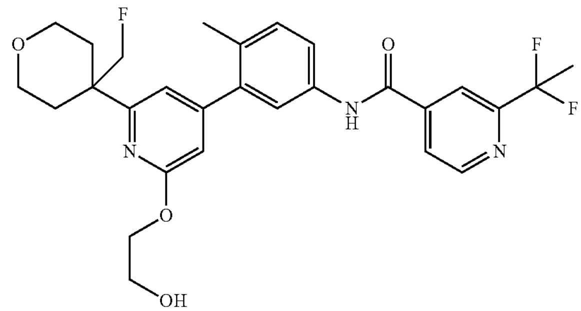 [SMILES: Cc1ccc(NC(=O)c2ccnc(C(C)(F)F)c2)cc1-c1cc(OCCO)nc(C2(CF)CCOCC2)c1] | 2-(1,1-difluoroethyl)-N-(3-(2-(4-(fluoromethyl)tetrahydro-2H-pyran-4-yl)-6-(2-hydroxyethoxy)pyridin-4-yl)-4-methylphenyl)isonicotinamide | ¹H NMR (400 MHz, DMSO-d6) δ ppm 10.65 (s, 1H) 8.88 (d, J = 5.14 Hz, 1H) 8.18 (s, 1H) 8.03 (dd, J = 5.01, 1.34 Hz, 1H) 7.77 (dd, J = 8.25, 2.26 Hz, 1H) 7.67 (d, J = 2.20 Hz, 1H) 7.34 (d, J = 8.44 Hz, 1H) 7.04 (d, J = 0.86 Hz, 1H) 6.65 (d, J = 0.86 Hz, 1H) 4.82 (t, J = 5.50 Hz, 1H) 4.42-4.64 (m, 2H) 4.32 (t, J = 5.20 Hz, 2H) 3.66-3.83 (m, 4H) 3.35-3.53 (m, 2H) 2.17-2.32 (m, 5H) 2.05 (t, J = 19.13 Hz, 3H) 1.81 (ddd, J = 13.82, 10.03, 4.03 Hz, 2H); LCMS (m/z) (M + H) = 530.3, Rt = 1.24 min. |
| 212 | 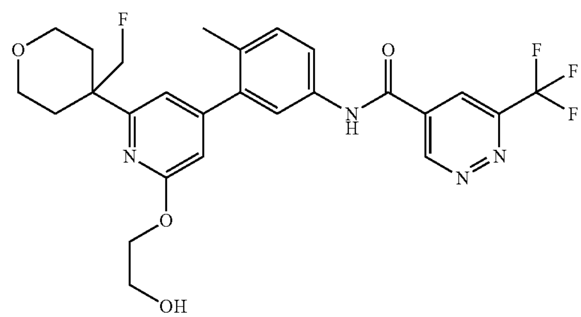 | N-(3-(2-(4-(fluoromethyl)tetrahydro-2H-pyran-4-yl)-6-(2-hydroxyethoxy)pyridin-4-yl)-4-methylphenyl)-6-(trifluoromethyl)pyridazine-4-carboxamide | ¹H NMR (400 MHz, DMSO-d6) δ ppm 10.87 (s, 1H) 9.92 (d, J = 1.96 Hz, 1H) 8.68 (d, J = 1.96 Hz, 1H) 7.76 (dd, J = 8.31, 2.20 Hz, 1H) 7.66 (d, J = 2.20 Hz, 1H) 7.37 (d, J = 8.44 Hz, 1H) 7.04 (d, J = 0.86 Hz, 1H) 6.66 (d, J = 0.98 Hz, 1H) 4.82 (t, J = 5.50 Hz, 1H) 4.43-4.61 (m, 2H) 4.33 (t, J = 5.20 Hz, 2H) 3.67-3.85 (m, 4H) 3.36-3.51 (m, 2H) 2.21-2.33 (m, 5H) 1.81 (ddd, J = 13.79, 10.00, 3.97 Hz, 2H); LCMS (m/z) (M + H) = 530.3, Rt = 1.24 mn. |
| 213 | 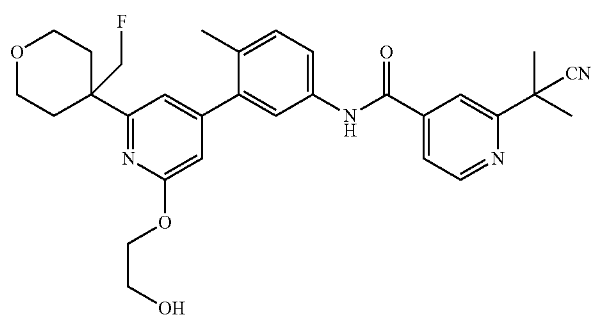 [SMILES: Cc1ccc(NC(=O)c2ccnc(C(C)(C)C#N)c2)cc1-c1cc(OCCO)nc(C2(CF)CCOCC2)c1] | 2-(2-cyanopropan-2-yl)-N-(3-(2-(4-(fluoromethyl)tetrahydro-2H-pyran-4-yl)-6-(2-hydroxyethoxy)pyridin-4-yl)-4-methylphenyl)isonicotinamide | ¹H NMR (400 MHz, DMSO-d6) δ ppm 10.56 (s, 1H) 8.81 (dd, J = 5.01, 0.73 Hz, 1H) 8.00 (s, 1H) 7.86 (dd, J = 5.01, 1.47 Hz, 1H) 7.75 (dd, J = 8.19, 2.20 Hz, 1H) 7.65 (d, J = 2.20 Hz, 1H) 7.34 (d, J = 8.56 Hz, 1H) 7.04 (d, J = 0.86 Hz, 1H) 6.65 (d, J = 0.86 hz, 1H) 4.42-4.66 (m, 2H) 4.32 (t, J = 5.20 Hz, 2H) 3.62-3.83 (m, 4H) 3.37-3.52 (m, 2H) 2.17-2.32 (m, 5H) 1.68-1.87 (m, 9H); LCMS (m/z) (M + H) = 533.3, Rt = 1.24 min. |
| 214 | 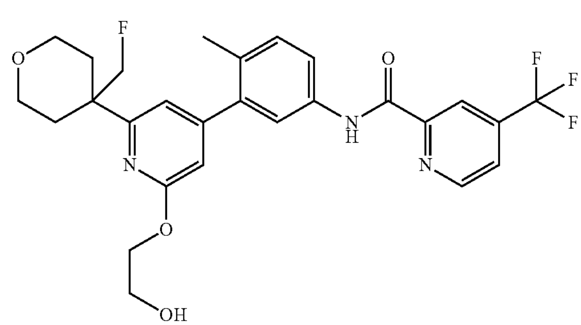 [SMILES: Cc1ccc(NC(=O)c2cc(C(F)(F)F)ccn2)cc1-c1cc(OCCO)nc(C2(CF)CCOCC2)c1] | N-(3-(2-(4-(fluoromethyl)tetrahydro-2H-pyran-4-yl)-6-(2-hydroxyethoxy)pyridin-4-yl)-4-methylphenyl)-4-(trifluoromethyl)picolinamide | ¹H NMR (400 MHz, DMSO-d6) δ ppm 10.84 (s, 1H) 9.03 (d, J = 5.01 Hz, 1H) 8.34 (d, J = 0.61 Hz, 1H) 8.09 (dd, J = 5.01, 1.01 Hz, 1H) 7.73-7.95(m, 2H) 7.33 (d, J = 8.44 Hz, 1H) 7.05 (d, J = 0.98 Hz, 1H) 6.67 (d, J = 0.98 Hz, 1H) 4.83 (t, J = 5.56 Hz, 1H) 4.42-4.65 (m, 2H) 4.33 (t, J = 5.20 Hz, 2H) 3.70-3.86 (m, 4H) 3.38-3.53 (m, 2H) 2.19-2.32 (m, 6H) 1.82 (ddd, J = 13.82, 10.03, 4.03 Hz, 2H); LCMS (m/z) (M + H) = 534.3, Rt = 1.32 min. |

TABLE 3-continued

| Example | Structure | Name | Physical Data |
|---|---|---|---|
| 215 | 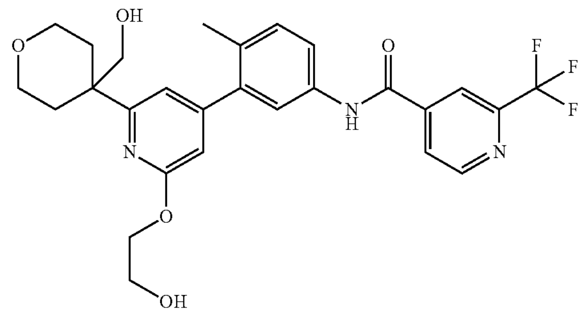 [SMILES: Cc1ccc(NC(=O)c2ccnc(C(F)(F)F)c2)cc1-c1cc(OCCO)nc(C2(CO)CCOCC2)c1] | N-(3'-(2-hydroxyethoxy)-6-methyl-5'-(4-methyltetrahydro-2H-pyran-4-yl)-[1,1'-biphenyl]-3-yl)-2-(trifluoromethyl)isonicotinamide | 1H NMR (400 MHz, DMSO-d6) δ ppm 10.69 (s, 1H) 8.99 (d, J = 5.01 Hz, 1H) 8.36 (s, 1H) 8.19 (dd, J = 4.95, 1.04 Hz, 1H) 7.75 (dd, J = 8.31, 2.20 Hz, 1H) 7.68 (d, J = 2.20 Hz, 1H) 7.34 (d, J = 8.44 Hz, 1H) 6.93 (d, J = 0.98 Hz, 1H) 6.58 (d, J = 0.98 Hz, 1H) 4.81 (t, J = 5.50 Hz, 1H) 4.56-4.70(m, 1H) 4.31 (t, J = 5.26 Hz, 2H) 3.65-3.82 (m, 4H) 3.49 (d, J = 5.62 Hz, 2H) 3.33-3.42 (m, 2H) 2.08-2.27 (m, 6H) 1.71-1.82 (m, 2H); LCMS (m/z) (M + H) = 532.1, Rt = 1.22 min. |
| 216 | 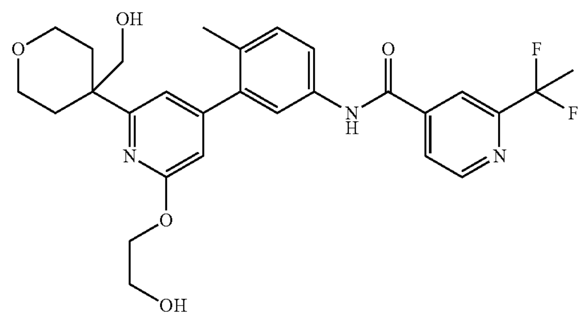 [SMILES: Cc1ccc(NC(=O)c2ccnc(C(C)(F)F)c2)cc1-c1cc(OCCO)nc(C2(CO)CCOCC2)c1] | 2-(1,1-difluoroethyl)-N-(3-(2-(2-hydroxyethoxy)-6-(4-(hydroxymethyl)tetrahydro-2H-pyran-4-yl)pyridin-4-yl)-4-methylphenyl)isonicotinamide | 1H NMR (400 MHz, DMSO-d6) δ ppm 10.65 (s, 1H) 8.88 (d, J = 5.01 Hz, 1H) 8.18 (s, 1H) 8.03 (dd, J = 5.01, 1.34 Hz, 1H) 7.75 (dd, J = 8.25, 2.26 Hz, 1H) 7.68 (d, J = 2.20 Hz, 1H) 7.33 (d, J = 8.56 Hz, 1H) 6.93 (d, J = 0.98 Hz, 1H) 6.59 (d, J = 0.98 Hz, 1H) 4.81 (t, J = 5.56 Hz, 1H) 4.57-4.68 (m, 1H) 4.31 (t, J = 5.26 Hz, 2H) 3.67-3.82 (m, 4H) 3.49 (d, J = 5.50 Hz, 2H) 3.34-3.42 (m, 2H) 2.16-2.29 (m, 5H) 2.05 (t, J = 19.13 Hz, 3H)1.79 (ddd, J = 13.72, 10.12, 3.91 Hz, 2H); LCMS (m/z) (M + H) = 528.1, Rt = 1.19 min. |
| 217 | 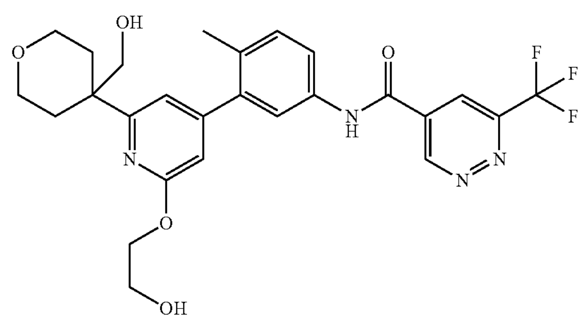 [SMILES: Cc1ccc(NC(=O)c2cnnc(C(F)(F)F)c2)cc1-c1cc(OCCO)nc(C2(CO)CCOCC2)c1] | N-(3-(2-(2-hydroxyethoxy)-6-(4-(hydroxymethyl)tetrahydro-2H-pyran-4-yl)-4-methylphenyl)-6-(trifluoromethyl)pyridazine-4-carboxamide | 1H NMR (400 MHz, DMSO-d6) δ ppm 10.87 (s, 1H) 9.92 (d, J = 1.96 Hz, 1H) 8.68 (d, J = 1.96 Hz, 1H) 7.74 (dd, J = 8.25, 2.26 Hz, 1H) 7.67 (d, J = 2.20 Hz, 1H) 7.37 (d, J = 8.44 Hz, 1H) 6.93 (d, J = 0.98 Hz, 1H) 4.81 (t, J = 5.50 Hz, 1H) 4.63 (t, J = 5.56 Hz, 1H) 4.31 (t, J = 5.26 Hz, 2H) 3.67-3.79 (m, 4H) 3.49 (d, J = 5.62 Hz, 2H) 3.34-3.42 (m, 2H) 2.25 (s, 3H) 2.19 (d, J = 13.82 Hz, 2H) 1.79 (ddd, J = 13.60, 9.93, 3.61 Hz, 2H); LCMS (m/z) (M + H) = 533.1, Rt = 1.16 min. |
| 218 | 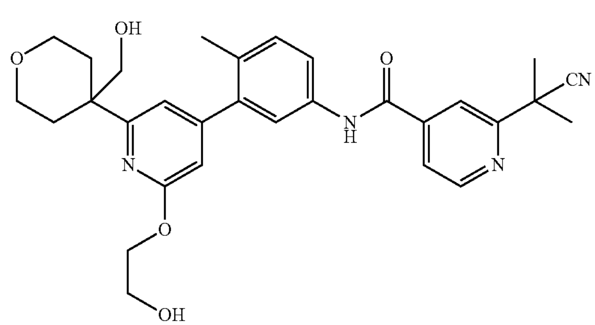 [SMILES: Cc1ccc(NC(=O)c2ccnc(C(C)(C)C#N)c2)cc1-c1cc(OCCO)nc(C2(CO)CCOCC2)c1] | 2-(2-cyanopropan-2-yl)-N-(3-(2-(2-hydroxyethoxy)-6-(4-(hydroxymethyl)tetrahydro-2H-pyran-4-yl)pyridin-4-yl)-4-methylphenyl)isonicotinamide | 1H NMR (400 MHz, DMSO-d6) δ ppm 10.87 (s, 1H) 9.92 (d, J = 1.96 Hz, 1H) 8.68 (d, J = 1.96 Hz, 1H) 7.74 (dd, J = 8.25, 2.26 Hz, 1H) 7.67 (d, J = 2.20 Hz, 1H) 7.37 (d, J = 8.44 Hz, 1H) 6.93 (d, J = 0.98 Hz, 1H) 6.59 (d, J = 0.98 Hz, 1H) 4.81 (t, J = 5.50 Hz, 1H) 4.63 (t, J = 5.56 Hz, 1H) 4.31 (t, J = 5.26 Hz, 2H) 3.67-3.79 (m, 4H) 3.49 (d, J = 5.62 Hz, 2H) 3.34-3.42 (m, 2H) 2.25 (s, 3H) 2.19 (d, J = 13.82 Hz, 2H) 1.79 (ddd, J = 13.60, 9.93, 3.61 Hz, 2H); LCMS (m/z) (M + H) = 533.1, Rt = 1.16 min. |

TABLE 3-continued

| Example | Structure | Name | Physical Data |
|---|---|---|---|
| 219 | 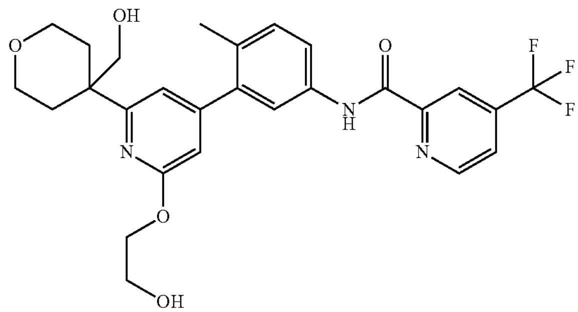 [SMILES: Cc1ccc(NC(=O)c2cc(C(F)(F)F)ccn2)cc1-c1cc(OCCO)nc(C2(CO)CCOCC2)c1] | N-(3-(2-(2-hydroxyethoxy)-6-(4-(hydroxymethyl)tetrahydro-2H-pyran-4-yl)-4-methylphenyl)-4-(trifluoromethyl)picolinamide | ¹H NMR (400 MHz, DMSO-d6) δ ppm 10.84 (s, 1H) 9.03 (d, J = 5.01 Hz, 1H) 8.34 (d, J = 0.73 Hz, 1H) 8.09 (dd, J = 5.07, 1.16 Hz, 1H) 7.82-7.95 (m, 2H) 7.32 (d, J = 8.44 Hz, 1H) 6.95 (d, J = 0.86 Hz, 1H) 6.60 (d, J = 0.98 Hz, 1H) 4.81 (t, J = 5.56 Hz, 1H) 4.56-4.66 (m, 1H) 4.31 (t, J = 5.26 Hz, 2H) 3.67-3.83 (m, 4H) 3.49 (d, J = 5.75 Hz, 2H) 3.34-3.43 (m, 2H) 2.16-2.29 (m, 5H) 1.79 (ddd, J = 13.75, 10.09, 3.91 Hz, 2H); LCMS (m/z) (M + H) = 532.3, Rt = 1.23 min. |
| 220 | 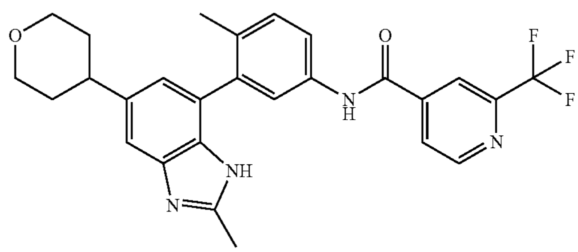 [SMILES: Cc1nc2cc(C3CCOCC3)cc(-c3cc(NC(=O)c4ccnc(C(F)(F)F)c4)ccc3C)c2[nH]1] | N-(4-methyl-3-(2-methyl-5-(tetrahydro-2H-pyran-4-yl)-1H-benzo[d]imidazol-7-yl)phenyl)-2-(trifluoromethyl)isonicotinamide | ¹H NMR (400 MHz, DMSO-d6) δ ppm 11.66-12.34 (m, 1H) 10.66 (d, J = 16.87 Hz, 1H) 8.81-9.15 (m, 1H) 8.37 (s, 1H) 8.20 (d, J = 4.89 Hz, 1H) 7.71-7.94 (m, 1H) 7.65 (dd, J = 7.21, 1.96 Hz, 1H) 7.18-7.46 (m, 2H) 6.88 (s, 1H) 3.89-4.08 (m, 2H) 3.46 (td, J = 11.19, 3.06 Hz, 2H) 2.82-3.00 (m, 1H) 2.42 (d, J = 1.96 Hz, 3H) 2.12 (d, J = 7.21 Hz, 3H) 1.65-1.87 (m, 4H).; LCMS (m/z) (M + H) = 495.2, Rt = 1.27 min. |
| 221 | 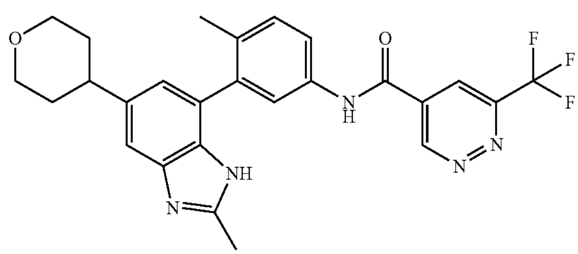 [SMILES: Cc1nc2cc(C3CCOCC3)cc(-c3cc(NC(=O)c4cnnc(C(F)(F)F)c4)ccc3C)c2[nH]1] | N-(4-methyl-3-(2-methyl-5-(tetrahydro-2H-pyran-4-yl)-1H-benzo[d]imidazol-7-yl)phenyl)-6-(trifluoromethyl)pyridazine-4-carboxamide | ¹H NMR (400 MHz, DMSO-d6) δ ppm 12.16 (br. s., 1H) 10.82 (br. s., 1H) 9.92 (d, J = 1.96 Hz, 1H) 8.68 (d, J = 2.08 Hz, 1H) 7.76 (br. s., 1H) 7.64(d, J = 2.20 Hz, 1H) 7.19-7.50 (m, 2H) 6.88 (d, J = 1.47 Hz, 1H) 3.97 (dd, J = 10.51, 2.93 Hz, 2H) 3.46 (td, J = 11.25, 2.93 Hz, 2H) 2.83-3.04 (m, 1H) 2.43 (s, 3H) 2.13 (s, 3H) 1.66-1.88 (m, 4H); LCMS (m/z) (M + H) = 496.2, Rt = 1.21 min. |
| 222 | 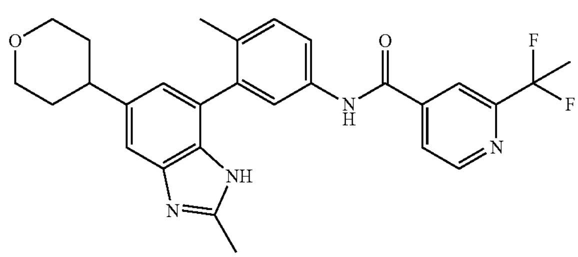 | 2-(1,1-difluoroethyl)-N-(4-methyl-3-(2-methyl-5-(tetrahydro-2H-pyran-4-yl)-1H-benzo[d]imidazol-7-yl)phenyl)isonicotinamide | ¹H NMR (400 MHz, DMSO-d6) δ ppm 12.15 (br. s., 1H) 10.61 (br. s., 1H) 8.87 (d, J = 5.13 Hz, 1H) 8.18 (s, 1H) 8.03 (dd, J = 5.07, 1.41 Hz, 1H) 7.66 (d, J = 1.83 Hz, 1H) 7.17-7.46 (m, 2H) 6.89 (d, J = 1.22 Hz, 1H) 3.97 (dd, J = 10.45, 3.00 Hz, 2H) 3.46 (td, J = 11.22, 3.12 Hz, 2H) 2.80-3.02 (m, 1H) 2.43 (s, 3H) 1.97-2.14 (m, 6H) 1.65-1.86 (m, 4H); LCMS (m/z) (M + H) = 496.2, Rt = 1.21 min. |
| 223 | 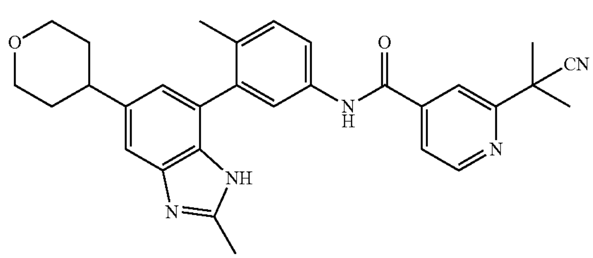 [SMILES: Cc1nc2cc(C3CCOCC3)cc(-c3cc(NC(=O)c4ccnc(C(C)(C)C#N)c4)ccc3C)c2[nH]1] | 2-(2-cyanopropan-2-yl)-N-(4-methyl-3-(2-methyl-5-(tetrahydro-2H-pyran-4-yl)-1H-benzo[d]imidazol-7-yl)phenyl)isonicotinamide | ¹H NMR (400 MHz, DMSO-d6) δ ppm 11.70-12.38 (m, 1H) 10.52 (d, J = 17.48 Hz, 1H) 8.68-8.99 (m, 1H) 8.00 (s, 1H) 7.60-7.91 (m, 3H)7.24-7.42 (m, 2H) 6.79-6.94 (m, 1H) 3.88-4.06 (m, 2H) 3.46 (td, J = 11.13, 2.81 Hz, 2H) 2.80-3.00 (m, 1H) 2.42 (d, J = 2.57 Hz, 3H) 2.12 (d, J = 6.72 Hz, 3H) 1.68-1.90 (m, 10H), LCMS (m/z) (M + H) = 494.3, Rt = 1.21 min. |

TABLE 3-continued

| Example | Structure | Name | Physical Data |
|---|---|---|---|
| 224 | 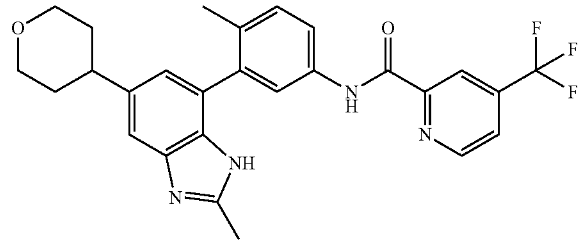 [SMILES: Cc1nc2cc(C3CCOCC3)cc(-c3cc(NC(=O)c4cc(C(F)(F)F)ccn4)ccc3C)c2[nH]1] | N-(4-methyl-3-(2-methyl-5-(tetrahydro-2H-pyran-4-yl)-1H-benzo[d]imidazol-7-yl)penyl)-4-(trifluoromethyl)picolinamide | $^1$H NMR (400 MHz, DMSO-d6) δ ppm 11.61-12.52 (m, 1H) 10.57-11.01 (m, 1H) 9.03 (dd, J = 4.95, 3.12 Hz, 1H) 8.34 (dd, J = 2.81, 0.73 Hz, 1H) 7.78-8.15 (m, 3H) 7.22-7.40 (m, 2H) 6.89 (t, J = 1.90, Hz, 1H) 3.86-4.09 (m, 2H) 3.46 (td, J = 11.13, 2.93 Hz, 2H) 2.89 (td, J = 11.00, 6.36 Hz, 1H) 2.43 (d, J = 1.71 Hz, 3H) 2.12 (d, J = 6.72 Hz, 3H) 1.67-1.96 (m, 4H); LCMS (m/z) (M + H) = 492.5, Rt = 1.37 min. |
| 225 | 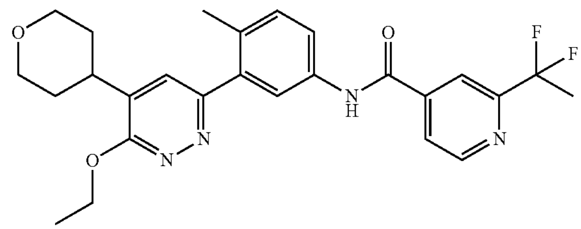 [SMILES: CCOc1nnc(-c2cc(NC(=O)c3ccnc(C(C)(F)F)c3)ccc2C)cc1C1CCOCC1] | 2-(1,1-difluoroethyl)-N-(3-(6-ethoxy-5-(tetrahydro-2H-pyran-4-yl)pyridazin-3-yl)-4-methylphenyl)isonicotinamide | $^1$H NMR (400 MHz, DMSO-d$_6$) δ ppm 10.68 (s, 1H) 8.84-8.93 (m, 1H) 8.20 (d, J = 0.61 Hz, 1 H) 8.04 (dd, J = 5.07, 1.41 Hz, 1 H) 7.76-7.89 (m, 2H) 7.59 (s, 1 H) 7.37 (d, J = 8.31 Hz, 1H) 4.59 (q, J = 7.09 Hz, 2H) 3.91-4.00 (m, 2H) 3.40-3.52 (m, 2H) 3.05 (s, 1H) 2.30 (s, 3H) 2.05 (t, J = 19.13 Hz, 3H) 1.66-1.80 (m, 4H) 1.43 (t, J = 7.03 Hz, 3 H). LCMS (m/z) (M + H) = 483.1, Rt = 1.40 min. |
| 226 | 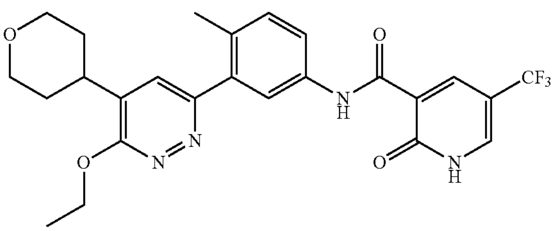 [SMILES: CCOc1nnc(-c2cc(NC(=O)c3cc(C(F)(F)F)c[nH]c3=O)ccc2C)cc1C1CCOCC1] | N-(3-(6-ethoxy-5-(tetrahydro-2H-pyran-4-yl)pyridazin-3-yl)-4-methylphenyl)-2-oxo-5-(trifluoromethyl)-1,2-dihydropyridine-3-carboxamide | $^1$H NMR (600 MHz, DMSO-d$_6$) δ ppm 13.42 (br. s., 1H) 11.78 (s, 1H) 8.50 (d, J = 2.11 Hz, 1 H) 8.40 (br. s., 1H) 7.75 (s, 1H) 7.71 (d, J = 8.16 Hz, 1H) 7.59 (s, 1H) 7.35 (d, J = 8.44 Hz, 1 H) 4.59 (q, J = 6.88 Hz, 2H) 3.96 (d, J = 10.91 Hz, 2H) 3.43-3.53 (m, 2H) 2.97-3.10 (m, 1H) 2.28 (s, 3H) 1.70-1.82 (m, 4H) 1.43 (t, J = 6.92 Hz, 3H). LCMS (m/z) (M + H) = 503.0, Rt = 1.35 min. |
| 227 | 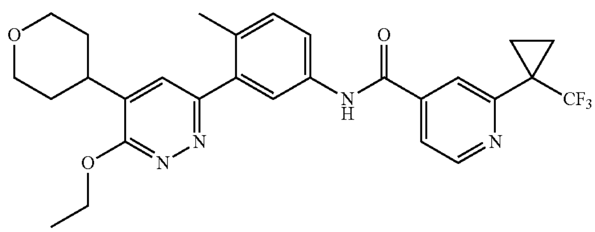 [SMILES: CCOc1nnc(-c2cc(NC(=O)c3ccnc(C4(C(F)(F)F)CC4)c3)ccc2C)cc1C1CCOCC1] | N-(3-(6-ethoxy-5-(tetrahydro-2H-pyran-4-yl)pyridazin-3-yl)-4-methylphenyl)-2-(1-(trifluoromethyl)cyclopropyl)isonicotinamide | $^1$H NMR (400 MHz, DMSO-d$_6$) δ ppm 10.58 (s, 1H) 8.76 (dd, J = 5.01, 0.73 Hz, 1H) 7.96 (s, 1H) 7.75-7.90 (m, 3H) 7.58 (s, 1H) 7.36 (d, J = 8.31 Hz, 1 H) 4.59 (q, J = 7.05 Hz, 3H) 3.91-4.02 (m, 2H) 3.41-3.54 (m, 2H) 3.06 (d, J = 5.01 Hz, 1H) 2.29 (s, 3H) 1.67-1.83 (m, 4H) 1.39-1.50 (m, 7H). LCMS (m/z) (M + H) = 527.1, Rt = 1.48 min. |
| 228 | 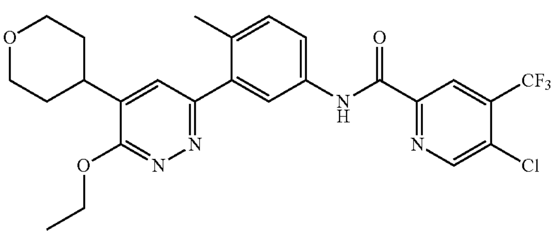 [SMILES: CCOc1nnc(-c2cc(NC(=O)c3cc(C(F)(F)F)c(Cl)cn3)ccc2C)cc1C1CCOCC1] | 5-chloro-N-(3-(6-ethoxy-5-(tetrahydro-2H-pyran-4-yl)pyridazin-3-yl)-4-methylphenyl)-4-(trifluoromethyl)picolinamide | $^1$H NMR (400 MHz, DMSO-d$_6$) δ ppm 10.86 (s, 1H) 9.10 (s, 1 H) 8.39 (s, 1H) 7.98 (d, J = 2.20 Hz, 1H) 7.93 (dd, J = 8.31, 2.32 Hz, 1H) 7.57 (s, 1H) 7.35 (d, J = 8.44 Hz, 1H) 4.59 (q, J = 6.97 Hz, 2H) 3.48 (td, J = 11.10, 3.36 Hz, 2H) 3.05 (tt, J = 10.32, 5.09 Hz, 1H) 2.31 (s, 3H) 1.67-1.81 (m, 4H) 1.43 (t, J = 7.03 Hz, 3H). LCMS (m/z) (M + H) = 521.2, Rt = 1.62 min. |
| 229 | 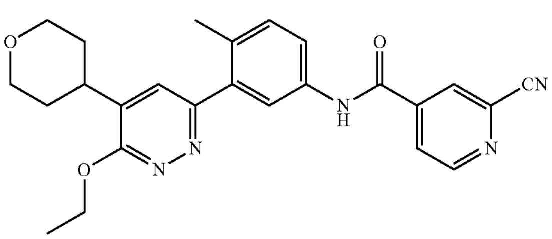 [SMILES: CCOc1nnc(-c2cc(NC(=O)c3ccnc(C#N)c3)ccc2C)cc1C1CCOCC1] | 2-cyano-N-(3-(6-ethoxy-5-(tetrahydro-2H-pyran-4-yl)pyridazin-3-yl)-4-methylphenyl) | $^1$H NMR (400 MHz, DMSO-d$_6$) δ ppm 10.68 (s, 1H) 8.97 (dd, J = 5.07, 0.79 Hz, 1H) 8.52 (dd, J = 1.65, 0.79 Hz. 1H) 8.19 (dd, J = 5.07, 1.65 Hz, 1H) 7.76-7.85 (m, 2H) 7.57 (s, 1H) 7.37 (d, J = 8.31 Hz, 1H) 4.59 (q, J = 7.05 Hz, 2H) 3.93-4.01 (m, 2H) 3.47 (td, J = 11.07, 3.42 Hz, 2H) 3.05 (tt, J = 10.30, 5.10 Hz, 1H) 2.30 (s, 3H) 1.66-1.79 (m, 4H) |

TABLE 3-continued

| Example | Structure | Name | Physical Data |
|---|---|---|---|
| | | | 1.43 (t, J = 7.03 Hz, 3H). LCMS (m/z) (M + H) 444.1, Rt = 1.30 min. |
| 230 | 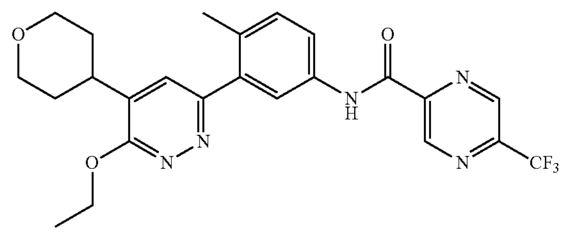 [SMILES: CCOc1nnc(-c2cc(NC(=O)c3cnc(C(F)(F)F)cn3)ccc2C)cc1C1CCOCC1] | N-(3-(6-ethoxy-5-(tetrahydro-2H-pyran-4-yl)pyridazin-3-yl)-4-methylphenyl)-5-(trifluoromethyl)pyrazine-2-carboxamide | ¹H NMR (400 MHz, DMSO-d₆) δ ppm 10.96 (s, 1H) 9.46 (d, J = 0.98 Hz, 1H) 9.31 (d, J = 0.86 Hz, 1H) 7.88-8.01 (m, 2H) 7.58 (s, 1H) 7.37 (d, J = 8.44 Hz, 1H) 4.59 (q, J = 6.97 Hz, 2H) 3.97 (dd, J = 10.33, 2.63 Hz, 2H) 3.48 (td, J = 11.10, 3.36 Hz, 2H) 2.99-3.12 (m, 1H) 2.31 (s, 3H) 1.66-1.81 (m, 4H) 1.44 (t, J = 7.03 Hz, 3H). LCMS (m/z) (M + H) = 488.1, Rt = 1.48 min. |
| 231 | 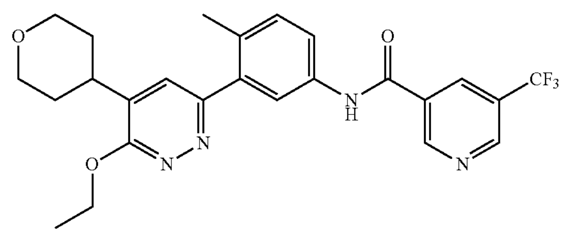 [SMILES: CCOc1nnc(-c2cc(NC(=O)c3cncc(C(F)(F)F)c3)ccc2C)cc1C1CCOCC1] | N-(3-(6-ethoxy-5-(tetrahydro-2H-pyran-4-yl)pyridazin-3-yl)-4-methylphenyl)-5-(trifluoromethyl)nicotinamide | ¹H NMR (400 MHz, DMSO-d₆) δ ppm 10.67 (s, 1H) 9.39 (d, J = 1.83 Hz, 1H) 9.19 (d, J = 1.22 Hz, 1H) 7.76-7.85 (m, 2H) 7.57 (s, 1H) 7.37 (d, J = 8.07 Hz, 1H) 4.59 (q, J = 6.97 Hz, 2H) 3.88-4.05 (m, 2H) 3.47 (td, J = 11.07, 3.42 Hz, 2H) 3.05 (s, 1H) 2.30 (s, 3H) 1.65-1.81 (m, 4H) 1.43 (t, J = 7.03 Hz, 3H). LCMS (m/z) (M + H) = 487.1, Rt = 1.40 min. |
| 232 | 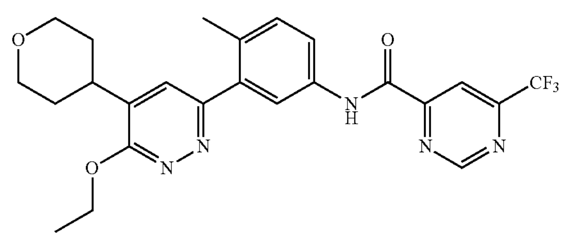 [SMILES: CCOc1nnc(-c2cc(NC(=O)c3cc(C(F)(F)F)ncn3)ccc2C)cc1C1CCOCC1] | N-(3-(6-ethoxy-5-(tetrahydro-2H-pyran-4-yl)pyridazin-3-yl)-4-methylphenyl)-5-(trifluoromethyl)pyrazine-2-carboxamide | ¹H NMR (400 MHz, DMSO-d₆) δ ppm 11.06 (s, 1H) 9.68 (d, J = 0.86 Hz, 1H) 8.47 (d, J = 1.22 Hz, 1H) 8.00 (d, J = 2.20 Hz, 1H) 7.94 (dd, J = 8.25, 2.26 Hz, 1H) 7.58 (s, 1H) 7.38 (d, J = 8.44 Hz, 1H) 4.59 (q, J = 6.97 Hz, 2H) 3.97 (dd, J = 10.27, 2.57 Hz, 2H) 3.47-3.51 (m, 1H) 3.05 (br. s., 2H) 2.32 (s, 3H) 1.67-1.81 (m, 4H) 1.44 (t, J = 7.03 Hz, 3H). LCMS (m/z) (M + H) = 488.1, Rt = 1.50 min. |
| 233 | 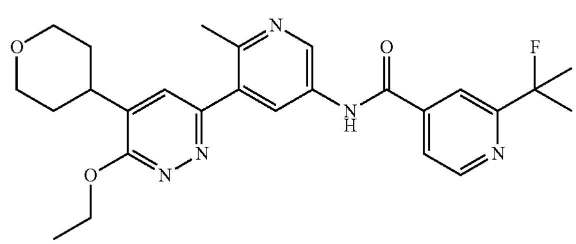 [SMILES: CCOc1nnc(-c2cc(NC(=O)c3ccnc(C(C)(C)F)c3)cnc2C)cc1C1CCOCC1] | N-(5-(6-ethoxy-5-(tetrahydro-2H-pyran-4-yl)pyridazin-3-yl)-6-methylpyridin-3-yl)-2-(2-fluoropropan-2-yl)isonicotinamide | ¹H NMR (400 MHz, DMSO-d₆) δ ppm 10.81 (s, 1H) 8.89-8.97 (m, 1H) 8.79 (d, J = 5.01 Hz, 1H) 8.20-8.29 (m, 1H) 8.07 (s, 1H) 7.82-7.88 (m, 1H) 7.70 (s, 1H) 4.60 (q, J = 7.05 Hz, 2H) 3.93-4.02 (m, 2H) 3.41-3.54 (m, 2H) 3.29 (s, 1H) 3.00-3.10 (m, 1H) 1.62-1.82 (m, 12H) 1.44 (t, J = 7.03 Hz, 3H). LCMS (m/z) (M + H)-480.1, Rt = 1.23 min. |
| 234 | 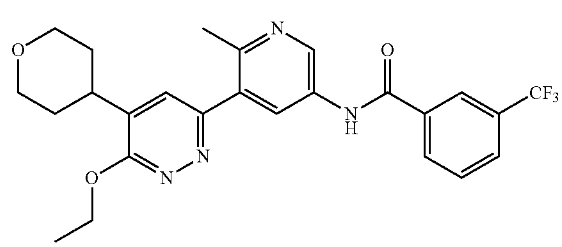 [SMILES: CCOc1nnc(-c2cc(NC(=O)c3cccc(C(F)(F)F)c3)cnc2C)cc1C1CCOCC1] | N-(5-(6-ethoxy-5-(tetrahydro-2H-pyran-4-yl)pyridazin-3-yl)-6-methylpyridin-3-yl)-3-(trifluoromethyl)benzamide | ¹H NMR (400 MHz, DMSO-d₆) δ ppm 10.71 (s, 1H) 8.93 (d, J = 2.45 Hz, 1H) 8.22-8.45 (m, 3H) 8.00 (d, J = 7.82 Hz, 1H) 7.82 (t, J = 7.76 Hz, 1H) 7.70 (s, 1H) 4.60 (q, J = 7.01 Hz, 2H) 3.93-4.01 (m, 2H) 3.43-3.53 (m, 2H) 3.01-3.11 (m, 1H) 1.68-1.85 (m, 4H) 1.44 (t, J = 6.97 Hz, 3H). LCMS (m/z) (M + H) = 487.3, Rt = 1.35 min. |

TABLE 3-continued

| Example | Structure | Name | Physical Data |
|---|---|---|---|
| 235 | 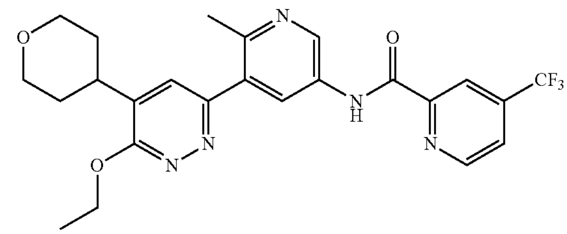 [SMILES: CCOc1nnc(-c2cc(NC(=O)c3cc(C(F)(F)F)ccn3)cnc2C)cc1C1CCOCC1] | N-(5-(6-ethoxy-5-(tetrahydro-2H-pyran-4-yl)pyridazin-3-yl)-6-methylpyridin-3-yl)-4-(trifluoromethyl)picolinamide | $^1$H NMR (400 MHz, DMSO-d$_6$) δ ppm 11.12 (s, 1H) 9.01-9.14 (m, 2H) 8.30-8.46 (m, 2H) 8.12 (dd, J = 5.01, 1.10 Hz, 1H) 7.69 (s, 1H) 4.61 (q, J = 6.97 Hz, 2H) 3.87-4.04 (m, 2H) 3.42-3.56 (m, 2H) 3.28 (s, 3H) 3.06 (s, 1H) 1.67-1.82 (m, 4H) 1.44 (t, J = 7.03 Hz, 3H). LCMS (m/z) (M + H) = 488.1, Rt = 1.33 min. |
| 236 | 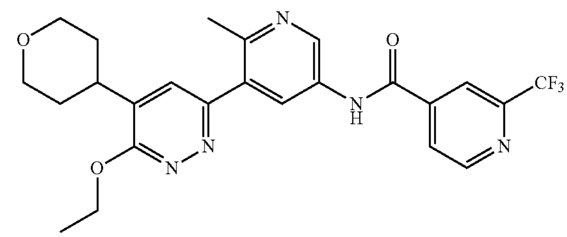 [SMILES: CCOc1nnc(-c2cc(NC(=O)c3ccnc(C(F)(F)F)c3)cnc2C)cc1C1CCOCC1] | N-(5-(6-ethoxy-5-(tetrahydro-2H-pyran-4-yl)pyridazin-3-yl)-6-methylpyridin-3-yl)-2-(trifluoromethyl)isonicotinamide | $^1$H NMR (400 MHz, DMSO-d$_6$) δ ppm 10.96 (s, 1H) 9.03 (d, J = 5.01 Hz, 1H) 8.49 (d, J = 2.45 Hz, 1H) 8.41 (s, 1H) 8.27 (d, J = 2.45 Hz, 1H) 8.23 (d, J = 5.01 Hz, 1H) 7.71 (s, 1H) 4.60 (q, J = 7.01 Hz, 2H) 3.92-4.02 (m, 3H) 3.37-3.52 (m, 5H) 2.96-3.12 (m, 1H) 1.65-1.82 (m, 4H) 1.44 (t, J = 7.03 Hz, 3H). LCMS (m/z) (M + H) = 488.0, Rt = 1.26 min. |
| 237 | 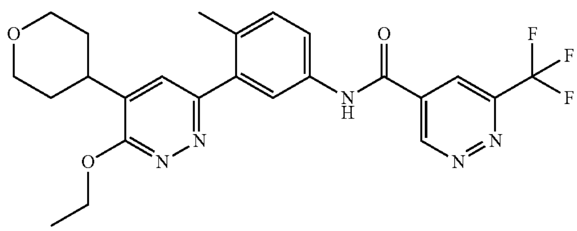 [SMILES: CCOc1nnc(-c2cc(NC(=O)c3cnnc(C(F)(F)F)c3)ccc2C)cc1C1CCOCC1] | N-(5-(6-ethoxy-5-(tetrahydro-2H-pyran-4-yl)pyridazin-3-yl)-4-methylphenyl)-6-(trifluoromethyl)pyridazine-4-carboxamide | $^1$H NMR (400 MHz, DMSO-d$_6$) δ ppm 10.90 (s, 1H) 9.93 (d, J = 1.96 Hz, 1H) 8.70 (d, J = 2.08 Hz, 1H) 7.73-7.91 (m, 2H) 7.59 (s, 1H) 7.40 (d, J = 8.19 Hz, 1H) 4.59 (q, J = 7.01 Hz, 2H) 3.85-4.05 (m, 2H) 3.32-3.57 (m, 2H) 3.06 (d, J = 4.77 Hz, 1H) 2.21-2.34 (m, 3H) 1.61-1.82 (m, 3H) 1.43 (t, J = 7.03 Hz, 3H). LCMS (m/z) (M + H) = 488.1, Rt = 1.38 min. |
| 238 | 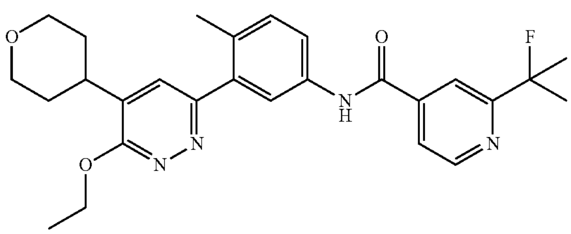 [SMILES: CCOc1nnc(-c2cc(NC(=O)c3ccnc(C(C)(C)F)c3)ccc2C)cc1C1CCOCC1] | N-(3-(6-ethoxy-5-(tetrahydro-2H-pyran-4-yl)pyridazin-3-yl)-4-methylphenyl)-2-(2-fluoropropan-2-yl)isonicotinamide | $^1$H NMR (400 MHz, DMSO-d$_6$) δ ppm 10.61 (s, 1H) 8.65-8.83 (m, 1H) 8.04 (d, J = 5.01 Hz, 1H) 7.74-7.87 (m, 3H) 7.60 (s, 1H) 7.36 (d, J = 8.31 Hz, 1H) 4.59 (q, J = 7.09 Hz, 2H) 3.90-4.01 (m, 2H) 3.36-3.54 (m, 2H) 3.05 (t, J = 5.01 Hz, 1H) 2.29 (s, 3H) 1.60-1.84 (m, 10H) 1.43 (t, J = 7.03 Hz, 3H). LCMS (m/z) (M + H) = 479.1, Rt = 1.40 min. |
| 239 | 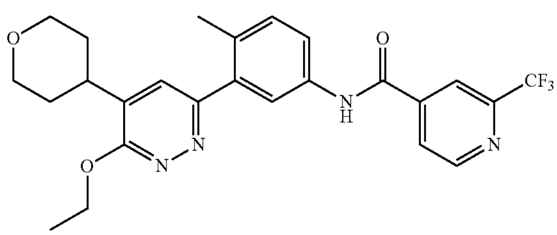 [SMILES: CCOc1nnc(-c2cc(NC(=O)c3ccnc(C(F)(F)F)c3)ccc2C)cc1C1CCOCC1] | N-(3-(6-ethoxy-5-(tetrahydro-2H-pyran-4-yl)pyridazin-3-yl)-4-methylphenyl)-2-(trifluoromethyl)isonicotinamide | $^1$H NMR (400 MHz, DMSO-d$_6$) δ ppm 10.73 (s, 1H) 9.00 (d, J = 5.01 Hz, 1H) 8.38 (s, 1H) 8.21 (dd, J = 5.01, 1.10 Hz, 1H) 7.72-7.97 (m, 2H) 7.59 (s, 1H) 7.38 (d, J = 8.31 Hz, 1H) 4.59 (q, J = 7.05 Hz, 2H) 3.84-4.07 (m, 2H) 3.47 (td, J = 11.10, 3.48 Hz, 2H) 3.05 (s, 1H) 2.30 (s, 3H) 1.65-1.86 (m, 4H) 1.43 (t, J = 7.03 Hz, 3H). LCMS (m/z) (M + H) = 487.1, Rt = 1.44 min. |
| 240 | 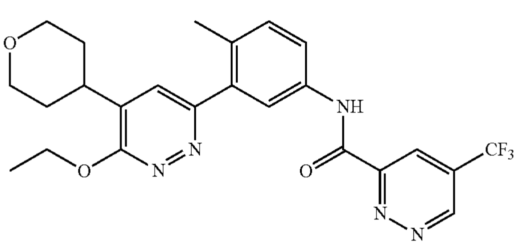 [SMILES: CCOc1nnc(-c2cc(NC(=O)c3cc(C(F)(F)F)cnn3)ccc2C)cc1C1CCOCC1] | N-(3-(6-ethoxy-5-(tetrahydro-2H-pyran-4-yl)pyridazin-3-yl)-4-methylphenyl)-5-(trifluoromethyl)pyridazine-3-carboxamide | $^1$H NMR (400 MHz, DMSO-d$_6$) δ ppm 11.29 (s, 1H), 9.96 (d, J = 1.8 Hz, 1H), 8.58 (m, 1H), 8.03 (d, J = 2.2 Hz, 1H), 7.96 (dd, J = 8.3, 2.2 Hz, 1H), 7.58 (s, 1H), 7.38 (d, J = 8.4 Hz, 1H), 4.60 (q, J = 7.0 Hz, 2H), 3.97 (m, 2H), 3.48 (td, J = 11.2, 3.1 Hz, 2H), 3.06 (m, 1H), 2.32 (s, 3H), 1.75 (m, 4H), 1.44 (t, J = 7.0 Hz, 3H). LCMS (m/z) (M + H) = 488.3, Rt = 1.41 min. |

TABLE 3-continued

| Example | Structure | Name | Physical Data |
|---|---|---|---|
| 241 | 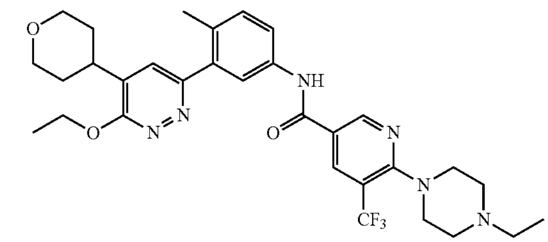 [SMILES: CCOc1nnc(-c2cc(NC(=O)c3cnc(N4CCN(CC)CC4)c(C(F)(F)F)c3)ccc2C)cc1C1CCOCC1] | N-(3-(6-ethoxy-5-(tetrahydro-2H-pyran-4-yl)pyridazin-3-yl)-4-methylphenyl)-6-(4-ethylpiperazin-1-yl)-5-(trifluoromethyl)nicotinamide | $^1$H NMR (400 MHz, DMSO-d$_6$) δ ppm 10.34 (s, 1H), 8.97 (d, J = 1.6 Hz, 1H), 8.53 (d, J = 1.7 Hz, 1H), 7.78 (m, 2H), 7.56 (s, 1H), 7.33 (d, J = 8.2 Hz, 1H), 4.59 (q, J = 7.0 Hz, 2H), 3.96 (m, 2H), 3.46 (m, 8H), 3.05 (m, 1H), 2.37 (q, J = 7.1 Hz, 2H), 2.28 (s, 3H), 1.75 (m, 4H), 1.43 (t, J = 7.0 Hz, 3H), 1.03 (t, J = 7.1 Hz, 3H). Signal for two aliphatic protons are hidden under solvent peak. LCMS (m/z) (M + H) = 599.5, Rt = 1.06 min. |
| 242 | 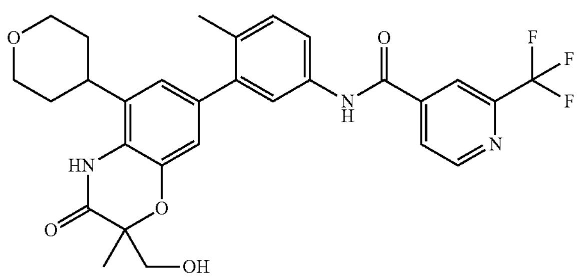 | N-(3-(2-(hydroxymethyl)-2-methyl-3-oxo-5-(tetrahydro-2H-pyran-4-yl)-3,4-dihydro-2H-benzo[b][1,4]oxazin-7-yl)-4-methylphenyl)-2-(trifluoromethyl)isonicotinamide | $^1$H NMR (400 MHz, DMSO-d6) δ ppm 10.63 (s, 1H) 10.39 (s, 1H) 8.99 (d, J = 5.01 Hz, 1H) 8.37 (s, 1H) 8.20 (dd, J = 4.95, 1.04 Hz, 1H) 7.61-7.77 (m, 2H) 7.30 (d, J = 8.44 Hz, 1H) 6.81 (dd, J = 16.44, 1.77 Hz, 2H) 3.91 (d, J = 11.25 Hz, 2H) 3.77 (d, J = 11.49 Hz, 1H) 3.43-3.63 (m, 3H) 3.25 (t, J = 7.15 Hz, 1 H) 2.25 (s, 3H) 2.07 (s, 1H) 1.55-1.71 (m, 4H) 1.34 (s, 3H). LCMS (m/z) (M + H) = 556.2, Rt = 1.30 min. |
| 243 | 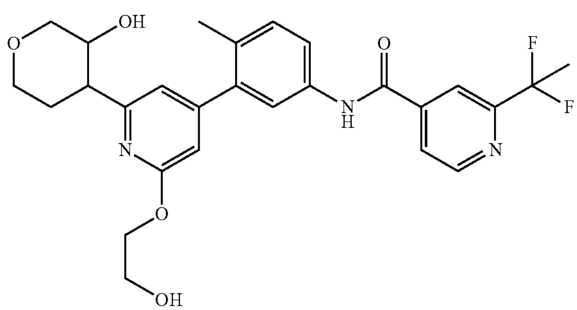 [SMILES: Cc1ccc(NC(=O)c2ccnc(C(C)(F)F)c2)cc1-c1cc(OCCO)nc(C2CCOCC2O)c1] | 2-(1,1-difluoroethyl)-N-(3-(2-(2-hydroxyethoxy)-6-(3-hydroxytetrahydro-2H-pyran-4-yl)pyridin-4-yl)-4-methylphenyl)isonicotinamide | $^1$H NMR (400 MHz, DMSO-d6) δ ppm 10.65 (s, 1H) 8.88 (d, J = 5.01 Hz, 1H) 8.18 (s, 1H) 8.03 (dd, J = 5.01, 1.35 Hz, 1H) 7.66-7.78 (m, 2H) 7.33 (d, J = 8.44 Hz, 1H) 6.85 (d, J = 0.73 Hz, 1H) 6.61 (d, J = 0.98 Hz, 1 H) 4.83 (t, J = 5.50 Hz, 1H) 4.66 (d, J = 5.14 Hz, 1H) 4.25-4.40 (m, 2H) 3.92-4.07 (m, 2H) 3.81 (dd, J = 11.68, 2.02 Hz, 1 H) 3.74 (q, J = 5.34 Hz, 2H) 3.55 (dd, J = 11.62, 1.10 Hz, 1H) 3.46 (td, J = 11.55, 2.08 Hz, 1H) 2.97 (dt, J = 12.32, 3.13 Hz, 1H) 2.16-2.30 (m, 4H) 1.94-2.10 (m, 3H) 1.65 (dd, J = 13.14, 2.63 Hz, 1H)); LCMS (m/z) (M + H) = 514.2, Rt = 1.19 min. |
| 244 | 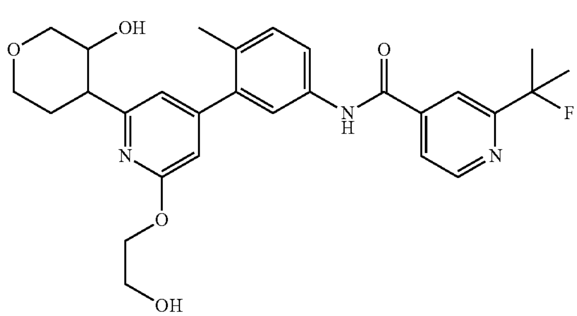 [SMILES: Cc1ccc(NC(=O)c2ccnc(C(C)(C)F)c2)cc1-c1cc(OCCO)nc(C2CCOCC2O)c1] | 2-(2-fluoropropan-2-yl)-N-(3-(2-(2-hydroxyethoxy)-6-(3-hydroxytetrahydro-2H-pyran-4-yl)pyridin-4-yl)-4-methylphenyl)isonicotinamide | $^1$H NMR (400 MHz, DMSO-d6) δ ppm 10.57 (s, 1H) 8.75 (d, J = 5.01 Hz, 1H) 8.02 (s, 1H) 7.82 (dd, J = 5.14, 1.59 Hz, 1H) 7.74 (dd, J = 8.31, 2.20 Hz, 1H) 7.69 (d, J = 2.08 Hz, 1H) 7.32 (d, J = 8.44 Hz, 1H) 6.85 (s, 1 H) 6.85 (s, 1H) 6.60 (d, J = 0.86 Hz, 1H) 4.82 (t, J = 5.50 Hz, 1 H) 4.66 (d, J = 5.14 Hz, 1H) 4.25-4.41 (m, 2H) 3.92-4.04 (m, 2H) 3.81 (dd, J = 11.68, 2.02 Hz, 1H) 3.74 (q, J = 5.26 Hz, 2H) 3.52-3.60 (m, 1H) 3.46 (td, J = 11.52, 2.02 Hz, 1H) 2.97 (dt, J = 12.41, 3.09 Hz, 1H) 2.16-2.30 (m, 4H) 1.61-1.78 (m, 7H); LCMS (m/z) (M + H) = 510.2, Rt = 1.50 min. |

TABLE 3-continued

| Example | Structure | Name | Physical Data |
|---|---|---|---|
| 245 | 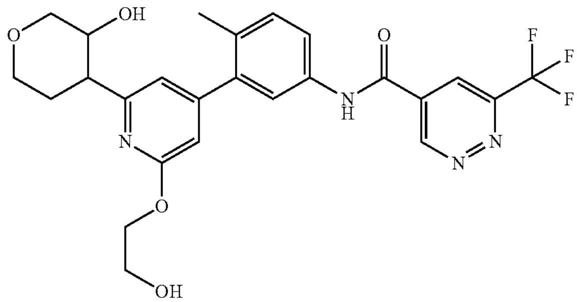 [SMILES: Cc1ccc(NC(=O)c2cnnc(C(F)(F)F)c2)cc1-c1cc(OCCO)nc(C2CCOCC2O)c1] | N-(3-(2-(2-hydroxyethoxy)-6-(3-(hydroxytetrahydro-2H-pyran-4-yl)pyridin-4-yl)-4-methylphenyl)-6-(trifluoromethyl)pyridazine-4-carboxamide | ¹H NMR (400 MHz, DMSO-d6) δ ppm 10.87 (s, 1H) 9.92 (d, J = 1.96 Hz, 1H) 8.68 (d, J = 1.96 Hz, 1H) 7.65-7.78 (m, 2H) 7.37 (d, J = 8.31 Hz, 1H) 6.84 (d, J = 0.86 Hz, 1H) 6.61 (d, J = 0.98 Hz, 1H) 4.82 (t, J = 5.50 Hz, 1H) 4.65 (d, J = 5.14 Hz, 1H) 4.25-4.41 (m, 2H) 3.91-4.07 (m, 2H) 3.81 (dd, J = 11.68, 2.02 Hz, 1H) 3.74 (q, J = 5.26 Hz, 2H) 3.55 (dd, J = 11.55, 1.16 Hz, 1H) 3.46 (td, J = 11.55, 2.08 Hz, 1H) 2.97 (dt, J = 12.35, 3.18 Hz, 1H) 2.18-2.31 (m, 4H) 1.65 (dd, J = 13.08, 2.57 Hz, 1H); LCMS (m/z) (M + H) = 519.2, Rt = 1.16 min |
| 246 | 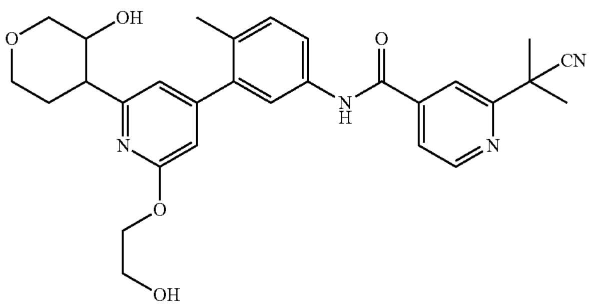 | 2-(2-cyanopropan-2-yl)-N-(3-(2-(2-hydroxyethoxy)-6-(3-(hydroxytetrahydro-2H-pyran-4-yl)pyridin-4-yl)-4-methylphenyl)isonicotinamide | ¹H NMR (400 MHz, DMSO-d6) δ ppm 10.57 (s, 1H) 8.81 (dd, J = 5.07, 0.67 Hz, 1H) 8.00 (s, 1H) 7.86 (dd, J = 5.07, 1.53 Hz, 1H) 7.72 (dd, J = 8.25, 2.26 Hz, 1H) 7.67 (d, J = 2.20 Hz, 1H) 7.34 (d, J = 8.44 Hz, 1H) 6.84 (d, J = 0.73 Hz, 1H) 6.61 (d, J = 0.98 Hz, 1H) 4.82 (br. s., 1H) 4.65 (br. s., 1H) 4.25-4.40 (m, 2H) 3.93-4.05 (m, 2H) 3.81 (dd, J = 11.62, 2.08 Hz, 1H) 3.74 (br. s., 2H) 3.55 (dd, J = 11.62, 1.10 Hz, 1H) 3.46 (td, J = 11.52, 2.02 Hz, 1H) 2.97 (dt, J = 12.35, 3.18 Hz, 1H) 2.16-2.30 (m, 4H) 1.77 (s, 7H) 1.65 (dd, J = 12.96, 2.57 Hz, 1H); LCMS (m/z) (M + H) = 556.1, Rt = 1.42 min |
| 247 | 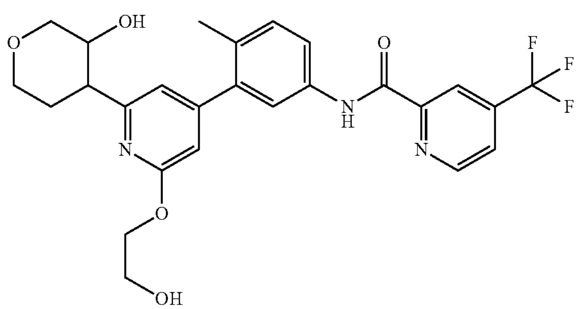 [SMILES: Cc1ccc(NC(=O)c2cc(C(F)(F)F)ccn2)cc1-c1cc(OCCO)nc(C2CCOCC2O)c1] | N-(3-(2-(2-hydroxyethoxy)-6-(3-(hydroxytetrahydro-2H-pyran-4-yl)pyridin-4-yl)-4-methylphenyl)-4-(trifluoromethyl)picolinamide | ¹H NMR (400 MHz, DMSO-d6) δ ppm 10.84 (s, 1H) 9.03 (d, J = 5.01 Hz, 1H) 8.32-8.37 (m, 1H) 8.09 (dd, J = 5.07, 1.16 Hz, 1H) 7.82-7.93 (m, 2H) 7.32 (d, J = 9.29 Hz, 1H) 6.87 (d, J = 0.73 Hz, 1H) 6.62 (d, J = 1.10 Hz, 1H) 4.26-4.41 (m, 2H) 3.92-4.04 (m, 2H) 3.81 (dd, J = 11.62, 2.08 Hz, 1H) 3.75 (t, J = 5.20 Hz, 2H) 3.55 (dd, J = 11.55, 1.16 Hz, 1H) 3.47 (td, J = 11.58, 2.14 Hz, 2H) 2.98 (dt, J = 12.29, 3.09 Hz, 1H) 2.19-2.31 (m, 4H) 1.60-1.75 (m, 1H); LCMS (m/z) (M + H) = 518.0, Rt = 1.33 min |
| 248 | 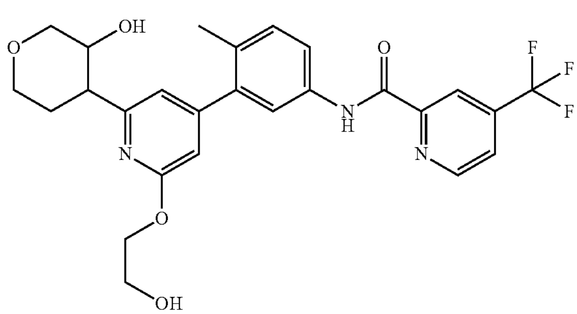 [SMILES: Cc1ccc(NC(=O)c2cc(C(F)(F)F)ccn2)cc1-c1cc(OCCO)nc(C2CCOCC2O)c1] | N-(3-(2-(2-hydroxyethoxy)-6-(3-(hydroxytetrahydro-2H-pyran-4-yl)pyridin-4-yl)-4-methylphenyl)-4-(trifluoromethyl)picolinamide (single enantiomer from chiral SFC) | ¹H NMR (400 MHz, DMSO-d6) δ ppm 10.84 (s, 1H) 9.03 (d, J = 5.01 Hz, 1H) 8.32-8.37 (m, 1H) 8.09 (dd, J = 5.07, 1.16 Hz, 1H) 7.82-7.93 (m, 2H) 7.32 (d, J = 9.29 Hz, 1H) 6.87 (d, J = 0.73 Hz, 1H) 6.62 (d, J = 1.10 Hz, 1H) 4.26-4.41 (m, 2H) 3.92-4.04 (m, 2H) 3.81 (dd, J = 11.62, 2.08 Hz, 1H) 3.75 (t, J = 5.20 Hz, 2H) 3.55 (dd, J = 11.55, 1.16 Hz, 1H) 3.47 (td, J = 11.58, 2.14 Hz, 2H) 2.98 (dt, J = 12.29, 3.09 Hz, 1H) 2.19-2.31 (m, 4H) 1.60-1.75 (m, 1H); LCMS (m/z) (M + H) = 518.0, Rt = 1.33 min |

TABLE 3-continued

| Example | Structure | Name | Physical Data |
|---|---|---|---|
| 249 | 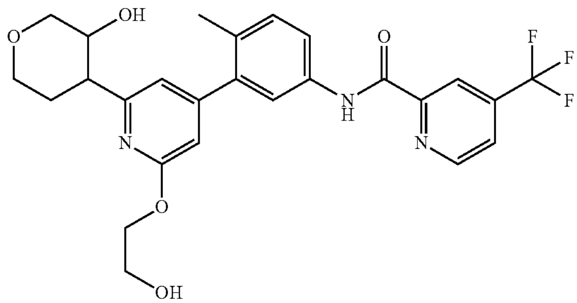 [SMILES: Cc1ccc(NC(=O)c2cc(C(F)(F)F)ccn2)cc1-c1cc(OCCO)nc(C2CCOCC2O)c1] | N-(3-(2-(2-hydroxyethoxy)-6-(3-(hydroxytetrahydro-2H-pyran-4-yl)pyridin-4-yl)-4-methylphenyl)-4-(trifluoromethyl)picolinamide (single enantiomer from chiral SFC) | ¹H NMR (400 MHz, DMSO-d6) δ ppm 10.84 (s, 1H) 9.03 (d, J = 5.01 Hz, 1H) 8.32-8.37 (m, 1H) 8.09 (dd, J = 5.07, 1.16 Hz, 1H) 7.82-7.93 (m, 2H) 7.32 (d, J = 9.29 Hz, 1H) 6.87 (d, J = 0.73 Hz, 1H) 6.62 (d, J = 1.10 Hz, 1H) 4.26-4.41 (m, 2H) 3.92-4.04 (m, 2H) 3.81 (dd, J = 11.62, 2.08 Hz, 1H) 3.75 (t, J = 5.20 Hz, 2H) 3.55 (dd, J = 11.55, 1.16 Hz, 1H) 3.47 (td, J = 11.58, 2.14 Hz, 2H) 2.98 (dt, J = 12.29, 3.09 Hz, 1H) 2.19-2.31 (m, 4H) 1.60-1.75 (m, 1H); LCMS (m/z) (M + H) = 518.0, Rt = 1.33 min |
| 250 | 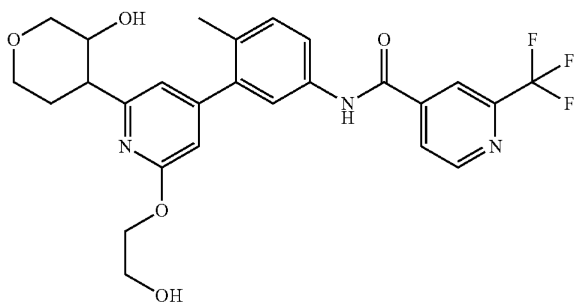 [SMILES: Cc1ccc(NC(=O)c2ccnc(C(F)(F)F)c2)cc1-c1cc(OCCO)nc(C2CCOCC2O)c1] | N-(3-(2-(2-hydroxyethoxy)-6-(3-(hydroxytetrahydro-2H-pyran-4-yl)pyridin-4-yl)-4-methylphenyl)-2-(trifluoromethyl)isonicotinamide (single enantiomer from chiral SFC) | 1H NMR (400 MHz, DMSO-d6) δ ppm 10.84 (s, 1H) 9.03 (d, J = 5.01 Hz, 1H) 8.32-8.37 (m, 1H) 8.09 (dd, J = 5.07, 1.16 Hz, 1H) 7.82-7.93 (m, 2H) 7.32 (d, J = 9.29 Hz, 1H) 6.87 (d, J = 0.73 Hz, 1H) 6.62 (d, J = 1.10 Hz, 1H) 4.26-4.41 (m, 2H) 3.92-4.04 (m, 2H) 3.81 (dd, J = 11.62, 2.08 Hz, 1H) 3.75 (t, J = 5.20 Hz, 2H) 3.55 (dd, J = 11.55, 1.16 Hz, 1H) 3.47 (td, J = 11.58, 2.14 Hz, 2H) 2.98 (dt, J = 12.29, 3.09 Hz, 1H) 2.19-2.31 (m, 4H) 1.60-1.75 (m, 1H); LCMS (m/z) (M + H) = 518.0, Rt = 1.33 min |
| 251 | 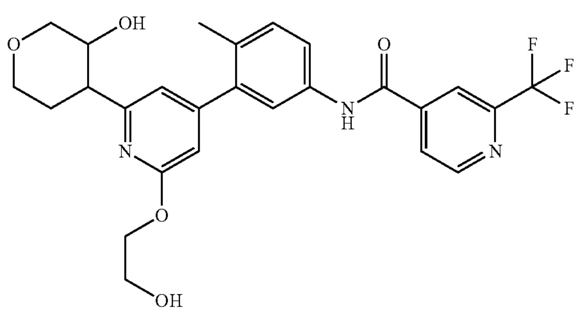 [SMILES: Cc1ccc(NC(=O)c2ccnc(C(F)(F)F)c2)cc1-c1cc(OCCO)nc(C2CCOCC2O)c1] | N-(3-(2-(2-hydroxyethoxy)-6-(3-(hydroxytetrahydro-2H-pyran-4-yl)pyridin-4-yl)-4-methylphenyl)-2-(trifluoromethyl)isonicotinamide (single enantiomer from chiral SFC) | 1H NMR (400 MHz, DMSO-d6) δ ppm 10.84 (s, 1H) 9.03 (d, J = 5.01 Hz, 1H) 8.32-8.37 (m, 1H) 8.09 (dd, J = 5.07, 1.16 Hz, 1H) 7.82-7.93 (m, 2H) 7.32 (d, J = 9.29 Hz, 1H) 6.87 (d, J = 0.73 Hz, 1H) 6.62 (d, J = 1.10 Hz, 1H) 4.26-4.41 (m, 2H) 3.92-4.04 (m, 2H) 3.81 (dd, J = 11.62, 2.08 Hz, 1H) 3.75 (t, J = 5.20 Hz, 2H) 3.55 (dd, J = 11.55, 1.16 Hz, 1H) 3.47 (td, J = 11.58, 2.14 Hz, 2H) 2.98 (dt, J = 12.29, 3.09 Hz, 1H) 2.19-2.31 (m, 4H) 1.60-1.75 (m, 1H); LCMS (m/z) (M + H) = 518.0, Rt = 1.33 min |
| 252 | 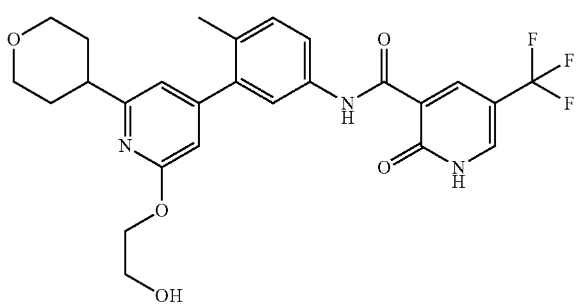 [SMILES: Cc1ccc(NC(=O)c2cc(C(F)(F)F)c[nH]c2=O)cc1-c1cc(OCCO)nc(C2CCOCC2)c1] | N-(3-(2-(2-hydroxyethoxy)-6-(terahydro-2H-pyran-4-yl)pyridin-4-yl)-4-methylphenyl)-2-oxo-5-(trifluoromethyl)-1,2-dihydropyridine-3-carboxamide | ¹H NMR (400 MHz, DMSO-d6) δ ppm 11.84 (s, 1H) 8.47 (d, J = 2.91 Hz, 1H) 8.38 (dd, J = 2.78, 1.14 Hz, 1H) 7.53-7.68 (m, 2H) 7.32 (d, J = 9.35 Hz, 1H) 6.84 (d, J = 1.01 Hz, 1H) 6.60 (d, J = 1.14 Hz, 1H) 4.82 (t, J = 5.56 Hz, 1H) 4.27-4.46 (m, 2H) 3.91-4.04 (m, 2H) 3.74 (q, J = 5.39 Hz, 2H) 3.37-3.51 (m, 2H) 2.80-3.09 (m, 1H) 2.22 (s, 3H 1.69-1.88 (m, 4H); LCMS (m/z) (M + H) = 518.2, Rt = 0.95 min. |

TABLE 3-continued

| Example | Structure | Name | Physical Data |
|---|---|---|---|
| 253 | 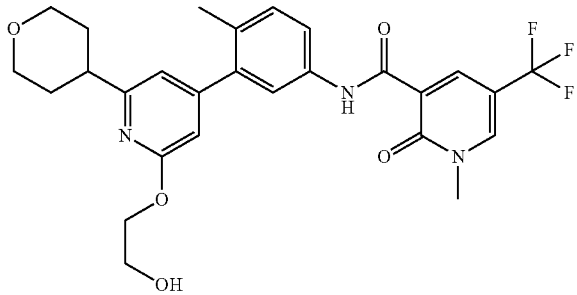 [SMILES: Cc1ccc(NC(=O)c2cc(C(F)(F)F)cn(C)c2=O)cc1-c1cc(OCCO)nc(C2CCOCC2)c1] | N-(3-(2-(2-hydroxyethoxy)-6-(terahydro-2H-pyran-4-yl)pyridin-4-yl)-4-methylphenyl)-1-methyl-2-oxo-5-(trifluoromethyl)-1,2-dihydropyridine-3-carboxamide | $^1$H NMR (400 MHz, DMSO-d6) δ ppm 11.75 (s, 1H) 8.84 (d, J = 1.59 Hz, 1H) 8.49 (d, J = 2.81 Hz, 1H) 7.51-7.74 (m, 2H) 7.32 (d, J = 8.07 Hz, 1H) 6.85 (d, J = 1.10 Hz, 1H) 6.61 (d, J = 1.22 Hz, 1H) 4.82 (br. s., 1H) 4.34 (t, J = 5.26 Hz, 2H) 3.96 (dt, J = 11.00, 3.12 Hz, 2H) 3.74 (t, J = 4.77 Hz, 2H) 3.68 (s, 3H) 3.45 (ddd, J = 11.19, 8.56, 6.05 Hz, 2H) 2.82-2.99 (m, 1H) 2.23 (s, 3H) 1.72-1.90 (m, 4H); LCMS (m/z) (M + H) = 532.0, Rt = 1.40 1.40 min. |
| 254 | 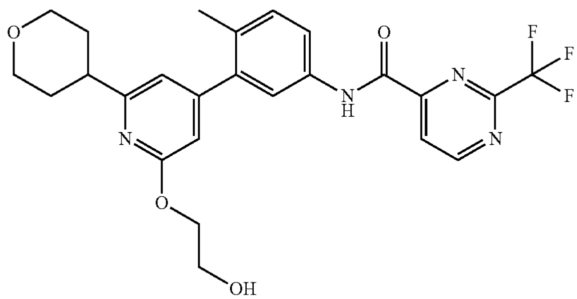 [SMILES: Cc1ccc(NC(=O)c2ccnc(C(F)(F)F)n2)cc1-c1cc(OCCO)nc(C2CCOCC2)c1] | N-(3-(2-(2-hydroxyethoxy)-6-(terahydro-2H-pyran-4-yl)pyridin-4-yl)-4-methylphenyl)-2-(trifluoromethyl)pyrimidine-4-carboxamide | $^1$H NMR (400 MHz, Methanol-d4) δ 9.47 (d, J = 1.0 Hz, 1H), 9.14 (d, J = 1.1 Hz, 1H), 7.79-7.68 (m, 2H), 7.33 (d, J = 8.2 Hz, 1H), 6.83 (d, J = 1.2 Hz, 1H), 4.47-4.43 (m, 2H), 4.08-4.03 (m, 2H), 3.91 (dd, J = 5.5, 4.3 Hz, 2H), 3.58 (td, J = 11.7, 2.5 Hz, 2H), 2.99-2.88 (m, 1H), 2.26 (s, 3H), 1.98-1.84 (m, 4H). LCMS (m/z) (M + H) = 503.1, Rt = 1.40 min. |
| 255 | 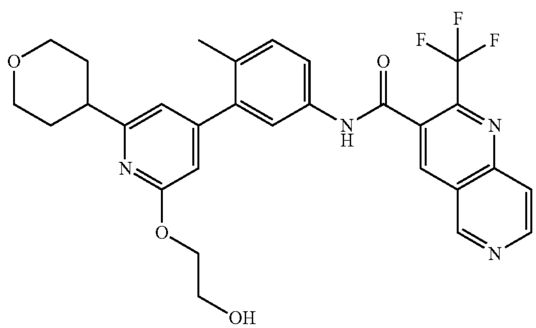 [SMILES: Cc1ccc(NC(=O)c2cc3cnccc3nc2C(F)(F)F)cc1-c1cc(OCCO)nc(C2CCOCC2)c1] | N-(3-(2-(2-hydroxyethoxy)-6-(terahydro-2H-pyran-4-yl)pyridin-4-yl)-4-methylphenyl)-2-(trifluoromethyl)-1,6-naphthyridine-3-carboxamide | $^1$H NMR (400 MHz, Methanol-d4) δ 9.59-9.50 (m, 1H), 8.97 (s, 1H), 8.91 (d, J = 6.0 Hz, 1H), 8.14 (d, J = 6.0 Hz, 1H), 7.61 (dd, J = 8.2, 2.3 Hz, 1H), 7.56 (d, J = 2.3 Hz, 1H), 7.33 (d, J = 8.3 Hz, 1H), 6.83 (d, J = 1.0 Hz, 1H), 6.63 (d, J = 1.2 Hz, 1H), 4.49-4.39 (m, 2H), 4.12-3.99 (m, 2H), 3.90 (dd, J = 5.5, 4.3 Hz, 2H), 3.58 (td, J = 11.7, 2.5 Hz, 2H), 3.01-2.86 (m, 1H), 2.27 (s, 3H), 2.02-1.81 (m, 4H); LCMS (m/z) (M + H) = 553.2, Rt = 1.28 min. |
| 256 | 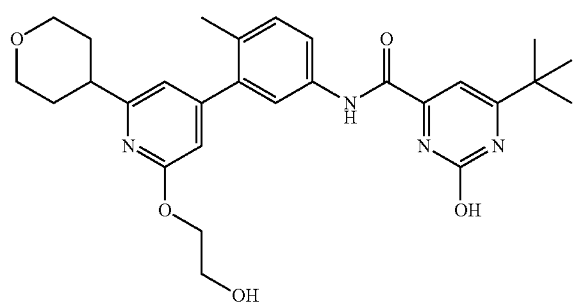 [SMILES: Cc1ccc(NC(=O)c2cc(C(C)(C)C)nc(O)n2)cc1-c1cc(OCCO)nc(C2CCOCC2)c1] | 6-(tert-butyl)-2-hydroxy-N-(3-(2-(2-hydroxyethoxy)-6-(tetrahydro-2H-pyran-4-yl)pyridin-4-yl)-4-methylphenyl)pyrimidine-4-carboxamide | $^1$H NMR (400 MHz, Methanol-d4) δ 7.74-7.63 (m, 2H), 7.31 (d, J = 8.1 Hz, 1H), 7.22 (s, 1H), 6.82 (d, J = 1.0 Hz, 1H), 6.62 (d, J = 1.2 Hz, 1H), 4.44 (dd, J = 5.5, 4.3 Hz, 2H), 4.11-3.99 (m, 2H), 3.95-3.85 (m, 2H), 3.58 (td, J = 11.7, 2.5 Hz, 2H), 3.02-2.86 (m, 1H), 2.25 (s, 3H), 2.01-1.83 (m, 4H); 1.39 (s, 9H); LCMS (m/z) (M + H) =507.2, Rt = 0.97 min. |
| 257 | 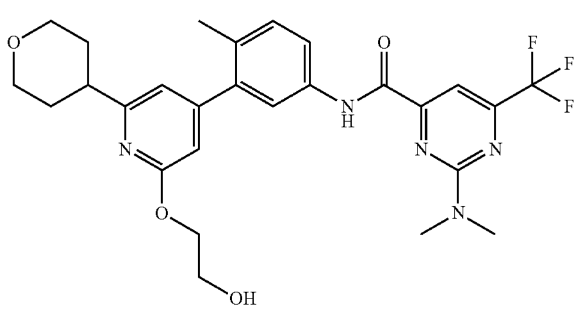 [SMILES: Cc1ccc(NC(=O)c2cc(C(F)(F)F)nc(N(C)C)n2)cc1-c1cc(OCCO)nc(C2CCOCC2)c1] | 2-(dimethylamino)-N-(3-(2-(2-hydroxyethoxy)-6-(tetrahydro-2H-pyran-4-yl)pyridin-4-yl)-4-methylphenyl)-6-(trifluoromethyl)pyrimidine-4-carboxamide | $^1$H NMR (400 MHz, Methylene Chloride-d2) δ 7.62 (dd, J = 8.2, 2.3 Hz, 1H), 7.52-7.41 (m, 2H), 7.22 (d, J = 8.3 Hz, 1H), 6.69 (d, J = 0.9 Hz, 1H), 6.53 (d, J = 1.1 Hz, 1H), 4.47-4.35 (m, 2H), 4.01-3.89 (m, 2H), 3.89-3.78 (m, 2H), 3.42 (td, J = 11.3, 3.3 Hz, 2H), 3.20 (s, 6H), 2.85-2.72 (m, 1H), 2.17 (s, 3H), 1.86-1.73 (m, 4H); HRMS (m/z) (M + H) = 546.2350, Rt = 3.04 min. |

TABLE 3-continued

| Example | Structure | Name | Physical Data |
|---|---|---|---|
| 258 | 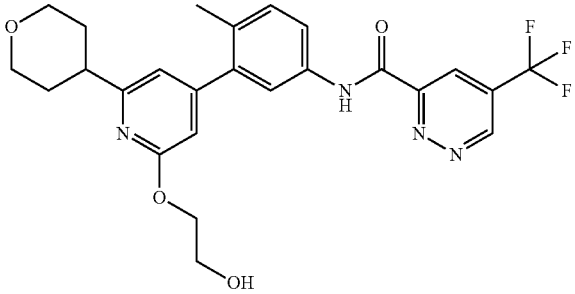 [SMILES: Cc1ccc(NC(=O)c2cc(C(F)(F)F)cnn2)cc1-c1cc(OCCO)nc(C2CCOCC2)c1] | N-(3-(2-(2-hydroxyethoxy)-6-(tetrahydro-2H-pyran-4-yl)pyridin-4-yl)-4-methylphenyl)-5-(trifluoromethyl)pyridazine-3-carboxamide | $^1$H NMR (400 MHz, Methanol-d4) δ 9.73 (d, J = 1.9 Hz, 1H), 8.63 (d, J = 1.4 Hz, 1H), 7.83-7.70 (m, 2H), 7.34 (d, J = 8.1 Hz, 1H), 6.84 (d, J = 1.0 Hz, 1H), 6.64 (d, J = 1.2 Hz, 1H), 4.48-4.42 (m, 2H), 4.06 (dd, J = 11.5, 2.6 Hz, 2H), 3.95-3.87 (m, 2H), 3.58 (td, J = 11.7, 2.5 Hz, 2H), 2.99-2.90 (m, 1H), 2.27 (s, 3H), 2.00-1.83 (m, 4H); LCMS (m/z) (M + H) = 503.0, Rt = 1.37 min. |
| 259 | 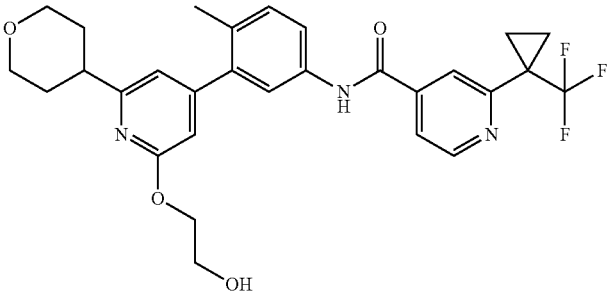 [SMILES: Cc1ccc(NC(=O)c2ccnc(C3(C(F)(F)F)CC3)c2)cc1-c1cc(OCCO)nc(C2CCOCC2)c1] | N-(3-(2-(2-hydroxyethoxy)-6-(tetrahydro-2H-pyran-4-yl)pyridin-4-yl)-4-methylphenyl)-2-(1-(trifluoromethyl)cyclopropyl)isonicotinamide | $^1$H NMR (400 MHz, Methanol-d4) δ 8.69 (dd, J = 5.1, 0.7 Hz, 1H), 8.05 (s, 1H), 7.79 (dd, J = 5.1, 1.6 Hz, 1H), 7.65 (dd, J = 8.2, 2.3 Hz, 1H), 7.59 (d, J = 2.2 Hz, 1H), 7.31 (d, J = 8.3 Hz, 1H), 6.82 (s, 1H), 6.62 (d, J = 1.1 Hz, 1H), 4.46-4.43 (m, 2H), 4.05 (dd, J = 11.5, 2.4 Hz, 2H), 3.92-3.88 (m, 2H), 3.58 (td, J = 11.7, 2.5 Hz, 2H), 2.97-2.89 (m, 1H), 1.97-1.84 (m, 4H); LCMS (m/z) (M + H) = 542.1, Rt = 1.41 min. |
| 260 | 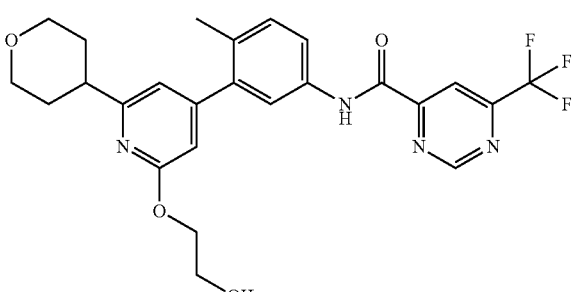 | N-(3-(2-(2-hydroxyethoxy)-6-(tetrahydro-2H-pyran-4-yl)pyridin-4-yl)-4-methylphenyl)-6-(trifluoromethyl)pyrimidine-4-carboxamide | 1H NMR (400 MHz, Methanol-d4) δ 9.54 (s, 1H), 8.50 (d, J = 1.3 Hz, 1H), 7.80-7.69 (m, 2H), 7.34 (d, J = 8.2 Hz, 1H), 6.83 (d, J = 1.0 Hz, 1H), 6.63 (d, J = 1.2 Hz, 1H), 4.45 (dd, J = 5.5, 4.3 Hz, 2H), 4.06 (dd, J = 10.6, 3.3 Hz, 2H), 3.91 (dd, J = 5.5, 4.3 Hz, 2H), 3.58 (td, J = 11.7, 2.6 Hz, 2H), 3.00-2.88 (m, 1H), 2.26 (s, 3H), 1.99-1.84 (m, 4H); LCMS (m/z) (M + H) = 503.0, Rt = 1.43 min. |
| 261 | 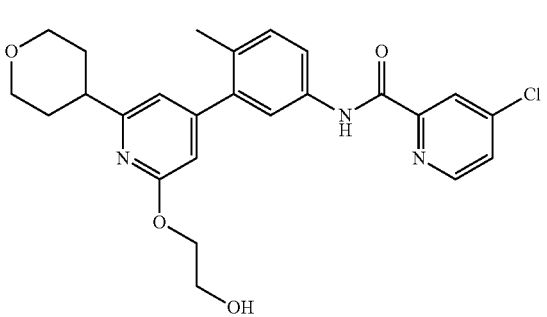 [SMILES: Cc1ccc(NC(=O)c2cc(Cl)ccn2)cc1-c1cc(OCCO)nc(C2CCOCC2)c1] | 4-chloro-N-(3-(2-(2-hydroxyethoxy)-6-(tetrahydro-2H-pyran-4-yl)pyridin-4-yl)-4-methylphenyl)picolinamide | 1H NMR (400 MHz, Methanol-d4) δ 8.64 (dd, J = 5.3, 0.5 Hz, 1H), 8.20 (dd, J = 2.1, 0.6 Hz, 1H), 7.73-7.64 (m, 3H), 7.34-7.29 (m, 1H), 6.83 (d, J = 1.0 Hz, 1H), 6.63 (d, J = 1.2 Hz, 1H), 4.47-4.41 (m, 2H), 4.06 (dd, J = 11.5, 2.4 Hz, 2H), 3.93-3.88 (m, 2H), 3.58 (td, J = 11.7, 2.5 Hz, 2H), 3.00-2.88 (m, 1H), 2.25 (s, 3H), 1.98-1.83 (m, 4H); LMCS (m/z) (M + H) = 468.0, Rt = 1.45 min. |
| 262 | 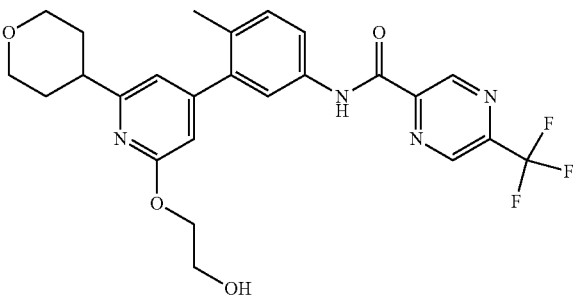 [SMILES: Cc1ccc(NC(=O)c2cnc(C(F)(F)F)cn2)cc1-c1cc(OCCO)nc(C2CCOCC2)c1] | N-(3-(2-(2-hydroxyethoxy)-6-(tetrahydro-2H-pyran-4-yl)pyridin-4-yl)-4-methylphenyl)-5-(trifluoromethyl)pyrazine-2-carboxamide | $^1$H NMR (400 MHz, Methanol-d4) δ 9.47 (d, J = 1.0 Hz, 1H), 9.14 (d, J = 1.1 Hz, 1H), 7.79-7.68 (m, 2H), 7.33 (d, J = 8.2 Hz, 1H), 6.83 (d, J = 1.0 Hz, 1H), 6.63 (d, J = 1.2 Hz, 1H), 4.47-4.43 (m, 2H), 4.08-4.03 (m, 2H), 3.91 (dd, J = 5.5, 4.3 Hz, 2H), (td, J = 11.7, 2.5 Hz, 2H), 2.99-2.88 (m, 1H), 2.26 (s, 3H), 1.98-1.84 (m, 4H); LCMS (m/z) (M + H) = 503.0, Rt = 1.42 min. |

| Example | Structure | Name | Physical Data |
|---|---|---|---|
| 263 | 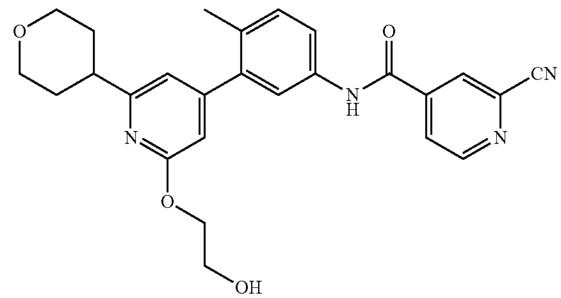 [SMILES: Cc1ccc(NC(=O)c2ccnc(C#N)c2)cc1-c1cc(OCCO)nc(C2CCOCC2)c1] | 2-cyano-N-(3-(2-(2-hydroxyethoxy)-6-(tetrahydro-2H-pyran-4-yl)pyridin-4-yl)-4-methylphenyl)isonicotinamide | 1H NMR (400 MHz, Methanol-d4) δ 8.88 (dd, J = 5.1, 0.8 Hz, 1H), 8.34 (dd, J = 1.6, 0.8 Hz, 1H), 8.11 (dd, J = 5.1, 1.7 Hz, 1H), 7.69-7.57 (m, 2H), 7.32 (d, J = 8.3 Hz, 1H), 6.82 (d, J = 1.0 Hz, 1H), 6.62 (d, J = 1.2 Hz, 1H), 4.44 (dd, J = 5.5, 4.3 Hz, 2H), 4.05 (dd, J = 11.6, 2.2 Hz, 2H), 3.90 (dd, J = 5.5, 4.3 Hz, 2H), 3.58 (td, J = 11.7, 2.6 Hz, 2H), 2.97-2.88 (m, 1H), 2.26 (s, 3H), 1.98-1.83 (m, 4H); LCMS (m/z) (M + H) = 459.0, Rt = 1.24 min. |
| 264 | 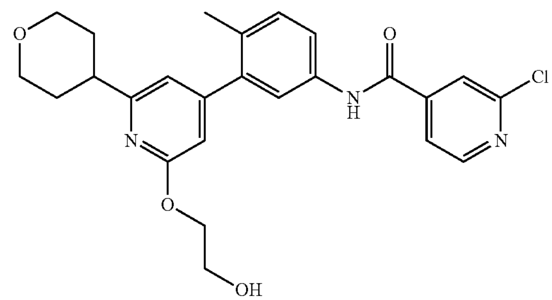 [SMILES: Cc1ccc(NC(=O)c2ccnc(Cl)c2)cc1-c1cc(OCCO)nc(C2CCOCC2)c1] | 2-chloro-N-(3-(2-(2-hydroxyethoxy)-6-(tetrahydro-2H-pyran-4-yl)pyridin-4-yl)-4-methylphenyl)isonicotinamide | $^1$H NMR (400 MHz, Methanol-d4) δ 8.54 (dd, J = 5.2, 0.6 Hz, 1H), 7.93 (d, J = 0.7 Hz, 1H), 7.81 (dd, J = 5.5, 1.5 Hz, 1H), 7.66-7.57 (m, 2H), 7.31 (d, J = 8.3 Hz, 1H), 6.81 (d, J = 1.0 Hz, 1H), 6.61 (d, J = 1.2 Hz, 1H), 4.44 (dd, J = 5.6, 4.3 Hz, 2H), 4.05 (dd, J = 11.5, 2.3 Hz, 2H), 3.90 (dd, J = 5.5, 4.3 Hz, 2H), 3.58 (td, J = 11.7, 2.5 Hz, 2H), 3.00-2.87 (m, 1H), 2.25 (s, 3H), 1.97-1.82 (m, 4H); LMCS (m/z) (M + H) = 468.0, Rt = 1.28 min. |
| 265 | 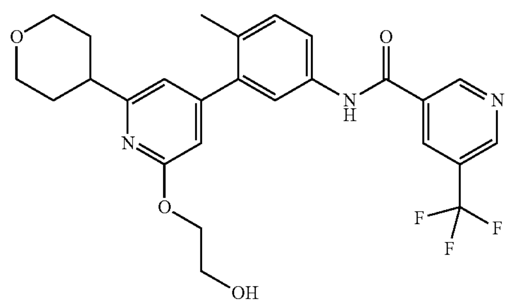 [SMILES: Cc1ccc(NC(=O)c2cncc(C(F)(F)F)c2)cc1-c1cc(OCCO)nc(C2CCOCC2)c1] | N-(3-(2-(2-hydroxyethoxy)-6-(tetrahydro-2H-pyran-4-yl)pyridin-4-yl)-4-methylphenyl)-5-(trifluoromethyl)nicotinamide | $^1$H NMR (400 MHz, Methanol-d4) δ 9.34 (d, J = 1.9 Hz, 1H), 9.06 (s, 1H), 8.65 (s, 1H), 7.69-7.59 (m, 2H), 7.32 (d, J = 8.3 Hz, 1H), 6.82 (d, J = 1.0 Hz, 1H), 6.62 (d, J = 1.2 Hz, 1H), 4.44 (dd, J = 5.6, 4.3 Hz, 2H), 4.08-4.02 (m, 2H) 3.90 (dd, J = 5.5, 4.3 Hz, 2H), 3.58 (td, J = 11.7, 2.5 Hz, 2H), 2.98-2.88 (m, 1H), 2.26 (s, 3H), 1.98-1.84 (m, 4H); LCMS (m/z) (M + H) = 502.0, Rt = 1.34 min. |
| 266 | 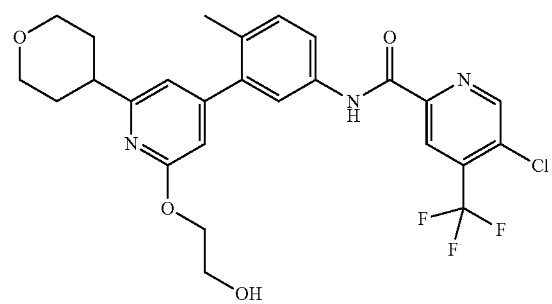 [SMILES: Cc1ccc(NC(=O)c2cc(C(F)(F)F)c(Cl)cn2)cc1-c1cc(OCCO)nc(C2CCOCC2)c1] | 5-chloro-N-(3-(2-(2-hydroxyethoxy)-6-(tetrahydro-2H-pyran-4-yl)pyridin-4-yl)-4-methylphenyl)-4-(trifluoromethyl)picolinamide | $^1$H NMR (400 MHz, Methanol-d4) δ 8.94 (s, 1H), 8.48 (s, 1H), 7.75-7.67 (m, 2H), 7.32 (d, J = 8.1 Hz, 1H), 6.83 (d, J = 1.0 Hz, 1H), 6.63 (d, J = 1.2 Hz, 1H), 4.45 (dd, J = 5.5, 4.3 Hz, 2H), 4.05 (dd, J = 10.6, 3.3 Hz, 2H), 3.90 (dd, J = 5.5, 4.3 Hz, 2H), 3.58 (td, J = 11.7, 2.5 Hz, 2H), 3.02-2.85 (m, 1H), 2.26 (s, 3H), 2.00-1.82 (m, 4H); LCMS (m/z) (M + H) = 536.0, Rt = 1.58 min. |
| 267 | 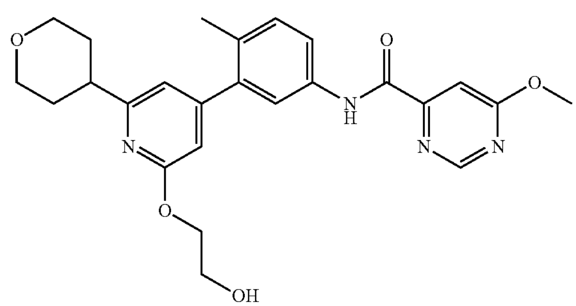 [SMILES: COc1cc(C(=O)Nc2ccc(C)c(-c3cc(OCCO)nc(C4CCOCC4)c3)c2)ncn1] | N-(3-(2-(2-hydroxyethoxy)-6-(tetrahydro-2H-pyran-4-yl)pyridin-4-yl)-4-methylphenyl)-6-methoxypyrimidine-4-carboxamide | $^1$H NMR (400 MHz, Methylene Chloride-d2) δ 8.73 (d, J = 1.1 Hz, 1H), 7.61 (dd, J = 8.2, 2.3 Hz, 1H), 7.56 (d, J = 2.3 Hz, 1H), 7.47 (d, J = 1.1 Hz, 1H), 7.23 (d, J = 8.3 Hz, 1H), 6.73 (d, J = 1.0 Hz, 1H), 6.56(d, J = 1.2 Hz, 1H), 4.49-4.38 (m, 2H), 4.02-3.90 (m, 5H), 3.89-3.81 (m, 2H), 3.49-3.37 (m, 2H), 2.94-2.79 (m, 1H), 2.18 (s, 3H), 1.86-1.75 (m, 4H); LCMS (m/z) (M + H) = 465.1, Rt = 1.35 min. |

TABLE 3-continued

| Example | Structure | Name | Physical Data |
|---|---|---|---|
| 268 | 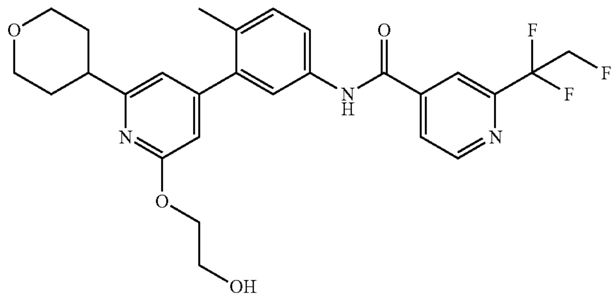 [SMILES: Cc1ccc(NC(=O)c2ccnc(C(F)(F)CF)c2)cc1-c1cc(OCCO)nc(C2CCOCC2)c1] | N-(3-(2-(2-hydroxyethoxy)-6-(tetrahydro-2H-pyran-4-yl)pyridin-4-yl)-4-methylphenyl)-2-(1,1,2-trifluoroethyl)isonicotinamide | $^1$H NMR (400 MHz, Methanol-d4) δ 8.85 (d, J = 4 Hz, 1H), 8.25 (s, 1H), 8.01 (d, J = 4.4 Hz, 1H) 7.66 (dd, J = 8.2, 2.3 Hz, 1H), 7.62 (d, J = 2.3 Hz, 1H), 7.32 (d, J = 8.3 Hz, 1H), 6.82 (d, J = 1.0 Hz, 1H), 6.62(d, J = 1.2 Hz, 1H), 5.02 (dt, J = 46.2, 12.7 Hz, 2H), 4.44 (dd, J = 5.5, 4.3 Hz, 2H), 4.11-4.00 (m, 2H), 3.90 (dd, J = 5.5, 4.3 Hz, 2H), 3.58 (td, J = 11.7, 2.5 Hz, 2H), 2.98-2.90 (m, 1H), 2.26 (s, 3H), 2.00-1.83 (m, 4H); LCMS (m/z) (M + H) = 516.2, Rt = 1.34 min. |
| 269 | 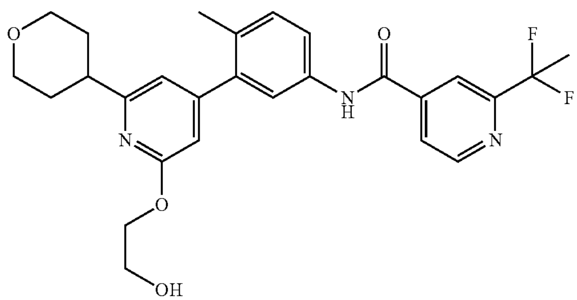 [SMILES: Cc1ccc(NC(=O)c2ccnc(C(C)(F)F)c2)cc1-c1cc(OCCO)nc(C2CCOCC2)c1] | 2-(1,1-difluoroethyl)-N-(3-(2-(2-hydroxyethoxy)-6-(tetrahydro-2H-pyran-4-yl)pyridin-4-yl)-4-methylphenyl)isonicotinamide | $^1$H NMR (400 MHz, DMSO-d6) δ ppm 10.64 (s, 1H) 8.77-8.98 (m, 1H) 8.18 (s, 1H) 8.03 (dd, J = 4.95, 1.41 Hz, 1H) 7.75 (dd, J = 8.25, 2.26 Hz, 1H) 7.68 (d, J = 2.20 Hz, 1H) 7.33 (d, J = 8.44 Hz, 1H) 6.84 (d, J = 1.10 Hz, 1H) 6.60 (d, J = 1.10 Hz, 1H) 4.82 (t, J = 5.56 Hz, 1H) 4.34 (t, J = 5.26 Hz, 2H) 3.96 (dt, J = 11.03, 3.04 Hz, 2H) 3.75 (q, J = 5.42 Hz, 2H) 3.45 (ddd, J = 11.25, 8.50, 6.05 Hz, 2H) 2.84-2.97 (m, 1H) 2.24 (s, 3H) 2.05 (t, J = 19.13 Hz, 3H) 1.75-1.86 (m, 4H); LCMS (m/z) (M + H) = 498.0, Rt = 1.38 min. |
| 270 | 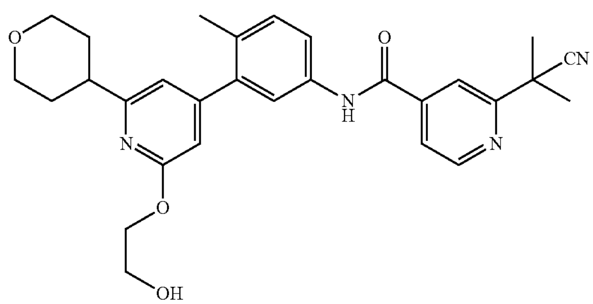 [SMILES: Cc1ccc(NC(=O)c2ccnc(C(C)(C)C#N)c2)cc1-c1cc(OCCO)nc(C2CCOCC2)c1] | 2-(2-cyanopropan-2-yl)-N-(3-(2-(2-hydroxyethoxy)-6-(tetrahydro-2H-pyran-4-yl)pyridin-4-yl)-4-methylphenyl)isonicotinamide | $^1$H NMR (400 MHz, DMSO-d6) δ ppm 10.55 (s, 1H) 8.81 (dd, J = 5.07, 0.67 Hz, 1H) 8.00 (s, 1H) 7.86 (dd, J = 5.01, 1.47 Hz, 1H) 7.73 (dd, J = 8.31, 2.20 Hz, 1H) 7.66 (d, J = 2.20 Hz, 1H) 7.34 (d, J = 8.44 Hz, 1H) 6.84 (d, J = 0.98 Hz, 1H) 6.60 (d, J = 1.10 Hz, 1H) 4.82 (t, J = 5.50 Hz, 1H) 4.34 (t, J = 5.26 Hz, 2 H) 3.96 (dt, J = 10.94, 3.03 Hz, 2H) 3.75 (q, J = 5.42 Hz, 2H) 3.45 (ddd, J = 11.25, 8.50, 6.05 Hz, 2H) 2.84-2.98 (m, 1H) 2.24 (s, 3H) 1.69-1.85 (m, 10H); LCMS (m/z) (M + H) = 501.1, Rt = 1.30 min. |
| 271 | 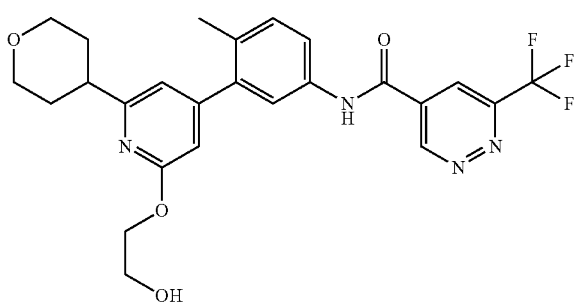 [SMILES: Cc1ccc(NC(=O)c2cnnc(C(F)(F)F)c2)cc1-c1cc(OCCO)nc(C2CCOCC2)c1] | N-(3-(2-(2-hydroxyethoxy)-6-(tetrahydro-2H-pyran-4-yl)pyridin-4-yl)-4-methylphenyl)-6-(trifluoromethyl)pyridazine-4-carboxamide | $^1$H NMR (400 MHz, DMSO-d6) δ ppm 10.86 (s, 1H) 9.92 (d, J = 1.96 Hz, 1H) 8.68 (d, J = 2.08 Hz, 1H) 7.73 (dd, J = 8.25, 2.26 Hz, 1H) 7.67 (d, J = 2.20 Hz, 1H) 7.37 (d, J = 8.44 Hz, 1H) 6.84 (d, J = 0.98 Hz, 1H) 6.60 (d, J = 1.10 Hz, 1H) 4.82 (t, J = 5.50 Hz, 1H) 4.34 (t, J = 5.20 Hz, 2H) 3.96(dt, J = 11.03, 3.04 Hz, 2H) 3.75 (q, J = 5.42 Hz, 2 H) 3.37-3.55 (m, 2H) 2.82-2.97 (m, 1H) 2.25 (s, 3H) 1.71-1.90 (m, 4H); LCMS (m/z) (M + H) = 503.0, Rt = 1.31 min. |

TABLE 3-continued

| Example | Structure | Name | Physical Data |
|---|---|---|---|
| 272 | 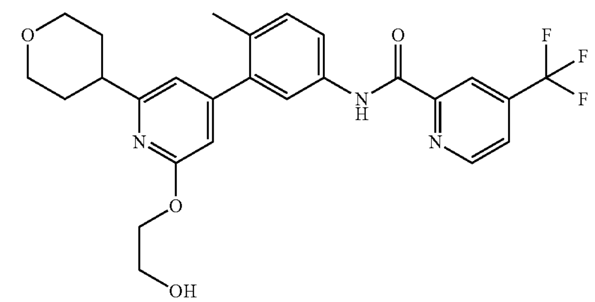 [SMILES: Cc1ccc(NC(=O)c2cc(C(F)(F)F)ccn2)cc1-c1cc(OCCO)nc(C2CCOCC2)c1] | N-(3-(2-(2-hydroxyethoxy)-6-(tetrahydro-2H-pyran-4-yl)pyridin-4-yl)-4-methylphenyl)-4-(trifluoromethyl) picolinamide | $^1$H NMR (400 MHz, DMSO-d6) δ ppm 10.83 (s, 1H) 9.03 (d, J = 5.01 Hz, 1H) 8.31-8.39 (m, 1H) 8.05-8.13 (m, 1H) 7.82-7.90 (m, 2H) 7.32 (d, J = 8.31 Hz, 1H) 6.86 (d, J = 1.10 Hz, 1H) 6.61 (d, J = 1.10 Hz, 1H) 4.82 (t, J = 5.50 Hz, 1H) 4.34 (t, J = 5.20 Hz, 2H) 3.96 (dt, J = 11.00, 3.00 Hz, 2H) 3.75 (q, J = 5.42 Hz, 2 H) 3.39-3.53 (m, 2H) 2.84-2.95 (m, 1H) 2.25 (s, 3H) 1.70-1.89 (m, 4H); LCMS (m/z) (M + H) = 503.0, Rt = 1.31 min. |
| 273 | 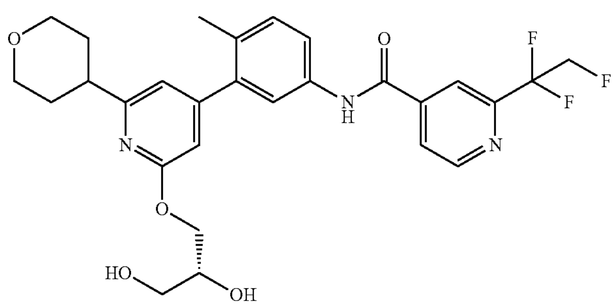 [SMILES: Cc1ccc(NC(=O)c2ccnc(C(F)(F)CF)c2)cc1-c1cc(OC[C@H](O)CO)nc(C2CCOCC2)c1] | (R)-N-(3-(2-(2,3-dihydroxypropoxy)-6-(tetrahydro-2H-pyran-4-yl)pyridin-4-yl)-4-methylphenyl)-2-(1,1,2-trifluoroethyl) isonicotinamide | $^1$H NMR (400 MHz, Methanol-d4) δ 8.85 (d, J = 5.1 Hz, 1H), 8.25 (s, 1H), 8.01 (d, J = 4.6 Hz, 1H) 7.66 (dd, J = 8.2, 2.3 Hz, 1H), 7.62 (d, J = 2.2 Hz, 1H), 7.32 (d, J = 8.3 Hz, 1H), 6.83 (s, 1H), 6.63 (d, J = 1.1 Hz, 1H), 5.02 (dt, J = 46.2, 12.7 Hz, 2H), 4.50-4.34 (m, 2H), 4.11-3.99 (m, 3H), 3.74-3.53 (m, 4H), 2.99-2.89 (m, 1H), 2.26 (s, 3H), 2.01-1.84 (m, 4H); LCMS (m/z) (M + H) = 546.1, Rt = 1.26 min. |
| 274 | 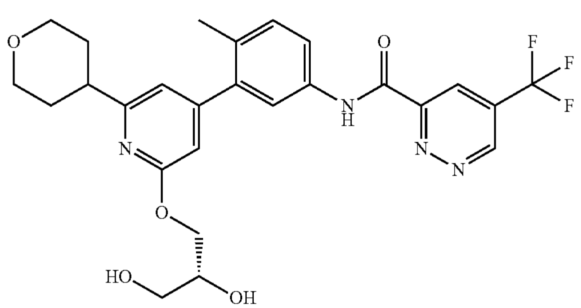 [SMILES: Cc1ccc(NC(=O)c2cc(C(F)(F)F)cnn2)cc1-c1cc(OC[C@H](O)CO)nc(C2CCOCC2)c1] | (R)-N-(3-(2-(2,3-dihydroxypropoxy)-6-(tetrahydro-2H-pyran-4-yl)pyridin-4-yl)-4-methylphenyl)-5-trifluoromethyl) pyridazine-3-carboxamide | $^1$H NMR (400 MHz, Methanol-d4) δ 9.77 (d, J = 1.7 Hz, 1H), 8.67 (dd, J = 2.2, 0.7 Hz, 1H), 7.87-7.74 (m, 2H), 7.38 (d, J = 8.0 Hz, 1H), 6.89 (d, J = 1.0 Hz, 1H), 6.69 (d, J = 1.2 Hz, 1H) 4.54-4.38 (m, 2H), 4.14-4.03 (m, 3H), 3.77-3.66 (m, 2H), 3.66-3.58 (m, 2H), 2.99 (s, 1H), 2.31 (s, 3H), 2.05-1.87 (m, 4H); LCMS (m/z) (M + H) = 533.1, Rt = 1.28 min. |
| 275 | 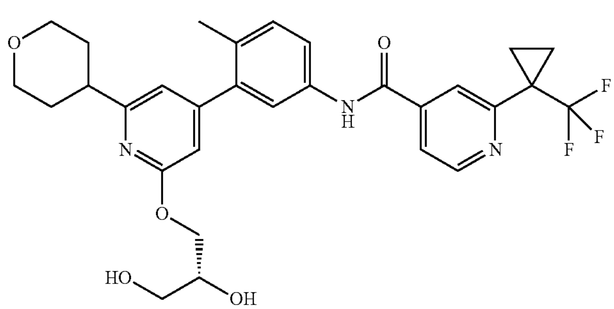 [SMILES: Cc1ccc(NC(=O)c2ccnc(C3(C(F)(F)F)CC3)c2)cc1-c1cc(OC[C@H](O)CO)nc(C2CCOCC2)c1] | (R)-N-(3-(2-(2,3-dihydroxypropoxy)-6-(tetrahydro-2H-pyran-4-yl)pyridin-4-yl)-4-methylphenyl)-2-(1-(trifluoromethyl) cyclopropyl) isonicotinamide | $^1$H NMR (400 MHz, Methanol-d4) δ 8.71-8.67 (m, 1H), 8.05 (s, 1H), 7.79 (dd, J = 5.1, 1.5 Hz, 1H), 7.65 (dd, J = 8.3, 2.2 Hz, 1H), 7.60 (d, J = 2.1 Hz, 1H), 7.31 (d, J = 8.3 Hz, 1H), 6.83 (s, 1H), 6.63 (d, J = 0.9 Hz, 1H), 4.50-4.33 (m, 2H), 4.10-3.99 (m, 3H), 3.71-3.53 (m, 4H), 3.00-2.88 (m, 1H), 2.26 (s, 3H), 1.99-1.83 (m, 4H), 1.52-1.39 (m, 4H); LCMS (m/z) (M + H) = 572.1, Rt = 1.32 min. |
| 276 | 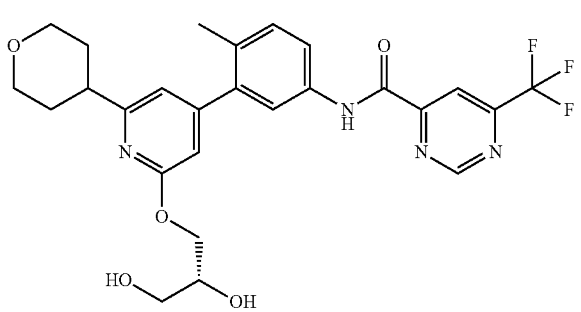 [SMILES: Cc1ccc(NC(=O)c2cc(C(F)(F)F)ncn2)cc1-c1cc(OC[C@H](O)CO)nc(C2CCOCC2)c1] | (R)-N-(3-(2-(2,3-dihydroxypropoxy)-6-(tetrahydro-2H-pyran-4-yl)pyridin-4-yl)-4-methylphenyl)-6-(trifluoromethyl) pyrimidine-4-carboxamide | $^1$H NMR (400 MHz, Methanol-d4) δ 9.54 (s, 1H), 8.50 (d, J = 1.3 Hz, 1H), 7.79-7.70 (m, 2H), 7.34 (d, J = 8.2 Hz, 1H), 6.84 (d, J = 1.0 Hz, 1H), 6.64 (d, J = 1.2 Hz, 1H), 4.49-4.35 (m, 2H), 4.04 (td, J = 10.3, 4.0 Hz, 3H), 3.72-3.62 (m, 2H), 3.61-3.55 (m, 2H), 2.98-2.90 (m, 1H), 2.26 (s, 3H), 1.98-1.84 (m, 4H); LCMS (m/z) (M + H) = 533.0, Rt = 1.33 min. |

TABLE 3-continued

| Example | Structure | Name | Physical Data |
|---|---|---|---|
| 277 | 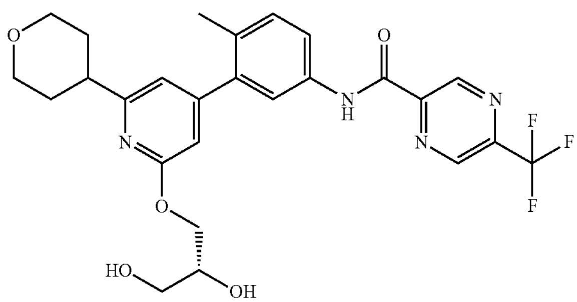 [SMILES: Cc1ccc(NC(=O)c2cnc(C(F)(F)F)cn2)cc1-c1cc(OC[C@H](O)CO)nc(C2CCOCC2)c1] | (R)-N-(3-(2-(2,3-dihydroxypropoxy)-6-(tetrahydro-2H-pyran-4-yl)pyridin-4-yl)-4-methylphenyl)-5-(trifluoromethyl)pyrazine-2-carboxamide | $^1$H NMR (400 MHz, Methanol-d4) δ 9.47 (d, J = 1.0 Hz, 1H), 9.14 (d, J = 1.1 Hz, 1H), 7.77-7.69 (m, 2H), 7.33 (d, J = 8.2 Hz, 1H), 6.84 (d, J = 1.0 Hz, 1H), 6.64 (d, J = 1.2 Hz, 1H), 4.51-4.32 (m, 2H), 4.10-3.98 (m, 3H), 3.71-3.55 (m, 4H), 2.99-2.89 (m, 1H), 2.27 (s, 3H), 1.99-1.82 (m, 4H); LCMS (m/z) (M + H) = 533.2, Rt = 1.32 min. |
| 278 | 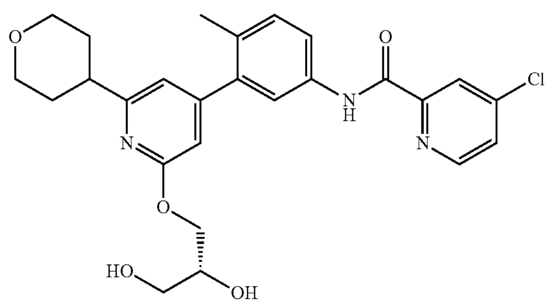 [SMILES: Cc1ccc(NC(=O)c2cc(Cl)ccn2)cc1-c1cc(OC[C@H](O)CO)nc(C2CCOCC2)c1] | (R)-4-chloro-N-(3-(2-(2,3-dihydroxypropoxy)-6-(tetrahydro-2H-pyran-4-yl)pyridin-4-yl)-4-methylphenyl)picolinamide | $^1$H NMR (400 MHz, Methanol-d4) δ 8.64 (dd, J = 5.3, 0.5 Hz, 1H), 8.20 (dd, J = 2.1, 0.5 Hz, 1H), 7.72-7.64 (m, 3H), 7.35-7.26 (m, 1H), 6.84 (d, J = 1.0 Hz, 1H), 6.64 (d, J = 1.2 Hz, 1H), 4.50-4.32 (m, 2H), 4.10-3.98 (m, 3H), 3.74-3.52 (m, 4H), 2.99-2.87 (m, 1H), 2.26 (s, 3H), 2.00-1.83 (m, 4H). LCMS (m/z) (M + H) = 498.2, Rt = 1.34 min. |
| 279 | 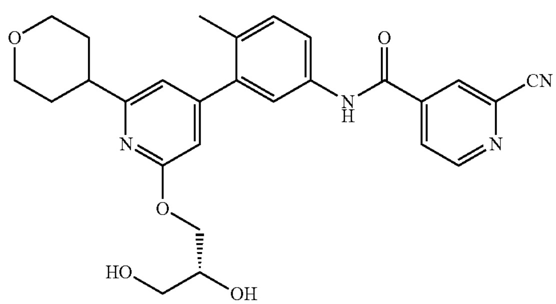 [SMILES: Cc1ccc(NC(=O)c2ccnc(C#N)c2)cc1-c1cc(OC[C@H](O)CO)nc(C2CCOCC2)c1] | (R)-2-cyano-N-(3-(2-(2,3-dihydroxypropoxy)-6-(tetrahydro-2H-pyran-4-yl)pyridin-4-yl)-4-methylphenyl)isonicotinamide | $^1$H NMR (400 MHz, Methanol-d4) δ 8.88 (dd, J = 5.1, 0.8 Hz, 1H), 8.34 (dd, J = 1.6, 0.8 Hz, 1H), 8.11 (dd, J = 5.1, 1.7 Hz, 1H), 7.65 (dd, J = 8.2, 2.3 Hz, 1H), 7.61 (d, J = 2.3 Hz, 1H), 7.32 (d, J = 8.3 Hz, 1H), 6.83 (d, J = 1.0 Hz, 1H), 6.63 (d, J = 1.2 Hz, 1H), 4.50-4.33 (m, 2H), 4.08-3.99 (m, 3H), 3.69-3.54 (m, 4H), 2.97-2.89 (m, 1H), 2.26 (s, 3H), 1.97-1.84 (m, 4H); LCMS (m/z) (M + H) = 489.3, Rt = 1.15 min. |
| 280 | 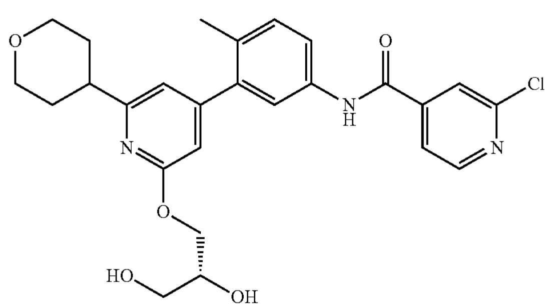 [SMILES: Cc1ccc(NC(=O)c2ccnc(Cl)c2)cc1-c1cc(OC[C@H](O)CO)nc(C2CCOCC2)c1] | (R)-2-chloro-N-(3-(2-(2,3-dihydroxypropoxy)-6-(tetrahydro-2H-pyran-4-yl)pyridin-4-yl)-4-methylphenyl)isonicotinamide | $^1$H NMR (400 MHz, Methanol-d4) δ 8.54 (dd, J = 5.2, 0.7 Hz, 1H), 7.93 (dd, J = 1.4, 0.6 Hz, 1H), 7.81 (dd, J = 5.2, 1.5 Hz, 1H), 7.64 (dd, J = 8.2, 2.3 Hz, 1H), 7.60 (d, J = 2.3 Hz, 1H), 7.31 (d, J = 8.3 Hz, 1H), 6.83 (d, J = 1.0 Hz, 1H), 6.63 (d, J = 1.2 Hz, 1H), 4.50-4.33 (m, 2H), 4.08-3.97 (m, 3H), 3.73-3.53 (m, 4H), 2.99-2.89 (m, 1H), 2.25 (s, 3H), 1.98-1.84 (m, 4H); LCMS (m/z) (M + H) = 498.0, Rt = 1.20 min. |
| 281 | 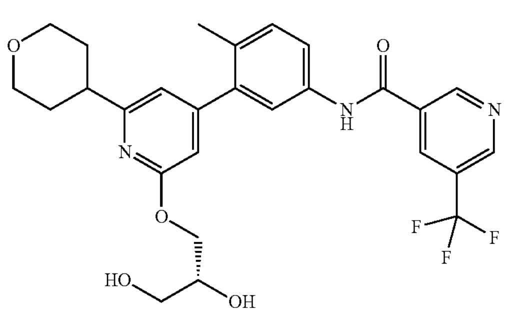 [SMILES: Cc1ccc(NC(=O)c2cncc(C(F)(F)F)c2)cc1-c1cc(OC[C@H](O)CO)nc(C2CCOCC2)c1] | (R)-N-(3-(2-(2,3-dihydroxypropoxy)-6-(tetrahydro-2H-pyran-4-yl)pyridin-4-yl)-4-methylphenyl)-5-(trifluoromethyl)nicotinamide | $^1$H NMR (400 MHz, Methanol-d4) δ 9.34 (d, J = 1.8 Hz, 1H), 9.07-9.05 (m, 1H), 8.65 (s, 1H), 7.69-7.59 (m, 2H), 7.32 (d, J = 8.3 Hz, 1H), 6.83 (d, J = 1.0 Hz, 1H), 6.63 (d, J = 1.2 Hz, 1H), 4.51-4.33 (m, 2H), 4.11-3.97 (m, 3H), 3.73-3.53 (m, 4H), 2.99-2.88 (m, 1H), 2.26 (s, 3H), 1.98-1.83 (m, 4H); LCMS (m/z) (M + H) = 532.1, Rt = 1.25 min. |

TABLE 3-continued

| Example | Structure | Name | Physical Data |
|---|---|---|---|
| 282 | 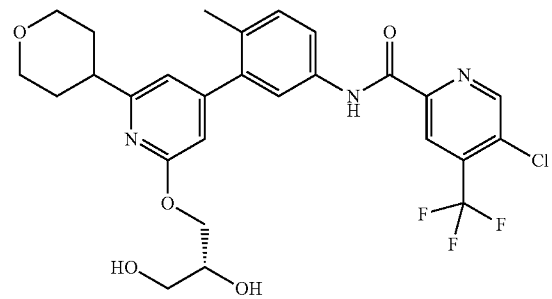 [SMILES: Cc1ccc(NC(=O)c2cc(C(F)(F)F)c(Cl)cn2)cc1-c1cc(OC[C@H](O)CO)nc(C2CCOCC2)c1] | (R)-5-chloro-N-(3-(2-(2,3-dihydroxypropoxy)-6-(tetrahydro-2H-pyran-4-yl)pyridin-4-yl)-4-methylphenyl)-4-(trifluoromethyl)picolinamide | ¹H NMR (400 MHz, Methanol-d4) δ 8.94 (s, 1H), 8.48 (s, 1H), 7.78-7.65 (m, 2H), 7.32 (d, J = 8.0 Hz, 1H), 6.84 (d, J = 1.0 Hz, 1H), 6.64 (d, J = 1.2 Hz, 1H), 4.50-4.33 (m, 2H), 4.09-3.98 (m, 3H), 3.72-3.53 (m, 4H), 2.99-2.88 (m, 1H), 2.26 (s, 3H), 1.99-1.82 (m, 4H); LCMS (m/z) (M + H) = 566.0, Rt = 1.48 min. |
| 283 | 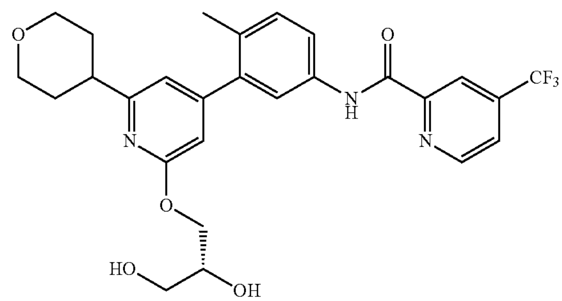 [SMILES: Cc1ccc(NC(=O)c2cc(C(F)(F)F)ccn2)cc1-c1cc(OC[C@H](O)CO)nc(C2CCOCC2)c1] | (R)-N-(3-(2-(2,3-dihydroxypropoxy)-6-(tetrahydro-2H-pyran-4-yl)pyridin-4-yl)-4-methylphenyl)-4-(trifluoromethyl)picolinamide | ¹H NMR (400 MHz, DMSO-d6) δ 10.83 (s, 1H) 9.03 (d, J = 5.01 Hz, 1H) 8.35 (d, J = 0.86 Hz, 1H) 8.09 (dd, J = 5.01, 1.10 Hz, 1H) 7.80-7.92 (m, 2H) 7.32 (d, J = 8.31 Hz, 1H) 6.86 (d, J = 0.98 Hz, 1H) 6.62 (d, J = 1.10 Hz, 1H) 4.91 (d, J = 5.26 Hz, 1H) 4.65 (t, J = 5.75 Hz, 1H) 4.34 (dd, J = 11.00, 4.40 Hz, 1H) 4.22 (dd, J = 10.94, 6.42 Hz, 1H) 3.96 (dt, J = 11.00, 2.93 Hz, 2H) 3.84 (dq, J = 10.87, 5.47 Hz, 1H) 3.38-3.52 (m, 4H) 3.31 (s, 1H) 2.80-3.00 (m, 1H) 2.25 (s, 3H) 1.72-1.88 (m, 4H); LCMS (m/z) (M + H) = 566.0, Rt = 1.48 min. |
| 284 | 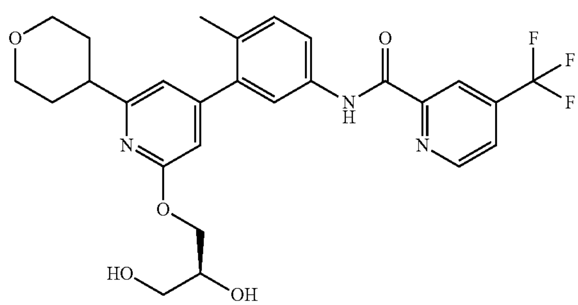 [SMILES: Cc1ccc(NC(=O)c2cc(C(F)(F)F)ccn2)cc1-c1cc(OC[C@@H](O)CO)nc(C2CCOCC2)c1] | (S)-N-(3-(2-(2,3-dihydroxypropoxy)-6-(tetrahydro-2H-pyran-4-yl)pyridin-4-yl)-4-methylphenyl)-2-(trifluoromethyl)isonicotinamide | ¹H NMR (400 MHz, Methanol-d4) δ 10.83 (s, 1H) 9.03 (d, J = 5.01 Hz, 1H) 8.35 (s, 1H) 8.09 (dd, J = 5.07, 1.04 Hz, 1H) 7.81-7.93 (m, 2H) 7.32 (d, J = 8.31 Hz, 1H) 6.86 (d, J = 0.86 Hz, 1H) 6.62 (d, J = 0.98 Hz, 1H) 4.50-5.09 (m, 2H) 4.35 (dd, J = 10.94, 4.46 Hz, 1H) 4.22 (dd, J = 11.00, 6.48 Hz, 1H) 3.97 (dt, J = 10.94, 2.84 Hz, 2H) 3.85 (quin, J = 5.50 Hz, 1H) 3.13-3.59 (m, 5H) 2.79-2.98 (m, 1H) 2.25 (s, 3H) 1.75-1.91 (m, 4H); LCMS (m/z) (M + H) = 532.1, Rt = 1.40 min. |
| 285 | 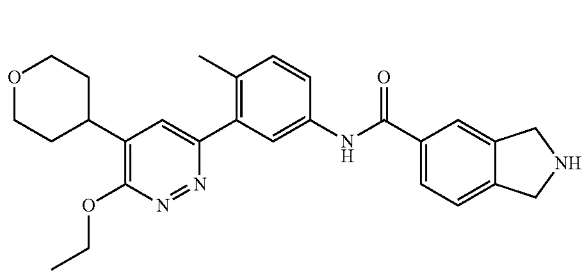 [SMILES: CCOc1nnc(-c2cc(NC(=O)c3ccc4c(c3)CNC4)ccc2C)cc1C1CCOCC1] | N-(3-(6-ethoxy-5-(tetrahydro-2H-pyran-4-yl)pyridazin-3-yl)-4-methylphenyl)isoindoline-5-carboxamid | ¹H NMR (600 MHz, DMSO-d₆) δ ppm 10.34 (s, 1H) 9.42 (br. s., 2H) 7.96-8.01 (m, 2H) 7.84 (d, J = 2.20 Hz, 1H) 7.79 (dd, J = 8.25, 2.20 Hz, 1H) 7.55-7.58 (m, 2H) 7.33 (d, J = 8.44 Hz, 1H) 4.59 (q, J = 7.00 Hz, 7H) 3.93-3.99 (m, 1H) 3.47 (td, J = 11.39, 2.80 Hz, 3H) 3.00-3.10 (m, 1H) 2.28 (s, 3H) 1.67-1.80 (m, 4H) 1.43 (t, J = 7.01 Hz, 3 H). LCMS (m/z) (M + H) = 459.1, Rt = 0.95 min. |

Examples 286 and 287

N-(3-(2-(4-hydroxytetrahydro-2H-pyran-4-yl)-6-(2-oxooxazolidin-3-yl)pyridin-4-yl)-4-methylphenyl)-2-(trifluoromethyl)isonicotinamide and N-(3-(2-((2-hydroxyethyl)amino)-6-(4-hydroxytetrahydro-2H-pyran-4-yl)pyridin-4-yl)-4-methylphenyl)-2-(trifluoromethyl)isonicotinamide

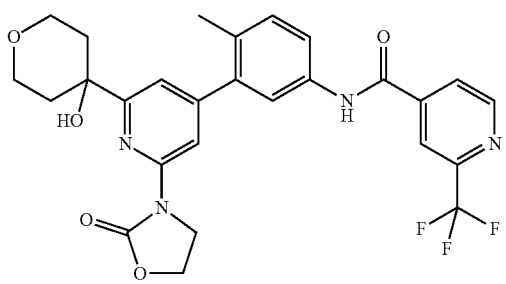

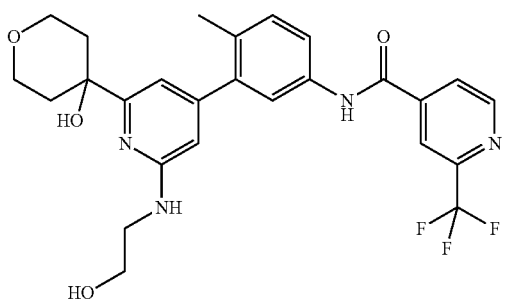

To a solution of 2-(4-hydroxytetrahydro-2H-pyran-4-yl)-6-(2-oxooxazolidin-3-yl)pyridin-4-yl trifluoromethanesulfonate (1.0 equiv.) and N-(4-methyl-3-(4,4,5,5-tetramethyl-1,3,2-dioxaborolan-2-yl)phenyl)-2-(trifluoromethyl) isonicotinamide (1.2 equiv.) in DME (0.2 M) and 2 M aq. Na$_2$CO$_3$ (5.0 equiv) was added PdCl$_2$(dppf)-DCM adduct (0.05 equiv.) and the reaction irradiated at 125° C. for 15 min and then cooled to rt. Sodium hydroxide (5.0 equiv.) was added, and the mixture was stirred at 100° C. for 40. The mixture was diluted with water and extracted with EtOAc. The organic layer was concentrated and the residue was dissolved in DMSO, filtered and purified via reverse phase prep-HPLC. The product fractions were lyophilized to give N-(3-(2-(4-hydroxytetrahydro-2H-pyran-4-yl)-6-(2-oxooxazolidin-3-yl)pyridin-4-yl)-4-methylphenyl)-2-(trifluoromethyl)isonicotinamide in 29% yield. $^1$H NMR (500 MHz Methanol-d4) δ 8.91 (d, J=5.09 Hz, 1H) 8.31 (s, 1H) 8.13 (d. J=3.91 Hz, 1H) 8.01 (s, 1H) 7.68-7.75 (m, 2H) 7.44 (d, J=0.78 Hz, 1H) 7.36 (d, J=8.61 Hz, 1H) 4.51-4.62 (m, 2H) 4.34-4.43 (m, 2H) 3.91-4.01 (m, 2H) 3.83-3.91 (m, 2H) 2.43 (td, J=12.91, 5.09 Hz, 2H) 2.30 (s, 3H) 1.65 (d, J=12.52 Hz, 2H). LC-MS: Rt—0.90, Mass—543.1 N-(3-(2-((2-hydroxyethyl)amino)-6-(4-hydroxytetrahydro-2H-pyran-4-yl)pyridin-4-yl)-4-methylphenyl)-2-(trifluoromethyl)isonicotinamide was also isolated in 24% yield. $^1$H NMR (500 MHz, Methanol-d4) δ 8.92 (d, J=4.69 Hz, 1H) 8.31 (s, 1H) 8.14 (dd, J=4.89, 1.37 Hz, 1H) 7.66 (dd, J=8.22, 2.35 Hz, 1H) 7.61-7.64 (m, 1H) 7.33 (d, J=8.22 Hz, 1H) 6.79 (d, J=1.17 Hz, 1H) 6.39 (d, J=1.17 Hz, 1H) 3.91-4.01 (m, 2H) 3.84-3.91 (m, 2H) 3.78 (t, J=5.87 Hz, 2H). 3.52-3.59 (m, 2H) 2.36 (td, J=12.91, 5.09 Hz, 2H) 2.29 (s, 3H) 1.60 (d, J=11.74 Hz, 2H). LC-MS:
Rt—0.71, Mass—517.1.

Example 288

2-(2-cyanopropan-2-yl)-N-(3-(6-ethoxy-5-(3-(fluoromethyl)tetrahydrofuran-3-yl)pyridin-3-yl)-4-methylphenyl)isonicotinamide

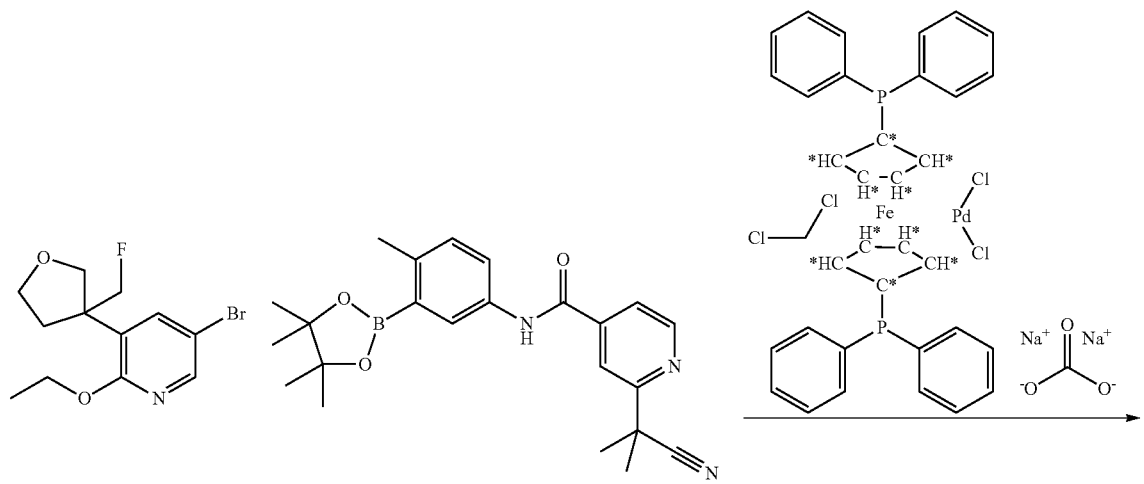

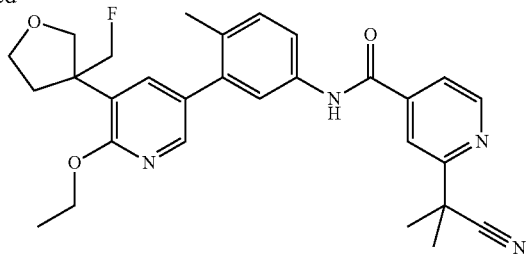

To a solution of 5-bromo-2-ethoxy-3-(3-(fluoromethyl)tetrahydrofuran-3-yl)pyridine (1.0 equiv.) and 2-(2-cyanopropan-2-yl)-N-(4-methyl-3-(4,4,5,5-tetramethyl-1,3,2-dioxaborolan-2-yl)phenyl)isonicotinamide (1.4 equiv.) in DME and 2M Na₂CO₃ (3:1, 0.08 M) was added PdCl₂(dppf)-DCM adduct (0.05 equiv.) and the reaction was purged with argon. The solution was heated to 100° C. for 1 hour, then cooled to rt, concentrated under vacuo, dissolved in DMSO, filtered and purified via reverse phase prep-HPLC. The pure fractions were lyophilized to give 2-(2-cyanopropan-2-yl)-N-(3-(6-ethoxy-5-(3-(fluoromethyl)tetrahydrofuran-3-yl)pyridin-3-yl)-4-methylphenyl)isonicotinamide in 39% yield. ¹H NMR (400 MHz, <cd3od>) δ ppm 1.42-1.49 (m, 3H) 1.81 (s, 6H) 2.27 (s, 3H) 2.29-2.35 (m, 1H) 2.40 (s, 1H) 3.91 (dd, J=9.39, 5.09 Hz, 2H) 4.01 (d, J=8.22 Hz, 1H) 4.28 (d, J=9.00 Hz, 1H) 4.46 (d, J=7.04 Hz, 2H) 4.51-4.68 (m, 2H) 7.33 (d, J=8.22 Hz, 1H) 7.56 (d, J=1.96 Hz, 1H) 7.59 (d, J=2.35 Hz, 1H) 7.67 (dd, J=8.22, 1.96 Hz, 1H) 7.82 (dd, J=5.09, 1.57 Hz, 1H) 8.05 (d, J=2.35 Hz, 1H) 8.07 (s, 1H) 8.76 (d, J=5.09 Hz, 1H). LCMS (m/z) (M+H)=503.3. Rt=1.03 min.

The compounds listed in Table 4, below, were prepared using methods similar to those described for the preparation of the above examples using the appropriate starting materials:

TABLE 4

| Example | Structure | Name | Physical Data |
|---|---|---|---|
| 289 | 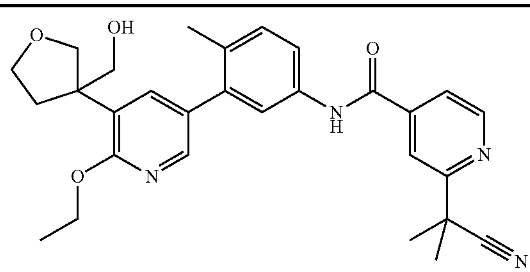 | 2-(2-cyanopropan-2-yl)-N-(3-(6-ethoxy-5-(3-(hydroxymethyl)tetrahydrofuran-3-yl)pyridin-3-yl)-4-methylphenyl)isonicotinamide | ¹H NMR (500 MHz, Methanol-d₄) δ 8.78 (d, J = 5.1 Hz, 1H), 8.09 (s, 1H), 8.03 (d, J = 2.2 Hz, 1H), 7.84 (d, J = 5.0 Hz, 1H), 7.72-7.59 (m, 2H), 7.56 (d, J = 2.2 Hz, 1H), 7.35 (d, J = 8.3 Hz, 1H), 4.74 (q, J = 10.7 Hz, 1H), 4.48 (dq, J = 14.1, 7.0 Hz, 2H), 4.10-3.85 (m, 3H), 3.85-3.73 (m, 1H), 2.54-2.34 (m, 2H), 2.31 (s, 2H), 1.84 (s, 6H), 1.47 (t, J = 7.5 Hz, 3H). LCMS (m/z) (M + H) = 501.3, Rt = 0.90 min |
| 290 | 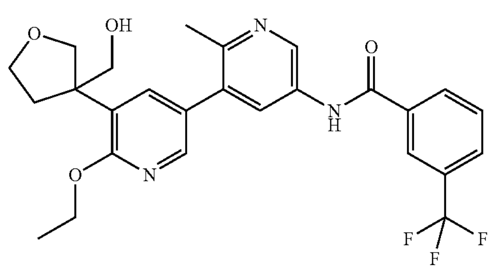 | N-(6'-ethoxy-5'-(3-(hydroxymethyl)tetrahydrofuran-3-yl)-2-methyl-[3,3'-bipyridin]-5-yl)-3-(trifluoromethyl)benzamide | ¹H NMR (500 MHz, METHANOL-d₄) δ ppm 1.45 (t, J = 7.09 Hz, 3H) 3.22 (dt, J = 12.61, 8.67 Hz, 1H) 2.41-2.48 (m, 1H) 2.68 (s, 3H) 3.80 (d, J = 3.15 Hz, 2 H) 3.87 (d, J = 9.14 Hz, 1H) 3.92 (dt, J = 8.83, 4.41 Hz, 1H) 3.99 (q, J = 7.67 Hz, 1H) 4.27 (d, J = 9.14 Hz, 1H) 4.48 (q, J = 7.04 Hz, 2H) 7.63 (d, J = 2.21 Hz, 1H) 7.79 (t, J = 7.72 Hz, 1H) 7.96 (d, J = 7.88 Hz, 1H) 8.16 (d, J = 1.89 Hz, 1H) 8.28 (d, J = 7.88 Hz, 1H) 8.35 (s, 1 H) 8.42 (d, J = 2.52 Hz, 1H) 9.31 (d, J = 2.21 Hz, 1H). LCMS (m/z) (M + H) = 502.2, Rt = 0.77 min. |
| 291 | 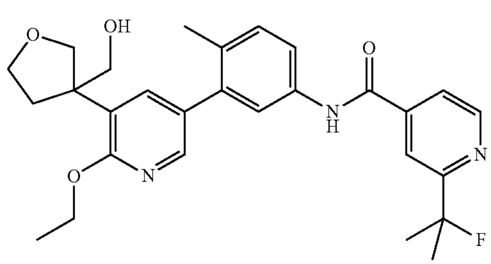 [SMILES: CCOc1ncc(-c2cc(NC(=O)c3ccnc(C(C)(C)F)c3)ccc2C)cc1C1(CO)CCOC1] | N-(3-(6-ethoxy-5-(3-(hydroxymethyl)tetrahydrofuran-3-yl)pyridin-3-yl)-4-methylphenyl)-2-(2-fluoropropan-2-yl)isonicotinamide | ¹H NMR (500 MHz, Methanol-d₄) δ 8.74 (d, J = 5.0 Hz, 1H), 8.12 (s, 1H), 8.05 (dd, J = 17.7, 2.1 Hz, 1H), 7.72-7.65 (m, 1H), 7.62 (dd, J = 10.4, 2.1 Hz, 1H), 7.57-7.50 (m, 1H), 7.35 (d, J = 8.3 Hz, 1H), 4.54-4.41 (m, 2H), 4.11-3.90 (m, 3H), 3.88 (d, J = 9.0 Hz, 1H), 3.85-3.73 (m, 2H), 2.54-2.34 (m, 2H), 2.29 (d, J = 25.9 Hz, 3H), 1.77 (d, J = 22.0 Hz, 6H), 1.53-1.40 (m, 3H). LCMS (m/z) (M + H) = 494.3, Rt = 0.90 min. |

TABLE 4-continued

| Example | Structure | Name | Physical Data |
|---|---|---|---|
| 292 | 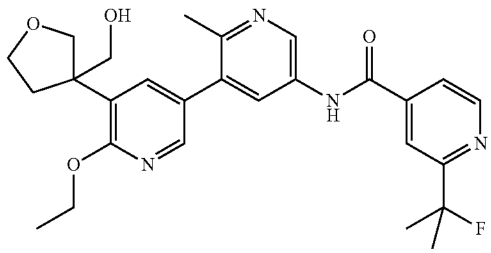 [SMILES: CCOc1ncc(-c2cc(NC(=O)c3ccnc(C(C)(C)F)c3)cnc2C)cc1C1(CO)CCOC1] | N-(6'-ethoxy-5'-(3-(hydroxymethyl)tetrahydrofuran-3-yl)-2-methyl-[3,3'-bipyridin]-5-yl)-2-(2-fluoropropan-2-yl)isonicotinamide | $^1$H NMR (500 MHz, Methanol-$d_4$) δ 9.44-9.37 (m, 1H), 8.82-8.76 (m, 1H), 8.51 (d, J = 2.3 Hz, 1H), 8.20 (d, J = 2.4 Hz, 1H), 8.16 (d, J = 11.0 Hz, 1H), 7.86 (dd, J = 5.0, 1.5 Hz, 1H), 7.66 (d, J = 2.3 Hz, 1H), 4.51 (q, J = 7.0 Hz, 2H), 4.29 (d, J = 9.0 Hz, 1H), 4.00 (p, J = 7.7 Hz, 1H), 3.94 (td, J = 8.8, 4.4 Hz, 1H), 3.89 (d, J = 9.0 Hz, 1H), 3.82 (d, J = 2.1 Hz, 2H), 2.73 (s, 3H), 2.50-2.40 (m, 2H), 2.24 (dt, J = 12.7, 8.6 Hz, 1H), 1.76 (d, J = 21.9 Hz, 8H), 1.53-1.45 (m, 3H). LCMS (m/z) (M + H) = 495.2, Rt = 0.69 min. |
| 293 | 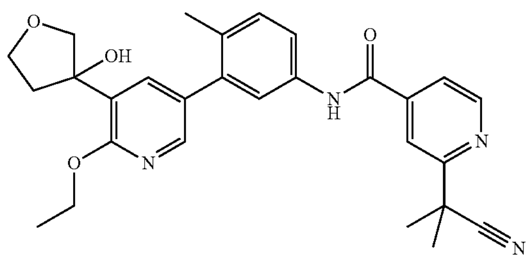 [SMILES: CCOc1ncc(-c2cc(NC(=O)c3ccnc(C(C)(C)C#N)c3)ccc2C)cc1C1(O)CCOC1] | 2-(2-cyanopropan-2-yl)-N-(3-(6-ethoxy-5-(3-hydroxytetrahydrofuran-3-yl)pyridin-3-yl)-4-methylphenyl)isonicotinamide | LCMS (m/z) (M + H) = 487.2, Rt = 0.88 min. |
| 294 | 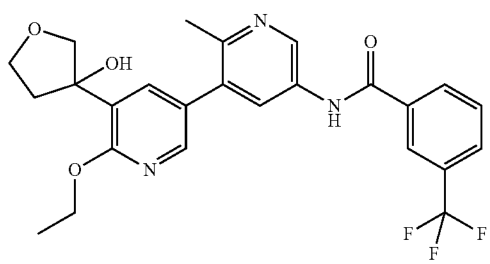 [SMILES: CCOc1ncc(-c2cc(NC(=O)c3cccc(C(F)(F)F)c3)cnc2C)cc1C1(O)CCOC1] | N-(6'-ethoxy-5'-(3-hydroxytetrahydrofuran-3-yl)-2-methyl-[3,3'-bipyridin]-5-yl)-3-(trifluoromethyl)benzamide | LCMS (m/z) (M + H) = 488.2, Rt = 0.76 min. |
| 295 | 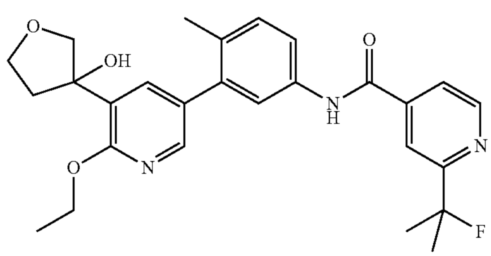 [SMILES: CCOc1ncc(-c2cc(NC(=O)c3ccnc(C(C)(C)F)c3)ccc2C)cc1C1(O)CCOC1] | N-(3-(6-ethoxy-5-(3-hydroxytetrahydrofuran-3-yl)pyridin-3-yl)-4-methylphenyl)-2-(2-fluoropropan-2-yl)isonicotinamide | LCMS (m/z) (M + H) = 480.2, Rt = 0.89 min. |
| 296 | 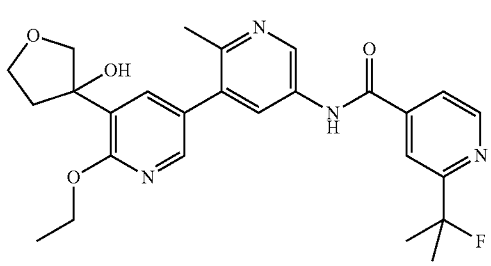 [SMILES: CCOc1ncc(-c2cc(NC(=O)c3ccnc(C(C)(C)F)c3)cnc2C)cc1C1(O)CCOC1] | N-(6'-ethoxy-5'-(3-hydroxytetrahydrofuran-3-yl)-2-methyl-[3,3'-bipyridin]-5-yl)-2-(2-fluoropropan-2-yl)isonicotinamide | LCMS (m/z) (M + H) = 481.1, Rt = 0.67 min. |

TABLE 4-continued

| Example | Structure | Name | Physical Data |
|---|---|---|---|
| 297 | 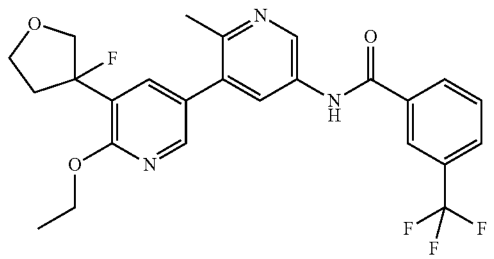 [SMILES: CCOc1ncc(-c2cc(NC(=O)c3cccc(C(F)(F)F)c3)cnc2C)cc1C1(F)CCOC1] | N-(6'-ethoxy-5'-(3-fluorotetrahydro-furan-3-yl)-2-methyl-[3,3'-bipyridin]-5-yl)-3-(trifluoro-methyl)benzamide | $^1$H NMR (400 MHz, <cd3od>) δ ppm 1.46 (t, J = 7.04 Hz, 3H) 2.29-2.44 (m, 1H) 2.67 (s, 3H) 2.75-2.93 (m, 1H) 4.04-4.32 (m, 4H) 4.51-4.58 (m, 2H) 7.78 (t, J = 7.83 Hz, 1H) 7.96 (dd, J = 7.83, 0.78 Hz, 1H) 8.01 (d, J = 2.35 Hz, 1H) 8.26-8.31 (m, 2H) 8.35 (s, 1H) 8.44 (d, J = 2.35 Hz, 1H) 9.32 (d, J = 2.35 Hz, 1H). LCMS (m/z) (M + H) = 490.1, Rt = 0.86 min. |
| 298 | 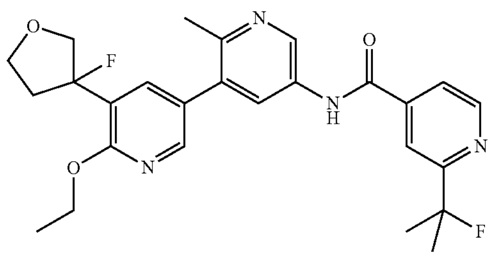 [SMILES: CCOc1ncc(-c2cc(NC(=O)c3ccnc(C(C)(C)F)c3)cnc2C)cc1C1(F)CCOC1] | N-(6'-ethoxy-5'-(3-fluorotetrahydro-furan-3-yl)-2-methyl-[3,3'-bipyridin]-5-yl)-2-(2-fluoropropan-2-yl)isonicotinamide | $^1$H NMR (400 MHz, <cd3od>) δ ppm 1.68-1.79 (m, 6H) 2.28-2.44 (m, 1H) 2.68 (s, 3H) 2.74-2.93 (m, 1H) 4.03-4.33 (m, 4H) 4.54 (dd, J = 7.04, 0.78 Hz, 2H) 7.84 (dd, J = 5.09, 1.56 Hz, 1H) 8.02 (d, J = 2.74 Hz, 1H) 8.12-8.15 (m, 1H) 8.28 (d, J = 2.35 Hz, 1H) 8.47 (d, J = 2.35 Hz, 1H) 8.74-8.77 (m, 1H) 9.34 (d, J = 2.35 Hz, 1H). LCMS (m/z) (M + H) = 483.2, Rt = 0.78 min. |
| 299 | 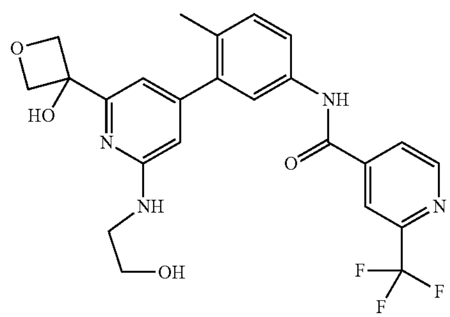 [SMILES: Cc1ccc(NC(=O)c2ccnc(C(F)(F)F)c2)cc1-c1cc(NCCO)nc(C2(O)COC2)c1] | N-(3-(2-((2-hydroxyethyl)amino)-6-(3-hydroxyoxetan-3-yl)pyridin-4-yl)-4-methylphenyl)-2-(trifluoromethyl)isonicotinamide | $^1$H NMR (400 MHz, <cd3od>) δ ppm 8.92 (d, J = 5.09 Hz, 1H) 8.31 (s, 1H) 8.13 (dd, J = 5.09, 1.17 Hz, 1H) 7.67 (dd, J = 8.22, 2.35 Hz, 1H) 7.64 (d, J = 2.35 Hz, 1H) 7.33 (d, J = 8.22 Hz, 1H) 6.89 (d, J = 1.17 Hz, 1H) 6.46 (d, J = 1.56 Hz, 1H) 5.07 (d, J = 6.65 Hz, 2H) 4.83 (d, J = 7.04 Hz, 2H) 3.76-3.82 (m, 2H) 3.55-3.62 (m, 2H) 2.30 (s, 3H). LCMS (m/z) (M + H) = 489.1, Rt = 0.67 min. |
| 300 | 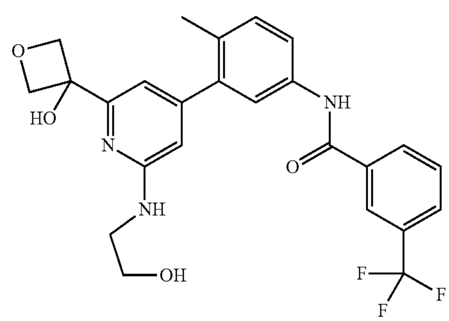 [SMILES: Cc1ccc(NC(=O)c2cccc(C(F)(F)F)c2)cc1-c1cc(NCCO)nc(C2(O)COC2)c1] | N-(3-(2-((2-hydroxyethyl)amino)-6-(3-hydroxyoxetan-3-yl)pyridin-4-yl)-4-methylphenyl)-3-(trifluoromethyl)benzamide | $^1$H NMR (400 MHz, <cd3od>) δ ppm 8.27 (s, 1H) 8.22 (d, J = 7.83 Hz, 1H) 7.91 (d, J = 7.83 Hz, 1H) 7.71-7.78 (m, 1H) 7.60-7.68 (m, 2H) 7.32 (d, J = 8.22 Hz, 1H) 6.89 (d, J = 1.17 Hz, 1H) 6.46 (d, J = 1.17 Hz, 1H) 5.07 (d, J = 6.65 Hz, 2H) 4.83 (d, J = 7.04 Hz, 2H) 3.75-3.82 (m, 2H) 3.55-3.62 (m, 2H) 2.30 (s, 3H). LCMS (m/z) (M + H) = 488.0, Rt = 0.76 min. |
| 301 | 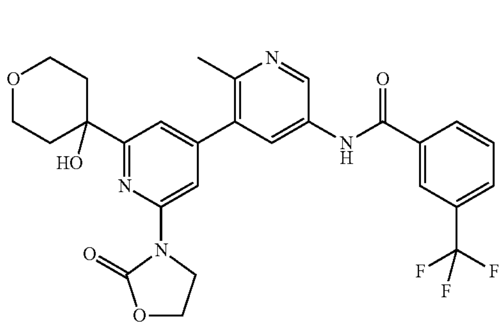 [SMILES: Cc1ncc(NC(=O)c2cccc(C(F)(F)F)c2)cc1-c1cc(N2CCOC2=O)nc(C2(O)CCOCC2)c1] | N-(2'-(4-hydroxytetrahydro-2H-pyran-4-yl)-2-methyl-6'-(2-oxooxazolidin-3-yl)-[3,4'-bipyridin]-5-yl)-3-(trifluoromethyl)benzamide | $^1$H NMR (500 MHz, Methanol-d4) δ 9.24 (d, J = 2.35 Hz, 1H) 8.43 (d, J = 2.35 Hz, 1H) 8.36 (s, 1H) 8.29 (d, J = 7.82 Hz, 1H) 8.17 (d, J = 1.57 Hz, 2H) 7.97 (d, J = 7.83 Hz, 1H) 7.76-7.83 (m, 1H) 7.53 (d, J = 1.57 Hz, 1H) 4.55-4.63 (m, 2H) 4.37-4.45 (m, 2H) 3.93-4.03 (m, 2H) 3.87-3.93 (m, 2H) 2.64 (s, 3H) 2.46 (td, J = 12.91, 4.70 Hz, 2H) 1.66 (d, J = 11.74 Hz, 2H). LC-MS: Rt-0.75, Mass-543.1 |

TABLE 4-continued

| Example | Structure | Name | Physical Data |
|---|---|---|---|
| 302 | 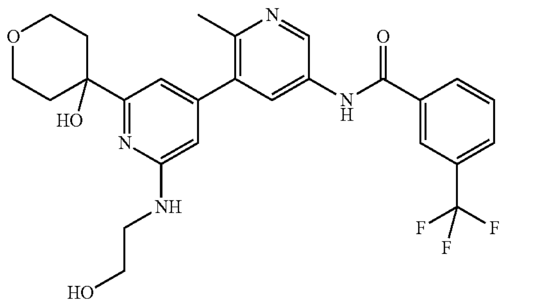 [SMILES: Cc1ncc(NC(=O)c2cccc(C(F)(F)F)c2)cc1-c1cc(NCCO)nc(C2(O)CCOCC2)c1] | N-(2'-((2-hydroxyethyl)amino)-6'-(4-hydroxytetrahydro-2H-pyran-4-yl)-2-methyl-[3,4'-bipyridin]-5-yl)-3-(trifluoromethyl)benzamide | $^1$H NMR (500 MHz, Methanol-d4) δ 8.84 (d, J = 2.35 Hz, 1H) 8.32 (s, 1H) 8.26 (d, J = 7.82 Hz, 1H) 8.14 (d, J = 2.35 Hz, 1H) 7.94 (dd, J = 7.83, 0.78 Hz, 1H) 7.73-7.81 (m, 1H) 6.83 (d, J = 1.17 Hz, 1H) 6.43 (d, J = 1.17 Hz, 1H) 3.91-4.00 (m, 2H) 3.84-3.91 (m, 2H) 3.75-3.81 (m, 2H) 3.53-3.61 (m, 2H) 2.51 (s, 3H) 2.33-2.45 (m, 2H) 1.60 (d, J = 12.13 Hz, 2H). LC-MS: Rt-0.60, Mass-517.1 |
| 303 | 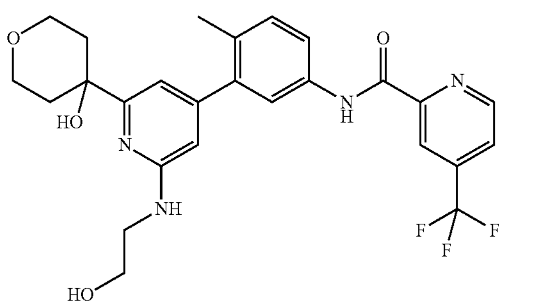 [SMILES: Cc1ccc(NC(=O)c2cc(C(F)(F)F)ccn2)cc1-c1cc(NCCO)nc(C2(O)CCOCC2)c1] | N-(3-(2-((2-hydroxyethyl)amino)-6-(4-hydroxytetrahydro-2H-pyran-4-yl)pyridin-4-yl)-4-methylphenyl)-4-(trifluoromethyl)picolinamide | $^1$H NMR (500 MHz, Methanol-d4) δ 8.98 (d, J = 4.69 Hz, 1H) 8.45 (d, J = 0.78 Hz, 1H) 7.94 (dd, J = 5.09, 1.17 Hz, 1H) 7.71-7.76 (m, 2H) 7.33 (d, J = 9.39 Hz, 1H) 6.80 (d, J = 1.17 Hz, 1H) 6.40 (d, J = 1.17 Hz, 1H) 3.91-4.01 (m, 2H) 3.84-3.91 (m, 2H) 3.78 (t, J = 5.67 Hz, 2H) 3.53-3.60 (m, 2H) 2.31-2.42 (m, 2H) 2.29 (s, 3H) 1.60 (d, J = 12.13 Hz, 2H). LC-MS: Rt-0.77, Mass-517.0 |
| 304 | 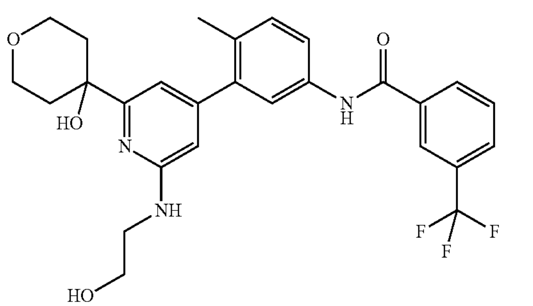 [SMILES: Cc1ccc(NC(=O)c2cccc(C(F)(F)F)c2)cc1-c1cc(NCCO)nc(C2(O)CCOCC2)c1] | N-(3-(2-((2-hydroxyethyl)amino)-6-(4-hydroxytetrahydro-2H-pyran-4-yl)pyridin-4-yl)-4-methylphenyl)-3-(trifluoromethyl)benzamide | $^1$H NMR (500 MHz, Methanol-d4) δ 8.27 (s, 1H) 8.22 (d, J = 7.83 Hz, 1H) 7.91 (d, J = 7.83 Hz, 1H) 7.71-7.78 (m, 1H) 7.60-7.66 (m, 2H) 7.31 (d, J = 8.22 Hz, 1H) 6.79 (d, J = 1.17 Hz, 1H) 6.40 (d, J = 1.17 Hz, 1H) 3.91-4.00 (m, 2H) 3.83-3.90 (m, 2H) 3.77 (t, J = 5.67 Hz, 2H) 3.51-3.59 (m, 2H) 2.36 (td, J = 12.91, 5.09 Hz, 2H) 2.29 (s, 3H) 1.60 (d, J = 11.74 Hz, 2H). LC-MS: Rt-0.78, Mass-516.1 |
| 305 | 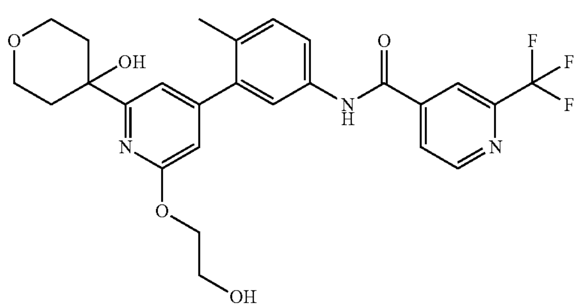 [SMILES: Cc1ccc(NC(=O)c2ccnc(C(F)(F)F)c2)cc1-c1cc(OCCO)nc(C2(O)CCOCC2)c1] | N-(3-(2-(2-hydroxyethoxy)-6-(4-hydroxytetrahydro-2H-pyran-4-yl)pyridin-4-yl)-4-methylphenyl)-2-(trifluoromethyl)isonicotinamide | $^1$H NMR (400 MHz, Methanol-d4) δ 0.07 (d, J = 12.52 Hz, 2H) 0.73 (s, 3H) 0.87 (td, J = 12.89, 5.23 Hz, 2H) 2.26-2.45 (m, 6H) 2.89-2.96 (m, 2H) 5.12 (s, 1H) 5.67 (s, 1H) 5.79 (d, J = 8.22 Hz, 1H) 6.06-6.16 (m, 2H) 6.57 (d, J = 5.09 Hz, 1H) 6.75 (s, 1H) 7.36 (d, J = 5.04 Hz, 1H). LC-MS: Rt-0.81, Mass-518.3 |
| 306 | 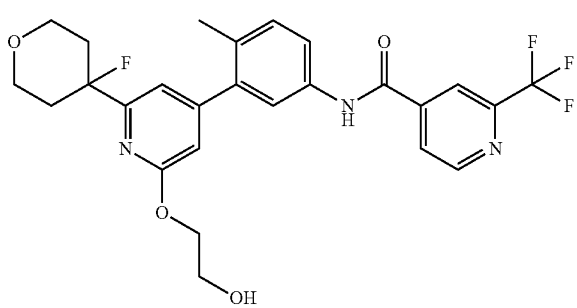 [SMILES: Cc1ccc(NC(=O)c2ccnc(C(F)(F)F)c2)cc1-c1cc(OCCO)nc(C2(F)CCOCC2)c1] | N-(3-(2-(4-fluorotetrahydro-2H-pyran-4-yl)-6-(2-hydroxyethoxy)pyridin-4-yl)-4-methylphenyl)-2-(trifluoromethyl)isonicotinamide | $^1$H NMR (400 MHz, Methanol-d4) δ 0.30 (t, J = 12.28 Hz, 2H) 0.72 (s, 3H) 0.88 (td, J = 13.38, 5.48 Hz, 1H) 0.98 (td, J = 13.39, 5.50 Hz, 1H) 2.25-2.34 (m, 2H) 2.34-2.45 (m, 4H) 2.83-2.95 (m, 2H) 5.19 (s, 1H) 5.59 (s, 1H) 5.80 (d, J = 8.31 Hz, 1H) 6.10 (d, J = 2.10 Hz, 1H) 6.15 (dd, J = 8.24, 2.18 Hz, 1H) 6.58 (d, J = 4.45 Hz, 1H) 6.76 (s, 1H) 7.36 (d, J = 5.04 Hz, 1H). LC-MS: Rt-0.97, Mass-520.3 |

Example 307

N-(3-(6-((2-methoxyethyl)amino)-5-(tetrahydro-2H-pyran-4-yl)pyridazin-3-yl)-4-methylphenyl)-2-(trifluoromethyl)isonicotinamide

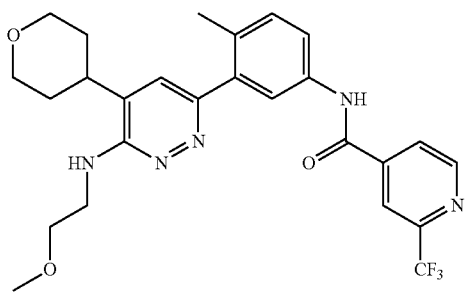 [SMILES: COCCNc1nnc(-c2cc(NC(=O)c3ccnc(C(F)(F)F)c3)ccc2C)cc1C1CCOCC1]

A vial was charged with N-(3-(6-chloro-5-(tetrahydro-2H-pyran-4-yl)pyridazin-3-yl)-4-methylphenyl)-2-(trifluoromethyl)isonicotinamide (1 equiv), 2-methoxyethylamine (1.2 equiv) and 1,4-Dioxane (0.15 M). The vial was purged with nitrogen and then BrettPhos (0.1 equiv), BrettPhos pre catalyst (0.1 equiv) and sodium tert-butoxide (3 equiv) were added. The reaction was heated overnight at 90° C. The reaction mixture was allowed to cool to room temperature, and was partitioned between EtOAc and water. The aqueous layer was washed with EtOAc and the combined organics were washed with brine, dried over magnesium sulfate, filtered and concentrated. The resulting material was dissolved in MeOH/DMSO (1:1), filtered through a 0.5 micron filter, and purified by reverse-phase HPLC (acidic). Fractions containing desired product were combined and lyophilized to give N-(3-(6-((2-methoxyethyl)amino)-5-(tetrahydro-2H-pyran-4-yl)pyridazin-3-yl)-4-methylphenyl)-2-(trifluoromethyl)isonicotinamide (4% yield). $^1$H NMR (400 MHz. DMSO-4) S ppm 10.79 (s, 1H), 9.00 (d. J=5.0 Hz, 1H), 8.37 (s, 1H), 8.21 (d. J=4.9 Hz, 1H), 7.90 (s, 1H), 7.78 (dd, J=8.3, 2.1 Hz, 1H), 7.62 (s, 1H), 7.39 (d, J=8.4 Hz, 1H), 3.97 (dd, J=11.2, 2.6 Hz, 2H), 3.71 (m, 2H), 3.55 (m, 5H), 3.31 (s, 3H), 3.06 (m, 1H), 2.33 (s, 3H), 1.71 (m, 4H). LCMS (m/z) (M+H)=516.1, Rt=1.04 min.

Example 308

N-(3-(6-((2-hydroxyethyl(methyl)amino)-5-(tetrahydro-2H-pyran-4-yl)pyridazin-3-yl)-4-methylphenyl)-2-(trifluoromethyl)isonicotinamide

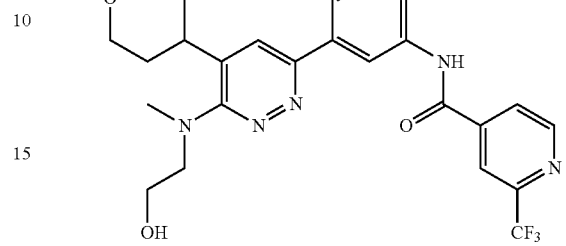

A vial was charged with N-(3-(6-chloro-5-(tetrahydro-2H-pyran-4-yl)pyridazin-3-yl)-4-methylphenyl)-2-(trifluoromethyl)isonicotinamide (1 equiv), 2-(methylamino)ethanol (1.2 equiv) and 1,4-Dioxane (0.15 M). The vial was purged with nitrogen and then RuPhos (0.1 equiv), RuPhos pre catalyst G2 (0.1 equiv) and sodium tert-butoxide (3 equiv) were added. The reaction was heated overnight at 90° C. The reaction mixture was allowed to cool to room temperature, and was partitioned between EtOAc and water. The aqueous layer was washed with EtOAc and the combined organics were washed with brine, dried over magnesium sulfate, filtered and concentrated. The resulting material was dissolved in MeOH/DMSO (1:1), filtered through a 0.5 micron filter, and purified by reverse-phase HPLC (acidic). Fractions containing desired product were combined and lyophilized to give N-(3-(6-((2-hydroxyethyl)(methyl)amino)-5-(tetrahydro-2H-pyran-4-yl)pyridazin-3-yl)-4-methylphenyl)-2-(trifluoromethyl)isonicotinamide (6.1% yield). $^1$H NMR (400 MHz, DMSO-d$_6$) δ ppm 10.76 (s, 1H), 9.00 (d, J=5.0 Hz, 1H), 8.37 (s, 1H), 8.20 (d. J=5.0 Hz, 1H), 7.89 (d, J=2.2 Hz, 1H), 7.76 (dd, J=8.3, 2.3 Hz, 1H), 7.66 (s, 1H), 7.39 (d, J=8.4 Hz, 1H), 4.79 (m, 2H), 3.99 (m, 2H), 3.17 (m, 1H), 2.71 (t, J=5.3 Hz, 3H), 2.30 (s, 3H), 1.74 (m, 4H). Signal for five aliphatic protons are hidden under solvent peaks. LCMS (m/z) (M+H)=516.3, Rt=0.98 min.

The compounds listed in Table 5, below, were prepared using methods similar to those described for the preparation of the above examples using the appropriate starting materials:

TABLE 5

| Example | Structure | Name | Physical Data |
|---|---|---|---|
| 309 | (structure) | (S)-N-(3-(6-((1-hydroxypropan-2-yl)amino)-5-(tetrahydro-2H-pyran-4-yl)pyridazin-3-yl)-4-methylphenyl)-2-(trifluoromethyl)isonicotinamide | $^1$H NMR (400 MHz, CD$_3$OD) δ ppm 8.91 (d, J = 5.0 Hz, 1H), 8.29 (s, 1H), 8.12 (d, J = 5.0 Hz, 1H), 7.88 (d, J = 2.2 Hz, 1H), 7.68 (m, 2H), 7.40 (d, J = 8.4 Hz, 1H), 4.79 (m, 1H), 4.65 (m, 1H), 4.08 (d, J = 11.2 Hz, 2H), 3.92 (td, J = 6.8, 3.9 Hz, 1H), 3.62 (td, J = 11.4, 3.3 Hz, 2H), 2.31 (s, 3H), 1.87 (m, 4H), 1.49 (d, J = 6.8 Hz, 3H). Signal for one aliphatic proton is hidden under solvent peak. Signals for exchangeable protons are not visible. LCMS (m/z) (M + H) = 516.1, Rt = 1.00 min. |

TABLE 5-continued

| Example | Structure | Name | Physical Data |
|---|---|---|---|
| 310 | 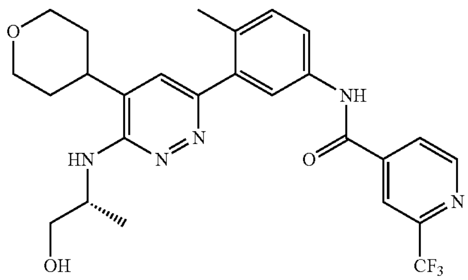 [SMILES: Cc1ccc(NC(=O)c2ccnc(C(F)(F)F)c2)cc1-c1cc(C2CCOCC2)c(N[C@H](C)CO)nn1] | (R)-N-(3-(6-((1-hydroxypropan-2-yl)amino)-5-(tetrahydro-2H-pyran-4-yl)pyridazin-3-yl)-4-methylphenyl)-2-(trifluoromethyl)isonicotinamide | $^1$H NMR (400 MHz, CD$_3$OD) δ ppm 8.91 (d, J = 5.0 Hz, 1H), 8.29 (s, 1H), 8.12 (d, J = 5.0 Hz, 1H), 7.88 (d, J = 2.3 Hz, 1H), 7.72-7.66 (m, 2H), 7.39 (d, J = 8.4 Hz, 1H), 4.79 (m, 1H), 4.65 (m, 1H), 4.08 (d, J = 11.3 Hz, 2H), 3.92 (m, 1H), 3.62 (td, J = 11.4, 3.3 Hz, 2H), 2.31 (s, 3H), 1.86 (m, 4H), 1.49 (d, J = 6.8 Hz, 3H). Signal for one aliphatic proton is hidden under solvent peak. Signals for exchangeable protons are not visible in MeOD. LCMS (m/z) (M + H) = 516.1, Rt = 1.00 min. |
| 311 | 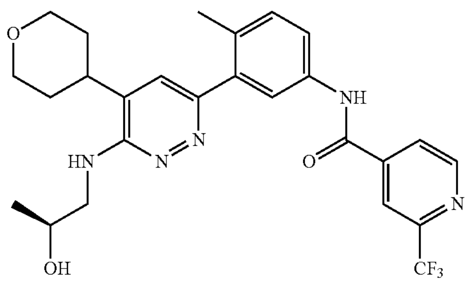 [SMILES: Cc1ccc(NC(=O)c2ccnc(C(F)(F)F)c2)cc1-c1cc(C2CCOCC2)c(NC[C@H](C)O)nn1] | (S)-N-(3-(6-((2-hydroxypropyl)amino)-5-(tetrahydro-2H-pyran-4-yl)pyridazin-3-yl)-4-methylphenyl)-2-(trifluoromethyl)isonicotinamide | $^1$H NMR (400 MHz, DMSO-d$_6$) ) δ ppm 10.80 (d, J = 28.0 Hz, 1H), 9.00 (dd, J = 4.8, 2.9 Hz, 1H), 8.37 (s, 1H), 8.21 (d, J = 4.9 Hz, 1H), 7.90 (d, J = 2.2 Hz, 1H), 7.78 (m, 2H), 7.41 (dd, J = 15.2, 8.5 Hz, 1H), 5.69 (m, 1H), 4.98 (m, 3H), 3.50 (m, 3H), 3.21 (m, 2H), 2.33 (s, 3H), 1.72 (m, 4H), 1.17 (d, J = 6.2 Hz, 3H). LCMS (m/z) (M + H) = 516.3, Rt = 0.99 min. |
| 312 | 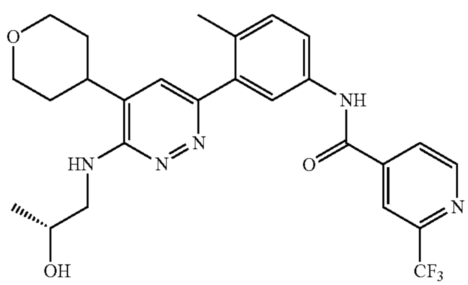 [SMILES: Cc1ccc(NC(=O)c2ccnc(C(F)(F)F)c2)cc1-c1cc(C2CCOCC2)c(NC[C@@H](C)O)nn1] | (R)-N-(3-(6-((2-hydroxypropyl)amino)-5-(tetrahydro-2H-pyran-4-yl)pyridazin-3-yl)-4-methylphenyl)-2-(trifluoromethyl)isonicotinamide | $^1$H NMR (400 MHz, DMSO-d$_6$) δ ppm 10.80 (d, J = 28.0 Hz, 1H), 9.00 (dd, J = 4.8, 2.9 Hz, 1H), 8.37 (s, 1H), 8.21 (d, J = 4.9 Hz, 1H), 7.93 (dd, J = 26.5, 2.1 Hz, 1H), 7.78 (m, 2H), 7.41 (dd, J = 15.0, 8.4 Hz, 1H), 5.69 (dq, J = 7.8, 3.7 Hz, 1H), 3.98 (m, 3H), 3.50 (m, 3H), 3.21 (m, 2H), 2.33 (s, 3H), 1.72 (m 4H), 1.17 (d, J = 4.0 Hz, 3H). Signal for one aliphatic proton is hidden under solvent peak. LCMS (m/z) (M + H) = 516.3, Rt = 0.99 min. |

Example 313

N-(4-methyl-3-(5-tetrahydro-2H-pyran-4-yl-6-((tetrahydro-2H-pyran-4-yl)oxy)pyridazin-3-yl)phenyl)-2-(trifluoromethyl)isonicotinamide

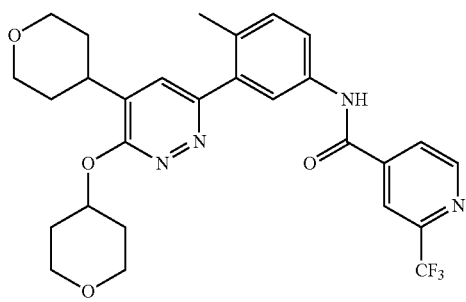 [SMILES: Cc1ccc(NC(=O)c2ccnc(C(F)(F)F)c2)cc1-c1cc(C2CCOCC2)c(OC2CCOCC2)nn1]

A solution of tetrahydro-4-pyranol (2 equiv) in THF (0.15 M) was cooled to 0° C., sodium hydride (2.5 equiv) was added and the reaction was stirred at 0° C. for 15 minutes. N-(3-(6-chloro-5-(tetrahydro-2H-pyran-4-yl)pyridazin-3-yl)-4-methylphenyl)-2-(trifluoromethyl)isonicotinamide (1 equiv) was added and the reaction was allowed to warm to room temperature and stirred overnight. The reaction was quenched with saturated sodium bicarbonate solution and was diluted with EtOAc and water. The aqueous phase was extracted with EtOAc, the combined organics were washed with brine, dried over magnesium sulfate, filtered and concentrated. The resulting material was dissolved in MeOH, filtered through a 0.5 micron filter, and purified by reverse-phase HPLC (basic). Fractions containing desired product were combined and lyophilized to give N-(4-methyl-3-(5-(tetrahydro-2H-pyran-4-yl)-6-((tetrahydro-2H-pyran-4-yl)oxy)pyridazin-3-yl)phenyl)-2-(trifluoromethyl)isonicotinamide (24.3% yield). $^1$H NMR (400 MHz, DMSO-4) δ ppm 10.73 (s, 1H), 9.00 (d, J=5.0 Hz, 1H), 8.38 (s, 1H), 8.21 (dd, J=4.9, 1.0 Hz, 1H), 7.84 (d. J=2.2 Hz, 1H), 7.80 (dd, J=8.2, 2.2 Hz, 1H), 7.58 (s, 1H), 7.37 (d. J=8.4 Hz, 1H), 5.54 (m, 1H), 3.98 (m, 2H), 3.88 (m, 2H), 3.61 (m, 2H), 3.48 (td, J=11.2, 3.1 Hz, 2H), 3.06 (m, 1H), 2.30 (s, 3H), 2.12 (m, 2H), 1.77 (m, 6H). LCMS (n z) (M+H)=543.1. Rt=1.40 min.

The compounds listed in Table 6, below, were prepared using methods similar to those described for the preparation of the above examples using the appropriate starting materials:

TABLE 6

| Example | Structure | Name | Physical Data |
|---|---|---|---|
| 314 | 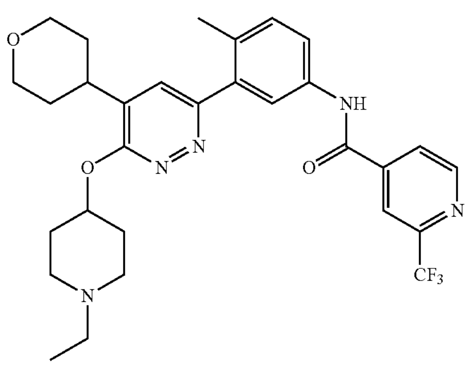 [SMILES: CCN1CCC(Oc2nnc(-c3cc(NC(=O)c4ccnc(C(F)(F)F)c4)ccc3C)cc2C2CCOCC2)CC1] | N-(3-(6-((1-ethylpiperidin-4-yl)oxy)-5-(tetrahydro-2H-pyran-4-yl)pyridazin-3-yl)-4-methylphenyl)-2-(trifluoromethyl)isonicotinamide | ¹H NMR (400 MHz, DMSO-d₆) δ ppm 10.73 (s, 1H), 9.00 (d, J = 5.0 Hz, 1H), 8.38 (s, 1H), 8.21 (d, J = 4.9 Hz, 1H), 7.84 (d, J = 2.0 Hz, 1H), 7.79 (dd, J = 8.3, 2.2 Hz, 1H), 7.58 (s, 1H), 7.37 (d, J = 8.4 Hz, 1H), 5.40 (s, 1H), 3.98 (m, 2H), 3.47 (td, J = 11.2, 3.1 Hz, 2H), 3.04 (dt, J = 10.1, 5.2 Hz, 1H), 2.70 (br s, 2H), 2.30 (s, 3H), 2.09 (br s, 2H), 1.76 (m, 6H), 1.06 (br s, 3H). Signal for four aliphatic are hidden under solvent peaks. LCMS (m/z) (M + H) = 570.4, Rt = 1.02 min. |
| 315 lp;2p | | N-(3-(6-(2-methoxyethoxy)-5-(tetrahydro-2H-pyran-4-yl)pyridazin-3-yl)-4-methylphenyl)-2-(trifluoromethyl)isonicotinamide | ¹H NMR (400 MHz, DMSO-d₆) δ ppm 10.73 (s, 1H), 9.00 (d, J = 5.0 Hz, 1H), 8.38 (s, 1H), 8.21 (d, J = 4.9 Hz, 1H), 7.84 (d, J = 2.1 Hz, 1H), 7.81 (dd, J = 8.2, 2.2 Hz, 1H), 7.59 (s, 1H), 7.37 (d, J = 8.3 Hz, 1H), 4.66 (m, 2H), 3.97 (m, 2H), 3.78 (m, 2H), 3.47 (td, J = 11.3, 2.7 Hz, 2H), 3.35 (s, 3H), 3.05 (m, 1H), 2.30 (s, 3H), 1.74 (m, 4H). LCMS (m/z) (M + H) = 517.0, Rt = 1.36 min. |
| 316 | 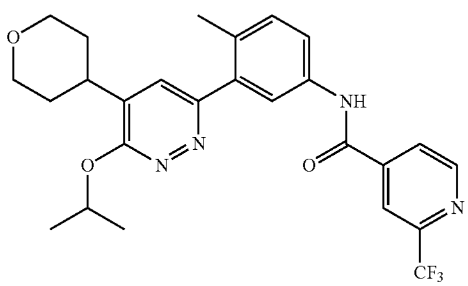 [SMILES: Cc1ccc(NC(=O)c2ccnc(C(F)(F)F)c2)cc1-c1cc(C2CCOCC2)c(OC(C)C)nn1] | N-(3-(6-isopropoxy-5-(tetrahydro-2H-pyran-4-yl)pyridazin-3-yl)-4-methylphenyl)-2-(trifluoromethyl)isonicotinamide | ¹H NMR (400 MHz, DMSO-d₆) δ ppm 10.73 (s, 1H), 9.00 (d, J = 5.0 Hz, 1H), 8.38 (s, 1H), 8.21 (m, 1H), 7.84 (d, J = 2.2 Hz, 1H), 7.80 (dd, J = 8.2, 2.3 Hz, 1H), 7.55 (s, 1H), 7.37 (d, J = 8.3 Hz, 1H), 5.56 (m, 1H), 3.97 (dd, J = 10.5, 2.7 Hz, 2H), 3.47 (td, J = 11.3, 3.0 Hz, 2H), 3.01 (m, 1H), 2.31 (s, 3H), 1.74 (m, 4H), 1.42 (s, 3H), 1.41 (s, 3H). LCMS (m/z) (M + H) = 501.3, Rt = 1.49 min. |

Example 317

N-(3-(6-ethoxy-5-(tetrahydro-2H-pyran-4-yl)pyridazin-3-yl)-4-methylphenyl)-4-(trifluoromethyl)picolinamide

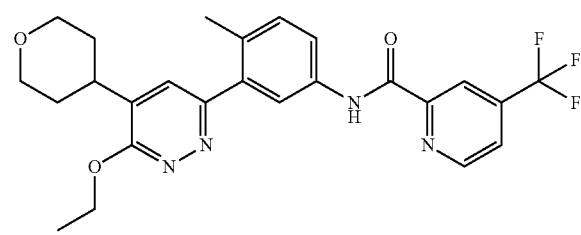 [SMILES: CCOc1nnc(-c2cc(NC(=O)c3cc(C(F)(F)F)ccn3)ccc2C)cc1C1CCOCC1]

A vial was charged with N-(3-(6-chloro-5-(tetrahydro-2H-pyran-4-yl)pyridazin-3-yl)-4-methylphenyl)-4-(trifluoromethyl)picolinamide (1 equiv), DMF (0.2 M), and sodium ethoxide 21% in ethanol (2.5 equiv). The vial was sealed and heated to 70° C. overnight. In the morning, the mixture was cooled, diluted with methanol, filtered through a 0.5 micron filter, and purified by reverse-phase HPLC (basic). Fractions containing desired product were combined and lyophilized to give N-(3-(6-ethoxy-5-(tetrahydro-2H-pyran-4-yl)pyridazin-3-yl)-4-methylphenyl)-4-(trifluoromethyl)picolinamide (12.74% yield). ¹H NMR (400 MHz, DMSO-d₆) δ ppm 10.84 (s, 1H) 9.04 (d, J=5.13 Hz, 1H) 8.30-8.40 (m, 1H) 8.04-8.14 (m, 1H) 7.99 (d, J=2.45 Hz, 1H) 7.94 (dd, J=8.31, 2.20 Hz, 1H) 7.58 (s, 1H) 7.35 (d, J=8.56 Hz, 1H) 4.59 (q, J=7.09 Hz, 2H) 3.90-4.02 (m, 2H) 3.48 (td, J=11.19, 3.30 Hz, 2H) 3.29 (s, 1H) 3.05 (td, J=10.39, 5.62 Hz, 1H) 2.31 (s, 3H) 1.67-1.80 (m, 3H) 1.44 (t, J=7.09 Hz, 3H). LCMS (m/z) (M+H)=487.1, Rt=1.52 min.

Example 318

1-(3,3-dimethylbutyl)-3-(3-(6-ethoxy-5-(tetrahydro-2H-pyran-4-yl)pyridazin-3-yl)-4-methylphenyl)urea

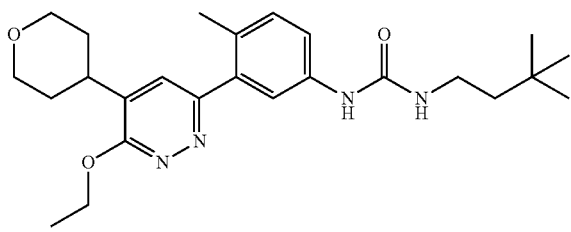 [SMILES: CCOc1nnc(-c2cc(NC(=O)NCCC(C)(C)C)ccc2C)cc1C1CCOCC1]

A vial was charged with 3-(6-ethoxy-5-(tetrahydro-2H-pyran-4-yl)pyridazin-3-yl)-4-methylaniline (1 equiv) and a 0.21M solution of I-isocyanato-3,3-dimethylbutane in DCM/toluene (3 equiv). The vial was sealed and heated to 50° C. for 3 days. After cooling, the mixture was diluted with MeOH and concentrated. The residue was taken up in MeOH and filtered through a 0.5 micron filter. The filtrate was purified by reverse-phase HPLC (basic method). Fractions containing the desired product were combined and lyophylized to give 1-(3,3-dimethylbutyl)-3-(3-(6-ethoxy-5-(tetrahydro-2H-pyran-4-yl)pyridazin-3-yl)-4-methylphenyl)urea (9.29% yield) as a white solid. $^1$H NMR (600 MHz, DMSO-$d_6$) δ ppm 8.40 (s, 1H) 7.49 (s, 1H) 7.44 (d, J=2.29 Hz, 1H) 7.35 (dd, J=8.30, 2.25 Hz, 1H) 7.16 (d, J=8.34 Hz, 1H) 5.99 (t, J=5.50 Hz, 1H) 4.57 (q, J=7.06 Hz, 2H) 3.95 (d, J=10.64 Hz, 2H) 3.46 (td, J=11.21, 2.98 Hz, 2H) 3.28 (s, 2H) 2.96-3.17 (m, 3H) 2.20 (s, 3H) 1.66-1.80 (m, 4H) 1.42 (t, J=6.97 Hz, 3H) 1.30-1.39 (m, 2H) 0.90 (s, 9H). LCMS (m/z) (M+H)=441.1. Rt=1.37 min.

Example 319

1-(3,3-dimethylbutyl)-3-(3-(2-(2-hydroxyethoxy)-6-(tetrahydro-2H-pyran-4-yl)pyridin-4-yl)-4-methylphenyl)urea

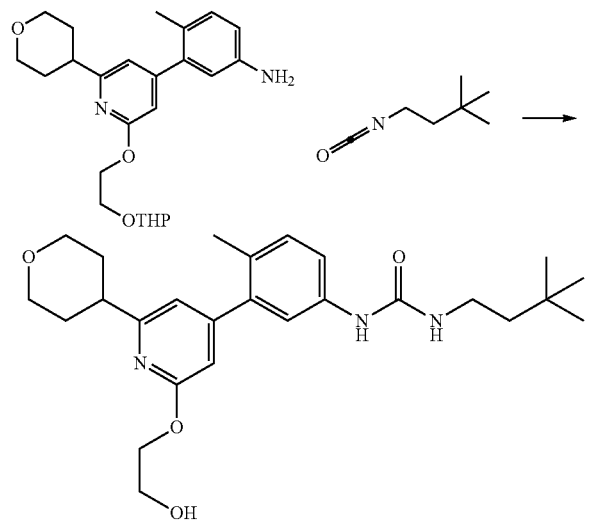

Into a 3-dram vial was added 4-methyl-3-(2-(2-((tetrahydro-2H-pyran-2-yl)oxy)ethoxy)-6-(tetrahydro-2H-pyran-4-yl)pyridin-4-yl)aniline (1.0 equiv.) and then 1-isocyanato-3,3-dimethylbutane (1.0 equiv.) and then DIEA (2.5 equiv.). The mixture was heated at 50° C. for 5 h and then the mixture was concentrated in vacuo and then treated with MeOH (0.05 M) and then 4N HCl in dioxane (40 equiv.). The mixture was agitated at room temperature for 30 min and concentrated in vacuo and the residue was purified by reverse-phase HPLC. The product fractions were combined and lyophillized to provide 1-(3,3-dimethylbutyl)-3-(3-(2-(2-hydroxyethoxy)-6-(tetrahydro-2H-pyran-4-yl)pyridin-4-yl)-4-methylphenyl)urea in 8.5% yield. 1H NMR (600 MHz, DMSO-d6) δ ppm 8.38 (s, 1H) 7.34 (d, J=2.20 Hz, 1H) 7.25 (dd, J=8.25, 2.29 Hz, 1H) 7.13 (d, J=8.34 Hz, 1H) 6.78 (d, J=0.73 Hz, 1H) 6.53 (d, J=1.01 Hz, 1H) 5.99 (t, J=5.59 Hz, 1H) 4.81 (br. s., 1H) 4.32 (t, J=5.23 Hz, 2H) 3.95 (dt, J=11.07, 2.95 Hz, 2H) 3.74 (d, J=4.77 Hz, 2H) 3.44 (ddd, J=1 1.21, 8.46, 6.10 Hz, 2H) 3.04-3.15 (m, 2H) 2.82-2.97 (m, 1H) 2.15 (s, 3H) 1.69-1.83 (m, 4H) 1.27-1.40 (m, 2H) 0.90 (s, 9H); LCMS (m/z) (M+H)=456.1, Rt=1.37 min.

Example 320

N-(3-(2-(4-amino-4-methylpiperidin-1-yl)-6-(tetrahydro-2H-pyran-4-yl)pyridin-4-yl-4-methylphenyl)-2-(trifluoromethyl)piperidine-4-carboxamide

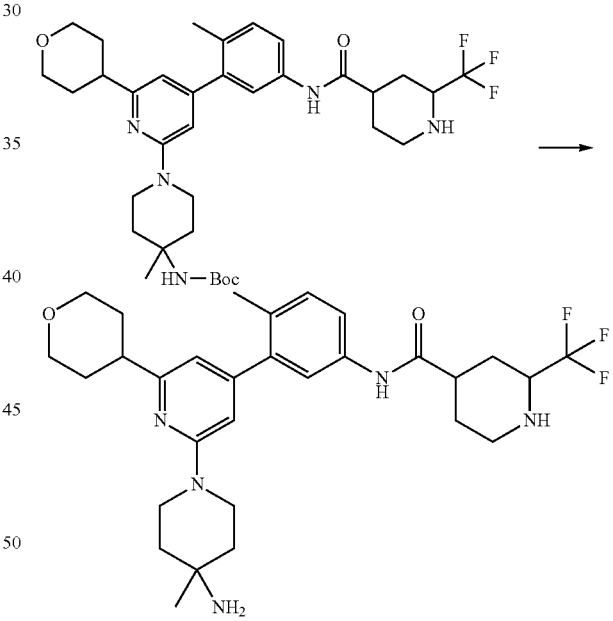

To tert-butyl (4-methyl-1-(4-(2-methyl-5-(2-(trifluoromethyl)piperidine-4-carboxamido)phenyl)-6-(tetrahydro-2H-pyran-4-yl)pyridin-2-yl)piperidin-4-yl)carbamate (1.0 equiv.) in DCM (0.06 M) was added TFA (25 equiv.) and stirred for 1.2 h. The reaction mixture was concentrated to dryness and purified via reverse phase prep-HPLC. The pure fractions were lyophilized to give the desired final product, N-(3-(2-(4-amino-4-methylpiperidin-1-yl)-6-(tetrahydro-2H-pyran-4-yl)pyridin-4-yl)-4-methylphenyl)-2-(trifluoromethyl)piperidine-4-carboxamide as a TFA salt (23.7%). $^1$H NMR (600 MHz, DMSO-d6) δ 10.15 (s, 1H), 7.91 (s, 2H), 7.51 (d, J=2.2 Hz, 1H), 7.46 (dd, J=8.2, 2.3 Hz, 1H), 7.24 (d, J=8.3 Hz, 1H), 6.60 (s, 1H), 6.47 (s, 1H), 4.08 (dt, J=13.7, 4.5 Hz, 2H), 3.95 (dt, J=11.3, 3.4 Hz, 2H), 3.25 (ddd, J=13.7, 9.3, 4.1 Hz, 3H), 3.09 (td, J=13.5, 12.9, 6.9 Hz, 1H), 2.85-2.70 (m, 2H), 2.18 (s, 4H), 2.07-2.01 (m, 1H), 1.83-1.65 (m, 10H), 1.37 (s, 3H); LCMS (m/z) (M+H)=560.4. Rt=0.70 min.

Example 321

N-(3-(2-(4-amino-4-methylpiperidin-1-yl)-6-(tetrahydro-2H-pyran-4-yl)pyridin-4-yl)-4-methylphenyl)-2-(trifluoromethyl)isonicotinamide

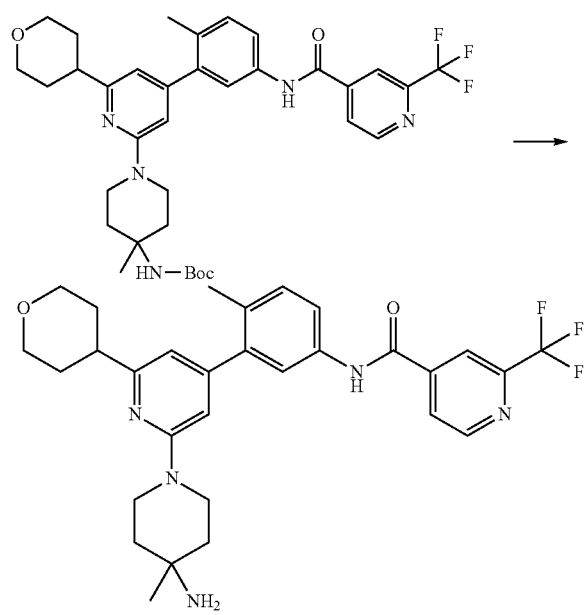

To tert-butyl (4-methyl-1-(4-(2-methyl-5-(2-(trifluoromethyl)isonicotinamido)phenyl)-6-(tetrahydro-2H-pyran-4-yl)pyridin-2-yl)piperidin-4-yl)carbamate (1.0 equiv.) in DCM (0.08 M) was added TFA (25 equiv.) and stirred for 1.2 h. The reaction mixture was concentrated to dryness and purified via reverse phase prep-HPLC. The pure fractions were lyophilized to give the desired final product, N-(3-(2-(4-amino-4-methylpiperidin-1-yl)-6-(tetrahydro-2H-pyran-4-yl)pyridin-4-yl)-4-methylphenyl)-2-(trifluoromethyl)isonicotinamide as a TFA salt (10.5%). $^1$H NMR (400 MHz, Methanol-d4) δ 8.91 (d, J=5.1 Hz, 1H), 8.31-8.26 (m, 1H), 8.14-8.08 (m, 1H), 7.73 (d, J=2.4 Hz, 1H), 7.57 (dd, J=8.2, 2.3 Hz, 1H), 7.33 (d, J=8.4 Hz, 1H), 6.78 (s, 1H), 6.67 (d, J=1.3 Hz, 1H), 4.17 (dt, J=13.9, 4.6 Hz, 2H), 4.09-4.02 (m, 2H), 3.57 (td, J=11.6, 2.7 Hz, 2H), 3.43-3.36 (m, 2H), 2.99-2.89 (m, 1H), 2.28 (s, 3H), 2.00-1.82 (m, 8H), 1.50 (s, 3H); LCMS (m/z) (M+H)=554.3, Rt=0.97 min.

Assays

The activity of a compound according to the present invention can be assessed by well-known in vitro & in vivo methods. Raf inhibition data provided herein was obtained using the following procedures.

In Vitro Raf Activity Determination: The RAF enzymes and the catalytically inactive MEK1 protein substrate were all made in-house using conventional methods. CRAF cDNA was subcloned as full length protein, with Y340E and Y341E activating mutations, into a baculovirus expression vector for Sf9 insect cell expression. h14-3-3 zeta cDNA was subcloned into a baculovirus expression vector for SF9 insect cell expression. Sf9 cells co-expressing both proteins were lysed and subjected to immobilized nickel chromatography and eluted with Imidazole. A second column (StrepII binding column) was used and eluted with desthiobiotin. Protein Tags were removed using Prescission enzyme and the protein was further purified using a flowthrough step to remove tags.

C-Raf TR refers to a truncated C-Raf protein, a Δ1-324 deletion mutant. C-Raf FL refers to the full-length C-Raf protein.

Full length MEK1 with an inactivating K97R ATP binding site mutation is utilized as a RAF substrate. The MEK1 cDNA was subcloned with an N-terminal (his)$_6$ tag into a vector for E. Coli expression. The MEK1 substrate was purified from E. Coli lysate by nickel affinity chromatography followed by anion exchange. The final MEK1 preparation was biotinylated (Pierce EZ-Link Sulfo-NHS-LC-Biotin) and concentrated.

Assay Materials: Assay buffer is 50 mM Tris, pH 7.5, 15 mM MgCl$_2$, 0.01% Bovine Serum Albumin (BSA) and 1 mM dithiothreitol (DTT); Stop buffer is 60 mM ethylenediaminetetraacetic acid (EDTA) and 0.01% Tween® 20: b-Raf (V600E), active; biotinylated Mek, kinase dead; Alpha Screen detection kit (available from PerkinElmer™, #6760617R); Anti phospho-MEK1/2 (available from Cell Signaling Technology, Inc. #9121); 384 well low volume assay plates (White Greiner® plates).

Assay conditions: b-Raf (V600E) approximately 4 μM; c-Raf approximately 4 nM; biotinylated Mek, kinase dead approximately 10 nM; ATP 10 μM for BRAF (V600E) and 1 μM for CRAF; Pre-incubation time with compounds 60 minutes at room temperature; Reaction time 1 or 3 hours at room temperature.

Assay protocol: Raf and biotinylated Mek (kinase dead) were combined at 2× final concentrations in assay buffer (50 mM Tris, pH 7.5, 15 mM MgCl$_2$, 0.01% BSA and 1 mM DTT) and dispensed 5 ml per well in assay plates (Greiner white 384 well assay plates #781207) containing 0.25 ml of 40× of a Raf kinase inhibitor test compound diluted in 100% DMSO. The plate was incubated for 60 minutes at room temperature. The Raf kinase activity reaction was started by the addition of 5 mL per well of 2×ATP diluted in assay buffer. After 3 hours (b-Raf(V600E)) or 1 hour (c-Raf). The reactions were stopped and the phosphorylated product was measured using a rabbit anti-p-MEK (Cell Signaling, #9121) antibody and the Alpha Screen IgG (ProteinA) detection Kit (PerkinElmer #6760617R), by the addition of 10 mL to the well of a mixture of the antibody (1:2000 dilution) and detection beads (1:2000 dilution of both beads) in Stop/bead buffer (25 mM EDTA, 50 mM Tris, pH 7.5, 0.01% Tween20). The additions were carried out under dark conditions to protect the detection beads from light. A lid was placed on top of the plate and incubated for 1 hour at room temperature, after which the luminescence was read on a PerkinElmer Envision instrument. The concentration of each compound for 50% inhibition (IC$_{50}$) was calculated by non-linear regression using XL Fit data analysis software.

Using the assays described above, compounds of the invention exhibit inhibitory efficacy for C-Raf and B-Raf. Table 7 details IC50 data for compounds of the invention.

TABLE 7

| Example No. | C-RAF IC50 mM | B-RAF IC50 mM |
|---|---|---|
| 1 | 0.001 | |
| 2 | 0.0007 | |
| 3 | 0.0005 | |
| 4 | 0.003 | |
| 5 | 0.002 | |
| 6 | 0.0003 | |
| 7 | 0.001 | |
| 8 | 0.001 | |
| 9 | 0.0003 | |
| 10 | 0.002 | |
| 11 | 0.0006 | |
| 12 | 0.002 | |
| 13 | 0.001 | |
| 14 | 0.0002 | |
| 15 | 0.001 | |
| 16 | 0.0004 | |
| 17 | 0.0007 | |
| 18 | 0.0006 | |
| 19 | 0.007 | |
| 20 | 6.28E−04 | 0.006883 |
| 21 | 3.73E−04 | 0.002728 |
| 22 | 5.95E−04 | 0.003764 |
| 23 | 25.00034 | 25.00034 |
| 24 | 4.55E−04 | 0.003521 |
| 25 | 1.54E−04 | 8.70E−04 |
| 26 | 3.72E−04 | 0.002298 |
| 27 | 0.26295128 | 1.210945 |
| 28 | 25.00034 | 25.00034 |
| 29 | 6.37E−04 | 0.004947 |
| 30 | 2.29E−04 | 0.001297 |
| 31 | 1.57E−04 | 4.46E−04 |
| 32 | 0.0003 | |
| 33 | 8.04E−04 | 0.002136 |
| 34 | 0.007627214 | 0.02048 |
| 35 | 2.97E−04 | 9.66E−04 |
| 36 | 0.001837686 | 0.011992 |
| 37 | 3.54E−04 | 0.001851 |
| 38 | 7.29E−04 | 0.004838 |
| 39 | 0.001173856 | 0.0059 |
| 40 | 0.003471606 | |
| 41 | 2.45E−04 | |
| 42 | 2.43E−04 | 0.001421 |
| 43 | 0.002672463 | 0.010228 |
| 44 | 0.008628467 | 0.067935 |
| 45 | 0.12057872 | 1.178656 |
| 46 | 0.05153823 | |
| 47 | 0.004347837 | |
| 48 | 0.0075267 | |
| 49 | 1.18E−04 | 4.69E−04 |
| 50 | 0.003289763 | |
| 51 | 0.002792441 | |
| 52 | 0.002148435 | |
| 53 | 6.24E−04 | |
| 54 | 2.11E−04 | |
| 55 | 7.47E−05 | |
| 56 | 2.81E−04 | |
| 57 | 1.49E−04 | |
| 58 | 1.55E−05 | |
| 59 | 1.03E−04 | |
| 60 | 2.03E−04 | |
| 61 | 0.001320694 | |
| 62 | 7.07E−04 | 0.003774 |
| 63 | 1.83E−04 | 6.13E−04 |
| 64 | 0.001180074 | 0.007124 |
| 65 | 0.001134928 | 0.007133 |
| 66 | 2.58E−04 | 0.001451 |
| 67 | 7.80E−05 | 3.04E−04 |
| 68 | 6.18E−04 | 0.003707 |
| 69 | 8.95E−04 | 0.005102 |
| 70 | 0.001590758 | 0.012935 |
| 71 | 3.51E−04 | 0.002838 |
| 72 | 0.00103504 | 0.004196 |
| 73 | 0.003092666 | 0.023382 |
| 74 | 3.60E−04 | 0.002066 |
| 75 | 0.006364049 | 0.076561 |
| 76 | 0.003926496 | 0.022782 |
| 77 | 0.003568822 | 0.02401 |
| 78 | 0.003230728 | 0.023498 |
| 79 | 4.93E−04 | 0.003999 |
| 80 | 0.002 | |
| 81 | 0.004848824 | 0.034902 |
| 82 | 0.001134069 | 0.003732 |
| 83 | 1.36E−05 | 5.93E−05 |
| 84 | 3.51E−04 | 0.002206 |
| 85 | 0.001173586 | 0.006473 |
| 86 | 0.002328187 | 0.014709 |
| 87 | 6.22E−04 | 0.003565 |
| 88 | 3.03E−04 | 9.34E−04 |
| 89 | 2.39E−04 | 0.001188 |
| 90 | 3.86E−04 | 0.003612 |
| 91 | 0.002391325 | 0.013035 |
| 92 | 3.33E−04 | 0.002202 |
| 93 | 0.001011737 | 0.008029 |
| 94 | 0.0042356 | 0.031774 |
| 95 | 5.14E−04 | 0.003921 |
| 96 | 4.82E−04 | 0.004165 |
| 97 | 0.001410454 | 0.010362 |
| 98 | 0.001106111 | 0.013061 |
| 99 | 4.15E−04 | 0.002665 |
| 100 | 3.00E−04 | 0.002203 |
| 101 | 0.001452945 | 0.006391 |
| 102 | 0.002677878 | 0.013153 |
| 103 | 8.44E−05 | 2.93E−04 |
| 104 | 1.28E−04 | 4.17E−04 |
| 105 | 9.15E−05 | 3.23E−04 |
| 106 | 1.46E−04 | 5.80E−04 |
| 107 | 7.25E−04 | 0.002964 |
| 108 | 4.24E−04 | 0.001803 |
| 109 | 0.002243914 | 0.0095 |
| 110 | 0.001518511 | 0.009983 |
| 111 | 7.16E−04 | 0.002746 |
| 112 | 2.25E−04 | 0.001214 |
| 113 | 9.00E−04 | 0.004745 |
| 114 | 0.003255496 | 0.017518 |
| 115 | 0.001055469 | 0.007008 |
| 116 | 0.00124781 | 0.006218 |
| 117 | 0.001425695 | 0.007191 |
| 118 | 5.62E−04 | 0.003894 |
| 119 | 1.76E−04 | 8.08E−04 |
| 120 | 0.002196845 | 0.010017 |
| 121 | 9.75E−04 | 0.00493 |
| 122 | 3.21E−04 | 0.001786 |
| 123 | 1.65E−04 | 0.001217 |
| 124 | 3.72E−04 | 0.002282 |
| 125 | | |
| 126 | 0.001965104 | 0.007736 |
| 127 | 9.87E−04 | 0.003152 |
| 128 | 6.33E−04 | 0.002146 |
| 129 | 0.00353637 | 0.023364 |
| 130 | 0.003088215 | 0.020064 |
| 131 | 3.10E−04 | 0.001299 |
| 132 | 8.53E−05 | |
| 133 | 0.00128187 | |
| 134 | 5.66E−04 | |
| 135 | 6.05E−04 | |
| 136 | 1.77E−04 | |
| 137 | 0.003319132 | |
| 138 | 0.002186751 | |
| 139 | 0.001181827 | |
| 140 | 0.008087768 | |
| 141 | 0.005898516 | |
| 142 | 0.011195754 | |
| 143 | 0.004361611 | |
| 144 | 3.64E−04 | 0.00167 |
| 145 | 0.007290524 | 0.04926 |
| 146 | 8.01E−04 | 0.003311 |
| 147 | 0.004507341 | |
| 148 | 0.009200948 | |
| 149 | 8.71E−04 | |
| 150 | 0.003 | |
| 151 | | |
| 152 | 0.00008 | |
| 153 | 0.00004 | |
| 154 | 0.00004 | |

TABLE 7-continued

| Example No. | C-RAF IC50 mM | B-RAF IC50 mM |
|---|---|---|
| 155 | | |
| 156 | | |
| 157 | 0.0003 | |
| 158 | 0.0004 | |
| 159 | | |
| 160 | 0.0007 | |
| 161 | 0.002 | |
| 162 | 0.001 | |
| 163 | 0.0003 | |
| 164 | 0.0004 | |
| 165 | 0.001 | |
| 166 | 0.002 | |
| 167 | 0.001 | |
| 168 | 0.0003 | |
| 169 | 0.002 | |
| 170 | 0.002 | |
| 171 | 0.001 | |
| 172 | 0.001991746 | |
| 173 | 3.83E−04 | |
| 174 | 3.31E−04 | |
| 175 | 8.30E−04 | |
| 176 | 6.84E−04 | |
| 177 | 6.21E−04 | |
| 178 | 1.36E−04 | |
| 179 | 7.95E−04 | |
| 180 | 2.97E−04 | |
| 181 | 3.93E−04 | |
| 182 | 9.51E−04 | |
| 183 | 0.001991746 | |
| 184 | 3.83E−04 | |
| 185 | 3.31E−04 | |
| 186 | 8.30E−04 | |
| 187 | 6.84E−04 | |
| 188 | 6.21E−04 | |
| 189 | 1.36E−04 | |
| 190 | 7.95E−04 | |
| 191 | 0.0001 | |
| 192 | 0.0003 | |
| 193 | 0.00002 | |
| 194 | 0.00007 | |
| 195 | 0.00003 | |
| 196 | 0.0004 | |
| 197 | 0.0004 | |
| 198 | 0.0002 | |
| 199 | 0.001 | |
| 200 | 0.0005 | |
| 201 | 0.0001 | |
| 202 | 0.0003 | |
| 203 | 0.0002 | |
| 204 | 0.00002 | |
| 205 | 0.0004 | |
| 206 | 0.0004 | |
| 207 | 0.0001 | |
| 208 | 0.0005 | |
| 209 | 0.0002 | |
| 210 | 0.0003 | |
| 211 | 0.0003 | |
| 212 | 0.00008 | |
| 213 | 0.0002 | |
| 214 | 0.0003 | |
| 215 | 0.0001 | |
| 216 | 0.0002 | |
| 217 | 0.0003 | |
| 218 | 0.0008 | |
| 219 | 0.0005 | |
| 220 | 0.0007 | |
| 221 | 0.002 | |
| 222 | 0.0004 | |
| 223 | 0.0006 | |
| 224 | 0.005 | |
| 225 | 0.00002 | |
| 226 | 0.004 | |
| 227 | 0.0002 | |
| 228 | 0.00006 | |
| 229 | 0.0007 | |
| 230 | 0.011 | |
| 231 | 0.0002 | |
| 232 | 0.00003 | |
| 233 | 0.002 | |
| 234 | 0.00008 | |
| 235 | NA | |
| 236 | 0.0003 | |
| 237 | 0.0001 | |
| 238 | 0.00007 | |
| 239 | 0.00004 | |
| 240 | 0.00004 | |
| 241 | 0.0001 | |
| 242 | 0.0001 | |
| 243 | 0.001 | |
| 244 | 0.003 | |
| 245 | 0.001 | |
| 246 | 0.006 | |
| 247 | 0.0004 | |
| 248 | 0.0007 | |
| 249 | | |
| 250 | 0.001 | |
| 251 | 0.001 | |
| 252 | 0.004 | |
| 253 | 0.0001 | |
| 254 | 0.0003 | |
| 255 | 0.0002 | |
| 256 | 0.0001 | |
| 257 | 0.001 | |
| 258 | 0.00002 | |
| 259 | 0.0003 | |
| 260 | 0.00008 | |
| 261 | 0.00003 | |
| 262 | 0.001 | |
| 263 | 0.0002 | |
| 264 | 0.0002 | |
| 265 | 0.0001 | |
| 266 | 0.002 | |
| 267 | 0.000005 | |
| 268 | 0.00002 | |
| 269 | 0.00003 | |
| 270 | 0.00009 | |
| 271 | 0.00002 | |
| 272 | 0.00005 | |
| 273 | 0.00001 | |
| 274 | 0.00003 | |
| 275 | 0.0002 | |
| 276 | 0.00006 | |
| 277 | 0.0002 | |
| 278 | 0.00005 | |
| 279 | 0.00007 | |
| 280 | 0.00007 | |
| 281 | 0.00005 | |
| 282 | 0.0003 | |
| 283 | 0.00007 | |
| 284 | 0.0002 | |
| 285 | 0.0009 | |
| 286 | 2.97E−04 | |
| 287 | 3.93E−04 | |
| 288 | 0.0006 | |
| 289 | 0.002 | |
| 290 | 0.002 | |
| 291 | 0.001 | |
| 292 | 0.009 | |
| 293 | 0.002 | |
| 294 | 0.002 | |
| 295 | 0.001 | |
| 296 | 0.004 | |
| 297 | 0.001 | |
| 298 | 0.002 | |
| 299 | 0.0001 | |
| 300 | 0.0001 | |
| 301 | 9.51E−04 | |
| 302 | 0.001527766 | |
| 303 | 0.001991746 | |
| 304 | 3.83E−04 | |
| 305 | 3.31E−04 | |
| 306 | 8.30E−04 | |
| 307 | 0.00008 | |
| 308 | 0.0005 | |

TABLE 7-continued

| Example No. | C-RAF IC50 mM | B-RAF IC50 mM |
|---|---|---|
| 309 | 0.00002 | |
| 310 | 0.00004 | |
| 311 | 0.00005 | |
| 312 | 0.0001 | |
| 313 | 0.00007 | |
| 314 | 0.00006 | |
| 315 | 0.0001 | |
| 316 | 0.0001 | |
| 317 | 0.0006 | |
| 318 | 0.0001 | |
| 319 | 0.0001 | |
| 320 | 0.35 | |
| 321 | 0.00009 | |

We claim:

1. A compound, or a pharmaceutically acceptable salt thereof, of formula I or II:

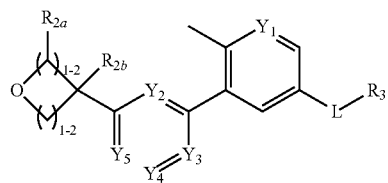

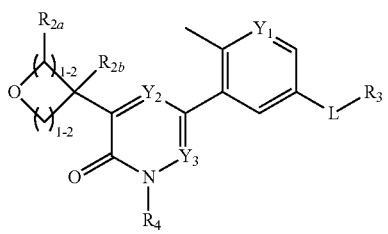

in which:

L is selected from NHC(O)— and —C(O)NH—;

$Y_1$ is selected from N and CH;

$Y_2$ is selected from N and CH;

$Y_3$ is selected from N and CH;

$Y_4$ is selected from N and $CR_8$; wherein $R_8$ is selected from H, hydroxy-ethoxy, 3-hydroxyoxetan-3-yl, 2,3-dihydroxypropoxy, bis(hydroxy-ethyl)-amino, 4-hydroxy-piperidin1-yl, hydroxy-ethyl-amino, 4-amino-4-methylpiperidin-1-yl, 2-oxooxazolidin-3-yl, methoxy and methyl;

$Y_5$ is selected from N and $CR_1$;

or $R_1$ and the nitrogen of $Y_4$ form a 5 member unsaturated ring containing and additional heteroatom selected from N, O and S;

or $R_1$ and $R_8$ together with the ring to which they are both attached form 2H-benzo[b][1,4]oxazin-3(4H)-one substituted with one to two $R_{20}$ groups independently selected from methyl and hydroxy-ethyl;

or $R_8$ and $Y_3$ together with the ring to which they are both attached form 1H-benzo[d]imidazole substituted with methyl;

$R_1$ is selected from H, ethoxy, isopropoxy, methoxy-ethyl-amino, (2-hydroxyethyl)(methyl)amino, (1-hydroxy-propan-2-yl)amino, methoxy-ethoxy, hydroxy-ethoxy, methoxy, (2-hydroxypropyl)amino, (tetrahydro-2H-pyran-4-yl)oxy, (tetrahydro-2H-pyran-4-yl)oxy, (1-eth-ylpiperidin-4-yl)oxy and pyrazolyl; wherein said pyrazolyl can be unsubstituted or substituted with 1 to 2 methyl groups; each $R_{2a}$ is independently selected from hydrogen and OH;

$R_{2b}$ is selected from H, methyl, halo, fluoro-methyl, hydroxy, hydroxymethyl, difluoromethyl, formyl, methoxy and cyano;

$R_3$ is selected from:

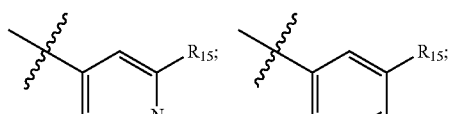

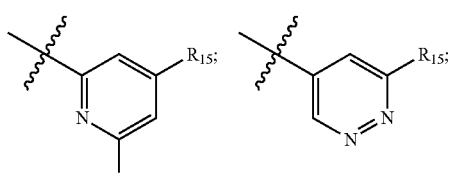

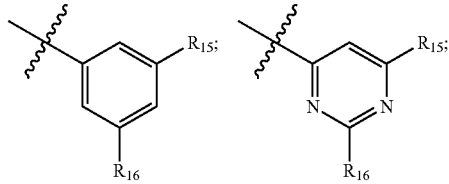

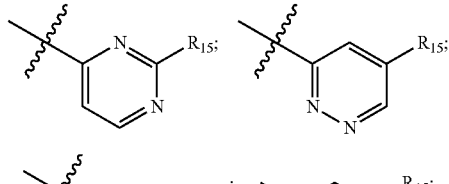

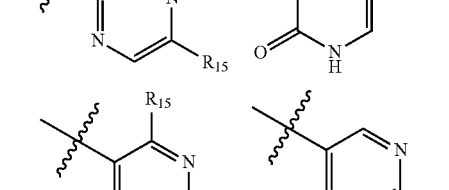

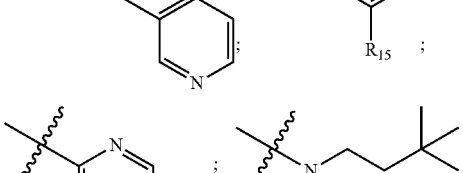

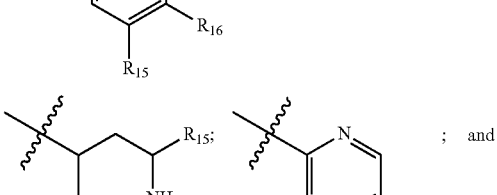

343

-continued

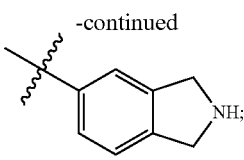

wherein

indicates the point of attachment with L;

R$_4$ is selected from H, methyl, hydroxy-ethyl, hydroxy-propyl and 2,3-dihydroxypropyl;

R$_{15}$ is selected from —CF$_3$, methoxy, —C(CH$_3$)$_2$F, —CF$_2$CH$_2$F, —C(CH$_3$)$_2$CN, —C(CH$_3$)F$_2$, —CHF$_2$, —C(CH$_3$)$_2$OH, t-butyl, 1-cyanocyclopropyl, 2-(trifluoromethyl)cyclopropyl, —C(F$_2$)C$_2$H$_5$, methyl-sulfonyl, 4-ethylpiperazin-1-yl, —C(CH$_3$)$_2$NH$_2$ and dimethyl-amino-methyl;

R$_{16}$ is selected from H, halo, hydroxy, dimethyl-amino, hydroxy-methyl, amino-methyl, —C(CH$_3$)$_2$NH$_2$ and —CF$_3$; or a pharmaceutically acceptable salt thereof; with the proviso that a compound of formula II is not 2-(2-cyanopropan-2-yl)-N-(4-methyl-3-(1-methyl-6-oxo-5-(tetrahydro-2H-pyran-4-yl)-1,6-dihydro-pyridazin-3-yl)phenyl)isonicotinamide or 2-(2-fluoropropan-2-yl)-N-(4-methyl-3-(1-methyl-6-oxo-5-(tetrahydro-2H-pyran-4-yl)-1,6-dihydropyridazin-3-yl)phenyl)isonicotinamide.

2. The compound of claim 1 of formula Ia:

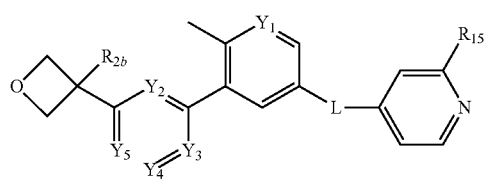

in which:

L is selected from —NHC(O)— and —C(O)NH—;
Y$_1$ is selected from N and CH;
Y$_2$ is selected from N and CH;
Y$_3$ is selected from N and CH;
Y$_4$ is selected from N and CR$_8$; wherein R$_8$ is selected from H, hydroxy-ethoxy, 3-hydroxyoxetan-3-yl, 2,3-dihydroxypropoxy, hydroxy-ethyl-amino, 4-amino-4-methylpiperidin-1-yl, 2-oxooxazolidin-3-yl, methoxy and methyl;
Y$_5$ is selected from N and CR$_1$;
R$_1$ is selected from H, ethoxy, hydroxy-ethoxy, methoxy, (tetrahydro-2H-pyran-4-yl)oxy and pyrazolyl; wherein said pyrazolyl can be unsubstituted or substituted with 1 to 2 methyl groups;
R$_{2b}$ is selected from H, methyl, halo, fluoro-methyl, hydroxy, difluoromethyl, formyl, methoxy and cyano;
R$_{15}$ is selected from —CF$_3$, methoxy, —C(CH$_3$)$_2$F, —CF$_2$CH$_2$F, —C(CH$_3$)$_2$CN, —C(CH$_3$)F$_2$, —CHF$_2$, —C(CH$_3$)$_2$OH, t-butyl, 1-cyanocyclopropyl, 2-(trifluoromethyl)cyclopropyl, —C(F$_2$)C$_2$H$_5$, methyl-sulfonyl,

344

4-ethylpiperazin-1-yl, —C(CH$_3$)$_2$NH$_2$ and dimethyl-amino-methyl; or a pharmaceutically acceptable salt thereof.

3. The compound of claim 2, or a pharmaceutically acceptable salt thereof, selected from:

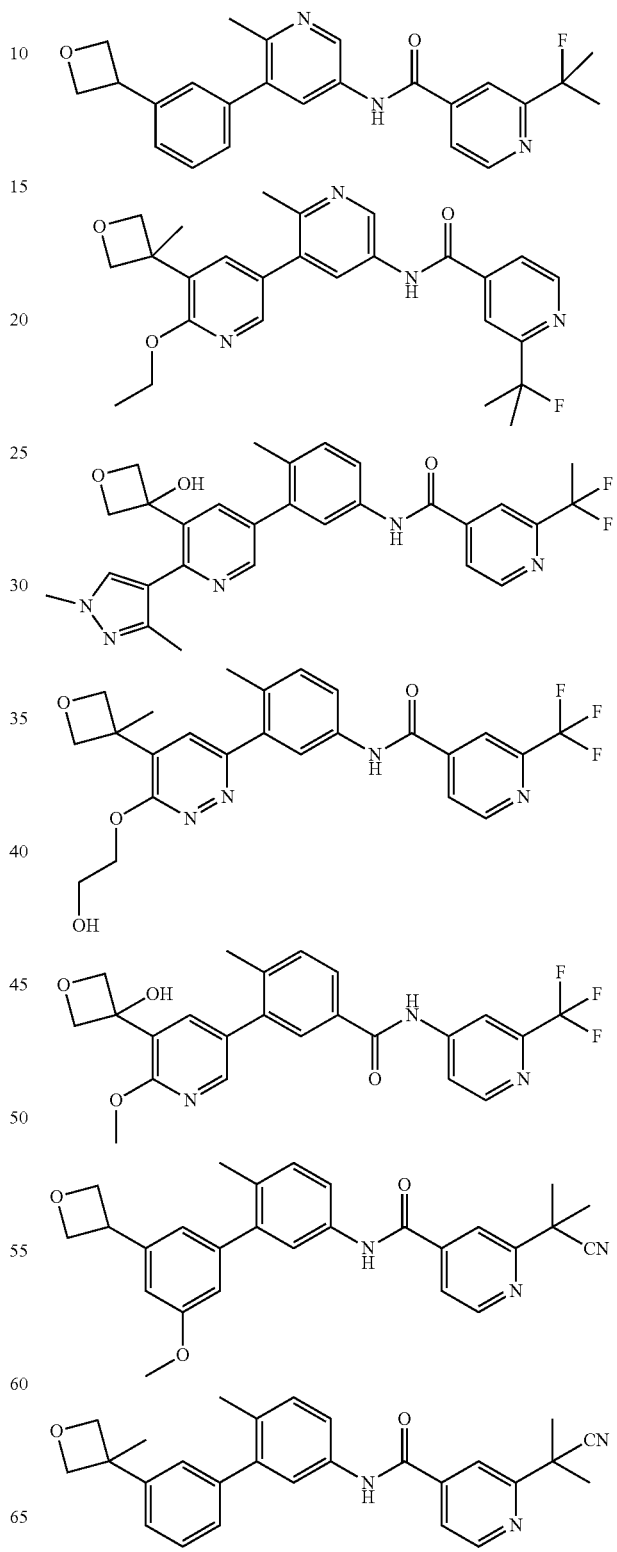

345
-continued
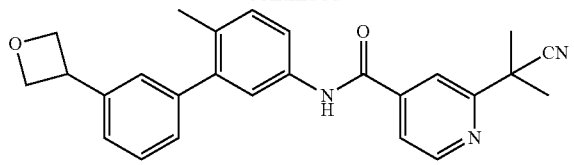
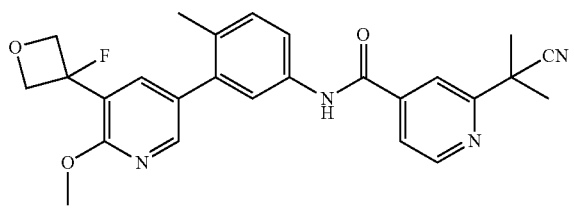
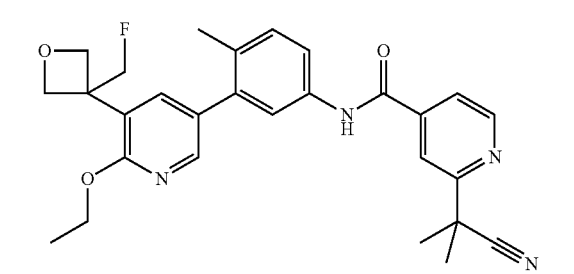
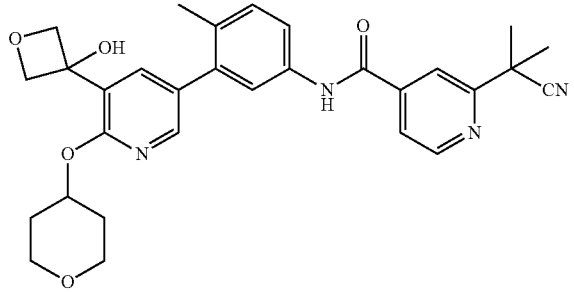
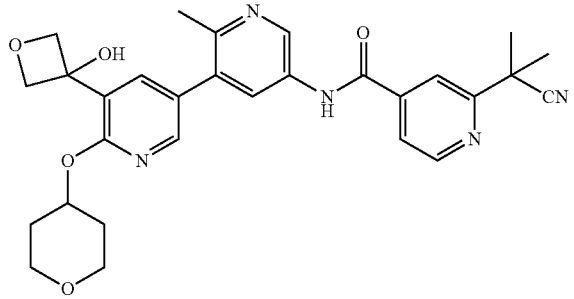
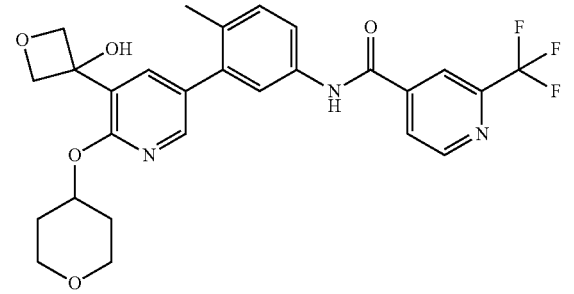
346
-continued
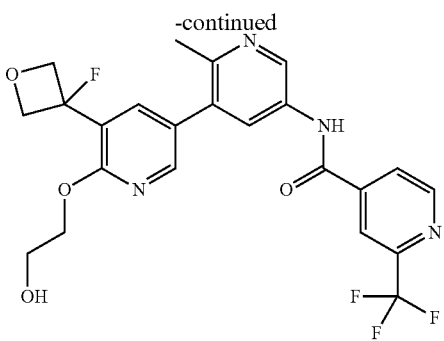
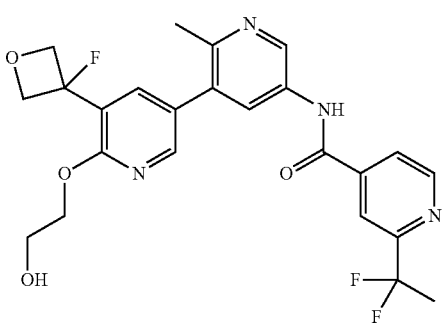
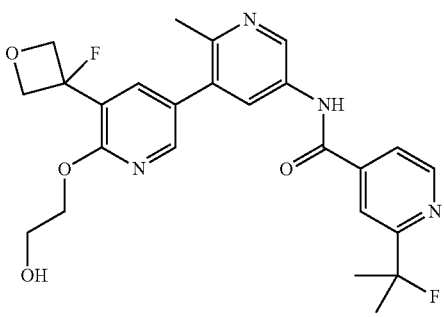
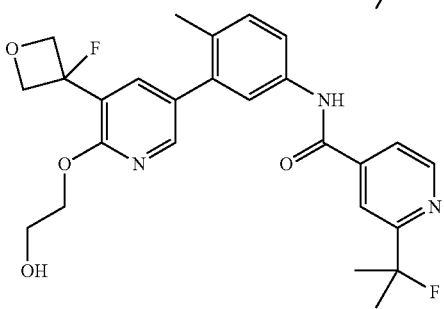
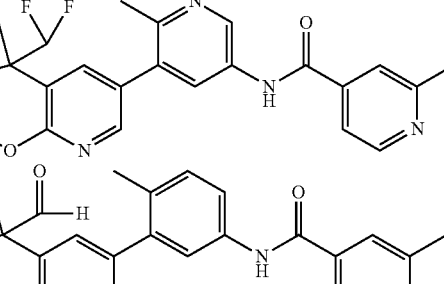
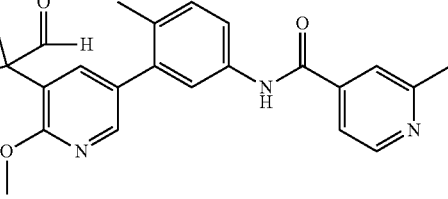

347
-continued
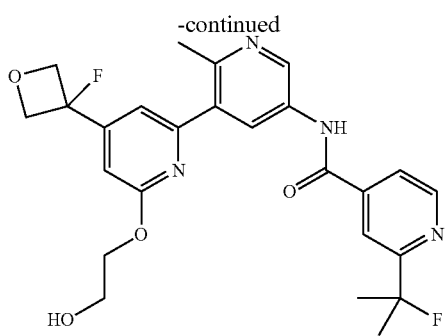
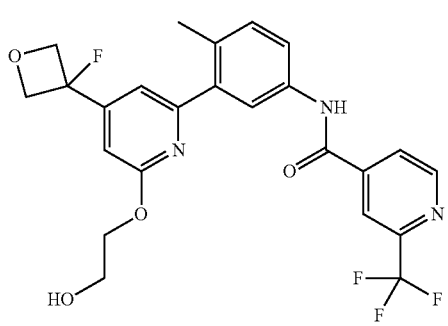
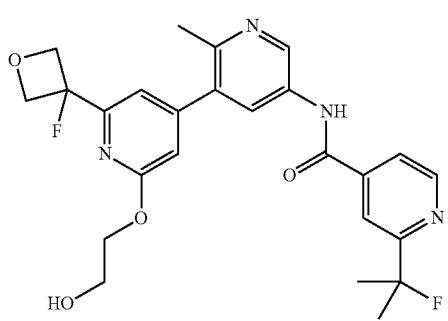
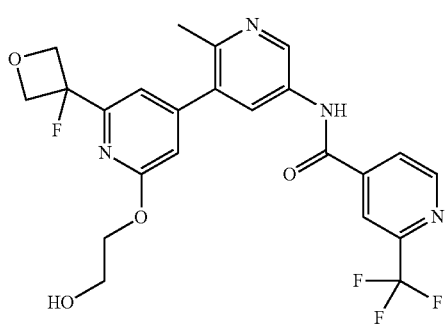
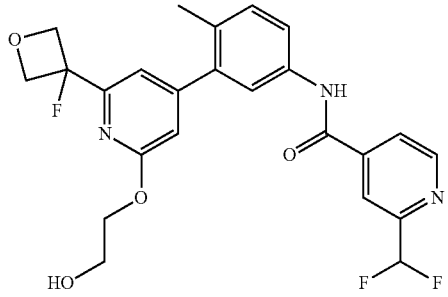
348
-continued
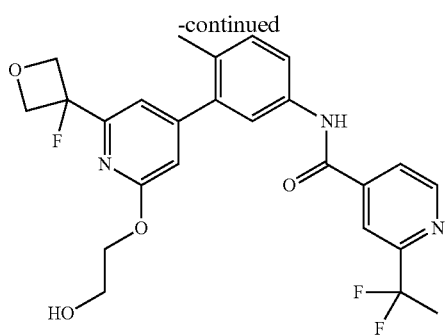
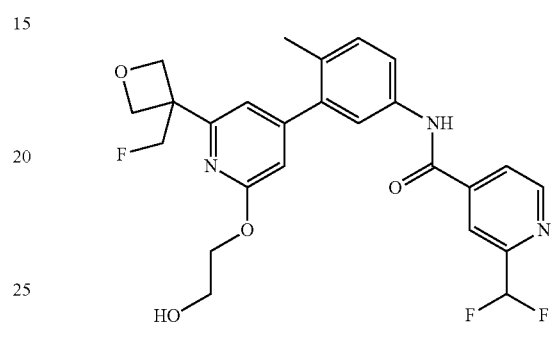
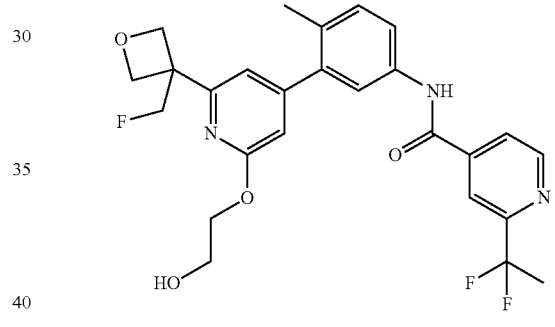
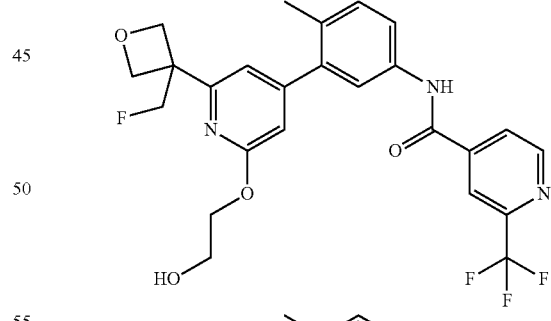
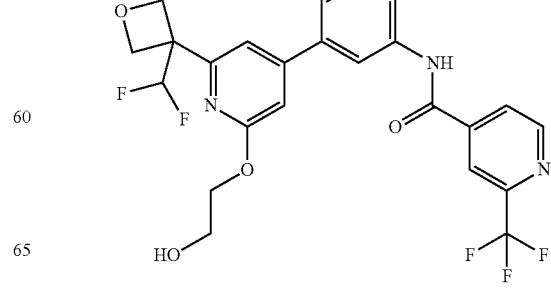

-continued
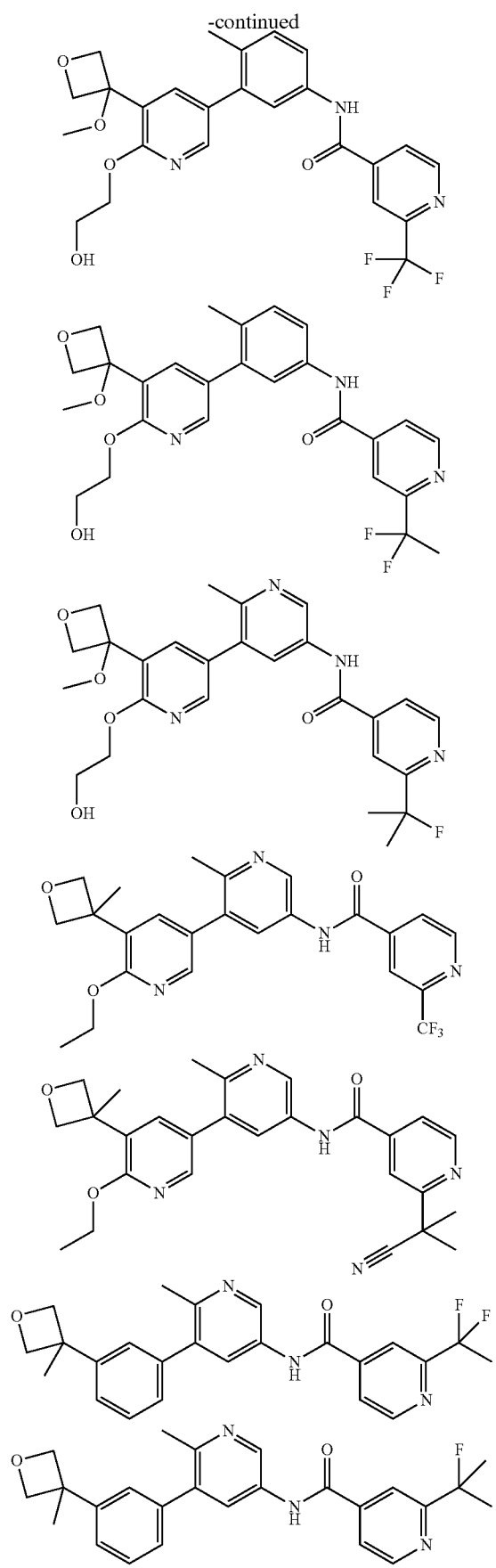
-continued
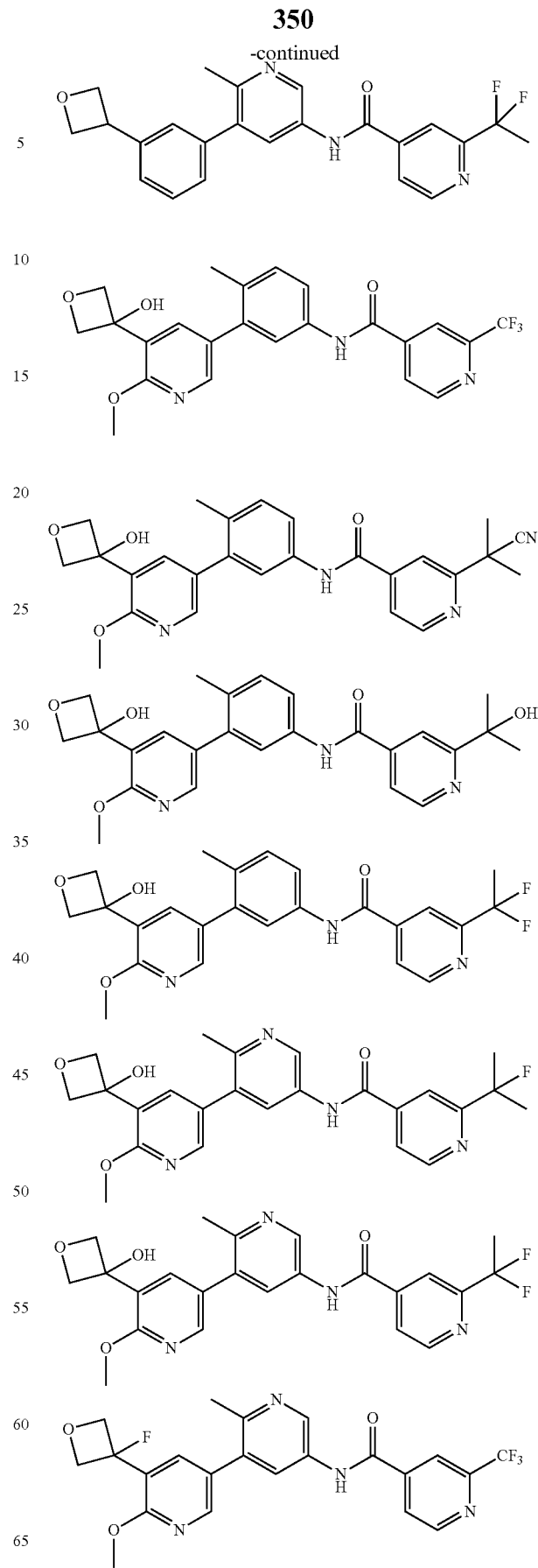

351
-continued
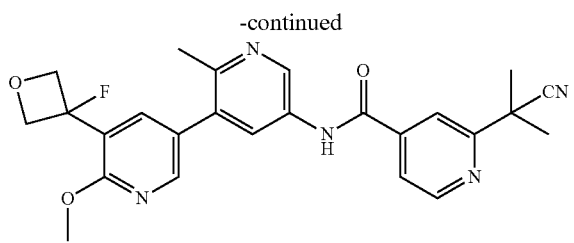
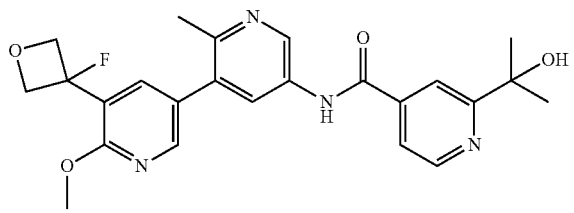
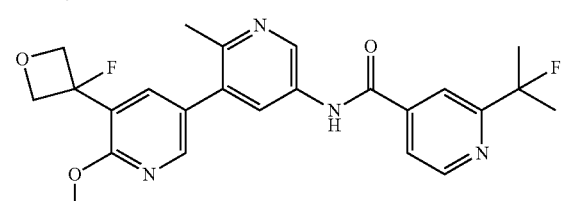
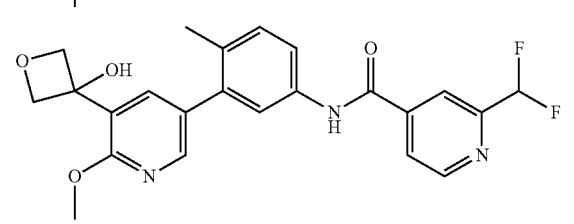
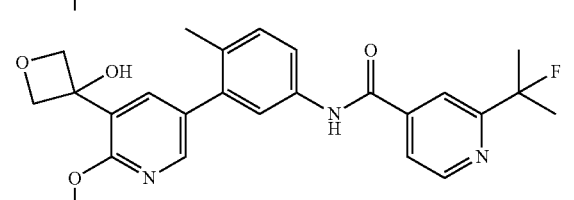
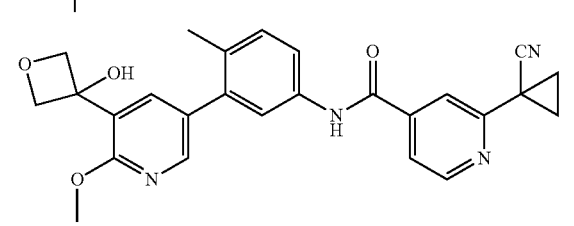
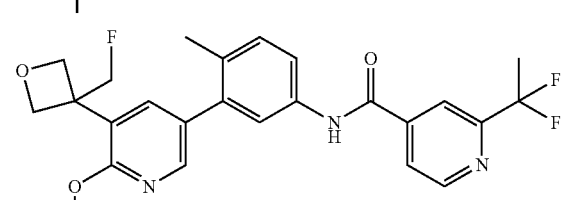
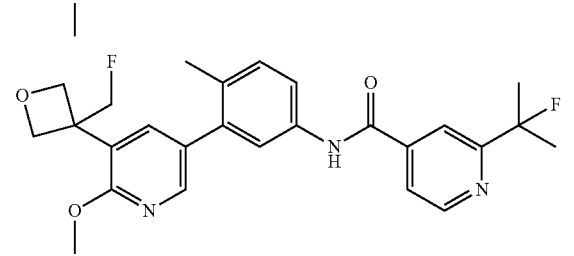
352
-continued
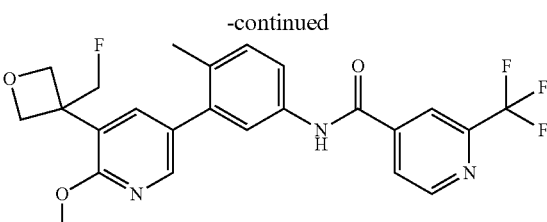
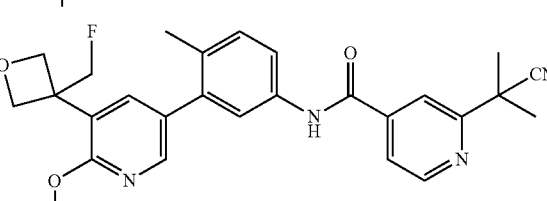
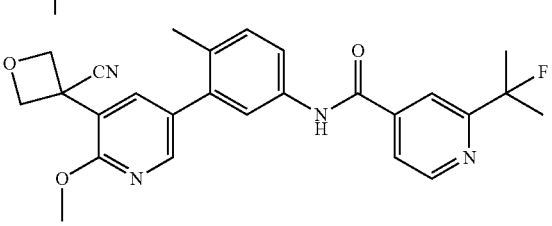
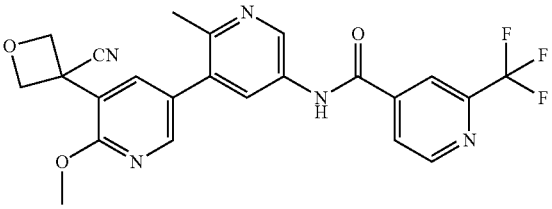
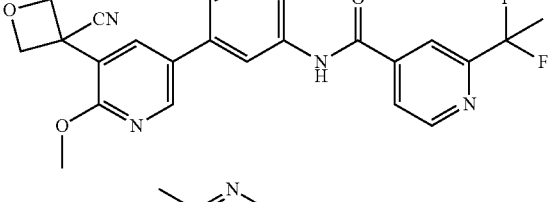
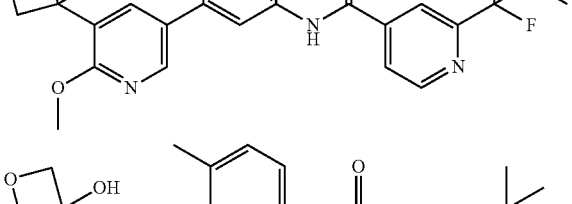
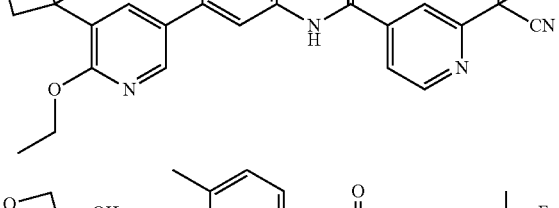
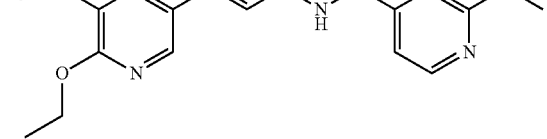

-continued
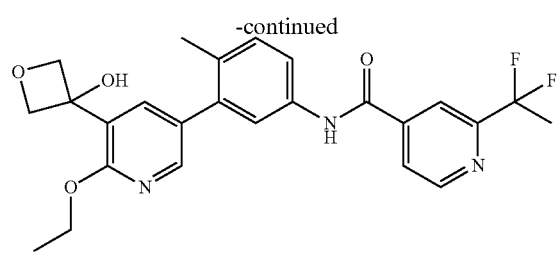
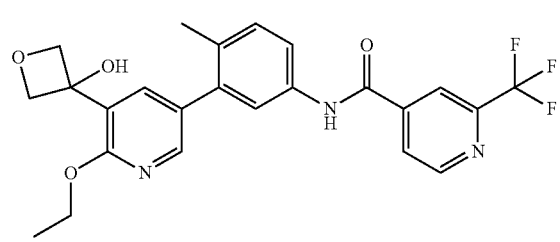
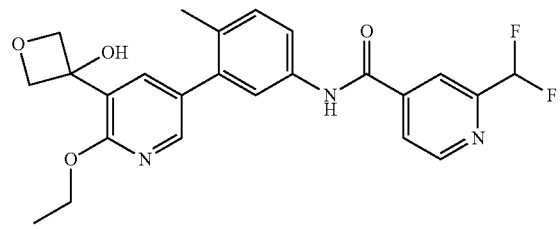
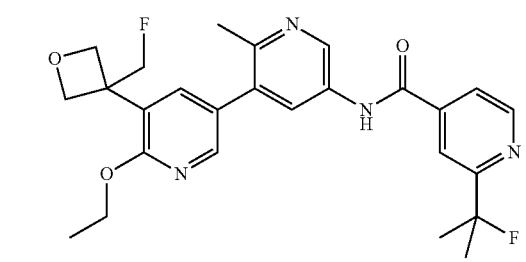
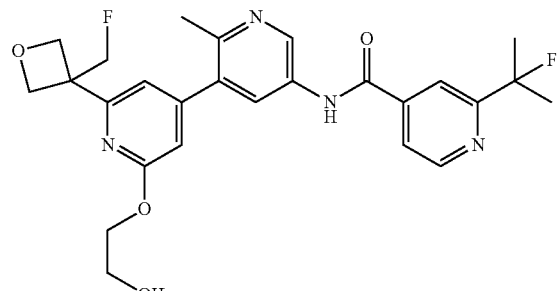
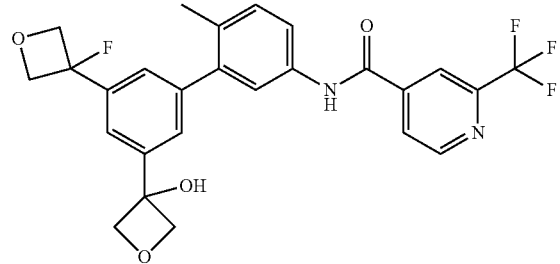
-continued
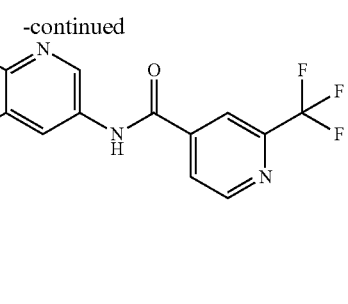
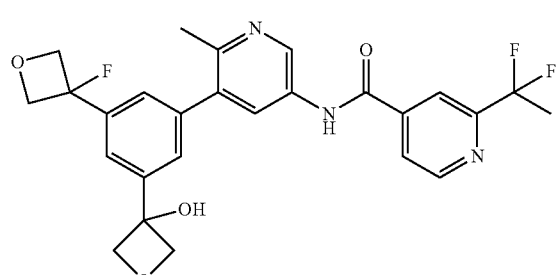
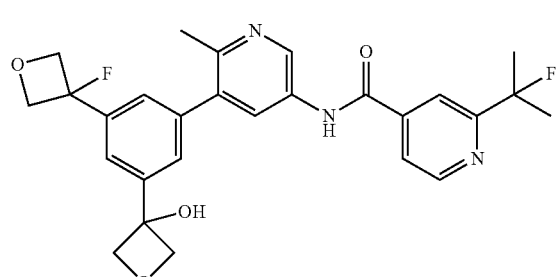
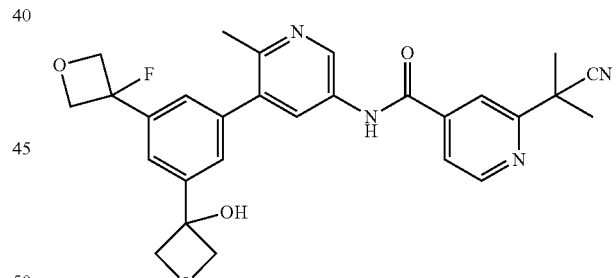
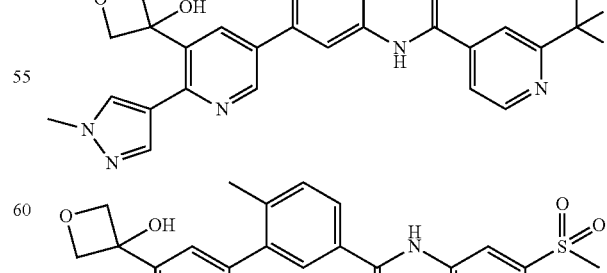

-continued

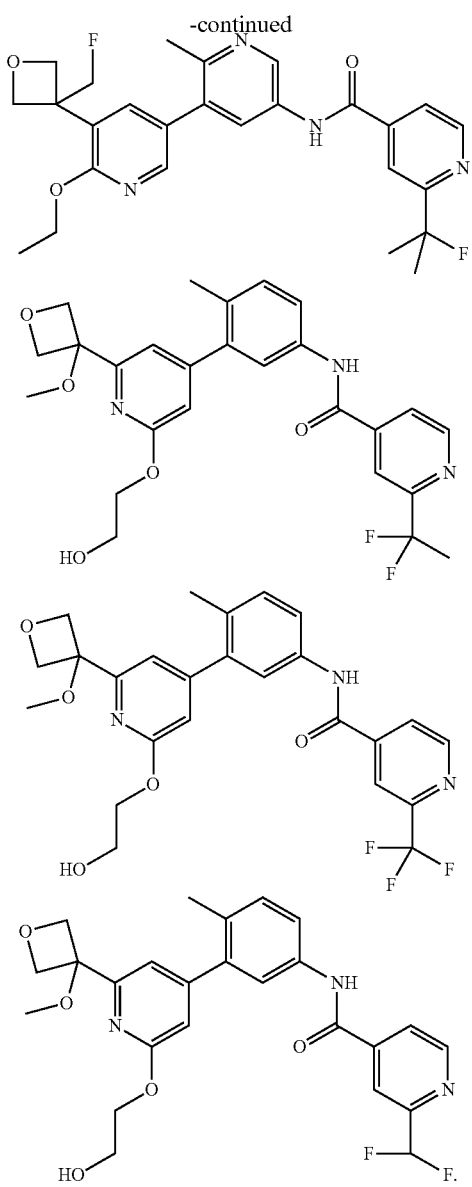

4. The compound of claim 1 of formula Ib:

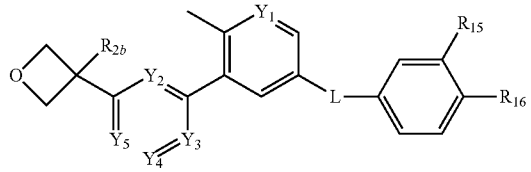

in which:
L is selected from —NHC(O)— and —C(O)NH—;
$Y_1$ is selected from N and CH;
$Y_2$ is selected from N and CH;
$Y_3$ is selected from N and CH;
$Y_4$ is selected from N and $CR_8$; wherein $R_8$ is selected from H, hydroxy-ethoxy, 3-hydroxyoxetan-3-yl, 2,3-dihydroxypropoxy, hydroxy-ethyl-amino, 4-amino-4-methylpiperidin-1-yl, 2-oxooxazolidin-3-yl, methoxy and methyl;

$Y_5$ is selected from N and $CR_1$;
$R_1$ is selected from H, ethoxy, hydroxy-ethoxy, methoxy, (tetrahydro-2H-pyran-4-yl)oxy and pyrazolyl; wherein said pyrazolyl can be unsubstituted or substituted with 1 to 2 methyl groups;
$R_{2b}$ is selected from H, methyl, halo, fluoro-methyl, hydroxy, difluoromethyl, formyl, methoxy and cyano;
$R_{15}$ is selected from —$CF_3$, methoxy, —$C(CH_3)_2F$, —$CF_2CH_2F$, —$C(CH_3)_2CN$, —$C(CH_3)F_2$, —$CHF_2$, —$C(CH_3)_2OH$, t-butyl, 1-cyanocyclopropyl, 2-(trifluoromethyl)cyclopropyl, —$C(F_2)C_2H_5$, methyl-sulfonyl, 4-ethylpiperazin-1-yl, —$C(CH_3)_2NH_2$ and dimethylamino-methyl;
$R_{16}$ is selected from H, halo, hydroxy, dimethyl-amino, hydroxy-methyl, amino-methyl, —$C(CH_3)_2NH_2$ and —$CF_3$; or a pharmaceutically acceptable salt thereof.

5. The compound of claim 4, or a pharmaceutically acceptable salts thereof, selected from:

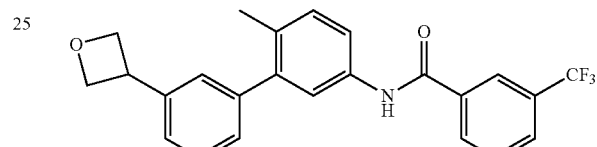

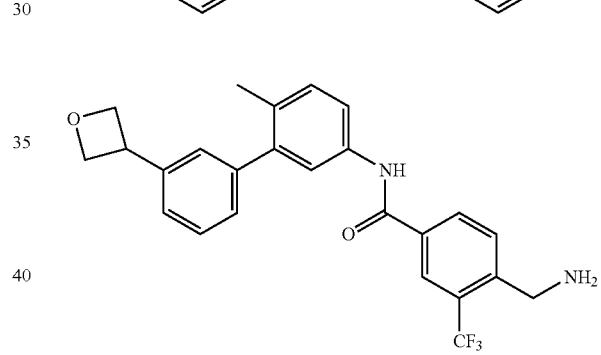

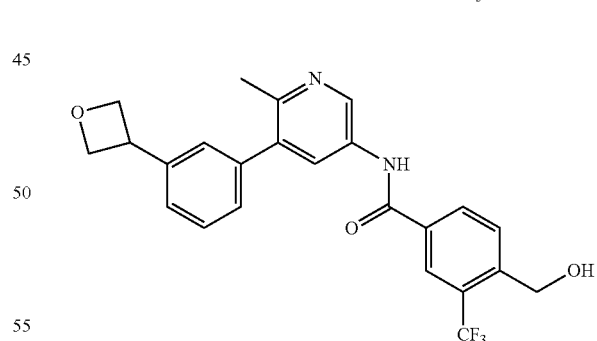

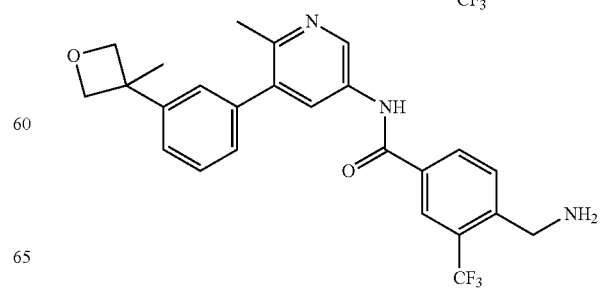

357
-continued
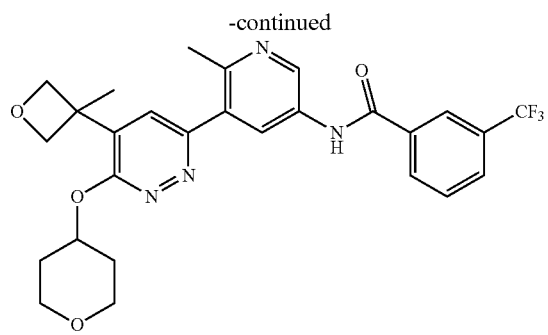
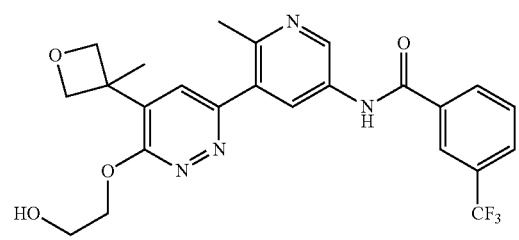
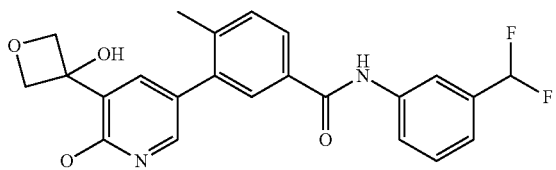
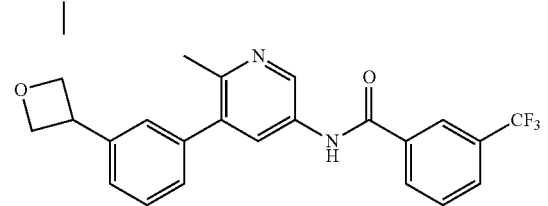
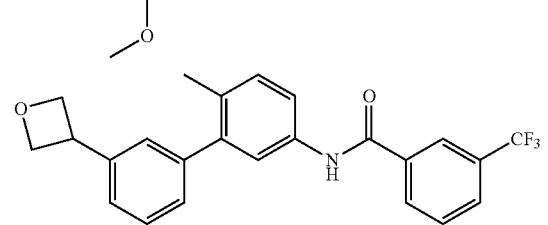
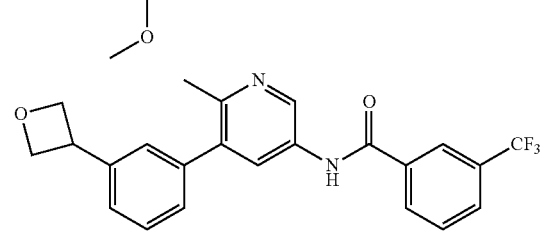
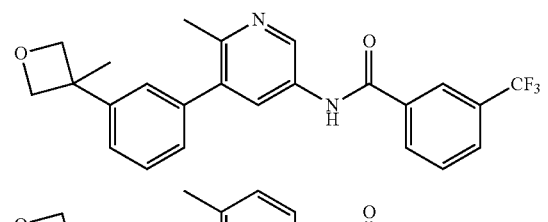
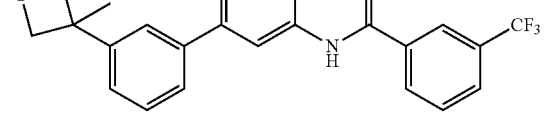
358
-continued
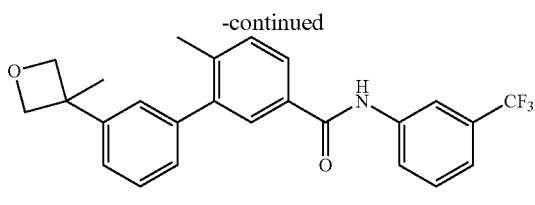
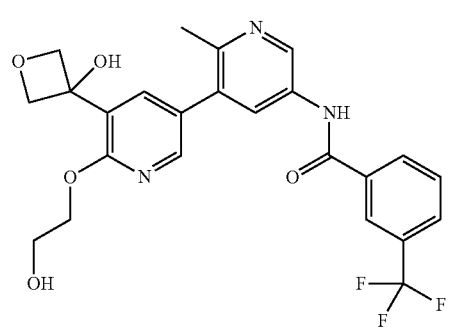
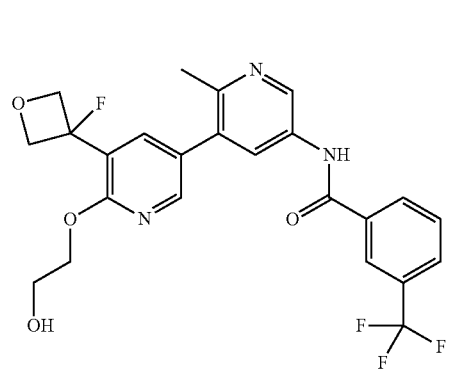
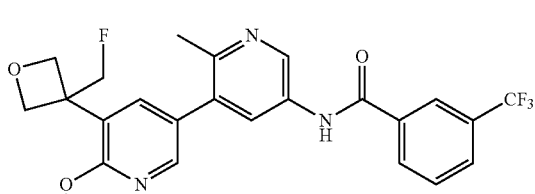
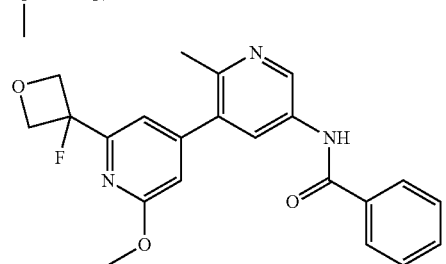
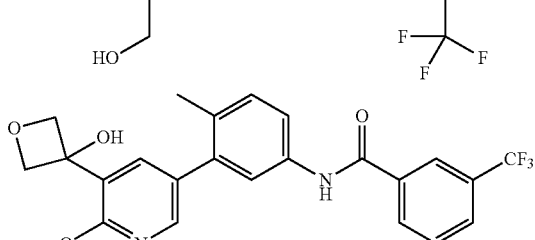

-continued
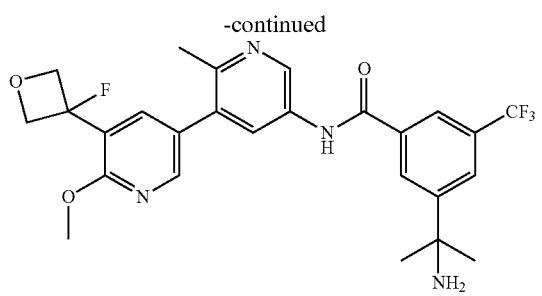
-continued
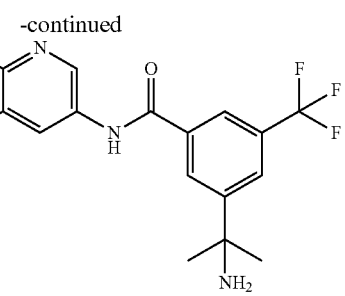
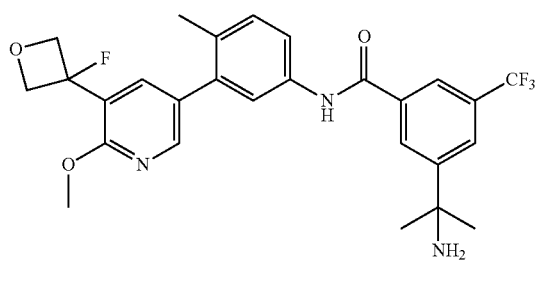
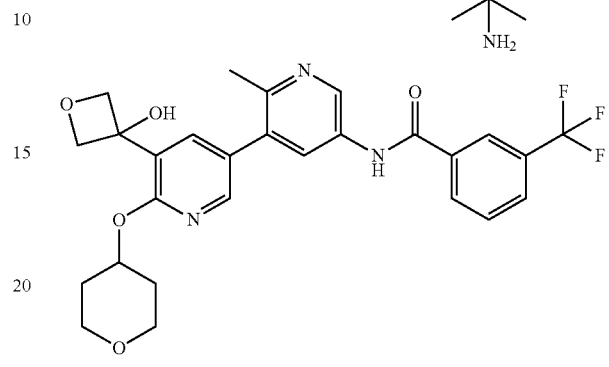
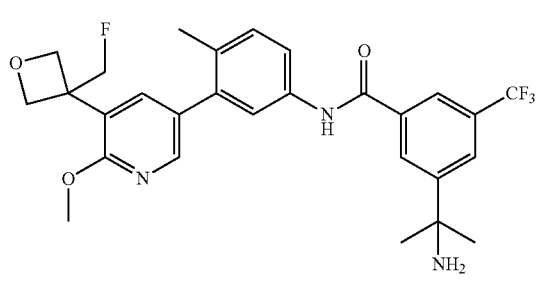
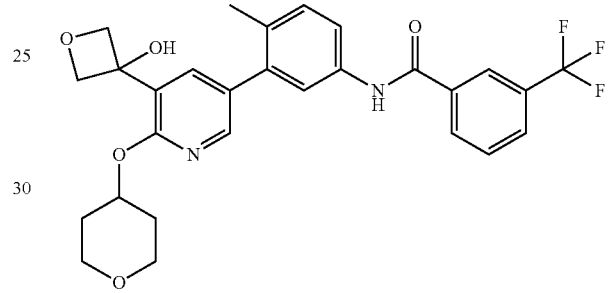
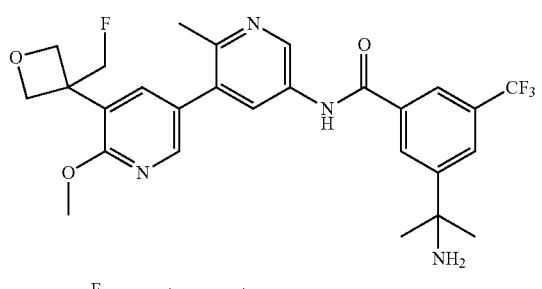
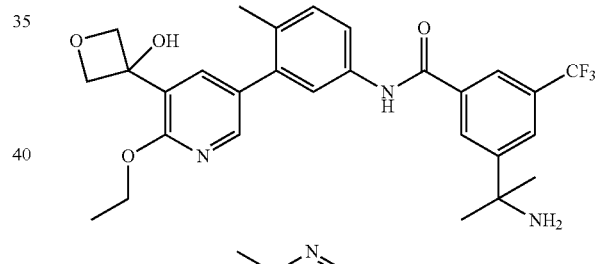
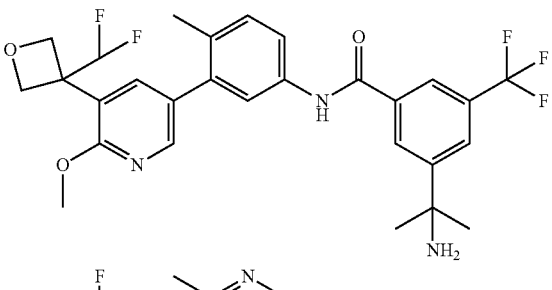
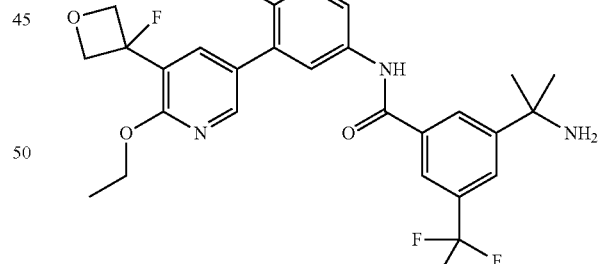
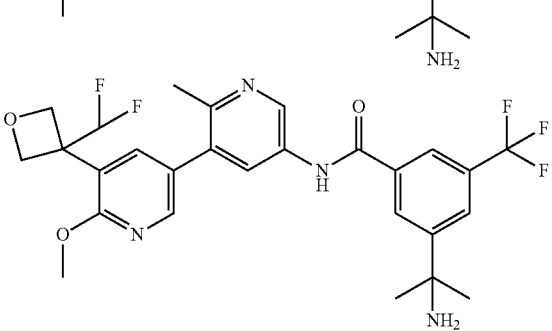
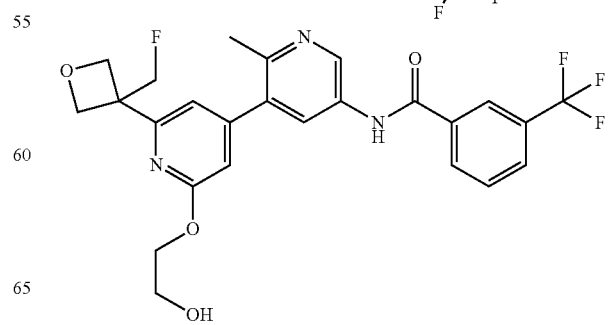

361

-continued

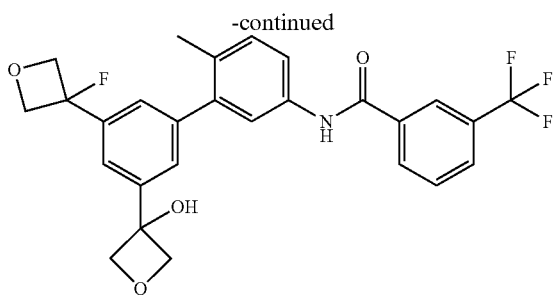

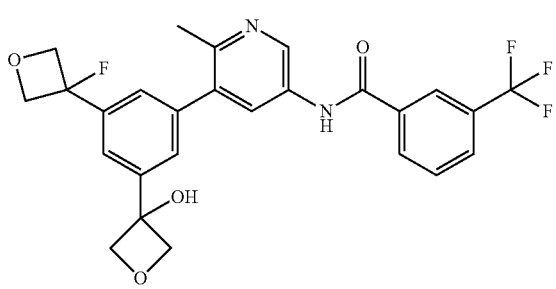

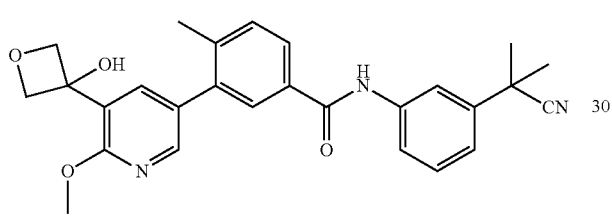

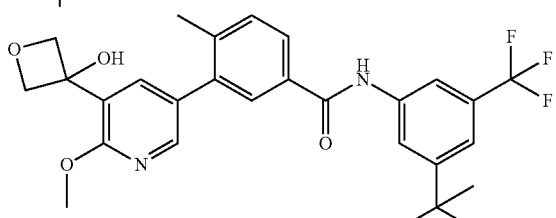

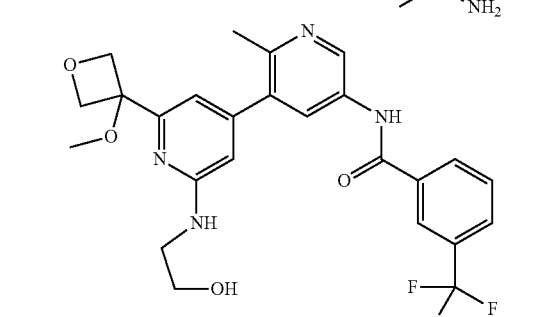

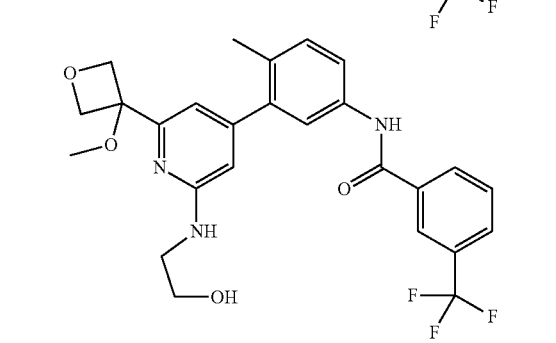

362

-continued

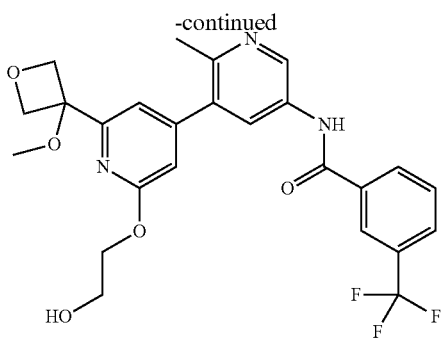

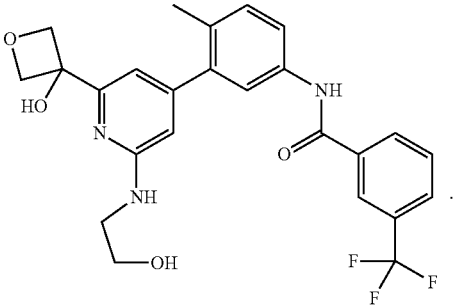 [SMILES: Cc1ccc(NC(=O)c2cccc(C(F)(F)F)c2)cc1-c1cc(NCCO)nc(C2(O)COC2)c1]

6. The compound of claim 1 of formula Ic:

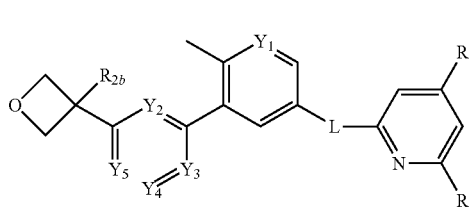

Ic in which:

L is selected from —NHC(O)— and —C(O)NH—;

$Y_1$ is selected from N and CH;

$Y_2$ is selected from N and CH;

$Y_3$ is selected from N and CH;

$Y_4$ is selected from N and $CR_8$; wherein $R_8$ is selected from H, hydroxy-ethoxy, 3-hydroxyoxetan-3-yl, hydroxy-ethyl-amine, methoxy and methyl;

$Y_5$ is selected from N and $CR_1$;

$R_1$ is selected from H, ethoxy, hydroxy-ethoxy, methoxy, (tetrahydro-2H-pyran-4-yl)oxy and pyrazolyl; wherein said pyrazolyl can be unsubstituted or substituted with 1 to 2 methyl groups;

$R_{2b}$ is selected from H, methyl, halo, fluoro-methyl, hydroxy, difluoromethyl, formyl, methoxy and cyano;

$R_{15}$ is selected from —$CF_3$, methoxy, —$C(CH_3)_2F$, —$CF_2CH_2F$, —$C(CH_3)_2CN$, —$C(CH_3)F_2$, —$CHF_2$, —$C(CH_3)_2OH$, t-butyl, 1-cyanocyclopropyl, 2-(trifluoromethyl)cyclopropyl, —$C(F_2)C_2H_5$, methyl-sulfonyl, 4-ethylpiperazin-1-yl, —$C(CH_3)_2NH_2$ and dimethylamino-methyl;

$R_{16}$ is selected from H, halo, hydroxy, dimethyl-amino, hydroxy-methyl, amino-methyl, —$C(CH_3)_2NH_2$ and —$CF_3$; or a pharmaceutically acceptable salt thereof.

7. The compound of claim 6, or a pharmaceutically acceptable salts thereof, selected from:

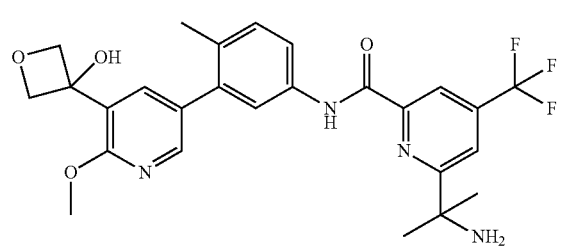
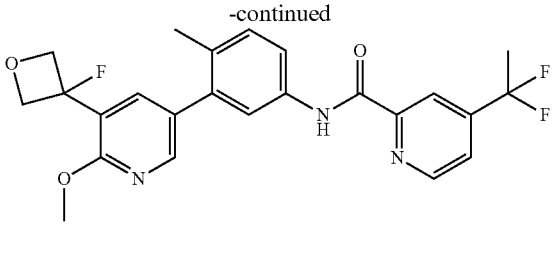
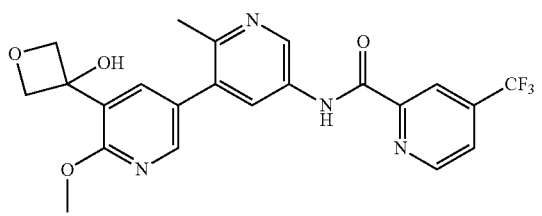
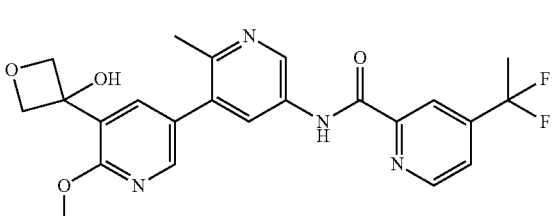
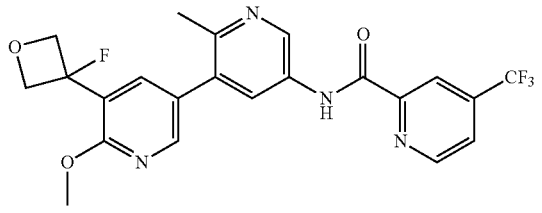
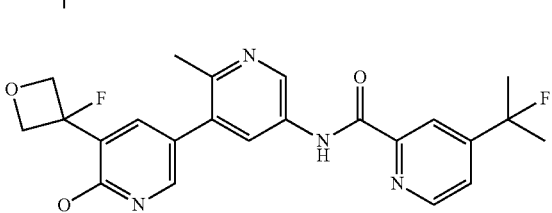
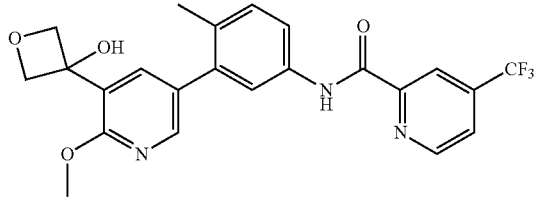
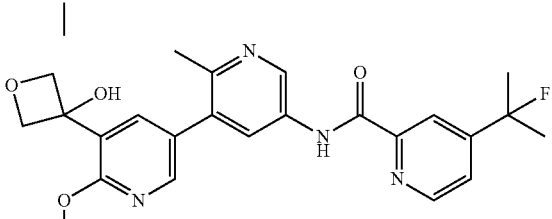
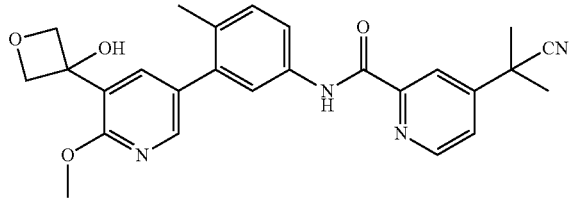
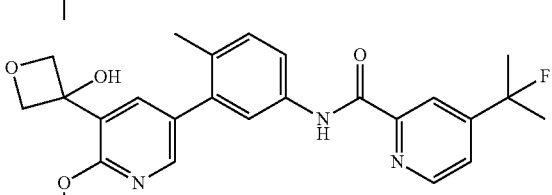
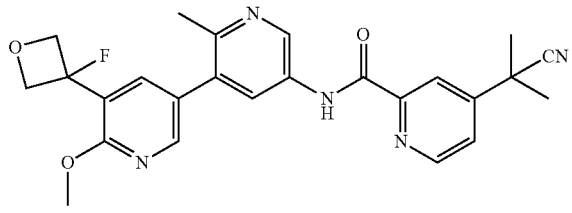
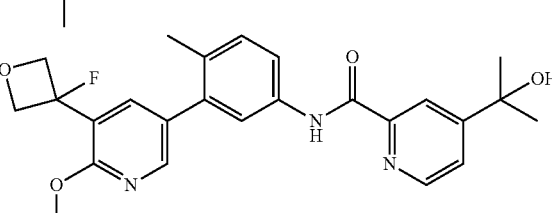
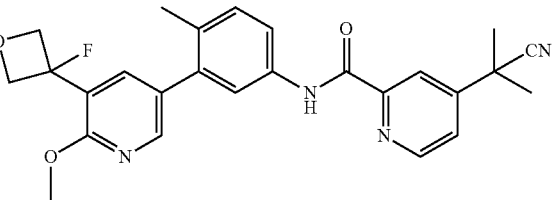
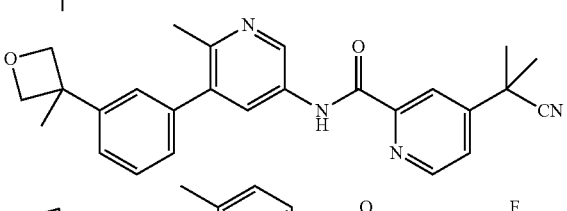

-continued
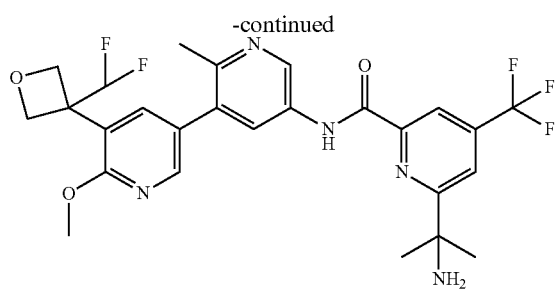
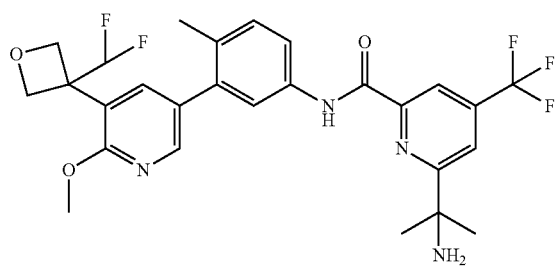
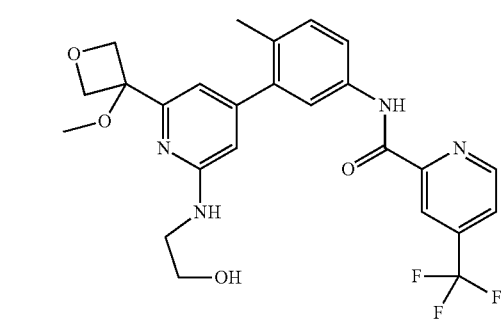
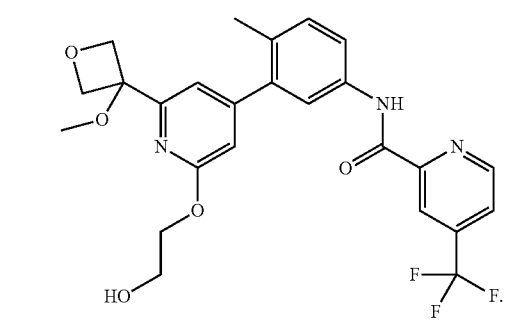
8. The compound of claim 1 of formula Id or Ie:
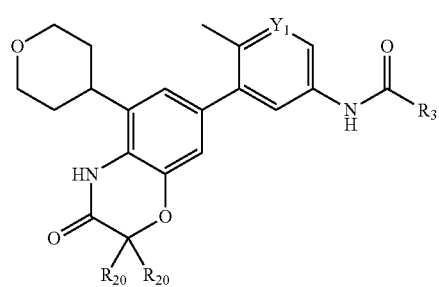
Id
-continued
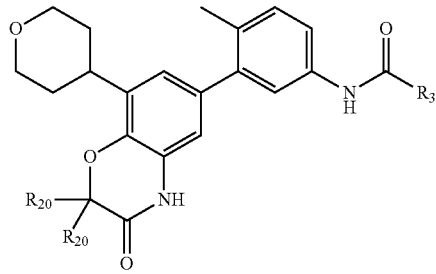
Ie
in which:
  $Y_1$ is selected from N and CH; each
  $R_{20}$ is independently selected from methyl and hydroxyethyl; and
  $R_3$ is selected from:
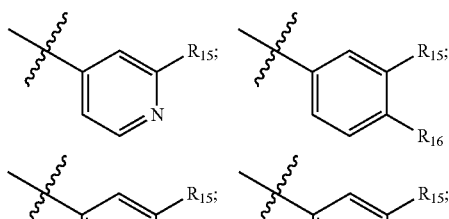
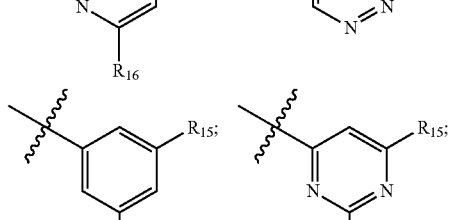
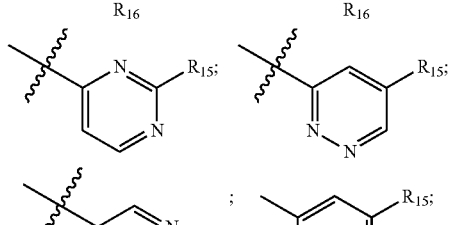
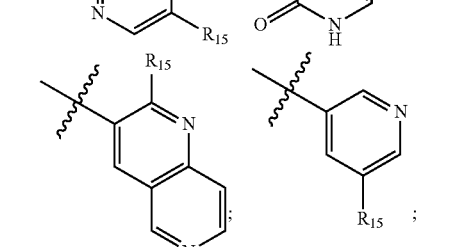
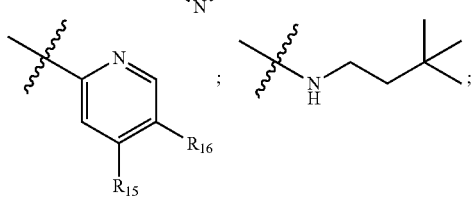

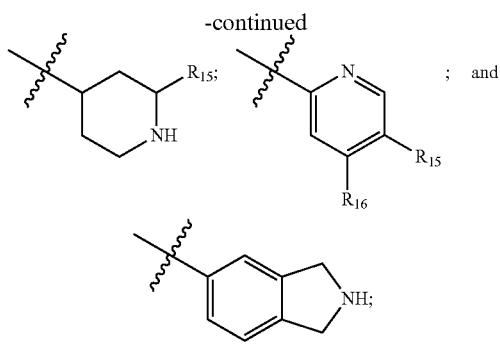

; and

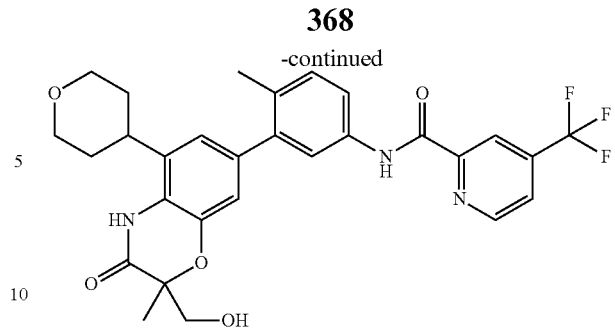

wherein indicates the point of attachment with L;

R$_{15}$ is selected from —CF$_3$, methoxy, —C(CH$_3$)$_2$F, —CF$_2$CH$_2$F, —C(CH$_3$)$_2$CN, —C(CH$_3$)F$_2$, —CHF$_2$, —C(CH$_3$)$_2$OH, t-butyl, 1-cyanocyclopropyl, 2-(trifluoromethyl)cyclopropyl, —C(F$_2$)C$_2$H$_5$, methyl-sulfonyl, 4-ethylpiperazin-1-yl, —C(CH$_3$)$_2$NH$_2$ and dimethyl-amino-methyl;

R$_{16}$ is selected from H, halo, hydroxy, dimethyl-amino, hydroxy-methyl, amino-methyl, —C(CH$_3$)$_2$NH$_2$ and —CF$_3$; or a pharmaceutically acceptable salt thereof.

9. The compound of claim 8, or a pharmaceutically acceptable salt thereof, selected from:

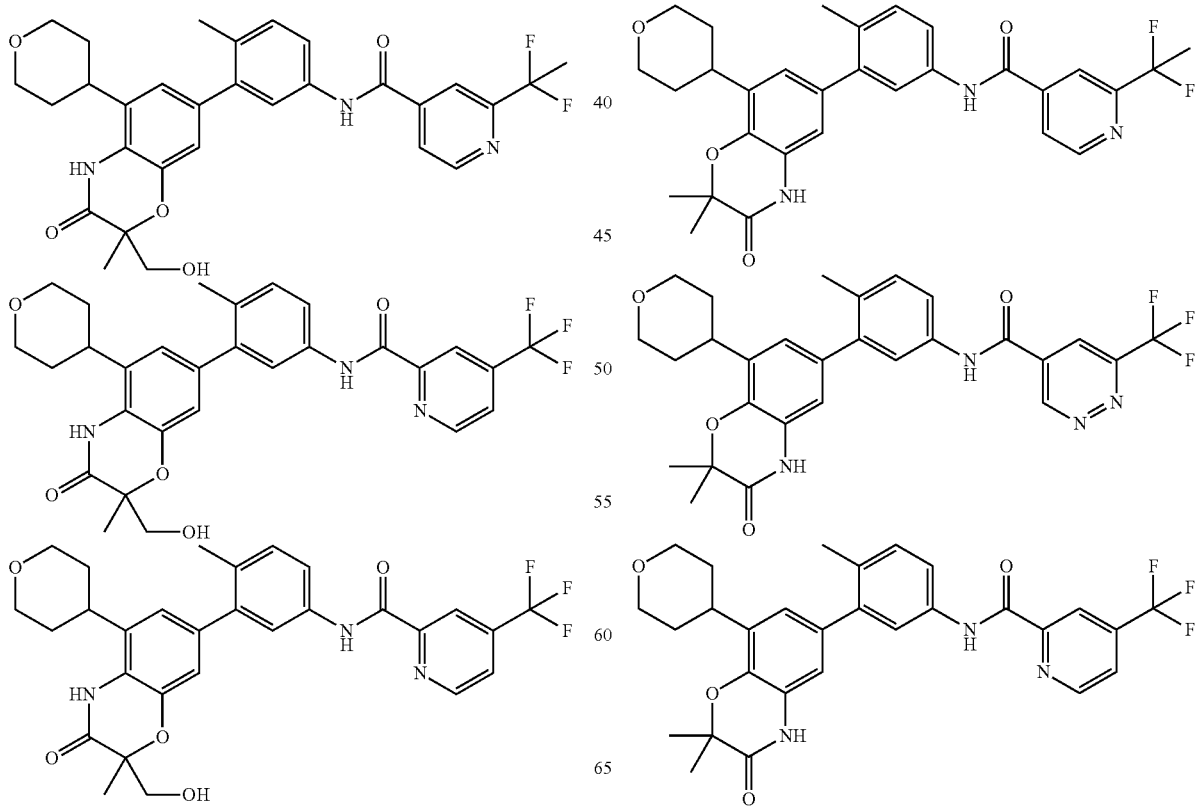

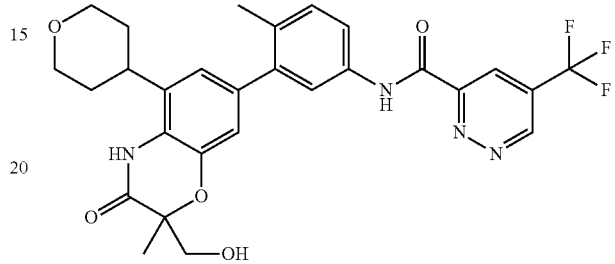

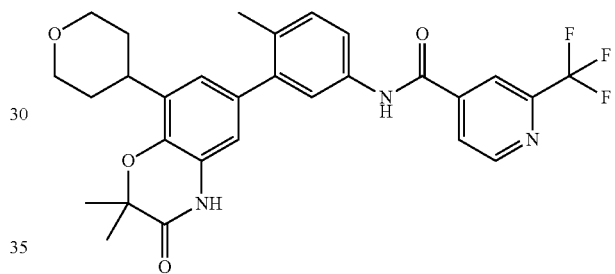

-continued

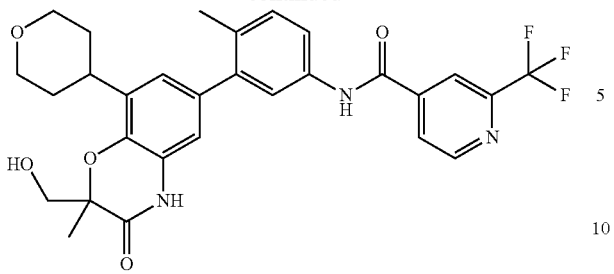

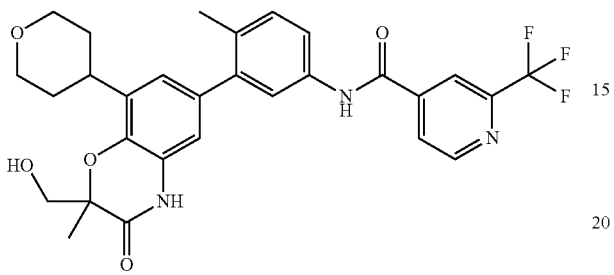

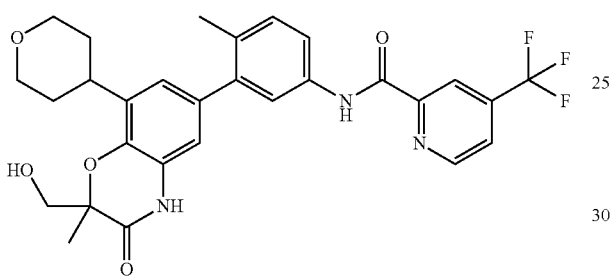

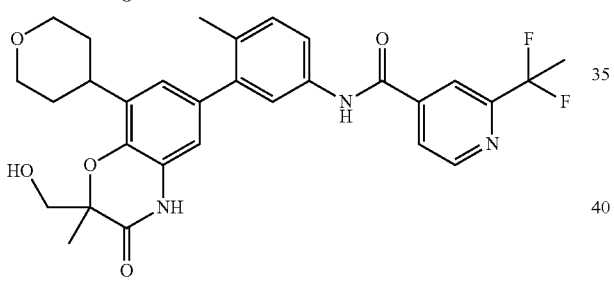

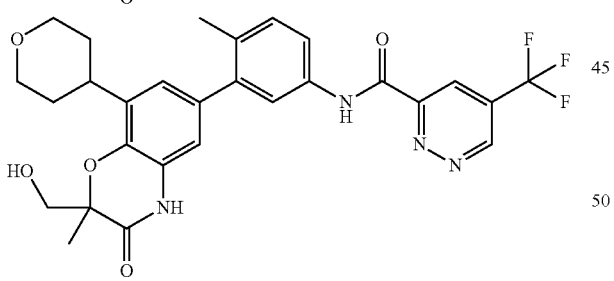

10. The compound of claim 1 of formula If:

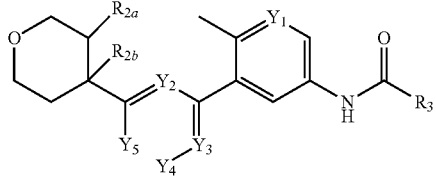

in which:
Y₁ is selected from N and CH;
Y₂ is selected from N and CH;
Y₃ is selected from N and CH;
Y₄ is selected from N and CR₈; wherein R₈ is selected from H, hydroxy-ethoxy, 3-hydroxyoxetan-3-yl, 2,3-dihydroxypropoxy, bis(hydroxy-ethyl)-amino, 4-hydroxy-piperidin1-yl, hydroxy-ethyl-amino, 4-amino-4-methylpiperidin-1-yl, 2-oxooxazolidin-3-yl, methoxy and methyl;
Y₅ is selected from N and CR₁;
or R₁ and the nitrogen of Y₄ form a 5 member unsaturated ring containing and additional heteroatom selected from N, O and S;
or R₁ and R₈ together with the ring to which they are both attached form 2H-benzo[b][1,4]oxazin-3(4H)-one substituted with one to two R₂₀ groups independently selected from methyl and hydroxy-ethyl;
or R₈ and Y₃ together with the ring to which they are both attached form 1H-benzo[d]imidazole substituted with methyl;
R₁ is selected from H, ethoxy, isopropoxy, methoxy-ethyl-amino, (2-hydroxyethyl)(methyl)amino, (1-hydroxypropan-2-yl)amino, methoxy-ethoxy, hydroxy-ethoxy, methoxy, (2-hydroxypropyl)amino, (tetrahydro-2H-pyran-4-yl)oxy, (tetrahydro-2H-pyran-4-yl)oxy, (1-ethylpiperidin-4-yl)oxy and pyrazolyl; wherein said pyrazolyl can be unsubstituted or substituted with 1 to 2 methyl groups; each
R₂ₐ is selected from hydrogen and OH;
R₂ᵦ is selected from H, methyl, halo, fluoro-methyl, hydroxy, hydroxymethyl, difluoromethyl, formyl, methoxy and cyano;
R₃ is selected from:

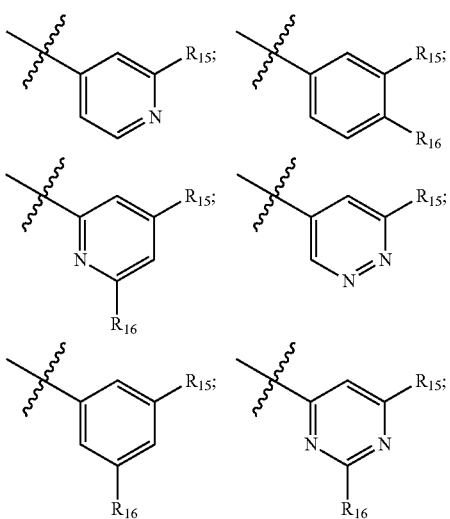

-continued

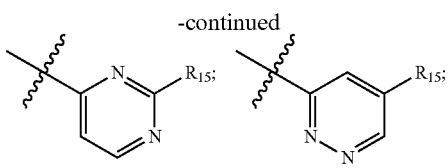

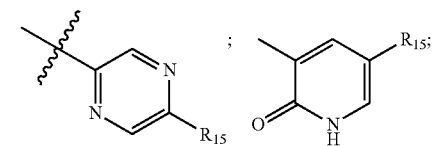

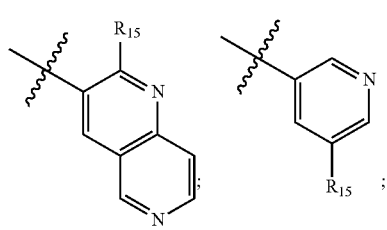

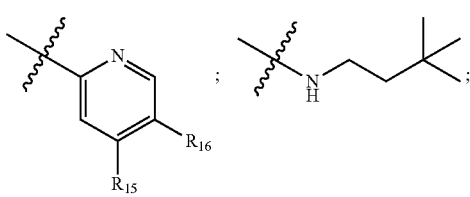

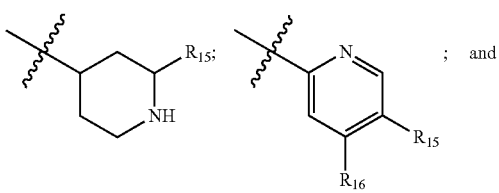

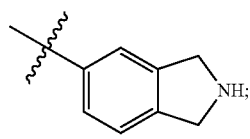

wherein

indicates the point of attachment with L;

$R_{15}$ is selected from —$CF_3$, methoxy, —$C(CH_3)_2F$, —$CF_2CH_2F$, —$C(CH_3)_2CN$, —$C(CH_3)F_2$, —$CHF_2$, —$C(CH_3)_2OH$, t-butyl, 1-cyanocyclopropyl, 2-(trifluoromethyl)cyclopropyl, —$C(F_2)C_2H_5$, methyl-sulfonyl, 4-ethylpiperazin-1-yl, —$C(CH_3)_2NH_2$ and dimethyl-amino-methyl;

$R_{16}$ is selected from H, halo, hydroxy, dimethyl-amino, hydroxy-methyl, amino-methyl, —$C(CH_3)_2NH_2$ and —$CF_3$; or a pharmaceutically acceptable salt thereof.

11. The compound of claim 10, or a pharmaceutically acceptable salt thereof, selected from:

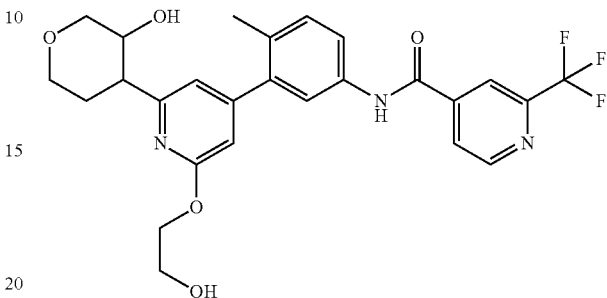

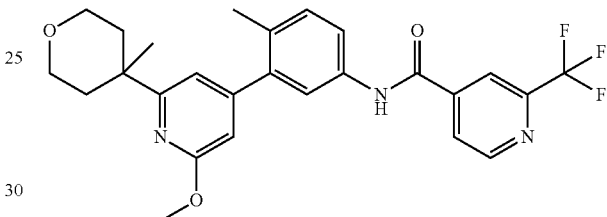

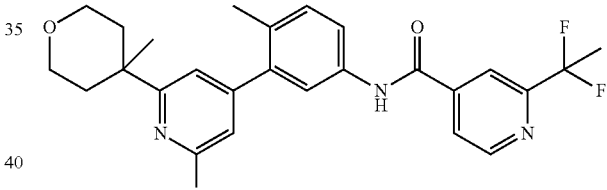

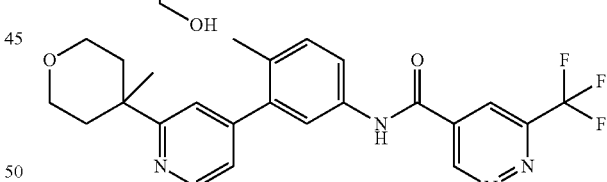

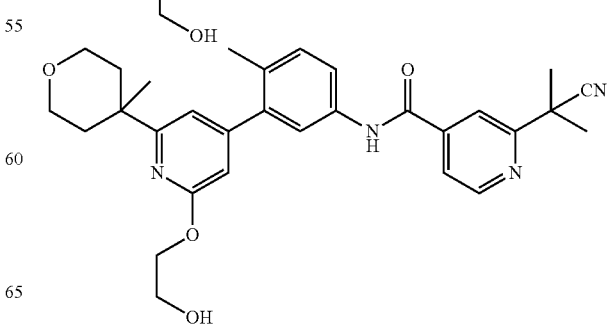

373
-continued
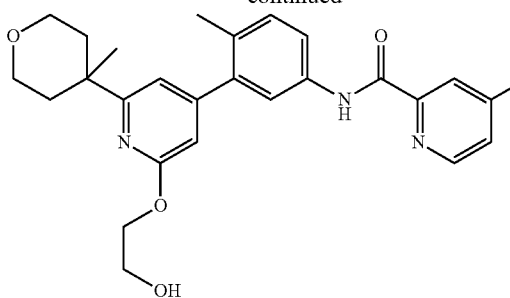
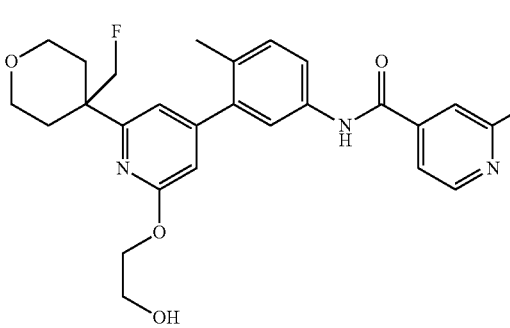
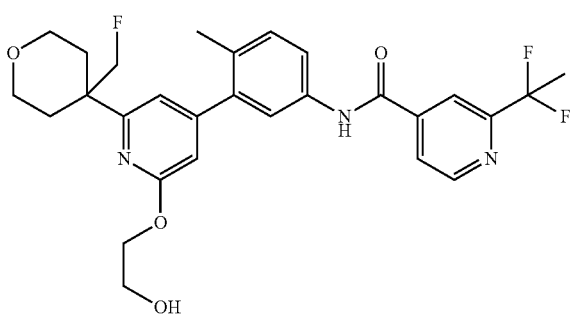
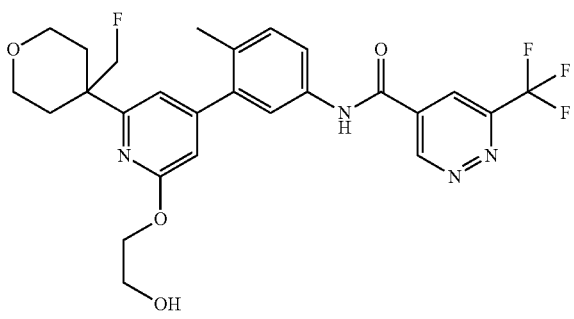
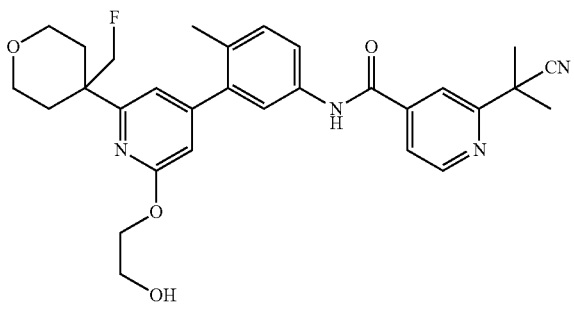
374
-continued
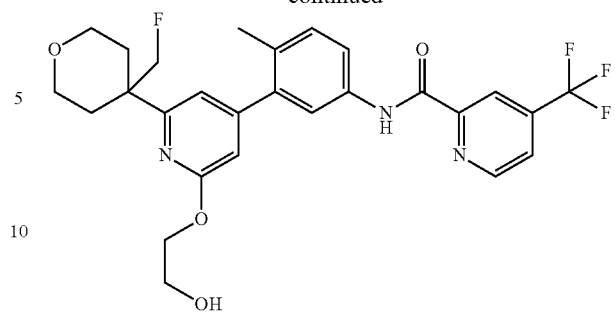
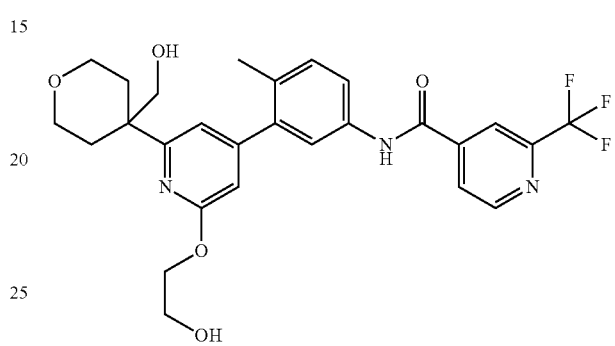
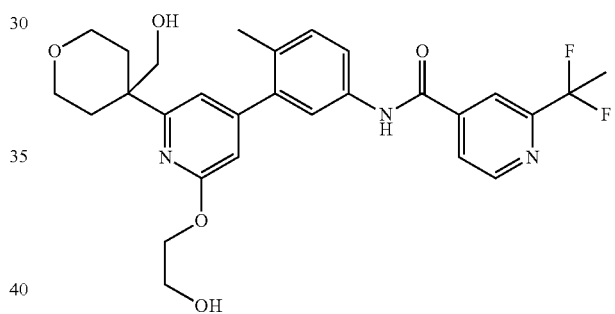
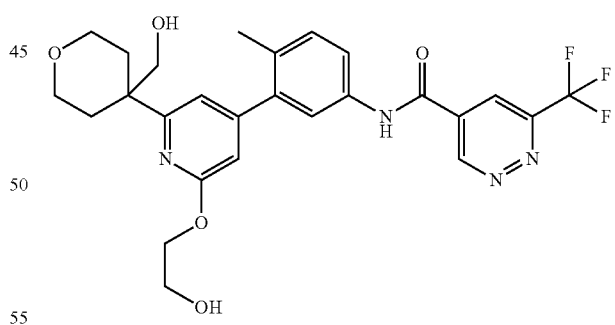
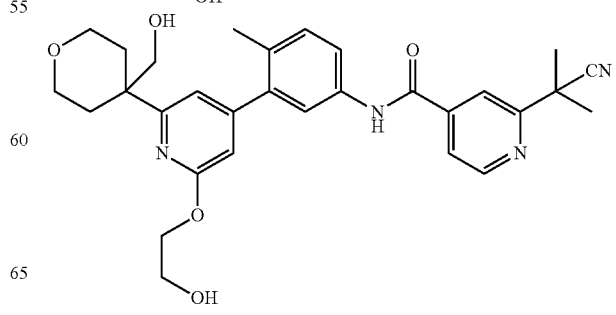

375
-continued
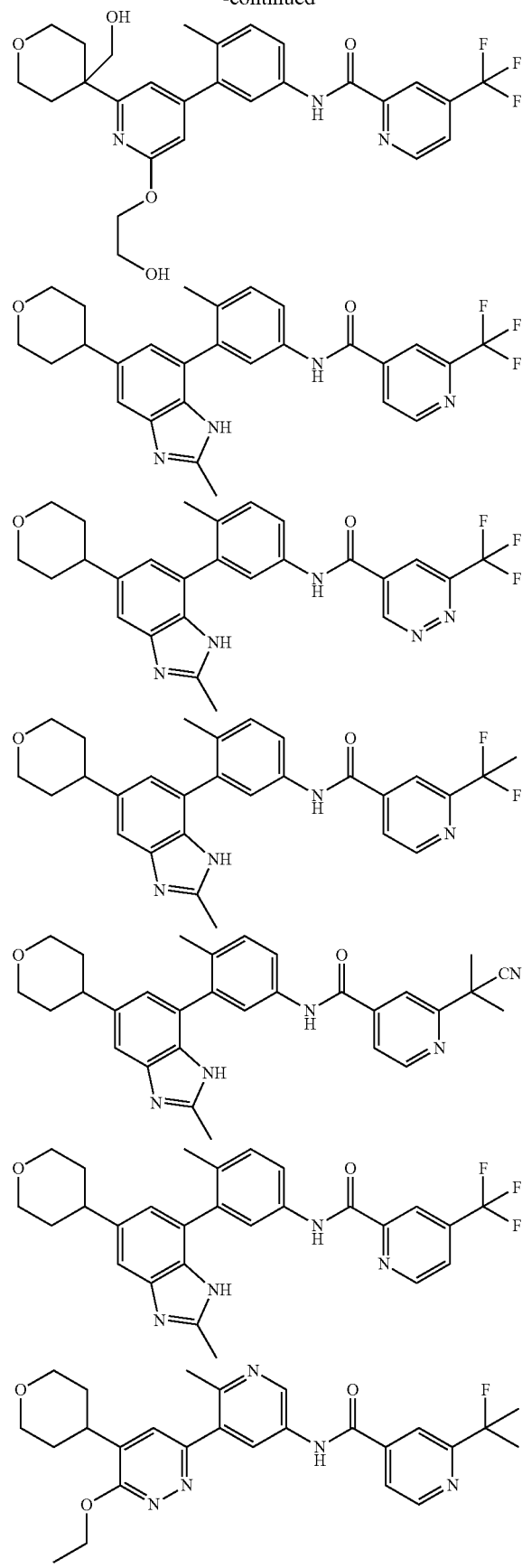
376
-continued
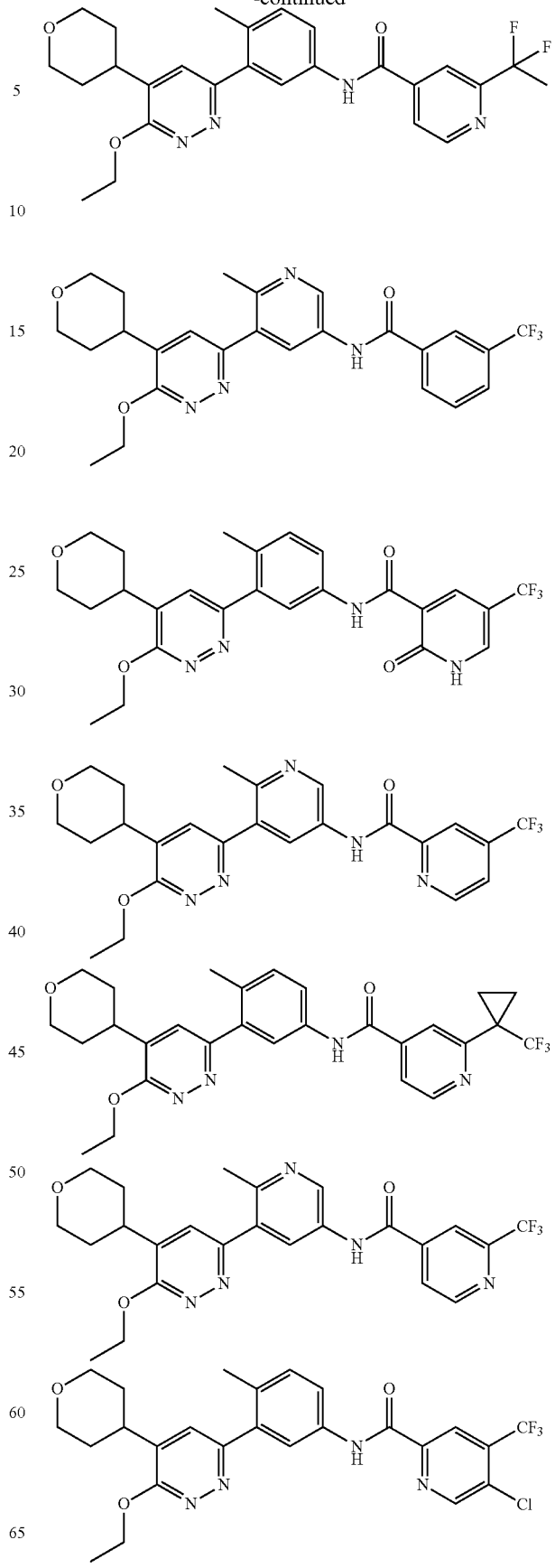

377
-continued
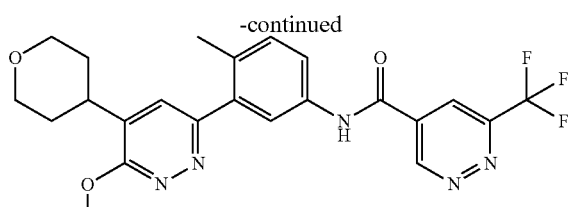
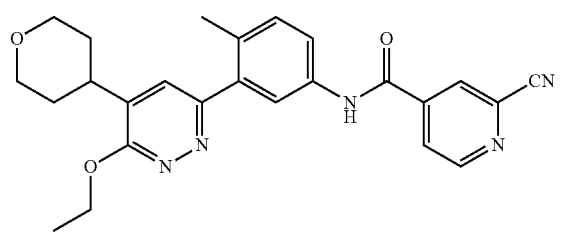
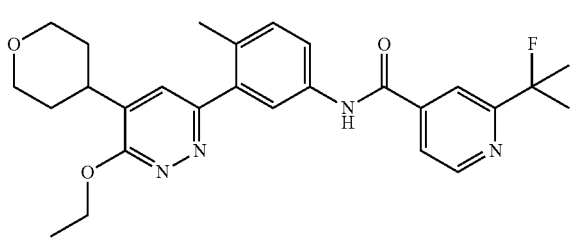
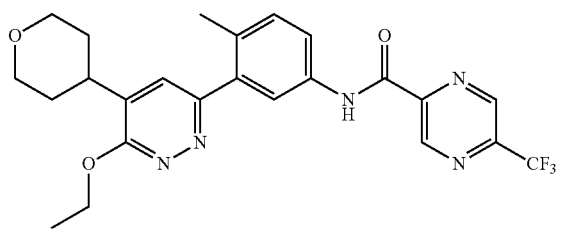
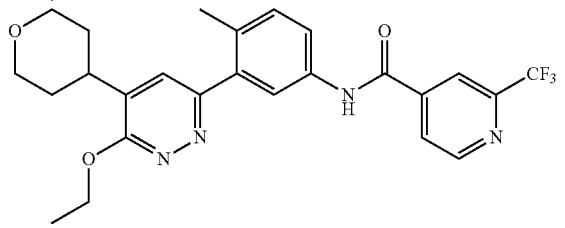
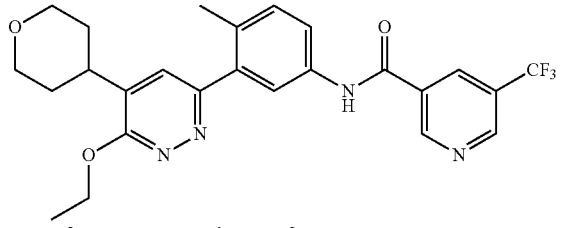
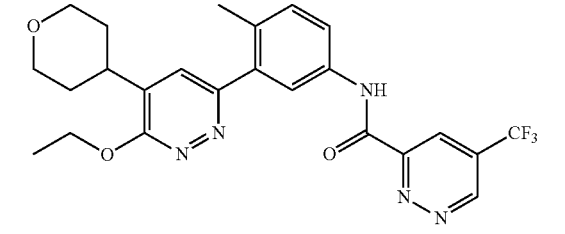
378
-continued
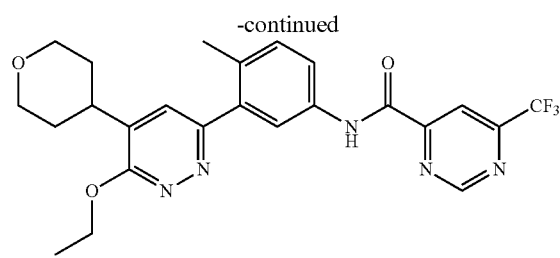
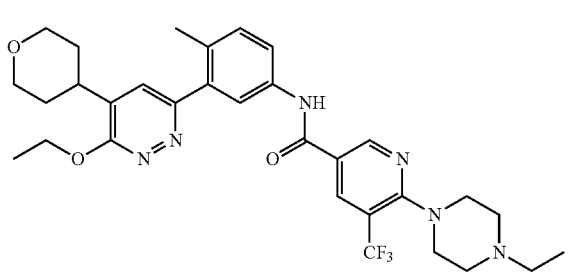
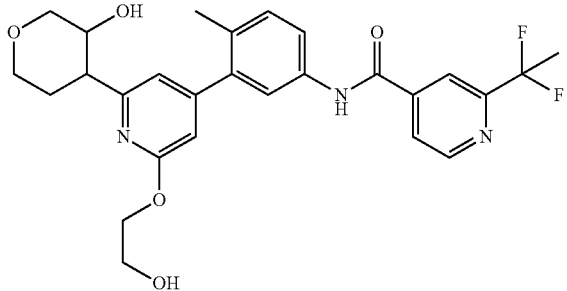
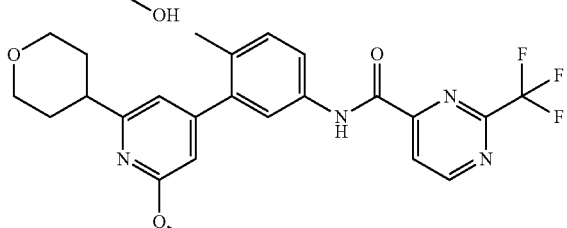
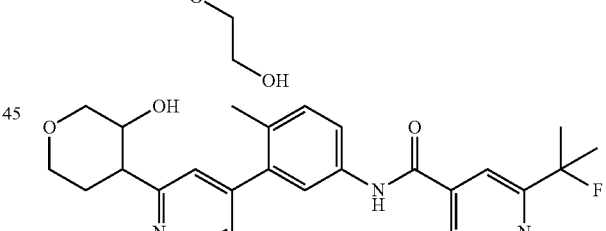
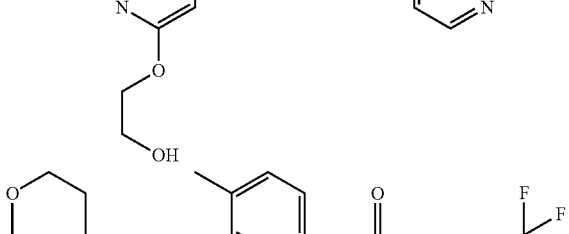
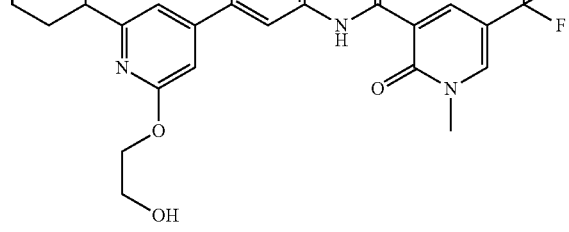

379
-continued
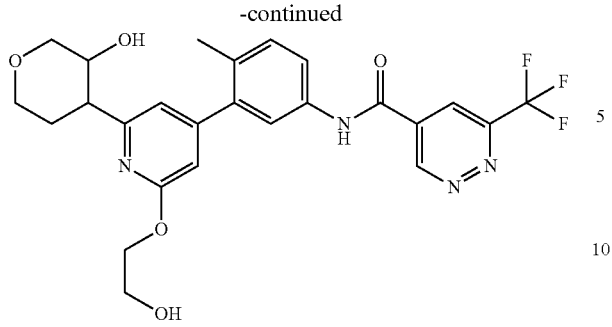
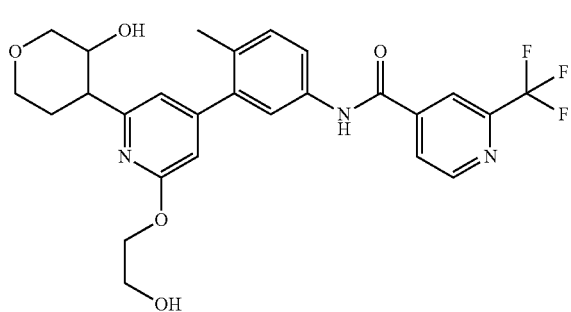
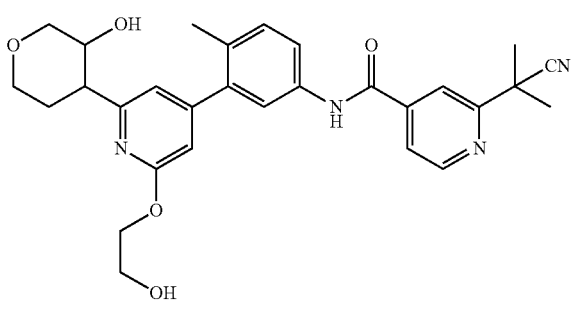
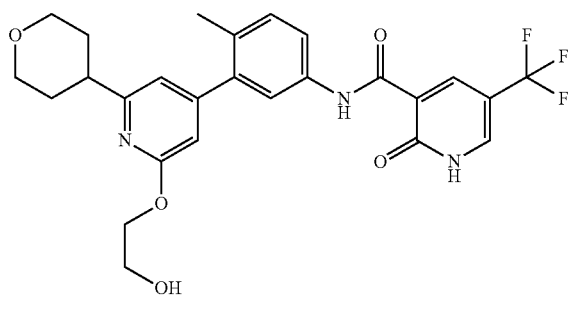
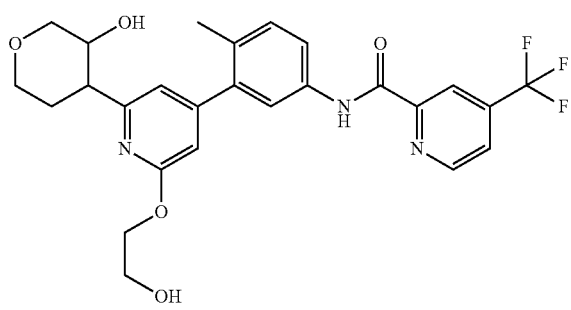
380
-continued
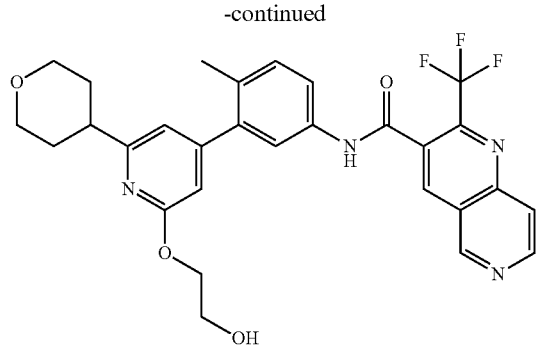
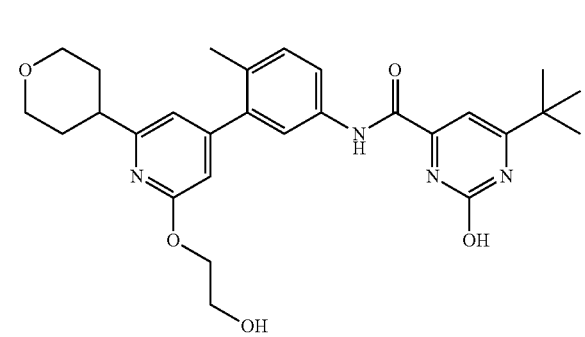
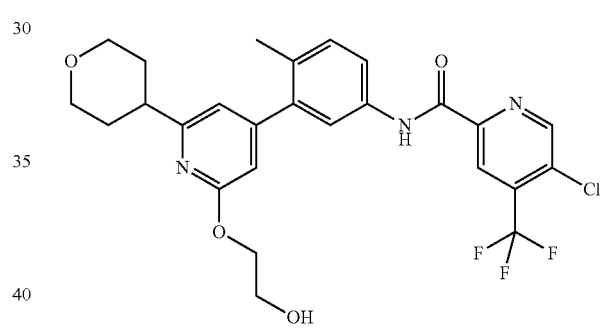
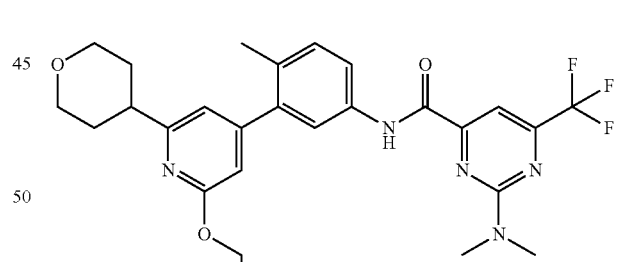
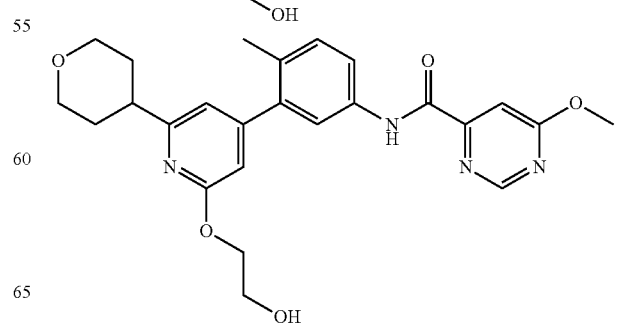

381
-continued
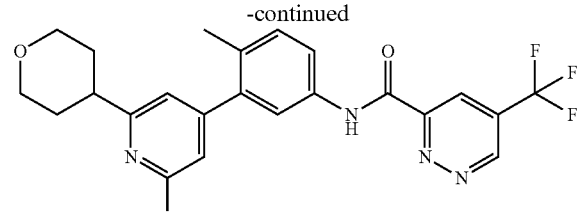
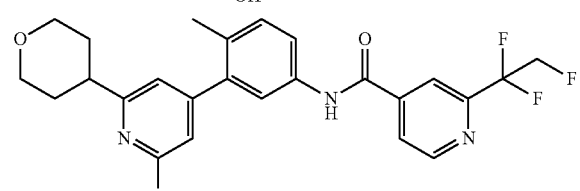
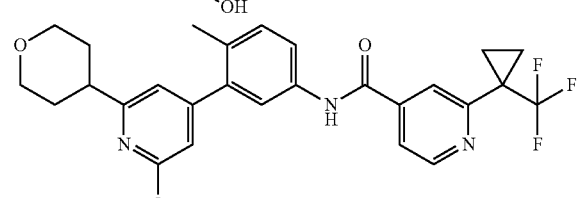
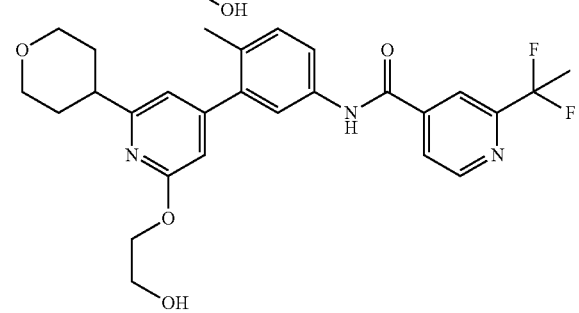
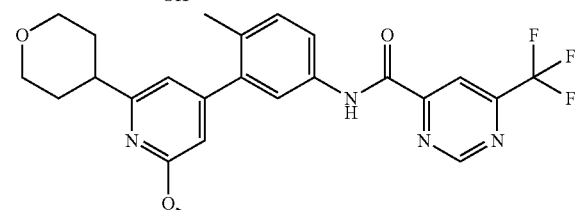
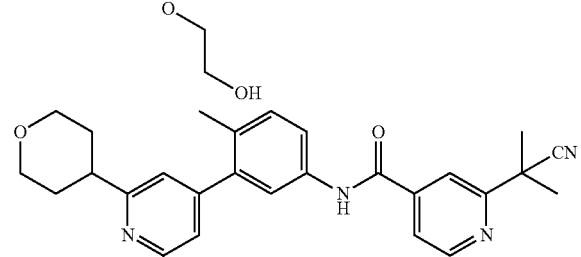
382
-continued
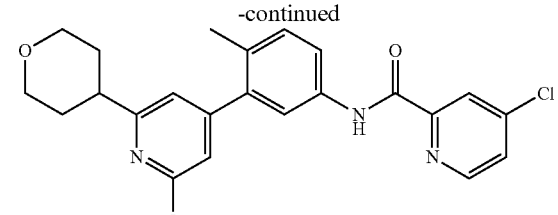
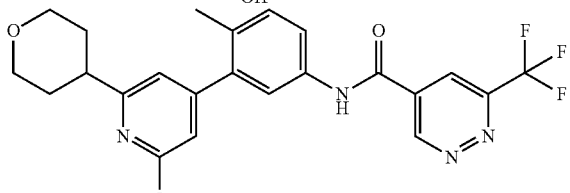
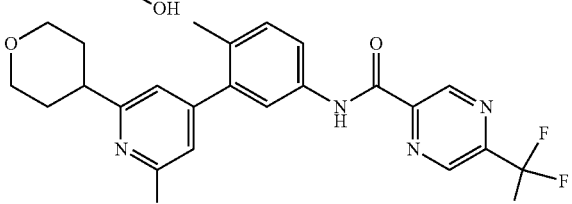
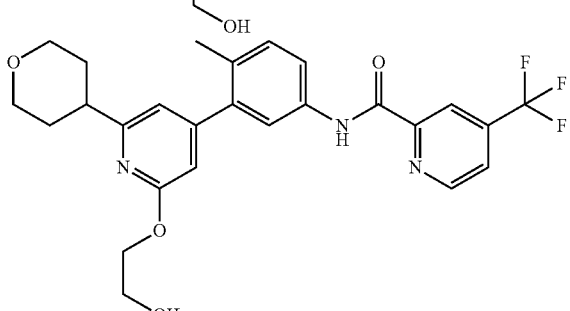
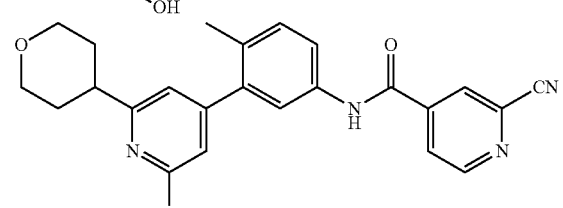
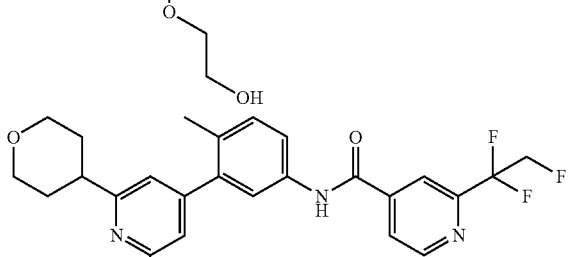

383
-continued
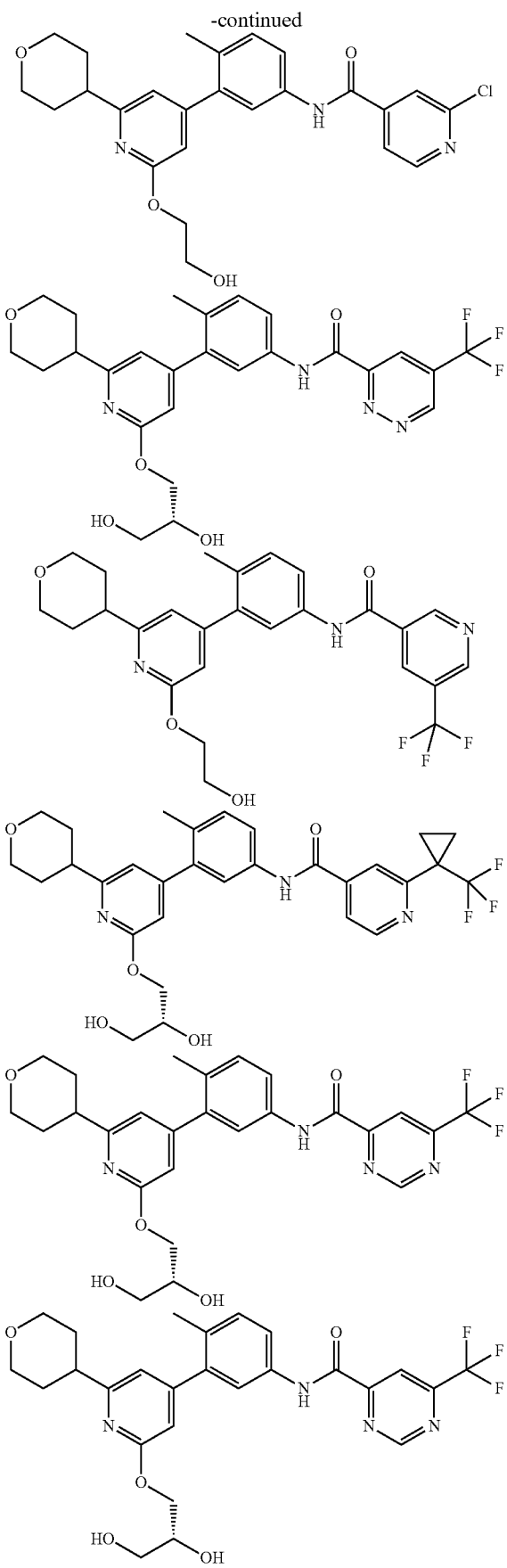
384
-continued
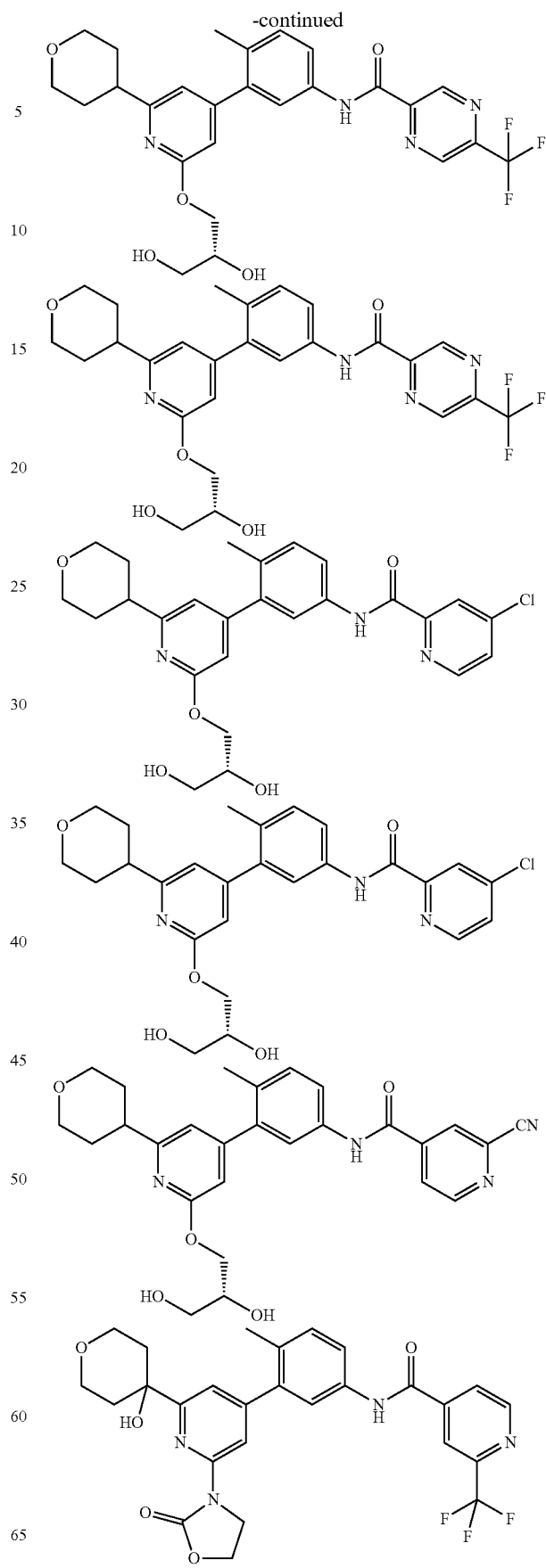

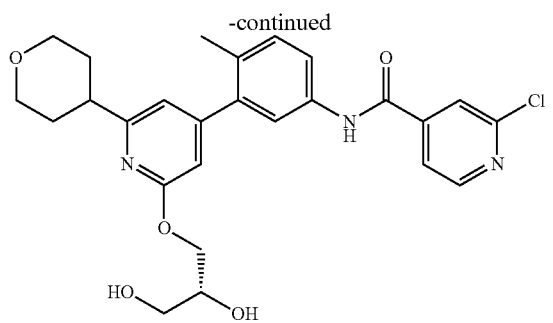
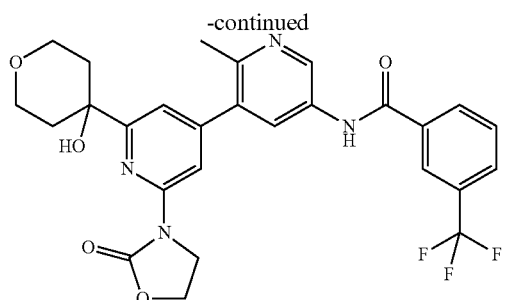
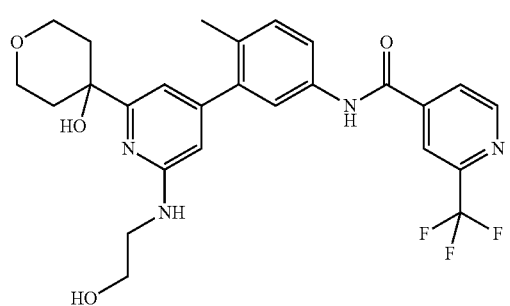
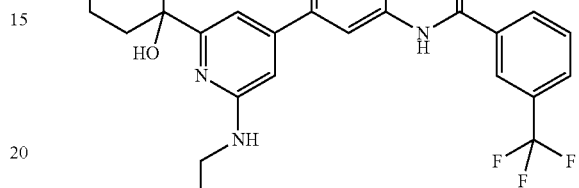
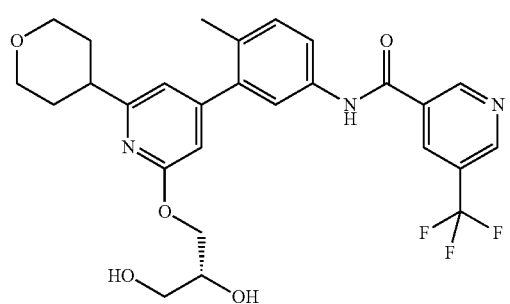
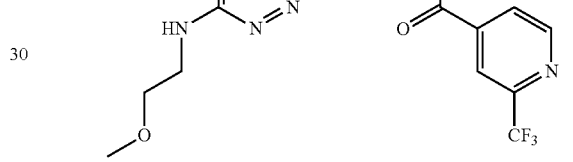
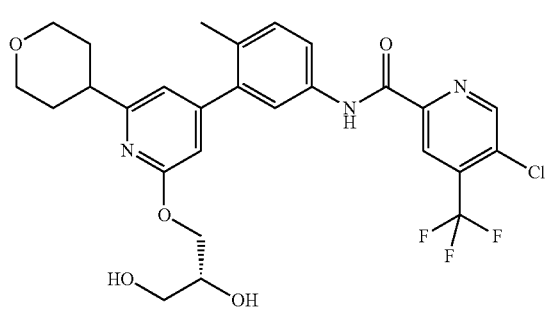
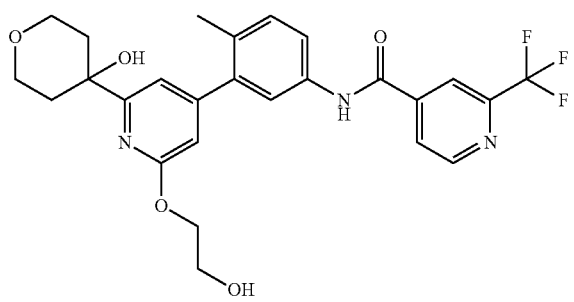
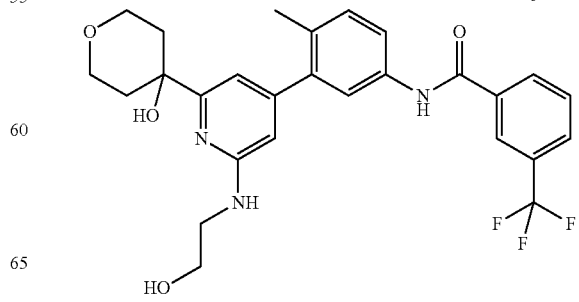

387
-continued
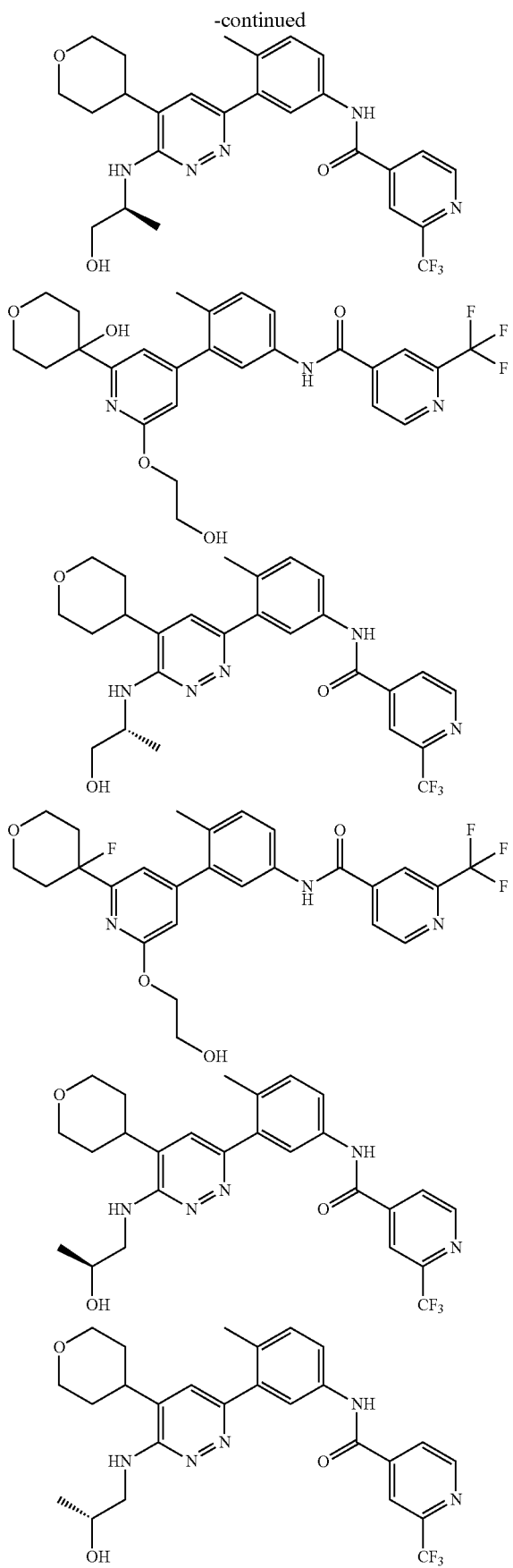
388
-continued
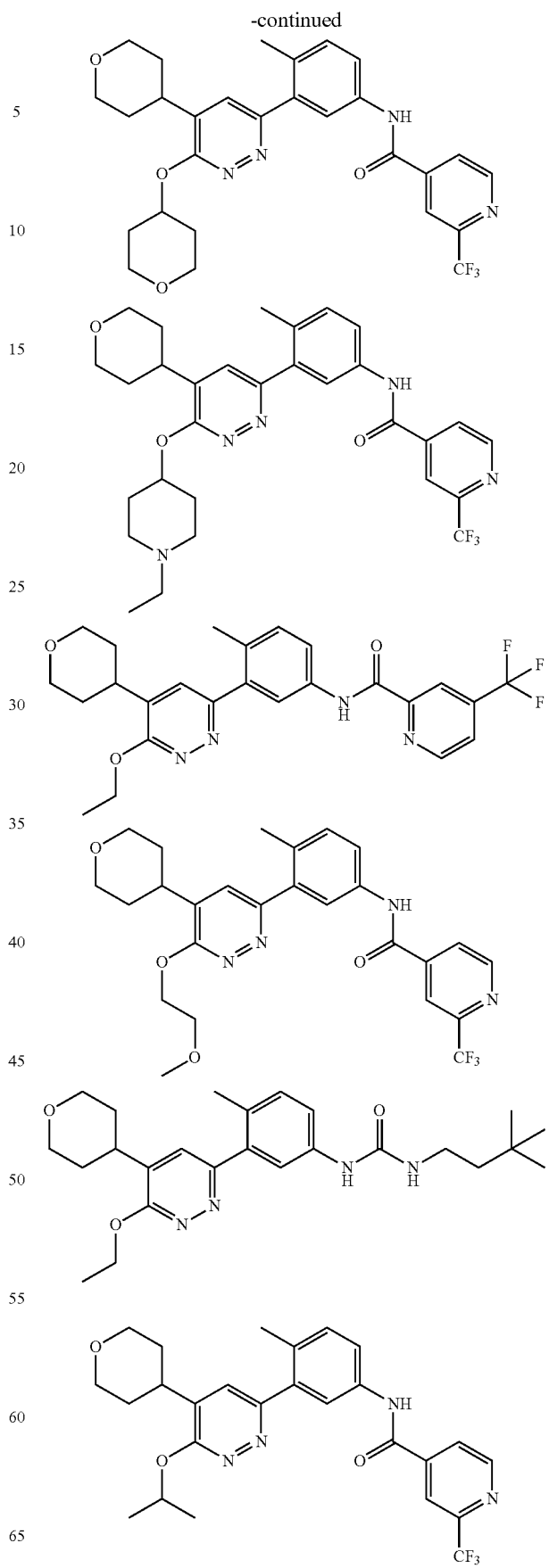

389
-continued
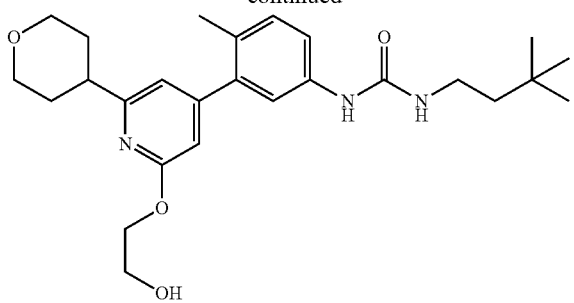
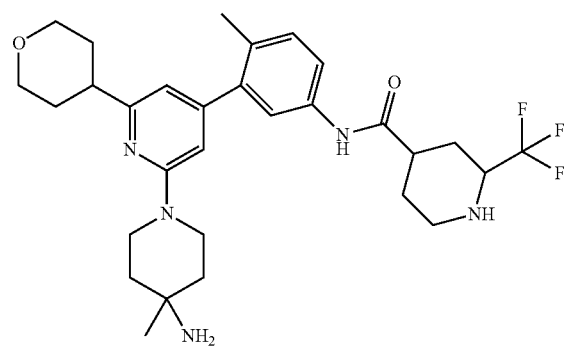
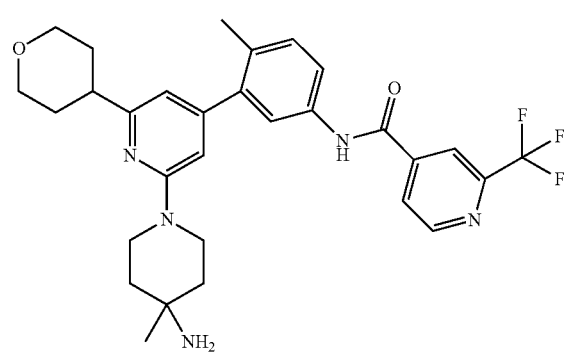
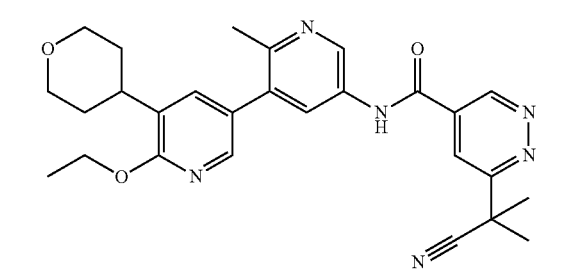
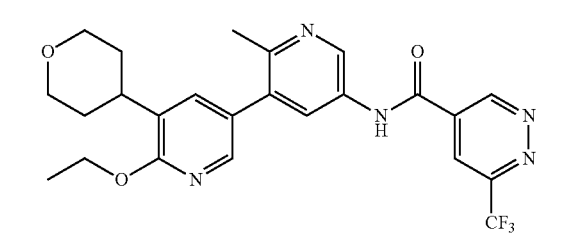
390
-continued
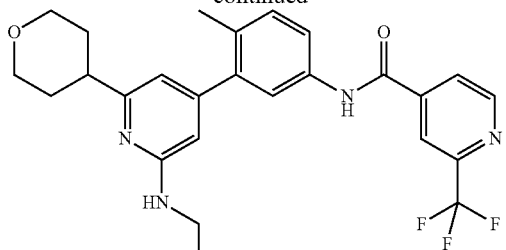
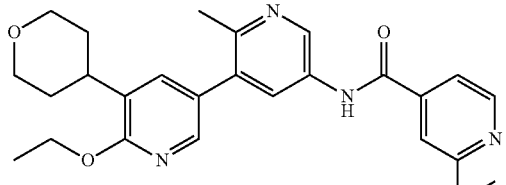
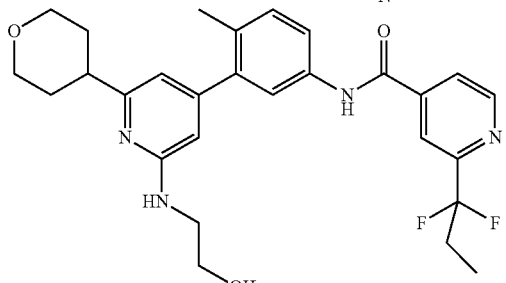
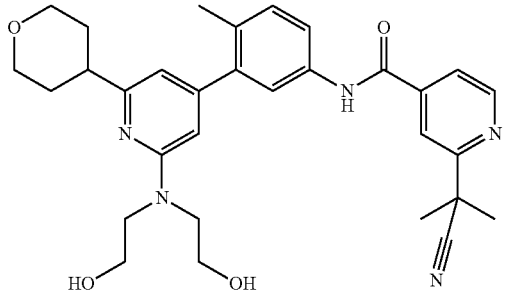
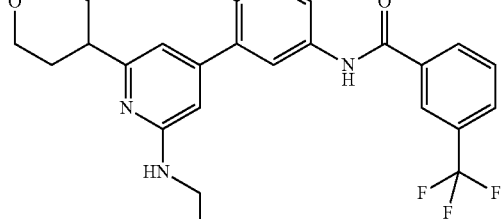
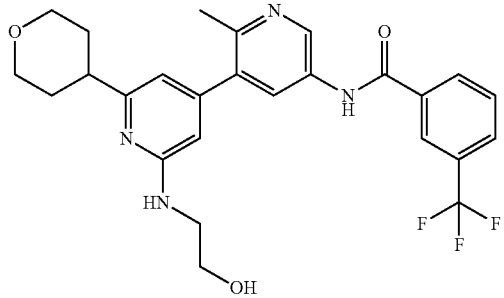

391
-continued
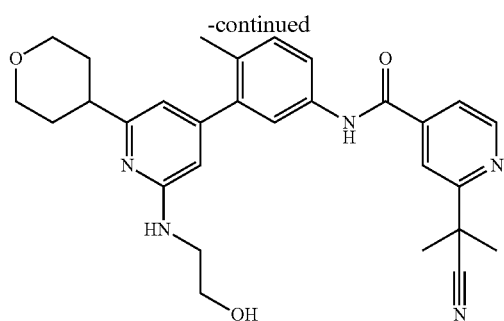
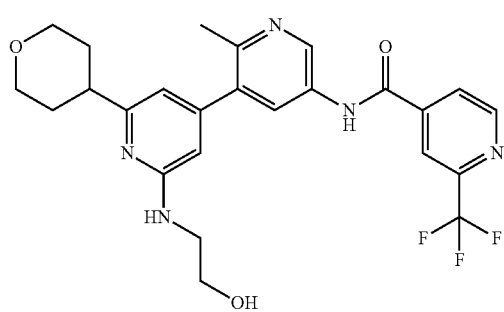
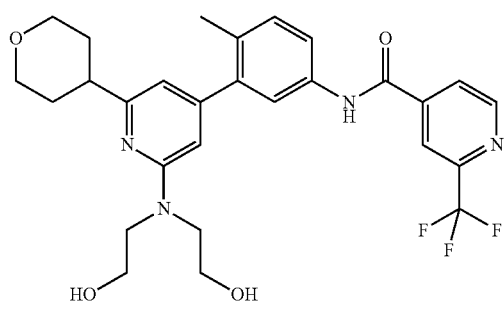
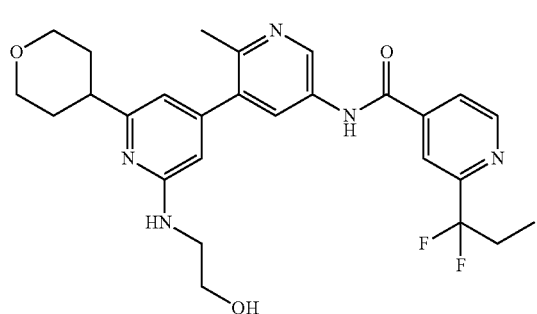
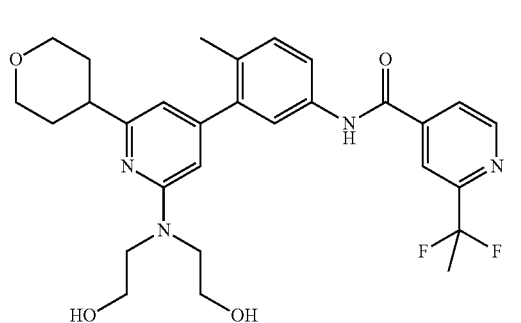
392
-continued
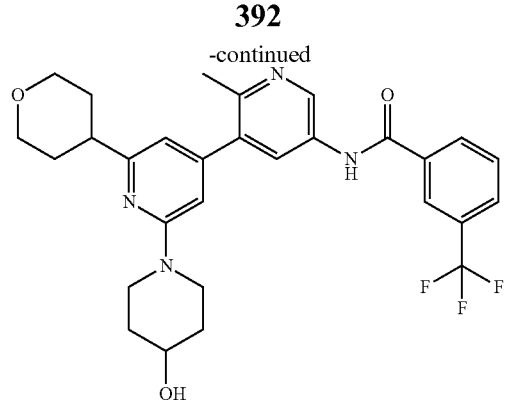
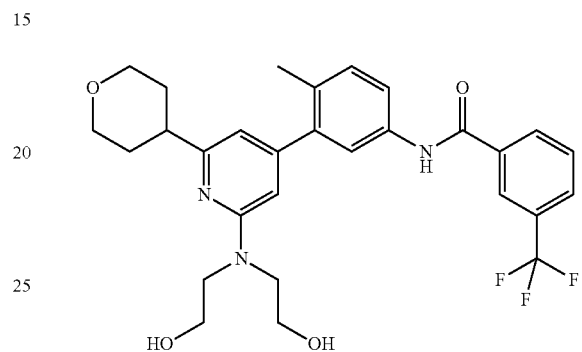
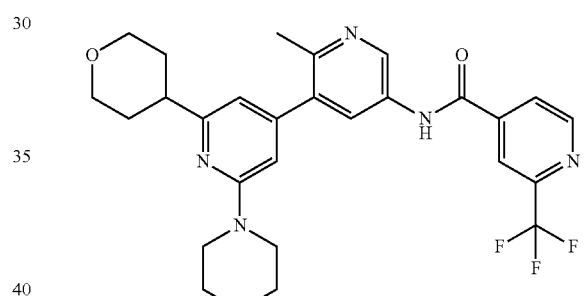
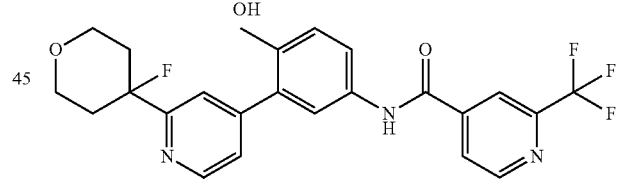
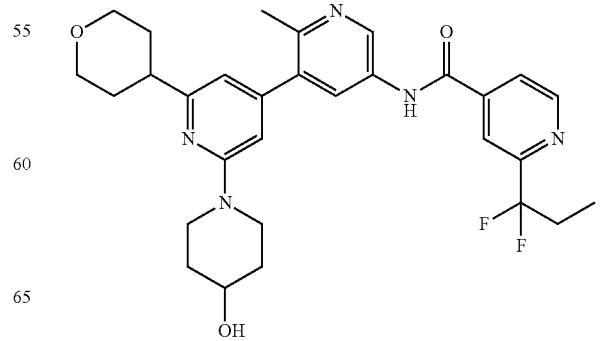

393
-continued
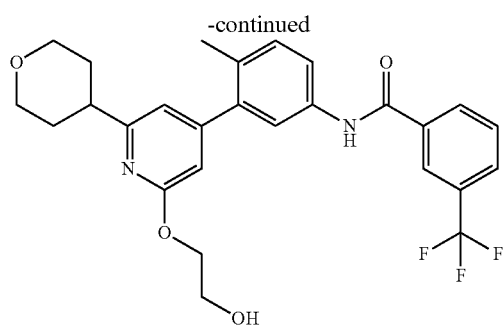
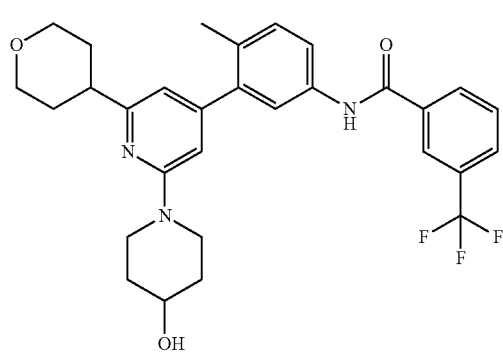
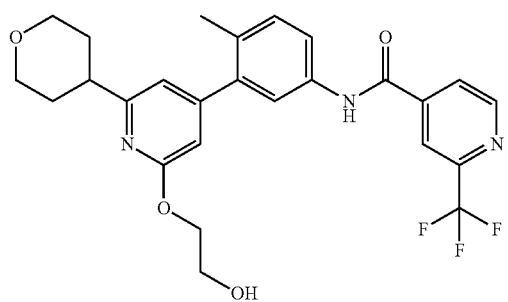
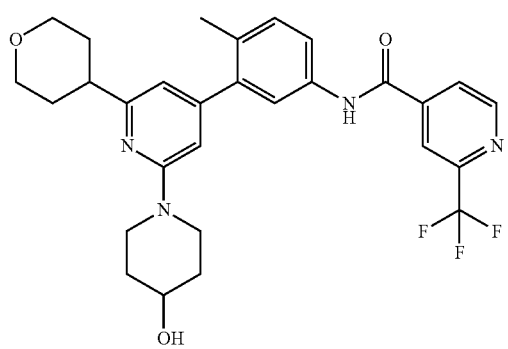
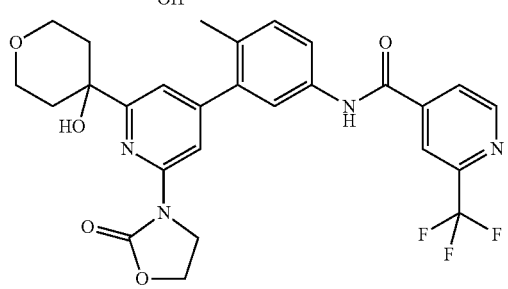
394
-continued
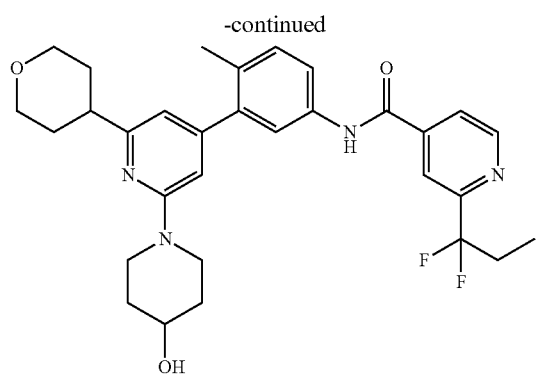
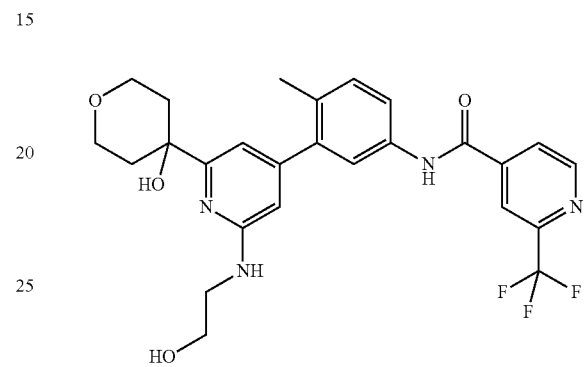
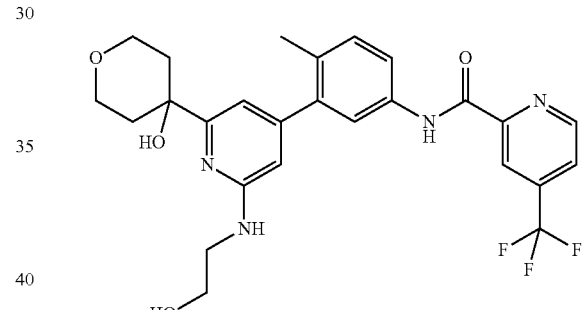
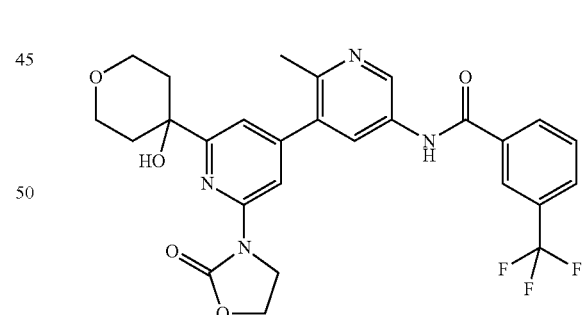
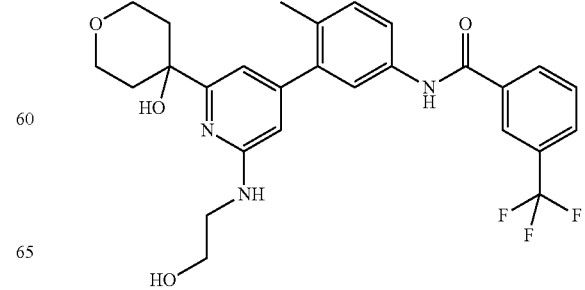

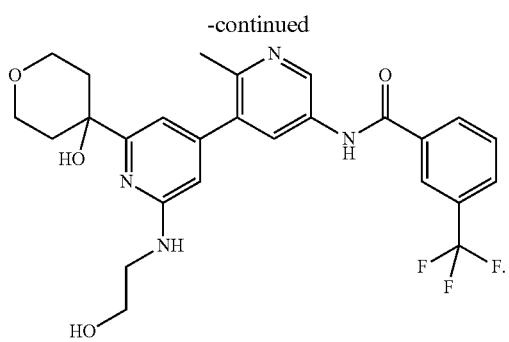
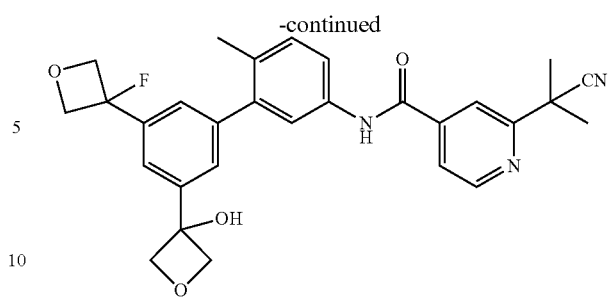
12. The compound of claim 1, or a pharmaceutically acceptable salt thereof, selected from:
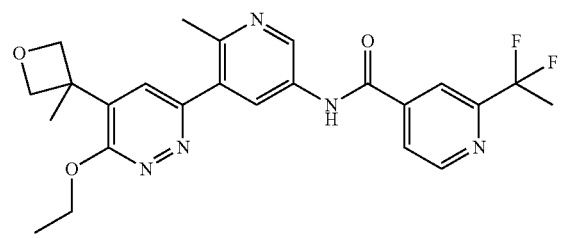
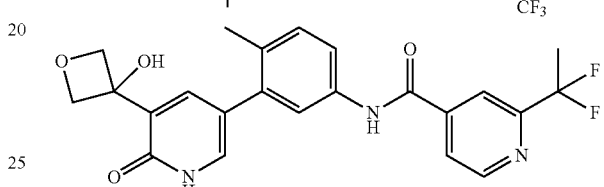
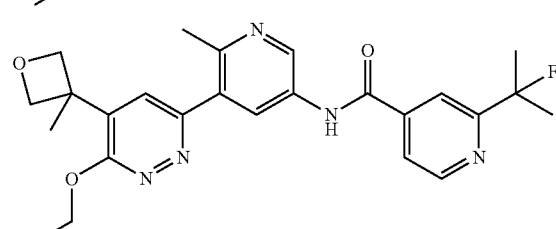
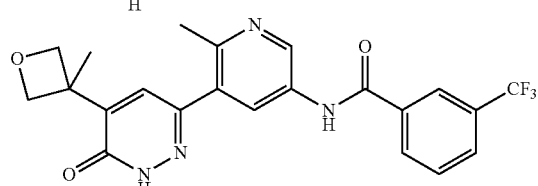
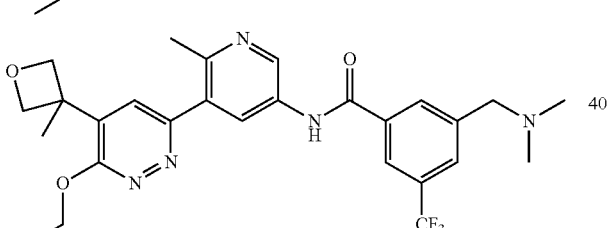
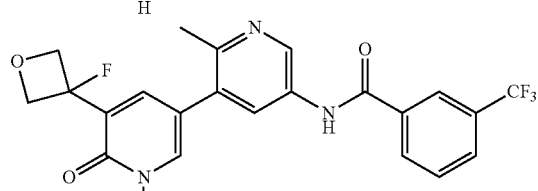
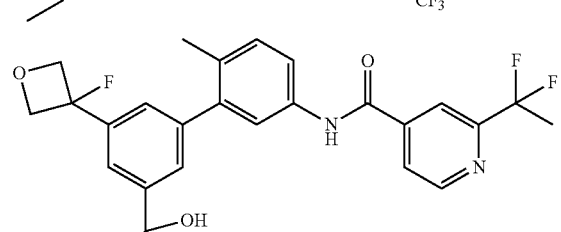
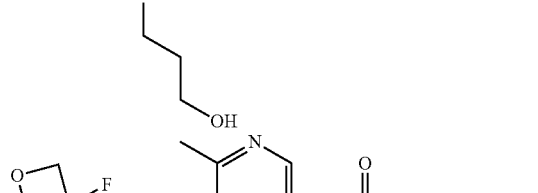
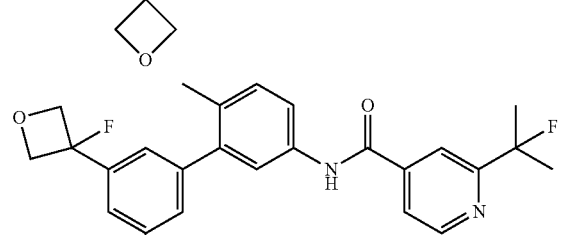
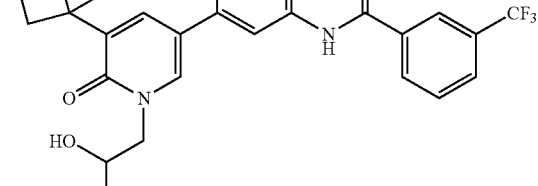
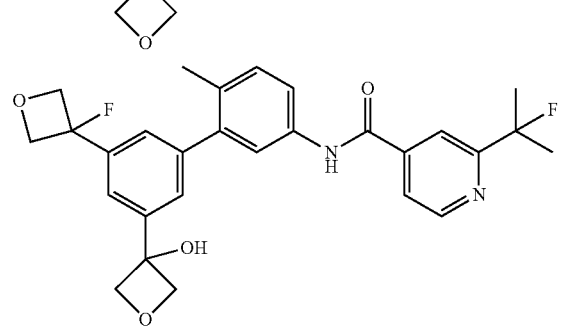
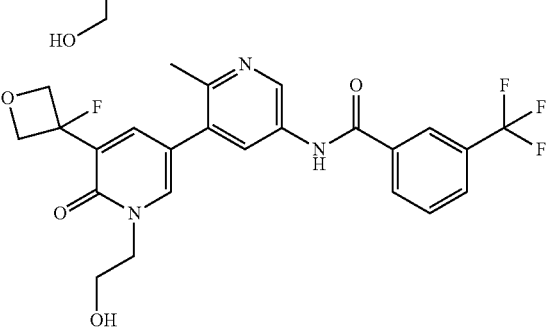

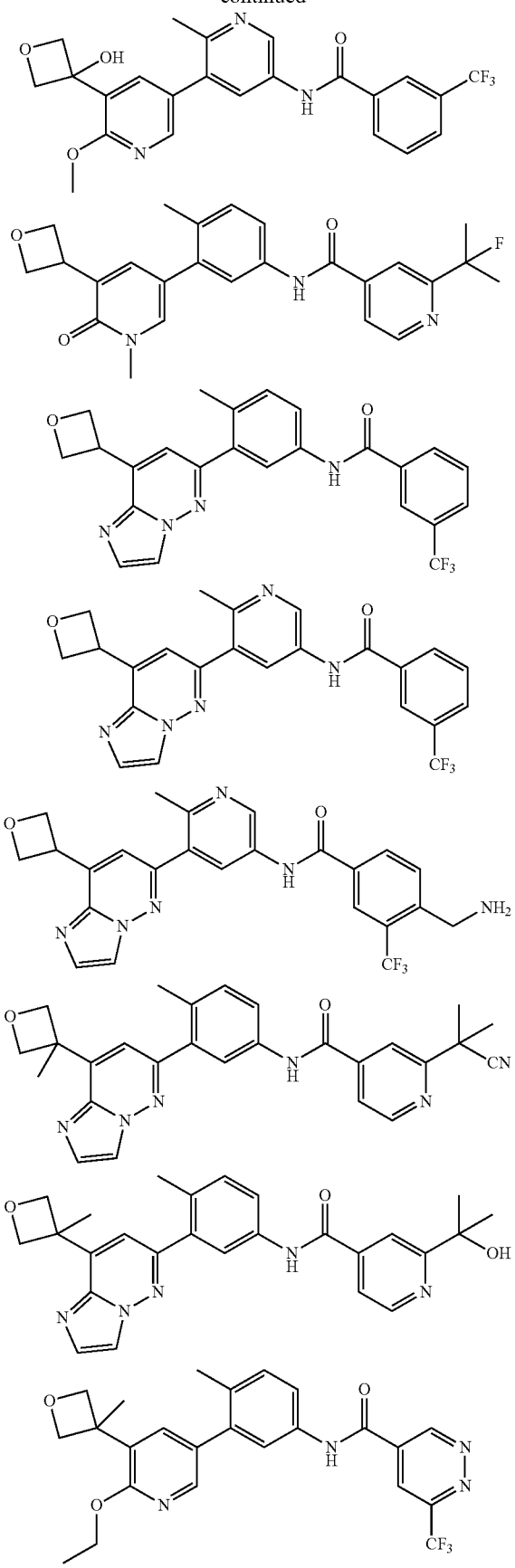
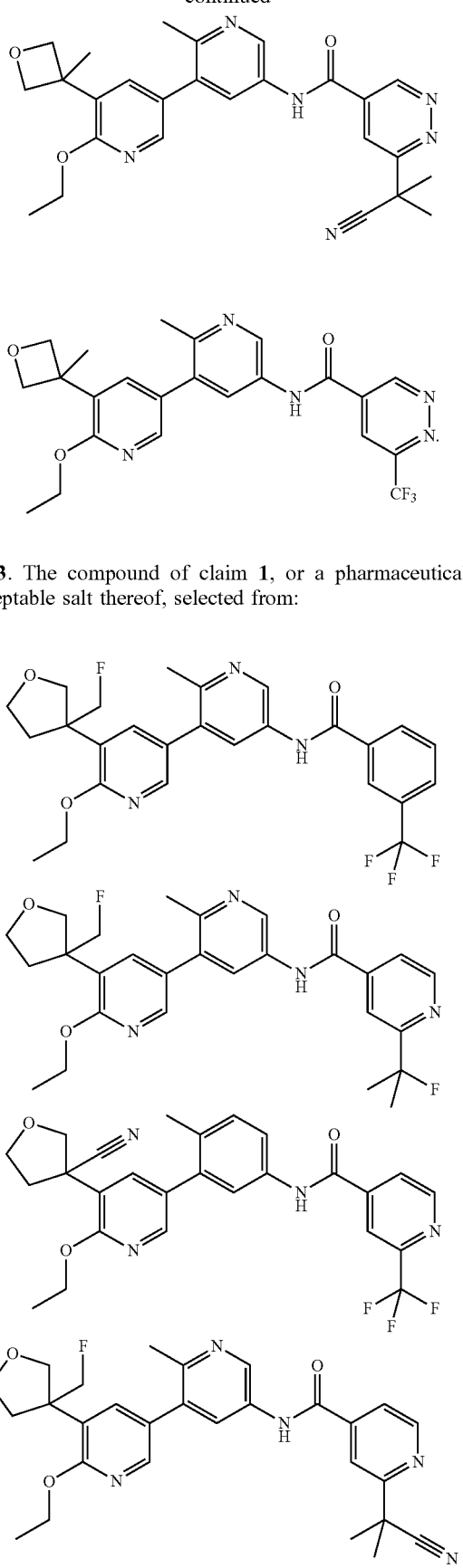
13. The compound of claim 1, or a pharmaceutically acceptable salt thereof, selected from:

399 -continued
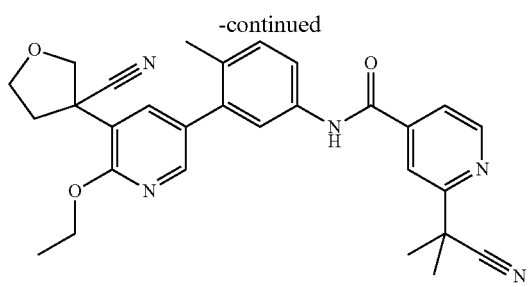
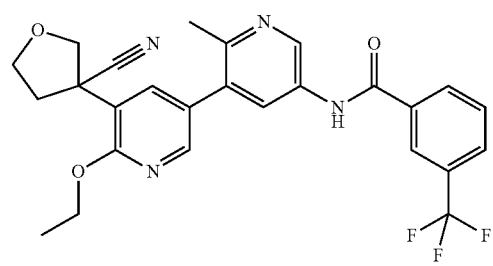
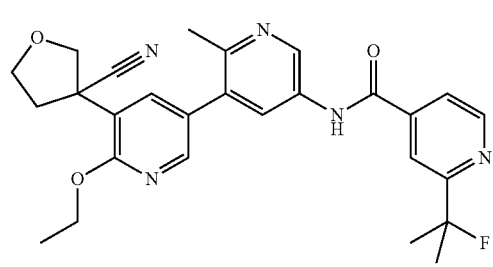
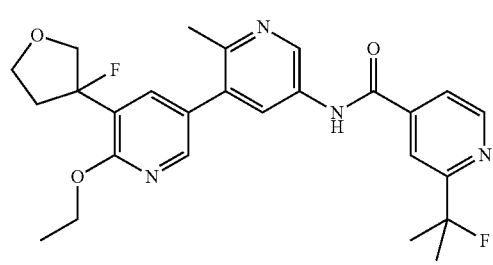
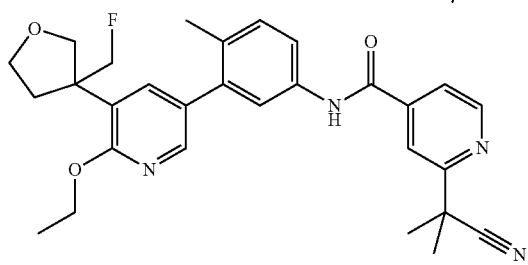
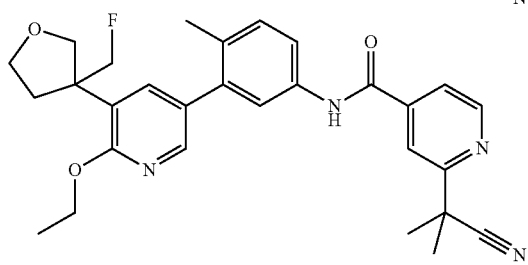
400 -continued
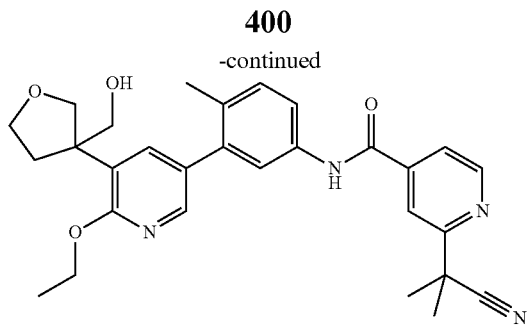
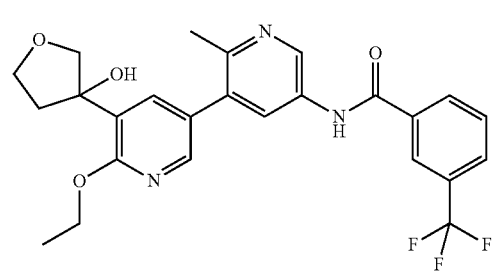
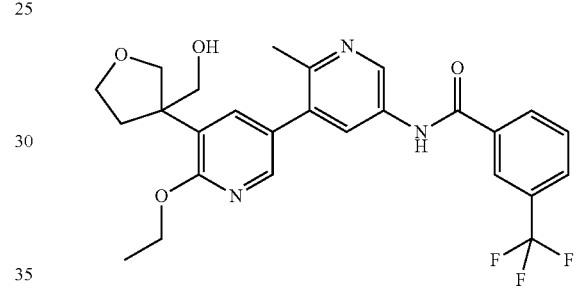
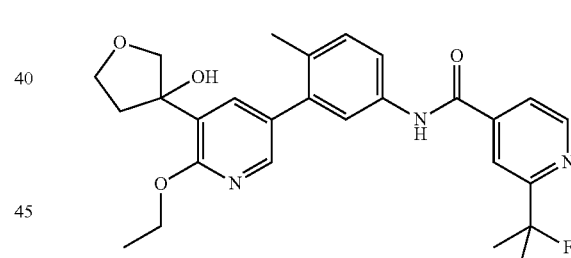
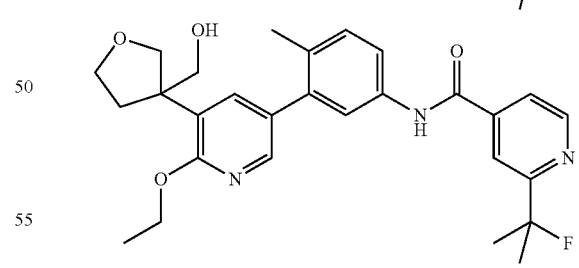
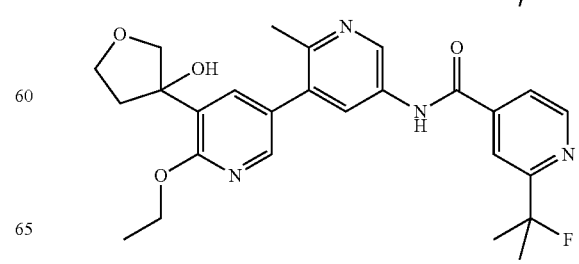

401
-continued

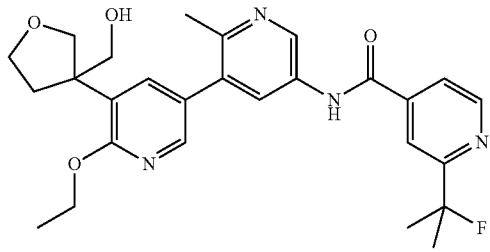

402
-continued

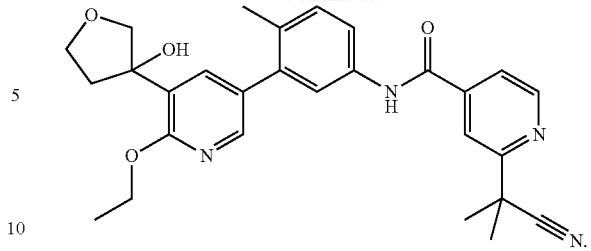

14. A pharmaceutical composition comprising a compound of claim 1 or a pharmaceutically acceptable salt thereof and one or more pharmaceutically acceptable carriers.

15. A combination comprising a therapeutically effective amount of a compound according to claim 1 or a pharmaceutically acceptable salt thereof and one or more therapeutically active co-agents.

16. A method of treating cancer, comprising administering to a subject in need thereof a therapeutically effective amount of a compound of claim 1 or a pharmaceutically acceptable salt thereof.

17. The method of claim 16 wherein the cancer is selected from melanoma.

* * * * *